(12) United States Patent
Piomelli et al.

(10) Patent No.: US 9,828,338 B2
(45) Date of Patent: *Nov. 28, 2017

(54) CARBAMATE DERIVATIVES OF LACTAM BASED N-ACYLETHANOLAMINE ACID AMIDASE (NAAA) INHIBITORS

(71) Applicants: The Regents of the University of California, Oakland, CA (US); Fondazione Istituto Italiano di Tecnologia, Genoa (IT); Universita Degli Studi di Parma, Parma (IT); Universita Degli Studi di Urbino "Carlo Bo", Urbino (IT)

(72) Inventors: Daniele Piomelli, Irvine, CA (US); Tiziano Bandiera, Gambolo (IT); Fabio Bertozzi, Genoa (IT); Andrea Nuzzi, Davoli (IT); Annalisa Fiasella, Pisa (IT); Stefano Ponzano, Florence (IT); Chiara Pagliuca, Arezzo (IT); Angelo Mario Reggiani, Recco (IT); Marco Mor, Ghedi (IT); Giorgio Tarzia, Petriano (IT)

(73) Assignees: The Regents of the University of California, Oakland, CA (US); Fondazione Istituto Italiano di Technologia, Genova (IT); Universita Degli Studi di Urbino "Carlo Bo", Urbino (IT); Universita Degli Studi di Parma, Parma (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/853,634

(22) Filed: Sep. 14, 2015

(65) Prior Publication Data

US 2016/0068482 A1 Mar. 10, 2016

Related U.S. Application Data

(63) Continuation of application No. PCT/US2014/029413, filed on Mar. 14, 2014.

(60) Provisional application No. 61/799,637, filed on Mar. 15, 2013.

(51) Int. Cl.
| | |
|---|---|
| *C07D 205/085* | (2006.01) |
| *C07D 403/12* | (2006.01) |
| *C07D 401/12* | (2006.01) |
| *C07D 405/12* | (2006.01) |
| *C07D 413/12* | (2006.01) |

(52) U.S. Cl.
CPC ....... *C07D 205/085* (2013.01); *C07D 401/12* (2013.01); *C07D 403/12* (2013.01); *C07D 405/12* (2013.01); *C07D 413/12* (2013.01)

(58) Field of Classification Search
None
See application file for complete search history.

(56) References Cited

U.S. PATENT DOCUMENTS

| | | | |
|---|---|---|---|
| 4,207,234 A | 6/1980 | Kamiya et al. | |
| 4,550,105 A | 10/1985 | Matsuo et al. | |
| 4,584,132 A | 4/1986 | Albrecht | |
| 4,665,171 A | 5/1987 | Evans et al. | |
| 4,683,303 A | 7/1987 | Pfaendler | |
| 4,831,130 A | 5/1989 | Albrecht et al. | |
| 4,870,169 A | 9/1989 | Evans et al. | |
| 4,931,556 A | 6/1990 | Boyer et al. | |
| 5,137,884 A | 8/1992 | Andrus et al. | |
| 5,260,310 A | 11/1993 | Derungs et al. | |
| 5,646,275 A | 7/1997 | Gardner et al. | |
| 5,962,012 A | 10/1999 | Lin et al. | |
| 6,261,595 B1 | 7/2001 | Stanley et al. | |
| 6,358,978 B1 | 3/2002 | Ritzeler et al. | |
| 9,321,743 B2 | 4/2016 | Piomelli et al. | |
| 9,353,075 B2 | 5/2016 | Piomelli et al. | |
| 2005/0131032 A1 | 6/2005 | Sit et al. | |

(Continued)

FOREIGN PATENT DOCUMENTS

| | | |
|---|---|---|
| EP | 0 742 223 A1 | 11/1996 |
| EP | 0 742 223 B1 | 11/1996 |

(Continued)

OTHER PUBLICATIONS

Beauve, Cecile. Tetrahedron 55 (1999) 13301-13320.*
Banker, Gilbert. Modern Pharmaceutics 3rd ed. Marcel Dekker, Inc. New York, 1996.*
Astarita, G. et al., "Pharmacological Characterization of Hydrolysis-Resistant Analogs of Oleoylethanolamide with Potent Anorexiant Properties," The Journal of Pharmacology and Experimental Therapeutics, vol. 318, No. 2, received Mar. 24, 2006, accepted May 12, 2006.
Armirotti, Andrea et al., "β-Lactones Inhibit N-acylethanolamine Acid Amidase by S-Acylation of the Catalytic N-Terminal Cysteine," ACS Medicinal Chemistry Letters (ACS), 2012, vol. 3, No. 5, pp. 422-426.

(Continued)

*Primary Examiner* — Deepak Rao
*Assistant Examiner* — Laura Daniel
(74) *Attorney, Agent, or Firm* — Zachary L. Terranova; Mintz, Levin, Cohn, Ferris, Glovsky and Popeo, P.C.

(57) ABSTRACT

Described herein are compounds and pharmaceutical compositions which inhibit N-acylethanolamine acid amidase (NAAA). Described herein are methods for synthesizing the compounds set forth herein and methods for formulating these compounds as pharmaceutical compositions which include these compounds. Also described herein are methods of inhibiting NAAA in order to sustain the levels of palmitoylethanolamide (PEA) and other N-acylethanolamines (NAE) that are substrates for NAAA, in conditions characterized by reduced concentrations of NAE. Also, described here are methods of treating and ameliorating pain, inflammation, inflammatory diseases, and other disorders in which modulation of fatty acid ethanolamides is clinically or therapeutically relevant or in which decreased levels of NAE are associated with the disorder.

15 Claims, 8 Drawing Sheets

(56) References Cited

U.S. PATENT DOCUMENTS

| | | |
|---|---|---|
| 2006/0281778 A1 | 12/2006 | Tagat et al. |
| 2007/0155747 A1 | 7/2007 | Dasse et al. |
| 2008/0050336 A1 | 2/2008 | Bachand et al. |
| 2009/0054526 A1 | 2/2009 | Hansen et al. |
| 2010/0311711 A1 | 12/2010 | Piomelli et al. |
| 2013/0281490 A1 | 10/2013 | Piomelli et al. |
| 2014/0094508 A1 | 4/2014 | Piomelli et al. |
| 2016/0068483 A1 | 3/2016 | Piomelli et al. |
| 2016/0235707 A1 | 8/2016 | Piomelli et al. |
| 2016/0256432 A1 | 9/2016 | Piomelli et al. |

FOREIGN PATENT DOCUMENTS

| | | |
|---|---|---|
| WO | WO-2009/049238 A1 | 4/2009 |
| WO | WO-2011/082285 A1 | 7/2011 |
| WO | WO-2013/078430 A1 | 5/2013 |
| WO | WO-2014/144547 A2 | 9/2014 |
| WO | WO-2014/144547 A3 | 9/2014 |
| WO | WO-2014/144836 A2 | 9/2014 |
| WO | WO-2014/144836 A3 | 9/2014 |

OTHER PUBLICATIONS

Banker, G.S. et al. (1996). *Modern Pharmaceutics*, Third Edition, Marcel Dekker, Inc. New York, 3 pages.

Berdyshev, E. et al. (1998). "Effects of Cannabinoid Receptor Ligands on LPS-Induced Pulmonary Inflammation in Mice," *Life Sciences* 63(8): PL125-129.

Cainelli, G. et al. (1997). "Penicillin G acylase mediated synthesis of the enantiopure (S)-3-amino-azetidin-2-one," *Tetrahedron:Asymmetry* 8(19):3231-3235.

Calignano, A. et al. (Jul. 16, 1998). "Control of pain initiation by endogenous cannabinoids," *Nature* 394(6690):277-281.

Calignano, A. et al. (May 11, 2001). "Antinociceptive activity of the endogenous fatty acid amide, palmitylethanolamide," *Eur J Pharmacol* 419(2-3):191-198.

Chalker, J.M. et al. (Nov. 18, 2009). "A convenient catalyst for aqueous and protein Suzuki-Miyaura cross-coupling," *J Am Chem Soc* 131(45):16346-16347.

Dias et al., "Antimicrobial properties of highly fluorinated silver (I) tis (pyrazoili) borates," Journal of Inorganic Biochemistry, 2006, vol. 100, pp. 158-160.

D'Agostino, G. et al. (Sep. 2007, e-published Jun. 12, 2007). "Acute intracerebroventricular administration of palmitoylethanolamide, an endogenous peroxisome proliferator-activated receptor-alpha agonist, modulates carrageenan-induced paw edema in mice," 322(3):1137-1143.

Duranti et al., "N-(2-Oxo-3-oxetanyl)carbamic Acid Esters as N-Acylethanolamine Acid Amidase Inhibitors: Synthesis and Structure-Activity and Structure—Property Relationships," Journal of Medicinal Chemistry, May 2012, pp. A-M.

Evans, D.A. et al. (1985). "The Asymmetric Synthesis of β-Lactam Antibiotics- I. Application of Chiral Oxazolidones in the Staudinger Reaction," *Tetrahedron Letters* 26:3783.

Fiasella, A. et al. (Jul. 2014, e-published May 14, 2014). "3-Aminoazetidin-2-one derivatives as N-acylethanolamine acid amidase (NAAA) inhibitors suitable for systemic administration," *ChemMedChem* 9(7):1602-1614.

Fleisher, D. et al. (1996). "Improved oral drug delivery: solubility limitations overcome b the use of prodrugs," Advanced Drug Delivery Reviews 19(2):115-130.

He, G. et al. (May 23, 2011, e-published Apr. 27, 2011). "A practical strategy for the structural diversification of aliphatic scaffolds through the palladium-catalyzed picolinamide-directed remote functionalization of unactivated C(sp3)—H bonds," Angewandte Chemie Int. Ed. 50(22):5192-5196.

Higashibayashi, Shuhei et al., Synthetic studies on thiostrepton family of peptide antibiotics: synthesis of the pentapeptide segment containing dihydroxyisoleucine, thiazoline and dehydroamino acid, Tetrahedron Letters (Elsevier B.V.), 2004, vol. 45, No. 19, pp. 3707-3712.

Holt et al., "Inhibition of fatty acid amide hydrolase, a key endocannabinoid metabolizing enzyme, by analogues of ibuprofen and indomethacin," Eur J Pharmacol., Jun. 2007, 565(1-3):26-36, Epub Mar. 2007.

International Search Report, dated Dec. 17, 2008, for International Application No. PCT/US2008/079621, filed Oct. 10, 2008, 1 page.

International Search Report and Written Opinion, dated Feb. 28, 2013, PCT application No. PCT/US2012/066421, pp. 13.

International Search Report dated Sep. 29, 2014, for PCT Application No. PCT/US2014/029007, filed Mar. 14, 2014, 4 pages.

International Search Report dated Oct. 10, 2014, for PCT Application No. PCT/US2014/029413, filed Mar. 14, 2014, 5 pages.

Kemeny, L. et al. (2007, e-published Jan. 17, 2007). "Endogenous phospholipid metabolite containing topical product inhibits ultraviolet light-induced inflammation and DNA damage in human skin," Skin Pharmacol Physiol 20(3):155-161.

Kumar, Y et al. (2003, e-published Oct. 2, 2003). "Process for Developing 3β-[4-(S)-Arylacetylamino-4β-(2-(2-furyl)ethyl]azetidin-2-one: A Carbacephem Key Intermediate," *Org. Proc. Res. Dev.*7(6):933-935.

Lall, Manjinder S. et al., Serine and Threonine [3 -Lactones: A New Class of Hepatitis A Virus 3C Cysteine Proteinase Inhibitors, Journal of Organic Chemistry (American Chemical Society), 2002, vol. 67, No. 5, pp. 1536-1547.

Li et al., "Design and Synthesis of Potent N-Acylethanolamine-hydrolyzing Acid Amidase (NAAA) Inhibitor as Anti-Inflammatory Compounds," PLoS One, Aug. 2012;7(8):e43023.

Lohse et al., "Incorporation of a phosphonic acid isostere of aspartic acid into peptides Using Fmoc-solid phase synthesis," Tetrahedron Letters, 1998, vol. 39, Issue 15, pp. 2067-2070.

Lo Verme, J. et al. (Jan. 2005, e-published Oct. 1, 2004). "The nuclear receptor peroxisome proliferator-activated receptor-alpha mediates the anti-inflammatory actions of palmitoylethanolamide," *Mol Pharmacol* 67(1):15-19.

Lo Verme, J. et al. (Dec. 2006, e-published Sep. 22, 2006). "Rapid broad-spectrum analgesia through activation of peroxisome proliferator-activated receptor-alpha," *J Pharmacol Exp Ther* 319(3):1051-1061.

Mazzari, S. et al. (Apr. 11, 1996). "N-(2-hydroxyethyl)hexadecanamide is orally active in reducing edema formation and inflammatory hyperalgesia by down-modulating mast cell activation," Eur J Pharmacol 300(3):227-236.

Mori, Tomonori et al., "Total Synthesis of Siomycin A: Construction of Synthetic Segments," Chemistry—An Asian Journal (Wiley—VCH Verlag), 2008, vol. 3, No. 6, pp. 984-1012.

Nissen, S.E. et al. (Mar. 28, 2007, e-published Mar. 25, 2007). "Effects of a potent and selective PPAR-α agonist in patients with atherogenic dyslipidemia or hypercholesterolemia: two randomized controlled trials," JAMA 297(12):1362-1373.

Office Actions and Responses for U.S. Appl. No. 13/684,017, filed Nov. 21, 2012, 110 pages.

Patani, G.A. et al. (Dec. 1996). "Bioisosterism: A Rational Approach in Drug Design," *Chem Rev* 96(8):3147-3176.

Pu et al.; Synthesis and Acylation of Salts of L-Threonine -Lactone: A route to _-Lactone Antibiotics; Journal of Organic Chemistry; vol. 56, vol. 3; pp. 1280-1283, published Feb. 1, 1991.

Pu et al.; Synthesis, Stability, and Antimicrobial Activity of (+)-Obafluorin and Related beta-Lactone Antibiotics; Journal of Organic Chemistry, vol. 59, No. 13, pp. 3642-3655 (1994).

Sasso, O. et al. (May 2012, e-published Mar. 7, 2012). "Peripheral FAAH inhibition causes profound antinociception and protects against indomethacin-induced gastric lesions," Pharmacol Res 65(5):553-563.

Saturnino et al., "Synthesis and biological evaluation of new potential inhibitors of N-acylethanolamine hydrolyzing acid amidase," Bioorganic & Medicinal Chemistry Letters, 2010, vol. 20, Issue 3, pp. 1210-1213.

Sliwa, A. et al. (2012). "12- TO 22-Membered Bridged β-Lactams as Potential Penicillin-Binding Protein Inhibitors," *Chem Asian J* 7:425-434.

(56) References Cited

OTHER PUBLICATIONS

Spetzler et al., "Preparation and application of 0-amino-serine, Ams, a new building block in chemoselective ligation chemistry," Journal of Peptide Science, 1999, vol. 5, Issue 12, pp. 582-592.

Solorzano, C. et al. (Dec. 8, 2009, e-published Nov. 19, 2009). "Selective N-acylethanolamine-hydrolyzing acid amidase inhibition reveals a key role for endogenous palmitoylethanolamide in inflammation," PNAS USA 106(49):20966-20971.

Solorzano, C. et al. (Aug. 12, 2010). "Synthesis and structure-activity relationships of N-(2-oxo-3-oxetanyl)amides as N-acylethanolamine-hydrolyzing acid amidase inhibitors," J Med Chem 53(15):5770-5781.

Stigers, Dannon J. et al., "Incorporation of chlorinated analogues of aliphatic amino acids during cell-free protein synthesis," Chemical Communications (Royal Soc of Chemistry), 2011, 47(6):1839-1841.

Tsuboi, K. et al. (Mar. 25, 2005, e-published Jan. 17, 2005). "Molecular characterization of N-acylethanolamine-hydrolyzing acid amidase, a novel member of the choloylglycine hydrolase family with structural and functional similarity to acid ceramidase," J Biol Chem 280(12):11082-11092.

Tsuboi, K. et al. (Aug. 2007). "The N-acylethanolamine-hydrolyzing acid amidase (NAAA)," Chem Biodivers 4(8):1914-1925.

Ueda et al. "A second N-acylethanolamine hydrolase in mammalian tissues," Neuropharmacology, 2005, vol. 48, pp. 1079-1085.

Valls, Nativitat et al., Synthesis of β-chloro α-amino acids: (2S,3R)- and (2S,3S)-3-chloroleucine, Tetrahedron Letters (Elsevier B.V.), 2006, vol. 47, No. 22, pp. 3701-3705.

Wang, Zheming et al., "β-Lactone probes identify a papain-like peptide ligase in *Arabidopsis thaliana*," Nature Chemical Biology (Nature Publishing Group), 2008, vol. 4, No. 9, pp. 557-563.

Written Opinion dated Sep. 29, 2014, for PCT Application No. PCT/US2014/029007, filed Mar. 14, 2014, 6 pages.

Written Opinion dated Oct. 10, 2014, for PCT Application No. PCT/US2014/029413, filed Mar. 14, 2014, 4 pages.

Written Opinion dated Dec. 17, 2008, for PCT Application No. PCT/US2008/079621, filed Oct. 10, 2008 4 pages.

* cited by examiner

CARBAMATE DERIVATIVES OF LACTAM BASED N-ACYLETHANOLAMINE ACID AMIDASE (NAAA) INHIBITORS

CROSS-REFERENCES TO RELATED APPLICATIONS

This application is a continuation of International Patent Application No. PCT/US2014/029413, filed Mar. 14, 2014, which in claims the benefit of U.S. Provisional Patent Application No. 61/799,637, filed Mar. 15, 2013, all of which are incorporated herein by reference in its entirety and for all purposes.

STATEMENT AS TO RIGHTS TO INVENTIONS MADE UNDER FEDERALLY SPONSORED RESEARCH AND DEVELOPMENT

This invention was made with Government support under Grant No. DA012413, awarded by the National Institutes of Health. The Government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 79828-901787_ST25.TXT, created Mar. 12, 2014, 966 bytes, machine format IBM-PC, MS-Windows operating system, is hereby incorporated by reference.

BACKGROUND OF THE INVENTION

While there are numerous compositions and methods known in the art to treat pain and inflammation, numerous difficulties remain. Most significantly, side effects over long administration periods and/or higher dosages often limit the use of such drugs. For example, certain COX-2 inhibitors are implicated in adverse cardiovascular events and aspirin-type pain medication often increase the risk of intestinal bleeding. In other examples, ibuprofen and acetaminophen tend to negatively impact hepatic function, especially at higher dosages.

Ethanolamides of long-chain fatty acids, usually referred to as N-acylethanolamines (NAEs), are present in numerous lower and higher organisms, and mammals with a wide variety of functions. For example, anandamide, a polyunsaturated fatty acid-type NAE, was demonstrated to have cannabimimetic activity. In contrast, saturated and monounsaturated NAEs are inactive as ligands of cannabinoid receptors. However, such compounds have been reported to possess a variety of other biological activities. For example, N-oleoylethanolamine, a monounsaturated fatty acid-type NAE, was shown to be anorexic via the peroxisome proliferator-activated receptor-α (PPAR-α), and N-stearoylethanolamine, a saturated fatty acid-type NAE, to be pro-apoptotic and anorexic.

N-palmitoylethanolamine (PEA), the naturally occurring amide of palmitic acid and ethanolamine, is a member of the saturated fatty acid-type NAE family. PEA has been shown to inhibit peripheral inflammation and mast cell degranulation (Mazzari et al., *European Journal of Pharmacology* 1996, 300, 227-36; Berdishev et al., *Life Science* 1998, 63, 125-129; D'Agostino et al., *Journal of Pharmacology and Experimental Therapeutics* 2007, 322, 1137-1143), as well as to exert antinociceptive effects in rats and mice (Calignano et al., *Nature* 1998, 394, 277-281; Calignano et al., *European Journal of Pharmacology* 2001, 419, 191-198).

These properties have been shown to be dependent on PPAR-α, and PEA activates this nuclear receptor with a potency comparable to the synthetic agonist WY14,643 (Lo Verme et al., *Molecular Pharmacology* 2005, 67, 15-19; Lo Verme et al., *Journal of Pharmacology and Experimental Therapeutics* 2006, 319, 1051-1061).

In the carrageenan-induced paw edema and phorbol ester-induced ear edema models, PEA applied as a drug attenuates inflammation in wild-type mice, but has no effect in mice lacking PPAR-α (see LoVerme et al., *Molecular Pharmacology* 2005, 67, 15-19). PEA was also found to suppress pain behaviors induced, in mice, by chemical tissue injury, nerve damage, or inflammation (see LoVerme et al., *Journal of Pharmacology and Experimental Therapeutics* 2006, 319, 1051-1061).

In addition to the pharmacological activities shown in animal models, PEA has been reported to attenuate skin inflammation in humans (Kemeny et al., *Skin Pharmacology and Physiology* 2007, 20, 155-161).

Activation of PPAR-α by selective receptor agonists could be envisaged as a viable approach for the treatment of inflammatory and pain states. However, the prolonged clinical use of PPAR-α agonists has been linked to serious adverse events, which include oncogenesis, renal dysfunction, and cardiovascular toxicity (Nissen et al., *JAMA* 2007, 297, 1362-1373). Sustaining PEA signaling at PPAR-α by protecting this lipid amide from degradation is envisaged as an alternative to direct PPAR-α activation by receptor agonists.

NAEs are substrate of the N-acylethanolamine acid amidase (NAAA), an enzyme that catalytically hydrolyzes the NAE to ethanolamine and the corresponding fatty acid. NAAA is a cysteine hydrolase that belongs to the N-terminal nucleophile (Ntn) family of enzymes (Tsuboi et al., *Journal of Biological Chemistry* 2005, 280, 11082-11092; Tsuboi et al., *Chemistry and Biodiversity* 2007, 4, 1914-1925). NAAA exhibits a substantial preference for PEA over other NAEs. Therefore, inhibition of NAAA is expected to decrease the inactivation and restore the levels of PEA in pathological conditions characterized by markedly reduced concentrations of this signaling molecule.

There exists a problem in the field to which the instant invention pertains related to the preparation of new inhibitors of NAAA for use in the preparation of pharmaceutical composition therapeutics. Surprisingly, the instant invention solves this as well as several other problems in the relevant field by providing, inter alia, small molecule chemical inhibitors of NAAA as well as methods for treating pain and inflammation.

BRIEF SUMMARY OF THE INVENTION

In one aspect, the present invention provides a compound having the structure of Formula I:

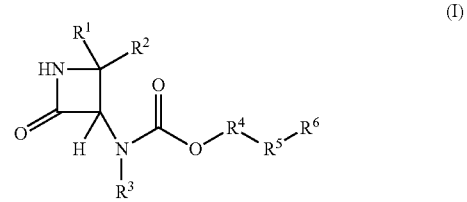

In Formula $R^1$ and $R^2$ are each independently selected from the group consisting of hydrogen, alkyl, aryl, cycloalkyl, arylalkyl, and cycloalkylalkyl. In some embodiments, $R^1$ and $R^2$ form a cycloalkyl substituent together with the carbon to which they are attached. $R^3$ is selected from the group consisting of hydrogen and alkyl. $R^4$ is selected from the group consisting of alkyl, alkenyl, alkynyl, aryl, arylalkyl, cycloalkyl, heteroaryl, heterocycloalkyl, heteroarylalkyl, and heterocycloalkylalkyl. $R^5$ is absent or is selected from the group consisting of alkyl, alkenyl, alkoxy, aryl, aryloxy, cycloalkyl, —O—, —S—, —C(O)—, —C(O)NH—, $NR^aR^b$, heteroaryl, and heterocycloalkyl. $R^6$ is absent or is selected from the group consisting of hydrogen, alkyl, alkoxy, aryl, aryl-alkylene, aryloxy, arylalkyloxy, arylalkyl, cycloalkyl, cycloalkyloxy, heterocycloalkyl, heterocycloalkyloxy, cycloalkylalkyl, heteroaryl, and —C(O)$NR^aR^b$. $R^1$, $R^2$, $R^3$, $R^4$, $R^5$, and $R^6$ are each independently optionally substituted with 1-4 substituents selected from the group consisting of lower alkyl, lower alkoxy, aryl, $NR^aR^b$, cyano, halogen, hydroxyl, trifluoromethyl, difluoromethyl, fluoromethyl. $R^a$ and $R^b$ are each independently selected from the group consisting of hydrogen and alkyl, and when $R^a$ and $R^b$ are taken together with the nitrogen atom to which they are bound, the group $NR^aR^b$ represents a heterocyclyl residue. Also included are the pharmaceutically acceptable salts, esters, or prodrugs thereof.

In a second aspect, the present invention provides a method of treating a mammal suffering from an inflammatory condition comprising administering to the mammal a compound having the structure selected from the group consisting of Formula I to XVII, as described herein.

In a third aspect, the present invention provides a method of treating a mammal suffering from pain or itch by administering to the mammal a compound having the structure selected from the group consisting of Formula I-XVII. In some embodiments, the painful or pruritogenic pathological state not attributable to inflammation (e.g., non-inflammatory pain or itch).

In a fourth aspect, the present invention provides a method of treating a mammal suffering from a neurodegenerative disorder, comprising administering to the mammal a compound having the structure selected from the group consisting of Formula I-XVII.

In a fifth aspect, the present invention provides a method of inhibiting NAAA comprising contacting the NAAA in vitro with a compound having the structure selected from the group consisting of Formula I-XVII.

DETAILED DESCRIPTION OF THE INVENTION

I. General

Figure 1:
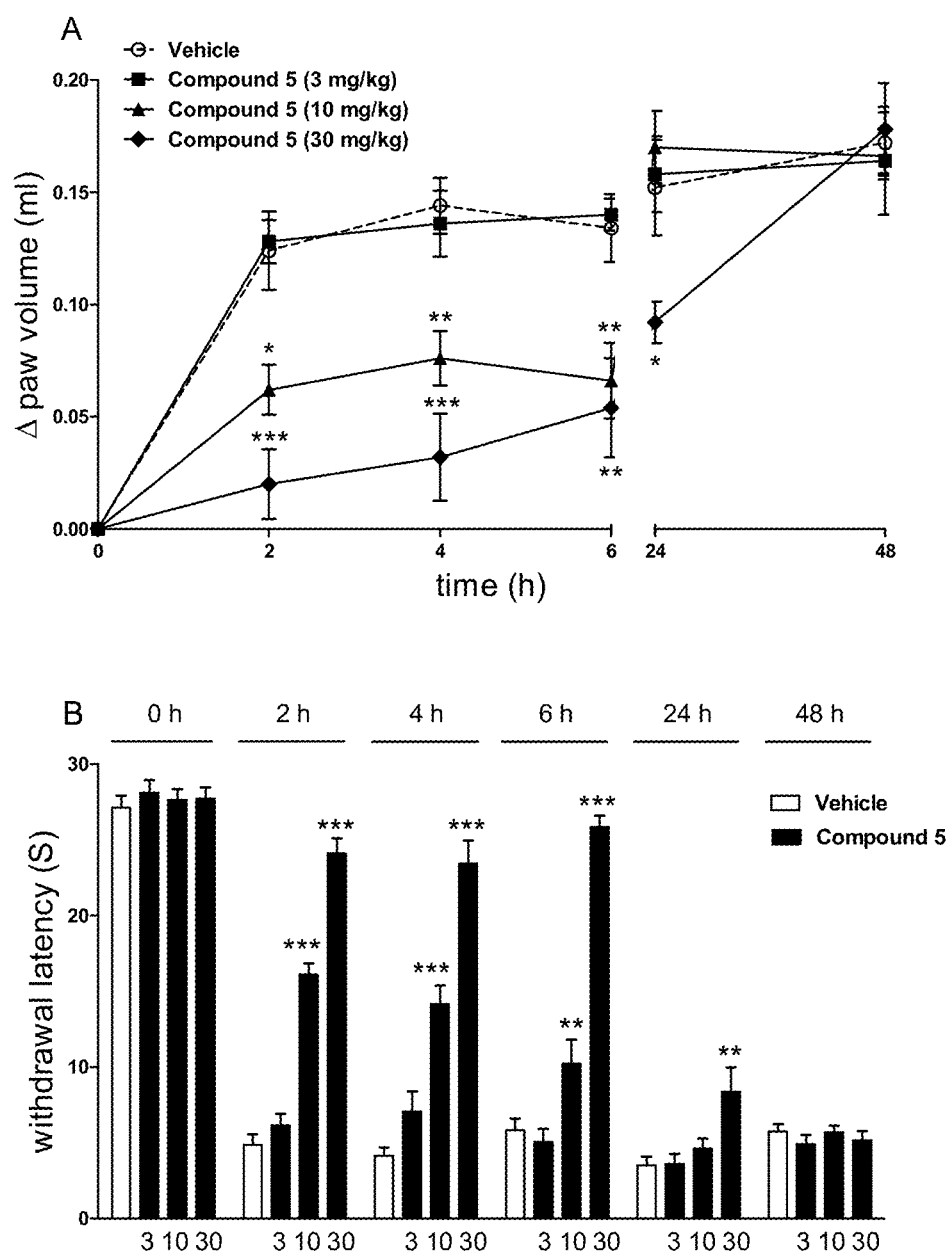
FIG. 1 shows the effects of oral administration of compound 5 on carrageenan-induced hyperalgesia and edema. Compound 5 (3-30 mg/kg) reduced paw edema (A) and heat hyperalgesia (B) measured immediately before (0 h) and at various times after compound 5 injection. Results are expressed as mean±SEM (n=6, each group).  $p<0.01$ and * $p<0.001$ vs. vehicle.
Figure 2:
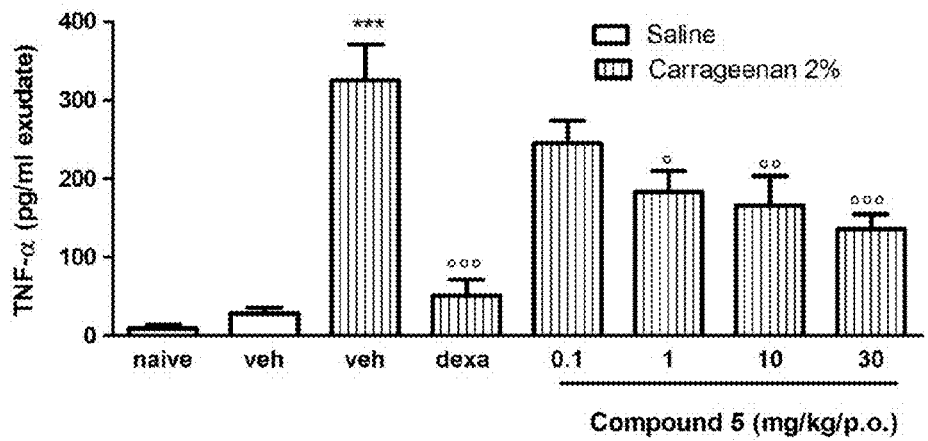
FIG. 2 shows that oral administration of compound 5 normalizes inflammation markers such as TNF-α concentration in pulmonary exudate. Carrageenan treatment induces a massive increase in inflammatory cytokine TNF-alpha concentration in the pulmonary exudate, as compared to saline treated animals. Treatment with dexamethasone (dexa, 0.5 mg/kg, i.p.) or compound 5 (30 mg/kg, p.o.) normalizes TNF-alpha concentration in the exudate of carrageenan-treated animals (n=6-10 per group). *** $p<0.001$ vs veh+saline; ° $p<0.05$, °° $p<0.01$, °°° $p<0.001$ vs veh+carrageenan 2%. 1 way ANOVA followed by Tukey's test.
Figure 3:
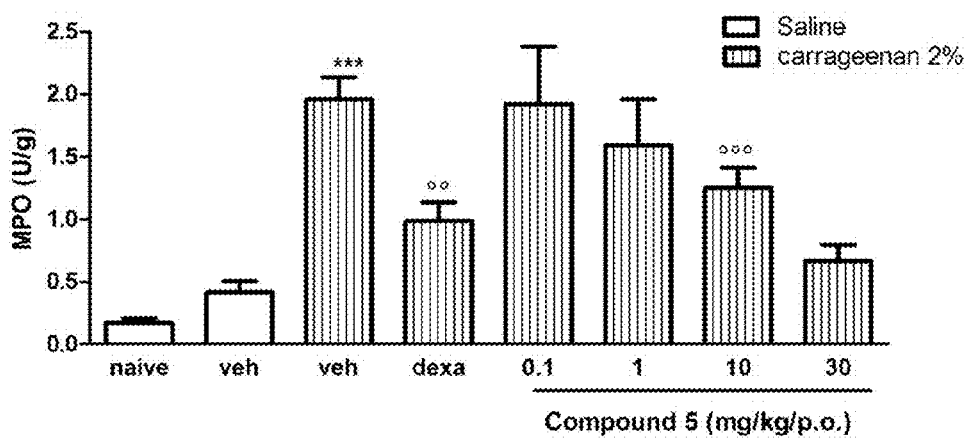
FIG. 3 shows that oral administration of compound 5 normalizes inflammation markers such as myeloperoxidase (MPO) activity in lung tissue. Carrageenan treatment induces an increase in myeloperoxidase (MPO) activity, a marker of neutrophil infiltration, in lung tissue, as compared to saline treated animals. Treatment with dexamethasone (dexa, 0.5 mg/kg, i.p.) and compound 5 (0.1-30 mg/kg, p.o.) normalizes MPO activity in the lungs of carrageenan-treated animals (n=6-10 per group). *** $p<0.001$ vs veh+saline; °° $p<0.01$, °°° $p<0.001$ vs veh+carrageenan 2%. 1 way ANOVA followed by Tukey's test.
Figure 4:
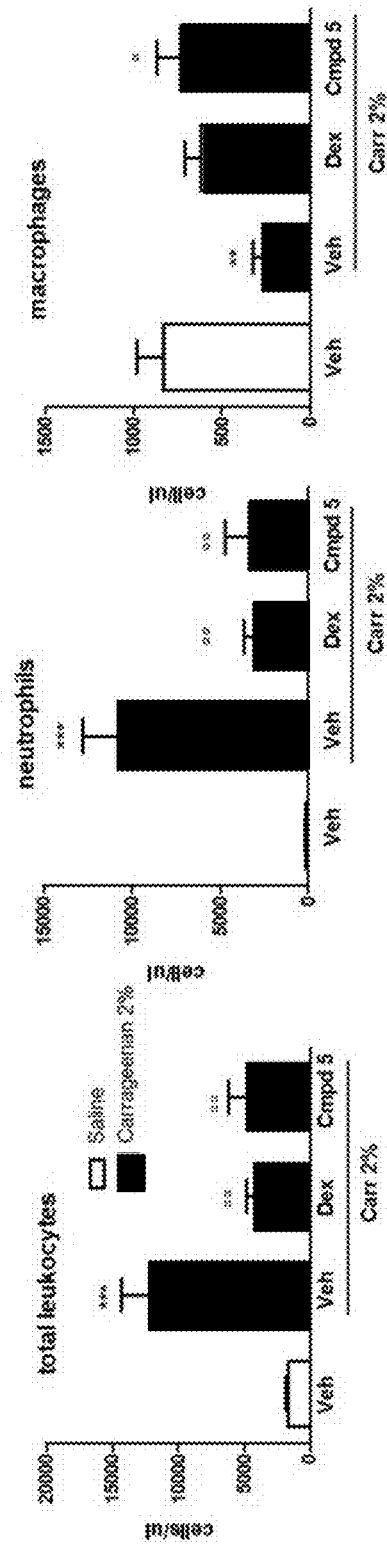
FIG. 4 shows that oral administration of compound 5 (30 mg/kg) restores number of leukocytes in the pulmonary exudate (FACS analysis). Carrageenan 2% treatment causes an increase in the number of leukocytes, in particular neutrophils, in the exudate as compared to saline treated animals. Treatment with dexamethasone (Dex, 0.5 mg/kg, i.p.) or compound 5 (30 mg/kg, p.o.) normalizes the number of leukocytes of carrageenan-treated animals (n=10 per group).
 $p<0.01$, * $p<0.001$ vs veh+saline; ° $p<0.01$, °° $p<0.01$ vs veh+carrageenan 2%. 1 way ANOVA followed by Tukey's test.
Figure 5:
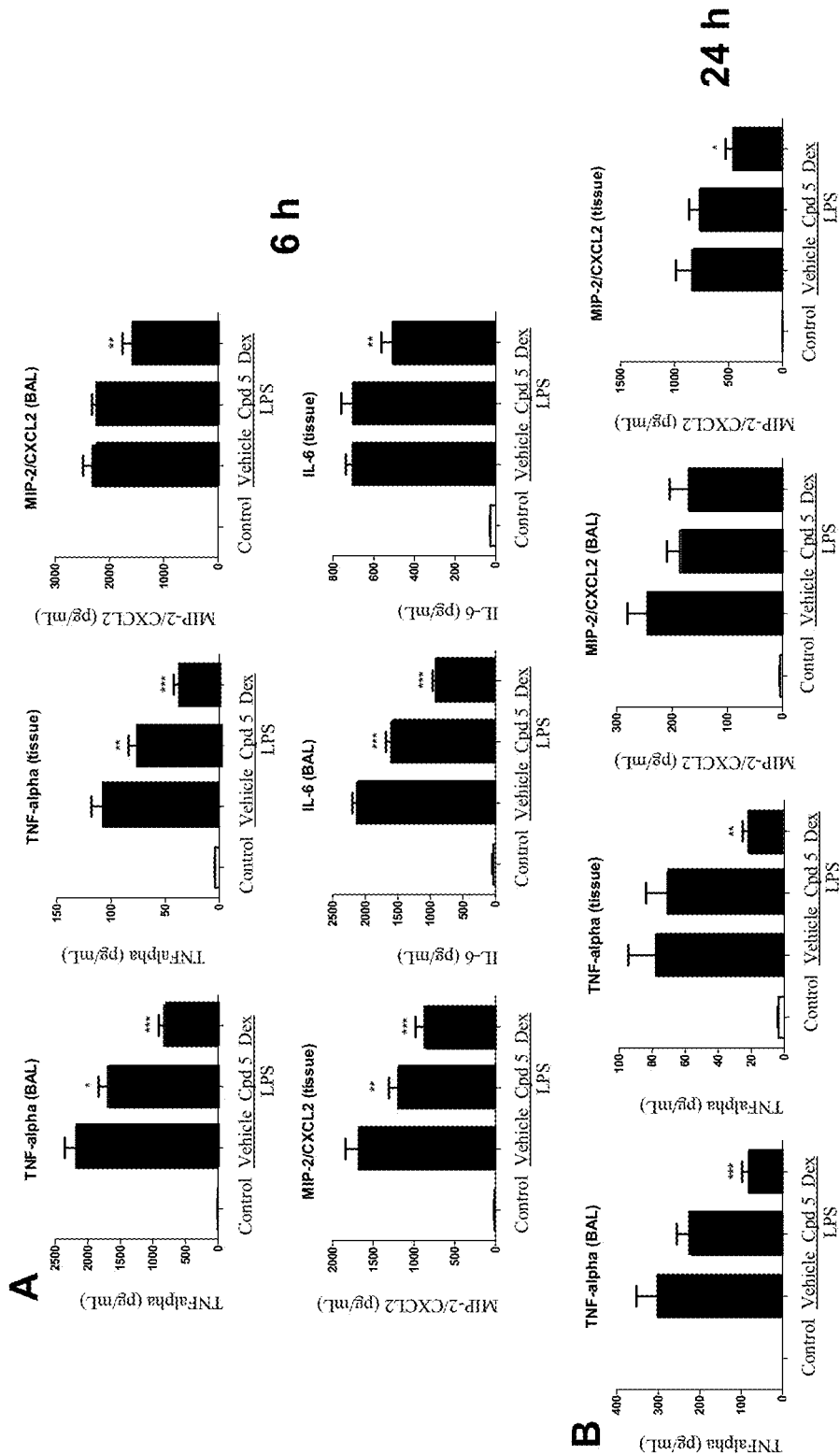
FIG. 5 shows that oral administration of compound 5 (30 mg/kg, 30 min) prevents production of cytokines/chemokines in the Broncho-Alveolar Lavage (BAL) and lung tissue in mice subjected to LPS-induced lung inflammation. Cytokines/chemokines are important to the inflammatory process and cellular migration. Dexamethasone (Dex, 0.5 mg/kg, i.p., 60 min). (A) TNF-alpha, MIP-2/CXCL2, and IL-6 concentration 6 h after the induction of inflammation; (B) TNF-alpha and MIP-2/CXCL2 concentration 24 h after the induction of inflammation. * $P<0.05$ compared to Vehicle+LPS group;  $P<0.01$ compared to Vehicle+LPS group; * $P<0.0001$ compared to Vehicle+LPS group. One way ANOVA followed by Newman-Keuls multiple comparison test.
Figure 6:
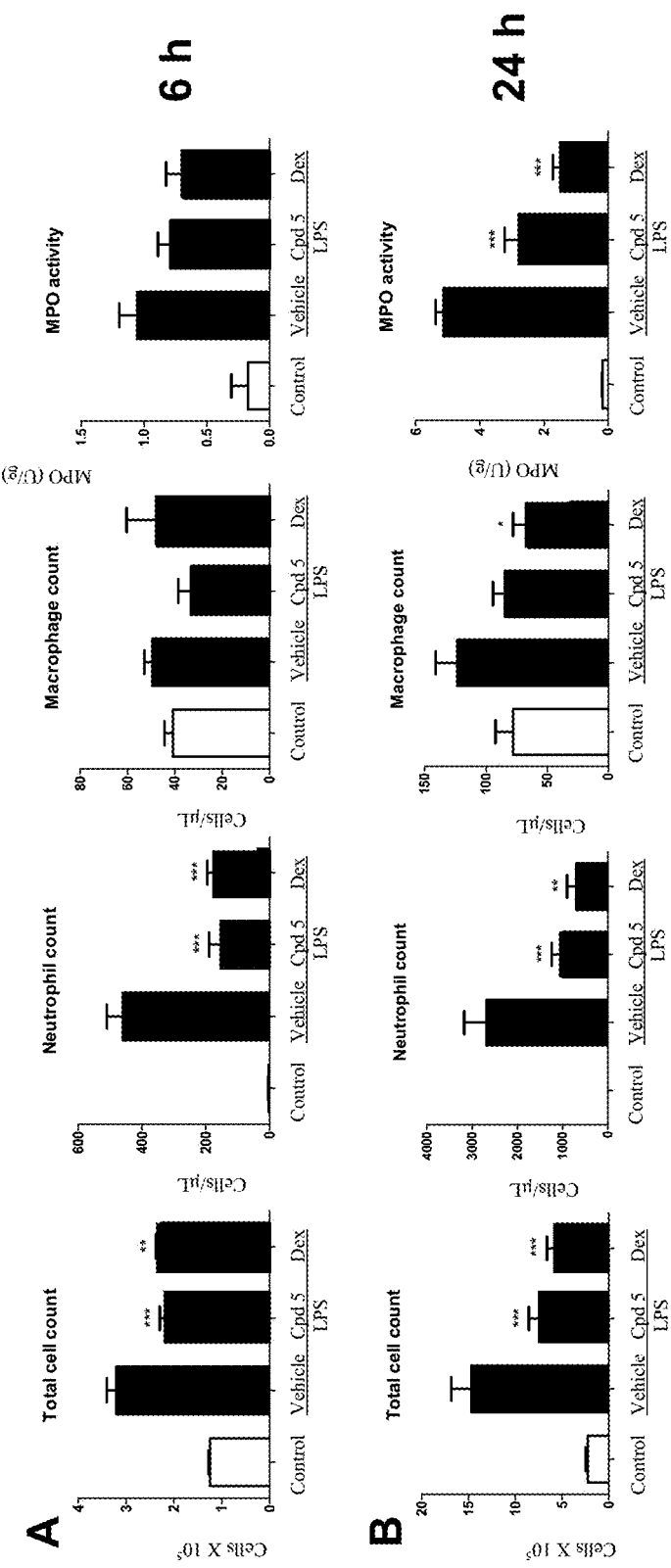
FIG. 6 shows that oral administration of compound 5 (30 mg/kg, 30 min) prevents the migration of neutrophils into the lungs of mice treated with LPS. Dexamethasone (Dex, 0.5 mg/kg i.p., 60 min). (A) Total cell count, neutrophil count, macrophage count, MPO activity 6 h after the induction of inflammation; (B) Total cell count, neutrophil count, macrophage count, MPO activity 24 h after the induction of inflammation. * $P<0.05$ compared to Vehicle+LPS group;  $P<0.01$ compared to Vehicle+LPS group; * $P<0.0001$ compared to Vehicle+LPS group. One way ANOVA followed by Newman-Keuls multiple comparison test.
Figure 7:
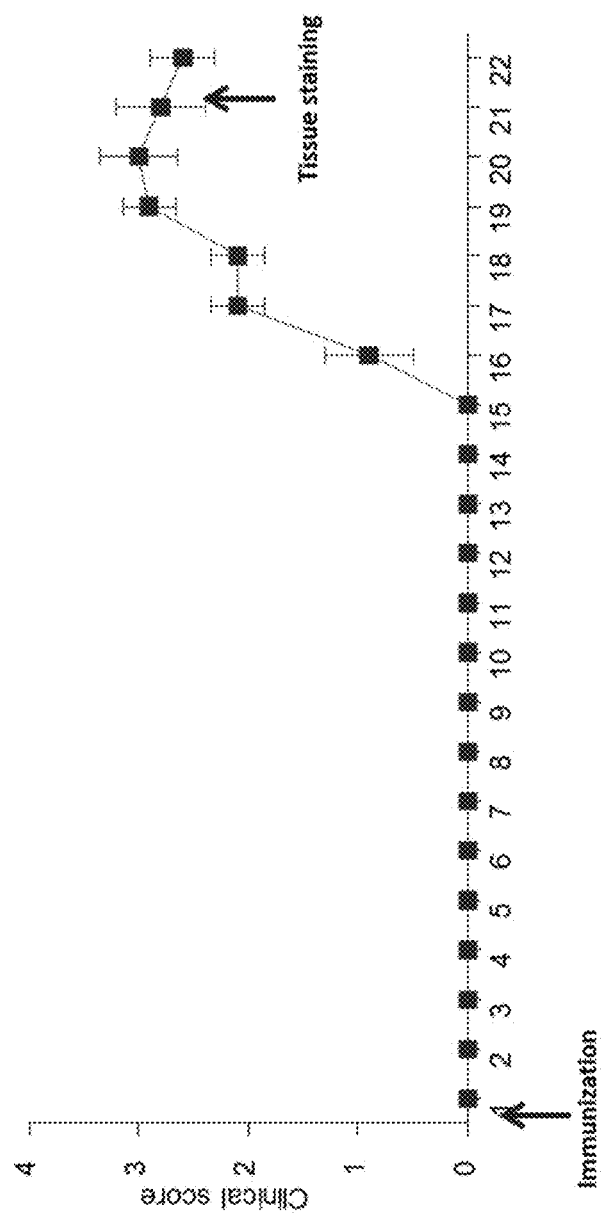
FIG. 7 shows the time course of Experimental Autoimmune Encephalomyelitis (EAE) in mice. The initial measurable signs of neurological impairment start to be detected at 2-2.5 weeks after MOG 35-55 peptide immunization. Disease rapidly develops up to a clear symptomatology characterized by an average score of 3.
Figure 8:
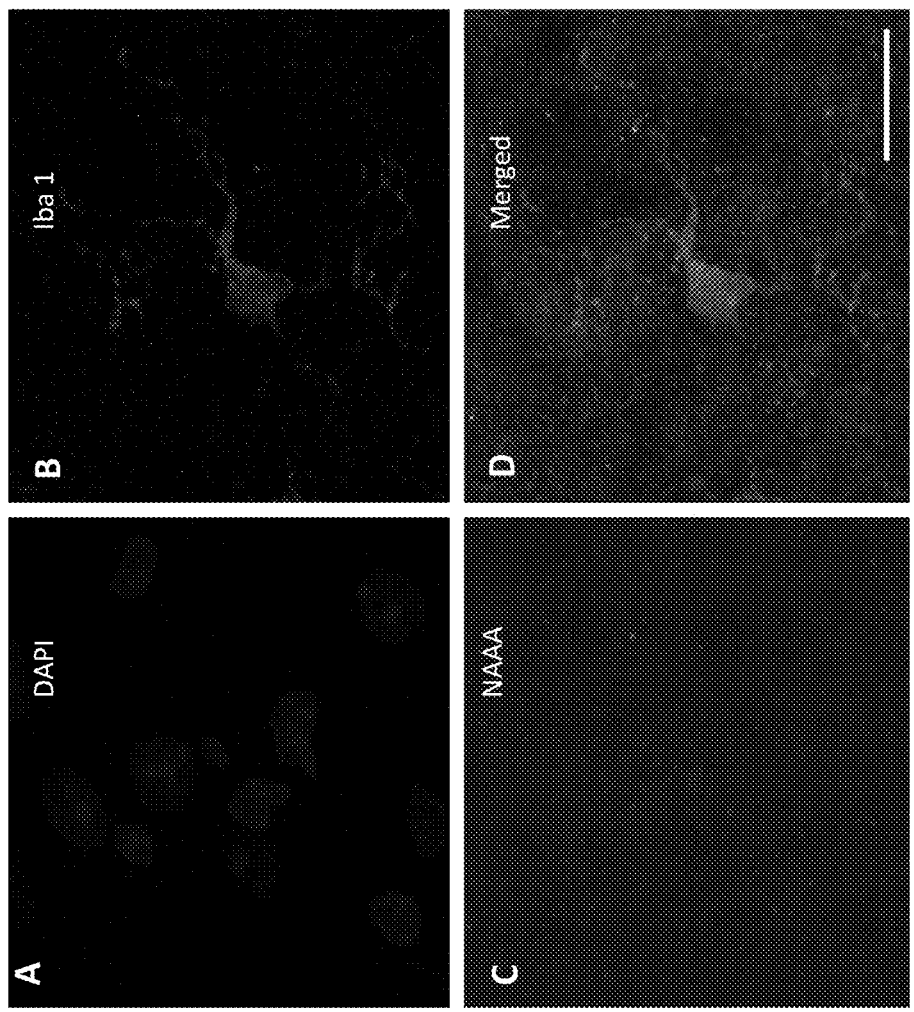
FIG. 8 shows that in control mice (no immunization) no evidence of microglia activation and NAAA expression was observed. The sections were analyzed with a Nikon A1 confocal microscope. A: DAPI staining for cell nuclei (blue). B: Iba1 staining for microglia. The Iba1 positive cell (red) shows a small soma and fine filaments. This ramified morphology defines the typical appearance of resting microglia in adult brain and spinal cord. C: NAAA staining. The absence of green fluorescent signal suggests that there is no NAAA expression in non-immunized mice (or is below the detection limits of the methodology). D: Merged A, B and C panels.
Figure 9:
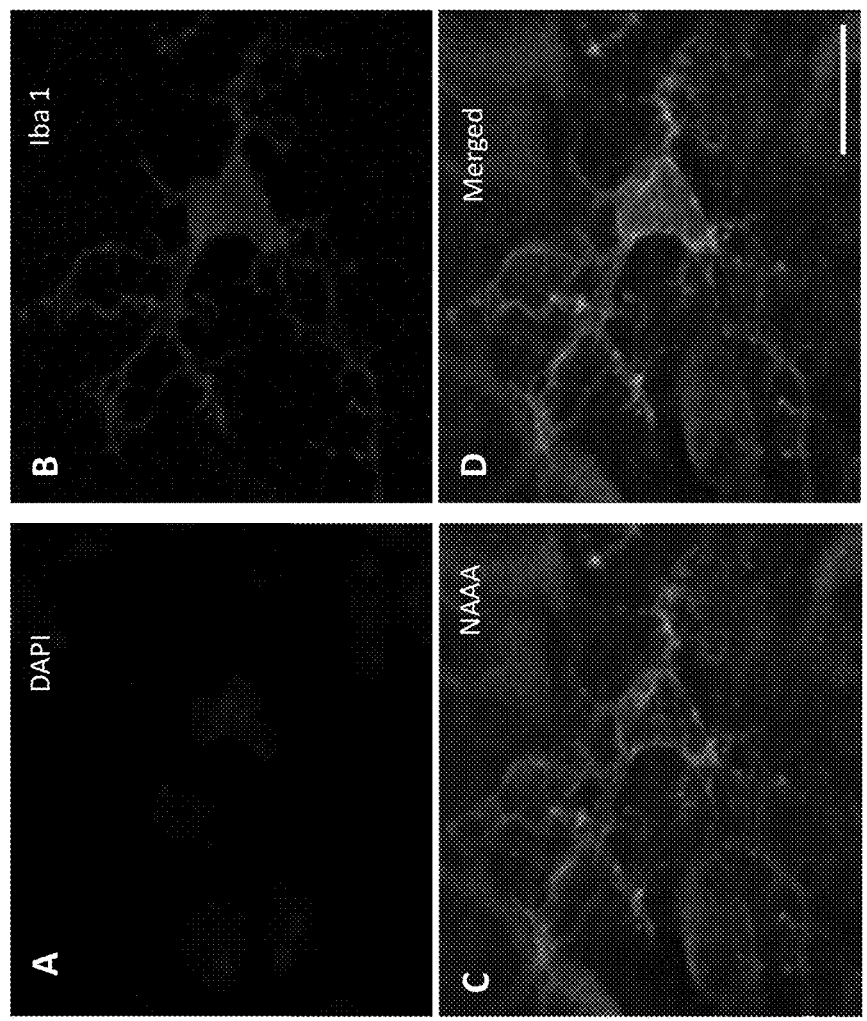
FIG. 9 shows the presence of both microglia activation and NAAA expression in EAE mice. The sections were analyzed with a Nikon A1 confocal microscope. A: DAPI staining for cell nuclei (blue). B: Iba1 staining for microglia. The change of morphology and shape of Iba1 positive cells (shorter and thicker processes) indicates activated microglia. C: NAAA staining. The appearance of green fluorescent signal suggests that NAAA overexpression occurs in EAE mice. D: Merged A, B and C panels. The colocalization (yellow) indicates that NAAA overexpression is found in Iba 1 positive cells.

The present invention provides compounds and pharmaceutical compositions which inhibit NAAA as well as methods of inhibiting NAAA using small organic compounds and pharmaceutical compositions. Also provided are compounds for use as a medicament in the treatment of pathologies where modulation of the levels of PEA and other NAE is needed, such as in the treatment of inflammation and pain and other disorders where modulation of palmitoylethanolamine levels is clinically relevant. Also provided are methods for modulating the levels of NAE in a subject by administering a composition set forth herein. Also provided are methods for treating conditions associated with reduced levels of NAE, including acute inflammation, chronic inflammation, acute pain, acute inflammatory pain, chronic inflammatory pain, and neuropathic pain, by administering a therapeutically effective amount of a compound of Formula I according to the invention. Also provided are pharmaceutical compositions which include a compound set forth herein, or a pharmaceutically acceptable salt thereof, and pharmaceutically acceptable excipients, carriers and/or diluents. Also provided are methods for preparing compounds of Formula I through a process consisting of suitable synthetic transformations.

II. Definitions

The practice of the present invention will employ, unless otherwise indicated, conventional methods of chemistry, biochemistry, molecular biology, cell biology, genetics, immunology and pharmacology, within the skill of the art. Such techniques are explained fully in the literature. See, e.g., Gennaro, A. R., ed. (1990) Remington's Pharmaceutical Sciences, 18th ed., Mack Publishing Co.; Hardman, J. G., Limbird, L. E., and Gilman, A. G., eds. (2001) The Pharmacological Basis of Therapeutics, 10th ed., McGraw-Hill Co.; Colowick, S. et al., eds., Methods In Enzymology, Academic Press, Inc.; Weir, D. M., and Blackwell, C. C., eds. (1986) Handbook of Experimental Immunology, Vols. I-IV, Blackwell Scientific Publications; Maniatis, T. et al., eds. (1989) Molecular Cloning: A Laboratory Manual, 2nd edition, Vols. I-III, Cold Spring Harbor Laboratory Press; Ausubel, F. M. et al., eds. (1999) Short Protocols in Molecular Biology, 4th edition, John Wiley & Sons; Ream et al., eds. (1998) Molecular Biology Techniques: An Intensive Laboratory Course, Academic Press; Newton, C. R., and Graham, A., eds. (1997) PCR (Introduction to Biotechniques Series), 2nd ed., Springer Verlag.

Unless defined otherwise, all technical and scientific terms used herein have the meaning commonly understood by a person skilled in the art to which this invention belongs. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger et al. (eds.), Springer Verlag (1991); and Hale & Marham, THE HARPER COLLINS DICTIONARY OF BIOLOGY (1991). As used herein, the following terms have the meanings ascribed to them unless specified otherwise.

In embodiments used in this specification and the appended claims, the singular forms "a," "an," and "the" include plural reference unless the context clearly dictates otherwise.

In embodiments, the term "composition" may include a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, in embodiments, the pharmaceutical compositions of the present invention encompass any composition made by admixing a compound of the present invention and a pharmaceutically acceptable carrier. In embodiments, the term "pharmaceutical composition" indicates a composition suitable for pharmaceutical use in a subject, including an animal or human. In embodiments, a pharmaceutical composition generally comprises an effective amount of an active agent and a pharmaceutically acceptable carrier.

In embodiments, the term "pharmaceutically acceptable carrier" may include standard pharmaceutical carriers, buffers and excipients, including phosphate-buffered saline solution, water, and emulsions (such as an oil/water or water/oil emulsion), and various types of wetting agents and/or adjuvants. In embodiments, suitable pharmaceutical carriers and their formulations are described in REMINGTON'S PHARMACEUTICAL SCIENCES (Mack Publishing Co., Easton, 19th ed. 1995). In embodiments, preferred pharmaceutical carriers depend upon the intended mode of administration of the active agent. Typical modes of administration used in embodiments are described below.

In embodiments, the term "effective amount" may include a dosage sufficient to produce a desired result on health, including, but not limited to, disease states. The desired result may comprise a subjective or objective improvement in the recipient of the dosage. A subjective improvement may be, for instance with respect to pain, decreased sensation of pain (e.g., noninflammatory pain, neuropathic pain). An objective improvement may be, for instance, an increased ability to move or use (e.g., place weight upon) an affected limb or a longer period of uninterrupted sleep, or a behavioral response indicating an increased tolerance of a painful stimuli.

In embodiments, a "prophylactic treatment" may include a treatment administered to a subject who does not have the subject condition (e.g., pain), wherein the treatment is administered for the purpose of decreasing the risk of developing the condition or to counter the severity of the condition (e.g., inflammation; pain, including but not limited to, acute pain, chronic pain, inflammatory pain, non-inflammatory pain, neuropathic pain and pain expected to result from the expected or likely occurrence of a painful event (e.g., surgery)) if one were to develop.

In embodiments, a "therapeutic treatment" may include a treatment administered to a subject who has the condition (e.g., pain, and/or exhibits signs or symptoms of pain including but not limited to, acute pain, chronic pain, cancer pain, inflammatory pain, non-inflammatory pain, neuropathic pain, wherein treatment is administered for the purpose of diminishing or eliminating those signs or symptoms) to be treated.

In embodiments, a "therapeutically effective amount" may include an amount of an agent sufficient to reduce the signs and/or symptoms of the disease or condition or to prevent, oppose, or reduce their progression. In embodiments, the compound is generally administered to a patient for treatment in a therapeutically effective amount.

In embodiments, the term "treating" may include combating, reducing, shortening, alleviating or eliminating a condition or symptoms thereof of the subject (e.g., pain, inflammation).

In embodiments, pain, particularly severe pain, can be a stressor. In embodiments, provided herein are methods of treating chronic pain conditions, including neuropathic pain, and chronic or intermittent pain associated with chronic health conditions as such conditions are often substantial stressors. In embodiments, "Neuropathic pain" may include pain caused by a primary lesion or dysfunction of the nervous system. Such pain may be chronic and involve a maintained abnormal state of increased pain sensation, in which a reduction of pain threshold and the like are continued, due to persistent functional abnormalities ensuing from an injury or degeneration of a nerve, plexus or perineural soft tissue. Such injury or degeneration may be caused by wound, compression, infection, cancer, ischemia, or a metabolic or nutritional disorder such as diabetes mellitus. Neuropathic pain may include, but is not limited to, neuropathic allodynia wherein a pain sensation is induced by mechanical, thermal or another stimulus that does not normally provoke pain, neuropathic hyperalgesia wherein an excessive pain occurs in response to a stimulus that is normally less painful than experienced. Examples of neuropathic pain include diabetic polyneuropathy, entrapment neuropathy, phantom pain, thalamic pain after stroke, post-herpetic neuralgia, atypical facial neuralgia pain after tooth extraction and the like, spinal cord injury, trigeminal neuralgia and cancer pain resistant to narcotic analgesics such as morphine. In embodiments, the neuropathic pain includes the pain caused by either central or peripheral nerve damage. In embodiments, it includes the pain caused by either mononeuropathy or polyneuropathy (e.g., familial amyloid polyneuropathy). In embodiments, as compared to inflammatory pain, neuropathic pain is relatively resistant to therapy with nonsteroidal anti-inflammatory agents and opioid substances (e.g, morphine).

Neuropathic pain may be bilateral in mirror image sites, or may be distributed approximately according to the innervation of the injured nerve, it may persist for months or years, and be experienced as a burning, stabbing, shooting, throbbing, piercing electric shock, or other unpleasant sensation.

The term "alkyl", as used herein, indicates a saturated aliphatic hydrocarbon radical, including straight chain and branched chain radicals of 1 to 16 carbon atoms. More preferably, an alkyl group has 1 to 12 carbon atoms. The term "lower alkyl", as used herein, refers to straight chain and branched chain radicals of 1 to 6 carbon atoms. Non-limiting examples of alkyl are, for instance, methyl, ethyl, propyl, isopropyl, n-butyl, iso-butyl, tert-butyl, n-amyl, iso-amyl, n-hexyl, n-heptyl, n-octyl and the like. Any alkyl group may be unsubstituted or substituted.

The term "alkenyl", as used herein, indicates an alkyl group, as defined herein, consisting of at least two carbon atoms and containing at least one carbon-carbon double bond. Representative examples include, but are not limited to, ethenyl, 1-propenyl, 2-propenyl, 1- or 2-butenyl, 1- or 2-pentenyl, 1-, 2- or 3-hexenyl, 2,4-hexadienyl and the like. Any alkenyl group may be unsubstituted or substituted.

The term "alkynyl", as used herein, indicates an alkyl group, as defined herein, consisting of at least two carbon atoms and containing at least one carbon-carbon triple bond. Representative examples include, but are not limited to, ethynyl, 1-propynyl, 2-propynyl, 1- or 2-butyryl, 1- or 2-pentynyl and the like. Any alkynyl group may be unsubstituted or substituted.

The term "cycloalkyl", as used herein, indicates a 3- to 10-membered all-carbon monocyclic or polycyclic ring, which may contain one or more double bonds but does not have a completely conjugated pi-electron system (e.g., 3 to 7 membered monocyclic ring or 3 to 7 membered polycyclic ring). Examples of cycloalkyl groups include, without limitation, cyclopropane, cyclobutane, cyclopentane, cyclopentene, cyclohexane, cyclohexene, cyclohexadiene, cycloheptane, norbornane. A cycloalkyl group may be unsubstituted or substituted.

The term "aryl", as used herein, indicates a hydrocarbon consisting of a mono-, bi- or tricyclic ring system, wherein the rings are fused together or linked to each other covalently and at least one of the carbocyclic rings is aromatic. Not limiting examples of aryl groups include, but are not limited to, phenyl, alpha- or beta-naphthyl, 1,2,3,4-tetrahydronaphthyl, 9,10-dihydroanthracenyl, indanyl, fluorenyl, biphenyl and the like. An aryl group may be unsubstituted or substituted.

The term "heteroaryl", as used herein, indicates a mono-, bi- or tricyclic ring system containing from one to three heteroatoms selected from nitrogen, oxygen and sulfur, wherein the rings are fused together or linked to each other covalently and at least one of the rings is aromatic. Not limiting examples of heteroaryl groups include pyrrolyl, furoyl, thiophenyl, imidazolyl, pyrazolyl, oxazolyl, isoxazolyl, thiazolyl, isothiazolyl, indolyl, benzofuranyl, benzothiophenyl, benzimidazolyl, benzopyrazolyl, benzoxazolyl, benzoisoxazolyl, benzothiazolyl, benzoisothiazolyl, triazolyl, oxadiazolyl, thiadiazolyl, tetrazolyl, pyridyl, pyrazinyl, pyrimidinyl, pyridazinyl, quinolinyl, isoquinolinyl, quinazolinyl, quinoxalinyl and the like. A heteroaryl group may be unsubstituted or substituted.

The terms "heterocycloalkyl," "heterocyclyl" or "heterocyclic ring", as used herein, mean a 3- to 7-membered, saturated or partially unsaturated carbocyclic ring wherein one or more carbon atoms are independently replaced by nitrogen, oxygen and sulfur. The heteroatom nitrogen and sulfur are optionally oxidized, and the nitrogen atom(s) are optionally quaternized. Not limiting examples of heterocyclyl groups include, for instance, radicals derived from oxirane, aziridine, oxetane, azetidine, tetrahydrofuran, dihydrofuran, tetrahydrothiophene, dihydrothiophene, pyrrolidine, dihydropyrrole, pyran, dihydropyran, tetrahydropyran, tetrahydrothiopyran, piperidine, pyrazoline, oxazoline, isoxazolidine, isoxazoline, thiazolidine, thiazoline, isothiazoline, dioxane, piperazine, morpholine, thiomorpholine, examethyleneimine, homopiperazine, and the like. A heterocyclyl group or a heterocyclic ring may be unsubstituted or substituted.

The term "substituted", as used herein, means that in each of the above alkyl, alkenyl, alkynyl, cycloalkyl, aryl, heteroaryl, heterocyclyl and heterocyclic radical, one or more hydrogen atoms can be independently replaced by a substituent selected from the group consisting of alkyl, substituted alkyl, aryl, substituted aryl, arylalkyl, alkoxy, cycloalkyloxy, aryloxy, arylalkyloxy, hydroxy, heteroaryloxy, heterocyclyloxy, trifluoromethoxy, carboxy, acyl, aroyl, heteroaroyl, halogen, nitro, cyano, alkoxycarbonyl, aryloxycarbonyl, aralkyloxycarbonyl, cycloalkyloxycarbonyl, heteroaryloxycarbonyl, heterocyclyloxycarbonyl, acyloxy, alkylthio, arylthio, alkysulfinyl, arylsulfinyl, alkylsulfonyl, arylsulfonyl, —O-Aroyl, —O-Heteroaroyl, —C(=O)—NR$^h$R$^k$, and —NR$^p$R$^q$, wherein each of R$^h$, R$^k$, R$^p$, and R$^q$ independently represents hydrogen, unsubstituted or substituted alkyl, unsubstituted or substituted cycloalkyl, unsubstituted or substituted aryl, unsubstituted or substituted aralkyl, unsubstituted or substituted heteroaryl, acyl, aroyl, heteroaroyl, unsubstituted or substituted heterocyclyl, and when R$^h$ and R$^k$, and R$^p$ and R$^q$ are taken together with the nitrogen atom to which they are bound, the group —NR$^h$R$^k$ and the group NR$^p$R$^q$ represent a heterocyclyl residue.

The term "aromatic" refers to a moiety wherein the constituent atoms make up an unsaturated ring system, all atoms in the ring system are sp$^2$ hybridized and the total number of π electrons is equal to 4n+2, wherein n is an integer.

The term "acyl", as used herein, means a group obtained by removing the hydroxy group from a carboxylic acid, where said carboxylic acid is an alkyl carboxylic acid, an alkenyl carboxylic acid, an alkynyl carboxylic acid, a cycloalkyl carboxylic acid or a heterocyclic carboxylic acid. Examples of such carboxylic acids include, but are not limited to, acetic acid, propanoic acid, 2-butenoic acid, 2-butynoic acid, cyclopropyl carboxylic acid, cyclobutyl carboxylic, oxetanyl carboxylic acid, tetrahydropyranyl carboxyic acid, and the like. ------

The term "acyloxy", as used herein, means a group —O-Acyl.

The term "alkoxy", as used herein, means an unsubstituted or substituted alkyl chain linked to the remainder of the molecule through an oxygen atom. Examples of alkoxy include, but are not limited to, methoxy, ethoxy, propyloxy, isopropyloxy, benzyloxy and the like.

The term "alkoxycarbonyl", as used herein, means a group —C(=O)O-Alkyl, wherein the alkyl is unsubstituted or substituted.

The term "alkysulfinyl", as used herein, means a group —S(O)-Alkyl.

The term "alkylsulfonyl", as used herein, means a group —SO$_2$-Alkyl.

The term "alkylthio", as used herein, means a group —S-Alkyl.

The terms "arylalkyl" and "aralkyl", as used herein, means an unsubstituted or substituted alkyl chain in which one of the hydrogen atom is substituted by and aryl group. Examples of aralkyl include, but are not limited to, benzyl, phenethyl, and the like.

The terms "arylalkoxy" "aralkyloxy", as used herein, means an unsubstituted or substituted aralkyl group linked to the remainder of the molecule through an oxygen atom. Examples of aralkyloxy include, but are not limited to, benzyloxy, phenethyloxy, and the like.

The terms "arylalkyloxycarbonyl" "aralkyloxycarbonyl", as used herein, means a group —C(=O)O-Aralkyl, wherein the aralkyl is unsubstituted or substituted.

The term "aroyl", as used herein, means a group obtained by removing the hydroxy group from an aryl carboxylic acid.

The term "aryloxy", as used herein, means an unsubstituted or substituted aryl group linked to the remainder of the molecule through an oxygen atom. Examples of aryloxy include, but are not limited to, phenoxy, alpha- or beta-naphthyloxy, biphenyloxy and the like.

The term "aryloxycarbonyl", as used herein, means a group —C(=O)O-Aryl, wherein the aryl is unsubstituted or substituted.

The term "arysulfinyl", as used herein, means a group —S(O)-Aryl.

The term "arylsulfonyl", as used herein, means a group —SO$_2$-Aryl.

The term "arylthio", as used herein, means a group —S-Aryl.

The term "carboxy" means a —COOH radical.

The term "cyano" means a —CN radical.

The term "cycloalkyloxy", as used therein, means an unsubstituted or substituted cycloalkyl group linked to the remainder of the molecule through an oxygen atom. Examples of cycloalkyloxy include, but are not limited, to cyclopropyloxy, cyclobutyloxy, cyclopentyloxy, cyclopentenyloxy, cyclohexyloxy, cyclohexenyloxy, cyclohexadienyloxy, cycloheptanyloxy and the like.

The term "cycloalkyloxycarbonyl", as used therein, means a group —C(=O)O-Cycloalkyl, wherein the cycloalkyl is unsubstituted or substituted.

The term "halogen", as used herein, indicates fluorine (F), chlorine (Cl), bromine (Br) or iodine (I).

The term "heteroaroyl", as used herein, indicates a group obtained by removing the hydroxy group from a heteroaryl carboxylic acid.

The term "heteroaryloxy", as used therein, means an unsubstituted or substituted heteroaryl group linked to the remainder of the molecule through an oxygen atom.

The term "heteroaryloxycarbonyl", as used therein, means a group —C(=O)O-Heteroaryl, wherein the heteroaryl is unsubstituted or substituted.

The terms heterocycloalkyloxy or "heterocyclyloxy", as used therein, means an unsubstituted or substituted heterocyclyl group linked to the remainder of the molecule through an oxygen atom.

The term "heterocyclyloxycarbonyl", as used therein, means a group —C(=O)O-Heterocyclyl, wherein the heterocyclyl is unsubstituted or substituted.

The term "hydroxy", as used herein, means a —OH radical.

The term "trifluoromethoxy" means a —OCF$_3$ radical.

A wavy bond depicted in a structure shown herein represents all possible stereochemical possibilities for the bond.

A person having ordinary skill in the art will immediately understand that the definitions of substituents (e.g. R groups) provided herein are intended to obey the standard rules of chemical valency. For clarity, where a formula provided herein requires a particular substituent, when present, to be divalent, (e.g. R$^4$ and R$^5$ in Formula I) a person having ordinary skill in the art will immediately understand that the definitions of that substituent are divalent in order to obey the standard rules of chemical valency. For example, in compounds of formula I below, when R$^4$ is set forth as being an R$^4$ substituent selected from alkyl, alkenyl, alkynyl, aryl, arylalkyl, cycloalkyl, heteroaryl, heterocycloalkyl, or heteroarylalkyl, the R$^4$ substituent may alternatively and equivalently be referred to as alkylene, alkenylene, alkynylene, arylene, arylalkylene, cycloalkylene, heteroarylene, heterocycloalkylene, and heteroarylalkylene, respectively. Thus, for example, where the standard rules of chemical valency require divalency for a particular substituent, that particular substituent may be equally referred to as alkyl or alkylene, alkenyl or alkenylene, alkynyl or alkynylene, aryl or arylene, arylalkyl or arylalkylene, cycloalkyl or cycloalkylene, heteroaryl or heteroarylene, heterocycloalkyl or heterocycloalkylene, or heteroaryl or heteroarylalkylene.

III. Compounds

In some embodiments, the present invention provides a compound having the structure of Formula I:

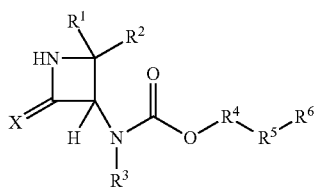

(I)

In Formula $R^1$ and $R^2$ are each independently selected from the group consisting of hydrogen, alkyl, aryl, cycloalkyl (e.g. 3 to 7 membered cycloalkyl), arylalkyl, and cycloalkylalkyl (e.g. 3 to 7 membered cycloalkyl). In some embodiments, $R^1$ and $R^2$ form a cycloalkyl (e.g. 3 to 7 membered cycloalkyl) substituent together with the carbon to which they are attached. $R^3$ is selected from the group consisting of hydrogen and alkyl. $R^4$ is selected from the group consisting of alkyl, alkenyl, alkynyl, aryl, arylalkyl, cycloalkyl (e.g. 3 to 7 membered cycloalkyl), heteroaryl, heterocycloalkyl, and heteroarylalkyl (e.g. also referred herein as alkylene, alkenylene, alkynylene, arylene, arylalkylene, cycloalkylene (e.g. 3 to 7 membered cycloalkylene), heteroarylene, heterocycloalkylene, heteroarylalkylene, and heterocycloalkylalkylene). $R^5$ is absent or is selected from the group consisting of alkyl, alkenyl, alkyoxy, aryl, aryloxy, cycloalkyl (e.g. 3 to 7 membered cycloalkyl), —O—, —S—, —C(O)—, —C(O)NH—, $NR^aR^b$, heteroaryl, and heterocycloalkyl (e.g. also referred herein as alkylene, alkenylene, alkyoxy, arylene, aryloxy, cycloalkylene (e.g. 3 to 7 membered cycloalkylene), —O—, —S—, —C(O)—, —C(O)NH—, $NR^aR^b$, heteroarylene, and heterocycloalkylene). $R^6$ is absent or is selected from the group consisting of hydrogen, alkyl, alkoxy, aryl, aryl-alkylene, arylalkenyl, aryloxy, arylalkoxy, arylalkyl, cycloalkyl (e.g. 3 to 7 membered cycloalkyl), cycloalkyloxy (e.g. 3 to 7 membered cycloalkyl), heterocycloalkyl, heterocycloalkyloxy, cycloalkylalkyl (e.g. 3 to 7 membered cycloalkyl), and heteroaryl. $R^1$, $R^2$, $R^3$, $R^4$, $R^5$, and $R^6$ are each independently optionally substituted with 1-4 substituents selected from the group consisting of hydrogen, lower alkyl, lower alkoxy, aryl, $NR^aR^b$, cyano, halogen, hydroxyl, trifluoromethyl, difluoromethyl, fluoromethyl. $R^a$ and $R^b$ are each independently selected from the group consisting of hydrogen and alkyl; X is selected from the group consisting of O and S (e.g. O). Also included are the pharmaceutically acceptable salts, esters, or prodrugs thereof. In embodiments, $R^6$ is selected from the group consisting of hydrogen, alkyl, alkoxy, aryl, aryl-alkylene, arylalkenyl, aryloxy, arylalkoxy, arylalkyl, cycloalkyl (e.g. 3 to 7 membered cycloalkyl), cycloalkyloxy (e.g. 3 to 7 membered cycloalkyl), heterocycloalkyl, heterocycloalkyloxy, cycloalkylalkyl (e.g. 3 to 7 membered cycloalkyl), and heteroaryl.

In some other embodiments, in Formula, $R^1$ and $R^2$ are each independently selected from the group consisting of hydrogen, alkyl, aryl, cycloalkyl, arylalkyl, and cycloalkylalkyl. In some embodiments, $R^1$ and $R^2$ form a cycloalkyl substituent together with the carbon to which they are attached. $R^3$ is selected from the group consisting of hydrogen and alkyl. $R^4$ is selected from the group consisting of alkyl, alkenyl, alkynyl, aryl, arylalkyl, cycloalkyl, heteroaryl, heterocycloalkyl, and heteroarylalkyl. $R^5$ is absent or is selected from the group consisting of alkyl, alkenyl, alkoxy, aryl, aryloxy, cycloalkyl, —O—, —S—, —C(O)—, —C(O)NH—, $NR^aR^b$, heteroaryl, and heterocycloalkyl. $R^6$ is absent or is selected from the group consisting of hydrogen, alkyl, alkoxy, aryl, aryl-alkylene, arylalkenyl, aryloxy, arylalkoxy, arylalkyl, cycloalkyl, cycloalkyloxy, heterocycloalkyl, heterocycloalkyloxy, cycloalkylalkyl, heteroaryl, and —C(O)$NR^aR^b$. $R^1$, $R^2$, $R^3$, $R^4$, $R^5$, and $R^6$ are each independently optionally substituted with 1-4 substituents selected from the group consisting of hydrogen, lower alkyl, lower alkoxy, aryl, $NR^aR^b$, cyano, halogen, hydroxyl, trifluoromethyl, difluoromethyl, fluoromethyl. $R^a$ and $R^b$ are each independently selected from the group consisting of hydrogen and alkyl, and when $R^a$ and $R^b$ are taken together (i.e. connected directly to each other) with the nitrogen atom to which they are bound, the group $NR^aR^b$ represent a heterocyclyl residue. Also included are the pharmaceutically acceptable salts, esters, or prodrugs thereof.

In some embodiments, the compounds of the present invention have the structure selected from the group of Formulae II-XVII:

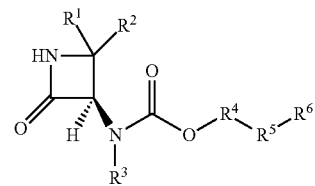

(II)

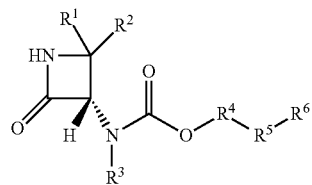

(III)

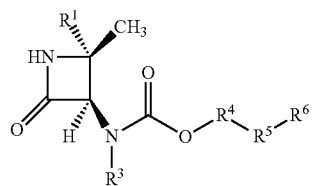

(IV)

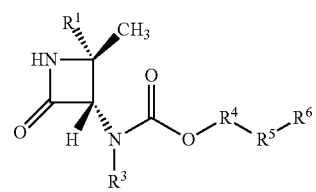

(V)

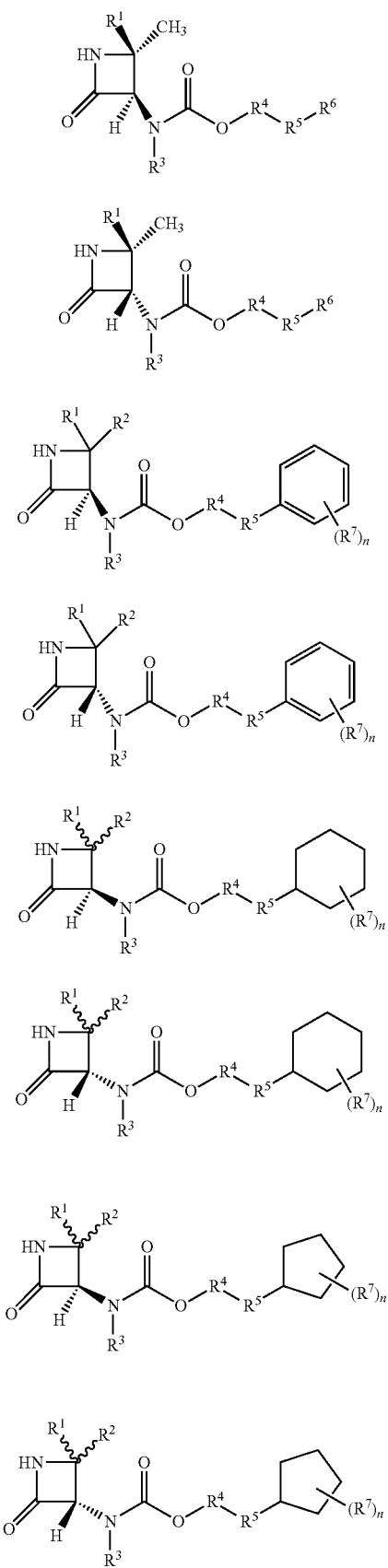

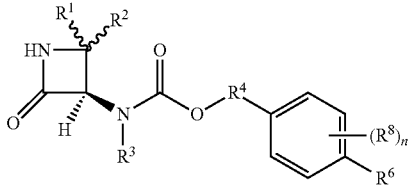

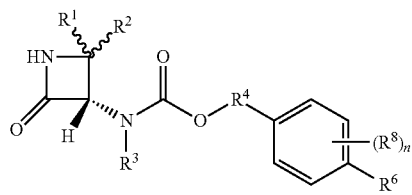

In the formulae described herein, $R^7$, $R^8$, and $R^9$ are each independently selected from the group consisting of hydrogen, halogen, hydroxyl, nitro, cyano, trifluoromethyl, alkyl, alkoxy and aryl. Subscript n is each independently an integer from 0-4. In some embodiments of any of the above, n is 0, 1, 2, 3, or 4. More preferably, n is 1 or 2. In further embodiments of the above when n is 1 or 2, $R^7$, $R^8$, and $R^9$ are each independently selected from the group consisting of hydrogen, halogen, and alkyl. In further embodiments of the above when n is 1 or 2, $R^7$, $R^8$, and $R^9$ are each independently selected from the group consisting of hydrogen, hydroxyl, nitro, cyano, and aryl. In other embodiments of the above, n is 0.

In some embodiments of the above $R^1$, $R^2$, $R^3$, $R^4$, $R^5$, and $R^6$ are each independently optionally substituted with 1 or 2 substituents selected from the group consisting of hydrogen, lower alkyl, lower alkoxy, aryl, $NR^aR^b$, cyano, halogen, hydroxyl, trifluoromethyl, difluoromethyl, fluoromethyl. In some embodiments of the above $R^1$, $R^2$, $R^3$, $R^4$, $R^5$, and $R^6$ are each unsubstituted. In other embodiments of the above $R^1$, $R^2$, $R^3$, $R^4$, $R^5$, and $R^6$ are each independently optionally substituted with 1 or 2 substituents selected from the group consisting of hydrogen, lower alkyl, and halogen. In some embodiments of the above $R^1$, $R^2$, $R^3$, $R^4$, $R^5$, and $R^6$ are each independently optionally substituted with 1 or 2 substituents selected from the group consisting of hydrogen, lower alkyl, lower alkoxy, $NR^aR^b$, cyano, halogen, hydroxyl, trifluoromethyl, difluoromethyl, fluoromethyl.

In some other embodiments, or in further of the above embodiments, the present invention provides that $R^3$ is hydrogen. In some other embodiments, or in any embodiment set forth herein, $R^3$ is methyl.

In some embodiments, or in further of the above embodiments, the present invention provides a compound wherein $R^4$ is alkyl. In other embodiments, $R^4$ is selected from the group consisting of methyl, ethyl, i-propyl, n-propyl, i-butyl, t-butyl, n-butyl, n-pentyl, i-pentyl, pentyl, hexyl, heptyl, octyl, nonyl, decyl, undecyl, and dodecyl. In some embodiments, $R^4$ is cycloalkyl. In yet others, $R^4$ is cyclohexyl. In other embodiments, $R^4$ is aryl. In some other embodiments, $R^4$ is benzyl. In some embodiments, or in further of the above embodiments, the present invention provides a compound wherein $R^4$ is alkenyl. In some embodiments, $R^4$ is selected from the group consisting of trans-3-nonene, cis-3-nonene, trans-1-butene, and cis-1-butene.

In some embodiments, or in further of the above embodiments, $R^5$ is absent.

In some other embodiments, or in further of the above embodiments, $R^5$ and $R^6$ are both absent.

In some embodiments, or in further of the above embodiments, the present invention provides a compound wherein $R^5$ is alkenyl. In some embodiments, $R^5$ is selected from the group consisting of trans-3-nonene, cis-3-nonene, trans-1-butene, and cis-1-butene. In yet other embodiments, $R^5$ selected from the group consisting of —O— or —C(O)—. In still other embodiments, $R^5$ is aryl. In some embodiments, $R^5$ is phenyl.

In some embodiments, or in further of the above embodiments, the present invention provides a compound wherein $R^6$ selected from the group consisting of aryl, arylalkenyl, and aryl-alkylene. In some other embodiments, $R^6$ is selected from the group consisting of phenyl, phenylethylene, benzyl, and biphenyl. In some embodiments, $R^6$ is phenyl. In other embodiments, $R^6$ is cycloalkyl. In some other embodiments, $R^6$ is selected from the group consisting of cyclohexyl, cyclopentyl, norbornanyl, adamantyl, and 1,2,3,4-tetrahydro-naphthyl. In some embodiments, $R^6$ is alkoxy. In yet other embodiments, $R^6$ is selected from the group consisting of methoxy, ethoxy, propoxy, butoxy, cyclopentyloxy, cyclohexyloxy, and norbornanyloxy. In certain embodiments, $R^6$ is alkyl.

In some embodiments, or in further of the above embodiments, the present invention provides a compound wherein $R^6$ is selected from the group consisting of methyl, ethyl, i-propyl, n-propyl, i-butyl, t-butyl, n-butyl, n-pentyl, i-pentyl, pentyl, and hexyl. In some other embodiments, $R^6$ heteroaryl. In other embodiments, $R^6$ is selected from the group consisting of pyridyl and benzo[d]oxazole. In some other embodiments, $R^6$ is heterocycloalkyl. In certain embodiments, $R^6$ is selected from the group consisting of pyranyl and morpholinyl. In certain embodiments, $R^6$ is tetrahydro-pyranyl.

In some embodiments, $R^6$ is —C(O)NR$^a$R$^b$, wherein R$^a$ and R$^b$ are each independently selected from the group consisting of hydrogen, alkyl, cycloalkyl, and aryl. In some other embodiments, R$^a$ and R$^b$ form a heterocycloalkyl substituent together with the nitrogen to which they are attached. In other embodiments, NR$^a$R$^b$ is selected from the group consisting of morpholinyl and piperidinyl.

In some embodiments, or in further of the above embodiments, the present invention provides a compound wherein $R^4$-$R^5$-$R^6$ is selected from the group consisting of

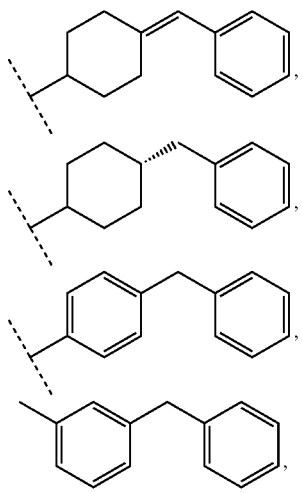

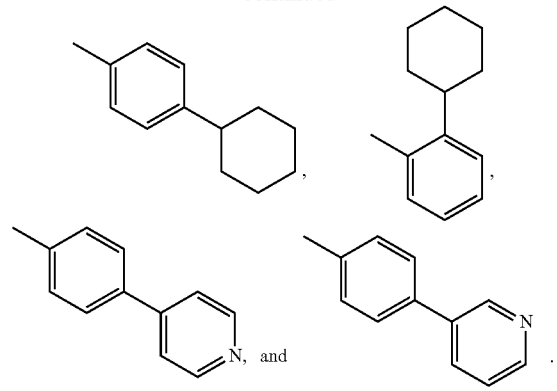

The present invention provides that in some embodiments the compound is selected from the group consisting of

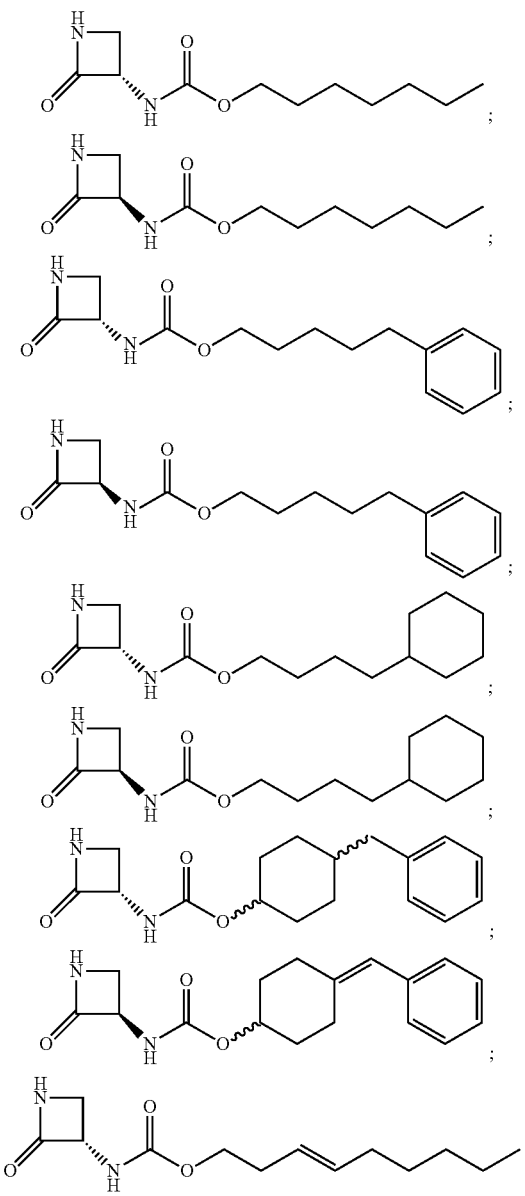

-continued
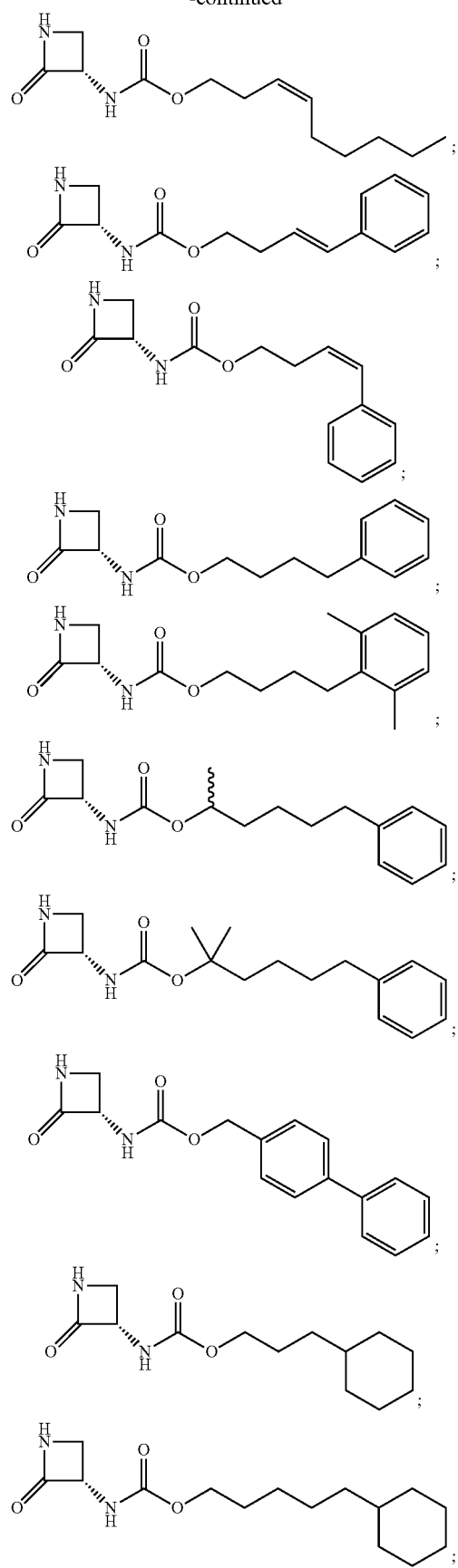
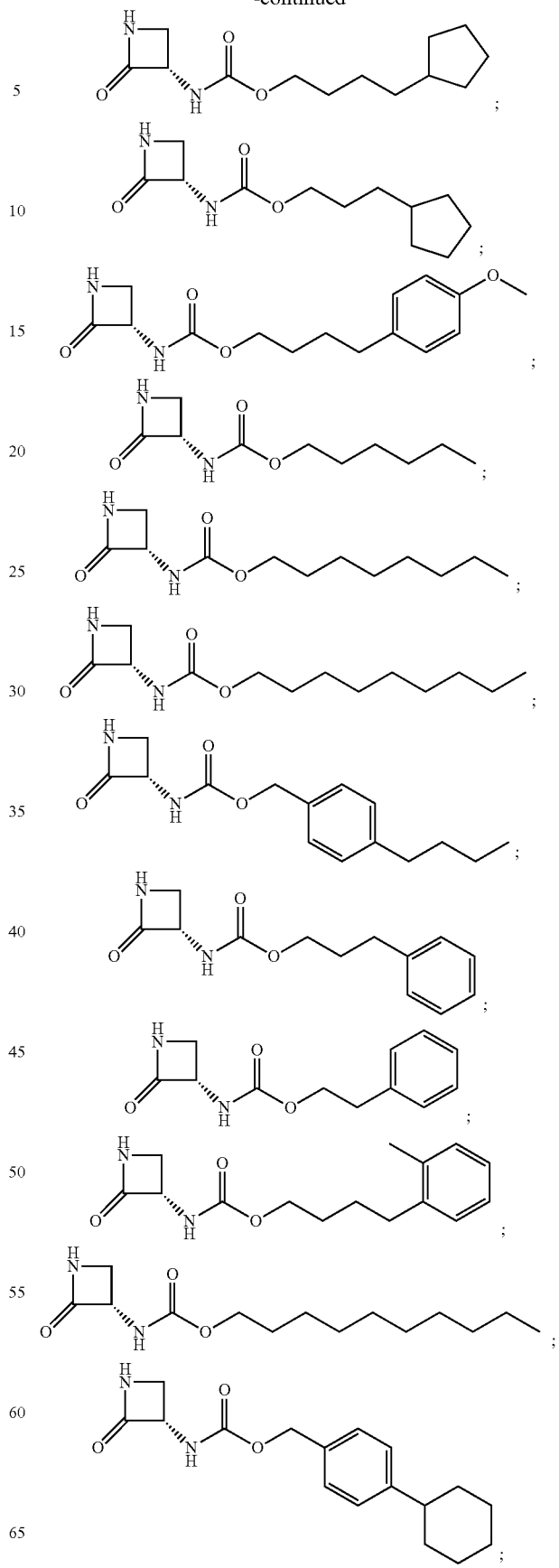

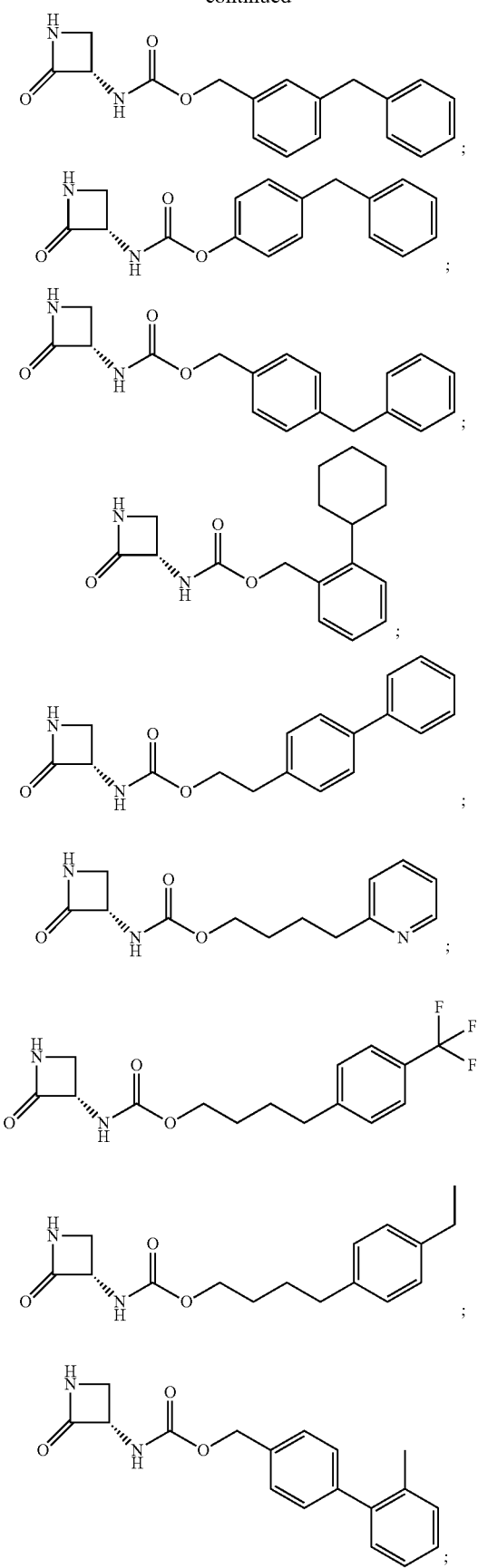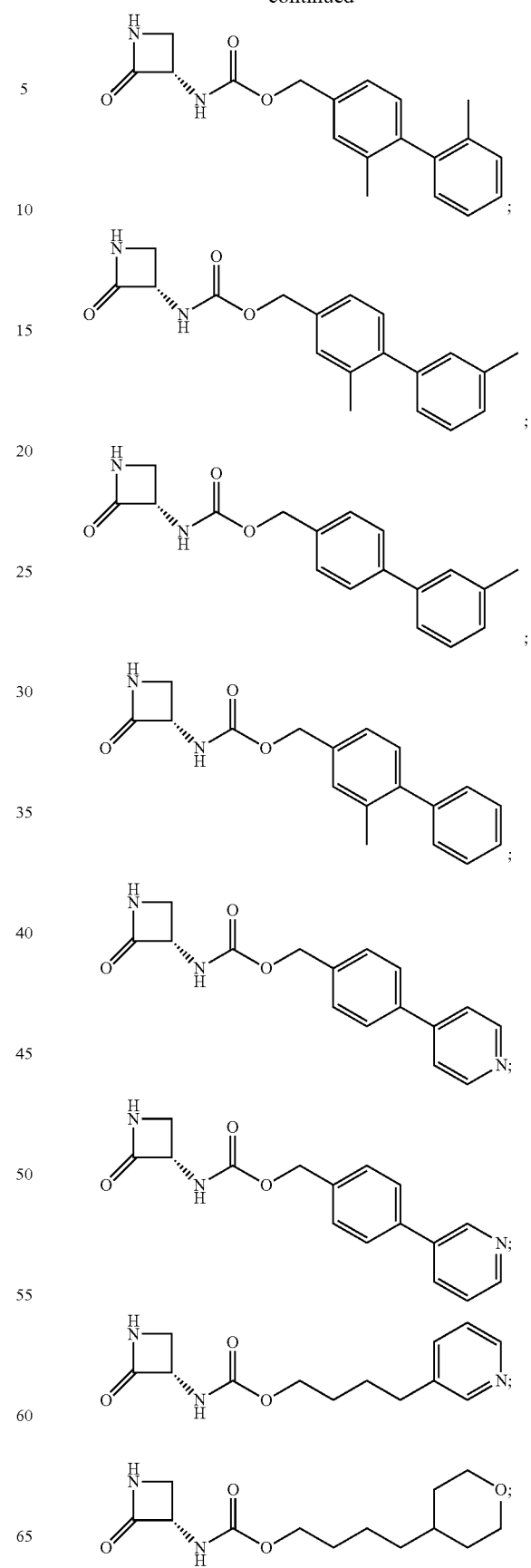

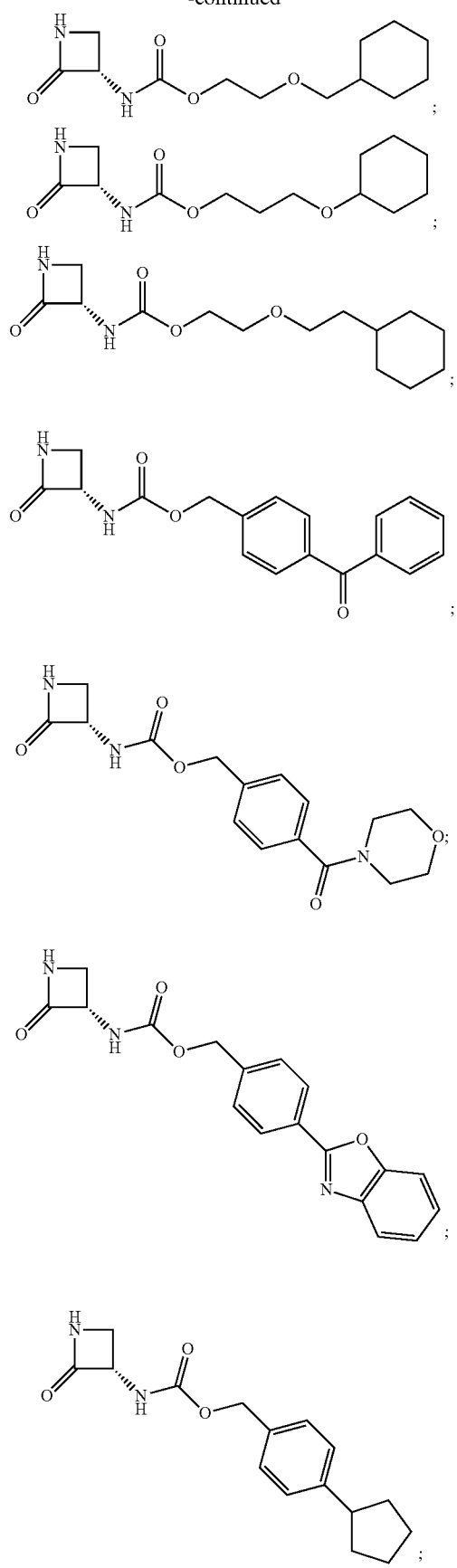
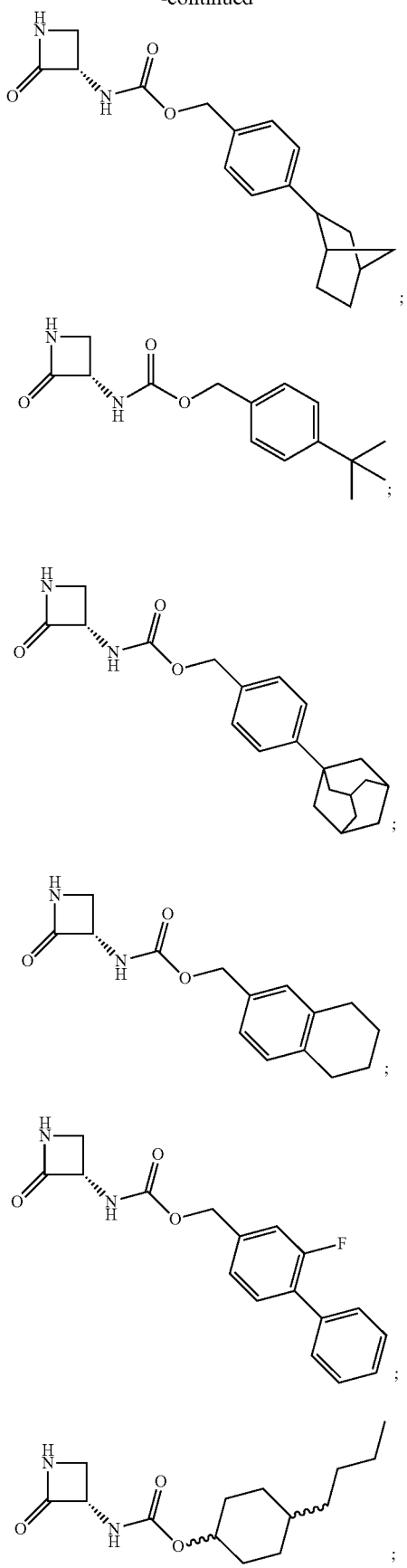

23
-continued
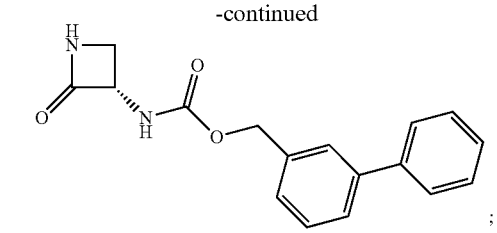
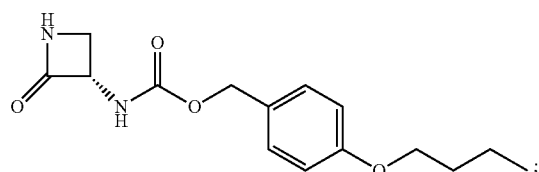
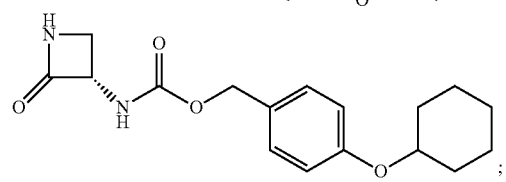
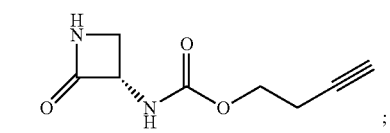
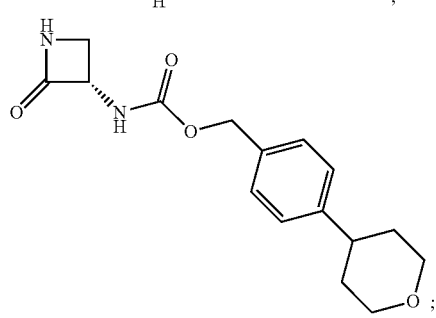
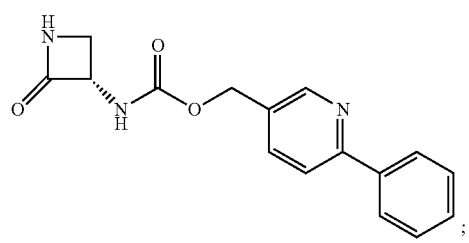
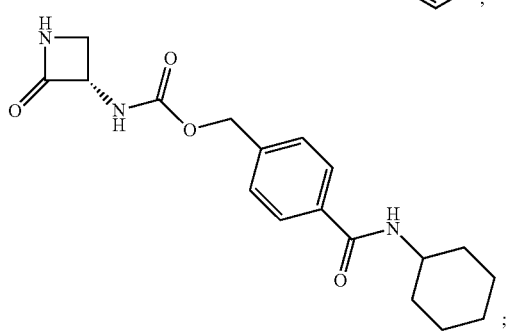
24
-continued
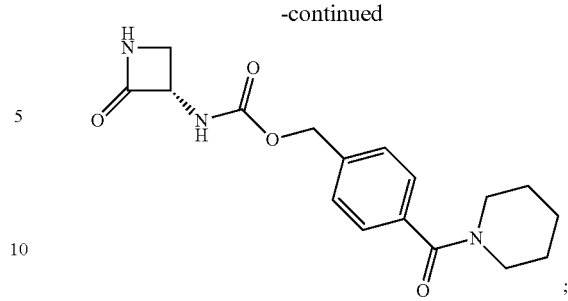
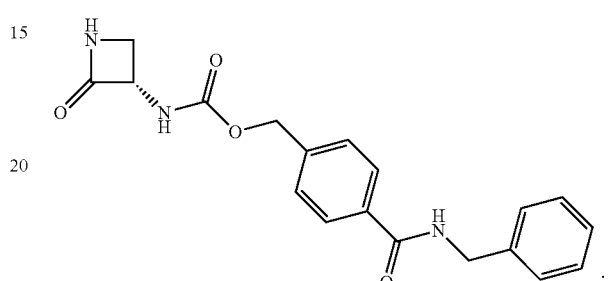
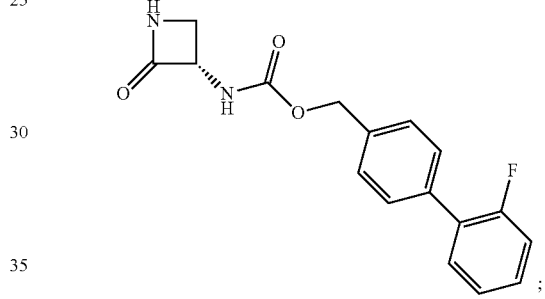
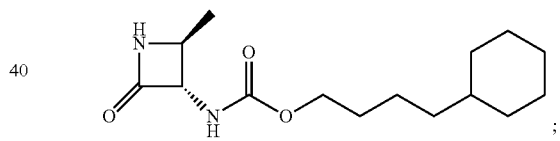
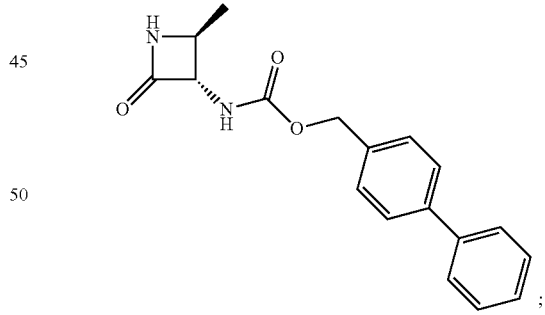
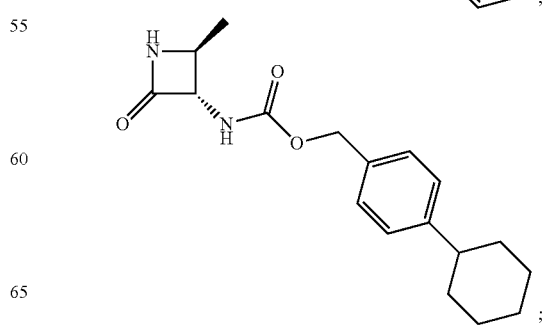

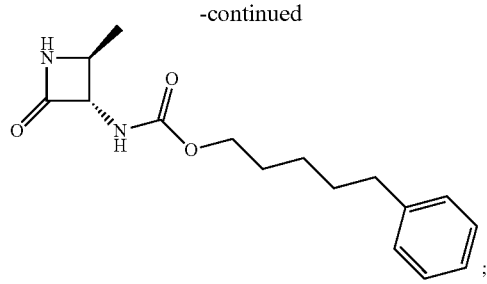
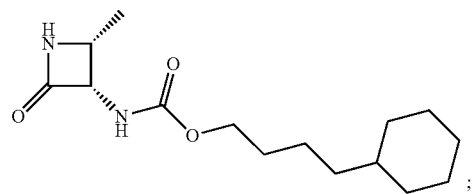
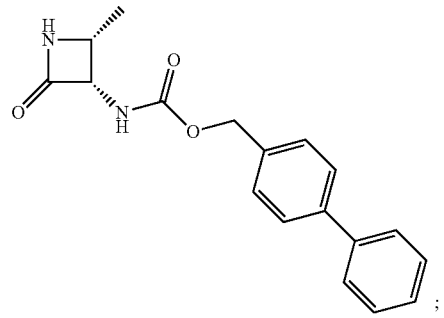
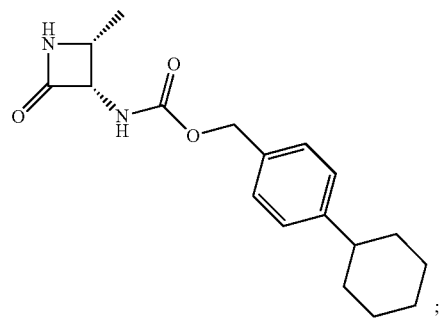
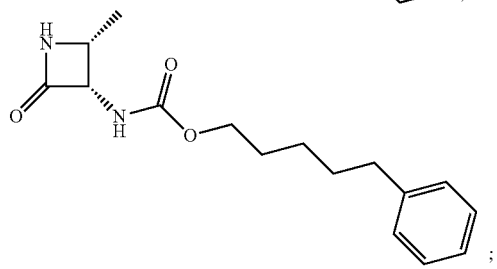
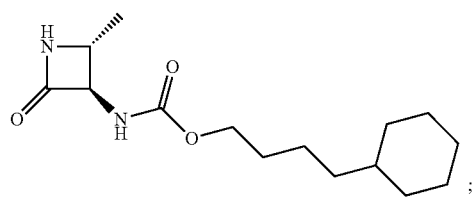
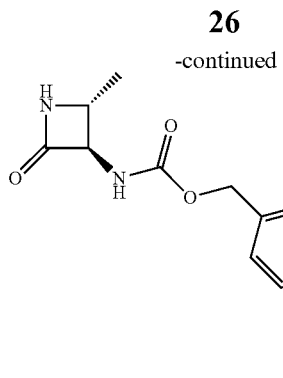
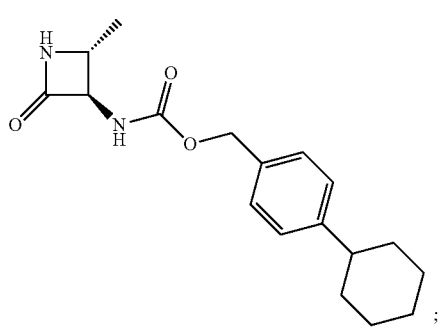
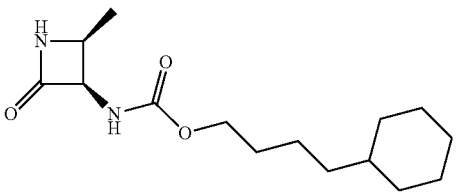
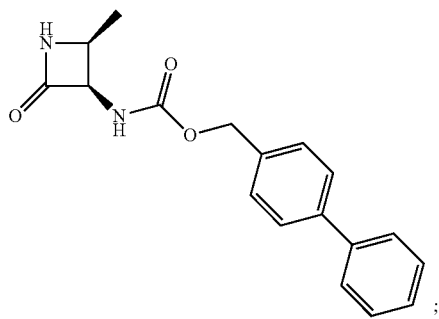
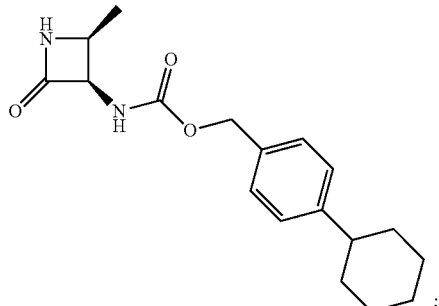
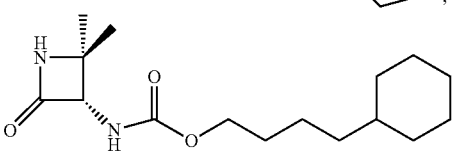

27
-continued
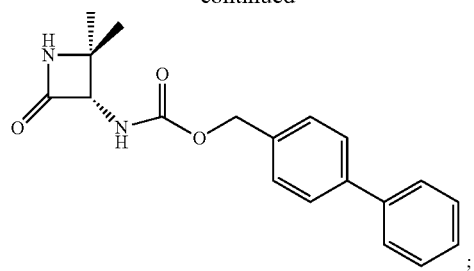
;
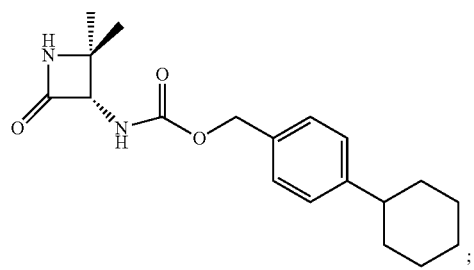
;
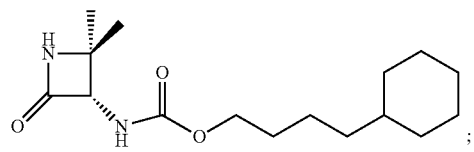
;
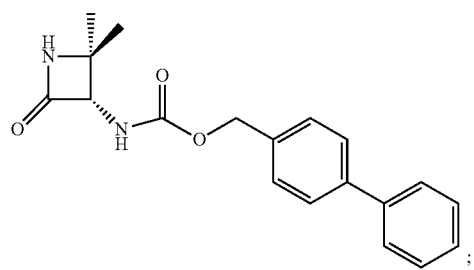
;
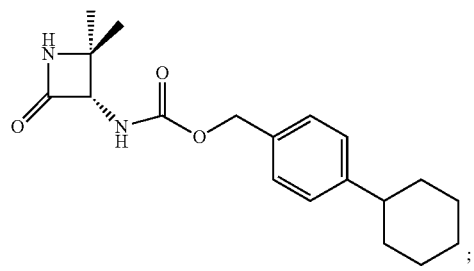
;
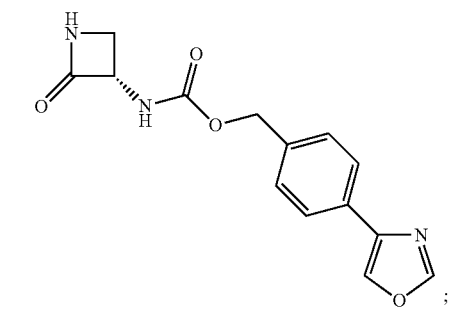
;
28
-continued
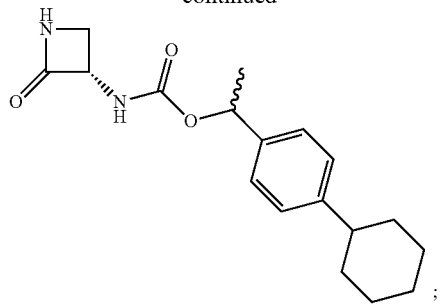
;
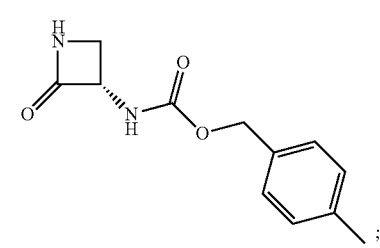
;
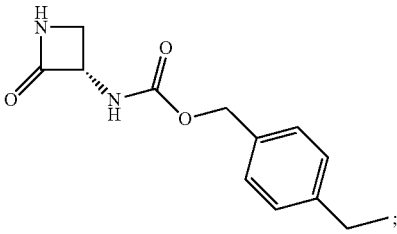
;
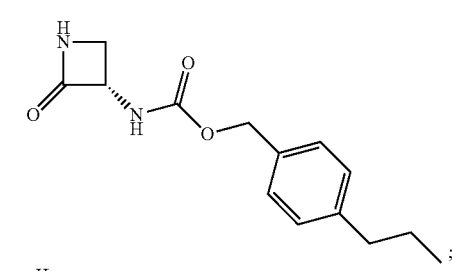
;
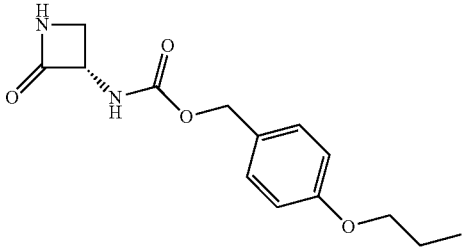
;
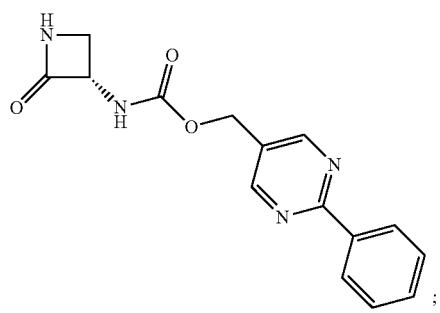
;

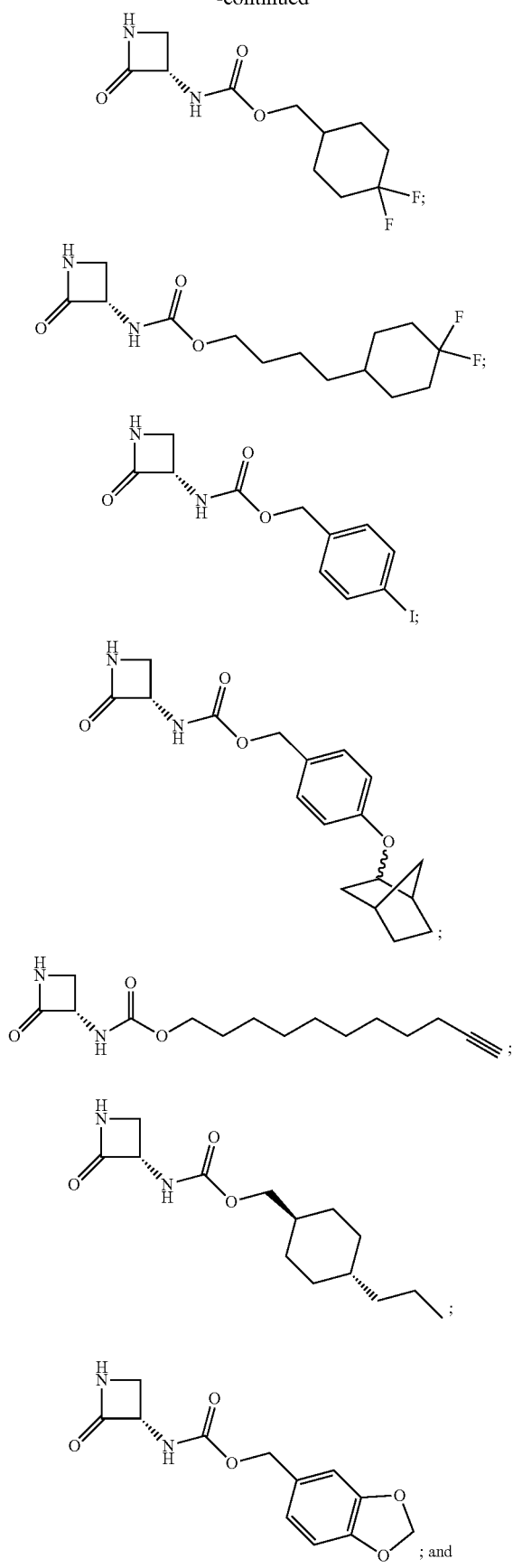

In some embodiments, or in further of the above embodiments, the present invention provides a pharmaceutical composition that includes one or more compounds having a structure selected from the group consisting of Formulae I-XVII, or a pharmaceutically acceptable salt thereof, and a pharmaceutically acceptable excipient, carrier or diluent.

In embodiments of the compounds or methods described herein, each cycloalkyl, cycloalkylene, cycloalkyloxy, and/or cycloalkylalkyl is a 3 to 7 membered ring cycloalkyl, 3 to 7 membered ring cycloalkylene, 3 to 7 membered ring cycloalkyloxy, and/or 3 to 7 membered ring cycloalkylalkyl, respectively.

In some embodiments of the invention, the compound is selected from the group consisting of:
Heptyl-N-[(3S)-2-oxoazetidin-3-yl]-carbamate;
Heptyl-N-[(3R)-2-oxoazetidin-3-yl]-carbamate;
5-phenylpentyl-N-[(3S)-2-oxoazetidin-3-yl]-carbamate;
5-phenylpentyl-N-[(3R)-2-oxoazetidin-3-yl]-carbamate;
4-cyclohexylbutyl-N-[(3S)-2-oxoazetidin-3-yl]-carbamate;
4-cyclohexylbutyl-N-[(3R)-2-oxoazetidin-3-yl]-carbamate;
(1s, 4R) and (1r, 4S)-(4-benzylcyclohexyl)-N-[(3S)-2-oxoazetidin-3-yl]-carbamate;
(R,Z) and (S,E)-(4-benzylidenecyclohexyl)-N-[(3S)-2-oxoazetidin-3-yl]-carbamate;
[(E)-non-3-enyl]-N-[(3S)-2-oxoazetidin-3-yl]-carbamate;
[(Z)-non-3-enyl]-N-[(3S)-2-oxoazetidin-3-yl]-carbamate;
[(E)-4-phenylbut-3-enyl]-N-[(3S)-2-oxoazetidin-3-yl]-carbamate;
[(Z)-4-phenylbut-3-enyl]-N-[(3S)-2-oxoazetidin-3-yl]-carbamate;
4-phenylbutyl-N-[(3S)-2-oxoazetidin-3-yl]-carbamate;
4-(2,6-dimethylphenyl)-butyl-N-[(3S)-2-oxoazetidin-3-yl]-carbamate;
[(1S)- and (1R)-1-methyl-5-phenyl-pentyl]-N-[(3S)-2-oxoazetidin-3-yl]-carbamate
(1,1-dimethyl-5-phenyl-pentyl)-N-[(3S)-2-oxoazetidin-3-yl]-carbamate
(4-phenylphenyl)-methyl-N-[(3S)-2-oxoazetidin-3-yl]-carbamate;
3-cyclohexylpropyl-N-[(3S)-2-oxoazetidin-3-yl]-carbamate;
5-cyclohexylpentyl-N-[(3S)-2-oxoazetidin-3-yl]-carbamate;
4-cyclopentylbutyl N-[(3S)-2-oxoazetidin-3-yl]-carbamate;
3-cyclopentylpropyl-N-[(3S)-2-oxoazetidin-3-yl]-carbamate;
4-(4-methoxyphenyl)-butyl-N-[(3S)-2-oxoazetidin-3-yl]-carbamate;
hexyl-N-[(3S)-2-oxoazetidin-3-yl]-carbamate;
octyl-N-[(3S)-2-oxoazetidin-3-yl]-carbamate;
nonyl-N-[(3S)-2-oxoazetidin-3-yl]-carbamate;
(4-butylphenyl)-methyl-N-[(3S)-2-oxoazetidin-3-yl]-carbamate;
3-phenylpropyl-N-[(3S)-2-oxoazetidin-3-yl]-carbamate;
Phenethyl-N-[(3S)-2-oxoazetidin-3-yl]-carbamate;
4-(o-tolyl)butyl-N-[(3S)-2-oxoazetidin-3-yl]-carbamate;

Decyl-N-[(3S)-2-oxoazetidin-3-yl]-carbamate;
(4-cyclohexylphenyl)-methyl-N-[(3S)-2-oxoazetidin-3-yl]-carbamate;
(3-benzylphenyl)-methyl-N-[(3S)-2-oxoazetidin-3-yl]-carbamate;
(4-benzylphenyl)-N-[(3S)-2-oxoazetidin-3-yl]-carbamate;
(4-benzylphenyl)-methyl-N-[(3S)-2-oxoazetidin-3-yl]-carbamate;
(2-cyclohexylphenyl)-methyl-N-[(3S)-2-oxoazetidin-3-yl]-carbamate;
2-(4-phenylphenyl)-ethyl-N-[(3S)-2-oxoazetidin-3-yl]-carbamate;
4-(2-pyridyl)-butyl-N-[(3S)-2-oxoazetidin-3-yl]-carbamate;
4-[4-(trifluoromethyl)-phenyl]-butyl-N-[(3S)-2-oxoazetidin-3-yl]-carbamate;
4-(4-ethylphenyl)-butyl-N-[(3S)-2-oxoazetidin-3-yl]-carbamate;
[4-(o-tolyl)-phenyl]-methyl-N-[(3S)-2-oxoazetidin-3-yl]-carbamate;
[3-methyl-4-(o-tolyl)-phenyl]-methyl-N-[(3S)-2-oxoazetidin-3-yl]-carbamate;
[3-methyl-4-(m-tolyl)-phenyl]-methyl-N-[(3S)-2-oxoazetidin-3-yl]-carbamate;
[4-(m-tolyl)-phenyl]-methyl-N-[(3S)-2-oxoazetidin-3-yl]-carbamate;
(3-methyl-4-phenyl-phenyl)-methyl-N-[(3S)-2-oxoazetidin-3-yl]-carbamate;
[4-(4-pyridyl)-phenyl]-methyl-N-[(3S)-2-oxoazetidin-3-yl]-carbamate;
[4-(3-pyridyl)-phenyl]-methyl-N-[(3S)-2-oxoazetidin-3-yl]-carbamate;
4-(3-pyridyl)-butyl-N-[(3S)-2-oxoazetidin-3-yl]-carbamate;
4-tetrahydropyran-4-yl-butyl-N-[(3S)-2-oxoazetidin-3-yl]-carbamate;
2-(cyclohexylmethoxy)-ethyl-N-[(3S)-2-oxoazetidin-3-yl]-carbamate;
3-(cyclohexoxy)-propyl-N-[(3S)-2-oxoazetidin-3-yl]-carbamate;
2-(2-cyclohexylethoxy)-ethyl-N-[(3S)-2-oxoazetidin-3-yl]-carbamate;
(4-benzoylphenyl)-methyl-N-[(3S)-2-oxoazetidin-3-yl]-carbamate;
[4-(morpholine-4-carbonyl)-phenyl]-methyl-N-[(3S)-2-oxoazetidin-3-yl]-carbamate;
[4-(1,3-benzoxazol-2-yl)-phenyl]-methyl-N-[(3S)-2-oxoazetidin-3-yl]-carbamate;
(4-cyclopentylphenyl)-methyl-N-[(3S)-2-oxoazetidin-3-yl]-carbamate;
(4-norbornan-2-yl-phenyl)-methyl-N-[(3S)-2-oxoazetidin-3-yl]-carbamate;
(4-tert-butylphenyl)-methyl-N-[(3S)-2-oxoazetidin-3-yl]-carbamate;
[4-(1-adamantyl)-phenyl]-methyl-N-[(3S)-2-oxoazetidin-3-yl]-carbamate;
tetralin-6-yl-methyl-N-[(3S)-2-oxoazetidin-3-yl]-carbamate;
(3-fluoro-4-phenyl-phenyl)-methyl-N-[(3S)-2-oxoazetidin-3-yl]-carbamate;
(1s,4R) and (1r,4S)-(4-butylcyclohexyl)-N-[(3S)-2-oxoazetidin-3-yl]-carbamate;
(3-phenylphenyl)-methyl-N-[(3S)-2-oxoazetidin-3-yl]-carbamate;
(4-butoxyphenyl)-methyl-N-[(3S)-2-oxoazetidin-3-yl]-carbamate;
[4-(cyclohexoxy)-phenyl]-methyl-N-[(3S)-2-oxoazetidin-3-yl]-carbamate;
but-3-ynyl-N-[(3S)-2-oxoazetidin-3-yl]-carbamate;
(4-tetrahydropyran-4-yl-phenyl)-methyl-N-[(3S)-2-oxoazetidin-3-yl]-carbamate;
(6-phenyl-3-pyridyl)-methyl-N-[(3S)-2-oxoazetidin-3-yl]-carbamate;
[4-(cyclohexylcarbamoyl)-phenyl]-methyl-N-[(3S)-2-oxoazetidin-3-yl]-carbamate;
[4-(piperidine-1-carbonyl)-phenyl]-methyl-N-[(3S)-2-oxoazetidin-3-yl]-carbamate;
[4-(benzylcarbamoyl)-phenyl]-methyl-N-[(3S)-2-oxoazetidin-3-yl]-carbamate;
[4-(2-fluorophenyl)-phenyl]-methyl-N-[(2S)-2-oxoazetidin-3-yl]-carbamate
4-cyclohexylbutyl-N-[(2S,3S)-2-methyl-4-oxo-azetidin-3-yl]-carbamate;
(4-phenylphenyl)-methyl-N-[(2S,3S)-2-methyl-4-oxo-azetidin-3-yl]-carbamate;
(4-cyclohexylphenyl)-methyl-N-[(2S,3S)-2-methyl-4-oxo-azetidin-3-yl]-carbamate;
5-phenylpentyl-N-[(2S,3S)-2-methyl-4-oxo-azetidin-3-yl]-carbamate;
4-cyclohexylbutyl-N-[(2R,3S)-2-methyl-4-oxo-azetidin-3-yl]-carbamate;
(4-phenylphenyl)-methyl-N-[(2R,3S)-2-methyl-4-oxo-azetidin-3-yl]-carbamate;
(4-cyclohexylphenyl)-methyl-N-[(2R,3S)-2-methyl-4-oxo-azetidin-3-yl]-carbamate;
5-phenylpentyl-N-[(2R,3S)-2-methyl-4-oxo-azetidin-3-yl]-carbamate;
4-cyclohexylbutyl-N-[(2R,3R)-2-methyl-4-oxo-azetidin-3-yl]-carbamate;
(4-phenylphenyl)-methyl-N-[(2R,3R)-2-methyl-4-oxo-azetidin-3-yl]-carbamate;
(4-cyclohexylphenyl)-methyl-N-[(2R,3R)-2-methyl-4-oxo-azetidin-3-yl]-carbamate;
4-cyclohexylbutyl-N-[(2S,3R)-2-methyl-4-oxo-azetidin-3-yl]-carbamate;
(4-phenylphenyl)-methyl-N-[(2S,3R)-2-methyl-4-oxo-azetidin-3-yl]-carbamate;
(4-cyclohexylphenyl)-methyl-N-[(2S,3R)-2-methyl-4-oxo-azetidin-3-yl]-carbamate;
4-cyclohexylbutyl-N-[(3S)-2,2-dimethyl-4-oxo-azetidin-3-yl]-carbamate;
(4-phenylphenyl)-methyl-N-[(3S)-2,2-dimethyl-4-oxo-azetidin-3-yl]-carbamate;
(4-cyclohexylphenyl)-methyl-N-[(3S)-2,2-dimethyl-4-oxo-azetidin-3-yl]-carbamate;
4-cyclohexylbutyl-N-[(3R)-2,2-dimethyl-4-oxo-azetidin-3-yl]-carbamate;
(4-phenylphenyl)-methyl-N-[(3R)-2,2-dimethyl-4-oxo-azetidin-3-yl]-carbamate; and
(4-cyclohexylphenyl)-methyl-N-[(3R)-2,2-dimethyl-4-oxo-azetidin-3-yl]-carbamate.
(4-oxazol-4-ylphenyl)-methyl-N-[(3S)-2-oxoazetidin-3-yl]-carbamate
[(1S)- and (1R)-1-(4-cyclohexylphenyl)-ethyl]-N-[(3S)-2-oxoazetidin-3-yl]-carbamate p-tolylmethyl-N-[(3S)-2-oxoazetidin-3-yl]-carbamate
(4-ethylphenyl)-methyl-N-[(3S)-2-oxoazetidin-3-yl]-carbamate
(4-propylphenyl)-methyl-N-[(3S)-2-oxoazetidin-3-yl]-carbamate
(4-propoxyphenyl)-methyl-N-[(3S)-2-oxoazetidin-3-yl]-carbamate
(2-Phenylpyrimidin-5-yl)-methyl-N-[(3S)-2-oxoazetidin-3-yl]-carbamate
(4,4-difluorocyclohexyl)-methyl-N-[(3S)-2-oxoazetidin-3-yl]-carbamate 4-(4,4-difluorocyclohexyl)-butyl-N-[(3S)-2-oxoazetidin-3-yl]-carbamate
(4-iodophenyl)-methyl-N-[(3S)-2-oxoazetidin-3-yl]-carbamate
4-[(1R,2R,4S)- and (1S,2S,4R)-norbornan-2-yl]-oxyphenyl]-methyl-N-[(3S)-2-oxoazetidin-3-yl]-carbamate
undec-10-ynyl-N-[(3S)-2-oxoazetidin-3-yl]-carbamate
[(1s,4S)-(4-propylcyclohexyl)]-methyl-N-[(3S)-2-oxoazetidin-3-yl]-carbamate
1,3-benzodioxol-5-ylmethyl-N-[(3S)-2-oxoazetidin-3-yl]-carbamate
(2,2-difluoro-1,3-benzodioxol-5-yl)-methyl-N-[(3S)-2-oxoazetidin-3-yl]-carbamate.

The compounds of the invention may be isolated in the form of their pharmaceutically acceptable acid addition salts, such as the salts derived from inorganic and organic acids. The term "pharmaceutically acceptable salts" refers to salts prepared from pharmaceutically acceptable, non-toxic acids including inorganic or organic acids. Such acids include hydrochloric, sulfuric, phosphoric, glycolic, malic, maleic, tartaric, succinic, citric, malonic acid and the like.

The compounds of the invention may be in crystalline forms. In certain embodiments, the crystalline forms of the compounds of the invention are polymorphs. In further embodiments, hydrates and solvates of the compounds of the invention or their pharmaceutically acceptable salts are contemplated by this invention.

The compounds of the invention may contain one or more chiral centers. Compounds containing one chiral center can occur as single enantiomers or mixtures of the two enantiomers. Such mixtures occur as racemates or racemic mixtures. Compounds containing more than one chiral center can occur as single enantiomers and pairs of enantiomers, and as stereoisomers which are not enantiomers, referred to as diastereoisomers. The compounds of the invention are meant to encompass all possible stereoisomers and mixtures thereof.

The compounds of the invention containing a carbon-carbon double bond can exist as E and Z geometric isomers. Geometric isomers of compounds of Formula (I) containing one or more carbon-carbon double bonds are within the scope of the present invention.

Some of the compounds described herein may exist with different points of attachment of a hydrogen atom, referred to as tautomers. Such an example may be a ketone and its enol form known as keto-enol tautomers. The individual tautomers as well as mixture thereof are encompassed by the Formula I.

The compounds of Formula I may have unnatural ratios of atomic isotopes at one or more of their atoms. For example, the compounds may be radiolabeled with isotopes such as tritium or carbon-14. All isotopic variations of the compounds of the present invention, whether radioactive or not, are within the scope of the present invention The invention also encompasses active metabolites of compounds of Formula I.

In addition, prodrugs of compounds of Formula I are also included within the scope of this invention. As used herein, the term "prodrug" means a compound which is converted within the body, e.g. by hydrolysis in the blood or by chemical conversion by metabolic processes, into its active form that has medical effects. Pharmaceutically acceptable prodrugs are described in T. Higuchi and V. Stella, *Prodrugs as Novel Delivery Systems*, Vol. 14 of the A.C.S. Symposium Series, Edward B. Roche, ed., *Bioreversible Carriers in Drug Design*, American Pharmaceutical Association and Pergamon Press, 1987, and in D. Fleisher, S. Ramon and H. Barbra "*Improved oral drug delivery: solubility limitations overcome by the use of prodrugs*", Advanced Drug Delivery Reviews (1996) 19(2) 115-130, which are incorporated herein by reference in its entirety for all purposes.

IV. Methods for Preparing Compounds

Described herein are methods for preparing the compounds set forth herein.

The present invention also provides methods for preparing compounds of Formula I.

The compounds of Formula I can be prepared through a process consisting of synthetic transformations reported, for instance, in Michael Smith, Jerry March—*March's Advanced Organic Chemistry: reactions mechanisms and structure* —6th Edition, John Wiley & Sons Inc., 2007, which is herein incorporated by reference in its entirety for all purposes. It is well known to one of ordinary skill in the art that transformation of a chemical function into another may require that one or more reactive centers in the compound containing this function be protected in order to avoid undesired side reactions. Protection of such reactive centers, and subsequent de-protection at the end of the synthetic transformations, can be accomplished following standard procedures described, for instance, in Theodora W. Green and Peter G. M. Wuts—*Protective Groups in Organic Synthesis, Fourth Edition*, John Wiley & Sons Inc., 2006, which is herein incorporated by reference in its entirety for all purposes.

In one embodiment, a compound of Formula I, can be obtained by reaction of a compound of Formula XVIII, or a salt thereof, wherein $R_1$, $R_2$, and $R_3$ are as defined above,

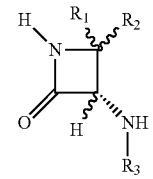

XVIII

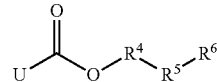

XIX with a compound of Formula XIX, wherein U represents chlorine, azido, a group selected from, but not limited to, 1-imidazolyl, p-nitrophenoxy, or 2-pyridyloxy, $R^1$ and $R^2$ are each independently selected from the group consisting of hydrogen, alkyl, aryl, cycloalkyl, arylalkyl, and cycloalkylalkyl. In some embodiments, $R^1$ and $R^2$ form a cycloalkyl substituent together with the carbon to which they are attached. $R^3$ is selected from the group consisting of hydrogen and alkyl. $R^4$ is selected from the group consisting of alkyl, alkenyl, alkynyl, aryl, arylalkyl, cycloalkyl, heteroaryl, heterocycloalkyl, heteroarylalkyl, and heterocycloalkylalkyl. $R^5$ is absent or is selected from the group consisting of alkyl, alkenyl, alkoxy, aryl, aryloxy, cycloalkyl, —O—, —S—, —C(O)—, —C(O)NH—, $NR^aR^b$, heteroaryl, and heterocycloalkyl. $R^6$ is absent or is selected from the group consisting of hydrogen, alkyl, alkoxy, aryl, aryl-alkylene, aryloxy, arylalkyloxy, arylalkyl, cycloalkyl, cycloalkyloxy, heterocycloalkyl, heterocycloalkyloxy, cycloalkylalkyl, heteroaryl, and —C(O)$NR^aR^b$. $R^1$, $R^2$, $R^3$, $R^4$, $R^5$, and $R^6$ are each independently optionally substituted with 1-4 substituents selected from the group consisting of lower alkyl, lower alkoxy, aryl, $NR^aR^b$, cyano, halogen, hydroxyl, trifluoromethyl, difluoromethyl, fluoromethyl. $R^a$ and $R^b$ are each independently selected from the group consisting of hydrogen and alkyl, and when $R^a$ and $R^b$ are taken together with the nitrogen atom to which they are bound, the group $NR^aR^b$ represents a heterocyclyl residue.

In some embodiments, a compound of Formula XIX, wherein $R_4$, $R_5$, $R_6$, and U are as defined above, can be obtained by reaction of a compound of Formula XX, wherein U is as defined above, and V represents a residue selected from chlorine, $OCH_2CH_3$, 1-imidazolyl, p-nitrophenoxy, 2-pyridyloxy, or the compound of Formula XX represents triphosgene, with a compound of Formula XXI,

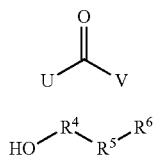

XX

XXI wherein $R_4$, $R_5$, and $R_6$ are as defined above.

A compound of Formula XX is generally a commercially available compound used in the activation of alcohols.

A compound of Formula XXI, wherein $R_4$, $R_5$, and $R_6$ are as defined above, is either a commercially available alcohol or can be prepared from suitable precursors, as known to a person skilled in the art, such as the corresponding halides or esters, according to standard synthetic methods as reported, for instance, in Michael Smith, Jerry March—*March's Advanced Organic Chemistry: reactions mechanisms and structure—6th Edition*, John Wiley & Sons Inc., 2007, and references cited therein, which is incorporated herein as reference.

A compound of Formula XVIII wherein $R_1$, $R_2$ and $R_3$ are as defined above, can be obtained from a compound of Formula I, wherein $R_1$, $R_2$, and $R_3$ are as defined above, and $R_4$ is —$CH_2$—, $R_5$ is absent, and and $R_6$ is phenyl, by hydrogenolysis reaction.

A compound of Formula XVIII wherein $R_1$, $R_2$ and $R_3$ are as defined above, can be obtained from a compound of Formula I, wherein $R_1$, $R_2$, and $R_3$ are as defined above, and $R_4$ is t-butyl, and $R_5$ and $R_6$ are absent, by reaction with trifluoroacetic acid (TFA).

In another embodiment a compound of Formula I, as defined above, can be obtained by removal of a suitable endocyclic nitrogen protecting group from a compound of Formula XXII, wherein $R_1$, $R_2$, $R_3$, $R_4$, $R_5$, and $R_6$ are as defined above, and PG represents a suitable nitrogen protecting group selected from, but not limited to, hydroxyl, methoxyl, p-methoxyphenyl, O-methylbenzensulfonyl, t-butyldimethylsilyl, bis-(trimethylsilyl)-methyl, 2,4-dimethoxybenzyl, and the like.

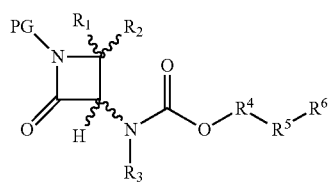

XXII

A compound of Formula XXII, as defined above, can be obtained by cyclyzation of a suitably protected compound of Formula XXIII, wherein $R_1$, $R_2$, $R_3$, $R_4$, $R_5$, and $R_6$ and PG are as defined above.

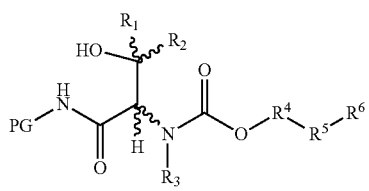

XXIII

A compound of Formula XXIII, as defined above, can be obtained by reaction of a compound of Formula XXIV wherein $R_1$, $R_2$, $R_3$, $R_4$, $R_5$, and $R_6$ are as defined above, by treatment with a suitable amine in the presence of a carboxylic acid activating agent.

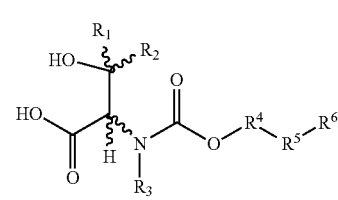

XXIV

A compound of Formula XXIV, as defined above, can be obtained by reaction of a compound of Formula XXV wherein $R_1$, $R_2$ and $R_3$ are as defined above, with a compound of Formula XIX, as defined above.

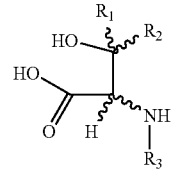

XXV

Amino acids of Formula XXV are either commercially available or can be obtained according to standard synthetic methods for the preparation of amino acids as described, for instance, in Blaskovich M A., *Handbook on Syntheses of Amino Acids—General Routes to Amino Acids* Oxford University Press, USA, 2010, and references cited therein, which is herein incorporated as reference.

In another embodiment, a compound of Formula XXII, wherein one of $R_1$ or $R_2$ represents H and the other represents an optionally substituted lower alkyl, an optionally substituted aryl, optionally substituted cycloalkyl, or $R_1$ and $R_2$ are both an optionally substituted lower alkyl, an optionally substituted aryl, optionally substituted cycloalkyl, $R_3$ represents H, $R_4$, $R_5$, $R_6$ and PG are as defined above, can be obtained by treatment of a compound of Formula XXVI, or a salt thereof, wherein $R_1$, $R_2$, $R_3$, and PG are as defined above, with a compound of Formula XIX, wherein $R_4$, $R_5$, $R_6$ and U are as defined above.

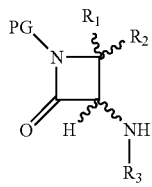

XXVI

A compound of Formula XXVI, or a salt thereof, wherein one of $R_1$ or $R_2$ represents H and the other represents an optionally substituted lower alkyl, an optionally substituted aryl, optionally substituted cycloalkyl, or R1 and R2 are both an optionally substituted lower alkyl, an optionally substituted aryl, optionally substituted cycloalkyl, and $R_3$ represents H, can be obtained from a compound of Formula XXVII wherein $R_1$, $R_2$ and PG are as defined above, and —NAUX represents a suitable chiral auxiliary. It is known to a person skilled in the art that the group —NAUX represents a nitrogen containing heterocycle bearing substituted stereogenic centers with a defined absolute configuration such as, but not limited to, substituted oxazolidin-2-ones, di-substituted pyrrolidines, and the like.

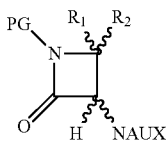

XXVII

A compound of Formula XXVII, as defined above, can be obtained from a compound of Formula XXVIII, wherein one of $R_1$ or $R_2$ represents H, and the other represents an optionally substituted lower alkyl, an optionally substituted aryl, optionally substituted cycloalkyl, or $R_1$ and $R_2$ are both an optionally substituted lower alkyl, an optionally substituted aryl, optionally substituted cycloalkyl, and PG is as defined above, by cycloaddition reaction with a compound of Formula XXIX.

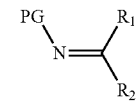

XXVIII

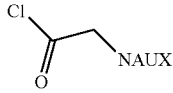

XXIX

Acyl chlorides of Formula XXIX, carrying a suitable chiral auxiliary (AUX), are either commercially available or can be prepared from suitable precursors, as known to a person skilled in the art, such as the corresponding carboxylic acids or esters, according to standard synthetic methods as reported, for instance, in Evans, D. A.; Sjögren, E. B. *Tetrahedron Lett.* 1985, 26, 3783, and references cited therein, which is incorporated herein as reference.

Imines of Formula XXVIII are either commercially available or can be prepared by synthetic methods reported, for instance, in Molina P., Tarraga A., Argues A. in Katritzky A. R., Taylor R. J. k., *Comprehensive Organic Functional Group Transformations II, Elsevier,* 2004, Vol. 5, pag. 949-973; or in Michael Smith, Jerry March—*March's Advanced Organic Chemistry: reactions mechanisms and structure*—6th Edition, John Wiley & Sons Inc., 2007, and references cited therein, which are herein incorporated as reference.

The synthesis of a compound of Formula I, according to the synthetic processes described above, can be conducted in a stepwise manner, whereby each intermediate is isolated and purified by standard purification techniques, like, for example, column chromatography, before carrying out the subsequent reaction. Alternatively, two or more steps of the synthetic sequence can be carried out in a so-called "one-pot" procedure, as known in the art, whereby only the compound resulting from the two or more steps is isolated and purified, using standard procedures, like column flash chromatography, reverse phase HPLC, preparative tin-layer-chromatography (TLC), crystallization, and the like.

The compounds described above can be prepared as exemplified in the following procedures.

A compound of Formula I, as defined above, can be obtained by separating diastereoisomers or enantiomers of Formula I. In a typical procedure, diastereoisomers can be separated by fractional crystallization from a suitable solvent or by standard chromatographic techniques. The pair of enantiomers thus obtained may be separated into individual stereoisomers by standard techniques described, for example, in J. Jacques, A. Collet, S. H. Wilen—*Enantiomers, Racemates, and Resolutions*, John Wiley & Sons Inc., New York (N.Y.), 1981 and in G. Subramanian (Ed.), *Chiral Separation Techniques: a practical approach—Wiley, Weinheim* 2007, which are herein incorporated as reference. Alternatively, an enantiomer of a compound of Formula I may be obtained by stereospecific synthesis using optically pure starting materials of known configuration.

A pharmaceutically acceptable salt of a compound of Formula I, containing a basic group, can be obtained by dissolving said compound in a solvent like, for instance, acetonitrile, dioxane, tetrahydrofuran, ethanol, methanol, or dichloromethane, or mixtures thereof, and adding the proper amount of an inorganic or organic acid, dissolved in a suitable solvent such as, for instance, acetonitrile, dioxane, tetrahydrofuran, ethanol, methanol, or dichloromethane, or mixtures thereof, at a temperature ranging from −20° C. to room temperature. The salt is usually isolated by filtration of the precipitate obtained by a) cooling; b) addition of a precipitating solvent, usually diethyl ether or diisopropyl ether; or c) partial evaporation of the solvent A compound of Formula I, as defined above, can be obtained by reaction of a compound of Formula XVIII, as defined above, with a compound of Formula XIX, as defined above. The reaction can be performed in a suitable solvent, such as dioxane, tetrahydrofuran, dichloromethane, acetonitrile, N,N-dimethylformamide, or mixtures thereof, in the presence of a suitable organic or inorganic base, such as triethylamine, di-isopropylethylamine or sodium hydrogen carbonate, and at a temperature ranging from −10° C. to 60° C., and for a period of time from 1 hour to 24 hours.

A compound of Formula XIX, as defined above, can be prepared by reaction of a compound of Formula XX, as defined above, with a compound represented by Formula XXI, as defined above, such as phosgene, ethyl choloroformate, p-nitrophenylchloroformate, 1,1'-carbonyldiimidazole, di-2-pyridyl carbonate, triphosgene, and the like. Such reaction is conducted in a suitable solvent such as dichloromethane, chloroform, acetonitrile, tetrahydrofuran, or mixtures thereof, in the presence of a suitable base such as triethylamine, di-isopropylethylamine, or pyridine, at a temperature ranging from −10° C. to 40° C., and for a period of time from 1 to 72 hours.

A compound of Formula XVIII, as defined above, or a salt thereof, can be obtained by hydrogenolysis reaction of a compound of Formula I, wherein $R_1$, $R_2$, $R_3$, are as defined above, $R_4$ is —$CH_2$—, $R_5$ is absent, and and $R_6$ is phenyl, by hydrogenolysis reaction, either by treatment with hydrogen ($H_2$) gas in the presence of a suitable catalyst, such as 10% Pd/C, 10% Pd(OH)$_2$, and the like, or alternatively using 10% Pd on activated charcoal in the presence of cyclohexadiene, and the like, in a suitable solvent, such as dichloromethane, ethanol, tetrahydrofuran, dioxane, or ethylacetate, at a temperature ranging from −10° C. to room temperature, and for a period of time from 10 minutes to 2 hours. A compound of Formula II is usually isolated as a salt after treatment with a dichloromethane, ethanol, or ethylacetate solution of acetic, hydrochloridric, or p-toluensulphonic acid, or the like.

A compound of Formula XVIII, as defined above, or a salt thereof, can be obtained by reaction of a compound of Formula I, wherein $R_1$, $R_2$, $R_3$, are as defined above, $R_4$ is t-butyl and $R_5$ and $R_6$ are absent, either by treatment with neat trifluoroacetic acid (TFA), or alternatively using hydrochloridric acid, and the like, in a suitable solvent, such as, ethanol, tetrahydrofuran, dioxane, or ethylacetate, at a temperature ranging from −10° C. to room temperature, and for a period of time from 10 minutes to 24 hours. A compound of Formula XVIII is usually isolated by precipitation as a salt after treatment with diethyl ether, dioxane, or the like.

A compound of Formula I, as defined above, can be obtained by selective deprotection of a compound of Formula XXII wherein $R_1$, $R_2$, $R_3$, $R_4$, $R_5$ and $R_6$ are as defined above, and PG is a nitrogen protecting group, by treatment with ceric ammonium nitrate, samarium iodide, ozone/$Na_2S_2O_4$, $NH_3$(liq.)/Na, sodium stabilized in silica gel (Na-SG)/t-BuOH, cesium fluoride or the like, in a suitable solvent, such as acetonitrile, water, dioxane, tetrahydrofuran, methanol, diethylether, methyl t-butyl ether, cyclohexane, or mixtures thereof, at a temperature ranging from −10° C. to room temperature, and for a period of time from 10 minutes to 2 hours.

A compound of Formula XXII, as defined above, can be obtained by cyclyzation reaction of a compound of Formula XXIII, as defined above, by previous activation of the hydroxyl group with suitable reagents, selected from, but not limited to, N,N'-sulfonyl-diimidazole, p-toluenesulfonyl chloride, methanesulfonyl chloride, and the like, in a solvent, such as dioxane, tetrahydrofuran, acetone, acetonitrile, N,N-dimethylformamide, or mixtures thereof, in the presence of an inorganic base, such as sodium hydride, potassium carbonate, or sodium hydrogen carbonate, at a temperature ranging from 0° C. to 50° C., and for a period of time from 1 hours to 24 hours.

A compound of Formula XXIII, as defined above, can be obtained by reaction of a compound of Formula XXIV, as defined above, with suitable amines, selected from, but not limited to, 4-methoxyaniline, methoxyamine, benzylamine, in the presence of a carboxyl-activating agent, such as 1-ethyl-3-(3-dimethylaminopropyl)-carbodiimide, N,N'-dicyclohexylcarbodiimide, N,N'-diisopropylcarbodiimide, and the like, in a solvent, such as water, tetrahydrofuran, dimethylformamide, dichloromethane or mixtures thereof, at a temperature ranging from −10° C. to room temperature, and for a period of time from 12 hours to 24 hours.

A compound of Formula XXIV, as defined above, can be obtained by reaction of a compound of Formula XXV, wherein $R_1$, $R_2$, $R_3$, are as defined above, with a compound of Formula XIX, as defined as above, wherein U represents chlorine, hydroxyl, azido, a group selected from, but not limited to, 1-imidazolyl, p-nitrophenoxy, or 2-pyridyloxy. The reaction can be performed in a suitable solvent, such as dioxane, tetrahydrofuran, dichloromethane, acetonitrile, N,N-dimethylformamide, or mixtures thereof, in the presence of a suitable organic or inorganic base, such as triethylamine, di-isopropylethylamine or sodium hydrogen carbonate, and at a temperature ranging from −10° C. to 60° C., and for a period of time from 1 hour to 24 hours.

A compound of Formula XXII, wherein A one of $R_1$ or $R_2$ represents H, and the other represents an optionally substituted lower alkyl, an optionally substituted aryl, optionally substituted cycloalkyl, or $R_1$, $R_2$ are both an optionally substituted lower alkyl, an optionally substituted aryl, optionally substituted cycloalkyl, and $R_3$ represents H, $R_4$, $R_5$ and $R_6$ and PG are as defined above, can be obtained by reaction of a compound of Formula XXVI, or a salt thereof, as defined above, with a compound of Formula XIX, as defined above. The reaction can be performed in an analogous manner as reported for the synthesis of a compound of Formula I from compounds of Formula XVIII with compounds of Formula XIX.

A compound of Formula XXVI, as defined above, wherein $R_3$ is H, can be prepared from a compound of Formula XXVII wherein one of $R_1$ or $R_2$ represents H, and the other represents an optionally substituted lower alkyl, an optionally substituted aryl, optionally substituted cycloalkyl, or $R_1$, $R_2$ are both an optionally substituted lower alkyl, an optionally substituted aryl, optionally substituted cycloalkyl, and $R_3$ represents H, $R_4$, $R_5$, $R_6$, PG and —NAUX are as defined above, by chemo-selective removal of the chiral auxiliary using $NH_3$(liq.)/Na, ethylenediamine/Li, bis-(methoxyethyl)-amine or n-butylamine/Li, sodium stabilized in silica gel (Na-SG) or the like, in a suitable solvent, such as, dioxane, tetrahydrofuran, diethylether, t-butanol, methyl t-butyl ether, cyclohexane, toluene or mixtures thereof, at a temperature ranging from −78° C. to room temperature, and for a period of time from 10 minutes to 2 hours.

A compound of Formula XXVII, as defined above, can be prepared by cycloaddition reaction of a compound of Formula XXVIII, as defined above, with a compound of Formula XXIX, as defined above. The reaction can be performed in a suitable solvent, such as dioxane, tetrahydrofuran, dicholomethene, chloroform, dicholoethane, or mixtures thereof, in the presence of a suitable organic or inorganic base, such as triethylamine, di-isopropylethylamine, and activated 4 Å molecular sieves, at a temperature ranging from 0° C. to 80° C., and for a period of time from 1 hour to 24 hours.

V. Pharmaceutical Compositions

The invention provides pharmaceutical compositions of the compounds described herein for modulation of the levels of PEA or other NAE in a subject. The pharmaceutical compositions of the present invention encompass compositions made by admixing a compound of the present invention and a pharmaceutically acceptable carrier and/or excipient or diluent. Such compositions are suitable for pharmaceutical use in an animal or human.

The pharmaceutical compositions of the present invention comprise a compound described herein, or a pharmaceutically acceptable salt thereof, as an active ingredient and a pharmaceutically acceptable carrier and/or excipient or diluent. A pharmaceutical composition may optionally contain other therapeutic ingredients.

The compounds of the present invention can be combined as the active ingredient in intimate admixture with a suitable pharmaceutical carrier and/or excipient according to conventional pharmaceutical compounding techniques. Any carrier and/or excipient suitable for the form of preparation desired for administration is contemplated for use with the compounds disclosed herein.

The compositions include compositions suitable for topical, parenteral, pulmonary, nasal, rectal or oral administration. The most suitable route of administration in any given case will depend in part on the nature and severity of the conditions being treated and on the nature of the active ingredient.

Some preferred compositions include compositions suitable for topical, subcutaneous, and pulmonary, in the form of nasal or buccal inhalation administration.

Other preferred compositions include compositions suitable for systemic (enteral or parenteral) administration. The systemic administration includes the oral, rectal, sublingual, sublabial administration.

The compositions may be prepared by any of the methods well-known in the art of pharmacy.

Compositions for topical administration include, but are not limited to, ointments, creams, lotions, solutions, pastes, gels, sticks, liposomes, nanoparticles, patches, bandages and wound dressings. In certain embodiments, the topical formulation comprises a penetration enhancer.

Compositions for pulmonary administration include, but are not limited to, dry powder compositions consisting of the powder of a compound described herein, or a salt thereof, and the powder of a suitable carrier and/or lubricant. The compositions for pulmonary administration can be inhaled from any suitable dry powder inhaler device known to a person skilled in the art.

Compositions for systemic administration include, but are not limited to, dry powder compositions consisting of the powder of a compound of Formula I, or a salt thereof, and the powder of a suitable carrier and/or excipient. The compositions for systemic administration can be represented by, but not limited to, tablets, capsules, pills, syrups, solutions, suspensions, films and suppository.

Administration of the compositions is performed under a protocol and at a dosage sufficient to reduce the inflammation and pain in the subject.

In some embodiments, in the pharmaceutical compositions of the present invention the active principle or active principles are generally formulated in dosage units. The dosage unit may contain from 0.1 to 1000 mg of a NAAA inhibitor per dosage unit.

In some embodiments, the amounts effective for topical or systemic administration will depend on the severity of the disease, disorder or condition, previous therapy, the individual's health status and response to the drug. In some embodiments, the dose is in the range from 0.001% by weight to about 60% by weight of the formulation.

When used in combination with one or more other active ingredients, the compound of the present invention and the other active ingredients may be used in lower doses than when each is used singly.

With respect to formulations with respect to any variety of routes of administration, methods and formulations for the administration of drugs are disclosed in *Remington: The Science and Practice of Pharmacy*, 21*st Edition*, Lippincott Williams & Wilkins Eds., 2005; and in *Ansel's Pharmaceutical Dosage Forms and Drug Delivery Systems*, 8$^{th}$ *Edition*. Lippincott Williams & Wilkins Eds., 2005, which are herein incorporated as reference.

VI. Administration

The compounds of the invention may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The compounds of the invention can be effective over a wide dosage range. For example, in the treatment of adult humans, dosages from about 1 to about 1000 mg, about 100 to about 500 mg, about 10 to about 100 mg, about 1 to 10 mg may be needed. These dosages may adjusted as to amounts and/or a schedule as needed to achieve relief (e.g., 4, 6, 8, 12 or 24 hour intervals; 1-, 2-, 3-, or 4-times per day). Depending on the compound, doses of the 0.05 to about 100 mg, or from about 0.1 to about 100 mg per day may be used. In choosing a regimen for patients, it may frequently be necessary to begin with a dosage of from about 2 to about 70 mg per day and when the condition is under control to reduce the dosage as low as from about 0.1 to about 10 mg per day. For example, in the treatment of adult humans, dosages from about 0.05 to about 100 mg, preferably from about 0.1 to about 100 mg, per day may be used. The exact dosage will depend upon the mode of administration, the compound of the invention involved, on the therapy desired, form in which administered, the subject to be treated and the body weight of the subject to be treated, and the preference and experience of the physician or veterinarian in charge.

Generally, the compounds of the present invention can be dispensed in unit dosage form comprising preferably from about 0.1 to about 1000 mg of active ingredient together with a pharmaceutically acceptable carrier per unit dosage. Dosage forms suitable for oral, nasal, pulmonary or transdermal administration may comprise from about 0.001 mg to about 100 mg, or from about 0.01 mg to about 50 mg of the compounds admixed with a pharmaceutically acceptable carrier or diluent. For storage and use, these preparations preferably contain a preservative to prevent the growth of microorganisms.

Kits providing a unit dosage of the compounds and compositions set forth herein are contemplated as within the present invention. Kits providing many unit dosages of the compounds and compositions set forth herein are contemplated as within the present invention. Still further, kits providing several unit dosages of the compounds and compositions set forth herein are contemplated as within the present invention. In some embodiments, the kits of the present invention include a unit dosage of a pharmaceutical composition of a compound set forth herein. In certain embodiments, the kits of the present invention include many unit dosages of a pharmaceutical composition of a compound set forth herein. In certain other embodiments, the kits of the present invention include a unit dosage of a pharmaceutical composition set forth herein.

Administration of an appropriate amount the candidate compound may be by any means known in the art such as, for example, oral or rectal, parenteral, intraperitoneal, intravenous, subcutaneous, subdermal, intranasal, or intramuscular. In some embodiments, administration is transdermal. In some other embodiments, the administration is for dermal delivery. An appropriate amount or dose of the candidate compound may be determined empirically as is known in the art. An appropriate or therapeutic amount is an amount sufficient to effect a loss of body fat or a loss in body weight in the animal over time. The candidate compound can be administered as often as required to effect a loss of body fat or loss in body weight, for example, hourly, every six, eight, twelve, or eighteen hours, daily, or weekly Formulations suitable for oral administration can consist of (a) liquid solutions, such as an effective amount of the active ingredient suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

Injection solutions and suspensions can be prepared from sterile powders, granules, and tablets of the kind previously described. Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

With respect to transdermal or dermal delivery routes of administration, methods for transdermal administration of drugs are disclosed in Remington's Pharmaceutical Sciences, Gennaro AR ed. 20th edition, 2000: Williams & Wilkins Pa., USA. Dermal or skin patches are a preferred means for transdermal delivery of the compounds of the invention. Patches preferably provide an absorption enhancer such as DMSO to increase the absorption of the compounds. Other methods for transdermal drug delivery are disclosed in U.S. Pat. Nos. 5,962,012, 6,261,595, and 6,261,595. Each of which is incorporated by reference in its entirety.

Preferred patches include those that control the rate of drug delivery to the skin. Patches may provide a variety of dosing systems including a reservoir system or a monolithic system, respectively. The reservoir design may, for example, have four layers: the adhesive layer that directly contacts the skin, the control membrane, which controls the diffusion of drug molecules, the reservoir of drug molecules, and a water-resistant backing Such a design delivers uniform amounts of the drug over a specified time period, the rate of delivery has to be less than the saturation limit of different types of skin.

The monolithic design, for example, typically has only three layers: the adhesive layer, a polymer matrix containing the compound, and a water-proof backing. This design brings a saturating amount of drug to the skin. Thereby, delivery is controlled by the skin. As the drug amount decreases in the patch to below the saturating level, the delivery rate falls.

Compounds of the invention may be used in combination with other compounds of the invention or with other drugs that may also be useful in the treatment, prevention, suppression of a neurological or psychological disorder. Such other drugs may be administered, by a route and in an amount commonly used therefor, contemporaneously or sequentially with a compound of the invention. When a compound of the invention is used contemporaneously with one or more other drugs, a pharmaceutical composition in unit dosage form containing such other drugs and the compound is preferred. When used in combination with one or more other active ingredients, the compound of the present invention and the other active ingredients may be used in lower doses than when each is used singly.

In the pharmaceutical compositions of the present invention for oral, sublingual, subcutaneous, intramuscular, intravenous, transdermal, dermal delivery, local or rectal administration, the active principle, by itself or in association with another active principle, can be administered to animals and humans in unit forms of administration mixed with conventional pharmaceutical carriers. The appropriate unit forms of administration include oral forms such as tablets, gelatin capsules, powders, granules and solutions or suspensions to be taken orally, sublingual and buccal forms of administration, aerosols, implants, subcutaneous, intramuscular, intravenous, intranasal or intraocular forms of administration and rectal forms of administration.

In other embodiments, the pharmaceutical compositions of the present invention, the active principle or active principles are generally formulated in dosage units. The dosage unit may contain from 0.1 to 1000 mg, advantageously from 1 to 500 mg and preferably from 2 to 200 mg per dosage unit for daily administration.

In certain embodiments, the pharmaceutical compositions of the present invention are suitable for dermal delivery.

VII. Method of Use

In some embodiments, the compounds described herien, and their pharmaceutical compositions and methods of administering them are useful in treating acute inflammation, chronic inflammation, pain (including acute pain, acute inflammatory pain, chronic inflammatory pain, and neuropathic pain), and other disorders in which decreased levels of NAE are associated with the disorder. The treatment may be prophylactic or therapeutic.

In other embodiments, the pharmaceutical compositions of the present invention, the active principle or active principles are generally formulated in dosage units. The dosage unit may contain from 0.1 to 1000 mg, advantageously from 1 to 500 mg and preferably from 2 to 200 mg per dosage unit.

NAAA inhibition can increase PEA and OEA levels to inhibit peripheral inflammation and mast cell degranulation (Mazzari et al., *European Journal of Pharmacology* 1996, 300, 227-36; Berdishev et al., *Life Science* 1998, 63, 125-129; D'Agostino et al., *Journal of Pharmacology and Experimental Therapeutics* 2007, 322, 1137-1143), as well as to exert antinociceptive effects in rats and mice (Calignano et al., *Nature* 1998, 394, 277-281; Calignano et al., *European Journal of Pharmacology* 2001, 419, 191-198). These properties have been shown to be dependent on PPAR-α, and PEA and OEA activate this nuclear receptor with high potency (Lo Verme et al., *Molecular Pharmacology* 2005, 67, 15-19; Lo Verme et al., *Journal of Pharmacology and Experimental Therapeutics* 2006, 319, 1051-1061). In the carrageenan-induced paw edema and phorbol ester-induced ear edema models, PEA applied as a drug attenuates inflammation in wild-type mice, but has no effect in mice lacking PPAR-α (see LoVerme et al., *Molecular Pharmacology* 2005, 67, 15-19). PEA was also found to suppress pain behaviors in mice induced by chemical tissue injury, nerve damage, or inflammation (see LoVerme et al., *Journal of Pharmacology and Experimental Therapeutics* 2006, 319, 1051-1061). In addition to the pharmacological activities shown in animal models, PEA has been reported to attenuate skin inflammation in humans (Kemeny et al., *Skin Pharmacology and Physiology* 2007, 20, 155-161). Certain methods of treating pain and inflammation by inhibiting NAAA have been disclosed in the Patent Application WO2009/049238. Some compounds disclosed in WO2009/049238 have been shown to prevent the carrageenan- and LPS-induced reduction in PEA and OEA levels in leukocytes and RAW264.7 macrophages, respectively, and attenuate inflammation and tissue damage produced in mice by traumatic spinal cord injury (Solorzano et al., *Proceedings of the National Academy of Science USA* 2009, 106, 20966-20971; Solorzano et al., *Journal of Medicinal Chemistry* 2010, 53, 5770-5781). Each of these publications and patent applications are specifically incorporated herein by reference particularly with respect to the biological properties and activities of NAAA inhibitors and PEA/OEA as well as of their therapeutic uses and their biological assay methods which can be used to assess the anti-inflammatory and anti-pain as well as the other therapeutic actions of the NAAA inhibitors of the present invention.

The compounds and compositions described herein are useful for treating arthritis, wherein arthritis may include osteoarthritis, rheumatoid arthritis, gout, fibromyalgia, general arthritis, psoriatic arthritis, systemic lupus erythematosus, or septic arthritis.

The compounds and compositions described herein are useful for treating asthma, wherein asthma may include exercise-induced asthma, asthma due to an allergy, cough-variant asthma, occupational asthma, or nocturnal asthma.

The compounds and compositions described herein are useful for treating neurogenerative inflammation, wherein neurodegenerative inflammation may include Parkinson's disease or multiple sclerosis.

The compositions of the present invention are useful for treaching neurodegenerative disorders such as Amyotrophic Lateral Sclerosis, Parkinson's, and Alzheimers. The compositions of the present invention are also useful for treating Multiple Sclerosis.

The compounds and compositions described herein are useful for treating neurodermatitis.

The irritable bowel syndrome (IBS) described herein may include, but is not limited to, IBS with constipation, IBS with diarrhea, or IBS with alternating constipation and diarrhea.

The inflammatory bowel disease (IBD) described herein may include Crohn's disease, ulcerative colitis, ileocolits, ileitis, gastroduodenal Crohn's disease, or jejunoileitis.

VIII. Inflammation and Inflammatory Pain

In some embodiments, the compounds described herein and their pharmaceutical compositions may be administered in therapeutically effective amounts to alleviate or treat inflammation in a subject. The treatment may be prophylactic or therapeutic. The treatment may be administered in a combination therapy with another pain reliever or anti-inflammatory agent. In some embodiments, the pain is a pain caused by inflammation or injury of a tissue. Inflammatory pain develops in response to tissue damage occurring from the noxious stimuli. The inflammation is associated with disease states including, but not limited to, acute inflammation, chronic inflammation, arthritis, rheumatoid arthritis, asthma, chronic obstructive pulmonary disease (COPD), adult respiratory disease, chronic bronchitis, emphysema, cough, inflammatory bowel disease, ulcerative colitis, lupus, graft vs. host reaction (i.e., graft vs. host disease), acute and chronic allograft rejection, acute respiratory distress syndrome, osteoarthritis, multiple sclerosis, restinosis, cystic fibrosis, crystal induced arthritis, ocular inflammation, hyperoxia-induced inflammations, dyslipidemia, myofasciitis, carpal tunnel, Alzheimer's disease, Parkinson's disease. In embodiments, the inflammation is associated with disease states including, but not limited to, acute inflammation, chronic inflammation, arthritis, rheumatoid arthritis, asthma, chronic obstructive pulmonary disease (COPD), adult respiratory disease, chronic bronchitis, emphysema, cough, inflammatory bowel disease, ulcerative colitis, Crohn's disease, ileocolits, ileitis, gastroduodenal Crohn's disease, jejunoileitis, lupus, graft vs. host reaction (i.e., graft vs. host disease), acute and chronic allograft rejection, acute respiratory distress syndrome, osteoarthritis, multiple sclerosis, restinosis, cystic fibrosis, crystal induced arthritis, ocular inflammation, (including dry eye), corneal damage, hyperoxia-induced inflammations, dyslipidemia, myofasciitis, carpal tunnel, Alzheimer's disease, Parkinson's disease.

In some embodiments, the present invention provides a method of treating a mammal suffering from an inflammatory condition comprising administering to the mammal a compound having the structure selected from the group consisting of Formula I to XVII.

In some other embodiments, the present invention provides a method set forth herein wherein the inflammatory condition is osteoarthritis, rheumatoid arthritis, asthma, chronic obstructive pulmonary disease (COPD), adult respiratory disease, chronic bronchitis, inflammatory bowel disease, ulcerative colitis, lupus, graft vs. host reaction (i.e., graft vs. host disease), acute and chronic allograft rejection, acute respiratory distress syndrome, multiple sclerosis, restinosis, cystic fibrosis, crystal induced arthritis, ocular inflammation, (including dry eye), corneal damage, hyperoxia-induced inflammation, myofascitis, polymyositis, carpal tunnel, sprains, contusions, dental pain, vasculitis, or periodontitis.

In some embodiments, the present invention provides that the inflammatory condition is contact dermatitis, atopic dermatitis, seborrhoic dermatitis, eczema, urticaria, rosacea, acne, psoriasis, lichen, psoriatic arthritis acne, skin burns deriving from various origins, surgical skin incisions, or delayed skin healing induced by diabetes, immunosuppression or other causes.

The compositions of the present invention can also be useful for treating the inflammation associated with neurodegenerative disorders such as ALS, Parkinson's, and Alzheimers.

The compositions of the present invention can also be useful for treating skin inflammation disorders. The compositions of the present invention can be applied locally, topically, or systemically for the treatments contemplated herein.

The compounds of the present invention are surprisingly beneficial at treating multiple sclerosis as compared to similar compounds. For example, the carbamate containing compounds which are described herein are surprisingly better than related amide containing compounds at treating multiple sclerosis. The claimed carbamate compounds were found to be surprisingly therapeutic for treating multiple sclerosis as compared to the related amides.

IX. Pain

In some embodiments, the compounds described herein and their pharmaceutical compositions may be administered in therapeutically effective amounts to alleviate or treat pain in a subject in need thereof. The treatment may be prophylactic or therapeutic. The treatment may be administered in a combination therapy with another pain reliever or anti-inflammatory agent. The treatment may be also administered in a combination with PEA and/or OEA, or other NAAA substrates with similar anti-inflammatory properties.

The compositions of the present invention are useful for treating neurodegenerative disorders such as ALS, Parkinson's, and Alzheimers. The compositions of the present invention are also useful for treating multiple sclerosis.

The compositions of the present invention are useful for treating skin inflammation disorders. The compositions of the present invention can be applied locally, topically, or systemically for the treatments contemplated herein.

In some embodiments, the pain is associated with disease states including, but not limited to migraine, sinus headaches, trigeminal disease, dental pain, multiple sclerosis, sarcoidosis, polymyositis, gingivitis, swelling occurring after injury, pre-term labor, sprains, contusions, surgery (prophylactically and therapeutically), trauma, bone damage, and cancer.

In other embodiments, the pain can be a neuropathic pain selected from the group of, but not limited to, post herpetic neuralgia, post trigeminal neuralgia, diabetic neuropathy, neuropathic low back pain, peripheral or polyneuropathic pain, toxic neuropathy, chronic neuropathy caused by chemotherapeutic agents, retinopathy of prematurity, diabetic retinopathy, polymyositis, vasculitis, and periodontitis.

In some embodiments, the present invention provides a method of treating a mammal suffering from a painful or pruritogenic pathological state not attributable to inflammation comprising administering to the mammal a compound having the structure selected from the group consisting of Formula I-XVII.

In some embodiments, the present invention provides that the pathological state to be treated is post herpetic neuralgia, trigeminal neuralgia, causalgia, diabetic neuropathy, neuropathic low back pain, peripheral or polyneuropathic pain, toxic neuropathy, chronic neuropathy caused by chemotherapeutic and antiviral agents, or pruritus induced by uremia, malignancies of various origin, polycythemia, jaundice or cholestasis, iron deficiency, athlete's foot, xerosis, wound healing, thyroid illness, hyperparathyroidism, or menopause.

X. Dermal Diseases, Disorders or Conditions

In some embodiments, the compositions of the invention may be administered in therapeutically effect amounts to alleviate or treat dermal diseases, disorders or conditions in a subject. The treatment may be prophylactic or therapeutic. The treatment may be administered in a combination therapy with another agent used in the treatment of dermatological diseases, disorders or conditions. In some embodiments, dermal diseases, disorders or conditions include, but are not limited to, contact dermatitis, atopic dermatitis, eczema, urticaria, rosacea, acne, psoriasis, pruritis, lichen, psoriatic arthritis acne, scarring, skin wound healing, skin burns deriving from various origins, such as sunburns or radiation therapy burns, and of various severities (first degree burn, second degree burn, third degree burn, fourth degree burns), scleroderma, solar keratosis, squamous cell carcinoma, and melanoma.

In some embodiments, the present invention provides a method of treating a mammal suffering from a neurodegenerative disorder, comprising administering to the mammal a compound having the structure selected from the group consisting of Formula I-XVII.

In some embodiments, the present invention provides that the neurodegenerative disorder is Alzheimer's disease (e g Alzheimer's dementia), Parkinson's disease, Huntington's disease, Amytrophic Lateral Sclerosis, or macular degeneration.

In other embodiments, the present invention provides a method of inhibiting NAAA comprising contacting the NAAA in vitro with a compound having the structure selected from the group consisting of Formula I-XVII.

In other embodiments, the present invention provides a method, as set forth herein, wherein the compound is selected from the group consisting of

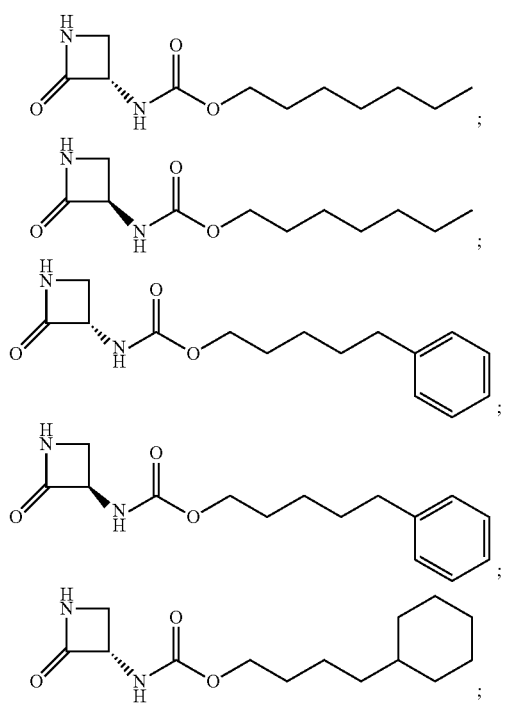

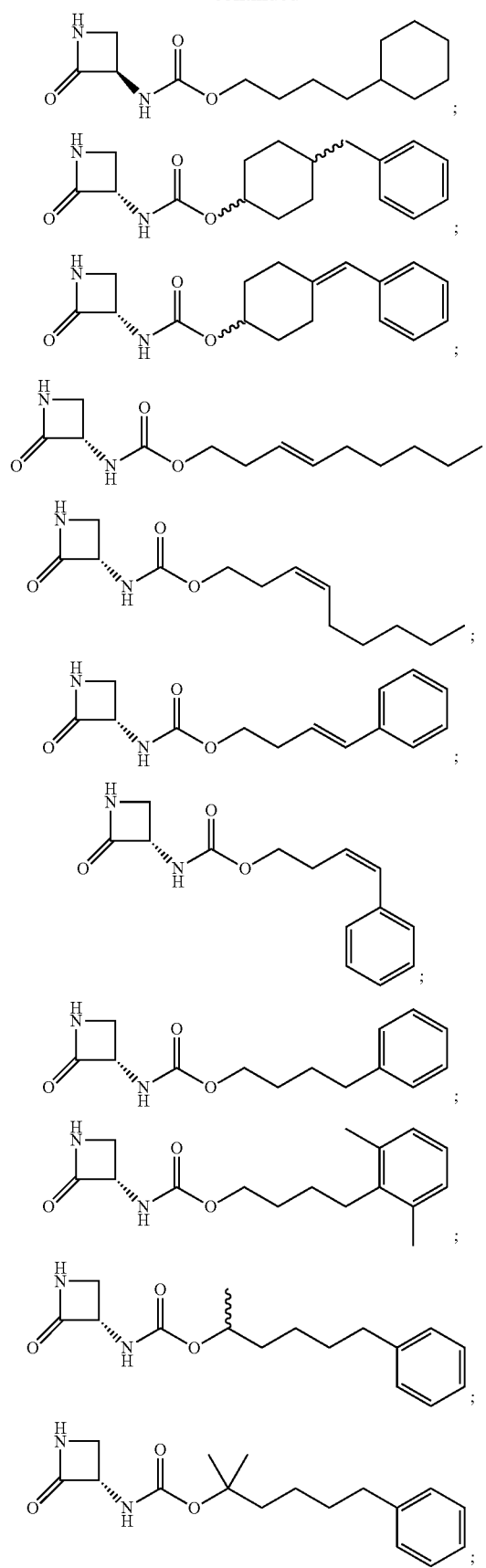
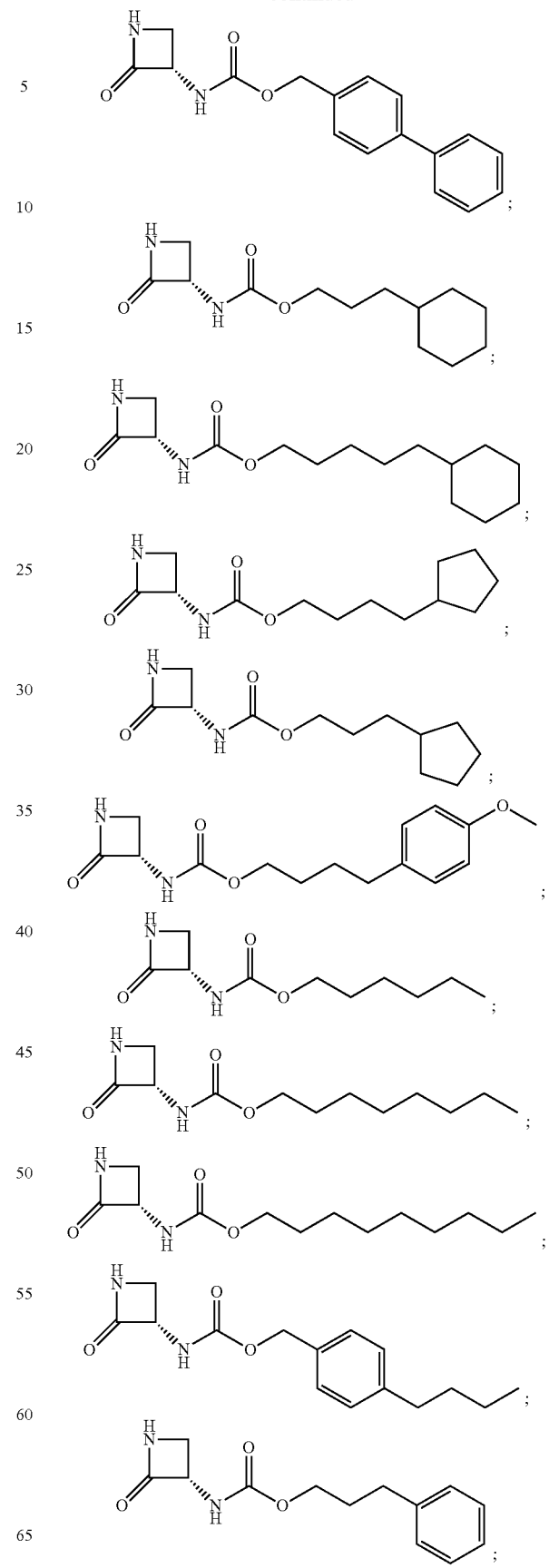

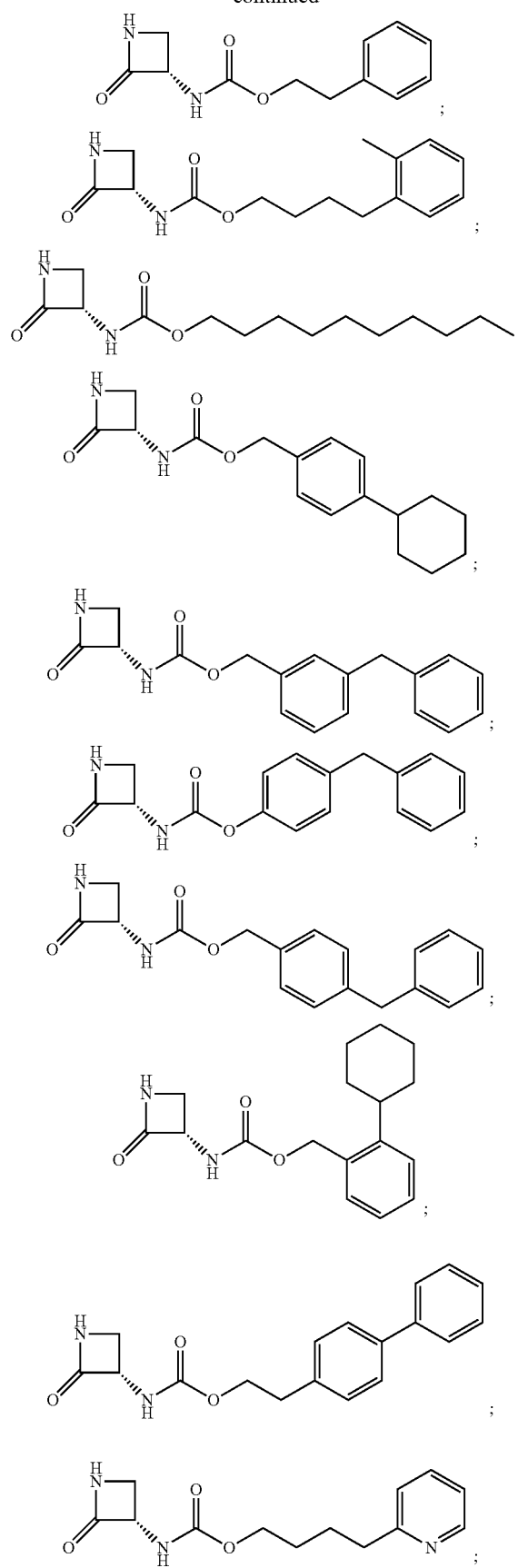
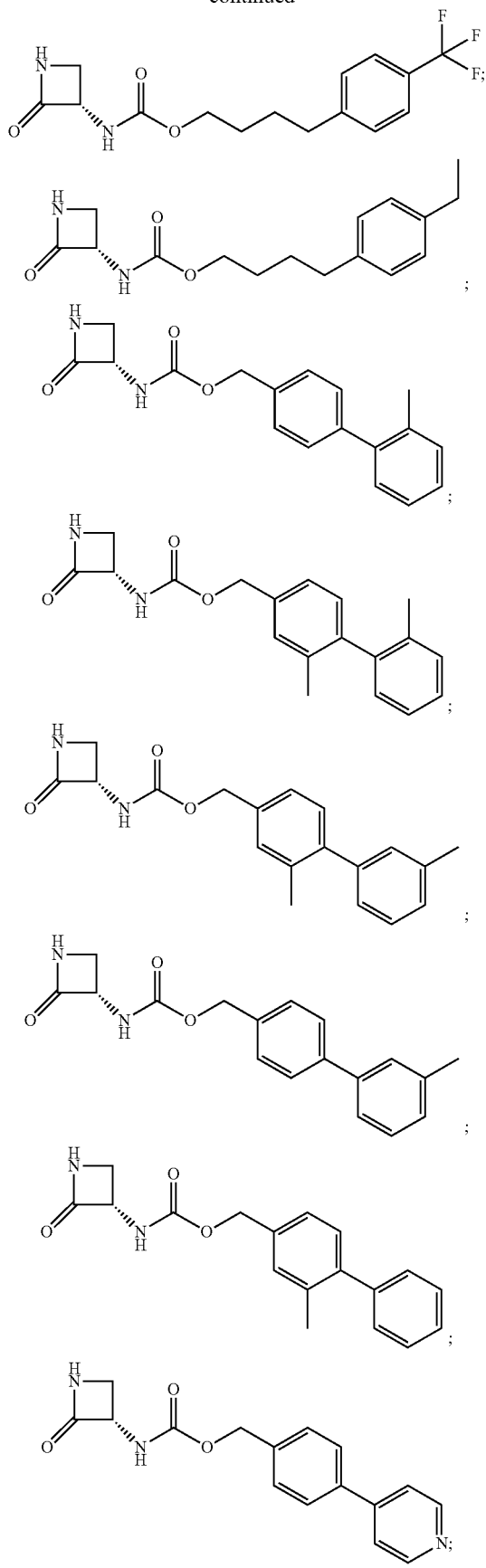

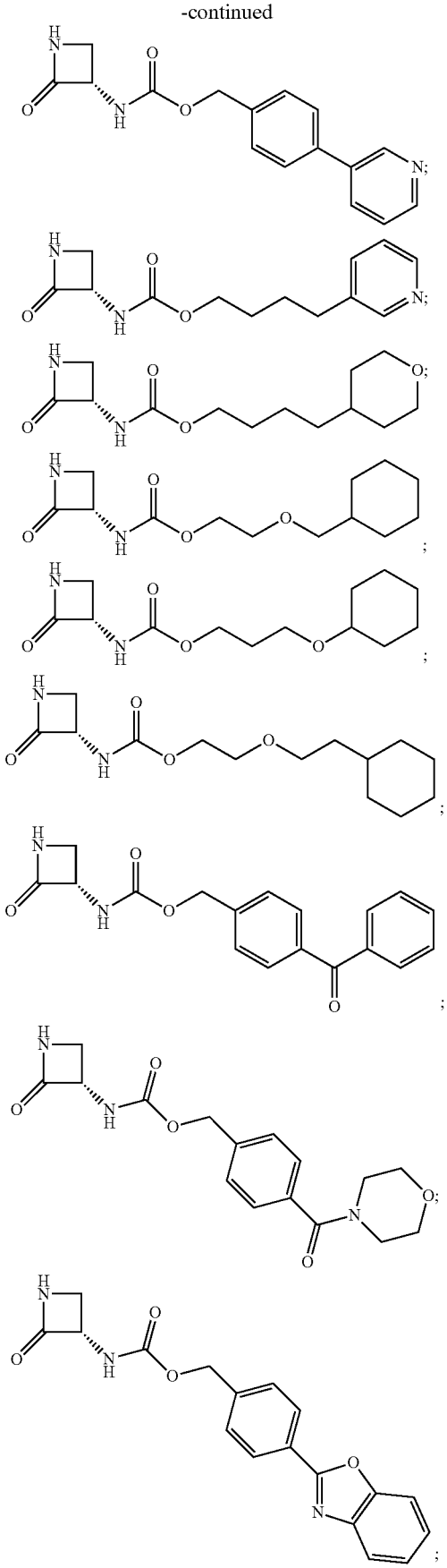
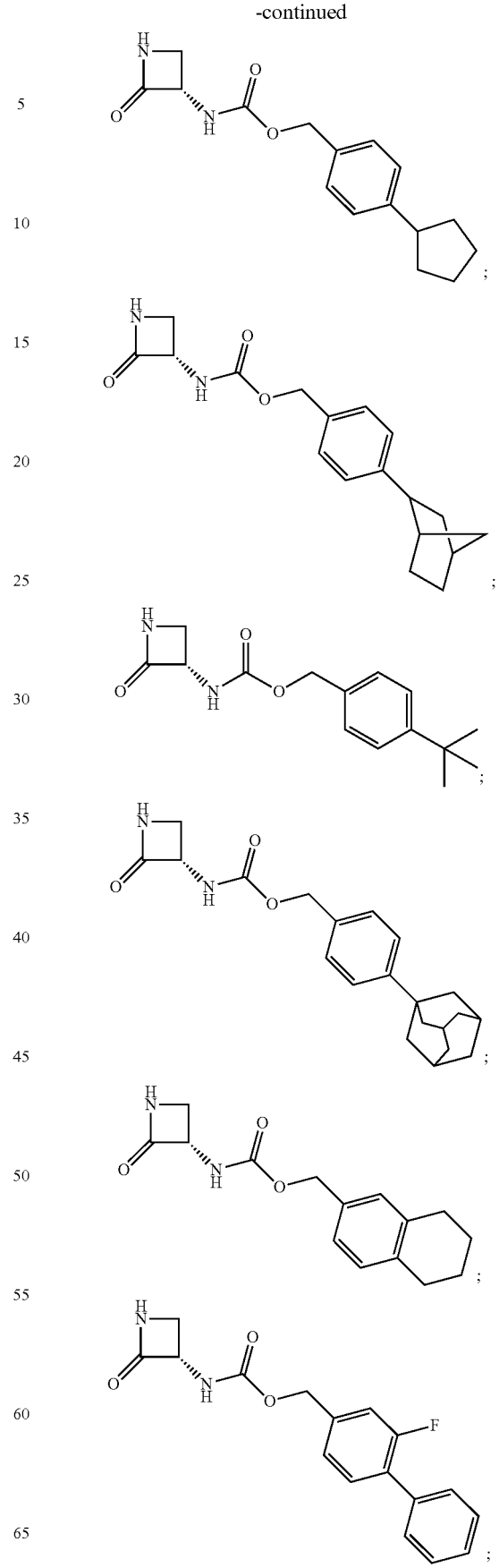

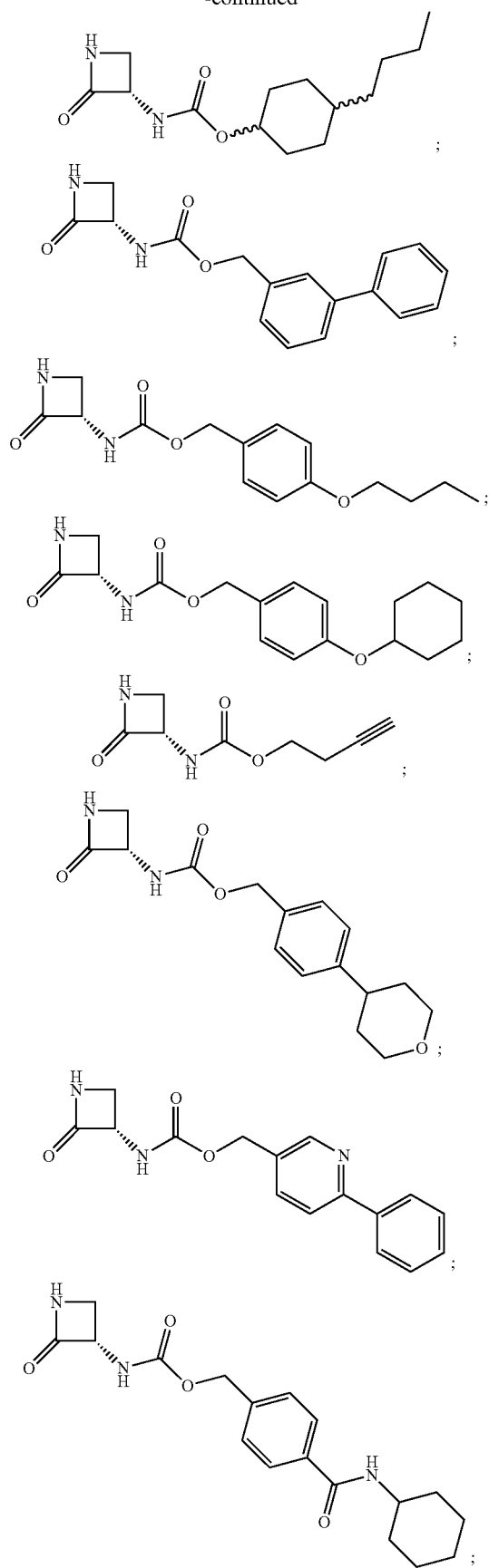
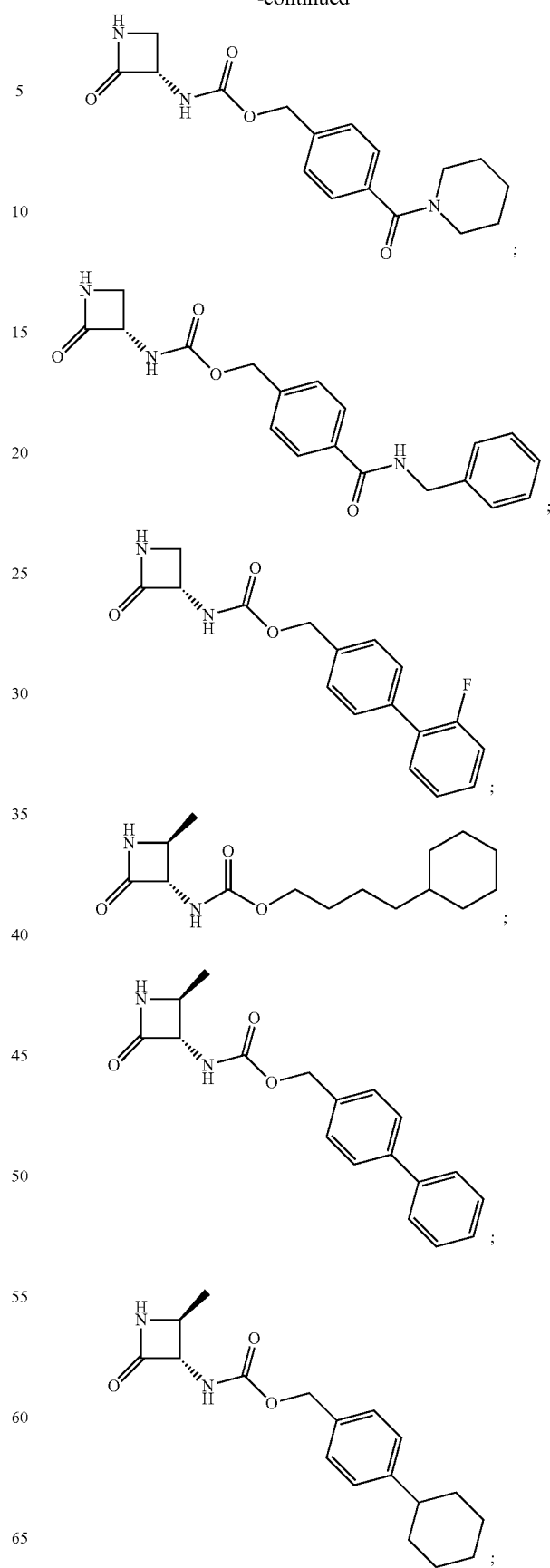

57
-continued
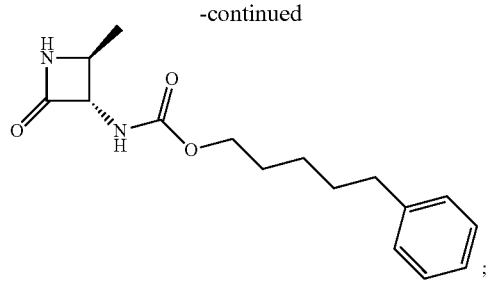
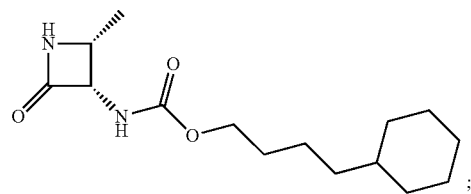
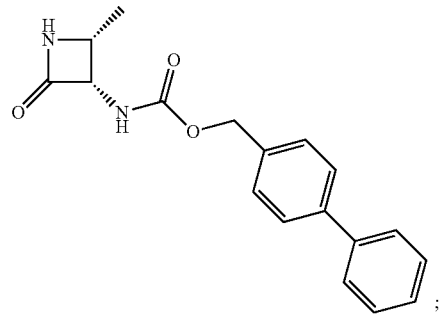
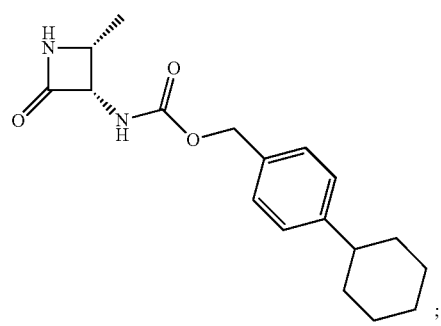
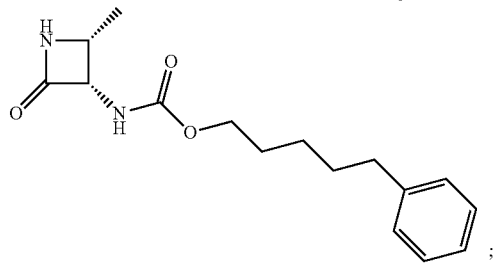
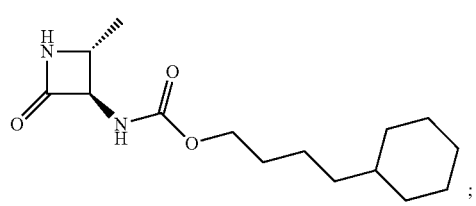
58
-continued
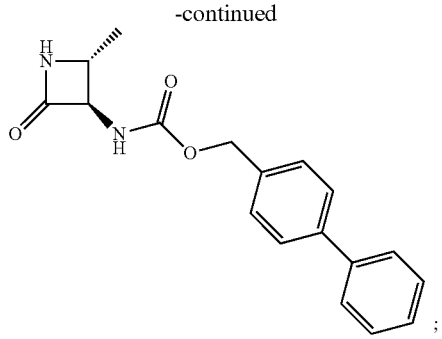
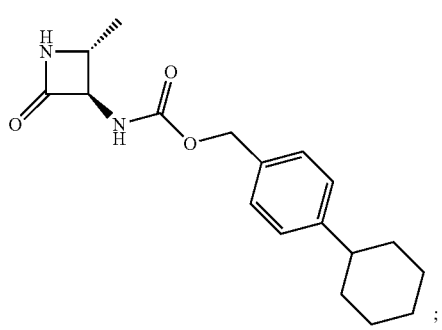
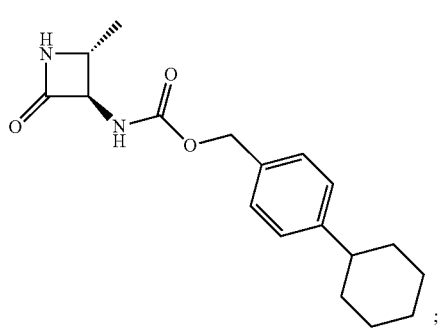
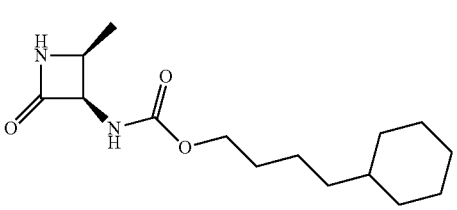
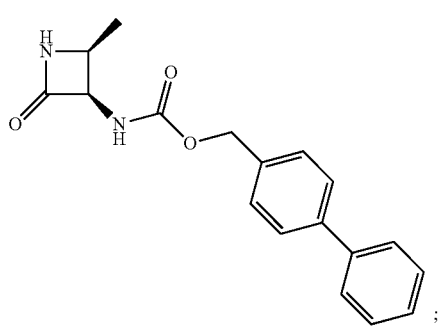

59
-continued
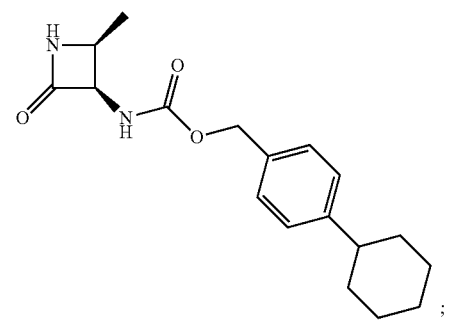
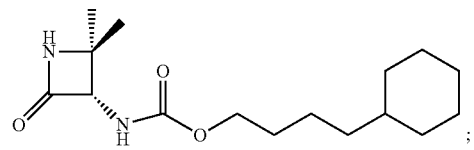
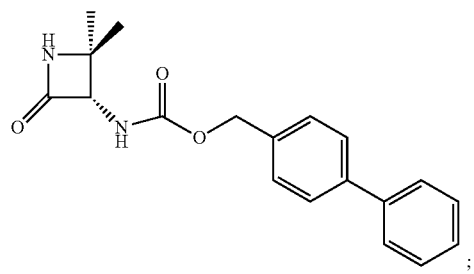
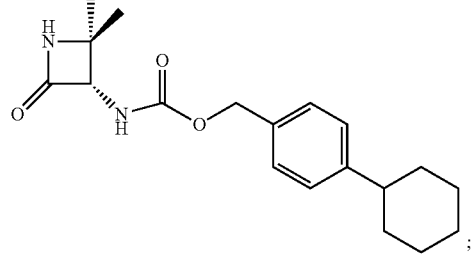
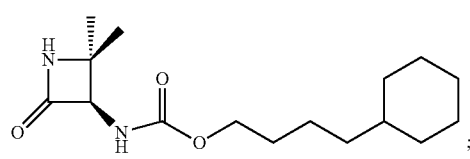
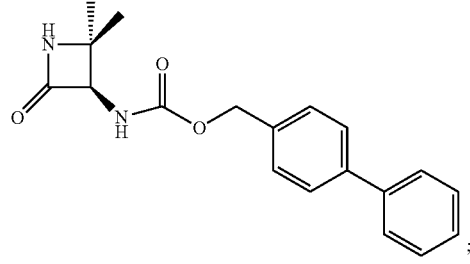
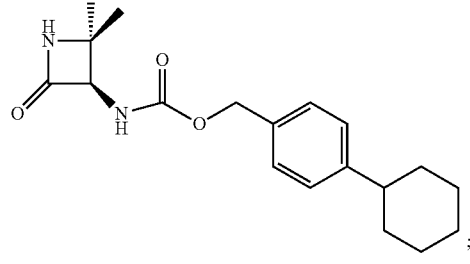
60
-continued
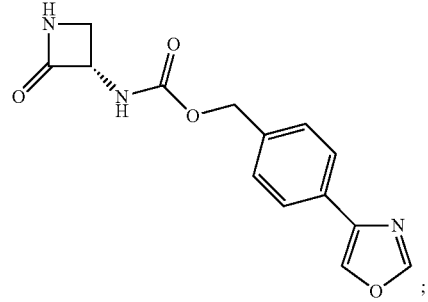
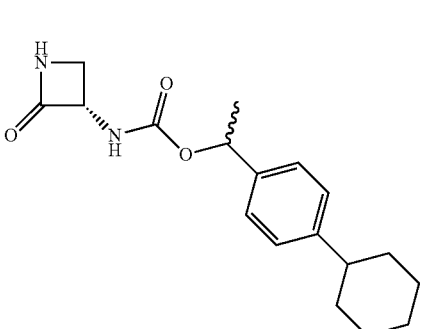
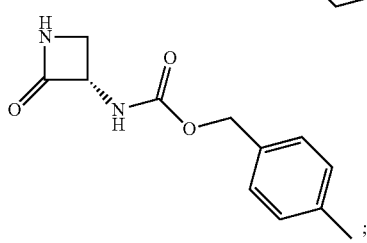
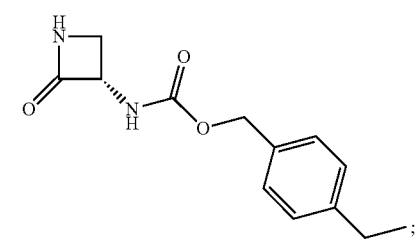
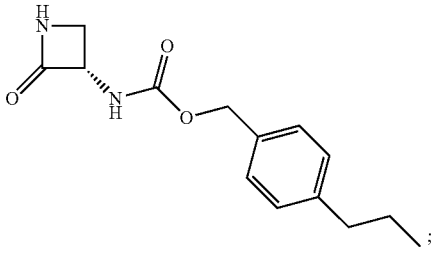
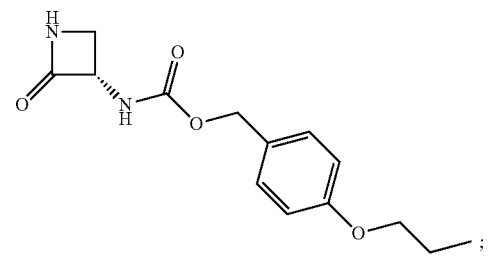

-continued

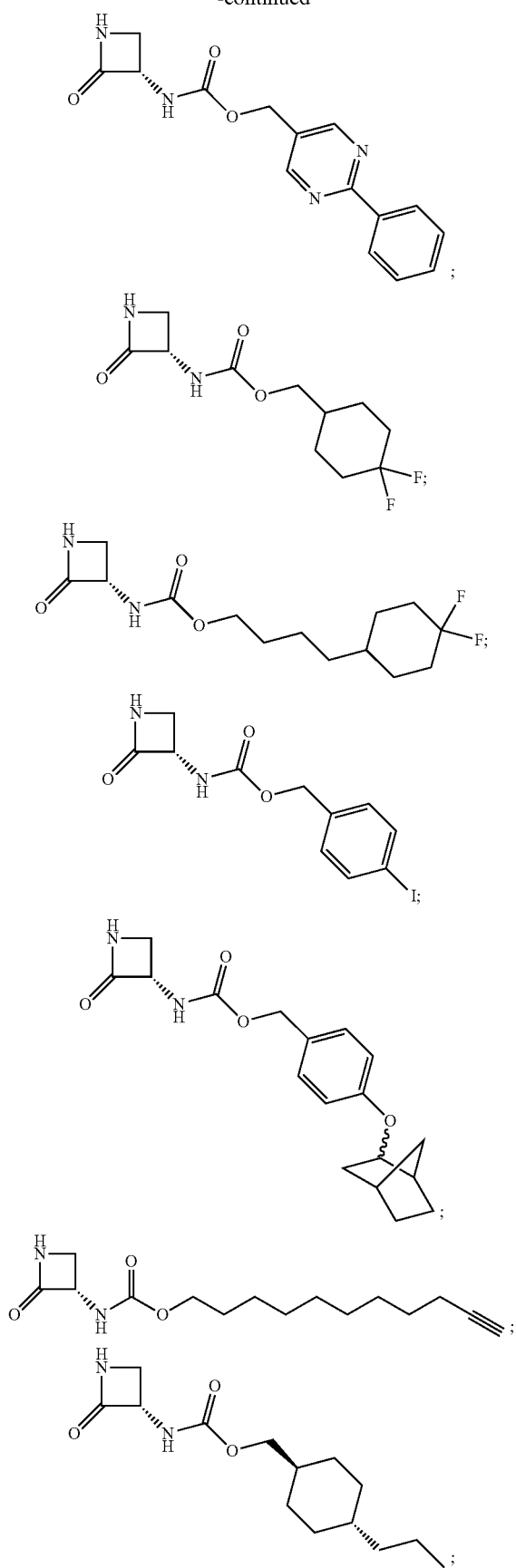

-continued

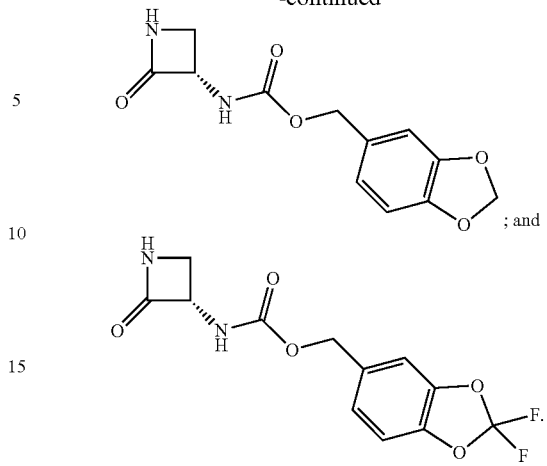

XI. Patient Populations

The compounds and compositions described herein are useful for treating diseases, conditions, and disorders. The present inventions includes methods for treating these disease, conditions, and disorders.

In some embodiments, the methods include administering the compounds and compositions of the present invention to men. In other embodiments, the methods include administering the compounds and compositions of the present invention to women. In certain embodiments, the methods include administering the compounds and compositions of the present invention to women of child-bearing age. In some other embodiments, the methods include administering the compounds and compositions to women who pregnant. In certain other embodiments, the methods include administering the compounds and compositions of the present invention to children.

In certain embodiments, the methods include administering the compounds and compositions to children under the age of 18 years old. In further embodiments, the methods include administering the compounds and compositions to children under the age of 16 years old. In certain embodiments, the methods include administering the compounds and compositions to children under the age of 14 years old. In further embodiments, the methods include administering the compounds and compositions to children under the age of 12 years old. In further other embodiments, the methods include administering the compounds and compositions to children under the age of 10 years old.

In some embodiments, the methods include administering the compounds and compositions to pre-pubescent children.

In other embodiments, the methods described herein are useful for treating a patient in need of treatment with a compound or composition set forth herein. In other embodiments, the methods include treating a patient in need thereof. In some embodiments, the patient in need thereof suffers from multiple conditions or disease. In other embodiment, the patient in need thereof includes a patient having pain. In some embodiments, the patient in need thereof includes a patient having an inflammatory disease.

In some embodiments, the compounds and compositions set forth herein are administered daily. In other embodiments, the compounds and compositions set forth herein are administered twice a day. In other embodiments, the compounds and compositions set forth herein are administered three times a day. In other embodiments, the compounds and compositions set forth herein are administered four times a day. In other embodiments, the compounds and compositions set forth herein are administered five times a day.

In some embodiments, the compounds and compositions set forth herein are administered weekly. In other embodiments, the compounds and compositions set forth herein are administered monthly. In other embodiments, the compounds and compositions set forth herein are administered twice a week. In other embodiments, the compounds and compositions set forth herein are administered three times a week. In other embodiments, the compounds and compositions set forth herein are administered four times a week. In other embodiments, the compounds and compositions set forth herein are administered five times a week. In other embodiments, the compounds and compositions set forth herein are administered six times a week. In other embodiments, the compounds and compositions set forth herein are administered seven times a week. In other embodiments, the compounds and compositions set forth herein are administered eight times a week. In other embodiments, the compounds and compositions set forth herein are administered nine times a week. In other embodiments, the compounds and compositions set forth herein are administered ten times a week. In other embodiments, the compounds and compositions set forth herein are administered eleven times a week. In other embodiments, the compounds and compositions set forth herein are administered twelve times a week. In other embodiments, the compounds and compositions set forth herein are administered thirteen times a week. In other embodiments, the compounds and compositions set forth herein are administered fourteen times a week.

XII. Additional Embodiments

1. A compound having the structure of Formula I:

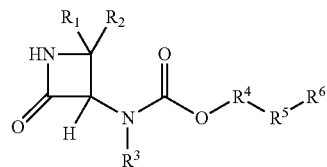

(I)

wherein: $R^1$ and $R^2$ are each independently selected from the group consisting of hydrogen, alkyl, aryl, cycloalkyl (e.g., 3 to 7 membered cycloalkyl), arylalkyl, and cycloalkylalkyl (e.g., 3 to 7 membered cycloalkyl); or $R^1$ and $R^2$ form a cycloalkyl (e.g., 3 to 7 membered cycloalkyl) substituent together with the carbon to which they are attached; $R^3$ is selected from the group consisting of hydrogen and alkyl; $R^4$ is selected from the group consisting of alkylene, alkenylene, alkynylene, arylene, arylalkylene, cycloalkylene (e.g., 3 to 7 membered cycloalkylene), heteroarylene, heterocycloalkylene, heteroarylalkylene, and heterocycloalkylalkylene; $R^5$ is absent or is selected from the group consisting of alkylene, alkenylene, alkyoxy, arylene, aryloxy, cycloalkylene (e.g., 3 to 7 membered cycloalkylene), —O—, —S—, —C(O)—, —C(O)NH—, $NR^aR^b$, heteroarylene, and heterocycloalkylene; $R^6$ is absent or is selected from the group consisting of hydrogen, alkyl, alkyloxy, aryl, aryl-alkyl, aryloxy, arylalkyloxy, arylalkyl, cycloalkyl (e.g., 3 to 7 membered cycloalkyl), cycloalkyloxy (e.g., 3 to 7 membered cycloalkyl), heterocycloalkyl, heterocycloalkyloxy, cycloalkylalkyl (e.g., 3 to 7 membered cycloalkyl), and heteroaryl, and —C(O) $NR^aR^b$; wherein $R^1$, $R^2$, $R^3$, $R^4$, $R^5$, and $R^6$ are each independently optionally substituted with 1-4 substituents selected from the group consisting of hydrogen, lower alkyl, lower alkoxy, aryl, $NR^aR^b$, cyano, halogen, hydroxyl, trifluoromethyl, difluoromethyl, fluoromethyl; $R^a$ and $R^b$ together with the nitrogen atom to which they bound are optionally a heterocyclyl residue; wherein $R^a$ and $R^b$ are each independently selected from the group consisting of hydrogen and alkyl; or a pharmaceutically acceptable salt, ester, or prodrug thereof.

2. A compound having the structure of Formula I:

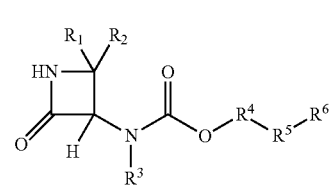

(I)

wherein: $R^1$ and $R^2$ are each independently selected from the group consisting of hydrogen, alkyl, aryl, cycloalkyl (e.g., 3 to 7 membered cycloalkyl), arylalkyl, and cycloalkylalkyl (e.g., 3 to 7 membered cycloalkyl); or $R^1$ and $R^2$ form a cycloalkyl (e.g., 3 to 7 membered cycloalkyl) substituent together with the carbon to which they are attached; $R^3$ is selected from the group consisting of hydrogen and alkyl; $R^4$ is selected from the group consisting of alkylene, alkenylene, alkynylene, arylene, arylalkylene, cycloalkylene (e.g., 3 to 7 membered cycloalkylene), heteroarylene, heterocycloalkylene, heteroarylalkylene, and heterocycloalkylalkylene; $R^5$ is absent or is selected from the group consisting of alkylene, alkenylene, alkyoxy, arylene, aryloxy, cycloalkylene (e.g., 3 to 7 membered cycloalkylene), —O—, —S—, —C(O)—, —C(O)NH—, $NR^aR^b$, heteroarylene, and heterocycloalkylene; $R^6$ is absent or is selected from the group consisting of hydrogen, alkyl, alkyloxy, aryl, aryl-alkyl, aryloxy, arylalkyloxy, arylalkyl, cycloalkyl (e.g., 3 to 7 membered cycloalkyl), cycloalkyloxy (e.g., 3 to 7 membered cycloalkyl), heterocycloalkyl, heterocycloalkyloxy, cycloalkylalkyl (e.g., 3 to 7 membered cycloalkyl), and heteroaryl, and —C(O) $NR^aR^b$; wherein $R^1$, $R^2$, $R^3$, $R^4$, $R^5$, and $R^6$ are each independently optionally substituted with 1-4 substituents selected from the group consisting of hydrogen, lower alkyl, lower alkoxy, aryl, $NR^aR^b$, cyano, halogen, hydroxyl, trifluoromethyl, difluoromethyl, fluoromethyl, and when $R^a$ and $R^b$ are taken together with the nitrogen atom to which they are bound, the group $NR^aR^b$ represents a heterocyclyl residue; wherein $R^a$ and $R^b$ are each independently selected from the group consisting of hydrogen and alkyl; and or a pharmaceutically acceptable salt, ester, or prodrug thereof.

3. A compound of one of embodiments 1 to 2, having the structure selected from the group of Formulae II-XVII:

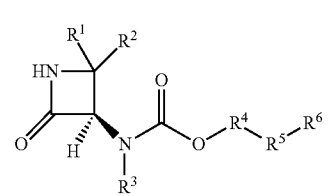

(II)

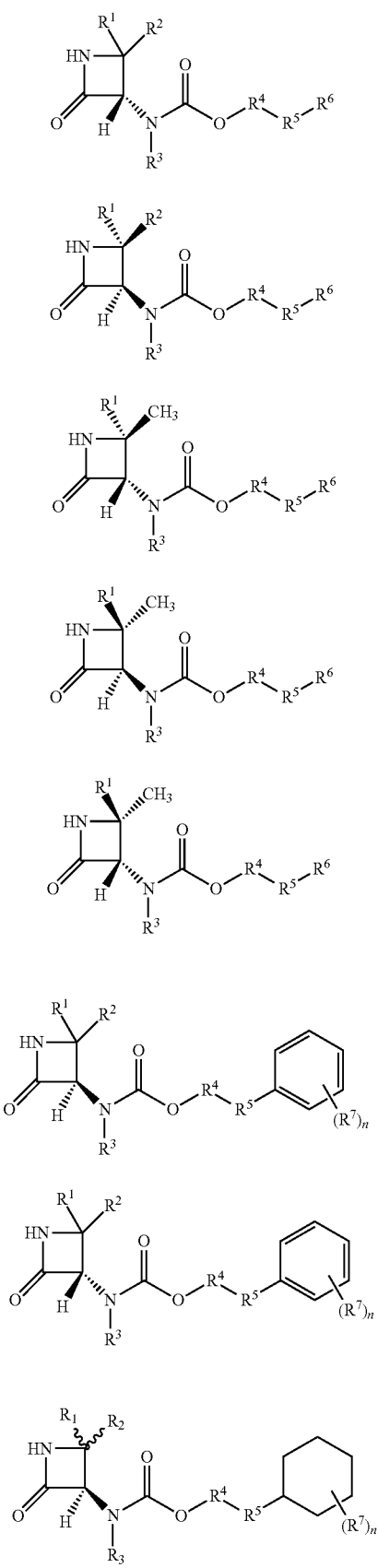
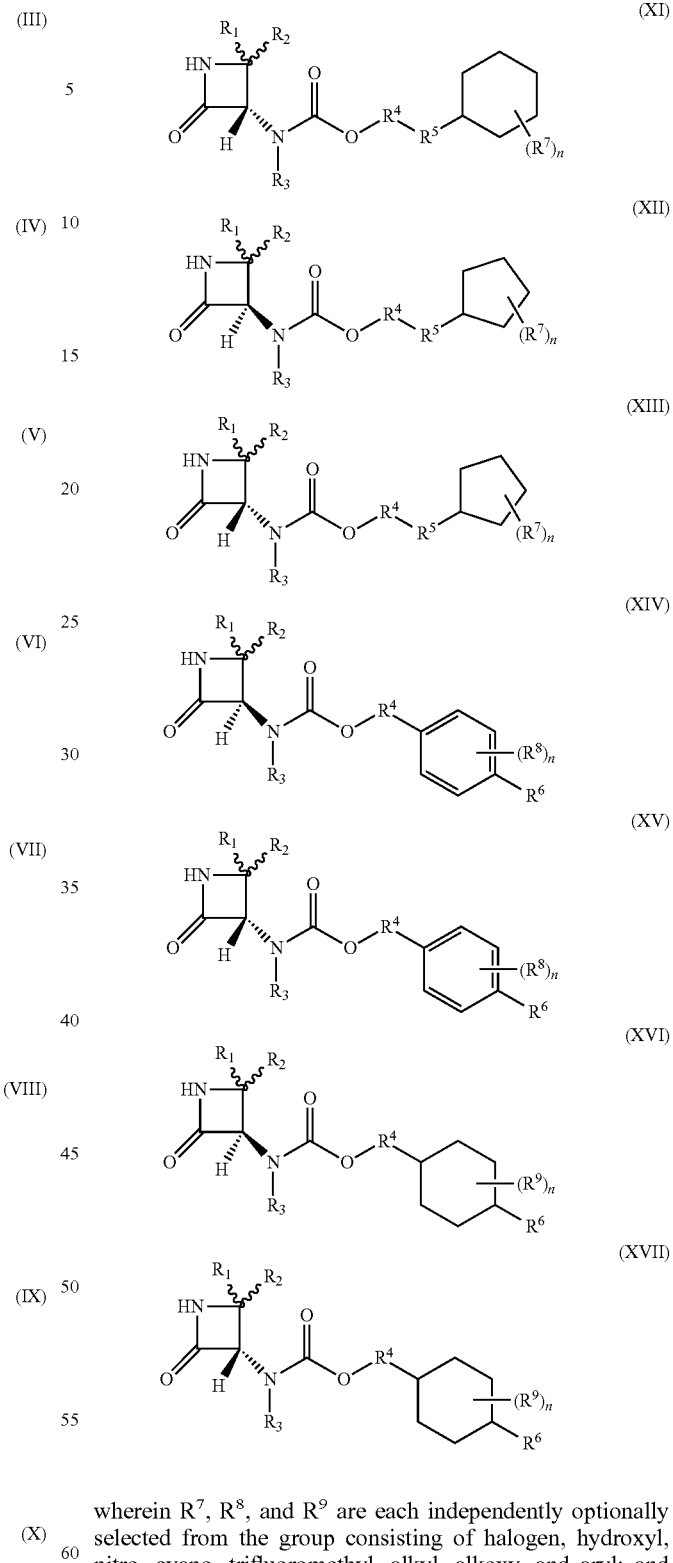

wherein $R^7$, $R^8$, and $R^9$ are each independently optionally selected from the group consisting of halogen, hydroxyl, nitro, cyano, trifluoromethyl, alkyl, alkoxy, and aryl; and subscript n is, in each instance, independently an integer from 1-4.

4. A compound of one of embodiments 1 to 3, wherein $R^1$ and $R^2$ are both hydrogen.

5. A compound of one of embodiments 1 to 3, wherein $R^1$ is hydrogen and $R^2$ is methyl 6. A compound of one of embodiments 1 to 5, wherein $R^3$ is hydrogen 7. A compound of one of embodiments 1 to 5, wherein $R^3$ is methyl.

8. A compound of one of embodiments 1 to 7, wherein $R^4$ is alkyl.

9. A compound of one of embodiments 1 to 8, wherein $R^4$ is selected from the group consisting of methyl, ethyl, i-propyl, n-propyl, i-butyl, t-butyl, n-butyl, n-pentyl, i-pentyl, pentyl, hexyl, heptyl, octyl, nonyl, decyl, undecyl, and dodecyl.

10. A compound of one of embodiments 1 to 7, wherein $R^4$ is cycloalkyl (e.g., 3 to 7 membered cycloalkyl).

11. A compound of one of embodiments 1 to 7, wherein $R^4$ is cyclohexyl.

12. A compound of one of embodiments 1 to 7, wherein $R^4$ is aryl

13. A compound of one of embodiments 1 to 7, wherein $R^4$ is benzyl.

14. A compound of one of embodiments 1 to 13, wherein $R^5$ is absent.

15. A compound of one of embodiments 1 to 13, wherein $R^5$ and $R^6$ are both absent.

16. A compound of one of embodiments 1 to 13, wherein $R^5$ is alkenyl.

17. A compound of one of embodiments 1 to 13, wherein $R^5$ is selected from the group consisting of trans-3-nonene, cis-3-nonene, trans-1-butene, and cis-1-butene.

18. A compound of one of embodiments 1 to 13, wherein $R^5$ selected from the group consisting of —O— or —C(O)—.

19. A compound of one of embodiments 1 to 13, wherein $R^5$ is aryl.

20. A compound of one of embodiments 1 to 13, wherein $R^5$ is phenyl.

21. A compound of one of embodiments 1 to 14 and 16 to 20, wherein $R^6$ is selected from the group consisting of aryl and aryl-alkylene.

22. A compound of one of embodiments 1 to 14 and 16 to 20, wherein $R^6$ is selected from the group consisting of phenyl, phenylethylene, benzyl, and biphenyl, 23. A compound of one of embodiments 1 to 14 and 16 to 20, wherein $R^6$ is phenyl.

24. A compound of one of embodiments 1 to 14 and 16 to 20, wherein $R^6$ is cycloalkyl (e.g., 3 to 7 membered cycloalkyl).

25. A compound of one of embodiments 1 to 14 and 16 to 20, wherein $R^6$ is selected from the group consisting of cyclohexyl, cyclopentyl, norbornanyl, adamantyl, and 1,2,3,4-tetrahydro-naphthyl.

26. A compound of one of embodiments 1 to 14 and 16 to 20, wherein $R^6$ is alkyloxy.

27. A compound of one of embodiments 1 to 14 and 16 to 20, wherein $R^6$ is selected from the group consisting of methoxy, ethoxy, propoxy, butoxy, cyclopentyloxy, cyclohexyloxy, and norbornanyloxy.

28. A compound of one of embodiments 1 to 14 and 16 to 20, wherein $R^6$ is alkyl.

29. A compound of one of embodiments 1 to 14 and 16 to 20, wherein $R^6$ is selected from the group consisting of methyl, ethyl, i-propyl, n-propyl, i-butyl, t-butyl, n-butyl, n-pentyl, i-pentyl, pentyl, and hexyl.

30. A compound of one of embodiments 1 to 14 and 16 to 20, wherein $R^6$ is heteroaryl.

31. A compound of one of embodiments 1 to 14 and 16 to 20, wherein $R^6$ is selected from the group consisting of pyridyl and benzo[d]oxazole.

32. A compound of one of embodiments 1 to 14 and 16 to 20, wherein $R^6$ is heterocycloalkyl.

33. A compound of one of embodiments 1 to 14 and 16 to 20, wherein $R^6$ is selected from the group consisting of tetrahydro-pyranyl.

34. A compound of one of embodiments 1 to 14 and 16 to 20, wherein $R^6$ is selected from the group consisting of —C(O)NR$^a$R$^b$.

35. A compound of one of embodiments 1 to 34, wherein NR$^a$R$^b$ is independently selected from the group consisting of morpholinyl and piperidinyl.

36. A compound of one of embodiments 1 to 7, wherein $R^4$-$R^5$-$R^6$ is selected from the group consisting of

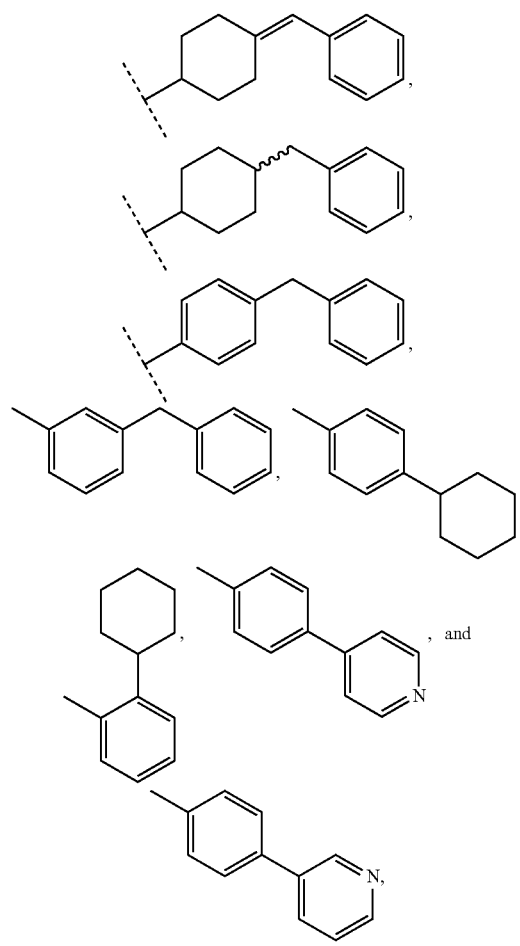

37. A compound of embodiment 1, wherein the compound is selected from the group consisting of

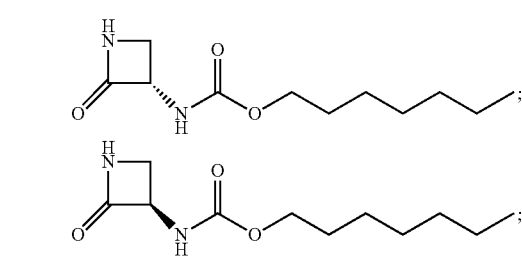

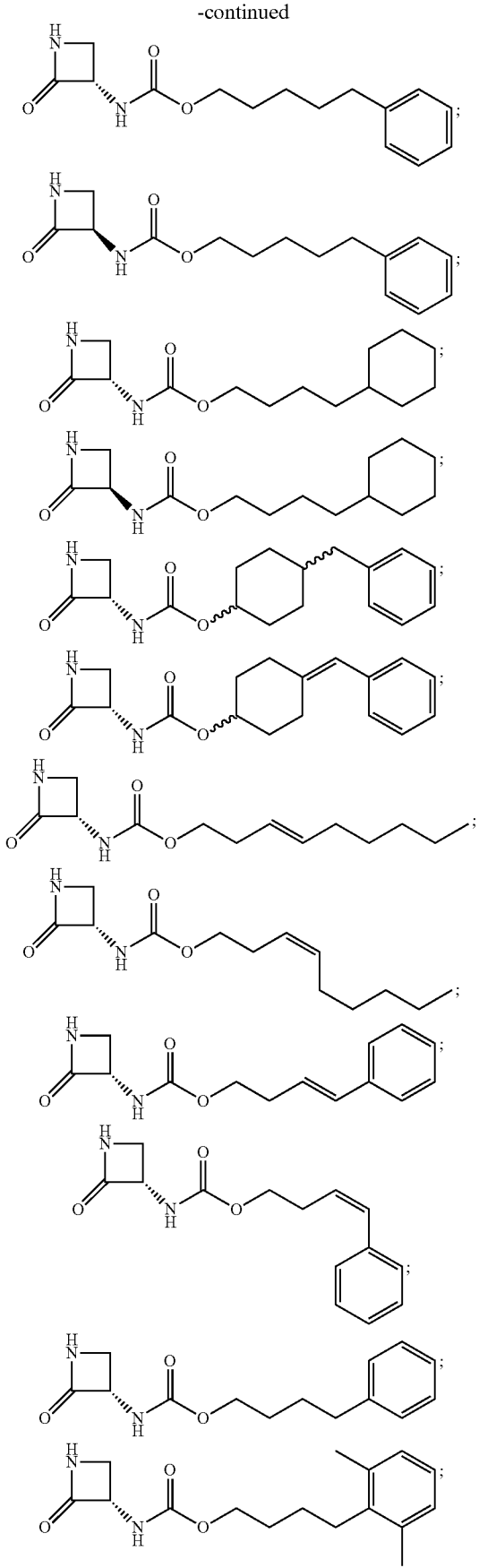
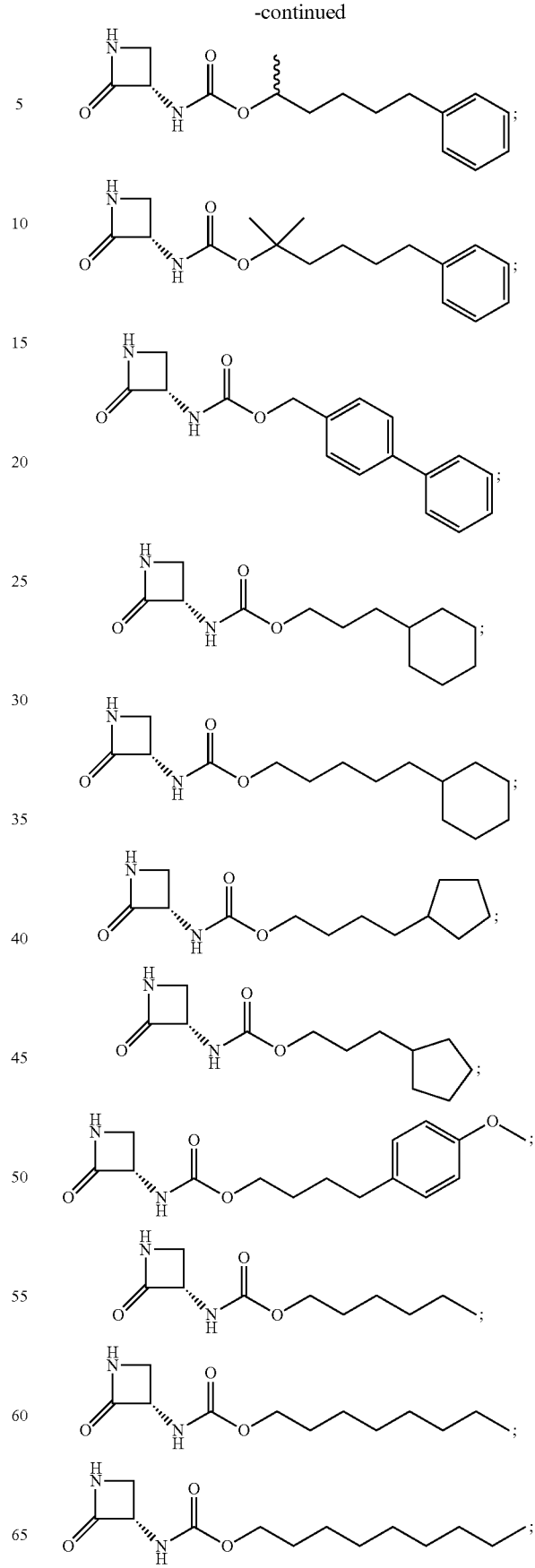

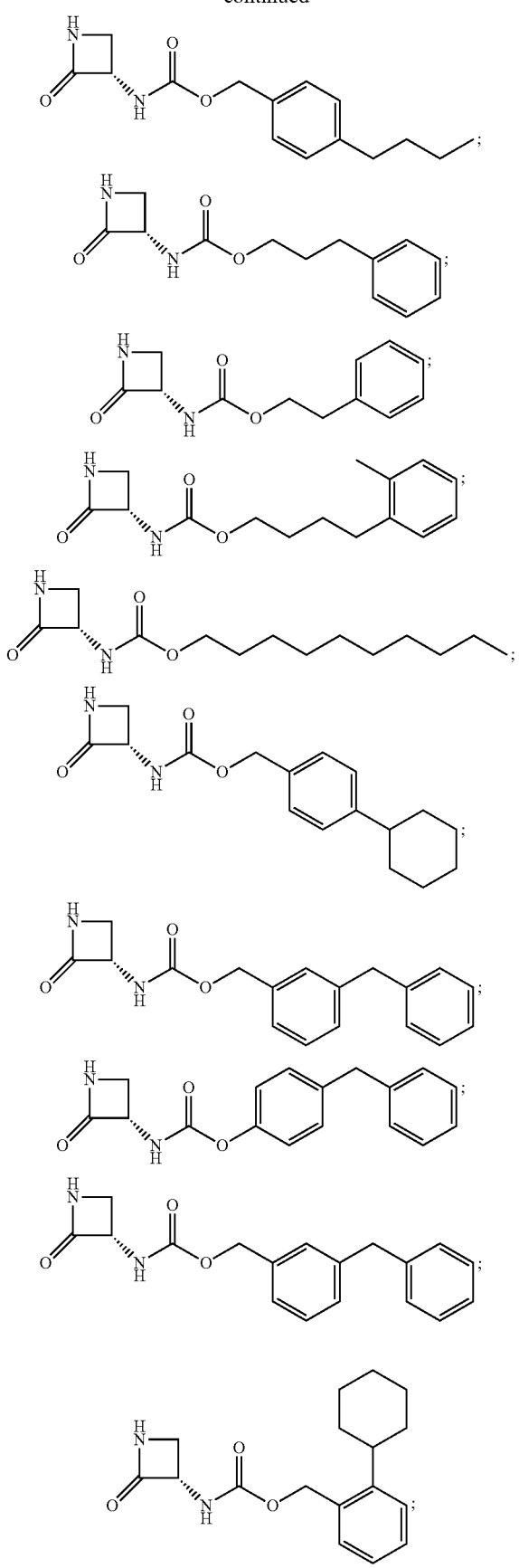
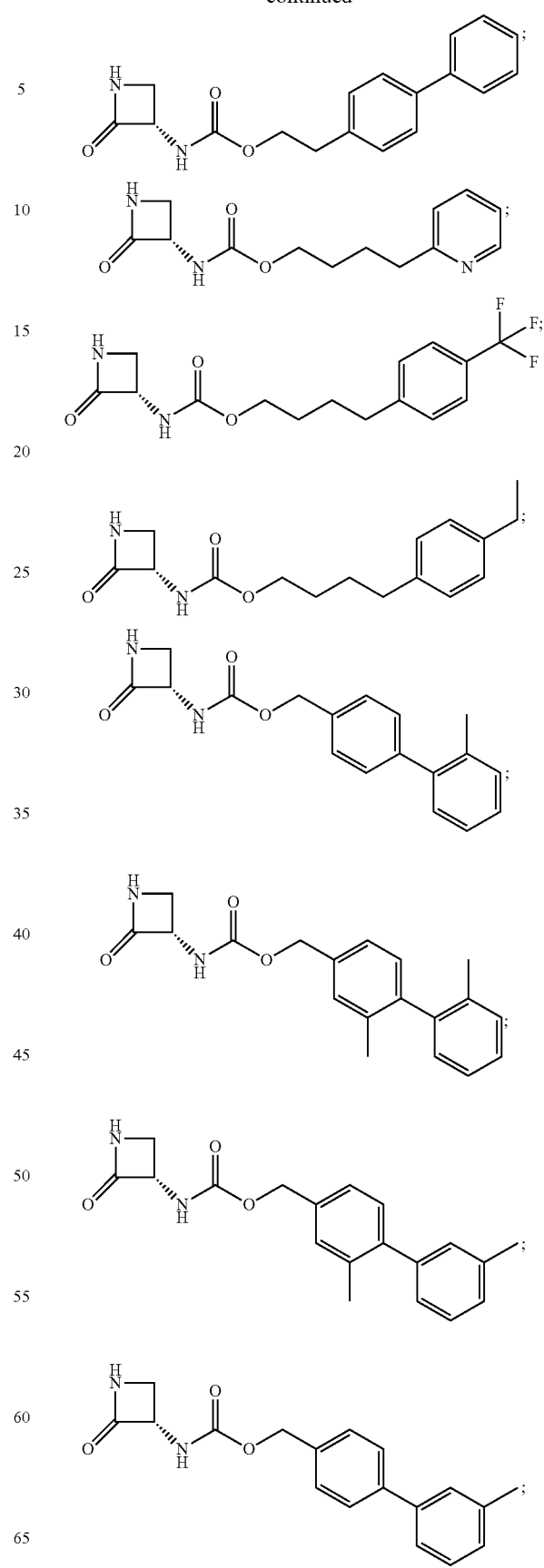

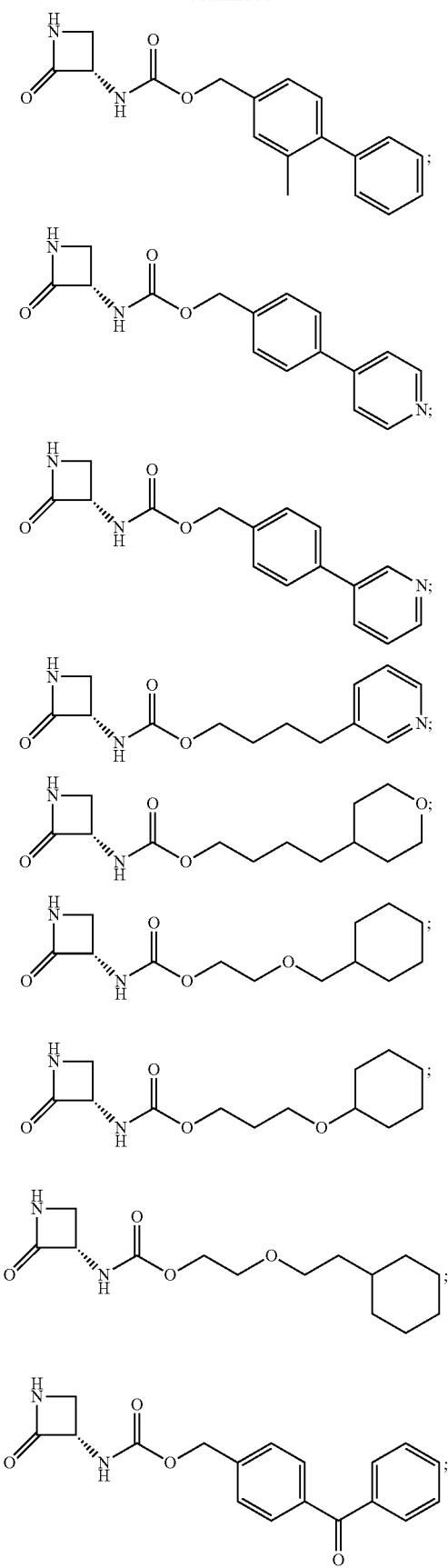
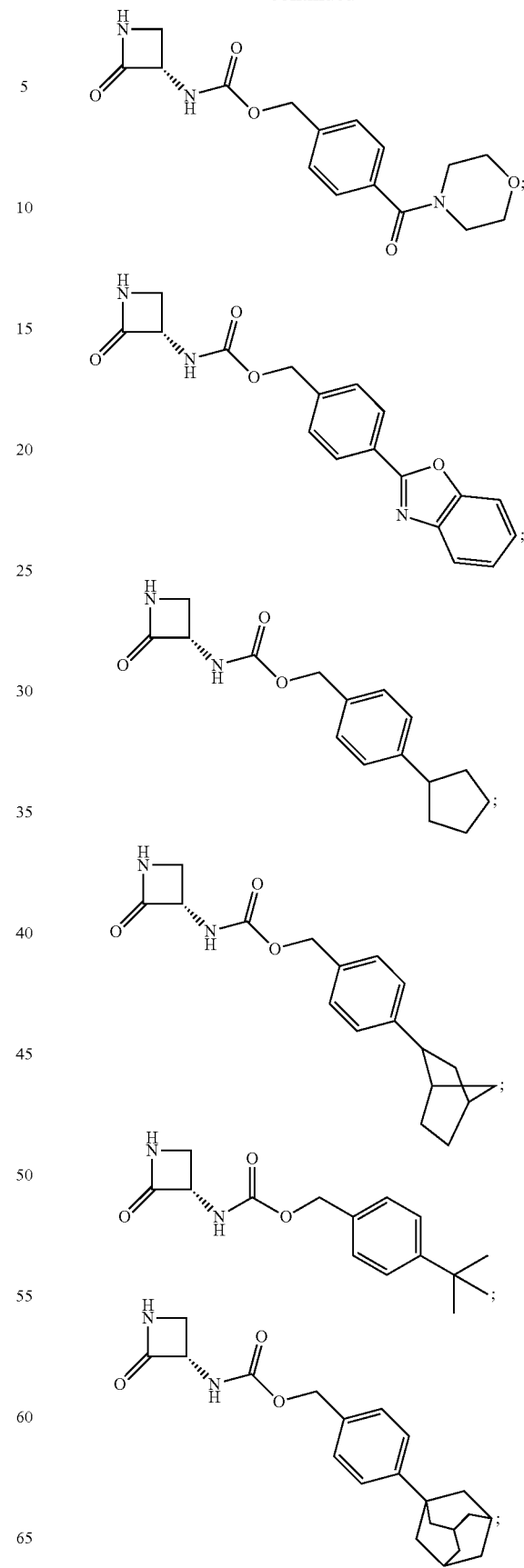

75
-continued
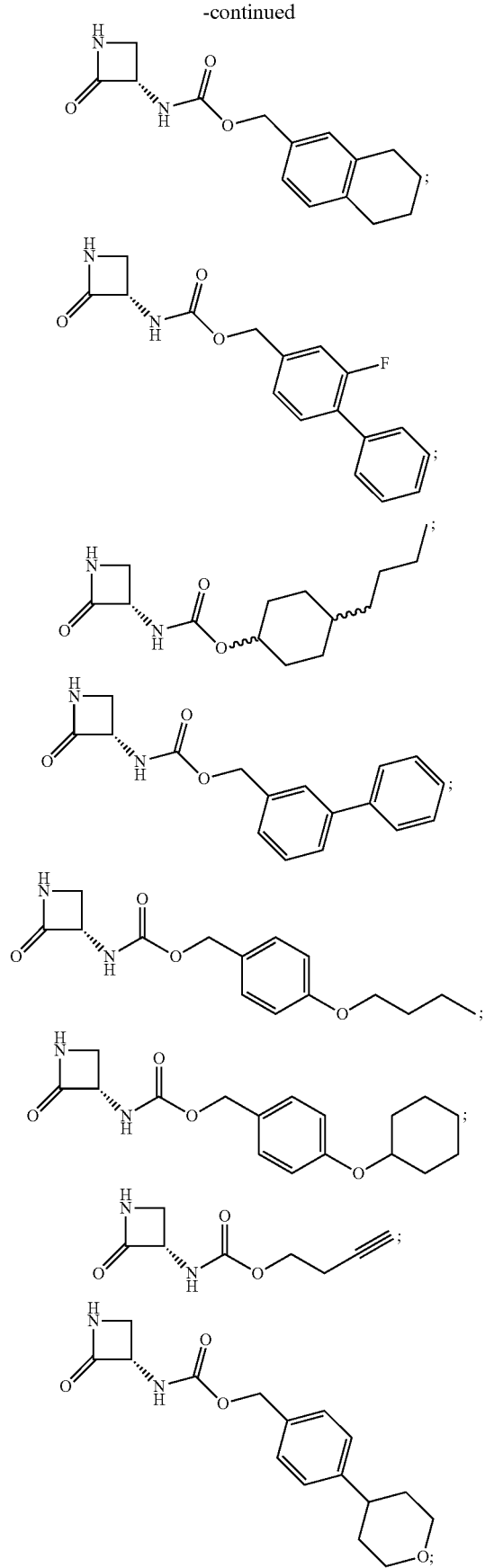
76
-continued
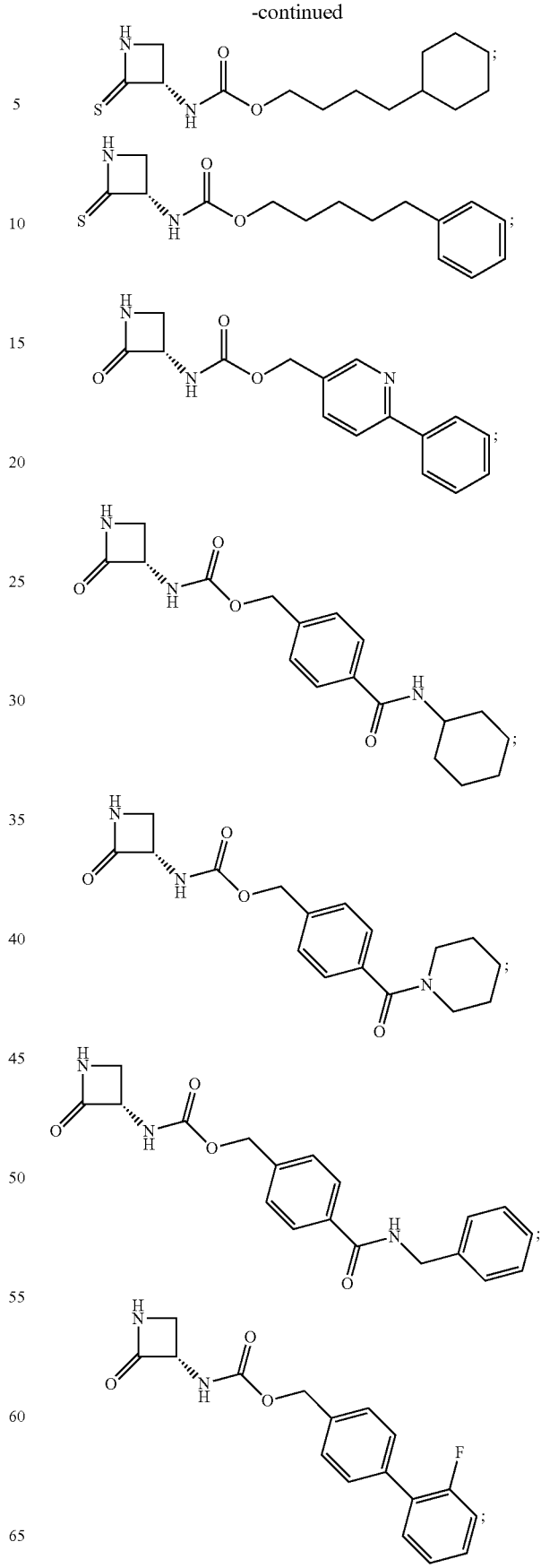

77
-continued
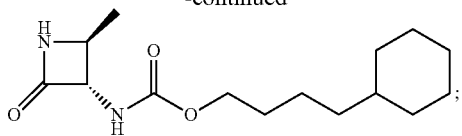
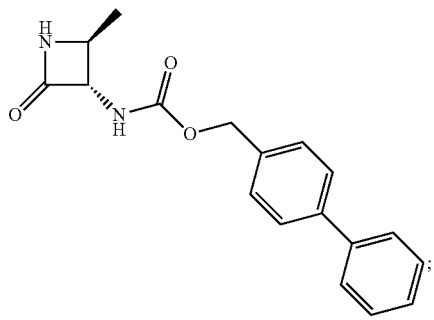
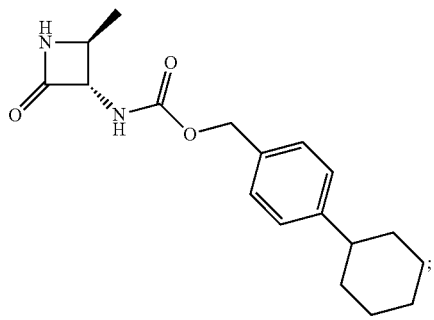
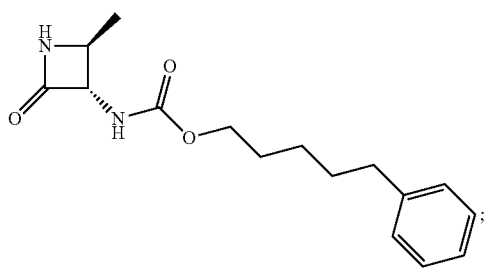
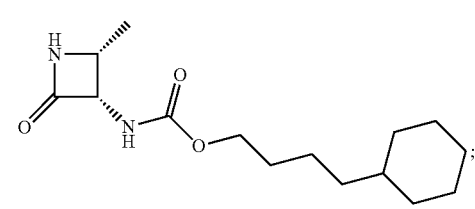
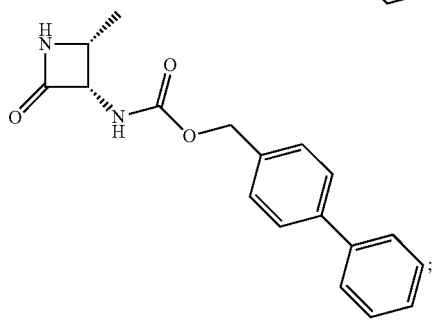
78
-continued
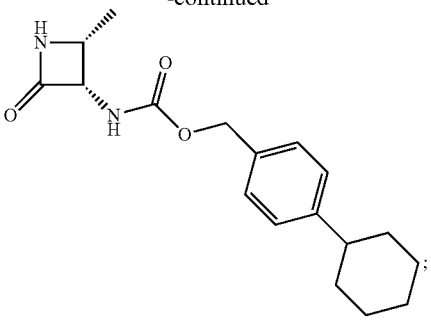
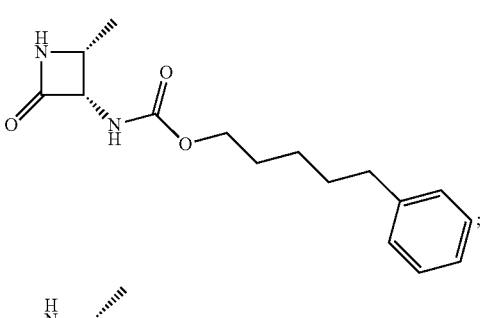
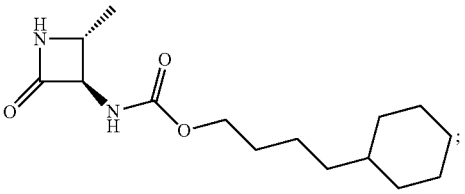
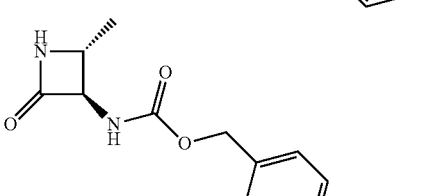
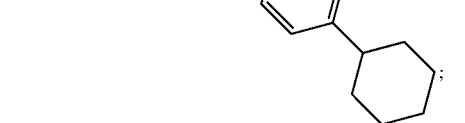
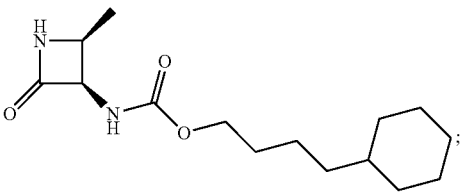

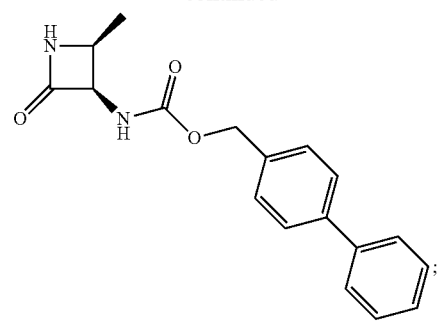
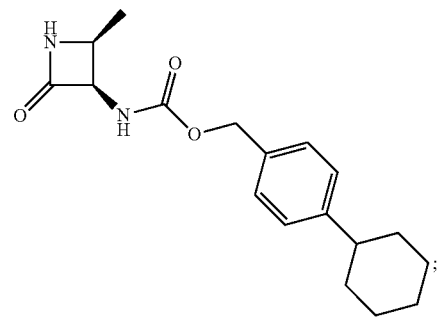
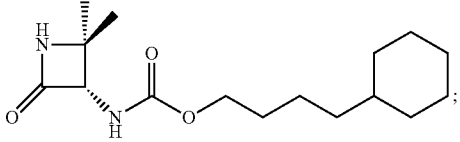
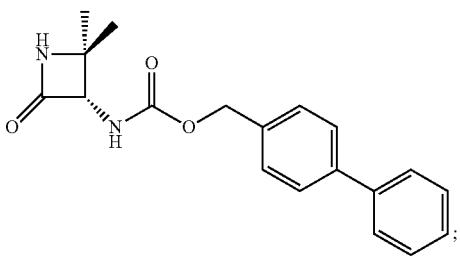
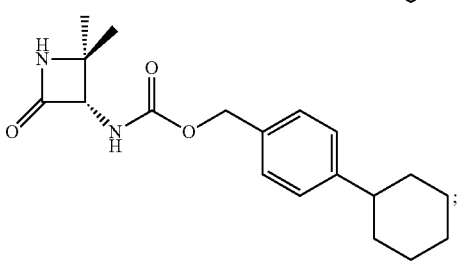
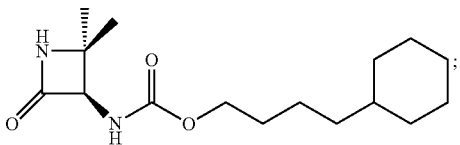
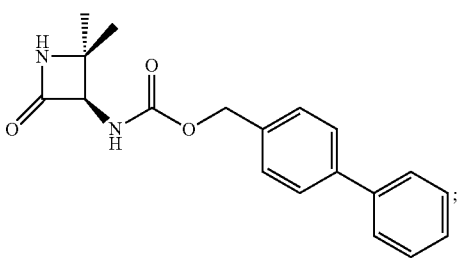
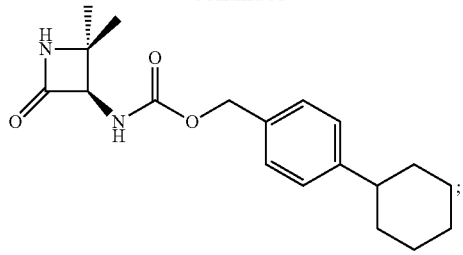
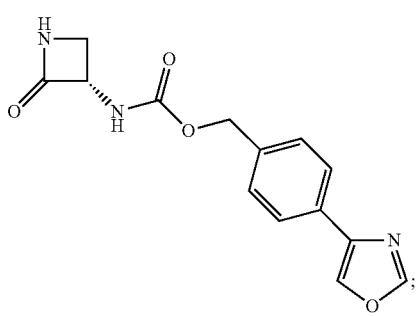
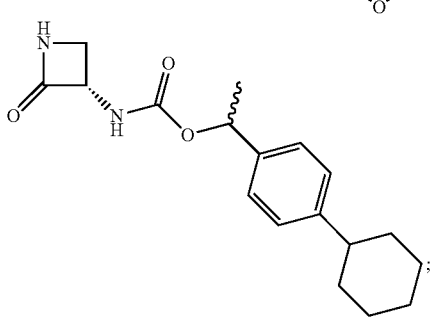
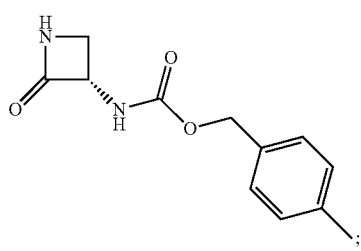
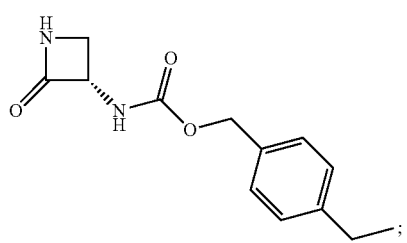
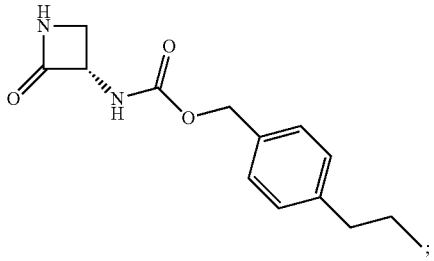

81
-continued

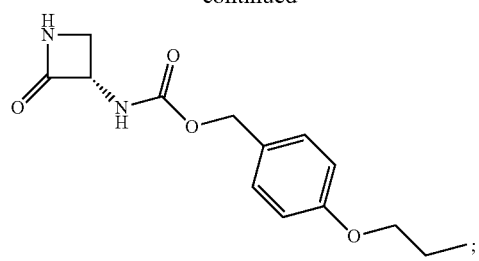

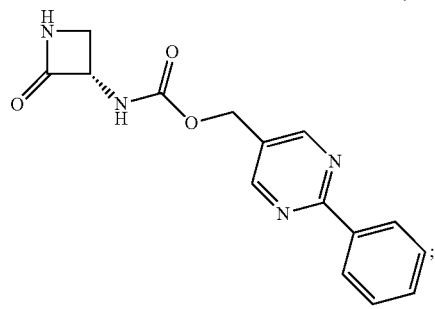

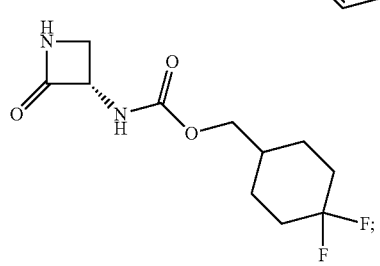

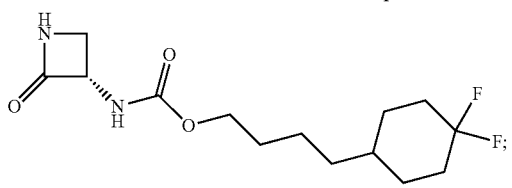

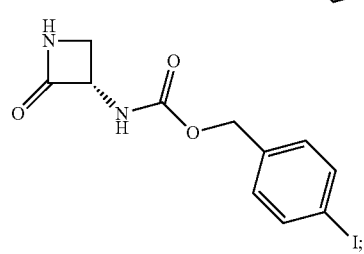

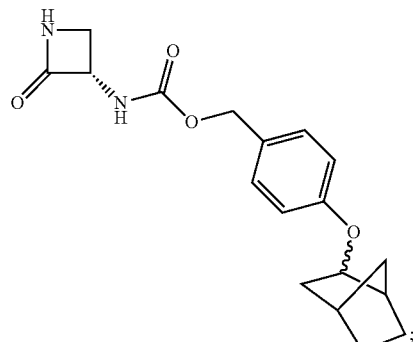

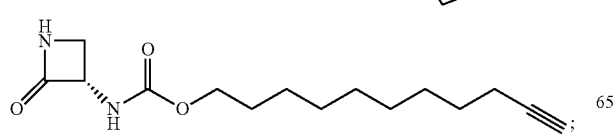

82
-continued

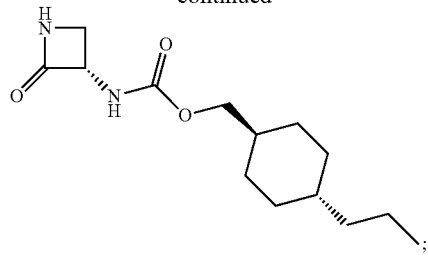

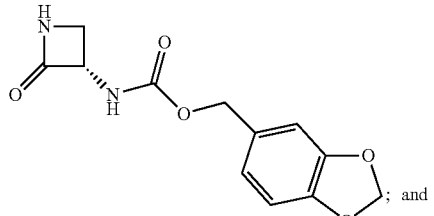

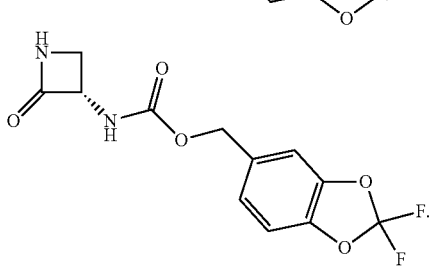

38. A pharmaceutical composition comprising one or more compounds having a structure selected from the group consisting of Formulae I-XVII, or a pharmaceutically acceptable salt thereof, and a pharmaceutically acceptable excipient, carrier or diluent.

39. The pharmaceutical composition of embodiment 38, wherein the compound is selected from the group consisting of

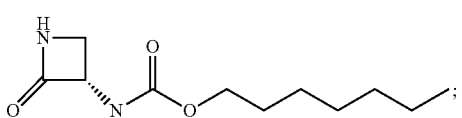

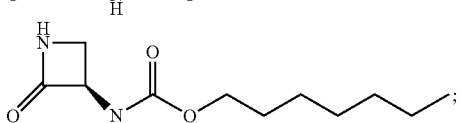

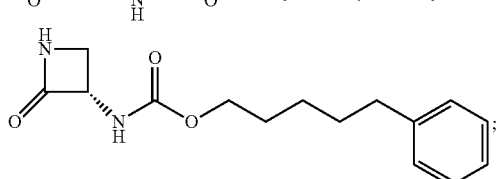

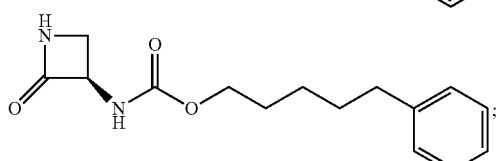

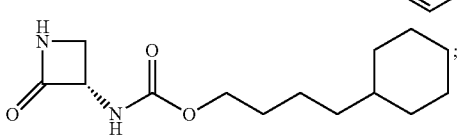

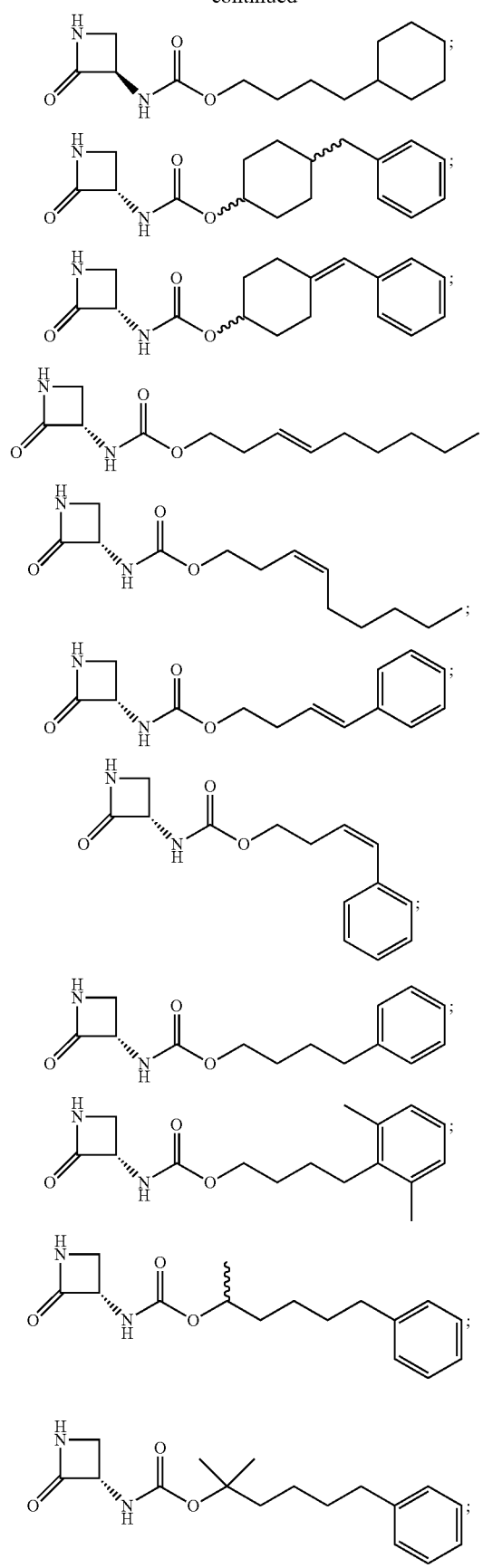
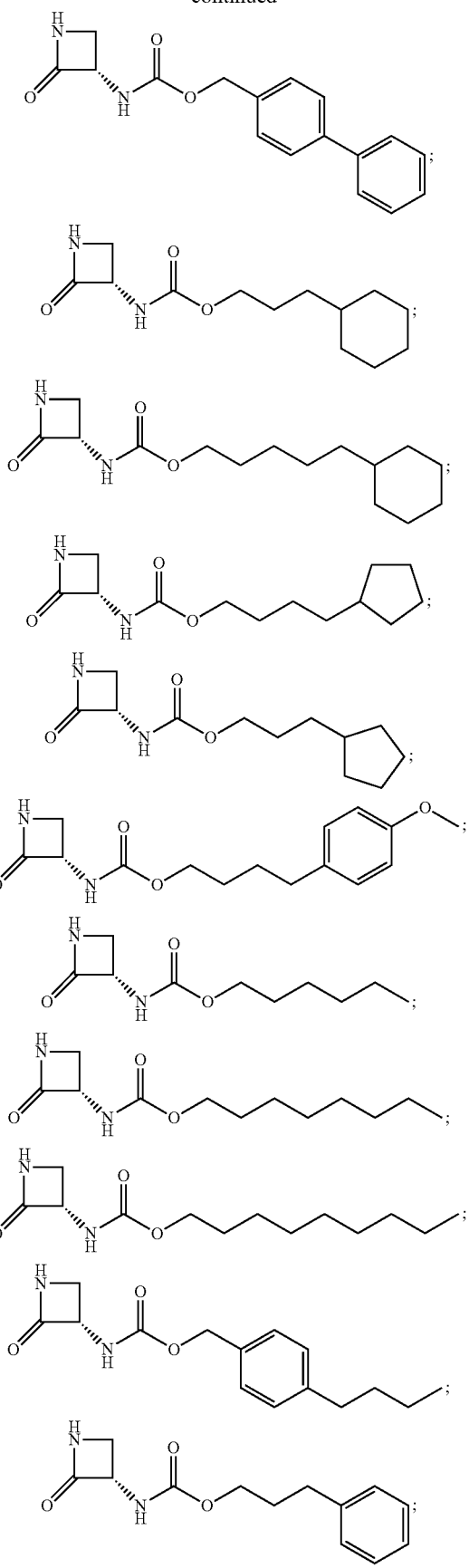

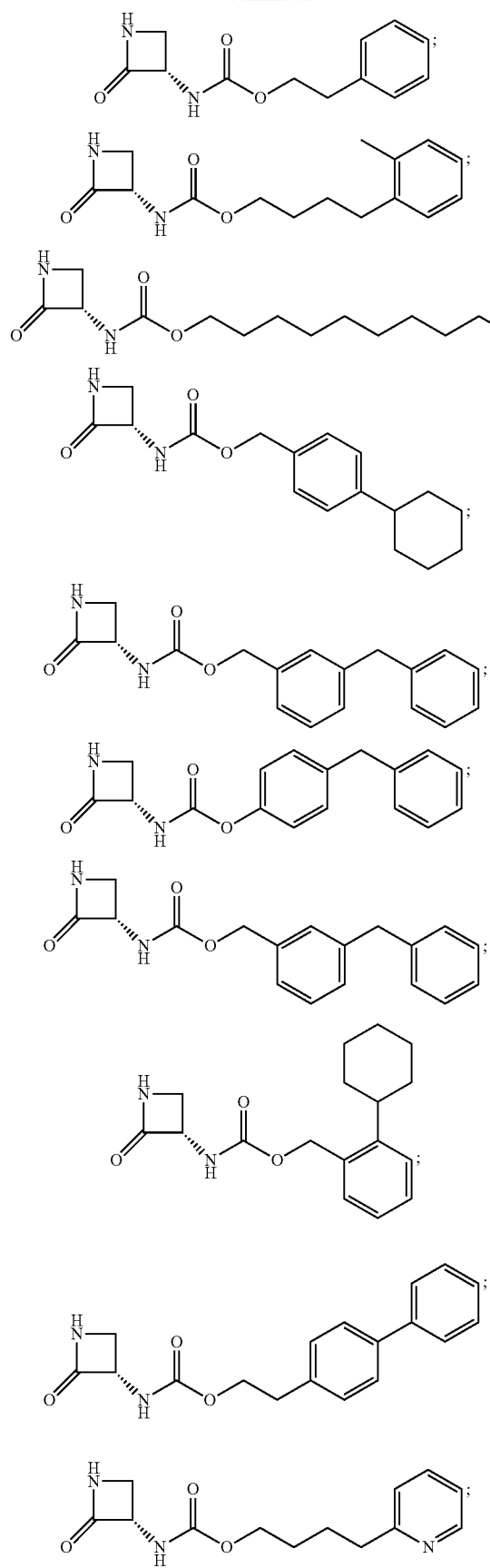
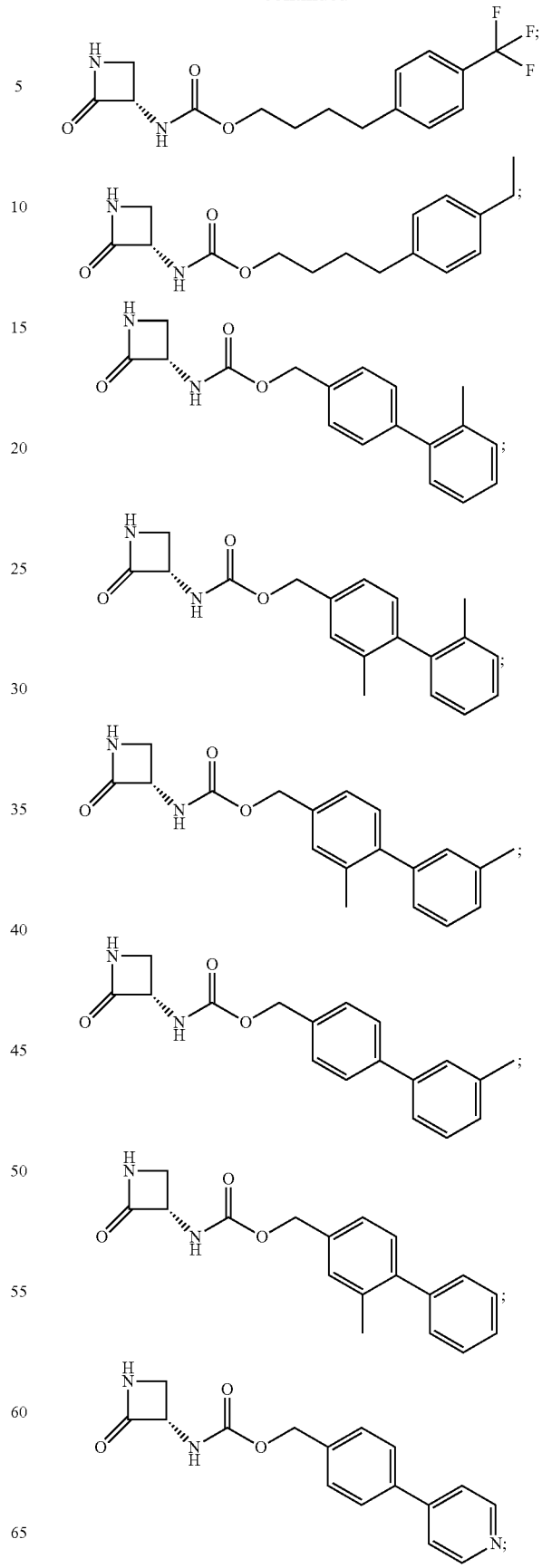

87
-continued
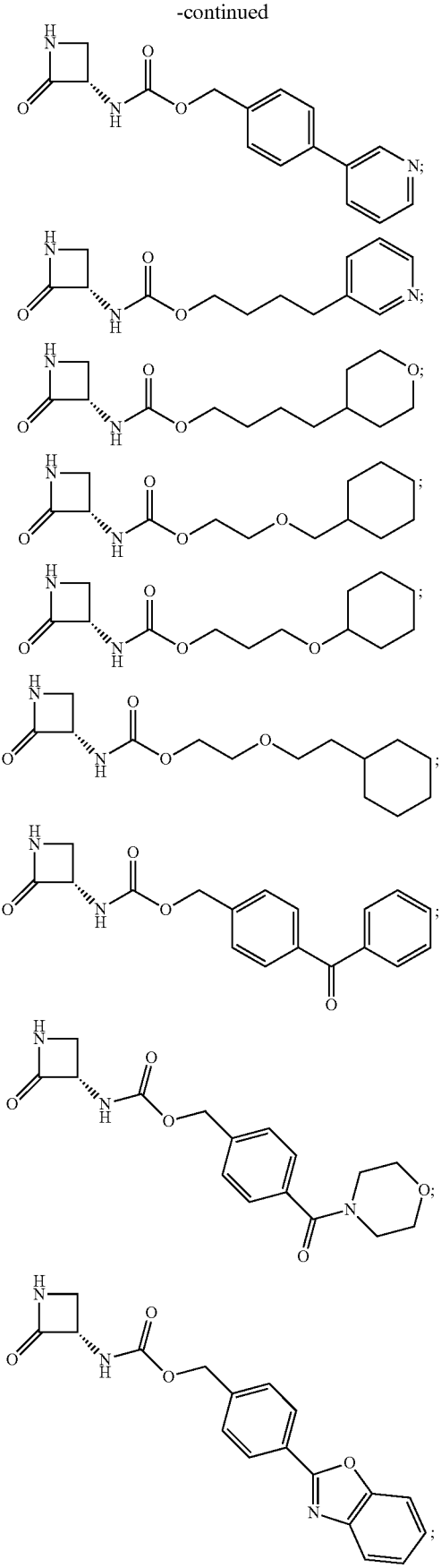
88
-continued
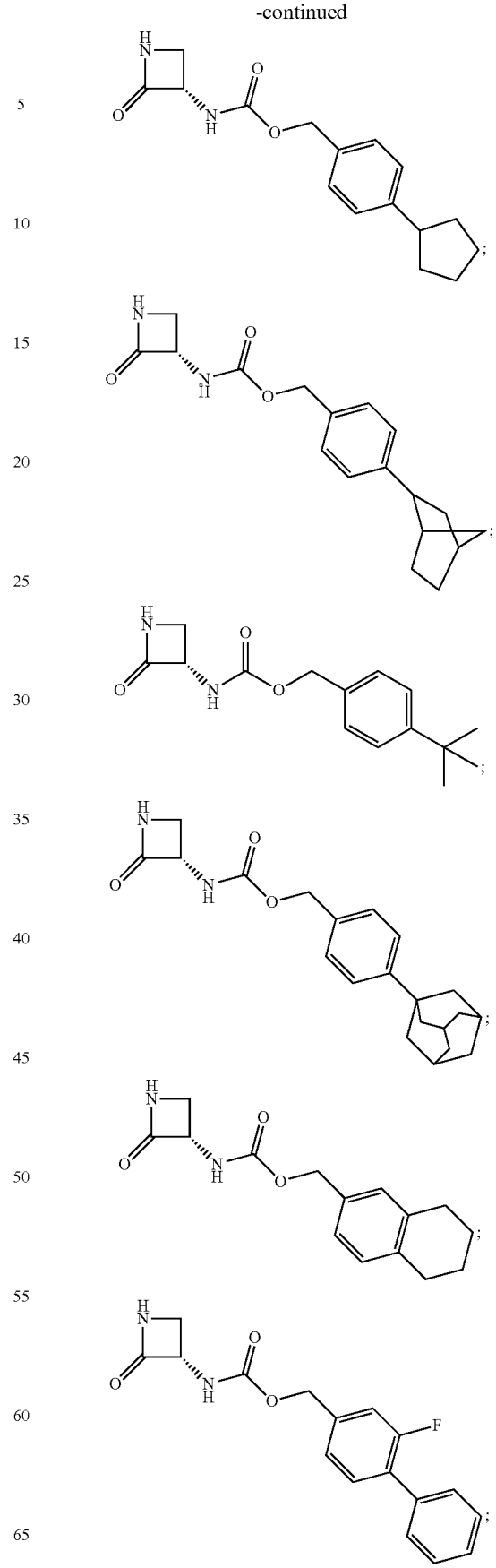

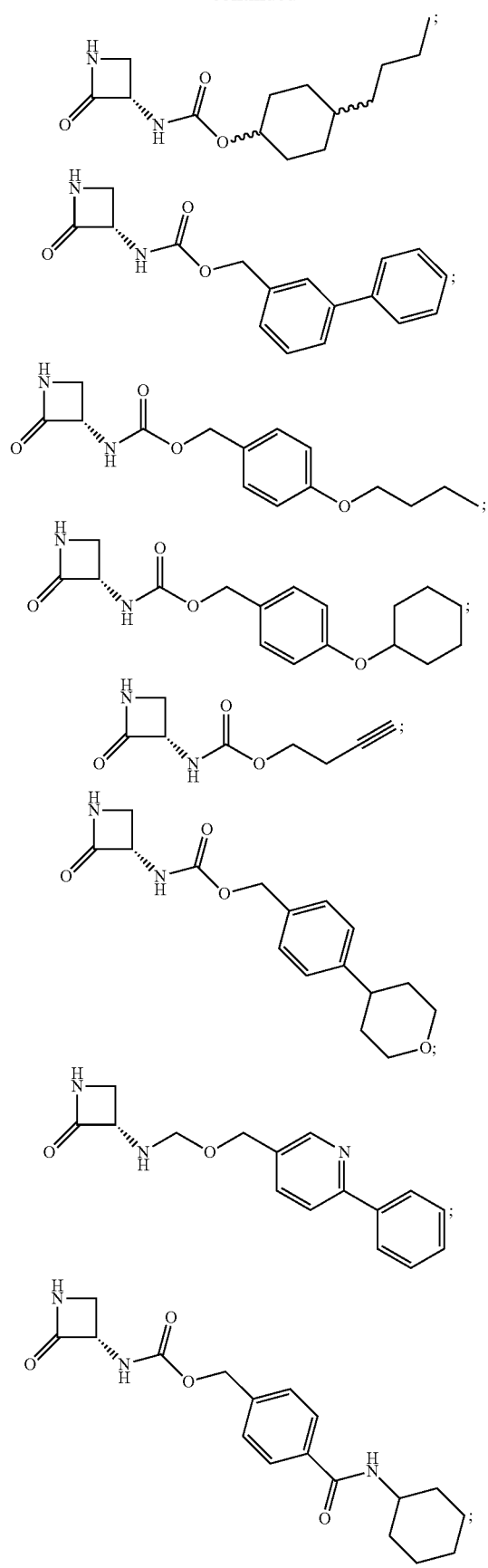
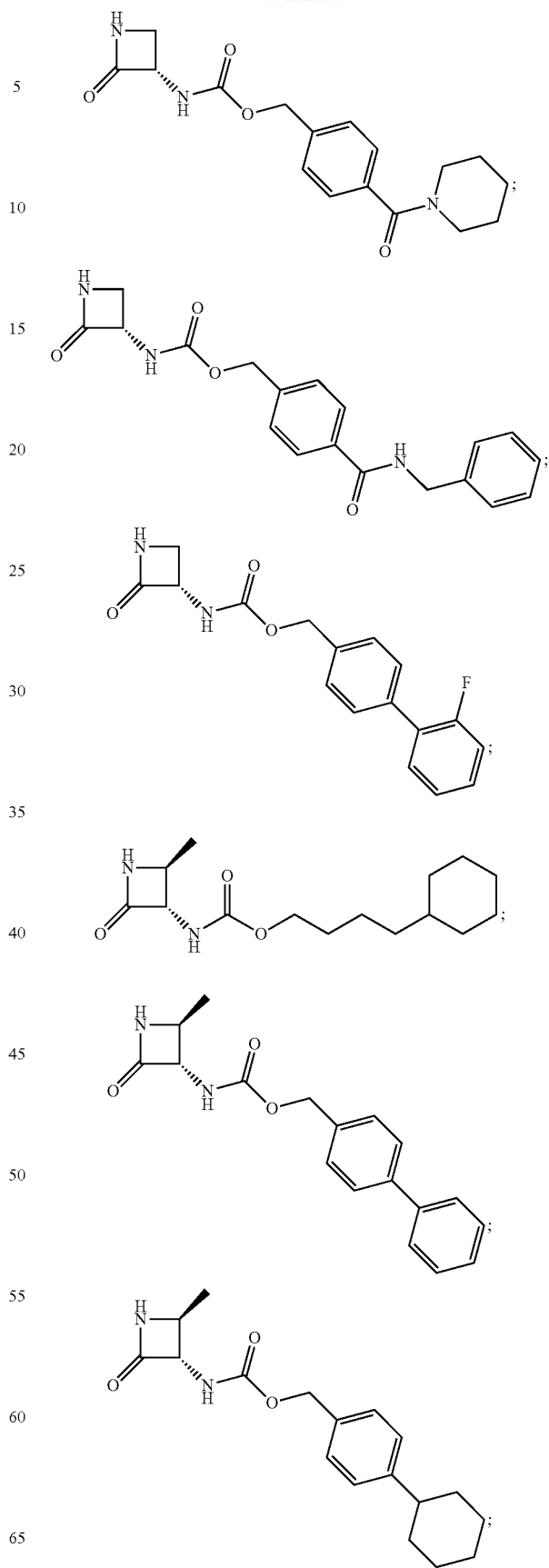

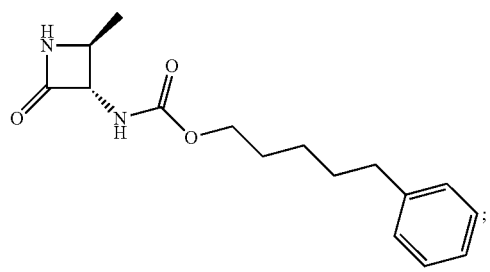
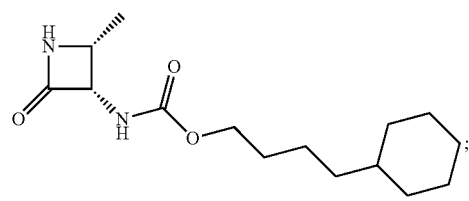
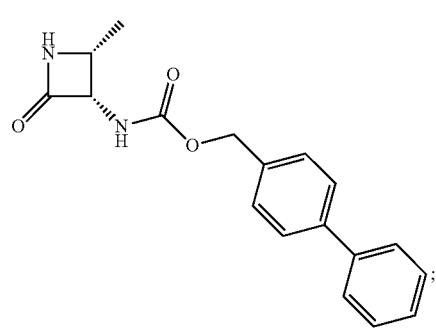
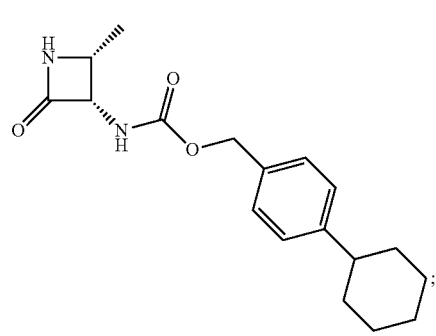
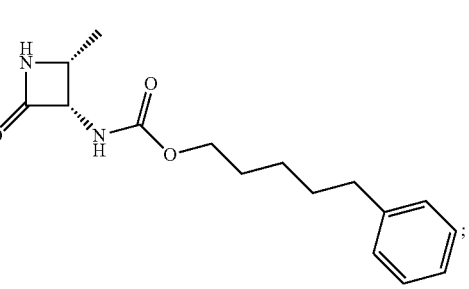
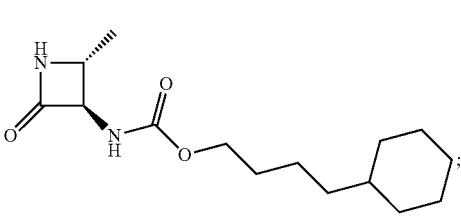
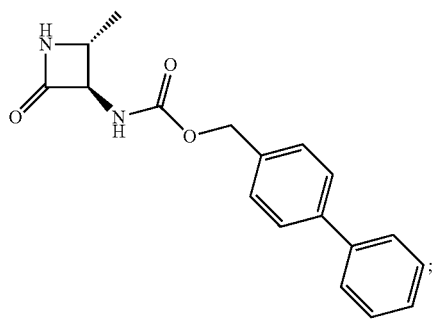
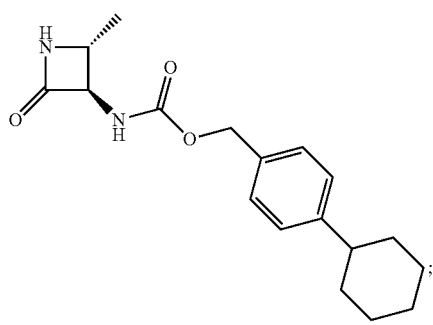
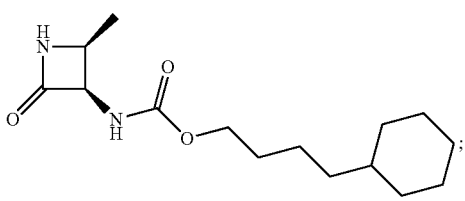
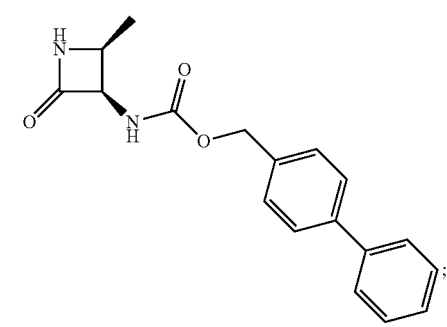
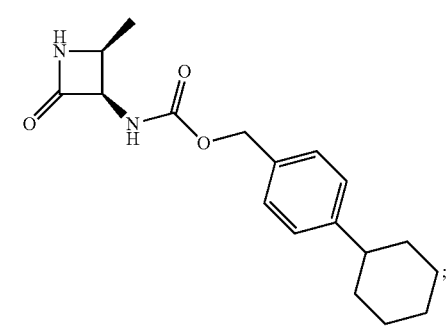
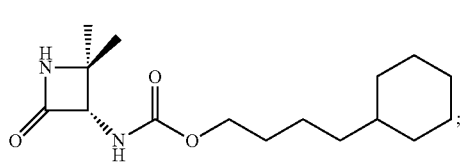

93
-continued
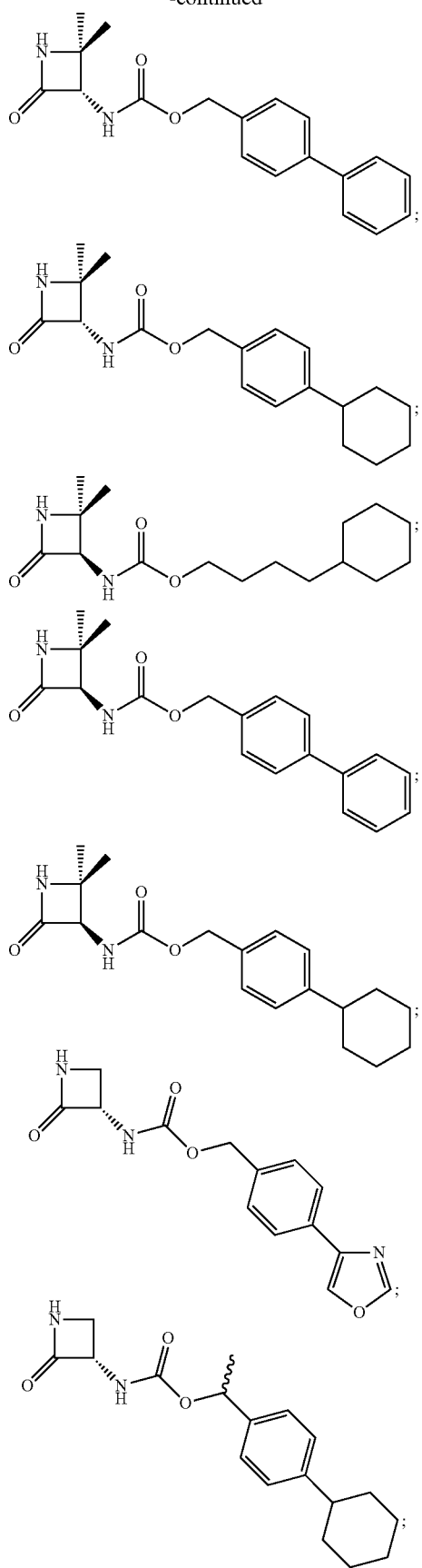
94
-continued
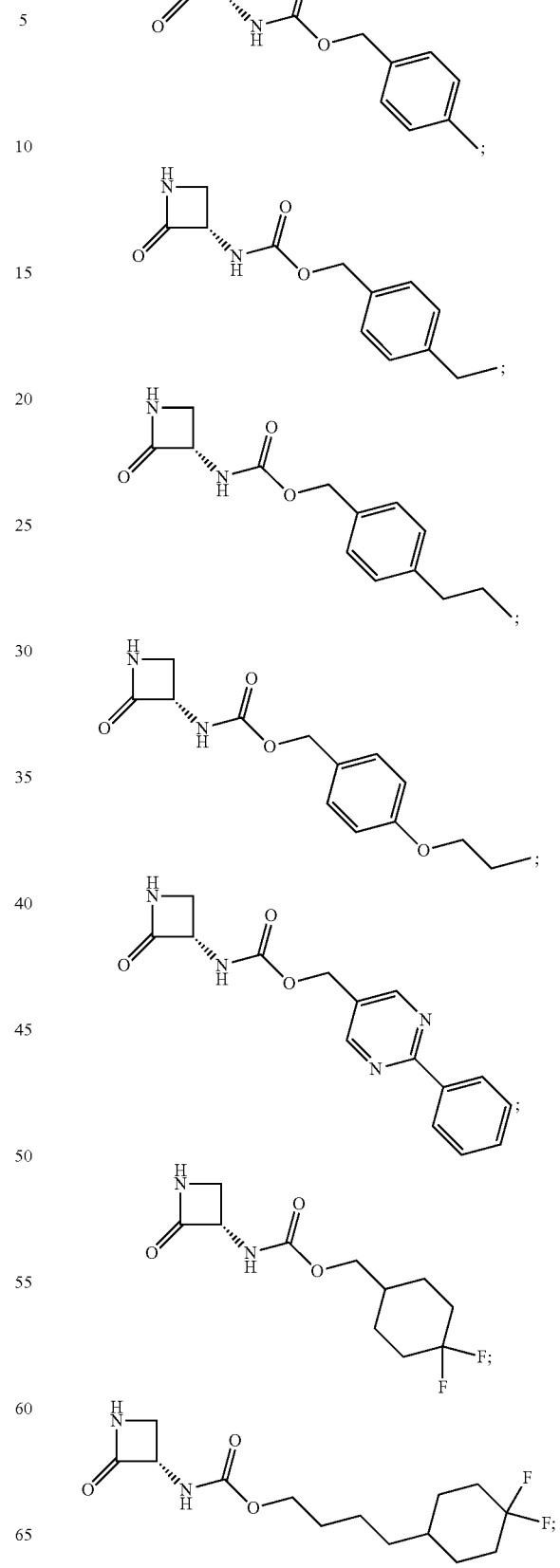

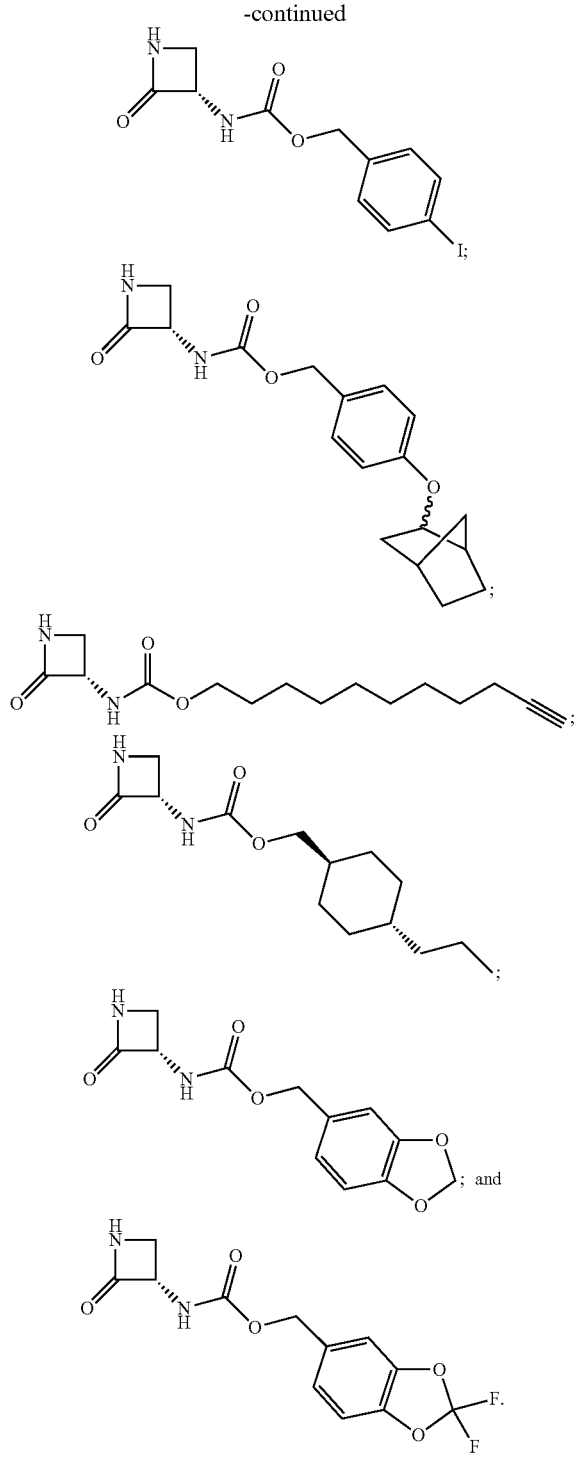

reaction (i.e., graft vs. host disease), acute and chronic allograft rejection, acute respiratory distress syndrome, multiple sclerosis, restinosis, cystic fibrosis, crystal induced arthritis, ocular inflammation, (including dry eye), corneal damage, hyperoxia-induced inflammation, myofascitis, polymyositis, carpal tunnel, sprains, contusions, dental pain, vasculitis, or periodontitis.

42. The method of embodiment 40, wherein the inflammatory condition is contact dermatitis, atopic dermatitis, seborrhoic dermatitis, urticaria, rosacea, acne, psoriasis, lichen, psoriatic arthritis acne, skin burns deriving from various origins, surgical skin incisions, or delayed skin healing induced by diabetes, immunosuppression or other causes.

43. A method of treating a mammal suffering from a painful or pruritogenic pathological state not attributable to inflammation, comprising administering to the mammal a compound having the structure selected from the group consisting of Formula I-XVII.

44. The method of embodiment 43, wherein the pathological state is post herpetic neuralgia, trigeminal neuralgia, causalgia, diabetic neuropathy, neuropathic low back pain, peripheral or polyneuropathic pain, toxic neuropathy, chronic neuropathy caused by chemotherapeutic or antiviral agents, or pruritus induced by uremia, malignancies of various origin, polycythemia, jaundice or cholestasis, iron deficiency, athlete's foot, xerosis, wound healing, thyroid illness, hyperparathyroidism, or menopause.

45. A method of treating a mammal suffering from a neurodegenerative disorder, comprising administering to the mammal a compound having the structure selected from the group consisting of Formula I-XVII.

46. The method of embodiment 45, wherein the neurodegenerative disorder is Alzheimer's disease (e g Alzheimer's dementia), Parkinson's disease, Huntington's disease, Amytrophic Lateral Sclerosis, or macular degeneration.

47. A method of inhibiting N-acylethanolamine acid amidase (NAAA) comprising contacting the NAAA in vitro with a compound having the structure selected from the group consisting of Formula I-XVII.

48. The method of one of embodiments 40 to 47, wherein the compound is selected from the group consisting of

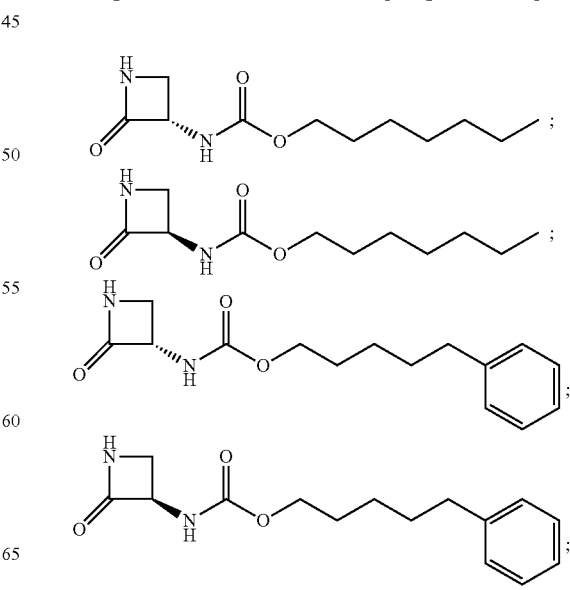

40. A method of treating a mammal suffering from an inflammatory condition comprising administering to the mammal a compound having the structure selected from the group consisting of Formula I-XVII.

41. The method of embodiment 40 wherein the inflammatory condition is osteoarthritis, rheumatoid arthritis, asthma, chronic obstructive pulmonary disease (COPD), adult respiratory disease, inflammatory bowel disease, ulcerative colitis, Crohn's disease, ileocolits, ileitis, gastroduodenal Crohn's disease, jejunoileitis, lupus, graft vs. host

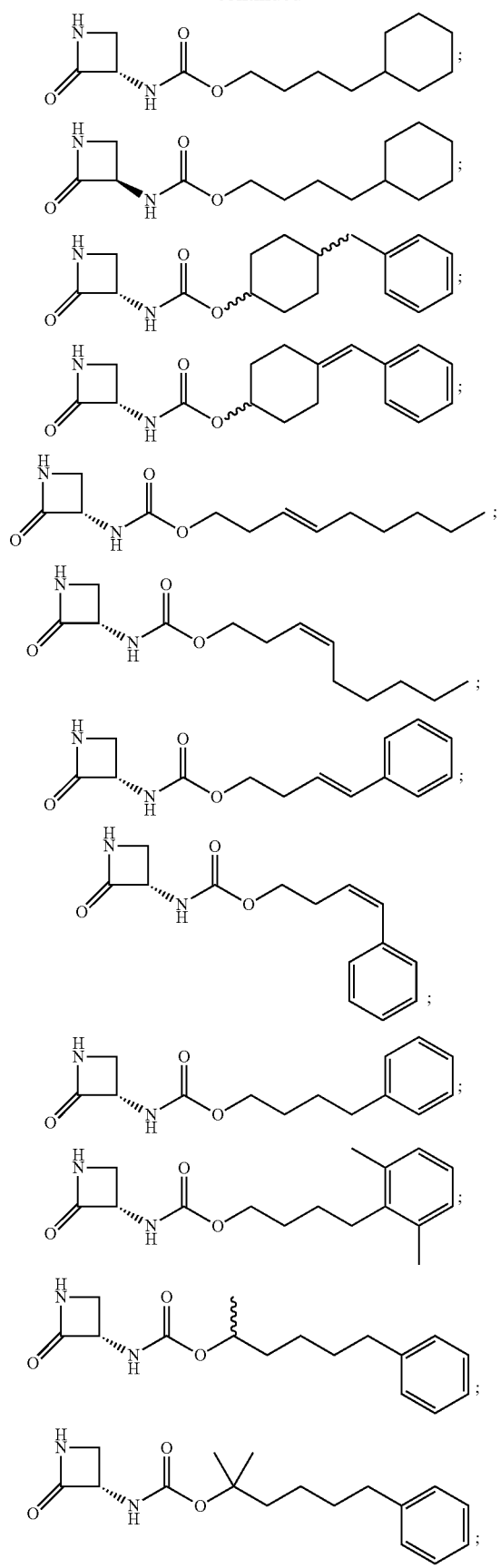
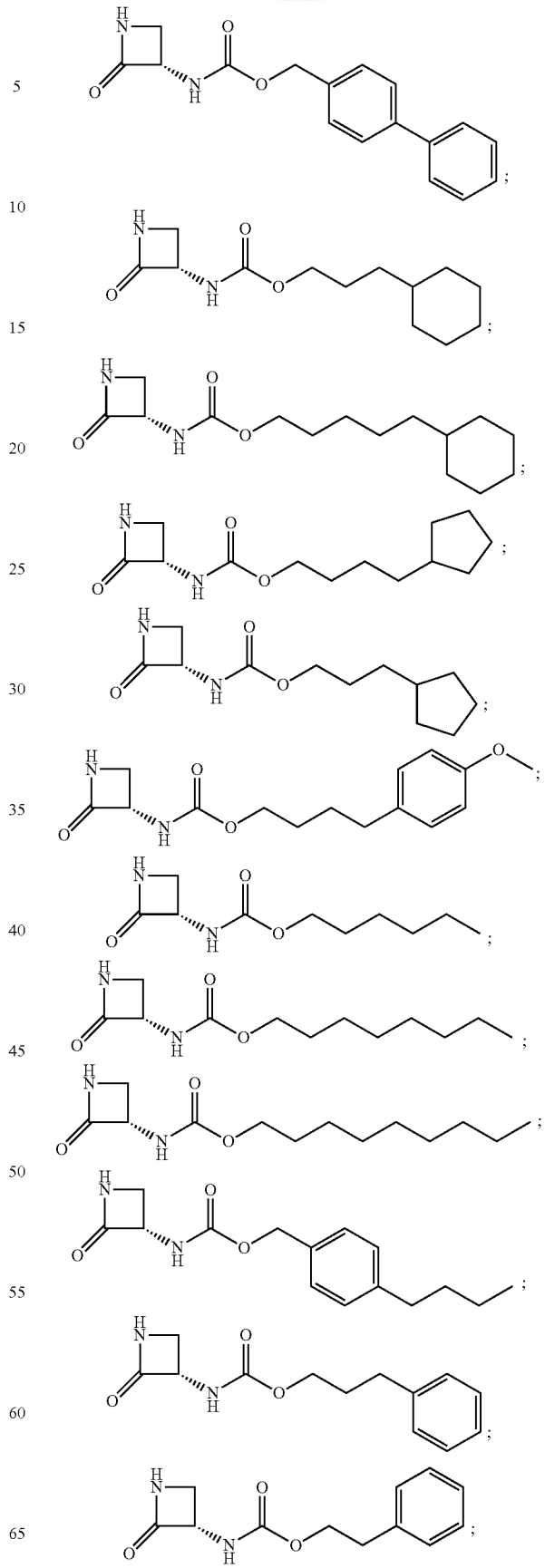

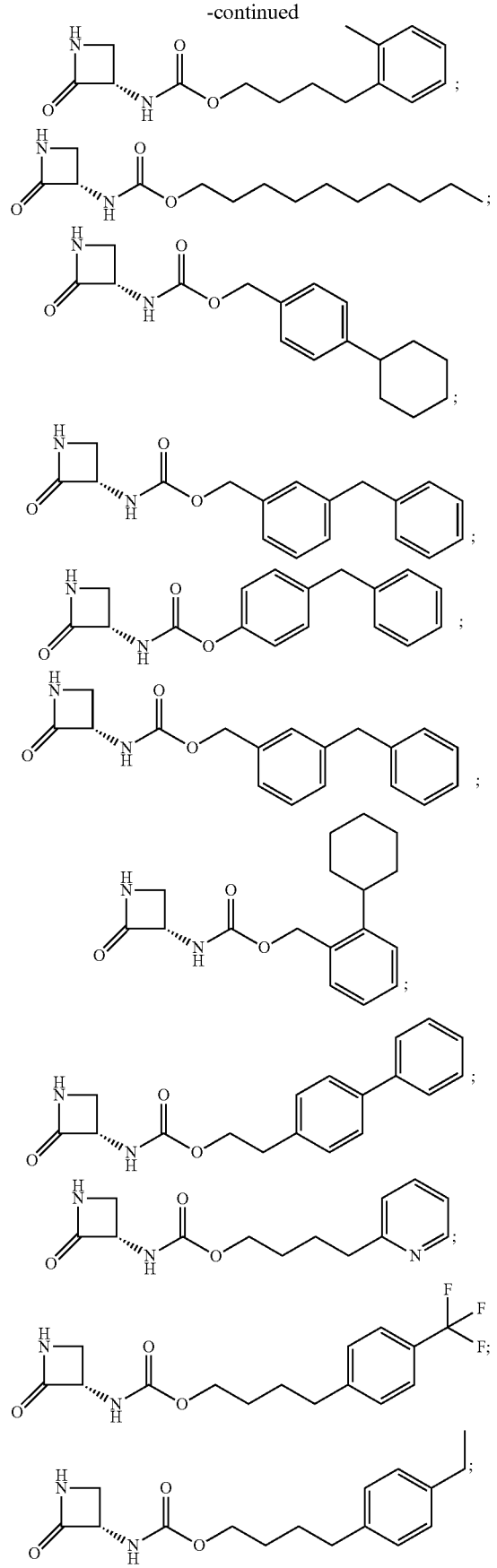
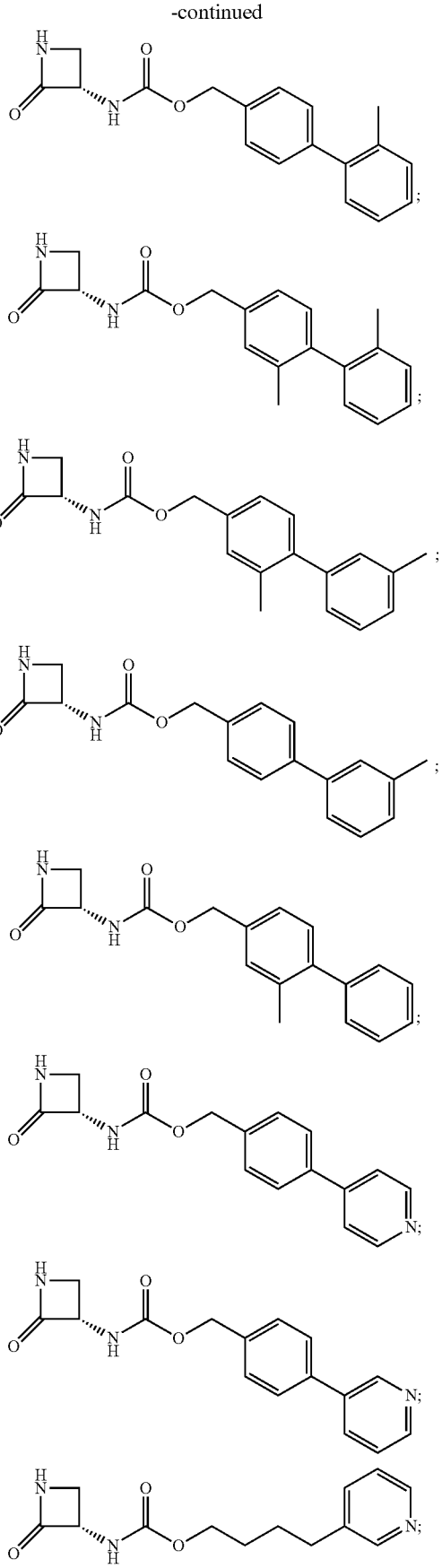

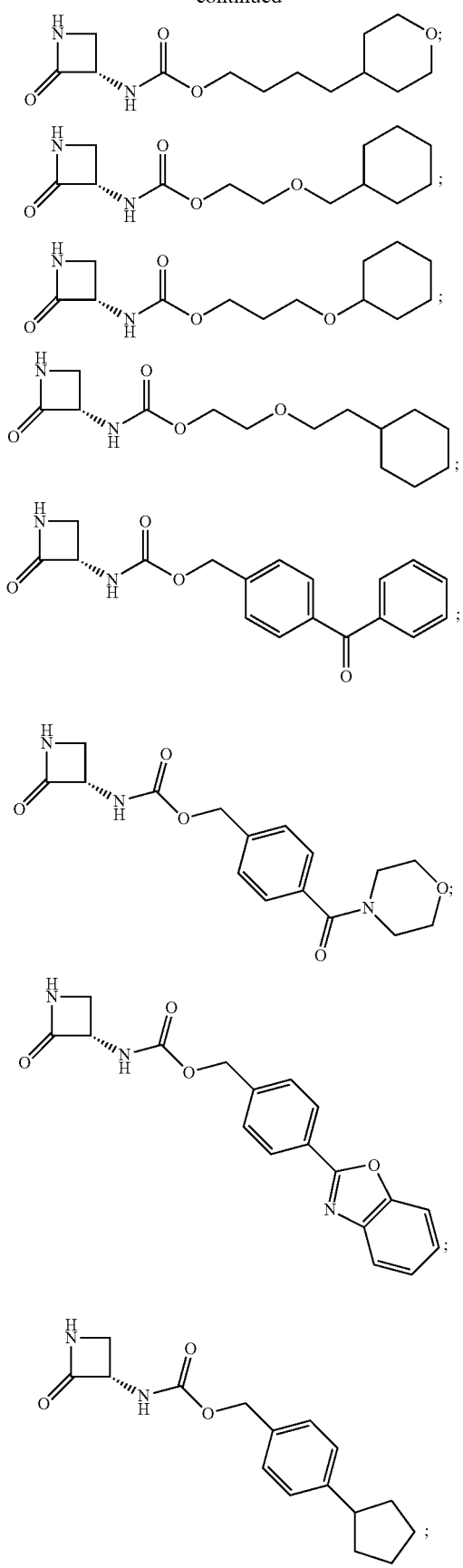
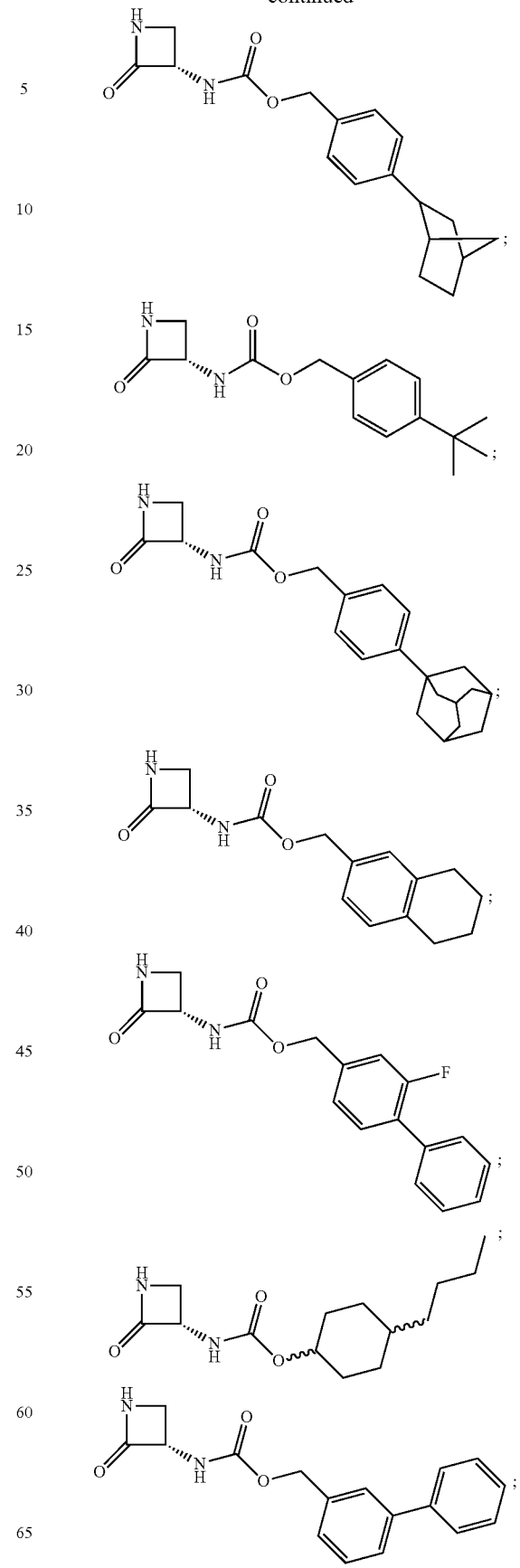

103
-continued
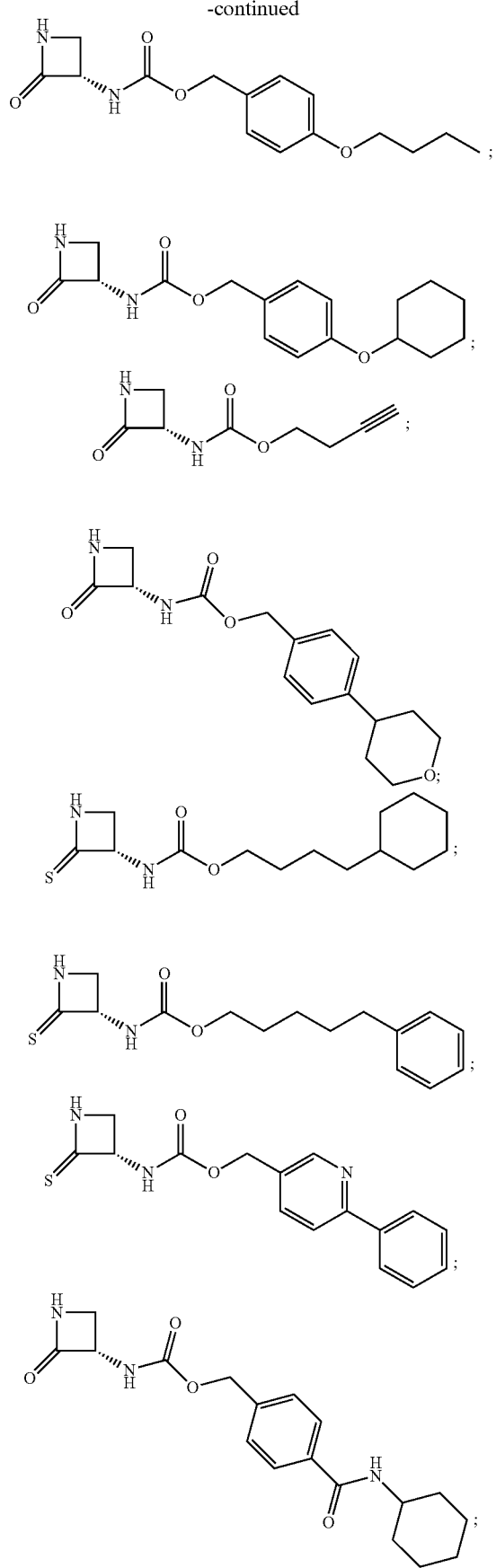
104
-continued
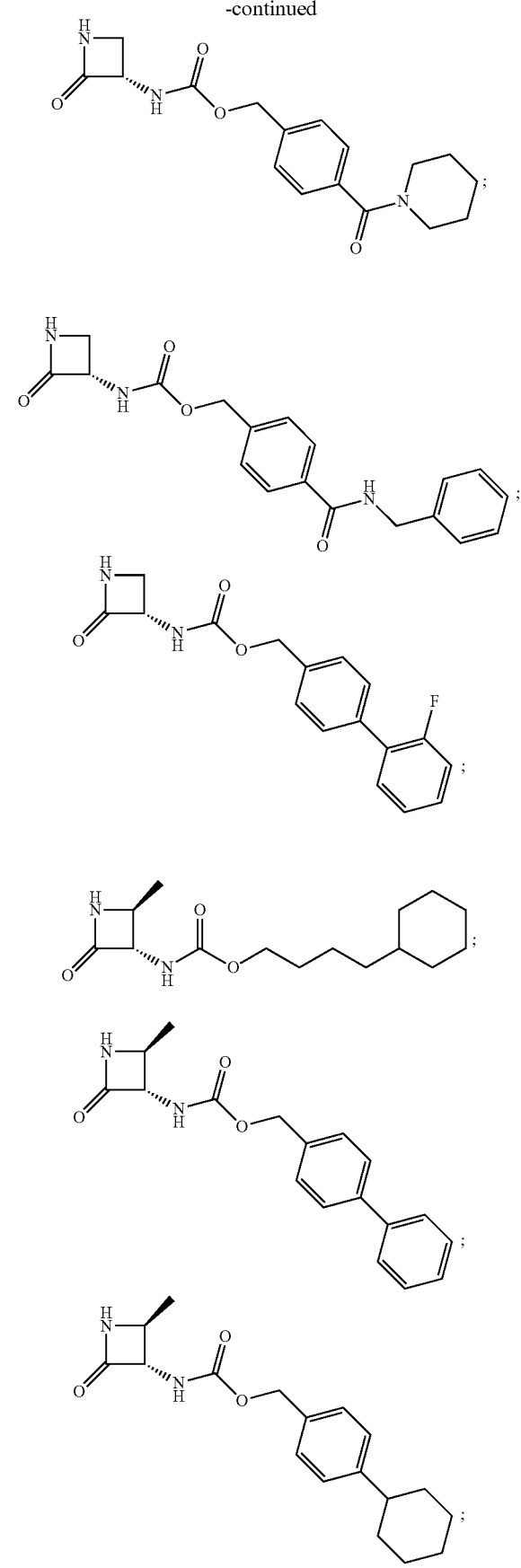

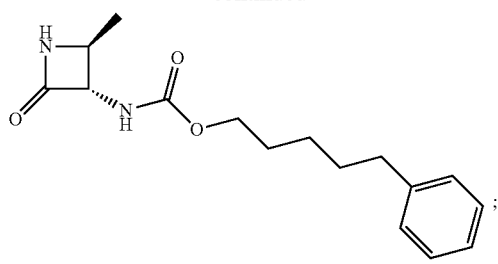
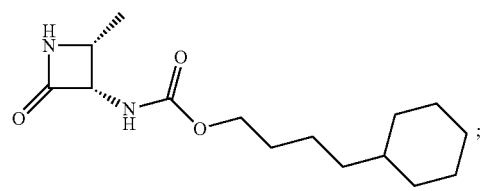
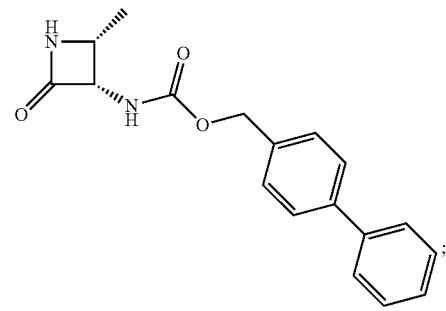
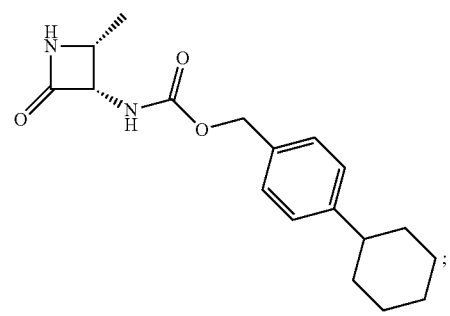
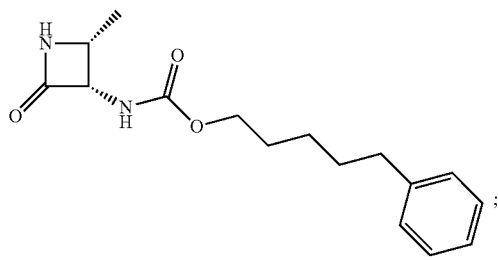
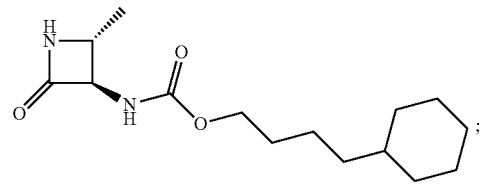
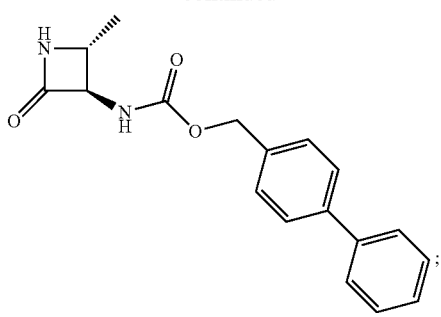
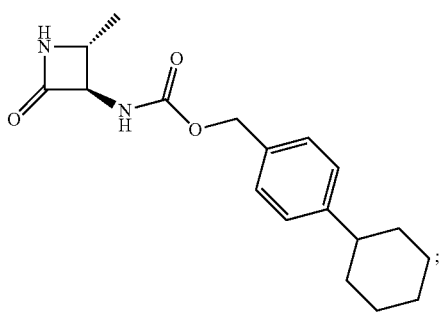
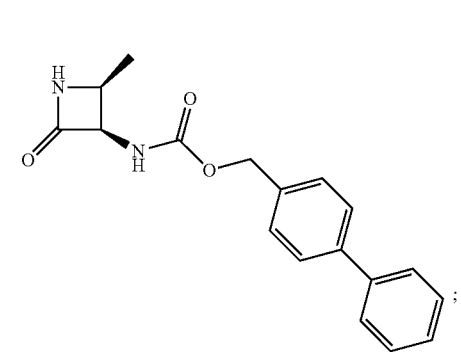
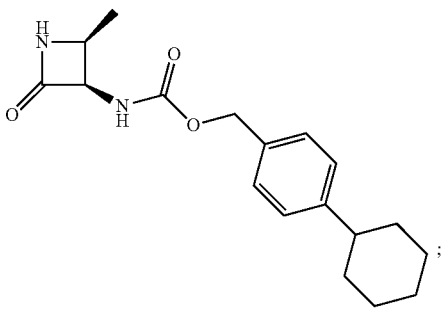
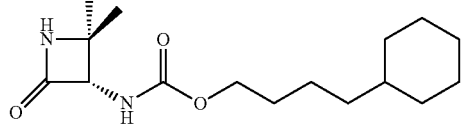

107
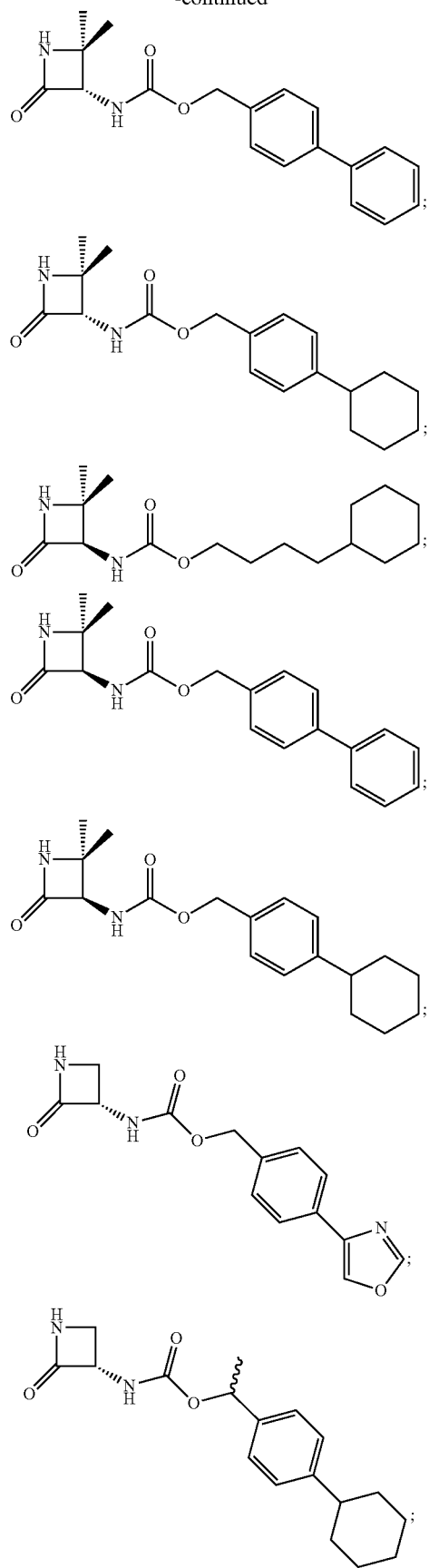
108
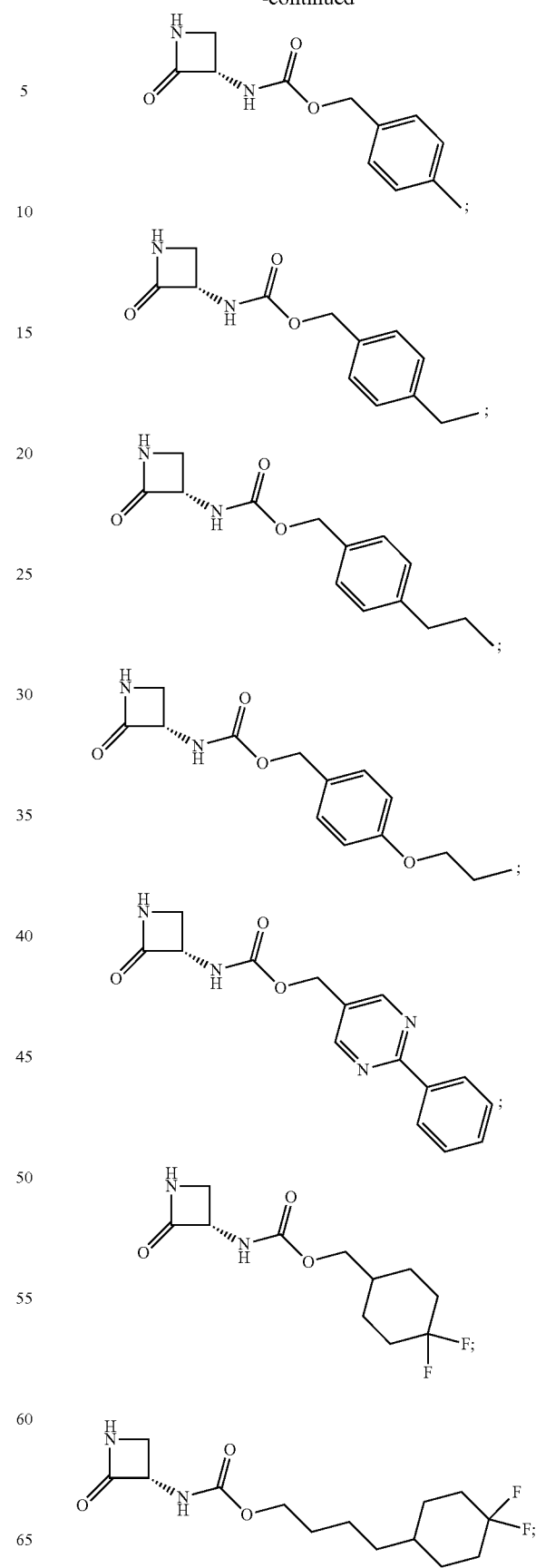

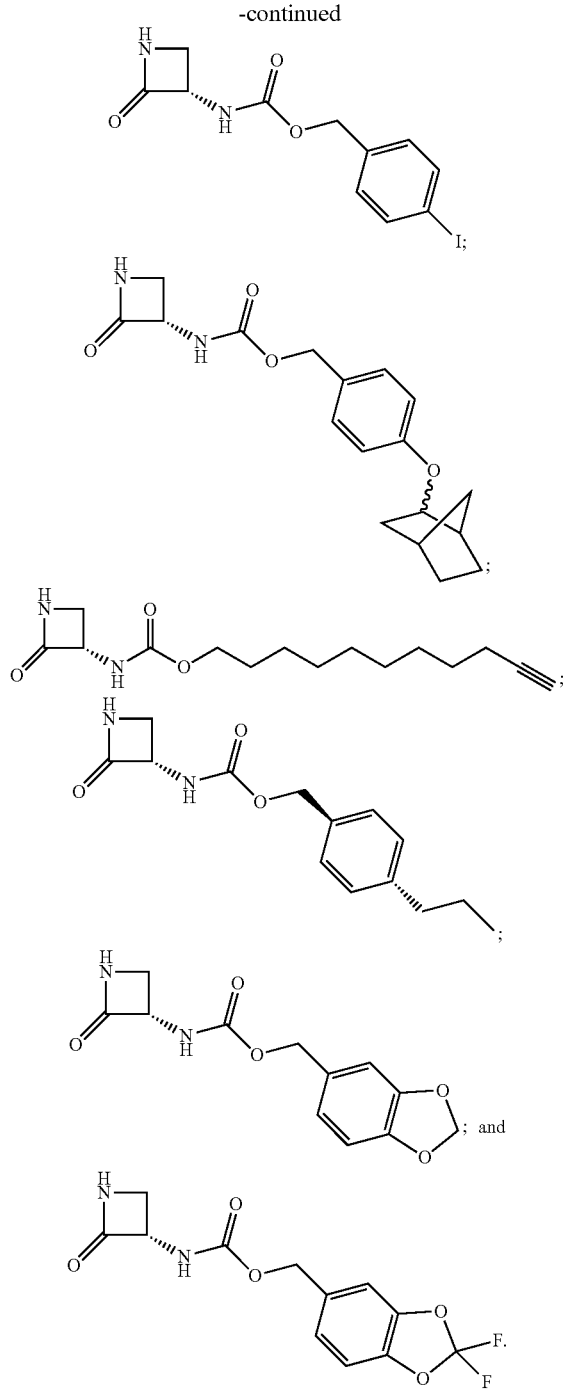

49. The compound of one of embodiments 1 to 39, wherein each cycloalkyl, cycloalkylene, cycloalkyloxy, and cycloalkylalkyl is a 3 to 7 membered cycloalkyl, 3 to 7 membered cycloalkylene, cycloalkyloxy (3 to 7 membered cycloalkyl), and cycloalkylalkyl (3 to 7 membered cycloalkyl), respectively.

50. The method of one of embodiments 40 to 48, wherein each cycloalkyl, cycloalkylene, cycloalkyloxy, and cycloalkylalkyl is a 3 to 7 membered cycloalkyl, 3 to 7 membered cycloalkylene, cycloalkyloxy (3 to 7 membered cycloalkyl), and cycloalkylalkyl (3 to 7 membered cycloalkyl), respectively.

XIII. Examples

Methods for Testing Compounds on NAAA
UPLC/MS r-NAAA Assay

Lysosomal NAAA protein preparation was obtained by homogenizing male Sprague-Dawley rat lungs (Charles River) in 20 mM Tris-HCl buffer pH 7.4 containing 0.32M sucrose. Samples were centrifuged at 800 g for 15 min at 4° C. Supernatants were then centrifuged at 12,000 xg for 30 min at 4° C. Pellets were then resuspended in PBS pH 7.4 and subjected to a freeze/thaw cycle at −80° C. The suspension was finally centrifuged at 105,000×g for 1 h at 4° C. The supernatant was then used in the enzymatic assay.

NAAA protein preparation was pre-incubated with various concentrations of test compounds or vehicle control in 100 mM $NaH_2PO_4$/Citrate buffer, 1% Triton-X, 3 mM DTT (pH 4.5) for 30 min at 37° C. Samples were then incubated with heptadecenoylethanolamide (50 μM, Avanti Polar Lipids) at 37° C. for 30 min. The reaction was terminated by addition of cold methanol containing heptadecanoic acid (NuCheck Prep) as internal standard. Samples were then analyzed by UPLC/MS (Acquity, Waters). Heptadecenoic and heptadecanoic acids were eluted on an Acquity UPLC BEH C18 column (50 mm length, 2.1 mm i.d., 1.7 μm pore size, Waters) isocratically at 0.5 mL/min for 1.5 min with a solvent mixture of 95% methanol and 5% $H_2O$, both containing 0.25% acetic acid and 5.0 mM ammonium acetate. The column temperature was 40° C. Electrospray ionization was in the negative mode, capillary voltage was 0.5 kV, cone voltage was 25 kV, desolvation temperature was 500° C. $N_2$ was used as drying gas at a flow rate of 1000 L/hour and a temperature of 500° C. The $[M-H]^-$ ion was monitored in the selected-ion monitoring mode (m/z values: heptadecenoic acid 267.37, heptadecanoic acid 269.37). Calibration curves were generated using commercial heptadecenoic acid (Nu-Check Prep) Inhibition of NAAA activity was calculated as reduction of heptadecenoic acid in the samples compared to vehicle controls. $IC_{50}$ values were calculated by non-linear regression analysis of log [concentration]/inhibition curves using GraphPad Prism 5 (GraphPad Software Inc., CA—USA) applying a standard slope curve fitting.

Fluorogenic h-NAAA Assay

Hek293 cells stably transfected with the human NAAA coding sequence cloned from a human spleen cDNA library were used as enzyme source. Recombinant HEK-hNAAA pellets were resuspended in homogenizing buffer, and sonicated. Samples were centrifuged at 800×g for 15 min at 4° C. and the resultant supernatants were then ultracentrifuged at 12,000×g for 30 min at 4° C. The pellets were resuspended in PBS pH 7.4 on ice and subjected to a freeze/thaw cycle at −80° C. The suspension was finally centrifuged at 105,000×g for 1 h at 4° C. Protein concentration was measured and samples aliquoted and stored at −80° C. until use.

The assay was run in Optiplate 96-wells black plates, in a total reaction volume of 200 μL. NAAA protein preparation (4.0 μg) was pre-incubated for 10 min with various concentrations of test compounds or vehicle control (5% DMSO) in 100 mM citrate/phosphate buffer (pH 4.5) containing 3.0 mM DTT, 0.1% Triton X-100, 0.05% BSA, 150 mM NaCl. N-(4-methyl-2-oxo-chromen-7-yl)-hexadecanamide was used as a substrate (5.0 μM) and the reaction carried over for 30 min at 37° C. The samples were then read in a Perkin Elmer Envision plate reader using an excitation wavelength of 360 nm and emission 460 nm. IC50 values were calculated by non-linear regression analysis of log

[concentration]/inhibition curves using GraphPad Prism 5 (GraphPad Software Inc., CA—USA) applying a standard slope curve fitting.

The selectivity of selected compounds versus Acid Ceramidase (AC) was determined.

Rat AC (r-AC) Assay

Rat AC (r-AC) was cloned from a brain cDNA library using primers based on the sequence obtained from the National Center for Biotechnology Information (NCBI) database: 5'rAC (5'-GACCATGCTGGGCCGTAGT-3') (SEQ ID NO:1) and 3'rAC (5'-CCAGCCTATA-CAAGGGTCT-3') (SEQ ID NO:2). The PCR (High Fidelity PCR Master, Roche) product was subcloned into a pEF6-V5/His vector (Invitrogen) to construct a mammalian expression vector encoding V5/His-tagged rat AC. HEK293 cells were transfected with pEF6-rAC-V5/His using Super-Fect reagent (Qiagen) and screened with G418 (0.3 mg/mL). Cells were suspended in 20 mM Tris HCl (pH 7.5) containing 0.32M sucrose, sonicated and centrifuged at 800×g for 15 minutes at 4° C. The supernatants were centrifuged again at 12,000×g for 30 minutes at 4° C. The pellets were suspended in phosphate-buffered saline (PBS) and subjected to 2 freeze-thaw cycles at −80° C. The suspensions were centrifuged at 105,000×g for 1 hour at 4° C. The supernatants containing recombinant AC were kept at −80° C. until use. Protein concentration was measured using the bicinchoninic acid (BCA) assay (Pierce). Recombinant rat AC (50 μg) was preincubated with inhibitors (final DMSO concentration 1%) in assay buffer (100 mM sodium phosphate, 0.1% Nonidet P-40, 150 mM NaCl, 3 mM DTT, 100 mM sodium citrate, pH 4.5) for 30 minutes at 37° C. Reactions were started by the addition of 100 μM N-lauroyl ceramide (Nu-Chek Prep, Elysian, Minn.) and carried on for 30 minutes at 37° C. Reactions were stopped by addition of a mixture of chloroform/methanol (2:1, vol/vol) containing 1 nmol of heptadecanoic acid (HDA; NuChek Prep). The organic phases were collected, dried under N2, and analyzed by LC-MS in the negative-ion mode using heptadecenoic acid (HDA) as internal standard (m/z=199 for lauric acid, m/z=269 for HDA). HDA was eluted on an XDB Eclipse C18 column isocratically at 2.2 mL/min for 1 minute with a solvent mixture of 95% methanol and 5% water, both containing 0.25% acetic acid and 5 mM ammonium acetate. The column temperature was 50° C. Electrospray ionization (ESI) was in the negative mode, capillary voltage as 4 kV, and fragmentor voltage was 100 V. N2 was used as drying gas at a flow rate of 13 L/min and a temperature of 350° C. Nebulizer pressure was set at 60 psi. We monitored [M-H]− in the selected-ion monitoring (SIM) mode using HDA as internal standard. Calibration curves were generated using commercial lauric acid (Nu-Chek Prep; m/z=199).

The $IC_{50}$ values of representative compounds of the invention on NAAA and AC are reported in Table 1.

The compounds of the present invention inhibited NAAA activity with $IC_{50}$ lower than 100 μM. The $IC_{50}$ values of representative compounds of the invention are reported in Table 1.

TABLE 1

$IC_{50}$ values of representative compounds of the invention

| Example | r-NAAA UPLC/MS assay $IC_{50}$ (μM) | h-NAAA Fluorogenic assay $IC_{50}$ (μM) | r-AC UPLC/MS assay $IC_{50}$ (μM) |
|---|---|---|---|
| 1 | 0.7 | 0.122 | 37% inhib. @ 1 μM |
| 2 | 66 | | |
| 3 | 0.62 | 0.298 | |
| 4 | 18.7 | | |
| 5 | 0.027 | 0.073 | 12.5 |
| 6 | 8.4 | | |
| 7 | 6.6 | | |
| 8 | 5.7 | | |
| 9 | 0.18 | 0.078 | |
| 10 | 0.25 | 0.076 | |
| 11 | 6.62 | | |
| 12 | 1.6 | | |
| 13 | 2.43 | 0.93 | |
| 14 | 8.1 | | |
| 15 | 3.9 | | |
| 16 | 8.0 | | |
| 17 | 0.31 | 0.513 | 20.1 |
| 18 | 0.04 | | |
| 19 | 0.058 | 0.049 | |
| 20 | 0.048 | 0.032 | |
| 21 | 0.22 | 0.097 | |
| 22 | 0.79 | 0.573 | |
| 23 | 1.6 | | |
| 24 | 0.016 | 0.037 | |
| 25 | 0.04 | 0.017 | |
| 26 | 0.046 | 0.023 | |
| 27 | | 45% Inhib. @ 2.5 μM | |
| 28 | | 65% Inhib. @ 50 μM | |
| 29 | 2.0 | | |
| 30 | 0.055 | 0.025 | |
| 31 | 0.028 | 0.041 | 21.7 |
| 32 | 1.2 | | |
| 33 | 21 | | |
| 34 | 0.3 | 0.23 | |
| 35 | n.a. | | |
| 36 | 5.05 | | |
| 37 | n.a. | | |

TABLE 1-continued

IC$_{50}$ values of representative compounds of the invention

| Example | r-NAAA UPLC/MS assay IC$_{50}$ (μM) | h-NAAA Fluorogenic assay IC$_{50}$ (μM) | r-AC UPLC/MS assay IC$_{50}$ (μM) |
|---|---|---|---|
| 38 | 0.67 | 0.073 | |
| 39 | 1.0 | 0.22 | |
| 40 | 0.51 | | |
| 41 | 0.91 | | |
| 42 | 0.62 | | |
| 43 | 0.87 | | |
| 44 | 0.59 | | |
| 45 | 48% inhib. @ 30 μM | | |
| 46 | | 40% inhib. @ 2.5 μM | |
| 47 | | 55% inhib. @ 50 μM | |
| 48 | 12.6 | | |
| 49 | 1.65 | | |
| 50 | | 25% inhib. @ 2.5 μM | |
| 51 | 0.77 | | |
| 52 | 0.42 | 0.639 | |
| 53 | | 55% inhib. @ 50 μM | |
| 54 | | 0.675 | |
| 55 | 0.031 | 0.077 | |
| 56 | 0.016 | 0.039 | |
| 57 | 0.18 | 0.31 | |
| 58 | 2.7 | 2.1 | |
| 59 | | 0.14 | |
| 60 | | 0.237 | |
| 61 | 0.7 | 0.323 | |
| 62 | 45% inhib. @ 30 μM | | |
| 63 | 0.24 | 0.104 | |
| 64 | 0.16 | 0.207 | |
| 65 | 20% inhib. @ 30 μM | | |
| 66 | | 0.746 | |
| 67 | | 60% inhib. @ 2.5 μM | |
| 68 | | 18% inhib. @ 2.5 μM | |
| 69 | | 12% inhib. @ 2.5 μM | |
| 70 | | 40% inhib. @ 2.5 μM | |
| 71 | | 0.365 | |
| 72 | 0.05 | 0.24 | 20% inhib. @ 10 μM |
| 73 | 0.9 | | 20% inhib. @ 10 μM |
| 74 | 0.046 | 0.107 | 20% inhib. @ 10 μM |
| 75 | 2.8 | | |
| 76 | 87 | | 5% inhib. @ 10 μM |
| 77 | n.a. | | |
| 78 | 55% inhib. @ 100 μM | | |
| 79 | 35% inhib. @ 30 μM | | |
| 80 | 21.5 | | |
| 81 | n.a. | | |
| 82 | 5.1 | | |
| 83 | 4.7 | | |
| 84 | | 18% inhib. @ 2.5 μM | |
| 85 | | 0.619 | |
| 86 | 18% inhib. @100 μM | | |
| 87 | n.a. | | |
| 88 | n.a. | | |
| 89 | n.a. | | |
| 90 | n.a. | | |
| 91 | n.a. | | |
| 92 | | 1.88 | |
| 93 | | 40% inhib. @2.5 μM | |
| 94 | | 1.23 | |
| 95 | | 0.16 | |
| 96 | | 0.052 | |
| 97 | | 0.25 | |
| 98 | | 26% inhib. @2.5 μM | |
| 99 | | 35% inhib. @2.5 μM | |
| 100 | | 0.337 | |
| 101 | | 95% inhib. @2.5 μM | |
| 102 | | 95% inhib. @2.5 μM | |
| 103 | | 0.006 | |
| 104 | | 0.006 | |
| 105 | | 43% inhib. @2.5 μM | |
| 106 | | 97% inhib. @2.5 μM | | n.a. = <10% inhib. @100 μM

Methods for Screening Compounds for a Therapeutic Activity

A variety of animal models can be used to test the compounds of the present invention for their therapeutic effectiveness in treating inflammatory and pain states. With the aim to better illustrate the present invention, without limiting it, a method for testing the compounds of the present invention for therapeutic effectiveness is reported hereunder.

Behavioral Testing

Carrageenan-Induced Inflammation

Paw edema was induced by injecting λ-carrageenan (1% weight/vol in sterile $H_2O$, 50 μL) into the left hind paw of lightly restrained mice (Sasso et al., *Pharmacol. Res.* 2012; 65: 553-632). All experiments were performed in a quiet room, and experimenters were blinded to the treatment protocol at the time of the test. Edema was measured with a plethysmometer (Ugo Basile, Comerio, Italy). Heat hyperalgesia was assessed measuring the latency to withdraw the hind paw from a focused beam of radiant heat (thermal intensity: infrared 3.0) applied to the plantar surface in a plantar test apparatus (Ugo Basile). The cutoff time was set at 30 s. Fresh drug solutions were prepared daily and given by intraperitoneal injection (in 80% sterile saline solution/ 10% PEG-400/10% Tween 80, 200 μL per animal), at the same time of carrageenan injection. Intraplantar administration of carrageenan in mice resulted in the development of paw edema and heat hyperalgesia. Both responses were markedly attenuated, in a dose- and time-dependent manner, by oral administration (p.o.) of compound 5 (3-30 mg/kg) as shown in FIG. 1.

Acute Inflammation Models

Carrageenan-Induced Lung Inflammation

Saline or saline containing 2% carrageenan (0.1 mL) was injected into the pleural cavity of mice, using a 1 mm needle at the level of the $6^{th}$ intercostal space. 4 hours after the injection of carrageenan, mice were killed by inhalation of $CO_2$. The chest was carefully opened and the pleural cavity was rinsed with 1 mL of saline solution containing heparin (5 U/mL). The exudate and washing solution were removed by aspiration and the total volume of the fluid was measured. Any exudate that was contaminated with blood was discarded. The amount of exudate was calculated by subtracting the volume of washing fluid injected from the total volume recovered. The oral administration of compound 5 (0.1-30 mg/kg po) dose-dependently normalized the increase of myeloperoxidase activity (MPO) in lung tissue and the associated increase of TNF-α in the pulmonary exudate. Similarly, compound 5 at the dose of 30 mg/kg po also normalized neutrophil infiltration in the exudate.

LPS-Induced Inflammation

Mice were anesthetized with ketamine and xylazine (100 and 10 mg/kg, respectively), and were subjected to intranasal instillation of LPS (1 μg/μL) or vehicle (saline 0.9%); the volume used was 1 μL/g body weight. In order to avoid drawing, the weight of each animal was divided by three; therefore each mouse received the respective volume of LPS or vehicle. Ex: animal 1 (24 g) received 3 times an intranasal instillation of 8 μL of LPS solution or vehicle.

The bronchoalveolar lavage and lung samples were collected 6 h or 24 h after the induction of inflammation. Compound 5 tested at the dose of 30 mg/kg po significantly reduced LPS induced increase of the inflammatory markers IL-6, TNF-α and MIP-2/CXCL2 in tissue and BAL at 6 hr but not at 24 h while it also prevented neutrophil infiltration in lung tissue at both time points.

General Purification and Analytical Methods

UPLC/MS analyses were run on a Waters ACQUITY UPLC/MS instrument consisting of a SQD Single Quadropole Mass Spectrometer equipped with an electrospray ionization interface and a photodiode array detector. The analyses were performed on an ACQUITY UPLC BEH C18 column (50×2.1 mmID, particle size 1.7 μm) with a Van-Guard BEH C18 pre-column (5×2.1 mmID, particle size 1.7 μm). The mobile phases were 10 mM NH4OAc at pH 5 adjusted with AcOH (A) and 10 mM $NH_4OAc$ in MeCN—$H_2O$ (95:5) at pH 5 (B). Electrospray ionization in positive and negative mode was used in the mass scan range 100-500 Da.

Purifications by preparative HPLC/MS were run on a Waters Autopurification system consisting of a 3100 Single Quadropole Mass Spectrometer equipped with an electrospray ionization interface and a 2998 Photodiode Array Detector. The HPLC system included a 2747 Sample Manager, 2545 Binary Gradient Module, System Fluidic Organizer and 515 HPLC Pump. The purifications were performed on a XBridge™ Prep $C_{18}$ OBD column (100×19 mmID, particle size 5 μm) with a XBridge™ Prep $C_{18}$ (10×19 mmID, particle size 5 μm) Guard Cartridge. The mobile phases were either 1) $H_2O$ and MeCN (B) or 2) 10 mM $NH_4OAc$ at pH 5 adjusted with AcOH (A) and 10 mM $NH_4OAc$ in MeCN—$H_2O$ (95:5) at pH 5 (B). Electrospray ionization in positive and negative mode was used in the mass scan range 100-500 Da.

Automated column chromatography purification was done using a Teledyne ISCO apparatus (CombiFlash® Rf) with normal phase pre-packed silica gel columns of different sizes (from 4 g until 120 g). Typical silica gel column chromatography is intended as a purification performed using normal glass columns filled with Merck silica gel 60 (230-400 mesh) as stationary phase. Mixtures of solvents used as eluents are reported below.

Hydrogenation reactions were performed using H-Cube® continuous flow hydrogenation equipment (SS-reaction line version), employing disposable cartridges (CatCart®), preloaded with the required heterogeneous catalyst.

Microwave heating was performed using Explorer®-48 positions instrument (CEM).

NMR experiments were run on a Bruker Avance III 400 system (400.13 MHz for $^1H$, and 100.62 MHz for $^{13}C$), equipped with a BBI inverse probe and Z-gradients. Unless indicated, spectra were acquired at 300 K, using deuterated dimethylsulfoxyde (DMSO-$d_6$) and deuterated chloroform (CDCl$_3$) as solvents.

TABLE 2

Examples of compounds of the invention

| Example | Structure | Formula | Name |
|---|---|---|---|
| 1 | 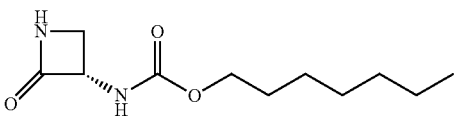 [SMILES: CCCCCCCOC(=O)N[C@H]1CNC1=O] | $C_{11}H_{20}N_2O_3$ | Heptyl-N-[(3S)-2-oxoazetidin-3-yl]-carbamate |
| 2 | 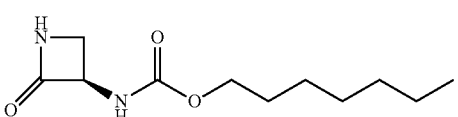 | $C_{11}H_{20}N_2O_3$ | Heptyl-N-[(3R)-2-oxoazetidin-3-yl]-carbamate |
| 3 | 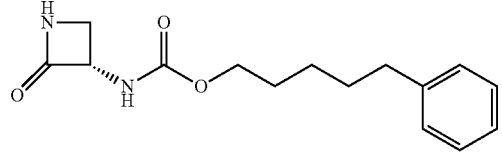 [SMILES: O=C(N[C@H]1CNC1=O)OCCCCCc1ccccc1] | $C_{15}H_{20}N_2O_3$ | 5-Phenylpentyl-N-[(3S)-2-oxoazetidin-3-yl]-carbamate |
| 4 | 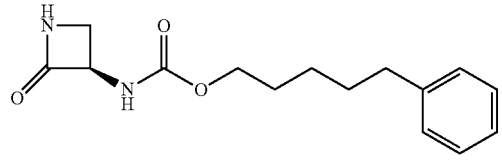 [SMILES: O=C(N[C@@H]1CNC1=O)OCCCCCc1ccccc1] | $C_{15}H_{20}N_2O_3$ | 5-Phenylpentyl-N-[(3R)-2-oxoazetidin-3-yl]-carbamate |
| 5 | 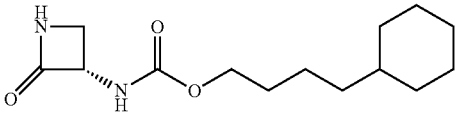 [SMILES: O=C(N[C@H]1CNC1=O)OCCCCC1CCCCC1] | $C_{14}H_{24}N_2O_3$ | 4-Cyclohexylbutyl-N-[(3S)-2-oxoazetidin-3-yl]-carbamate |
| 6 | 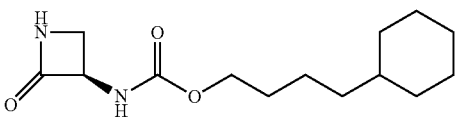 [SMILES: O=C(N[C@@H]1CNC1=O)OCCCCC1CCCCC1] | $C_{14}H_{24}N_2O_3$ | 4-Cyclohexylbutyl-N-[(3R)-2-oxoazetidin-3-yl]-carbamate |
| 7 | 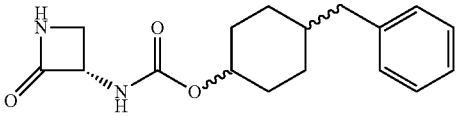 [SMILES: O=C(N[C@H]1CNC1=O)OC1CCC(Cc2ccccc2)CC1] | $C_{17}H_{22}N_2O_3$ | (1s,4R) and (1r,4S)-(4-Benzylcyclohexyl)-N-[(3S)-2-oxoazetidin-3-yl]-carbamate |
| 8 | 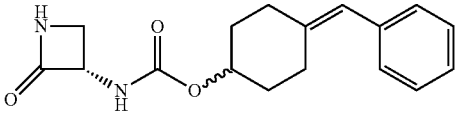 [SMILES: O=C(N[C@H]1CNC1=O)OC1CCC(=Cc2ccccc2)CC1] | $C_{17}H_{20}N_2O_3$ | (R,Z) and (S,E)-(4-Benzylidenecyclohexyl)-N-[(3S)-2-oxoazetidin-3-yl]-carbamate |
| 9 | 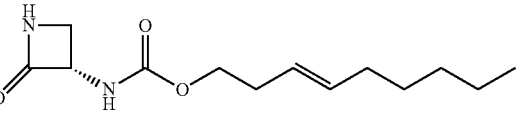 | $C_{13}H_{22}N_2O_3$ | [(E)-Non-3-enyl]-N-[(3S)-2-oxoazetidin-3-yl]-carbamate |
| 10 | 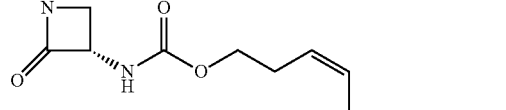 | $C_{13}H_{22}N_2O_3$ | [(Z)-Non-3-enyl]-N-[(3S)-2-oxoazetidin-3-yl]-carbamate |
| 11 | 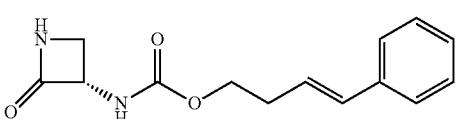 | $C_{14}H_{16}N_2O_3$ | [(E)-4-Phenylbut-3-enyl]-N-[(3S)-2-oxoazetidin-3-yl]-carbamate |

TABLE 2-continued

Examples of compounds of the invention

| Example | Structure | Formula | Name |
|---|---|---|---|
| 12 | 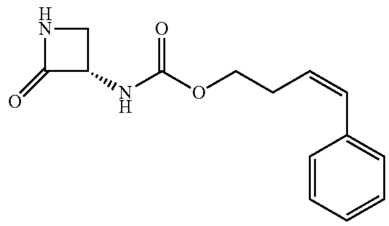 [SMILES: O=C(N[C@H]1CNC1=O)OCC/C=C\c1ccccc1] | $C_{14}H_{16}N_2O_3$ | [(Z)-4-Phenylbut-3-enyl]-N-[(3S)-2-oxoazetidin-3-yl]-carbamate |
| 13 | 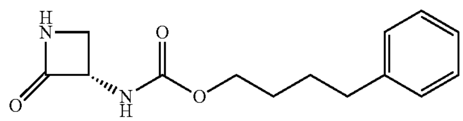 [SMILES: O=C(N[C@H]1CNC1=O)OCCCCc1ccccc1] | $C_{14}H_{18}N_2O_3$ | 4-Phenylbutyl-N-[(3S)-2-oxoazetidin-3-yl]-carbamate |
| 14 | 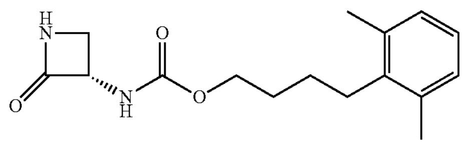 [SMILES: Cc1cccc(C)c1CCCCOC(=O)N[C@H]1CNC1=O] | $C_{16}H_{22}N_2O_3$ | 4-(2,6-Dimethylphenyl)-butyl-N-[(3S)-2-oxoazetidin-3-yl]-carbamate |
| 15 | 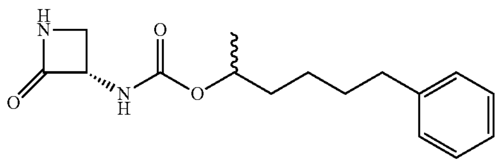 [SMILES: CC(CCCCc1ccccc1)OC(=O)N[C@H]1CNC1=O] | $C_{16}H_{22}N_2O_3$ | [(1S)- and (1R)-1-Methyl--5-phenyl-pentyl)]-N-[(3S)-2-oxoazetidin-3-yl]-carbamate |
| 16 | 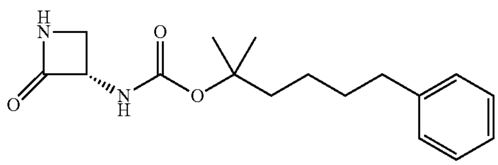 [SMILES: CC(C)(CCCCc1ccccc1)OC(=O)N[C@H]1CNC1=O] | $C_{17}H_{24}N_2O_3$ | (1,1-Dimethyl-5-phenyl-pentyl)-N-[(3S)-2-oxoazetidin-3-yl]-carbamate |
| 17 | 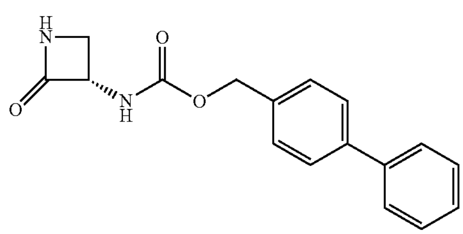 [SMILES: O=C(N[C@H]1CNC1=O)OCc1ccc(-c2ccccc2)cc1] | $C_{17}H_{16}N_2O_3$ | (4-Phenylphenyl)-methyl-N-[(3S)-2-oxoazetidin-3-yl]-carbamate |
| 18 | 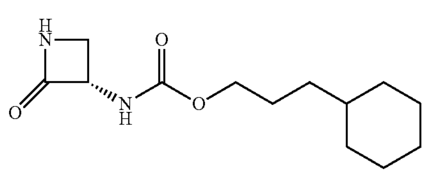 [SMILES: O=C(N[C@H]1CNC1=O)OCCCC1CCCCC1] | $C_{13}H_{22}N_2O_3$ | 3-Cyclohexylpropyl-N-[(3S)-2-oxoazetidin-3-yl]-carbamate |
| 19 | 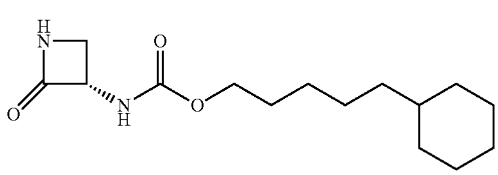 [SMILES: O=C(N[C@H]1CNC1=O)OCCCCCC1CCCCC1] | $C_{15}H_{26}N_2O_3$ | 5-Cyclohexylpentyl-N-[(3S)-2-oxoazetidin-3-yl]-carbamate |
| 20 | 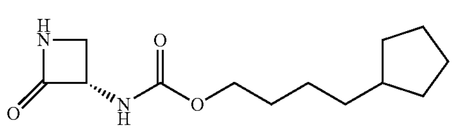 [SMILES: O=C(N[C@H]1CNC1=O)OCCCCC1CCCC1] | $C_{13}H_{22}N_2O_3$ | 4-Cyclopentylbutyl-N-[(3S)-2-oxoazetidin-3-yl]-carbamate |

TABLE 2-continued

Examples of compounds of the invention

| Example | Structure | Formula | Name |
|---|---|---|---|
| 21 | 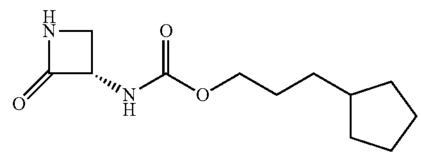 [SMILES: O=C(N[C@H]1CNC1=O)OCCCC1CCCC1] | $C_{12}H_{20}N_2O_3$ | 3-Cyclopentylpropyl-N-[(3S)-2-oxoazetidin-3-yl]-carbamate |
| 22 | 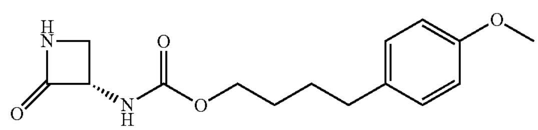 [SMILES: COc1ccc(CCCCOC(=O)N[C@H]2CNC2=O)cc1] | $C_{15}H_{20}N_2O_4$ | 4-(4-Methoxyphenyl)-butyl-N-[(3S)-2-oxoazetidin-3-yl]-carbamate |
| 23 | 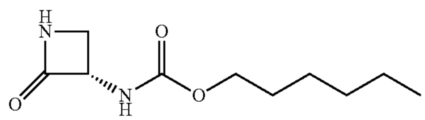 | $C_{10}H_{18}N_2O_3$ | Hexyl-N-[(3S)-2-oxoazetidin-3-yl]-carbamate |
| 24 | 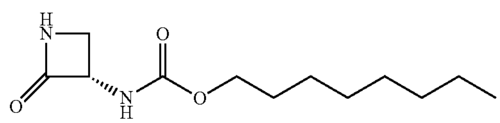 [SMILES: CCCCCCCCOC(=O)N[C@H]1CNC1=O] | $C_{12}H_{22}N_2O_3$ | Octyl-N-[(3S)-2-oxoazetidin-3-yl]-carbamate |
| 25 | 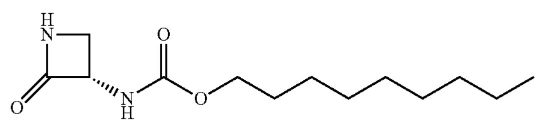 [SMILES: CCCCCCCCCOC(=O)N[C@H]1CNC1=O] | $C_{13}H_{24}N_2O_3$ | Nonyl-N-[(3S)-2-oxoazetidin-3-yl]-carbamate |
| 26 | 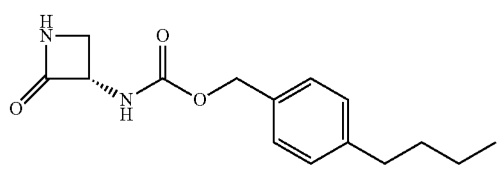 [SMILES: CCCCc1ccc(COC(=O)N[C@H]2CNC2=O)cc1] | $C_{15}H_{20}N_2O_3$ | (4-Butylphenyl)-methyl-N-[(3S)-2-oxoazetidin-3-yl]-carbamate |
| 27 | 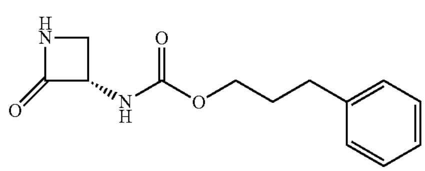 [SMILES: O=C(N[C@H]1CNC1=O)OCCCc1ccccc1] | $C_{13}H_{16}N_2O_3$ | 3-Phenylpropyl-N-[(3S)-2-oxoazetidin-3-yl]-carbamate |
| 28 | 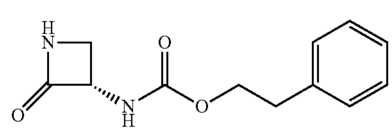 [SMILES: O=C(N[C@H]1CNC1=O)OCCc1ccccc1] | $C_{12}H_{14}N_2O_3$ | Phenethyl-N-[(3S)-2-oxoazetidin-3-yl]-carbamate |
| 29 | 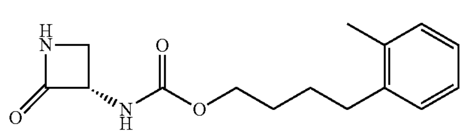 [SMILES: Cc1ccccc1CCCCOC(=O)N[C@H]1CNC1=O] | $C_{15}H_{20}N_2O_3$ | 4-(o-Tolyl)-butyl-N-[(3S)-2-oxoazetidin-3-yl]-carbamate |
| 30 | 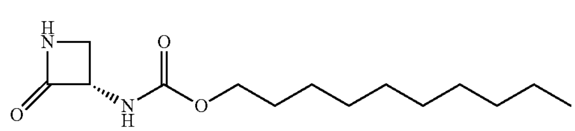 [SMILES: CCCCCCCCCCOC(=O)N[C@H]1CNC1=O] | $C_{14}H_{26}N_2O_3$ | Decyl-N-[(3S)-2-oxoazetidin-3-yl]-carbamate |

TABLE 2-continued

Examples of compounds of the invention

| Example | Structure | Formula | Name |
|---|---|---|---|
| 31 | 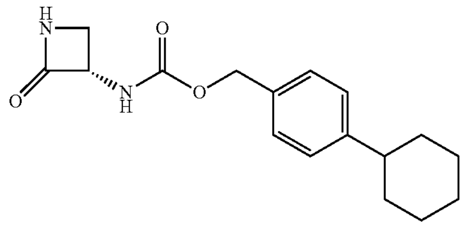 [SMILES: O=C(N[C@H]1CNC1=O)OCc1ccc(C2CCCCC2)cc1] | $C_{17}H_{22}N_2O_3$ | (4-Cyclohexylphenyl)-methyl-N-[(3S)-2-oxoazetidin-3-yl]-carbamate |
| 32 | 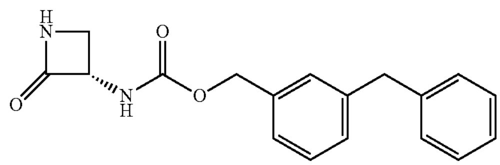 [SMILES: O=C(N[C@H]1CNC1=O)OCc1cccc(Cc2ccccc2)c1] | $C_{18}H_{18}N_2O_3$ | (3-Benzylphenyl)-methyl-N-[(3S)-2-oxoazetidin-3-yl]-carbamate |
| 33 | 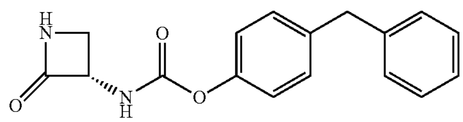 [SMILES: O=C(N[C@H]1CNC1=O)Oc1ccc(Cc2ccccc2)cc1] | $C_{17}H_{16}N_2O_3$ | (4-Benzylphenyl)-N-[(3S)-2-oxoazetidin-3-yl]-carbamate |
| 34 | 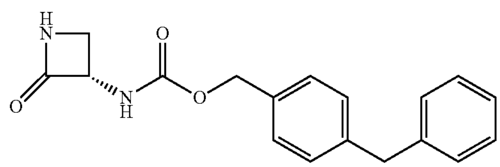 [SMILES: O=C(N[C@H]1CNC1=O)OCc1ccc(Cc2ccccc2)cc1] | $C_{18}H_{18}N_2O_3$ | (4-Benzylphenyl)-methyl-N-[(3S)-2-oxoazetidin-3-yl]-carbamate |
| 35 | 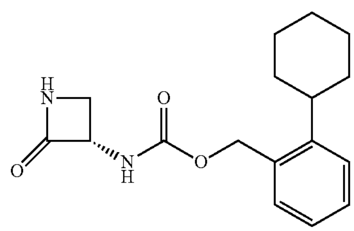 [SMILES: O=C(N[C@H]1CNC1=O)OCc1ccccc1C1CCCCC1] | $C_{17}H_{22}N_2O_3$ | (2-Cyclohexylphenyl)-methyl-N-[(3S)-2-oxoazetidin-3-yl]-carbamate |
| 36 | 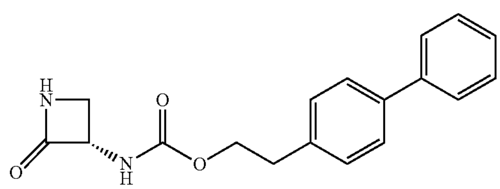 [SMILES: O=C(N[C@H]1CNC1=O)OCCc1ccc(-c2ccccc2)cc1] | $C_{18}H_{18}N_2O_3$ | 2-(4-Phenylphenyl)-ethyl-N-[(3S)-2-oxoazetidin-3-yl]-carbamate |
| 37 | 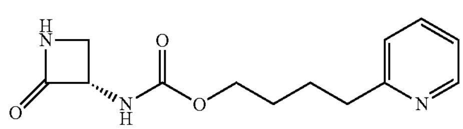 [SMILES: O=C(N[C@H]1CNC1=O)OCCCCc1ccccn1] | $C_{13}H_{17}N_3O_3$ | 4-(2-Pyridyl)-butyl-N-[(3S)-2-oxoazetidin-3-yl]-carbamate |
| 38 | 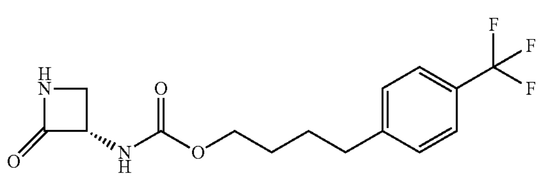 [SMILES: O=C(N[C@H]1CNC1=O)OCCCCc1ccc(C(F)(F)F)cc1] | $C_{15}H_{17}F_3N_2O_3$ | 4-[4-(Trifluoromethyl)-phenyl]butyl-N-[(3S)-2-oxoazetidin-3-yl]-carbamate |

TABLE 2-continued

Examples of compounds of the invention

| Example | Structure | Formula | Name |
|---|---|---|---|
| 39 | 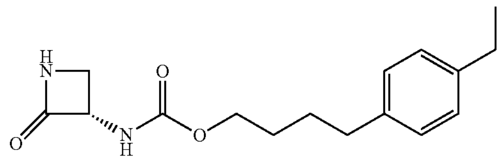 [SMILES: CCc1ccc(CCCCOC(=O)N[C@H]2CNC2=O)cc1] | $C_{16}H_{22}N_2O_3$ | 4-(4-Ethylphenyl)butyl-N-[(3)-2-oxoazetidin-3-yl]-carbamate |
| 40 | 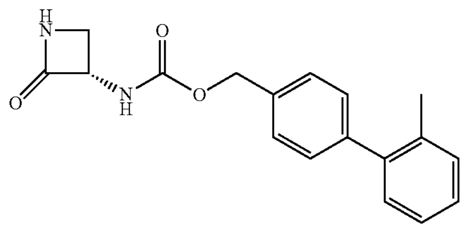 [SMILES: Cc1ccccc1-c1ccc(COC(=O)N[C@H]2CNC2=O)cc1] | $C_{18}H_{18}N_2O_3$ | [4-(o-Tolyl)-phenyl]-methyl-N-[(3S)-2-oxoazetidin-3-yl]-carbamate |
| 41 | 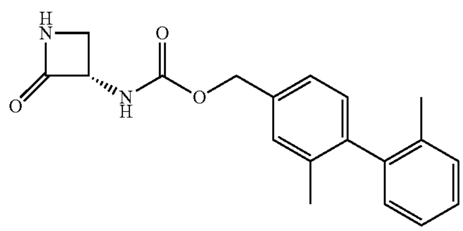 [SMILES: Cc1ccccc1-c1ccc(COC(=O)N[C@H]2CNC2=O)cc1C] | $C_{19}H_{20}N_2O_3$ | [3-Methyl-4-(o-Tolyl)-phenyl]-methyl-N-[(3S)-2-oxoazetidin-3-yl]-carbamate |
| 42 | 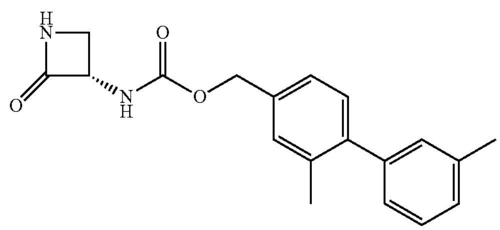 [SMILES: Cc1cccc(-c2ccc(COC(=O)N[C@H]3CNC3=O)cc2C)c1] | $C_{19}H_{20}N_2O_3$ | [3-Methyl-4-(m-tolyl)-phenyl]-methyl-N-[(3S)-2-oxoazetidin-3-yl]-carbamate |
| 43 | 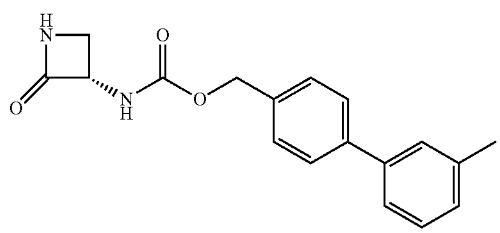 [SMILES: Cc1cccc(-c2ccc(COC(=O)N[C@H]3CNC3=O)cc2)c1] | $C_{18}H_{18}N_2O_3$ | [4-(m-Tolyl)-phenyl]-methyl-N-[(3S)-2-oxoazetidin-3-yl]carbamate |
| 44 | 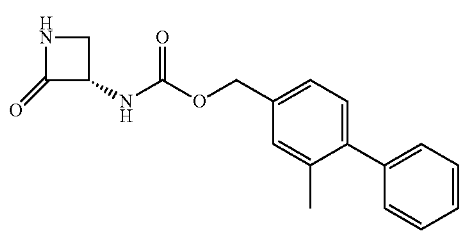 [SMILES: Cc1cc(COC(=O)N[C@H]2CNC2=O)ccc1-c1ccccc1] | $C_{18}H_{18}N_2O_3$ | (3-Methyl-4-phenyl-phenyl)-methyl-N-[(3S)-2-oxoazetidin-3-yl]-carbamate |
| 45 | 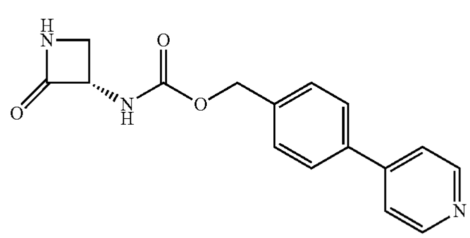 [SMILES: O=C(N[C@H]1CNC1=O)OCc1ccc(-c2ccncc2)cc1] | $C_{16}H_{15}N_3O_3$ | [4-(4-Pyridyl)-phenyl]-methyl-N-[(3S)-2-oxoazetidin-3-yl]-carbamate |

TABLE 2-continued

Examples of compounds of the invention

| Example | Structure | Formula | Name |
|---|---|---|---|
| 46 | 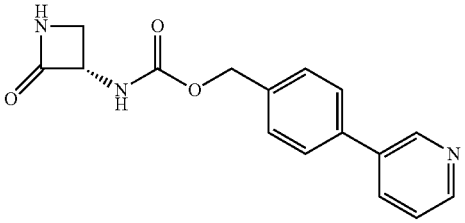 [SMILES: O=C(N[C@H]1CNC1=O)OCc1ccc(-c2cccnc2)cc1] | $C_{16}H_{15}N_3O_3$ | [4-(3-Pyridyl)-phenyl]-methyl-N-[(3S)-2-oxoazetidin-3-yl]-carbamate |
| 47 | 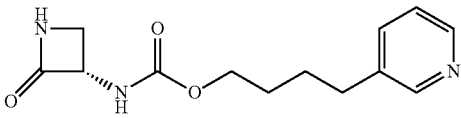 [SMILES: O=C(N[C@H]1CNC1=O)OCCCCc1cccnc1] | $C_{13}H_{17}N_3O_3$ | 4-(3-Pyridyl)-butyl-N-[(3S)-2-oxoazetidin-3-yl]-carbamate |
| 48 | 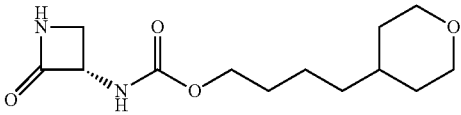 | $C_{13}H_{22}N_2O_4$ | 4-Tetrahydropyran-4-yl-butyl-N-[(3S)-2-oxoazetidin-3-yl]-carbamate |
| 49 | 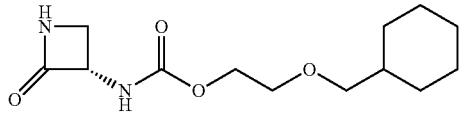 | $C_{13}H_{22}N_2O_4$ | 2-(Cyclohexylmethoxy)-ethyl-N-[(3S)-2-oxoazetidin-3-yl]-carbamate |
| 50 | 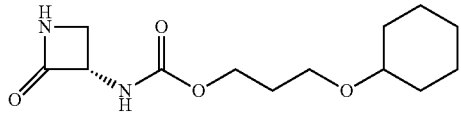 | $C_{13}H_{22}N_2O_4$ | 3-(Cyclohexoxy)-propyl-N-[(3S)-2-oxoazetidin-3-yl]-carbamate |
| 51 | 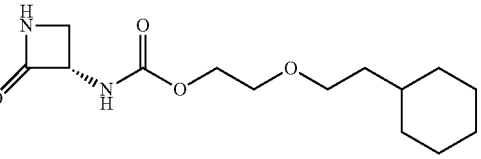 | $C_{14}H_{24}N_2O_4$ | 2-(2-Cyclohexylethoxy)-ethyl-N-[(3S)-2-oxoazetidin-3-yl]-carbamate |
| 52 | 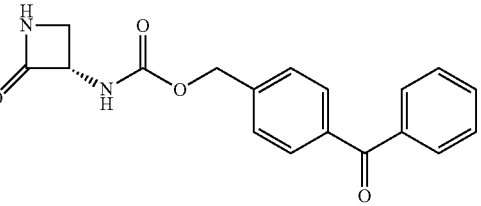 | $C_{18}H_{16}N_2O_4$ | (4-Benzoylphenyl)-methyl-N-[(3S)-2-oxoazetidin-3-yl]-carbamate |
| 53 | 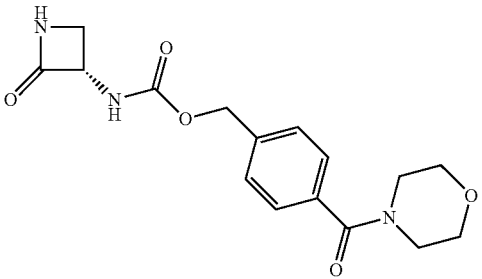 [SMILES: O=C(N[C@H]1CNC1=O)OCc1ccc(C(=O)N2CCOCC2)cc1] | $C_{16}H_{19}N_3O_5$ | [4-(Morpholine-4-carbonyl)-phenyl]-methyl-N-[(3S)-2-oxoazetidin-3-yl]-carbamate |

TABLE 2-continued

Examples of compounds of the invention

| Example | Structure | Formula | Name |
|---|---|---|---|
| 54 | 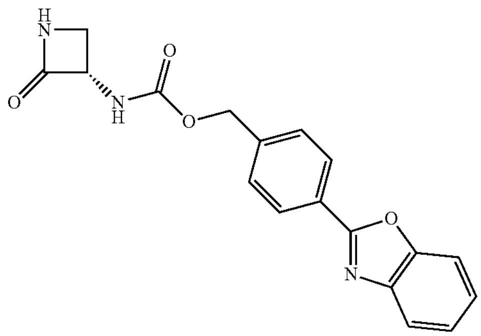 [SMILES: O=C(N[C@H]1CNC1=O)OCc1ccc(-c2nc3ccccc3o2)cc1] | $C_{18}H_{15}N_3O_4$ | [4-(1,3-Benzoxazol-2-yl)-phenyl]-methyl-N-[(3S)-2-oxoazetidin-3-yl]-carbamate |
| 55 | 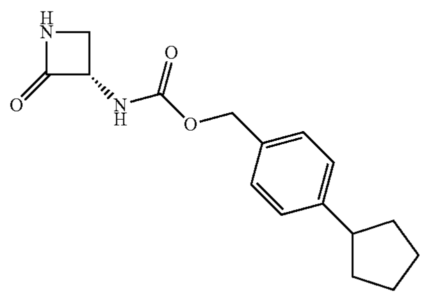 [SMILES: O=C(N[C@H]1CNC1=O)OCc1ccc(C2CCCC2)cc1] | $C_{16}H_{20}N_2O_3$ | (4-Cyclopentylphenyl)-methyl-N-[(3S)-2-oxoazetidin-3-yl]-carbamate |
| 56 | 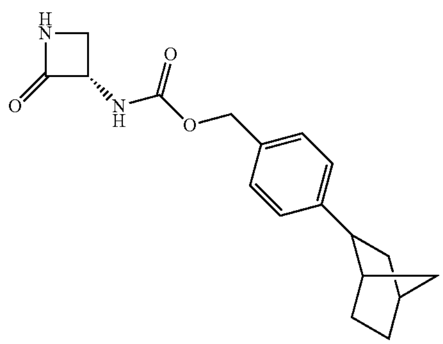 [SMILES: O=C(N[C@H]1CNC1=O)OCc1ccc(C2CC3CCC2C3)cc1] | $C_{18}H_{22}N_2O_3$ | exo-(4-Norbornan-2-yl-phenyl)-methyl-N-[(3S)-2-oxoazetidin-3-yl]-carbamate |
| 57 | 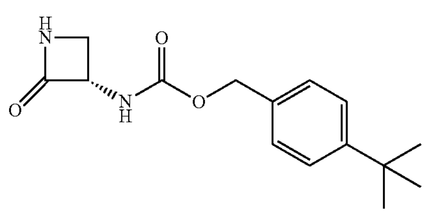 [SMILES: CC(C)(C)c1ccc(COC(=O)N[C@H]2CNC2=O)cc1] | $C_{15}H_{20}N_2O_3$ | (4-tert-Butylphenyl)-methyl-N-[(3S)-2-oxoazetidin-3-yl]-carbamate |
| 58 | 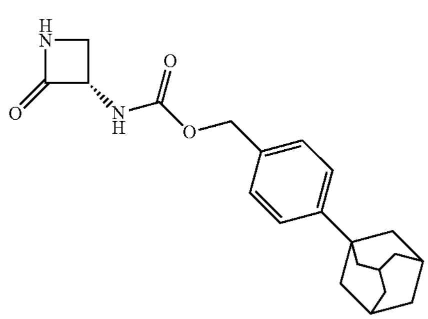 [SMILES: O=C(N[C@H]1CNC1=O)OCc1ccc(C23CC4CC(CC(C4)C2)C3)cc1] | $C_{21}H_{26}N_2O_3$ | [4-(1-Adamantyl)-phenyl]-methyl-N-[(3S)-2-oxoazetidin-3-yl]-carbamate |

TABLE 2-continued

Examples of compounds of the invention

| Example | Structure | Formula | Name |
|---|---|---|---|
| 59 | 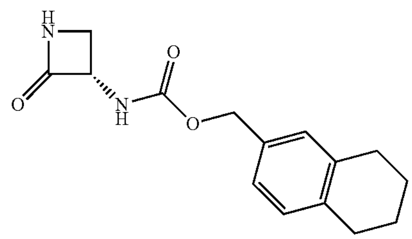 [SMILES: O=C(N[C@H]1CNC1=O)OCc1ccc2c(c1)CCCC2] | $C_{15}H_{18}N_2O_3$ | Tetralin-6-yl-methyl-N-[(3S)-2-oxoazetidin-3-yl]-carbamate |
| 60 | 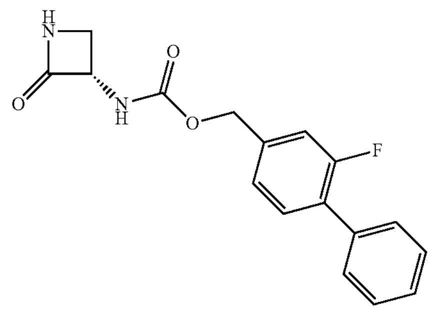 [SMILES: O=C(N[C@H]1CNC1=O)OCc1ccc(-c2ccccc2)c(F)c1] | $C_{17}H_{15}FN_2O_3$ | (3-Fluoro-4-phenyl-phenyl)-methyl-N-[(3S)-2-oxoazetidin-3-yl]-carbamate |
| 61 | 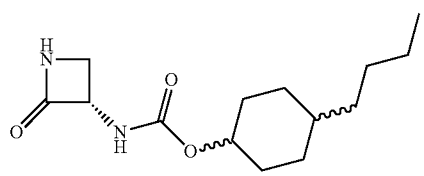 [SMILES: CCCCC1CCC(OC(=O)N[C@H]2CNC2=O)CC1] | $C_{14}H_{24}N_2O_3$ | (1s,4R) and (1r,4S)-(4-Butylcyclohexyl)-N-[(3S)-2-oxoazetidin-3-yl]-carbamate |
| 62 | 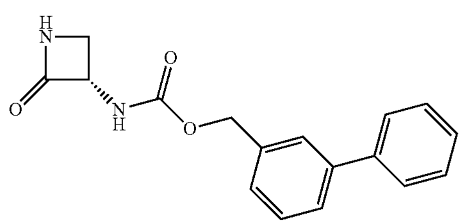 [SMILES: O=C(N[C@H]1CNC1=O)OCc1cccc(-c2ccccc2)c1] | $C_{17}H_{16}N_2O_3$ | (3-Phenylphenyl)-methyl-N-[(3S)-2-oxoazetidin-3-yl]-carbamate |
| 63 | 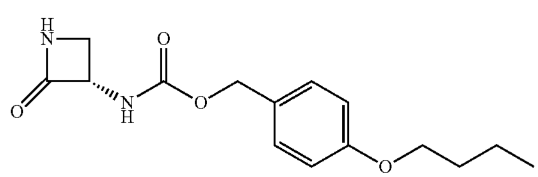 [SMILES: CCCCOc1ccc(COC(=O)N[C@H]2CNC2=O)cc1] | $C_{15}H_{20}N_2O_4$ | (4-Butoxyphenyl)-methyl-N-[(3S)-2-oxoazetidin-3-yl]-carbamate |
| 64 | 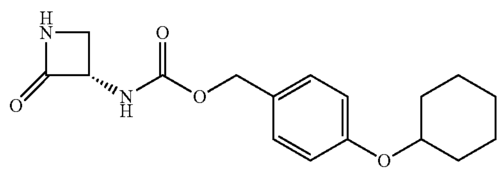 [SMILES: O=C(N[C@H]1CNC1=O)OCc1ccc(OC2CCCCC2)cc1] | $C_{17}H_{22}N_2O_4$ | [4-(Cyclohexoxy)-phenyl]-methyl-N-[(3S)-2-oxoazetidin-3-yl]-carbamate |
| 65 | 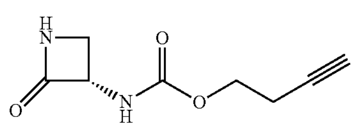 | $C_8H_{10}N_2O_3$ | But-3-ynyl-N-[(3S)-2-oxoazetidin-3-yl]-carbamate |

TABLE 2-continued

Examples of compounds of the invention

| Example | Structure | Formula | Name |
|---|---|---|---|
| 66 | 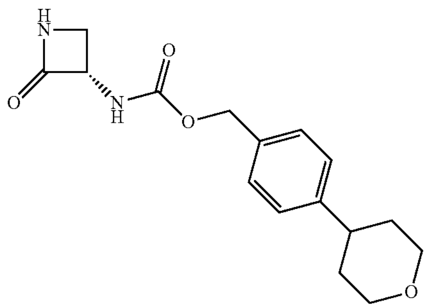 [SMILES: O=C(N[C@H]1CNC1=O)OCc1ccc(C2CCOCC2)cc1] | $C_{16}H_{20}N_2O_4$ | (4-Tetrahydropyran-4-yl-phenyl)-methyl-N-[(3S)-2-oxoazetidin-3-yl]-carbamate |
| 67 | 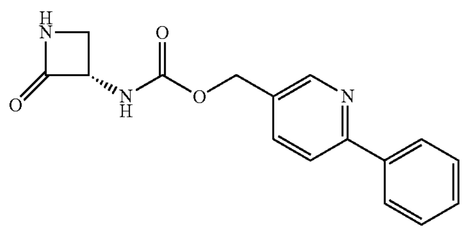 [SMILES: O=C(N[C@H]1CNC1=O)OCc1ccc(-c2ccccc2)nc1] | $C_{16}H_{15}N_3O_3$ | (6-Phenyl-3-pyridyl)-methyl-N-[(3S)-2-oxoazetidin-3-yl]-carbamate |
| 68 | 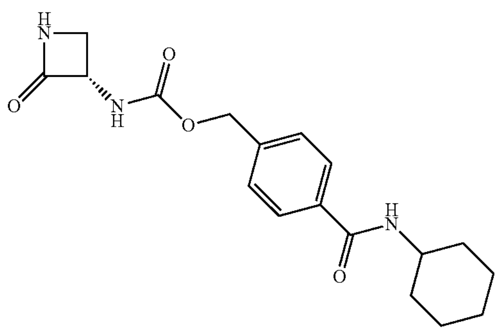 [SMILES: O=C(N[C@H]1CNC1=O)OCc1ccc(C(=O)NC2CCCCC2)cc1] | $C_{18}H_{23}N_3O_4$ | [4-(Cyclohexylcarbamoyl)-phenyl]-methyl-N-[(3S)-2-oxoazetidin-3-yl]-carbamate |
| 69 | 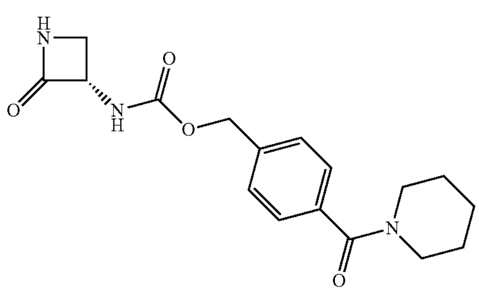 [SMILES: O=C(N[C@H]1CNC1=O)OCc1ccc(C(=O)N2CCCCC2)cc1] | $C_{17}H_{21}N_3O_4$ | [4-(Piperidine-1-carbonyl)-phenyl]-methyl-N-[(3S)-2-oxoazetidin-3-yl]-carbamate |
| 70 | 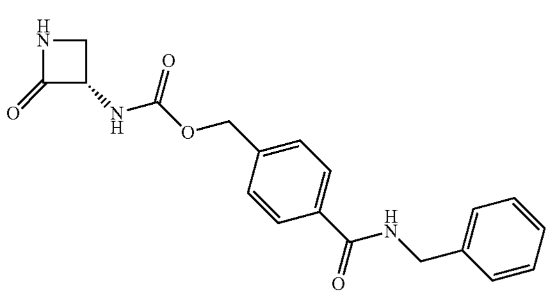 [SMILES: O=C(N[C@H]1CNC1=O)OCc1ccc(C(=O)NCc2ccccc2)cc1] | $C_{19}H_{19}N_3O_4$ | [4-(Benzylcarbamoyl)-phenyl]-methyl-N-[(3S)-2-oxoazetidin-3-yl]-carbamate |

TABLE 2-continued

Examples of compounds of the invention

| Example | Structure | Formula | Name |
|---|---|---|---|
| 71 | 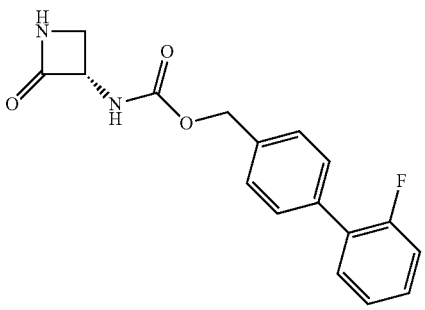 [SMILES: O=C(N[C@H]1CNC1=O)OCc1ccc(-c2ccccc2F)cc1] | $C_{17}H_{15}FN_2O_3$ | [4-(2-Fluorophenyl)-phenyl]-methyl-N-[(3S)-2-oxoazetidin-3-yl]-carbamate |
| 72 | 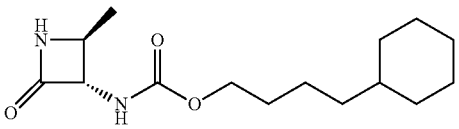 [SMILES: C[C@@H]1NC(=O)[C@H]1NC(=O)OCCCCC1CCCCC1] | $C_{15}H_{26}N_2O_3$ | 4-Cyclohexylbutyl-N-[(2S,3S)-2-methyl-4-oxo-azetidin-3-yl]-carbamate |
| 73 | 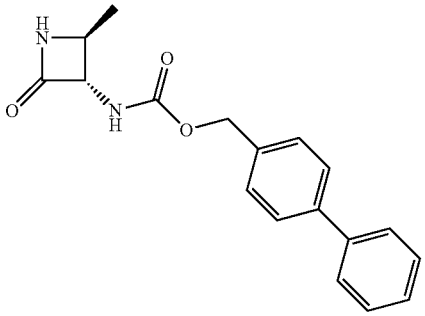 [SMILES: C[C@@H]1NC(=O)[C@H]1NC(=O)OCc1ccc(-c2ccccc2)cc1] | $C_{18}H_{18}N_2O_3$ | (4-Phenylphenyl)-methyl-N-[(2S,3S)-2-methyl-4-oxo-azetidin-3-yl]-carbamate |
| 74 | 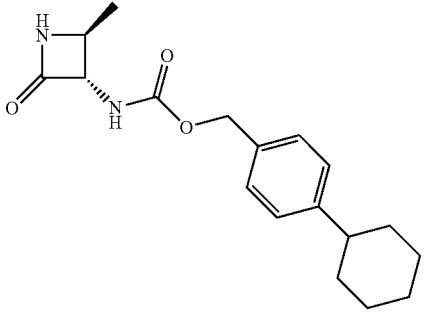 [SMILES: C[C@@H]1NC(=O)[C@H]1NC(=O)OCc1ccc(C2CCCCC2)cc1] | $C_{18}H_{24}N_2O_3$ | (4-Cyclohexylphenyl)-methyl-N-[(2S,3S)-2-methyl-4-oxo-azetidin-3-yl]-carbamate |
| 75 | 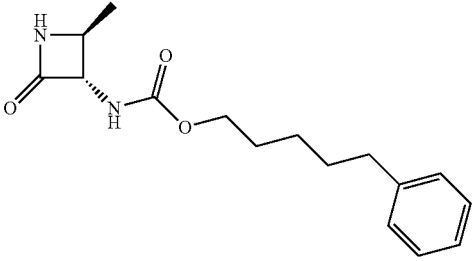 [SMILES: C[C@@H]1NC(=O)[C@H]1NC(=O)OCCCCCc1ccccc1] | $C_{16}H_{22}N_2O_3$ | 5-Phenylpentyl-N-[(2S,3S)-2-methyl-4-oxo-azetidin-3-yl]-carbamate |
| 76 | 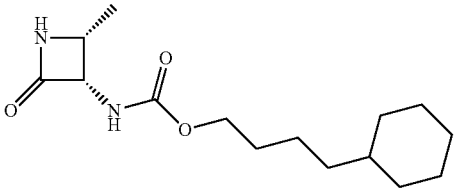 [SMILES: C[C@H]1NC(=O)[C@H]1NC(=O)OCCCCC1CCCCC1] | $C_{15}H_{26}N_2O_3$ | 4-Cyclohexylbutyl-N-[(2R,3S)-2-methyl-4-oxo-azetidin-3-yl]-carbamate |

TABLE 2-continued

Examples of compounds of the invention

| Example | Structure | Formula | Name |
|---|---|---|---|
| 77 | 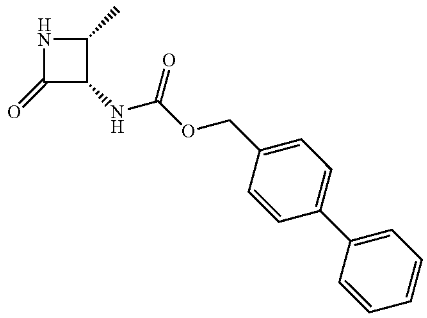 [SMILES: C[C@H]1NC(=O)[C@H]1NC(=O)OCc1ccc(-c2ccccc2)cc1] | $C_{18}H_{18}N_2O_3$ | (4-Phenylphenyl)-methyl-N-[(2R,3S)-2-methyl-4-oxo-azetidin-3-yl]-carbamate |
| 78 | 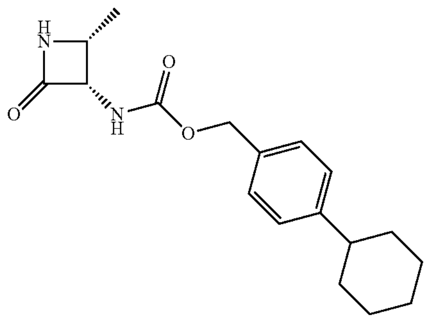 [SMILES: C[C@H]1NC(=O)[C@H]1NC(=O)OCc1ccc(C2CCCCC2)cc1] | $C_{18}H_{24}N_2O_3$ | (4-Cyclohexylphenyl)-methyl-N-[(2R,3S)-2-methyl-4-oxo-azetidin-3-yl]-carbamate |
| 79 | 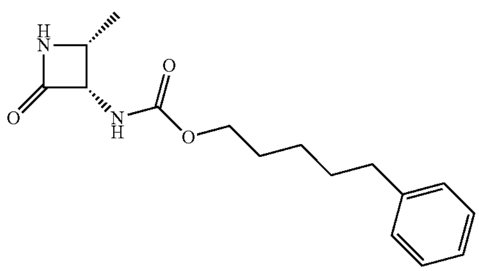 [SMILES: C[C@H]1NC(=O)[C@H]1NC(=O)OCCCCCc1ccccc1] | $C_{16}H_{22}N_2O_3$ | 5-Phenylpentyl-N-[(2R,3S)-2-methyl-4-oxo-azetidin-3-yl]-carbamate |
| 80 | 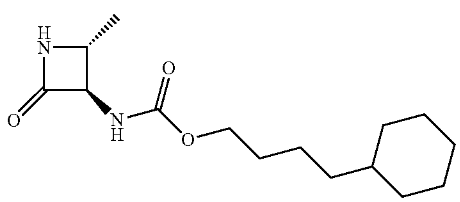 [SMILES: C[C@H]1NC(=O)[C@@H]1NC(=O)OCCCCC1CCCCC1] | $C_{15}H_{26}N_2O_3$ | 4-Cyclohexylbutyl-N-[(2R,3R)-2-methyl-4-oxo-azetidin-3-yl]-carbamate |
| 81 | 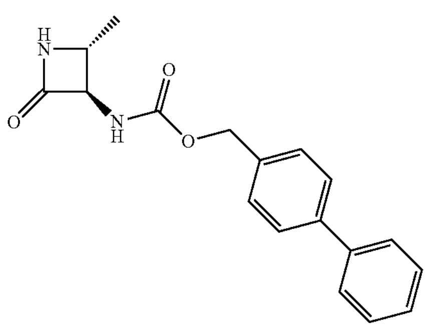 [SMILES: C[C@H]1NC(=O)[C@@H]1NC(=O)OCc1ccc(-c2ccccc2)cc1] | $C_{18}H_{18}N_2O_3$ | (4-Phenylphenyl)-methyl-N-[(2R,3R)-2-methyl-4-oxo-azetidin-3-yl]-carbamate |

TABLE 2-continued

Examples of compounds of the invention

| Example | Structure | Formula | Name |
|---|---|---|---|
| 82 | 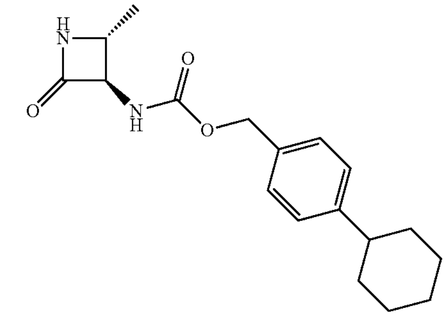 [SMILES: C[C@H]1NC(=O)[C@@H]1NC(=O)OCc1ccc(C2CCCCC2)cc1] | C{18}H{24}N{2}O{3} | (4-Cyclohexylphenyl)-methyl-N-[(2R,3R)-2-methyl-4-oxo-azetidin-3-yl]-carbamate |
| 83 | 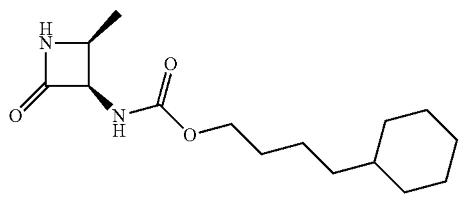 [SMILES: C[C@@H]1NC(=O)[C@@H]1NC(=O)OCCCCC1CCCCC1] | C{15}H{26}N{2}O{3} | 4-Cyclohexylbutyl-N-[(2S,3R)-2-methyl-4-oxo-azetidin-3-yl]-carbamate |
| 84 | 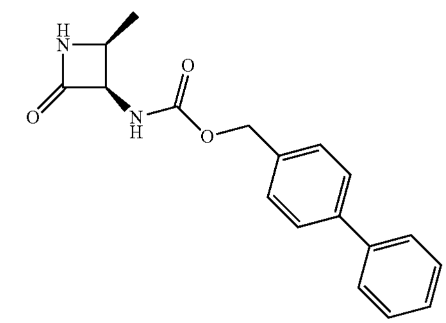 [SMILES: C[C@@H]1NC(=O)[C@@H]1NC(=O)OCc1ccc(-c2ccccc2)cc1] | C{18}H{18}N{2}O{3} | (4-Phenylphenyl)-methyl-N-[(2S,3R)-2-methyl-4-oxo-azetidin-3-yl]-carbamate |
| 85 | 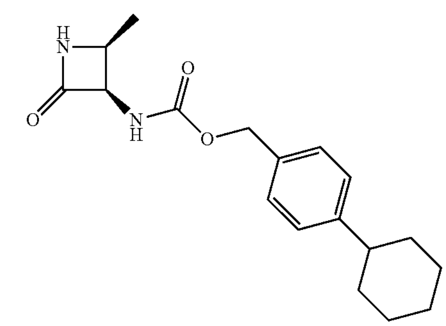 [SMILES: C[C@@H]1NC(=O)[C@@H]1NC(=O)OCc1ccc(C2CCCCC2)cc1] | C{18}H{24}N{2}O{3} | (4-Cyclohexylphenyl)-methyl-N-[(2S,3R)-2-methyl-4-oxo-azetidin-3-yl]-carbamate |
| 86 | 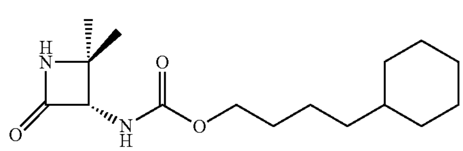 | C{16}H{28}N{2}O{3} | 4-Cyclohexylbutyl-N-[(3S)-2,2-dimethyl-4-oxo-azetidin-3-yl]-carbamate |
| 87 | 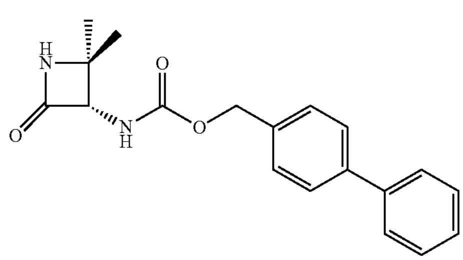 | C{19}H{20}N{2}O{3} | (4-Phenylphenyl)-methyl-N-[(3S)-2,2-dimethyl-4-oxo-azetidin-3-yl]-carbamate |

TABLE 2-continued

Examples of compounds of the invention

| Example | Structure | Formula | Name |
|---|---|---|---|
| 88 | 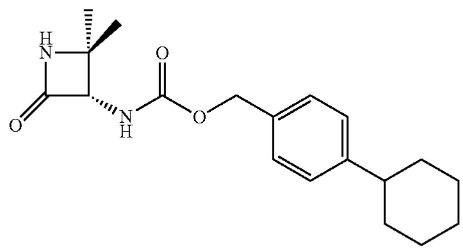 | $C_{19}H_{26}N_2O_3$ | (4-Cyclohexylphenyl)-methyl-N-[(3R)-2,2-dimethyl-4-oxo-azetidin-3-yl]-carbamate |
| 89 | 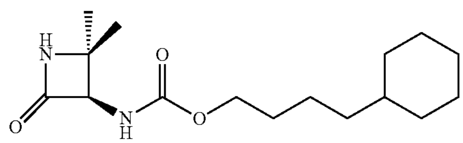 | $C_{16}H_{28}N_2O_3$ | 4-Cyclohexylbutyl-N-[(3R)-2,2-dimethyl-4-oxo-azetidin-3-yl]-carbamate |
| 90 | 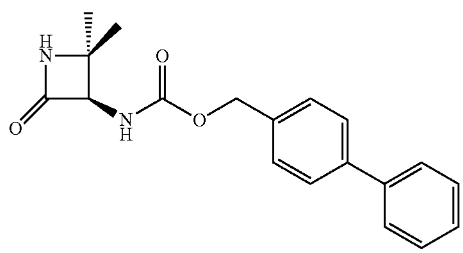 | $C_{19}H_{20}N_2O_3$ | (4-Phenylphenyl)-methyl-N-[(3R)-2,2-dimethyl-4-oxo-azetidin-3-yl]-carbamate |
| 91 | 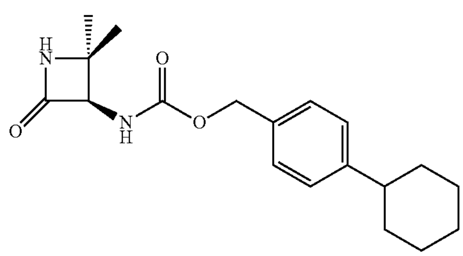 | $C_{19}H_{26}N_2O_3$ | (4-Cyclohexylphenyl)-methyl-N-[(3S)-2,2-dimethyl-4-oxo-azetidin-3-yl]-carbamate |
| 92 | 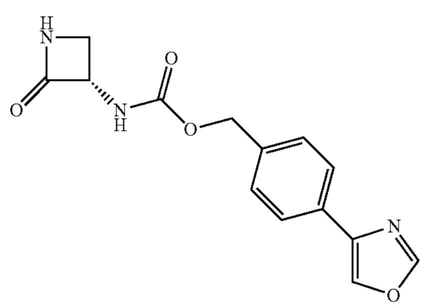 [SMILES: O=C(N[C@H]1CNC1=O)OCc1ccc(-c2cocn2)cc1] | $C_{14}H_{13}N_3O_4$ | (4-Oxazol-4-ylphenyl)-methyl-N-[(3S)-2-oxoazetidin-3-yl]-carbamate |
| 93 | 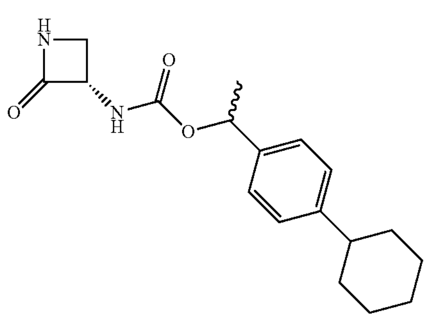 [SMILES: CC(OC(=O)N[C@H]1CNC1=O)c1ccc(C2CCCCC2)cc1] | $C_{18}H_{24}N_2O_3$ | [(1S)- and (1R)-1-(4-cyclohexylphenyl)-ethyl]-N-[(3S)-2-oxoazetidin-3-yl]-carbamate |

TABLE 2-continued

Examples of compounds of the invention

| Example | Structure | Formula | Name |
|---|---|---|---|
| 94 | 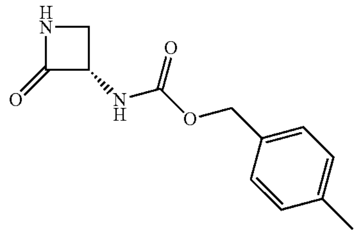 [SMILES: Cc1ccc(COC(=O)N[C@H]2CNC2=O)cc1] | $C_{12}H_{14}N_2O_3$ | p-Tolylmethyl-N-[(3S)-2-oxoazetidin-3-yl]-carbamate |
| 95 | 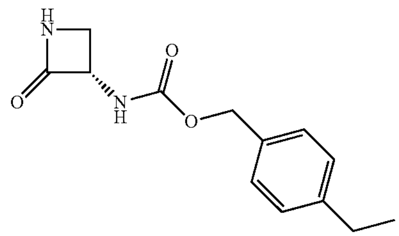 [SMILES: CCc1ccc(COC(=O)N[C@H]2CNC2=O)cc1] | $C_{13}H_{16}N_2O_3$ | (4-Ethylphenyl)-methyl-N-[(3S)-2-oxoazetidin-3-yl]-carbamate |
| 96 | 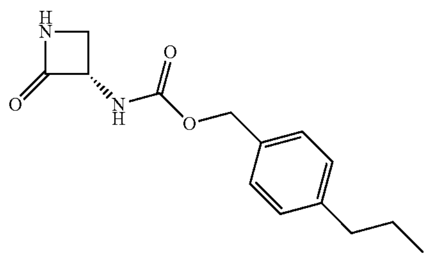 [SMILES: CCCc1ccc(COC(=O)N[C@H]2CNC2=O)cc1] | $C_{14}H_{18}N_2O_3$ | (4-Propylphenyl)-methyl-N-[(3S)-2-oxoazetidin-3-yl]-carbamate |
| 97 | 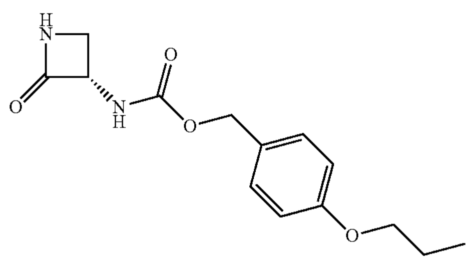 [SMILES: CCCOc1ccc(COC(=O)N[C@H]2CNC2=O)cc1] | $C_{14}H_{18}N_2O_4$ | (4-Propoxyphenyl)-methyl-N-[(3S)-2-oxoazetidin-3-yl]-carbamate |
| 98 | 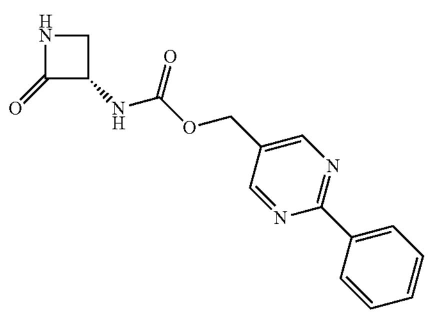 [SMILES: O=C(N[C@H]1CNC1=O)OCc1cnc(-c2ccccc2)nc1] | $C_{15}H_{14}N_4O_3$ | (2-Phenylpyrimidin-5-yl)-methyl-N-[(3S)-2-oxoazetidin-3-yl]-carbamate |
| 99 | 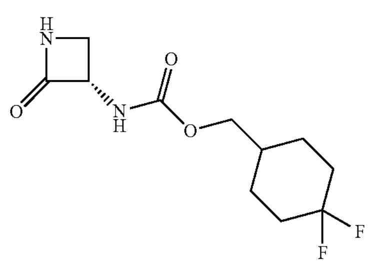 [SMILES: O=C(N[C@H]1CNC1=O)OCC1CCC(F)(F)CC1] | $C_{11}H_{16}F_2N_2O_3$ | (4,4-Difluorocyclohexyl)-methyl-N-[(3S)-2-oxoazetidin-3-yl]-carbamate |

TABLE 2-continued

Examples of compounds of the invention

| Example | Structure | Formula | Name |
|---|---|---|---|
| 100 | 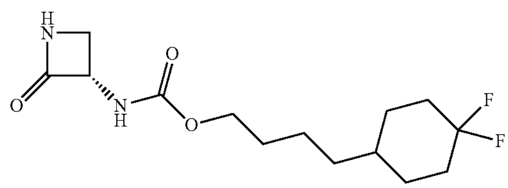 [SMILES: O=C(N[C@H]1CNC1=O)OCCCCC1CCC(F)(F)CC1] | $C_{14}H_{22}F_2N_2O_3$ | 4-(4,4-Difluorocyclohexyl)-butyl-N-[(3S)-2-oxoazetidin-3-yl]-carbamate |
| 101 | 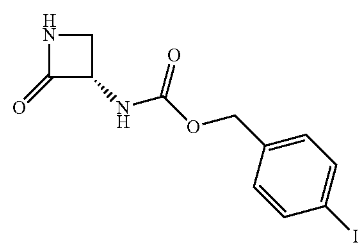 [SMILES: O=C(N[C@H]1CNC1=O)OCc1ccc(I)cc1] | $C_{11}H_{11}IN_2O_3$ | (4-Iodophenyl)-methyl-N-[(3S)-2-oxoazetidin-3-yl]-carbamate |
| 102 | 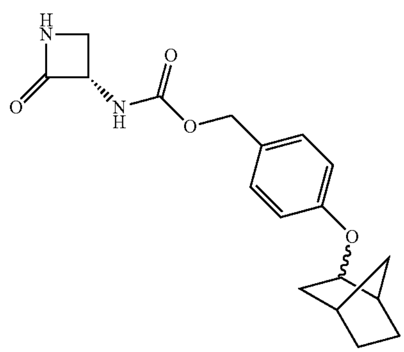 [SMILES: O=C(N[C@H]1CNC1=O)OCc1ccc(OC2CC3CCC2C3)cc1] | $C_{18}H_{22}N_2O_4$ | 4-[(1R,2R,4S)- and (1S,2S,4R)-Norbornan-2-yl]-oxyphenyl]-methyl-N-[(3S)-2-oxoazetidin-3-yl]-carbamate |
| 103 | 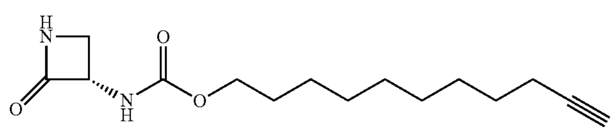 [SMILES: C#CCCCCCCCCCOC(=O)N[C@H]1CNC1=O] | $C_{15}H_{24}N_2O_3$ | Undec-10-ynyl-N-[(3S)-2-oxoazetidin-3-yl]-carbamate |
| 104 | 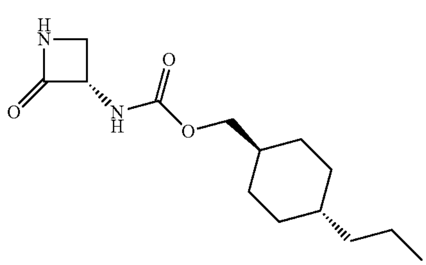 [SMILES: CCC[C@H]1CC[C@H](COC(=O)N[C@H]2CNC2=O)CC1] | $C_{14}H_{24}N_2O_3$ | [(1s,4S)-(4-propylcyclohexyl]-methyl-N-[(3S)-2-oxoazetidin-3-yl]-carbamate |
| 105 | 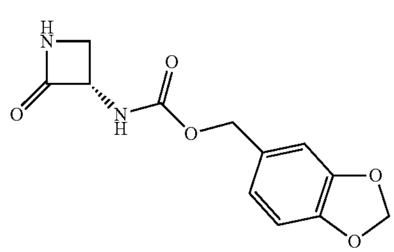 [SMILES: O=C(N[C@H]1CNC1=O)OCc1ccc2c(c1)OCO2] | $C_{12}H_{12}N_2O_5$ | 1,3-Benzodioxol-5-ylmethyl-N-[(3S)-2-oxoazetidin-3-yl]-carbamate |

TABLE 2-continued

Examples of compounds of the invention

| Example | Structure | Formula | Name |
| --- | --- | --- | --- |
| 106 | 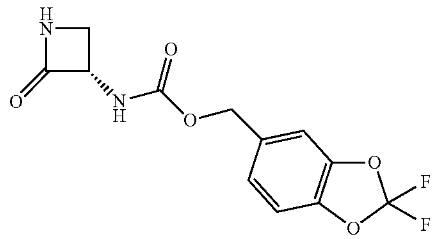 [SMILES: O=C(N[C@H]1CNC1=O)OCc1ccc2c(c1)OC(F)(F)O2] | $C_{12}H_{10}F_2N_2O_5$ | (2,2-Difluoro-1,3-benzodioxol-5-yl)-methyl-N-[(3S)-2-oxoazetidin-3-yl]-carbamate |

The compounds reported in Table 2 were synthesized as described below.

Solvents and reagents were obtained from commercial suppliers and were used without further purification. For simplicity, solvents and reagents were indicated as follows: Tetrahydrofuran (THF), diethyl ether (Et₂O), ethyl acetate (EtOAc), dichlorometane (CH₂Cl₂), isopropanol (iPrOH), dimethylsulfoxyde (DMSO) hydrochloric acid (HCl), cyclohexane (Cy), acetic acid (CH₃COOH), trifluoroacetic acid (TFA), N,N-dimethylformamide (DMF), triethylamine (Et₃N), methanol (MeOH), acetonitrile (CH₃CN), methyl tert-butyl ether (MTBE), ethanol (EtOH), N,N-Diisopropylethylamine (DIPEA), sodium bicarbonate (NaHCO₃), sodium solfate (Na₂SO₄), sodium hydroxide (NaOH), ammonium chloride (NH₄Cl), silica gel (SiO₂), sodium nitrite (NaNO₂), sodium carbonate (Na₂CO₃), potassium carbonate (K₂CO₃), potassium hydrogen sulfate (KHSO₄), 4-(dimethylamino)-pyridine (DMAP), di-2-pyridyl carbonate (2-DPC), carbonyl-diimidazole (CDI), lithium bis-(trimethylsilyl)-amide (LHMDS), n-butyllithium (BuLi), lithium aluminum hydride (LiAlH₄), sodium borohydride (NaBH₄), benzotriazol-1-yl-oxytripyrrolidinophosphonium hexafluorophosphate (PyBOP), O-benzotriazole-N,N,N',N'-tetramethyl-uronium hexafluorophosphate (HBTU), O-(benzotriazol-1-yl)-N,N,N',N'-tetra methyluronium tetra fluoroborate (TBTU), 1,3-dimethyl-3,4,5,6-tetrahydro-2(1H)-pyrimidinone (DMPU), triphenylphosphine (PPh₃), cerium (IV) ammonium nitrate (CAN), sodium hydride (NaH), cesium fluoride (CsF), tert-butyldimethylsilyl chloride (TBDM-SCl), potassium bis-(trimethylsilyl)-amide (KHMDS).

Preparation of [(3S)-2-oxoazetidin-3-yl]-ammonium acetate

The compound was synthesized according to a modified procedure described by Hanessian et al., *Can. J. Chem.* 1985, 63, 3613.

Step 1. Preparation of benzyl-N-[(1S)-1-(hydroxymethyl)-2-[(4-methoxyphenyl)-amino]-2-oxoethyl]-carbamate Under nitrogen atmosphere, to a cooled (0° C.), vigorously stirred solution of commercially available p-anisidine (141.5 g, 1.15 mol) in a 3:1 mixture of dry THF:CH₂Cl₂ (2.0 L), commercially available carbobenzyloxy-L-serine (50.0 g, 0.21 mol) and commercially available EDCI (43.9 g, 0.23 mol) were sequentially added. The resulting mixture was stirred at 0° C. for additional 0.5 h and then at r.t. for 16 h. After evaporation of the solvents, trituration with a 1:1 mixture Cy:EtOAc (3×0.4 L) mostly removed the excess of p-anisidine, and the resulting gummy residue was taken up in EtOAc (0.5 L) and washed with a 0.1 M HCl solution (10×0.4 L). The organic layer was dried over Na₂SO₄, filtered and concentrated to dryness affording the pure title compound (58.6 g, 82%), as a white solid. $R_t$=1.97 min. MS (ESI) m/z: 345 [M-H]⁺, 367 [M-Na]⁺, 383 [M-K]⁺. ¹H NMR (CDCl₃): δ 8.50-8.27 (bs, 1H), 7.44-7.29 (m, 6H), 6.90-6.81 (d, 2H, J=9.1 Hz), 5.97-5.80 (bs, 1H), 5.17 (s, 2H), 4.37-4.21 (m, 2H), 3.80 (s, 3H), 3.77-3.66 (m, 1H), 2.92-2.75 (bs, 1H).

Step 2. Preparation of benzyl-N-[(3S)-1-(4-methoxyphenyl)-2-oxo-azetidin-3-yl]-carbamate Under nitrogen atmosphere, to a cooled (0° C.), stirred solution of benzyl-N-[(1S)-1-(hydroxymethyl)-2-[(4-methoxyphenyl)-amino]-2-oxo-ethyl]-carbamate (58.6 g, 0.170 mol) in dry DMF (1.6 L), commercially available 1,1'-sulfonyldiimidazole (50.6 g, 0.256 mol) was added. The resulting mixture was stirred at 0° C. for additional 0.5 h and then cooled to −20° C. Under vigorous stirring, commercially available NaH (60% in mineral oil, 10.2 g, 0.256 mol) was added portion wise. The resulting suspension was vigorously stirred at −20° C. for additional 1 h, followed by the addition of MeOH (2.0 mL) and distilled H₂O (1.0 L). A precipitate was observed and filtered off. The solid was washed with additional H₂O (0.2 L) and the collected solid fractions were dried under reduced pressure at 40° C. for 5 h, affording the pure title compound (42.2 g, 76%), as a white solid. $R_t$=2.31 min. MS (ESI) m/z: 327 [M-H]⁺, 349 [M-Na]⁺, 365 [M-K]⁺. ¹H NMR (DMSO-d₆): δ 8.08 (d, 1H, J=8.5 Hz), 7.42-7.28 (m, 5H), 7.30 (d, 2H, J=8.9 Hz), 6.95 (d, 2H, J=8.9 Hz), 5.06 (s, 2H), 4.86 (ddd, 1H, J=8.5, 5.6, 2.6 Hz), 3.90 (t, 1H, J=5.6 Hz), 3.73 (s, 3H), 3.55 (dd, 1H, J=5.6, 2.6 Hz).

Step 3. Preparation of benzyl-N-[(3S)-2-oxoazetidin-3-yl]-carbamate

To a cooled (0° C.), vigorously stirred suspension of benzyl-N-[(3S)-1-(4-methoxyphenyl)-2-oxo-azetidin-3-yl]-carbamate (9.0 g, 0.028 mol) in MeCN (0.5 L) and H₂O (0.4 L), a solution of commercially available CAN (45.4 g, 0.083 mol) in H₂O (100 mL) was added dropwise over 45 min. The resulting mixture was stirred at 0° C. for additional 0.5 h and then NaHCO₃ saturated solution (0.5 L) was cautiously added followed by EtOAc (0.5 L). A colloidal precipitate was observed, filtered off and washed with additional EtOAc (0.2 L). The collected biphasic solution was partitioned and the organic phase was dried over Na₂SO₄. Activated charcoal was added to the solution and the organic phase was filtered through a pad of Celite and evaporated. Immediate trituration with Et$_2$O afforded the pure title compound (4.85 g, 80%), as an off-white solid. R$_t$=1.54 min. MS (ESI) m/z: 221 [M−H]$^+$, 243 [M−Na]$^+$, 259 [M−K]$^+$. $^1$H NMR (DMSO-d$_6$): δ 7.97 (d, 1H, J=8.7 Hz), 7.94 (bs, 1H), 7.42-7.30 (m, 5H), 5.05 (s, 2H), 4.67 (ddd, 1H, J=8.7, 5.4, 2.7 Hz), 3.40 (t, 1H, J=5.4 Hz), 3.09 (dd, 1H, J=5.4, 2.7 Hz).

Step 4. Preparation of [(3S)-2-oxoazetidin-3-yl]-ammonium acetate

Under nitrogen atmosphere, to a 0.05 M solution of benzyl-N-[(3S)-2-oxoazetidin-3-yl]-carbamate (3.28 g, 0.015 mol) in EtOH (0.3 L), cyclohexadiene (14.1 mL, 0.149 mol) and 10% Pd on activated charcoal (3.27 g) were sequentially added. The resulting suspension was stirred at r.t. for 12 h, then filtered off on a short pad of Celite. The outcoming solution was immediately trapped into a solution of AcOH (0.93 mL, 0.0164 mol) in EtOAc (0.245 L). Evaporation of solvents under reduced pressure, at a temperature below 35° C., gave a solid crude product (1.90 g). Trituration with THF afforded the pure title compound (1.72 g, 79%), as a white solid. $^1$H NMR (DMSO-d$_6$): δ 7.68 (bs, 1H), 3.99 (ddd, 1H, J=5.2, 2.4, 1.2 Hz), 3.32 (t, 1H, J=5.2 Hz), 2.79 (dd, 1H, J=5.2, 2.4 Hz), 1.90 (s, 3H).

Preparation of [(3R)-2-oxoazetidin-3-yl]-ammonium acetate

Step 1. Preparation of benzyl-N-[(1R)-1-(hydroxymethyl)-2-[(4-methoxyphenyl)-amino]-2-oxo-ethyl]-carbamate Under nitrogen atmosphere, to a cooled (0° C.), vigorously stirred solution of commercially available p-anisidine (14.15 g, 0.115 mol) in a 3:1 mixture of dry THF:CH$_2$Cl$_2$ (0.2 L), commercially available carbobenzyloxy-D-serine (5.0 g, 0.021 mol) and commercially available EDCI (4.39 g, 0.023 mol) were sequentially added. The resulting mixture was stirred at 0° C. for additional 0.5 h and then at r.t. for 16 h. After evaporation of the solvents, trituration with a 1:1 mixture Cy:EtOAc (3×40 mL) mostly removed the excess of p-anisidine, and the resulting gummy residue was taken up in EtOAc (1.0 L) and washed with a 0.1 M HCl solution (10×0.4 L). The organic layer was dried over Na$_2$SO$_4$, filtered and concentrated to dryness affording the pure title compound (6.46 g, 90%), as a white solid. R$_t$=1.97 min. MS (ESI) m/z: 345 [M−H]$^+$, 367 [M−Na]$^+$, 383 [M−K]$^+$. $^1$H NMR (CDCl$_3$): δ 8.50-8.27 (bs, 1H), 7.44-7.29 (m, 6H), 6.90-6.81 (d, 2H, J=9.1 Hz), 5.97-5.80 (bs, 1H), 5.17 (s, 2H), 4.37-4.21 (m, 2H), 3.80 (s, 3H), 3.77-3.66 (m, 1H), 2.92-2.75 (bs, 1H).

Step 2. Preparation of benzyl-N-[(3R)-1-(4-methoxyphenyl)-2-oxo-azetidin-3-yl]-carbamate Under nitrogen atmosphere, to a cooled (0° C.), stirred solution of benzyl-N-[(1R)-1-(hydroxymethyl)-2-[(4-methoxyphenyl)-amino]-2-oxo-ethyl]-carbamate (6.46 g, 0.019 mol) in dry DMF (0.17 L), commercially available 1,1'-sulfonyldiimidazole (5.69 g, 0.028 mol) was added. The resulting mixture was stirred at 0° C. for additional 0.5 h and then cooled to −20° C. Under vigorous stirring, commercially available NaH (60% in mineral oil, 1.125 g, 0.028 mol) was added portion wise. The resulting suspension was vigorously stirred at −20° C. for additional 1 h, followed by the addition of MeOH (0.5 mL) and distilled H$_2$O (0.22 L).

A precipitate was observed and filtered off. The solid was washed with additional H$_2$O (4×0.05 L) and the collected solid fractions were dried under reduced pressure at 40° C. for 16 h, affording the pure title compound (4.616 g, 75%), as a white solid. R$_t$=2.31 min. MS (ESI) m/z: 327 [M−H]$^+$, 349 [M−Na]$^+$, 365 [M−K]$^+$. $^1$H NMR (DMSO-d$_6$): δ 8.08 (d, 1H, J=8.5 Hz), 7.42-7.28 (m, 5H), 7.30 (d, 2H, J=8.9 Hz), 6.95 (d, 2H, J=8.9 Hz), 5.06 (s, 2H), 4.86 (ddd, 1H, J=8.5, 5.6, 2.6 Hz), 3.90 (t, 1H, J=5.6 Hz), 3.73 (s, 3H), 3.55 (dd, 1H, J=5.6, 2.6 Hz).

Step 3. Preparation of benzyl-N-[(3R)-2-oxoazetidin-3-yl]-carbamate

To a cooled (0° C.), vigorously stirred suspension of benzyl-N-[(3R)-1-(4-methoxyphenyl)-2-oxo-azetidin-3-yl]-carbamate (4.616 g, 0.014 mol) in MeCN (260 mL) and H$_2$O (200 mL), a solution of commercially available CAN (23.26 g, 0.042 mol) in H$_2$O (50 mL) was added dropwise over 45 min. The resulting mixture was stirred at 0° C. for additional 0.5 h and then NaHCO$_3$ saturated solution (250 mL) was cautiously added followed by EtOAc (150 mL). A colloidal precipitate was observed, filtered off and washed with additional EtOAc (150 mL). The collected biphasic solution was partitioned and the organic phase was dried over Na$_2$SO$_4$. Activated charcoal was added to the solution and the organic phase was filtered through a pad of Celite and evaporated. Immediate trituration with Et$_2$O afforded the pure title compound (2.29 g, 74%), as an off-white solid. R$_t$=1.54 min. MS (ESI) m/z: 221 [M−H]$^+$, 243 [M−Na]$^+$, 259 [M−K]$^+$. $^1$H NMR (DMSO-d$_6$): δ 7.97 (d, 1H, J=8.7 Hz), 7.94 (bs, 1H), 7.42-7.30 (m, 5H), 5.05 (s, 2H), 4.67 (ddd, 1H, J=8.7, 5.4, 2.7 Hz), 3.40 (t, 1H, J=5.4 Hz), 3.09 (dd, 1H, J=5.4, 2.7 Hz).

Step 4. Preparation of [(3R)-2-oxoazetidin-3-yl]-ammonium acetate

Under nitrogen atmosphere, to a 0.05 M solution of benzyl-N-[(3R)-2-oxoazetidin-3-yl]-carbamate (2.29 g, 0.01 mol) in EtOH (210 mL), cyclohexadiene (10.2 mL, 0.104 mol) and 10% Pd on activated charcoal (2.29 g) were sequentially added. The resulting suspension was stirred at r.t. for 16 h, then filtered off on a short pad of Celite. The outcoming solution was immediately trapped into a solution of AcOH (0.66 mL, 0.0115 mmol) in EtOAc (170 mL). Evaporation of solvents under reduced pressure afforded the pure title compound (1.46 g, quant.), as a white solid. $^1$H NMR (DMSO-d$_6$): δ 7.68 (bs, 1H), 3.99 (ddd, 1H, J=5.2, 2.4, 1.2 Hz), 3.32 (t, 1H, J=5.2 Hz), 2.79 (dd, 1H, J=5.2, 2.4 Hz), 1.90 (s, 3H).

Example 1.
Heptyl-N-[(3S)-2-oxoazetidin-3-yl]-carbamate

Step 1. Preparation of heptyl-2-pyridyl carbonate and heptyl-2-oxopyridine-1-carboxylate Under nitrogen atmosphere, to a stirred mixture of commercially available 1-heptanol (0.566 mL, 4.0 mmol) in dry CH$_2$Cl$_2$ (20 mL), dry Et$_3$N (0.67 mL, 4.8 mmol) and 2-DPC (1.04 g, 4.8 mmol) were added. The reaction mixture was stirred at r.t. for 16 h, then diluted with CH$_2$Cl$_2$ (50 mL) and sequentially washed with sat. NH$_4$Cl solution (25 mL), sat. NaHCO$_3$ solution (3×25 mL) and brine (25 mL). The organic layer was dried over Na$_2$SO$_4$, filtered and concentrated to dryness affording an orange oil (0.8 g), as a mixture (1:10 ratio) of heptyl-2-pyridyl carbonate and heptyl-2- oxopyridine-1-carboxylate. The mixture of isomers was not separated and used in the next step without any further purification. $R_t$=2.61 min. MS (ESI) m/z: 238 [M-H]$^+$, 260 [M–Na]$^+$, 276 [M–K]$^+$.

Step 2. Preparation of heptyl-N-[(3S)-2-oxoazetidin-3-yl]-carbamate

Under nitrogen atmosphere, to a suspension of [(3S)-2-oxoazetidin-3-yl]-ammonium acetate (0.04 g, 0.27 mmol) in dry CH$_2$Cl$_2$ (4.0 mL), DIPEA (0.053 mL, 0.32 mmol) was added dropwise. Subsequently, the crude mixture (0.704 g) containing heptyl-2-oxopyridine-1-carboxylate (0.064 g, 0.27 mmol) in dry CH$_2$Cl$_2$ (2.0 mL) was added. The reaction mixture was stirred at r.t. for 15 h, then concentrated to dryness giving an oily product (0.20 g). Purification by typical silica gel flash chromatography (Cy/EtOAc, from 100:0 to 40:60) afforded the pure title compound (0.02 g, 30%), as a white solid. $R_t$=2.18 min. MS (ESI) m/z: 229 [M-H]$^+$, 251 [M–Na]$^+$, 267 [M–K]$^+$. $^1$H NMR (DMSO-d$_6$): δ 7.90 (bs, 1H), 7.78 (d, 1H, J=8.6 Hz), 4.58-4.62 (m, 1H), 3.95 (t, 2H, J=6.7 Hz), 3.37 (t, 1H, J=5.4 Hz), 3.07 (dd, 1H, J=5.4, 2.7 Hz), 1.59-1.48 (m, 2H), 1.35-1.21 (m, 8H), 0.86 (t, 3H, J=6.9 Hz).

Example 2. Heptyl-N-[(3R)-2-oxoazetidin-3-yl]-carbamate

Step 1. Preparation of heptyl-N-[(3R)-2-oxoazetidin-3-yl]-carbamate

Under nitrogen atmosphere, to a suspension of [(3R)-2-oxoazetidin-3-yl]-ammonium acetate (0.02 g, 0.14 mmol) in dry CH$_2$Cl$_2$ (2.0 mL), DIPEA (0.027 mL, 0.16 mmol) was added dropwise. Subsequently, the crude mixture (0.36 g) containing heptyl-2-oxopyridine-1-carboxylate (0.033 g, 0.14 mmol) [see example 1, step 1] in dry CH$_2$Cl$_2$ (2.0 mL) was added. The reaction mixture was stirred at r.t. for 16 h, concentrated to dryness affording an oily product (0.20 g). Purification by typical silica gel flash chromatography afforded the pure title compound (0.02 g, 30%), as a white solid. $R_t$=2.19 min. MS (ESI) m/z: 229 [M-H]$^+$, 251 [M–Na]$^+$, 267 [M–K]$^+$. $^1$H NMR (DMSO-d$_6$): δ 7.90 (bs, 1H), 7.78 (d, 1H, J=8.6 Hz), 4.58-4.62 (m, 1H), 3.95 (t, 2H, J=6.7 Hz), 3.37 (t, 1H, J=5.4 Hz), 3.07 (dd, 1H, J=5.4, 2.7 Hz), 1.59-1.48 (m, 2H), 1.35-1.21 (m, 8H), 0.86 (t, 3H, J=6.9 Hz).

Example 3. 5-Phenylpentyl-N-[(3S)-2-oxoazetidin-3-yl]-carbamate

Step 1. Preparation of 5-phenylpentyl-2-pyridyl carbonate and 5-phenylpentyl-2-oxopyridine-1-carboxylate Under nitrogen atmosphere, to a stirred solution of commercially available 5-phenyl-1-heptanol (0.300 mL, 1.83 mmol) in dry CH$_2$Cl$_2$ (12.0 mL), dry Et$_3$N (0.31 mL, 2.2 mmol) and 2-DPC (0.474 g, 2.2 mmol) were added. The reaction mixture was stirred at r.t. for 16 h, then diluted with CH$_2$Cl$_2$ (50 mL) and sequentially washed with sat. NH$_4$Cl solution (25 mL), sat. NaHCO$_3$ solution (3×25 mL) and brine (25 mL). The organic layer was dried over Na$_2$SO$_4$, filtered and concentrated to dryness giving an oily product (0.521 g), as a mixture (1:3.7 ratio) of 5-phenylpentyl-2-pyridyl carbonate and 5-phenylpentyl-2-oxopyridine-1-carboxylate. The mixture of isomers was not separated and used in the next step without any further purification. $R_t$=2.62 min. MS (ESI) m/z: 286 [M-H]$^+$, 308 [M–Na]$^+$, 324 [M–K]$^+$.

Step 2. Preparation of 5-phenylpentyl-N-[(3S)-2-oxoazetidin-3-yl]-carbamate

Under nitrogen atmosphere, to a suspension of [(3S)-2-oxoazetidin-3-yl]-ammonium acetate (0.06 g, 0.41 mmol) in dry CH$_2$Cl$_2$ (4.0 mL), DIPEA (0.081 mL, 0.49 mmol) was added dropwise. Subsequently, the crude mixture (0.550 g) containing 5-phenylpentyl-2-oxopyridine-1-carboxylate (0.117 g, 0.41 mmol) in dry CH$_2$Cl$_2$ (2.0 mL) was added. The reaction mixture was stirred at r.t. for 16 h, then concentrated to dryness giving an oily product (0.32 g). Purification by preparative HPLC afforded the pure title compound (0.034 g, 30%), as a white solid. $R_t$=2.23 min. MS (ESI) m/z: 277 [M-H]$^+$, 299 [M–Na]$^+$, 315 [M–K]$^+$. $^1$H NMR (DMSO-d$_6$): δ 7.90 (s, 1H), 7.78 (d, 1H, J=8.7 Hz), 7.30-7.24 (m, 2H), 7.21-7.13 (m, 3H), 4.66-4.46 (m, 1H), 3.95 (t, 2H, J=6.4 Hz), 3.37 (t, 1H, J=5.3 Hz), 3.06 (dd, 1H, J=5.3, 2.8 Hz), 2.57 (t, 2H, J=7.6 Hz), 1.63-1.52 (m, 4H), 1.37-1.27 (m, 2H).

Example 4. 5-Phenylpentyl-N-[(3R)-2-oxoazetidin-3-yl]-carbamate

Step 1. Preparation of 5-phenylpentyl-N-[(3R)-2-oxoazetidin-3-yl]-carbamate

Under nitrogen atmosphere, to a suspension of [(3R)-2-oxoazetidin-3-yl]-ammonium acetate (0.035 g, 0.24 mmol) in dry CH$_2$Cl$_2$ (4.0 mL), DIPEA (0.048 mL, 0.29 mmol) was added dropwise. Subsequently, the crude mixture (0.32 g) containing 5-phenylpentyl-2-oxopyridine-1-carboxylate (0.068 g, 0.24 mmol) [see example 3, step 1] in dry CH$_2$Cl$_2$ (2.0 mL) was added dropwise. The reaction mixture was stirred at r.t. for 16 h, concentrated to dryness affording an oily product (0.32 g), which was purified by preparative HPLC affording the pure title compound (0.018 g, 27%), as a white solid. $R_t$=2.24 min; MS (ESI) m/z: 277 [M-H]$^+$, 299 [M–Na]$^+$, 315 [M–K]$^+$. $^1$H NMR (DMSO-d$_6$): δ 7.90 (s, 1H), 7.78 (d, 1H, J=8.7 Hz), 7.30-7.24 (m, 2H), 7.21-7.13 (m, 3H), 4.66-4.46 (m, 1H), 3.95 (t, 2H, J=6.4 Hz), 3.37 (t, 1H, J=5.3 Hz), 3.06 (dd, 1H, J=5.3, 2.8 Hz), 2.57 (t, 2H, J=7.6 Hz), 1.63-1.52 (m, 4H), 1.37-1.27 (m, 2H).

Example 5. 4-Cyclohexylbutyl-N-[(3S)-2-oxoazetidin-3-yl]-carbamate

Step 1. Preparation of 4-cyclohexylbutyl-2-pyridyl carbonate and 4-cyclohexylbutyl-2-oxopyridine-1-carboxylate Under nitrogen atmosphere, to a stirred solution of commercially available 4-cyclohexyl-1-butanol (0.89 mL, 5.13 mmol) in dry CH$_2$Cl$_2$ (30 mL), DMAP (0.063 g, 0.51 mmol) and 2-DPC (1.33 g, 6.16 mmol) were added. The reaction mixture was stirred at r.t. for 16 h, then diluted with CH$_2$Cl$_2$ (50 mL) and sequentially washed with sat. NH$_4$Cl solution (25 mL), sat. NaHCO$_3$ solution (3×25 mL) and brine (25 mL). The organic layer was dried over Na$_2$SO$_4$, filtered and concentrated to dryness affording a pale yellow oil (1.6 g), as a mixture (1:1.7 ratio) of 4-cyclohexylbutyl-2-pyridyl carbonate and 4-cyclohexylbutyl-2-oxopyridine-1-carboxylate. The mixture of isomers was not separated and used in the next step without any further purification. $R_t$=3.00 min. MS (ESI) m/z: 278 [M-H]+, 300 [M-Na]+, 316 [M-K]+.

Step 2. Preparation of 4-cyclohexylbutyl-N-[(3S)-2-oxoazetidin-3-yl]-carbamate

Under nitrogen atmosphere, to a suspension of [(3S)-2-oxoazetidin-3-yl]-ammonium acetate (0.05 g, 0.34 mmol) in dry $CH_2Cl_2$ (4.0 mL), DIPEA (0.067 mL, 0.41 mmol) was added dropwise. Subsequently, the crude mixture (0.254 g) containing 4-cyclohexylbutyl-2-oxopyridine-1-carboxylate (0.094 g, 0.34 mmol) in dry $CH_2Cl_2$ (2.0 mL) was added. The reaction mixture was stirred at r.t. for 16 h, then concentrated to dryness giving an oily product (0.33 g). Purification by typical silica gel flash chromatography (Cy/EtOAc 33:67) afforded the pure title compound (0.053 g, 58%), as a white solid. $R_t$=2.56 min. MS (ESI) m/z: 269 [M-H]+, 291 [M-Na]+, 307 [M-K]+. $^1$H NMR (DMSO-$d_6$): δ 7.90 (s, 1H), 7.78 (d, 1H, J=8.8 Hz), 4.67-4.50 (m, 1H), 3.94 (t, 2H, J=6.7 Hz), 3.37 (t, 1H, J=5.4 Hz), 3.06 (dd, 1H, J=5.4, 2.8 Hz), 1.72-1.45 (m, 7H), 1.36-1.07 (m, 8H), 0.91-0.77 (m, 2H).

Example 6. 6-Cyclohexylbutyl-N-[(3R)-2-oxoazetidin-3-yl]-carbamate

Step 1. Preparation of 4-cyclohexylbutyl-N-[(3R)-2-oxoazetidin-3-yl]-carbamate

Under nitrogen atmosphere, to a suspension of [(3R)-2-oxoazetidin-3-yl]-ammonium acetate (0.05 g, 0.34 mmol) in dry $CH_2Cl_2$ (4.0 mL), DIPEA (0.067 mL, 0.41 mmol) was added dropwise. Subsequently, the crude mixture (0.25 g) [see example 5, step 1] containing 4-cyclohexylbutyl-2-oxopyridine-1-carboxylate (0.094 g, 1.0 mmol) in dry $CH_2Cl_2$ (2.0 mL) was added. The reaction mixture was stirred at r.t. for 16 h, concentrated to dryness affording an oily product (0.50 g). Purification by typical silica gel flash chromatography (Cy/EtOAc 33:67) afforded the pure title compound (0.048 g, 53%), as a white solid. $R_t$=2.56 min; MS (ESI) m/z: 269 [M-H]+, 291 [M-Na]+, 307 [M-K]+. MS (ESI) m/z: 269 [M-H]+, 291 [M-Na]+, 307 [M-K]+.]+. $^1$H NMR (DMSO-$d_6$): δ 7.90 (s, 1H), 7.78 (d, 1H, J=8.8 Hz), 4.67-4.50 (m, 1H), 3.94 (t, 2H, J=6.7 Hz), 3.37 (t, 1H, J=5.4 Hz), 3.06 (dd, 1H, J=5.4, 2.8 Hz), 1.72-1.45 (m, 7H), 1.36-1.07 (m, 8H), 0.91-0.77 (m, 2H).

Example 7. (1s,4R) and (1r,4S)-(4-Benzylcyclohexyl)-N-[(3S)-2-oxoazetidin-3-yl]-carbamate Step 1. Preparation of 8-benzylidene-1,4-dioxaspiro-[4.5]-decane To a stirred suspension of NaH (60% in mineral oil, 0.306 g, 12.8 mmol) in DMSO (10 mL), a solution of benzyltriphenylphosphonium bromide (5.44 g, 12.8 mmol) in DMSO (30 mL) was slowly added. The solution was stirred at r.t. for 30 min and then at 50° C. for further 30 min. Upon the crude mixture turning into dark red color, a solution of 1,4-dioxaspiro-[4.5]-decan-8-one (2.0 g, 12.8 mmol) in DMSO (14 mL) was added. The solution was stirred at 50° C. for 16 h. The reaction mixture was quenched with $H_2O$ and the aqueous layer extracted with EtOAc (3×20 mL). The combined organic layers were washed with brine, dried over $Na_2SO_4$, filtered and concentrated to dryness. Purification by typical silica gel flash chromatography using a Teledyne ISCO apparatus, eluting with Cy/AcOEt (from 100:0 to 40:60) afforded the pure title compound (1.8 g, 61%) as a white solid. $^1$H NMR (CDCl$_3$): δ 7.35-7.28 (m, 2H), 7.23-7.17 (m, 3H), 6.31 (s, 1H), 3.99 (s, 4H), 2.57-2.49 (m, 2H), 2.47-2.40 (m, 2H), 1.84-1.77 (m, 2H), 1.73-1.66 (m, 2H).

Step 2. Preparation of 4-benzylidenecyclohexanone

Under vigorous stirring, 8-benzylidene-1,4-dioxaspiro-[4.5]-decane (1.8 g, 7.8 mmol) was dissolved in a acetone/HCl (10% v/v) mixture (70 mL:35 mL) and left to stir for 4 h. The crude mixture was diluted in $H_2O$ and extracted with EtOAc (3×40 mL). The combined organic layers were washed with brine, dried over $Na_2SO_4$, filtered and concentrated to dryness to afford pure title compound (1.4 g, 96%) as a colorless oil. $^1$H NMR (CDCl$_3$): δ 7.39-7.32 (m, 2H), 7.27-7.21 (m, 3H), 6.49 (s, 1H), 2.80-2.74 (m, 2H), 2.72-2.65 (m, 2H), 2.53 (t, 2H, J=6.8 Hz), 2.44 (t, 2H, J=7.0 Hz).

Step 3. Preparation of (S,E)- and (R,Z)-4-benzylidenecyclohexanol

To a stirred mixture of NaBH$_4$ in dry MeOH (10 mL), at 0° C., under nitrogen atmosphere, 4-benzylidenecyclohexanone (1.4 g, 7.50 mmol) dissolved in dry MeOH (30 mL) was added. The crude mixture was left to stir at 0° C. for 1 h and subsequently quenched with $H_2O$ (5.0 mL). Methanol was rotary evaporated and the crude mixture was dissolved in AcOEt (20 mL). The organic solution was extracted with brine, dried over $Na_2SO_4$, filtered and concentrated to dryness. Purification by typical silica gel flash chromatography using a Teledyne ISCO apparatus, eluting with Cy/AcOEt (from 100:0 to 50:50) afforded the title compounds (1.2 g, 91%) as a mixture (ratio 1:1) of two isomers, as transparent oils. $^1$H NMR (CDCl$_3$) (as a 1:1 mixture of isomers): δ 7.37-7.29 (m, 4H), 7.24-7.18 (m, 6H), 6.30 (s, 2H), 3.94-3.85 (m, 2H), 2.78 (dt, 2H, J=13.9, 5.0 Hz), 2.47 (dt, 2H, J=13.5, 4.9 Hz), 2.30-2.20 (m, 2H), 2.19-2.08 (m, 2H), 2.07-1.98 (m, 2H), 1.98-1.88 (m, 2H), 1.88-1.75 (m, 2H), 1.62-1.51 (m, 2H), 1.50-1.39 (m, 2H).

Step 4. Preparation of (1r,4r)- and (1s,4s)-4-benzylcyclohexanol

A solution of AcOEt (60 mL) containing (S,E)- and (R,Z)-4-benzylidenecyclohexanol (0.3 g, 1.59 mmol) was passed through an H-Cube® hydrogenator flow reactor provided with a 10% Pd/C cartridge (flow rate: 1.0 mL/min; P=1.0 bar; T=30° C.). The recovered organic solution was concentrated to dryness to afford the pure title compounds (0.29 g, 95%) as a mixture (ratio 1:1) of two isomers, as transparent oil. $^1$H NMR (CDCl$_3$) (as a 1:1 mixture of isomers): δ 7.32-7.24 (m, 4H), 7.22-7.10 (m, 6H), 2.55 (d, 2H, J=7.2 Hz), 2.49 (d, 2H, J=7.1 Hz), 2.01-1.89 (m, 2H), 1.80-1.68 (m, 4H), 1.65-1.35 (m, 12H), 1.30-1.14 (m, 2H), 1.11-0.95 (m, 2H).

Step 5. Preparation of (1r,4r)- and (1s,4s)-4-benzylcyclohexyl-2-pyridyl carbonate and (1r,4r)- and (1s,4s)-4-benzylcyclohexyl-2-oxopyridine-1-carboxylate Under nitrogen atmosphere, to a stirred mixture of (1r,4r)- and (1s,4s)-4-benzylcyclohexanol (0.67 g, 3.5 mmol) in dry $CH_2Cl_2$ (7.0 mL), DMAP (0.043 g, 0.35 mmol) and 2-DPC (0.91 g, 4.22 mmol) were added. The reaction mixture was left to react at r.t. for 15 h, then diluted with $CH_2Cl_2$ and sequentially washed with a sat. NH$_4$Cl solution (3.0 mL) and a sat. NaHCO$_3$ solution (3×3.0 mL). The organic layer was dried over Na$_2$SO$_4$, filtered and concentrated to dryness to afford a yellow oil (1.0 g), as a mixture (1:1.5 ratio) of (1r,4r)- and (1s,4s)-4-benzylcyclohexyl-2-pyridyl carbonate and (1r,4r)- and (1s,4s)-4-benzylcyclohexyl-2-oxopyridine-1-carboxylate. The mixture of isomers was not separated and used in the next step without any further purification. R$_t$=3.03 min. MS (ESI) m/z: 312 [M-H]$^+$, 334 [M–Na]$^+$.

Step 6. Preparation of (1s,4R) and (1r,4S)-(4-benzylcyclohexyl)-N-[(3S)-2-oxoazetidin-3-yl]-carbamate Under nitrogen atmosphere, to a suspension of [(3S)-2-oxoazetidin-3-yl]-ammonium acetate (0.05 g, 0.34 mmol) in dry CH$_2$Cl$_2$ (4.0 mL), DIPEA (0.067 mL, 0.41 mmol) was dropwise added. Subsequently, the crude mixture (0.35 g) containing (1r,4r)- and (1s,4s)-4-benzylcyclohexyl-2-oxopyridine-1-carboxylate (0.10 g, 0.34 mmol) in dry CH$_2$Cl$_2$ (2.0 mL) was added. The reaction mixture was stirred at r.t. for 16 h and concentrated to dryness giving an oily residue (0.32 g). Purification by typical silica gel flash chromatography (Cy/EtOAc from 100:0 to 30:70) afforded the pure title compounds (0.053 g, 58%), as a mixture (1:1 ratio) of isomers, as white solids. Isomer 1:R$_t$=2.31 min. MS (ESI) m/z: 303 [M-H]$^+$, 325 [M–Na]$^+$, 341 [M–K]$^+$; (ESI) m/z: 301 [M-H]$^-$ Isomer 2: R$_t$=2.37 min. MS (ESI) m/z: 303 [M-H]$^+$, 325 [M–Na]$^+$, 341 [M–K]$^+$. $^1$H NMR (DMSO-d$_6$): δ 7.89 (bs, 2H), 7.74 (bs, 2H), 7.34-7.24 (m, 4H), 7.19-7.16 (m, 6H), 4.75 (bs, 1H), 4.63 (bs, 2H), 4.44-4.40 (m, 1H), 3.43-3.36 (m, 2H), 3.12 (dd, 1H, J=4.9, 2.7 Hz), 3.08 (dd, 1H, J=5.1, 2.8 Hz), 1.90-1.86 (m, 2H), 1.77-1.57 (m, 6H), 1.52-1.40 (m, 6H), 1.36-1.18 (m, 4H), 1.14-0.97 (m, 4H).

Example 8. (R,E) and (S,Z)-(4-Benzylidenecyclohexyl)-N-[(3S)-2-oxoazetidin-3-yl]-carbamate Step 1. Preparation of (S,E) and (R,Z)-4-benzylidenecyclohexyl-2-pyridyl-carbonate and (S,E) and (R,Z)-4-benzylidenecyclohexyl-2-oxopyridine 1-carboxylate Under nitrogen atmosphere, to a stirred mixture of (S,E)- and (R,Z)-4-benzylidenecyclohexanol [see example 7, step 3] (0.45 g, 2.38 mmol) in dry CH$_2$Cl$_2$ (5.0 mL), DMAP (0.029 g, 0.24 mmol) and 2-DPC (0.61 g, 2.86 mmol) were added. The reaction mixture was left to react at r.t. for 16 h, then diluted with CH$_2$Cl$_2$ and sequentially washed with sat. NH$_4$Cl solution (3.0 mL) and a sat. NaHCO$_3$ solution (3×3.0 mL). The organic layer was dried over Na$_2$SO$_4$, filtered and concentrated to dryness giving a yellow oil (0.73 g), as a mixture of (S,E) and (R,Z)-4-benzylidenecyclohexyl-2-pyridyl-carbonate and (S,E) and (R,Z)-4-benzylidenecyclohexyl-2-oxopyridine 1-carboxylate (1:1.8 ratio). The mixture of isomers was not separated and used in the next step without any further purification. R$_t$=2.74 min. MS (ESI) m/z: 310 [M-H]$^+$, 332 [M–Na]$^+$.

Step 2. Preparation of (R,E) and (S,Z)-(4-benzylidenecyclohexyl) N-[(3S)-2-oxoazetidin-3-yl]-carbamate Under nitrogen atmosphere, to a suspension of [(3S)-2-oxoazetidin-3-yl]-ammonium acetate (0.05 g, 0.34 mmol) in dry CH$_2$Cl$_2$ (4.0 mL), DIPEA (0.07 mL, 0.41 mmol) was added dropwise. Subsequently, the crude mixture (0.29 g) containing (S,E) and (R,Z)-4-benzylidenecyclohexyl-2-pyridyl-carbonate and (S,E) and (R,Z)-4-benzylidenecyclohexyl-2-oxopyridine 1-carboxylate (0.11 g, 0.34 mmol) in dry CH$_2$Cl$_2$ (2.0 mL) was added. The reaction mixture was stirred at r.t. for 16 h, then concentrated to dryness giving an oily residue (0.36 g). Purification by typical silica gel flash chromatography (Cy/EtOAc from 100:0 to 30:70) afforded the pure title compounds (0.073 g, 71%), as a mixture (1:1 ratio) of isomers, as white solids. R$_t$=2.29. MS (ESI) m/z: 301 [M-H]$^+$, 323 [M–Na]$^+$, 339 [M–K]$^+$; $^1$H NMR (DMSO-d$_6$): δ 7.91 (s, 2H), 7.82 (d, 2H, J=8.8 Hz), 7.39-7.29 (m, 4H), 7.20 (t, 6H, J=6.5 Hz), 6.30 (s, 2H), 4.78-4.76 (m, 2H), 4.67-4.64 (m, 2H), 3.38 (t, 2H, J=5.3 Hz), 3.09-3.07 (m, 2H), 2.46-2.40 (m, 4H), 1.99-1.66 (m, 6H), 1.63-1.41 (m, 6H).

Example 9. [(E)-Non-3-enyl]-N-[(3S)-2-oxoazetidin-3-yl]-carbamate

Step 1. Preparation of (E)-non-3-en-1-ol

Under nitrogen atmosphere, to a stirred and cooled (0° C.) suspension of LiAlH$_4$ (2.0 M THF solution, 11.8 mL, 23.53 mmol) in dry Et$_2$O (65 mL), commercially available methyl (E)-non-3-enoate (1.13 g, 5.88 mmol) in dry Et$_2$O (5.0 mL) was added dropwise. The resulting reaction mixture was stirred at r.t. for 4 h, and then cooled to 0° C. H$_2$O (0.9 mL) was slowly added, followed by 3.0 M KOH solution (0.89 mL) and additional H$_2$O (3.0 mL). The mixture was stirred at 0° C. for 1 h and then filtered off. The organic layer was dried over Na$_2$SO$_4$, filtered and concentrated to dryness, affording the title compound (0.85 g, quant.), which was used in the next step without any further purification. $^1$H NMR (DMSO-d$_6$): δ 5.47-5.33 (m, 2H), 4.41 (t, 1H, J=5.3 Hz), 3.38 (td, 2H, J=6.9, 5.3 Hz), 2.13-2.07 (m, 2H), 1.98-1.90 (m, 2H), 1.36-1.18 (m, 6H), 0.86 (t, 3H, J=7.1 Hz).

Step 2. Preparation of [(E)-non-3-enyl]-2-pyridyl carbonate and [(E)-non-3-enyl]-2-oxopyridine-1-carboxylate Under nitrogen atmosphere, to a stirred solution of (E)-non-3-en-1-ol (0.2 g, 1.41 mmol) in dry CH$_2$Cl$_2$ (8.0 mL), DMAP (0.017 g, 0.14 mmol) and 2-DPC (0.365 g, 1.69 mmol) were added. The reaction mixture was stirred at r.t. for 16 h, then diluted with CH$_2$Cl$_2$ and sequentially washed with sat. NH$_4$Cl solution (20 mL) and sat. NaHCO$_3$ solution (3×20 mL). The organic layer was dried over Na$_2$SO$_4$, filtered and concentrated to dryness affording a yellow oil (0.37 g), as a mixture (1:1.8 ratio) of [(E)-non-3-enyl]-2-pyridyl carbonate and [(E)-non-3-enyl]-2-oxopyridine-1-carboxylate. The mixture of isomers was not separated and used in the next step without any further purification. R$_t$=2.84 min. MS (ESI) m/z: 264 [M-H]$^+$, 286 [M–Na]$^+$, 302 [M–K]$^+$.

Step 3. Preparation of [(E)-non-3-enyl]-N-[(3S)-2-oxoazetidin-3-yl]-carbamate

Under nitrogen atmosphere, to a suspension of [(3S)-2-oxoazetidin-3-yl]-ammonium acetate (0.05 g, 0.34 mmol) in dry CH$_2$Cl$_2$ (4.0 mL), DIPEA (0.067 mL, 0.41 mmol) was added dropwise. Subsequently, the crude mixture (0.250 g) containing [(E)-non-3-enyl]-2-oxopyridine-1-carboxylate (0.089 g, 0.34 mmol) in dry CH$_2$Cl$_2$ (2.0 mL) was added. The reaction mixture was stirred at r.t. for 16 h, then concentrated to dryness giving an oily residue (0.24 g).

Trituration with Cy/EtOAc (50:50) afforded the pure title compound (0.051 g, 59%), as a white solid. $R_t$=2.44 min. MS (ESI) m/z: 255 [M-H]$^+$, 277 [M−Na]$^+$, 293 [M−K]$^+$. $^1$H NMR (DMSO-d$_6$): δ 7.90 (s, 1H), 7.80 (d, 1H, J=8.8 Hz), 5.59-5.31 (m, 2H), 4.67-4.48 (m, 1H), 3.95 (t, 2H, J=6.8 Hz), 3.37 (t, 1H, J=5.2 Hz), 3.06 (dd, 1H, J=5.2, 2.8 Hz), 2.24 (q, 2H, J=6.8 Hz), 2.01-1.91 (m, 2H), 1.37-1.18 (m, 6H), 0.86 (t, 3H, J=7.1 Hz).

Example 10. [(Z)-Non-3-enyl]-N-[(3S)-2-oxoazetidin-3-yl]-carbamate

Step 1. Preparation of [(Z)-non-3-enyl]-2-pyridyl carbonate and [(Z)-non-3-enyl]-2-oxopyridine-1-carboxylate Under nitrogen atmosphere, to a stirred solution of commercially available (Z)-non-3-en-1-ol (0.236 mL, 1.40 mmol) in dry CH$_2$Cl$_2$ (9.0 mL), DMAP (0.017 g, 0.14 mmol) and 2-DPC (0.36 g, 1.68 mmol) were added. The reaction mixture was stirred at r.t. for 16 h, then diluted with CH$_2$Cl$_2$ (40 mL) and sequentially washed with sat. NH$_4$Cl solution (10 mL) and sat. NaHCO$_3$ solution (3×10 mL). The organic layer was dried over Na$_2$SO$_4$, filtered and concentrated to dryness affording a yellow oil (0.34 g), as a mixture (1:1.9 ratio) of [(Z)-non-3-enyl]-2-pyridyl carbonate and [(Z)-non-3-enyl]-2-oxopyridine-1-carboxylate. The mixture of isomers was not separated and used in the next step without any further purification. $R_t$=2.80 min. MS (ESI) m/z: 264 [M-H]$^+$, 286 [M−Na]$^+$, 302 [M−K]$^+$.

Step 2. Preparation of [(Z)-non-3-enyl]-N-[(3S)-2-oxoazetidin-3-yl]-carbamate Under nitrogen atmosphere, to a suspension of [(3S)-2-oxoazetidin-3-yl]-ammonium acetate (0.05 g, 0.34 mmol) in dry CH$_2$Cl$_2$ (4.0 mL), DIPEA (0.067 mL, 0.41 mmol) was added dropwise. Subsequently, the crude mixture (0.26 g) containing [(Z)-non-3-enyl]-2-oxopyridine-1-carboxylate (0.09 g, 0.34 mmol) in dry CH$_2$Cl$_2$ (1.0 mL) was added. The reaction mixture was stirred at r.t. for 16 h, then concentrated to dryness giving a solid residue (0.34 g). Purification by typical silica gel flash chromatography (Cy/EtOAc, from 60:40 to 40:60) afforded the pure title compound (0.077 g, 89%), as a white solid. $R_t$=2.54 min. MS (ESI) m/z: 255 [M-H]$^+$, 277 [M−Na]$^+$, 293 [M−K]$^+$. $^1$H NMR (DMSO-d$_6$): δ 7.91 (s, 1H), 7.80 (d, 1H, J=8.7 Hz), 5.54-5.41 (m, 1H), 5.40-5.29 (m, 1H), 4.68-4.59 (m, 1H), 3.94 (t, 2H, J=6.8 Hz), 3.38 (d, 1H, J=5.4 Hz), 3.07 (dd, 1H, J=5.4, 2.7 Hz), 2.29 (q, 2H, J=6.9 Hz), 2.00 (q, 2H, J=6.9 Hz), 1.42-1.17 (m, 10H), 0.86 (t, 3H, J=6.9 Hz).

Example 11. [(E)-4-Phenylbut-3-enyl]-N-[(3S)-2-oxoazetidin-3-yl]-carbamate

Step 1. Preparation of (E)-4-phenylbut-3-en-1-ol

Under nitrogen atmosphere, to a cooled (0° C.) suspension of LiAlH$_4$ (2.0 M THF solution, 6.2 mL, 12.35 mmol) in dry Et$_2$O (30 mL), commercially available methyl (E)-4-phenylbut-3-enoate (0.5 g, 3.09 mmol) in dry Et$_2$O (5 mL) was added dropwise. The resulting reaction mixture was stirred at r.t. for 2 h, and then cooled to 0° C. H$_2$O (0.47 mL) was slowly and cautiously added, followed by 3.0 M KOH solution (0.47 mL) and additional H$_2$O (1.6 mL). The mixture was stirred at 0° C. for 1 h and then filtered off. The organic layer was dried over Na$_2$SO$_4$, filtered and concentrated to dryness, affording the title compound (0.43 g, 94%), which was used in the next step without any further purification. $^1$H NMR (DMSO-d$_6$): δ 7.41-7.36 (m, 2H), 7.34-7.28 (m, 2H), 7.23-7.17 (m, 1H), 6.44 (d, 1H, J=16.0 Hz), 6.30 (dt, 1H, J=16.0, 6.9 Hz), 4.59 (t, 1H, J=5.3 Hz), 3.57-3.50 (m, 2H), 2.35 (qd, 2H, J=6.8, 1.1 Hz).

Step 2. Preparation of [(E)-4-phenylbut-3-enyl]-2-pyridyl carbonate and [(E)-4-phenylbut-3-enyl]-2-oxopyridine-1-carboxylate Under nitrogen atmosphere, to a stirred solution of (E)-non-3-en-1-ol (0.21 g, 1.40 mmol) in dry CH$_2$Cl$_2$ (9.0 mL), DMAP (0.017 g, 0.14 mmol) and 2-DPC (0.36 g, 1.69 mmol) were added. The reaction mixture was stirred at r.t. for 16 h, then diluted with CH$_2$Cl$_2$ (45 mL) and sequentially washed with sat. NH$_4$Cl solution (10 mL) and sat. NaHCO$_3$ solution (3×10 mL). The organic layer was dried over Na$_2$SO$_4$, filtered and concentrated to dryness affording a yellow oil (0.37 g), as a mixture (1:2.2 ratio) of [(E)-4-phenylbut-3-enyl]-2-pyridyl carbonate and [(E)-4-phenylbut-3-enyl]-2-oxopyridine-1-carboxylate. The mixture of isomers was not separated and used in the next step without any further purification. $R_t$=2.33 min. MS (ESI) m/z: 270 [M-H]$^+$, 292 [M−Na]$^+$, 308 [M−K]$^+$.

Step 3. Preparation of [(E)-4-phenylbut-3-enyl]-N-[(3S)-2-oxoazetidin-3-yl]-carbamate Under nitrogen atmosphere, to a suspension of [(3S)-2-oxoazetidin-3-yl]-ammonium acetate (0.05 g, 0.34 mmol) in dry CH$_2$Cl$_2$ (4.0 mL), DIPEA (0.067 mL, 0.41 mmol) was added dropwise. Subsequently, the crude mixture (0.293 g) containing [(E)-4-phenylbut-3-enyl]-2-oxopyridine-1-carboxylate (0.91 g, 0.34 mmol) in dry CH$_2$Cl$_2$ (2.0 mL) was added. The reaction mixture was stirred at r.t. for 16 h, then concentrated to dryness giving a solid residue (0.156 g). Purification by preparative HPLC afforded the pure title compound (0.034 g, 40%), as a white solid. $R_t$=1.96 min. MS (ESI) m/z: 261 [M-H]$^+$, 283 [M−Na]$^+$, 299 [M−K]$^+$. $^1$H NMR (DMSO-d$_6$): δ 7.91 (s, 1H), 7.85 (d, 1H, J=8.9 Hz), 7.38 (d, 2H, J=7.6 Hz), 7.31 (t, 2H, J=7.6 Hz), 7.24-7.18 (m, 1H), 6.48 (d, 1H, J=16.0 Hz), 6.32-6.21 (m, 1H), 4.68-4.50 (m, 1H), 4.09 (t, 2H, J=6.5 Hz), 3.36 (t, 1H, J=5.2 Hz), 3.06 (dd, 1H, J=5.2, 2.7 Hz), 2.47 (t, 2H, J=6.5 Hz).

Example 12. [(Z)-4-Phenylbut-3-enyl]-N-[(3S)-2-oxoazetidin-3-yl]-carbamate

Step 1. Preparation of (Z)-4-phenylbut-3-en-1-ol

To a dry powder of (PPh$_3$)$_3$NiCl$_2$ (0.047 g, 0.07 mmol), commercially available 2,3-dihydrofuran (0.27 mL, 3.57 mmol) in dry Et$_2$O (4.0 mL) was transferred dropwise via a cannula. The resulting suspension was cooled to 0° C. and PhMgBr (2.8 M in 2-methyl-THF, 1.28 mL, 3.57 mmol) was slowly added dropwise. After stirring for 1 h at 0° C., the mixture was stirred at r.t. for 6 h, and then poured into sat. NH$_4$Cl solution (40 mL). The crude product was extracted with Et$_2$O (3×20 mL), then the organic layer was dried over Na$_2$SO$_4$, filtered and concentrated to dryness giving a crude residue (0.57 g). Purification by typical silica gel flash chromatography (Cy/EtOAc, 80:20) afforded the pure title compound (0.375 g, 71%), as a colorless liquid. $R_t$=1.97 min. $^1$H NMR (DMSO-d$_6$): δ 7.38-7.29 (m, 4H), 7.27 (tt, 1H, J=7.0, 1.7 Hz), 6.46 (dt, 1H, J=11.8, 1.8 Hz), 5.71 (dt, 1H, J=11.8, 7.3 Hz), 4.61 (t, 1H, J=5.3 Hz), 3.52 (td, 2H, J=6.7, 5.4 Hz), 2.46 (qd, 2H, J=6.9, 1.9 Hz).

Step 2. Preparation of [(Z)-4-phenylbut-3-enyl]-2-pyridyl carbonate and [(Z)-4-phenylbut-3-enyl]-2-oxopyridine-1-carboxylate Under nitrogen atmosphere, to a stirred solution of (Z)-non-3-en-1-ol (0.375 g, 2.53 mmol) in dry $CH_2Cl_2$ (14 mL), DMAP (0.031 g, 0.25 mmol) and 2-DPC (0.657 g, 3.04 mmol) were added. The reaction mixture was stirred at r.t. for 16 h, then diluted with $CH_2Cl_2$ (55 mL) and sequentially washed with sat. $NH_4Cl$ solution (15 mL) and sat. $NaHCO_3$ solution (3×15 mL). The organic layer was dried over $Na_2SO_4$, filtered and concentrated to dryness affording an oily residue (0.65 g), as a mixture (1:1.9 ratio) of [(Z)-4-phenylbut-3-enyl]-2-pyridyl carbonate and [(Z)-4-phenyl-but-3-enyl]-2-oxopyridine-1-carboxylate. The mixture of isomers was not separated and used in the next step without any further purification. $R_t$=2.33 min. MS (ESI) m/z: 270 $[M-H]^+$, 292 $[M-Na]^+$, 308 $[M-K]^+$.

Step 3. Preparation of [(Z)-4-phenylbut-3-enyl]-N-[(3S)-2-oxoazetidin-3-yl]-carbamate Under nitrogen atmosphere, to a suspension of [(3S)-2-oxoazetidin-3-yl]-ammonium acetate (0.05 g, 0.34 mmol) in dry $CH_2Cl_2$ (4.0 mL), DIPEA (0.067 mL, 0.41 mmol) was added dropwise. Subsequently, the crude mixture (0.265 g) containing [(Z)-4-phenylbut-3-enyl]-2-oxopyridine-1-carboxylate (0.091 g, 0.34 mmol) in dry $CH_2Cl_2$ (2.0 mL) was added. The reaction mixture was stirred at r.t. for 16 h, then concentrated to dryness giving a solid residue (0.193 g). Purification by typical silica gel flash chromatography ($CH_2Cl_2$/MeOH, from 100:0 to 95:5) afforded the pure title compound (0.063 g, 71%), as a white solid. $R_t$=1.95 min. MS (ESI) m/z: 261 $[M-H]^+$, 283 $[M-Na]^+$, 299 $[M-K]^+$. $^1H$ NMR (DMSO-$d_6$): δ 7.91 (s, 1H), 7.85 (d, 1H, J=8.8 Hz), 7.40-7.23 (m, 5H), 6.52 (dt, 1H, J=11.7, 1.8 Hz), 5.71-5.62 (m, 1H), 4.67-4.50 (m, 1H), 4.08 (td, 2H, J=6.8, 1.8 Hz), 3.37 (t, 1H, J=5.3 Hz), 3.06 (dd, 1H, J=5.3, 2.8 Hz), 2.59 (qd, 2H, J=6.8, 1.8 Hz).

Example 13. 4-Phenylbutyl-N-[(3S)-2-oxoazetidin-3-yl]-carbamate

Step 1. Preparation of 4-phenylbutyl-2-pyridyl carbonate and 4-phenylbutyl-2-oxopyridine-1-carboxylate Under nitrogen atmosphere, to a stirred solution of commercially available 4-phenylbutan-1-ol (0.3 mL, 2.0 mmol) in dry $CH_2Cl_2$ (12 mL), DMAP (0.024 g, 0.20 mmol) and 2-DPC (0.518 g, 2.40 mmol) were added. The reaction mixture was stirred at r.t. for 16 h, then diluted with $CH_2Cl_2$ (55 mL) and sequentially washed with sat. $NH_4Cl$ solution (15 mL) and sat. $NaHCO_3$ solution (3×15 mL). The organic layer was dried over $Na_2SO_4$, filtered and concentrated to dryness affording an oily residue (0.54 g), as a mixture (1:1.8 ratio) of 4-phenylbutyl-2-pyridyl carbonate and 4-phenylbutyl-2-oxopyridine-1-carboxylate. The mixture of isomers was not separated and used in the next step without any further purification. $R_t$=2.43 min. MS (ESI) m/z: 272 $[M-H]^+$, 294 $[M-Na]^+$, 310 $[M-K]^+$.

Step 2. Preparation of 4-phenylbutyl-N-[(3S)-2-oxoazetidin-3-yl]-carbamate

Under nitrogen atmosphere, to a suspension of [(3S)-2-oxoazetidin-3-yl]-ammonium acetate (0.05 g, 0.34 mmol) in dry $CH_2Cl_2$ (4.0 mL), DIPEA (0.067 mL, 0.71 mmol) was added dropwise. Subsequently, the crude mixture (0.258 g) containing 4-phenylbutyl-2-oxopyridine-1-carboxylate (0.092 g, 0.34 mmol) in dry $CH_2Cl_2$ (2.0 mL) was added. The reaction mixture was stirred at r.t. for 16 h, then concentrated to dryness giving a solid residue (0.18 g). Purification by typical silica gel flash chromatography ($CH_2Cl_2$/MeOH, from 100:00 to 97:3) afforded the pure title compound (0.071 g, 80%), as a white solid. $R_t$=2.03 min. MS (ESI) m/z: 263 $[M-H]^+$, 285 $[M-Na]^+$, 302 $[M-K]^+$. $^1H$ NMR (DMSO-$d_6$): δ 7.90 (s, 1H), 7.79 (d, 1H, J=8.8 Hz), 7.31-7.24 (m, 2H), 7.22-7.15 (m, 3H), 4.66-4.50 (m, 1H), 3.98 (t, 2H, J=5.8 Hz), 3.38 (t, 1H, J=5.4 Hz), 3.06 (dd, 1H, J=5.1, 2.8 Hz), 2.59 (t, 2H, J=7.4 Hz), 1.67-1.50 (m, 4H).

Example 14. 4-(2,6-Dimethylphenyl)-butyl-N-[(3S)-2-oxoazetidin-3-yl]-carbamate

Step 1. Preparation of 2-[(E)-4-benzyloxybut-1-enyl]-1,3-dimethyl-benzene and 2-[(Z)-4-benzyloxybut-1-enyl]-1,3-dimethyl-benzene Under nitrogen atmosphere, to a cooled (−30° C.) solution of commercially available 3-benzyloxypropyl-(triphenyl)-phosphonium bromide (2.7 g, 5.5 mmol) in dry THF (50 mL), n-BuLi (2.5 M in hexane, 2.2 mL, 5.5 mmol) was added dropwise. The solution was stirred at −30° C. for 45 min, then commercially available 2,6-dimethylbenzaldehyde (0.67 g, 5.0 mmol) in dry THF (5.0 mL) was slowly added. The reaction mixture stirred at −30° C. for 30 min and then at r.t. for 16 h. The solution was diluted with $CH_2Cl_2$ (50 mL) and washed with sat. $NH_4Cl$ solution (3×15 mL). The organic layer was dried over $Na_2SO_4$, filtered and concentrated to dryness giving a crude residue (2.191 g). Purification by typical silica gel flash chromatography ($CH_2Cl_2$) afforded the pure title compounds (1.0 g, 75%), as a mixture (ratio 15:85) of E/Z diastereoisomers. $R_t$=2.62 min (minor) and 2.67 min (major). MS (ESI) m/z: 267 $[M-H]^+$, 284 $[M-NH_4]^+$. $^1H$ NMR (DMSO-$d_6$): δ 7.37-7.23 (m, 10H), 7.09-6.96 (m, 6H), 6.40 (d, 1H, J=16.2 Hz, minor), 6.35 (d, 1H, J=11.2 Hz, major), 5.81 (dt, 1H, J=11.2, 7.1 Hz Hz, major), 5.68 (dt, 1H, J=16.2, 7.1 Hz, minor), 4.50 (s, 2H, minor), 4.38 (s, 2H, major), 3.58 (t, 2H, J=6.5 Hz, minor), 3.40 (t, 2H, J=6.6 Hz, major), 2.52-2.48 (m, 2H, minor), 2.22 (s, 6H, minor), 2.12 (s, 6H, major), 2.03 (qd, 2H, J=6.7, 1.6 Hz).

Step 2. Preparation of 4-(2,6-dimethylphenyl)-butan-1-ol

A solution containing a mixture of 2-[(E)-4-benzyloxy-but-1-enyl]-1,3-dimethyl-benzene and 2-[(Z)-4-benzyloxy-but-1-enyl]-1,3-dimethyl-benzene (0.36 g, 1.35 mmol) in EtOH (28 mL) was passed through a H-Cube® hydrogenator flow reactor provided with a 20% $Pd(OH)_2$/C cartridge [flow rate: 1.0 mL/min; P=1.0 bar, T=60° C.]. The outcoming solution was concentrated to dryness, affording a colorless oil (0.27 g, quant.), which was used in the next step without any further purification. $R_t$=2.38 min. $^1H$ NMR (DMSO-$d_6$): δ 6.98-6.93 (m, 3H), 4.36 (t, 1H, J=5.2 Hz), 3.44 (q, 2H, J=6.3 Hz), 2.59-2.53 (m, 2H), 2.26 (s, 6H), 1.57-1.48 (m, 2H), 1.47-1.39 (m, 2H).

Step 3. Preparation of 4-(2,6-dimethylphenyl)-butyl 2-pyridyl carbonate and 4-(2,6-dimethylphenyl)-butyl-2-oxopyridine-1-carboxylate Under nitrogen atmosphere, to a stirred solution of 4-(2,6-dimethylphenyl)-butan-1-ol (0.25 g, 1.4 mmol) in dry CH₂Cl₂ (7.5 mL), DMAP (0.017 g, 0.14 mmol) and 2-DPC (0.364 g, 1.68 mmol) were added. The reaction mixture was stirred at r.t. for 16 h, then diluted with CH₂Cl₂ (55 mL) and sequentially washed with sat. NH₄Cl solution (15 mL) and sat. NaHCO₃ solution (3×15 mL). The organic layer was dried over Na₂SO₄, filtered and concentrated to dryness affording an oily residue (0.420 g), as a mixture (1:1.7 ratio) of 4-(2,6-dimethylphenyl)-butyl 2-pyridyl carbonate and 4-(2,6-dimethylphenyl)-butyl-2-oxopyridine-1-carboxylate. The mixture of isomers was not separated and used in the next step without any further purification. $R_t$=2.69 min. MS (ESI) m/z: 300 [M-H]⁺, 322 [M-Na]⁺, 338 [M-K]⁺.

Step 4. Preparation of 4-(2,6-dimethylphenyl)-butyl-N-[(3S)-2-oxoazetidin-3-yl]-carbamate Under nitrogen atmosphere, to a suspension of [(3S)-2-oxoazetidin-3-yl]-ammonium acetate (0.05 g, 0.34 mmol) in dry CH₂Cl₂ (4.0 mL), DIPEA (0.067 mL, 0.41 mmol) was added dropwise. Subsequently, the crude mixture (0.274 g) containing 4-(2,6-dimethylphenyl)-butyl-2-oxopyridine-1-carboxylate (0.102 g, 0.34 mmol) in dry CH₂Cl₂ (2.0 mL) was added. The reaction mixture was stirred at r.t. for 16 h, then concentrated to dryness giving a solid residue (0.16 g). Purification by typical silica gel flash chromatography (CH₂Cl₂/MeOH, from 100:00 to 96:4) afforded the pure title compound (0.016 g, 16%), as a white solid. $R_t$=2.30 min. MS (ESI) m/z: 291 [M-H]⁺, 313 [M-Na]⁺, 329 [M-K]⁺. ¹H NMR (DMSO-d₆): δ 7.90 (s, 1H), 7.80 (d, 1H, J=8.8 Hz), 6.98-6.92 (m, 3H), 4.66-4.50 (m, 1H), 4.02 (t, 2H, J=6.6 Hz), 3.37 (t, 1H, J=5.4 Hz), 3.06 (dd, 1H, J=5.2, 2.8 Hz), 2.61-2.54 (m, 2H), 2.26 (s, 6H), 1.71-1.62 (m, 2H), 1.49-1.38 (m, 2H).

Example 15. [(1S)- and (1R)-(1-Methyl-5-phenyl-pentyl)]-N-[(3S)-2-oxoazetidin-3-yl]-carbamate Step 1. Preparation of 5-phenyl-nonal-1-al Under nitrogen atmosphere, to a cooled (−78° C.) solution of oxalyl chloride (0.6 mL, 7.13 mmol) in dry CH₂Cl₂ (65.0 mL), DMSO (0.47 mL, 6.59 mmol) was added dropwise. After stirring at −78° C. for 15 min, a solution of commercially available 5-phenyl-pentanol (0.9 g, 5.49 mmol) in dry CH₂Cl₂ (10 mL) was added dropwise. The reaction mixture was stirred at −78° C. for 1 h, then Et₃N (2.2 mL, 16.46 mmol) was added dropwise. The resulting reaction mixture was warmed up to r.t., then concentrated to dryness. The crude product was taken up in Et₂O (100 mL) and washed with sat. NH₄Cl solution (75 mL). The organic layer was dried over Na₂SO₄, filtered and concentrated to dryness affording the title compound (0.88 g, quant.), which was used in the next step without any further purification. $R_t$=2.54 min. ¹H NMR (DMSO-d₆): δ 9.65 (t, 1H, J=1.6 Hz), 7.30-7.23 (m, 2H), 7.22-7.14 (m, 3H), 2.58 (t, 2H, J=7.1 Hz), 2.49-2.41 (m, 2H), 1.64-1.49 (m, 4H).

Step 2. Preparation of (2S)- and (2R)-6-phenylhexan-2-ol

Under nitrogen atmosphere, to a cooled (−65° C.) stirred solution of 5-phenyl-nonal-1-al (0.30 g, 1.85 mmol) in dry Et₂O (50 mL), MeMgBr (1.0 M in Bu₂O, 5.5 mL, 5.56 mmol) was added dropwise. The reaction mixture was warmed up to −10° C. in 30 min, then stirred for additional 4 h. After dilution with H₂O (5.0 mL) and extraction with EtOAc (50 mL), the collected organic layers were dried over Na₂SO₄, filtered and concentrated, affording the title compound (0.29 g, 89%) as a racemic mixture, which was used in the next step without any further purification. $R_t$=2.45 min. ¹H NMR (DMSO-d₆): δ 7.29-7.23 (m, 2H), 7.20-7.12 (m, 3H), 4.29 (d, 1H, J=4.7 Hz), 3.61-3.51 (m, 1H), 2.56 (t, 2H, J=7.7 Hz), 1.62-1.48 (m, 2H), 1.41-1.22 (m, 4H), 1.02 (d, 3H, J=6.1 Hz).

Step 3. Preparation of (1S)- and (1R)-(1-methyl-5-phenyl-pentyl)-2-pyridyl carbonate and (1S)- and (1R)-(1-methyl-5-phenyl-pentyl)-2-oxopyridine-1-carboxylate Under nitrogen atmosphere, to a stirred solution of (2S)- and (2R)-6-phenylhexan-2-ol (0.25 g, 1.4 mmol) in dry CH₂Cl₂ (9.0 mL), DMAP (0.017 g, 0.14 mmol) and 2-DPC (0.364 g, 1.69 mmol) were added. The reaction mixture was stirred at r.t. for 16 h, then diluted with CH₂Cl₂ (50 mL) and sequentially washed with sat. NH₄Cl solution (15 mL) and sat. NaHCO₃ solution (3×15 mL). The organic layer was dried over Na₂SO₄, filtered and concentrated to dryness affording an oily residue (0.36 g), as a mixture (1:1.9 ratio) of (1S)- and (1R)-(1-methyl-5-phenyl-pentyl)-2-pyridyl carbonate and (1S)- and (1R)-(1-methyl-5-phenyl-pentyl)-2-oxopyridine-1-carboxylate. The mixture of isomers was not separated and used in the next step without any further purification. $R_t$=2.74 min. MS (ESI) m/z: 300 [M-H]⁺, 322 [M-Na]⁺, 338 [M-K]⁺.

Step 4. Preparation of [(1S)-1-methyl-5-phenyl-pentyl]-N-[(3S)-2-oxoazetidin-3-yl]-carbamate and [(1R)-1-methyl-5-phenyl-pentyl]-N-[(3S)-2-oxoazetidin-3-yl]-carbamate Under nitrogen atmosphere, to a suspension of [(3S)-2-oxoazetidin-3-yl]-ammonium acetate (0.05 g, 0.34 mmol) in dry CH₂Cl₂ (4.0 mL), DIPEA (0.067 mL, 0.71 mmol) was added dropwise. Subsequently, the crude mixture (0.295) containing (1S)- and (1R)-[1-methyl-5-phenyl-pentyl]-2-oxopyridine-1-carboxylate (0.102 g, 0.34 mmol) in dry CH₂Cl₂ (2.0 mL) was added. The reaction mixture was stirred at r.t. for 16 h, then concentrated to dryness giving a solid residue (0.19 g). Purification by typical silica gel flash chromatography (CH₂Cl₂/MeOH, from 100:00 to 96:4) afforded the title compounds (0.051 g, 42%), as a mixture (1:1 ratio) of diastereoisomers, as a white solid. $R_t$=2.34 min. MS (ESI) m/z: 291 [M-H]⁺, 313 [M-Na]⁺, 329 [M-K]⁺. ¹H NMR (DMSO-d₆): δ 7.90 (bs, 2H), 7.71 (bs, 2H), 7.34-7.09 (m, 10H), 4.76-4.39 (m, 4H), 3.38 (bs, 2H), 3.07 (bs, 2H), 2.57 (bs, 4H), 1.67-1.06 (m, 18H).

Example 16. (1,1-Dimethyl-5-phenyl-pentyl)-N-[(3S)-2-oxoazetidin-3-yl]-carbamate Step 1. Preparation of (1,1-dimethyl-5-phenyl-pentyl)-2-pyridyl carbonate and (1,1-dimethyl-5-phenyl-pentyl)-2-oxopyridine-1-carboxylate Under nitrogen atmosphere, to a stirred mixture of 2-methyl-6-phenyl-hexan-2-ol (0.3 g, 1.56 mmol), [prepared as described in Khalaf et al. *J. Org. Chem.* 1972, 37, 4227-4235, compound 9] in dry CH₂Cl₂ (9.0 mL), DMAP (0.019 g, 0.16 mmol) and 2-DPC (0.405 g, 1.88 mmol) were added. The reaction mixture was stirred at r.t. for 16 h, then diluted with CH₂Cl₂ (50 mL) and sequentially washed with sat. NH₄Cl solution (15 mL) and sat. NaHCO₃ solution (3×15 mL). The organic layer was dried over Na₂SO₄, filtered and concentrated to dryness affording a yellow oil (0.5 g), as a mixture (1:2.3 ratio) of (1,1-dimethyl-5-phenyl-pentyl)-2-pyridyl carbonate and (1,1-dimethyl-5-phenyl-pentyl)-2-oxopyridine-1-carboxylate. The mixture of isomers was not separated and used in the next step without any further purification. $R_t$=2.90 min. MS (ESI) m/z: 314 [M-H]$^+$, 336 [M-Na]$^+$, 352 [M-K]$^+$.

Step 2. Preparation of (1,1-dimethyl-5-phenyl-pentyl)-N-[(3S)-2-oxoazetidin-3-yl]-carbamate Under nitrogen atmosphere, to a suspension of [(3S)-2-oxoazetidin-3-yl]-ammonium acetate (0.05 g, 0.34 mmol) in dry CH$_2$Cl$_2$ (4.0 mL), DIPEA (0.067 mL, 0.41 mmol) was added dropwise. Subsequently, the crude mixture (0.35 g) containing (1,1-dimethyl-5-phenyl-pentyl)-2-oxopyridine-1-carboxylate (0.106 g, 0.34 mmol) in dry CH$_2$Cl$_2$ (2.0 mL) was added. The reaction mixture was stirred at r.t. for 16 h, then concentrated to dryness giving an oily residue (0.18 g). Purification by preparative HPLC afforded the pure title compound (0.03 g, 29%), as a white solid. $R_t$=2.48 min. MS (ESI) m/z: 305 [M-H]$^+$, 327 [M-Na]$^+$, 343 [M-K]$^+$. $^1$H NMR (DMSO-d$_6$): δ 7.86 (s, 1H), 7.52 (d, 1H, J=9.0 Hz), 7.29-7.13 (m, 5H), 4.64-4.29 (m, 1H), 3.37-3.33 (m, 1H), 3.02 (dd, 1H, J=5.0, 2.9 Hz), 2.57 (t, 2H, J=7.7 Hz), 1.76-1.68 (m, 2H), 1.54 (p, 2H, J=7.7 Hz), 1.38-1.26 (m, 8H).

Example 17. (4-Phenylphenyl)-methyl-N-[(3S)-2-oxoazetidin-3-yl]-carbamate

Step 1. Preparation of (4-phenylphenyl)-methyl-2-pyridyl carbonate and (4-phenylphenyl)-methyl-2-oxopyridine-1-carboxylate Under nitrogen atmosphere, to a stirred mixture of commercially available 4-phenylbenzyl alcohol (0.300 g, 1.63 mmol) in dry CH$_2$Cl$_2$ (9.0 mL), DMAP (0.02 g, 0.16 mmol) and 2-DPC (0.42 g, 1.96 mmol) were added. The reaction mixture was stirred at r.t. for 16 h, then diluted with CH$_2$Cl$_2$ (50 mL) and sequentially washed with sat. NH$_4$Cl solution (15 mL) and sat. NaHCO$_3$ solution (3×15 mL). The organic layer was dried over Na$_2$SO$_4$, filtered and concentrated to dryness affording an oily residue (0.5 g), as a mixture (1:1.6 ratio) of (4-phenylphenyl)-methyl-2-pyridyl carbonate and (4-phenylphenyl)-methyl-2-oxopyridine-1-carboxylate. The mixture of isomers was not separated and used in the next step without any further purification. $R_t$=2.58 min. MS (ESI) m/z: 328 [M-Na]$^+$, 344 [M-K]$^+$.

Step 2. Preparation of (4-phenylphenyl)-methyl-N-[(3S)-2-oxoazetidin-3-yl]-carbamate Under nitrogen atmosphere, to a suspension of [(3S)-2-oxoazetidin-3-yl]-ammonium acetate (0.05 g, 0.34 mmol) in dry CH$_2$Cl$_2$ (4.0 mL), DIPEA (0.067 mL, 0.41 mmol) was added dropwise. Subsequently, the crude mixture (0.270 g) containing (4-phenylphenyl)-methyl-2-oxopyridine-1-carboxylate (0.104 g, 0.34 mmol) in dry CH$_2$Cl$_2$ (2.0 mL) was added. The reaction mixture was stirred at r.t. for 16 h. Filtration from the reaction medium afforded the pure title compound (0.063 g, 62%), as a white solid. $R_t$=2.20 min. MS (ESI) m/z: 297 [M-H]$^+$, 319 [M-Na]$^+$, 335 [M-K]$^+$. $^1$H NMR (DMSO-d$_6$): δ 7.99 (d, 1H, J=8.7 Hz), 7.94 (s, 1H), 7.69-7.62 (m, 4H), 7.50-7.33 (m, 5H), 5.09 (s, 2H), 4.76-4.61 (m, 1H), 3.41 (t, 1H, J=5.3 Hz), 3.09 (dd, 1H, J=5.2, 2.8 Hz).

Example 18. 3-Cyclohexylpropyl-N-[(3S)-2-oxoazetidin-3-yl]-carbamate

Step 1. Preparation of 3-cyclohexylpropyl-2-pyridyl carbonate and 3-cyclohexylpropyl-2-oxopyridine-1-carboxylate Under nitrogen atmosphere, to a stirred solution of commercially available 3-cyclohexylpropan-1-ol (0.25 g, 1.76 mmol) in dry CH$_2$Cl$_2$ (9.0 mL), DMAP (0.021 g, 0.18 mmol) and 2-DPC (0.456 g, 2.11 mmol) were added. The reaction mixture was stirred at r.t. for 16 h, then diluted with CH$_2$Cl$_2$ (50 mL) and sequentially washed with sat. NH$_4$Cl solution (15 mL) and sat. NaHCO$_3$ solution (3×15 mL). The organic layer was dried over Na$_2$SO$_4$, filtered and concentrated to dryness affording an oily residue (0.480 g), as a mixture (1:1.8 ratio) of 3-cyclohexylpropyl-2-pyridyl carbonate and 3-cyclohexylpropyl-2-oxopyridine-1-carboxylate. The mixture of isomers was not separated and used in the next step without any further purification. $R_t$=2.81 min. MS (ESI) m/z: 264 [M-H]$^+$, 286 [M-Na]$^+$, 302 [M-K]$^+$.

Step 2. Preparation of 3-cyclohexylpropyl-N-[(3S)-2-oxoazetidin-3-yl]-carbamate

Under nitrogen atmosphere, to a suspension of [(3S)-2-oxoazetidin-3-yl]-ammonium acetate (0.05 g, 0.34 mmol) in dry CH$_2$Cl$_2$ (4.0 mL), DIPEA (0.067 mL, 0.41 mmol) was added dropwise. Subsequently, the crude mixture (0.25 g) containing 3-cyclohexylpropyl-2-oxopyridine-1-carboxylate (0.089 g, 0.34 mmol) in dry CH$_2$Cl$_2$ (2.0 mL) was added. The reaction mixture was stirred at r.t. for 16 h, then concentrated to dryness giving a solid residue (0.18 g). Purification by typical silica gel flash chromatography (CH$_2$Cl$_2$/MeOH, from 100:00 to 96:4) afforded the pure title compound (0.064 g, 74%), as a white solid. $R_t$=2.36 min. MS (ESI) m/z: 255 [M-H]$^+$, 277 [M-Na]$^+$, 293 [M-K]$^+$. $^1$H NMR (DMSO-d$_6$): δ 7.90 (s, 1H), 7.78 (d, 1H, J=8.7 Hz), 4.66-4.48 (m, 1H), 3.93 (t, 2H, J=6.7 Hz), 3.37 (t, 1H, J=5.1 Hz), 3.06 (dd, 1H, J=5.1, 2.8 Hz), 1.72-1.48 (m, 7H), 1.26-1.04 (m, 6H), 0.93-0.77 (m, 2H).

Example 19. 5-Cyclohexylpentyl-N-[(3S)-2-oxoazetidin-3-yl]-carbamate

Step 1. Preparation of 5-cyclohexylpentan-1-ol

Under nitrogen atmosphere, at 0° C., to a suspension of LiAlH$_4$ (2.0 M in THF, 13.0 mL, 26.08 mmol) in dry Et$_2$O (67 mL), commercially available 5-cyclohexylpentanoic acid (1.2 g, 6.52 mmol) in dry Et$_2$O (2.0 mL) was added dropwise. The resulting reaction mixture was stirred at r.t. for 4 h, then cooled to 0° C. H$_2$O (0.5 mL) was slowly added, followed by 3.0 M KOH solution (0.5 mL) and additional H$_2$O (0.5 mL). The mixture was stirred additional 1 h at 0° C. and filtered off. The organic layer was dried over Na$_2$SO$_4$, filtered and concentrated to dryness, affording the title compound (0.98 g, 88%), which was used in the next step without any further purification. $^1$H NMR (DMSO-d$_6$): δ 3.36 (t, 2H, J=6.6 Hz), 1.73-1.53 (m, 5H), 1.39-1.37 (m, 2H), 1.31-1.04 (m, 10H), 0.82-0.84 (m, 2H).

Step 2. Preparation of 5-cyclohexylpentyl-2-pyridyl carbonate and 5-cyclohexylpentyl-2-oxopyridine-1-carboxylate Under nitrogen atmosphere, to a stirred solution of 5-cyclohexylpentan-1-ol (0.55 g, 3.23 mmol) in dry CH$_2$Cl$_2$ (18.0 mL), DMAP (0.039 g, 0.323 mmol) and 2-DPC (0.907 g, 4.19 mmol) were added. The reaction mixture was left at r.t. for 16 h, then diluted with CH$_2$Cl$_2$ (50 mL) and sequentially washed with sat. NH$_4$Cl solution (15 mL) and sat. NaHCO$_3$ solution (3×15 mL). The organic layer was dried over Na$_2$SO$_4$, filtered and concentrated to dryness giving an oily residue (0.92 g), as a mixture (1:1.9 ratio) of 5-cyclohexylpentyl-2-pyridyl carbonate and 5-cyclohexylpentyl-2-oxopyridine-1-carboxylate. The mixture of isomers was not separated and used in the next step without any further purification. R$_t$=3.23 min; MS (ESI) m/z: 292 [M-H]$^+$, 314 [M–Na]$^+$, 330 [M–K]$^+$; (ESI) m/z: 290 [M-1]$^-$.

Step 3. Preparation of 5-cyclohexylpentyl-N-[(3S)-2-oxoazetidin-3-yl]-carbamate

Under nitrogen atmosphere, to a suspension of [(3S)-2-oxoazetidin-3-yl]-ammonium acetate (0.05 g, 0.34 mmol) in dry CH$_2$Cl$_2$ (4.0 mL), DIPEA (0.067 mL, 0.41 mmol) was added dropwise. Subsequently, the crude mixture (0.29 g) containing 5-cyclohexylpentyl-2-oxopyridine-1-carboxylate (0.099 g, 0.34 mmol) in dry CH$_2$Cl$_2$ (2.0 mL) was added. The reaction mixture was stirred at r.t. for 16 h, concentrated to dryness affording an solid residue (0.18 g). Purification by typical silica gel flash chromatography (Cy/EtOAc, from 100:0 to 30:100) afforded the pure title compound (0.015 g, 16%), as a white solid. R$_t$=2.83 min. MS (ESI) m/z: 283 [M-H]$^+$, 305 [M–Na]$^+$, 321 [M–K]$^+$; MS (ESI) m/z: 281 [M-H]$^-$. $^1$H NMR (DMSO-d$_6$): δ 7.90 (s, 1H), 7.77 (d, 1H, J=8.7 Hz), 4.64-4.60 (m, 1H), 3.94 (t, 2H, J=6.6 Hz), 3.37 (t, 1H, J=5.4 Hz), 3.07 (dd, 1H, J=5.4, 2.7 Hz), 1.71-1.60 (m, 4H), 1.55 (dt, 2H, J=13.4, 8.1 Hz), 1.37-1.07 (m, 11H), 0.86-0.80 (m, 2H).

Example 20. 4-Cyclopentylbutyl-N-[(3S)-2-oxoazetidin-3-yl]-carbamate

Step 1. Preparation of 2-[(Z)-3-cyclopentylallyl]-1,3-dioxolane and 2-[(E)-3-cyclopentylallyl]-1,3-dioxolane Under nitrogen atmosphere, to a cooled (−30° C.) solution of commercially available 2-(1,3-dioxolan-2-yl)-ethyl(triphenyl)-phosphonium bromide (3.48 g, 7.9 mmol) in dry THF (82 mL), n-BuLi (2.5 M in Hexane, 3.1 mL, 7.9 mmol) was added dropwise. The solution was stirred at −30° C. for 45 min, then cyclopentanecarboxaldehyde (0.76 mL, 7.14 mmol) in dry THF (5.0 mL) was added dropwise. The reaction mixture was stirred for 30 min and then at r.t. for 16 h. Then, the solution was diluted with CH$_2$Cl$_2$ (100 mL) and washed with sat. NH$_4$Cl solution (3×50 mL). The organic layer was dried over Na$_2$SO$_4$, filtered and concentrated to dryness giving an oily residue (2.91 g). Purification by typical silica gel flash chromatography (CH$_2$Cl$_2$) afforded the pure title compounds (0.84 g, 65%), as a mixture (ratio 7:93) of E/Z diastereoisomers. $^1$H NMR (DMSO-d$_6$): δ 5.54-5.31 (m, 3H), 5.30-5.23 (m, 1H, major), 4.77 (t, 1H, J=4.7 Hz, major), 4.78 (t, 1H, J=6.0 Hz, minor), 3.92-3.71 (m, 8H), 2.72-2.60 (m, 1H, major), 2.35 (dd, 1H, J=4.8, 1.5 Hz, major), 2.33 (dd, 1H, J=4.8, 1.5 Hz, major), 2.27-2.23 (m, 2H, minor), 1.77-1.68 (m, 4H), 1.66-1.46 (m, 9H), 1.28-1.11 (m, 4H).

Step 2. Preparation of 2-(3-cyclopentylpropyl)-1,3-dioxolane

A 0.02 M solution of 2-[(Z)-3-cyclopentylallyl]-1,3-dioxolane and 2-[(E)-3-cyclopentylallyl]-1,3-dioxolane (0.72 g, 1.87 mmol) in EtOH (80 mL) was passed through the H-Cube® hydrogenator flow reactor provided with a 10% Pd/C cartridge [flow rate: 1.0 mL/min; P=1.0 bar; T=35° C.]. The outcoming solution was concentrated to dryness, affording the title compound (0.68 g, 94%) as a colorless oil. $^1$H NMR (DMSO-d$_6$): δ 4.74 (t, 1H, J=4.7 Hz), 3.91-3.81 (m, 2H), 3.79-3.69 (m, 2H), 1.76-1.65 (m, 3H), 1.62-1.39 (m, 6H), 1.38-1.24 (m, 4H), 1.11-0.96 (m, 2H).

Step 3. Preparation of 4-cyclopentylbutanal

A solution of 2-(3-cyclopentylpropyl)-1,3-dioxolane (0.68 g, 3.74 mmol) and 70% AcOH (42 mL) in THF (14 mL) was warmed up to 65° C. and stirred for 16 h, then diluted with Et$_2$O (25 mL), neutralized and washed with cold sat. NaHCO$_3$ solution (3×15 mL). The organic layer was dried over Na$_2$SO$_4$, filtered and concentrated to dryness affording the title compound (1.1 g, quant.), as a colorless oil, which was used in the next step without any further purification. $^1$H NMR (DMSO-d$_6$): δ 9.66 (t, 1H, J=1.7 Hz), 2.41 (td, 2H, J=7.3, 1.6 Hz), 1.78-1.66 (m, 2H), 1.61-1.40 (m, 5H), 1.31-1.22 (m, 4H), 1.11-0.98 (m, 2H).

Step 4. Preparation of 4-cyclopentylbutan-1-ol

To a cooled (0° C.) solution of 4-cyclopentylbutanal (0.52 g, 3.71 mmol) in EtOH (15.0 mL), NaBH$_4$ (0.155 g, 4.09 mmol) was added in one portion. The reaction mixture was stirred at r.t. for 30 min, then diluted with Et$_2$O (40 mL), neutralized and washed with sat. NH$_4$Cl solution (3×25 mL). The organic layer was dried over Na$_2$SO$_4$, filtered and concentrated to dryness giving a crude oily residue (0.5 g). Purification by typical silica gel flash chromatography (Cy/EtOAc, from 90:10 to 83:17) afforded the pure title compound (0.41 g, 60%), as a colorless liquid. $^1$H NMR (DMSO-d$_6$): δ 4.30 (t, 1H, J=5.2 Hz), 3.40-3.34 (m, 2H), 1.76-1.66 (m, 3H), 1.61-1.35 (m, 6H), 1.33-1.22 (m, 4H), 1.11-0.97 (m, 2H).

Step 5. Preparation of 4-cyclopentylbutyl-2-pyridyl carbonate and 4-cyclopentylbutyl 2-oxopyridine-1-carboxylate Under nitrogen atmosphere, to a stirred solution of 4-cyclopentylbutan-1-ol (0.41 g, 2.89 mmol) in dry CH$_2$Cl$_2$ (15 mL), DMAP (0.035 g, 0.29 mmol) and 2-DPC (0.748 g, 3.46 mmol) were added. The reaction mixture was stirred at r.t. for 16 h, then diluted with CH$_2$Cl$_2$ (50 mL) and sequentially washed with sat. NH$_4$Cl solution (15 mL) and sat. NaHCO$_3$ solution (3×15 mL). The organic layer was dried over Na$_2$SO$_4$, filtered and concentrated to dryness affording an oily residue (0.42 g), as a mixture (1:1.7 ratio) of 4-cyclopentylbutyl-2-pyridyl carbonate and 4-cyclopentylbutyl 2-oxopyridine-1-carboxylate. The mixture of isomers was not separated and used in the next step without any further purification. R$_t$=2.84 min. MS (ESI) m/z: 264 [M-H]$^+$, 286 [M–Na]$^+$, 302 [M–K]$^+$.

Step 6. Preparation of 4-cyclopentylbutyl-N-[(3S)-2-oxoazetidin-3-yl]-carbamate

Under nitrogen atmosphere, to a suspension of [(3S)-2-oxoazetidin-3-yl]-ammonium acetate (0.05 g, 0.34 mmol) in dry CH$_2$Cl$_2$ (4.0 mL), DIPEA (0.067 mL, 0.41 mmol) was added dropwise. Subsequently, the crude mixture (0.241 g) containing 4-cyclopentylbutyl-2-oxopyridine-1-carboxylate (0.089 g, 0.34 mmol) in dry CH$_2$Cl$_2$ (2.0 mL) was added.

The reaction mixture was stirred at r.t. for 16 h, then concentrated to dryness giving a solid residue (0.21 g). Trituration with Et$_2$O afforded the pure title compound (0.032 g, 37%), as a white solid. R$_t$=2.42 min. MS (ESI) m/z: 255 [M−H]$^+$, 277 [M−Na]$^+$, 293 [M−K]$^+$. $^1$H NMR (DMSO-d$_6$): δ 7.90 (s, 1H), 7.78 (d, 1H, J=8.7 Hz), 4.65-4.58 (m, 1H), 3.95 (t, 2H, J=6.7 Hz), 3.37 (t, 1H, J=5.2 Hz), 3.06 (dd, 1H, J=5.2, 2.8 Hz), 1.77-1.65 (m, 3H), 1.60-1.42 (m, 6H), 1.35-1.22 (m, 4H), 1.10-0.97 (m, 2H).

Example 21. 3-Cyclopentylpropyl-N-[(3S)-2-oxoazetidin-3-yl]-carbamate

Step 1. Preparation of 3-cyclopentylpropyl-2-pyridyl carbonate and 3-cyclopentylpropyl-2-oxopyridine-1-carboxylate Under nitrogen atmosphere, to a stirred solution of commercially available 3-cyclopentylpropan-1-ol (0.3 g, 2.34 mmol) in dry CH$_2$Cl$_2$ (14 mL), DMAP (0.029 g, 0.23 mmol) and 2-DPC (0.608 g, 2.81 mmol) were added. The reaction mixture was stirred at r.t. for 16 h, then diluted with CH$_2$Cl$_2$ (50 mL) and sequentially washed with sat. NH$_4$Cl solution (15 mL) and sat. NaHCO$_3$ solution (3×15 mL). The organic layer was dried over Na$_2$SO$_4$, filtered and concentrated to dryness affording an oily residue (0.6 g), as a mixture (1:1.8 ratio) of 3-cyclopentylpropyl-2-pyridyl carbonate and 3-cyclopentylpropyl-2-oxopyridine-1-carboxylate. The mixture of isomers was not separated and used in the next step without any further purification. R$_t$=2.62 min. MS (ESI) m/z: 250 [M-H]$^+$, 272 [M−Na]$^+$, 288 [M−K]$^+$.

Step 2. Preparation of 3-cyclopentylpropyl-N-[(3S)-2-oxoazetidin-3-yl]-carbamate Under nitrogen atmosphere, to a suspension of [(3S)-2-oxoazetidin-3-yl]-ammonium acetate (0.05 g, 0.34 mmol) in dry CH$_2$Cl$_2$ (4.0 mL), DIPEA (0.067 mL, 0.41 mmol) was added dropwise. Subsequently, the crude mixture (0.237 g) containing 3-cyclopentylpropyl-2-oxopyridine-1-carboxylate (0.085 g, 0.34 mmol) in dry CH$_2$Cl$_2$ (2.0 mL) was added. The reaction mixture was stirred at r.t. for 16 h, concentrated to dryness giving an oily residue (0.18 g). Purification by typical silica gel flash chromatography (CH$_2$Cl$_2$/MeOH, 98:2) afforded the title compound (0.057 g, 70%), as a white solid. R$_t$=2.18 min. MS (ESI) m/z: 241 [M-H]$^+$, 263 [M−Na]$^+$, 279 [M−K]$^+$. $^1$H NMR (DMSO-d$_6$): δ 7.90 (s, 1H), 7.78 (d, 1H, J=8.9 Hz), 4.67-4.48 (m, 1H), 3.94 (t, 2H, J=6.5 Hz), 3.37 (t, 1H, J=5.2 Hz), 3.07 (dd, 1H, J=5.2, 2.7 Hz), 1.80-1.66 (m, 3H), 1.62-1.41 (m, 6H), 1.35-1.22 (m, 2H), 1.11-0.98 (s, 2H).

Example 22. 4-(4-Methoxyphenyl)-butyl-N-[(3S)-2-oxoazetidin-3-yl]-carbamate

Step 1. Preparation of 4-(4-methoxyphenyl)-butyl-2-pyridyl carbonate and 4-(4-methoxyphenyl)-butyl-2-oxopyridine-1-carboxylate Under nitrogen atmosphere, to a stirred solution of commercially available 4-methoxyphenylbutanol (0.3 g, 1.67 mmol) in dry CH$_2$Cl$_2$ (9.0 mL), DMAP (0.02 g, 0.17 mmol) and 2-DPC (0.43 g, 2.0 mmol) were added. The reaction mixture was stirred at r.t. for 16 h, then diluted with CH$_2$Cl$_2$ (50 mL) and sequentially washed with sat. NH$_4$Cl solution (15 mL) and sat. NaHCO$_3$ solution (3×15 mL). The organic layer was dried over Na$_2$SO$_4$, filtered and concentrated to dryness affording an oily residue (0.511 g), as a mixture (1:1.7 ratio) of 4-(4-methoxyphenyl)-butyl-2-pyridyl carbonate and 4-(4-methoxyphenyl)-butyl-2-oxopyridine-1-carboxylate. The mixture of isomers was not separated and used in the next step without any further purification. R$_t$=2.40 min. MS (ESI) m/z: 302 [M-H]$^+$, 324 [M−Na]$^+$, 340 [M−K]$^+$.

Step 2. Preparation of 4-(4-methoxyphenyl)-butyl-N-[(3S)-2-oxoazetidin-3-yl]-carbamate Under nitrogen atmosphere, to a suspension of [(3S)-2-oxoazetidin-3-yl]-ammonium acetate (0.05 g, 0.34 mmol) in dry CH$_2$Cl$_2$ (4.0 mL), DIPEA (0.067 mL, 0.41 mmol) was added dropwise. Subsequently, the crude mixture (0.276 g) containing 4-(4-methoxyphenyl)-butyl-2-oxopyridine-1-carboxylate (0.102 g, 0.34 mmol) in dry CH$_2$Cl$_2$ (2.0 mL) was added. The reaction mixture was stirred at r.t. for 16 h, then concentrated to dryness giving an oily residue (0.195 g). Purification by typical silica gel flash chromatography (CH$_2$Cl$_2$/MeOH, from 100:0 to 95:5) afforded the pure title compound (0.075 g, 76%), as a white solid. R$_t$=2.02 min. MS (ESI) m/z: 293 [M-H]$^+$, 315 [M−Na]$^+$, 331 [M−K]$^+$. MS (ESI) m/z: 291 [M-H]$^-$. $^1$H NMR (DMSO-d$_6$): δ 7.90 (s, 1H), 7.79 (d, 1H, J=8.8 Hz), 7.13-7.06 (m, 2H), 6.86-6.80 (m, 2H), 4.66-4.49 (m, 1H), 3.97 (t, 2H, J=5.7 Hz), 3.71 (s, 3H), 3.37 (t, 1H, J=5.2 Hz), 3.06 (dd, 1H, J=5.2, 2.6 Hz), 2.55-2.50 (m, 2H), 1.60-1.49 (m, 4H).

Example 23. Hexyl-N-[(3S)-2-oxoazetidin-3-yl]-carbamate

Step 1. Preparation of hexyl-2-pyridyl carbonate and hexyl-2-oxopyridine-1-carboxylate Under nitrogen atmosphere, to a stirred mixture of commercially available 1-hexanol (0.246 mL, 1.96 mmol) in dry CH$_2$Cl$_2$ (8.0 mL), DMAP (0.024 g, 0.19 mmol) and 2-DPC (0.507 g, 2.35 mmol) were added. The reaction mixture was left at r.t. for 16 h, then diluted with CH$_2$Cl$_2$ (50 mL) and sequentially washed with sat. NH$_4$Cl solution (50 mL), a sat. NaHCO$_3$ solution (3×50 mL) and brine (50 mL). The organic layer was dried over Na$_2$SO$_4$, filtered and concentrated to dryness to afford an oily crude product (0.426 g), as a mixture (1:1.8 ratio) of hexyl-2-pyridyl carbonate and hexyl-2-oxopyridine-1-carboxylate. The mixture of isomers was not separated and used in the next step without any further purification. R$_t$=2.33 min; MS (ESI) m/z: 224 [M-H]$^+$, 246 [M−Na]$^+$; (ESI) m/z: 222 [M-H]$^-$.

Step 2. Preparation of hexyl-N-[(3S)-2-oxoazetidin-3-yl]-carbamate

Under nitrogen atmosphere, to a suspension of [(3S)-2-oxoazetidin-3-yl]-ammonium acetate (0.054 g, 0.37 mmol) in dry CH$_2$Cl$_2$ (5.0 mL), DIPEA (0.076 mL, 0.44 mmol) was dropwise added. Subsequently, the crude mixture (0.23 g) containing hexyl-2-oxopyridine-1-carboxylate (0.082 g, 0.37 mmol) in dry CH$_2$Cl$_2$ (2.0 mL) was added. The reaction mixture was stirred at r.t. for 16 h, concentrated to dryness affording an oily residue. Trituration with Et$_2$O afforded the pure title compound (0.045 g, 57%), as a white solid. R$_t$=1.95 min; MS (ESI) m/z: 215 [M-H]$^+$, 237 [M−Na]$^+$. $^1$H NMR (DMSO-d$_6$): δ 7.90 (bs, 1H), 7.78 (d, 1H, J=8.7 Hz), 4.70-4.48 (m, 1H), 4.01-3.89 (m, 2H), 3.37 (t, 1H, J=5.4 Hz), 3.09-3.04 (m, 1H), 1.58-1.45 (m, 2H), 1.35-1.20 (m, 6H), 0.88-0.85 (m, 3H

Example 24.
Octyl-N-[(3S)-2-oxoazetidin-3-yl]-carbamate

Step 1. Preparation of octyl-2-pyridyl carbonate and octyl-2-oxopyridine-1-carboxylate Under nitrogen atmosphere, to a stirred solution of commercially available octan-1-ol (0.24 mL, 1.53 mmol) in dry $CH_2Cl_2$ (15 mL), DMAP (0.02 g, 0.15 mmol) and 2-DPC (0.39 g, 1.84 mmol) were added. The reaction mixture was stirred at r.t. for 16 h, then diluted with $CH_2Cl_2$ (15 mL) and sequentially washed with sat. $NH_4Cl$ solution (15 mL) and sat. $NaHCO_3$ solution (3×15 mL). The organic layer was dried over $Na_2SO_4$, filtered and concentrated to dryness giving an oily residue (0.37 g), as a mixture (1:2 ratio) of octyl-2-pyridyl carbonate and octyl-2-oxopyridine-1-carboxylate. The mixture of isomers was not separated and used in the next step without any further purification. $R_t$=2.82 min. MS (ESI) m/z: 252 $[M-H]^+$. MS (ESI) m/z: 250 $[M-H]^-$.

Step 2. Preparation of octyl-N-[(3S)-2-oxoazetidin-3-yl]-carbamate

Under nitrogen atmosphere, to a suspension of [(3S)-2-oxoazetidin-3-yl]-ammonium acetate (0.05 g, 0.34 mmol) in dry $CH_2Cl_2$ (1.5 mL), DIPEA (0.07 mL, 0.41 mmol) was dropwise added. Subsequently, the crude mixture (0.24 g) containing octyl-2-oxopyridine-1-carboxylate (0.08 g, 0.34 mmol) in dry $CH_2Cl_2$ (2.0 mL) was added. The reaction mixture was stirred at r.t. for 16 h, then diluted with $CH_2Cl_2$ and sequentially washed with sat. $NH_4Cl$ solution (15 mL) and sat. $NaHCO_3$ solution (3×15 mL). The organic layer was dried over $Na_2SO_4$, filtered and concentrated to dryness to give a crude product. Trituration with $Et_2O$ afforded the pure title compound (0.035 g, 42%), as a white solid. $R_t$=2.40 min; MS (ESI) m/z: 243 $[M-H]^+$, 260 $[M-NH_4]^+$, 265 $[M-Na]^+$. MS (ESI) m/z: 241 $[M-H]^-$. $^1H$ NMR (DMSO-$d_6$) δ 7.96-7.88 (m, 1H), 7.78 (d, 1H, J=8.8 Hz), 4.72-4.54 (m, 1H), 3.94 (t, 2H, J=6.7 Hz), 3.37 (t, 1H, J=5.4 Hz), 3.06 (dd, 1H, J=5.2, 2.7 Hz), 1.62-1.44 (m, 2H), 1.36-1.21 (m, 12H), 0.86 (t, 3H, J=7.2 Hz).

Example 25.
Nonyl-N-[(3S)-2-oxoazetidin-3-yl]-carbamate

Step 1. Preparation of nonyl-2-pyridyl carbonate and nonyl-2-oxopyridine-1-carboxylate Under nitrogen atmosphere, to a stirred mixture of commercially available 1-nonanol (0.242 mL, 1.39 mmol) in dry $CH_2Cl_2$ (8.0 mL), DMAP (0.017 g, 0.14 mmol) and 2-DPC (0.359 g, 1.66 mmol) were added. The reaction mixture was left at r.t. for 16 h, then diluted with $CH_2Cl_2$ (50 mL) and sequentially washed with sat. $NH_4Cl$ solution (50 mL), sat. $NaHCO_3$ solution (3×50 mL) and brine (50 mL). The organic layer was dried over $Na_2SO_4$, filtered and concentrated to dryness to afford an oily residue (0.346 g), as a mixture (1:1.8 ratio) of nonyl-2-pyridyl carbonate and nonyl-2-oxopyridine-1-carboxylate. The mixture of isomers was not separated and used in the next step without any further purification. $R_t$=3.02 min; MS (ESI) m/z: 266 $[M-H]^+$, 288 $[M-Na]^+$.

Step 2. Preparation of 5-phenylpentyl-N-[(3S)-2-oxoazetidin-3-yl]-carbamate

Under nitrogen atmosphere, to a suspension of [(3S)-2-oxoazetidin-3-yl]-ammonium acetate (0.038 g, 0.26 mmol) in dry $CH_2Cl_2$ (5.0 mL), DIPEA (0.05 mL, 0.31 mmol) was dropwise added. Subsequently, the crude mixture (0.193 g) containing nonyl-2-oxopyridine-1-carboxylate (0.069 g, 0.26 mmol) in dry $CH_2Cl_2$ (3.0 mL) was added. The reaction mixture was stirred at r.t. for 16 h, concentrated to dryness affording an oily crude product. Trituration with $Et_2O$ afforded the pure title compound (0.038 g, 57%), as a white solid. $R_t$=2.62 min; MS (ESI) m/z: 257 $[M-H]^+$, 279 $[M-Na]^+$. $^1H$ NMR (DMSO-$d_6$): δ 7.90 (bs, 1H), 7.78 (d, 1H, J=8.8 Hz), 4.75-4.49 (m, 1H), 3.94 (t, 1H, J=6.7 Hz), 3.37 (t, 2H, J=5.4 Hz), 3.09-3.04 (m, 1H), 1.58-1.45 (m, 2H), 1.35-1.15 (m, 12H), 0.94-0.82 (m, 3H).

Example 26. (4-Butylphenyl)-methyl-N-[(3S)-2-oxoazetidin-3-yl]-carbamate

Step 1. Preparation of (4-butylphenyl)-methyl-2-pyridyl carbonate and (4-butylphenyl)-methyl-2-oxopyridine-1-carboxylate Under nitrogen atmosphere, to a stirred mixture of commercially available (4-butylbenzyl) alcohol (0.208 mL, 1.22 mmol) in dry $CH_2Cl_2$ (15.0 mL), DMAP (0.015 g, 0.12 mmol) and 2-DPC (0.32 g, 1.46 mmol) were added. The reaction mixture was left at r.t. for 16 h, then diluted with $CH_2Cl_2$ (50 mL) and sequentially washed with sat. $NH_4Cl$ solution (50 mL), sat. $NaHCO_3$ solution (3×50 mL) and brine (50 mL). The organic layer was dried over $Na_2SO_4$, filtered and concentrated to dryness to afford an oily residue (0.426 g), as a mixture (1:1.65 ratio) of (4-butylphenyl)-methyl-2-pyridyl carbonate and (4-butylphenyl)-methyl-2-oxopyridine-1-carboxylate. The mixture of isomers was not separated and used in the next step without any further purification. $R_t$=2.79 min; MS (ESI) m/z: 286 $[M-H]^+$.

Step 2. Preparation of (4-cyclohexylphenyl)-methyl-N-[(3S)-2-oxoazetidin-3-yl]-carbamate Under nitrogen atmosphere, to a suspension of [(3S)-2-oxoazetidin-3-yl]-ammonium acetate (0.056 g, 0.38 mmol) in dry $CH_2Cl_2$ (5.0 mL), DIPEA (0.09 mL, 0.51 mmol) was dropwise added. Subsequently, the crude mixture (0.28 g) containing (4-butylphenyl)-methyl-2-oxopyridine-1-carboxylate (0.10 g, 0.38 mmol) in dry $CH_2Cl_2$ (2.0 mL) was added. The reaction mixture was stirred at r.t. for 16 h, concentrated to dryness affording an oily crude product. Purification by typical silica gel column chromatography (Cy/EtOAc 66:34) afforded the pure title compound (0.07 g, 66%), as a white solid. $R_t$=2.39 min; MS (ESI) m/z: 277 $[M-H]^+$, 294 $[M-NH_4]^+$. $^1H$ NMR (DMSO-$d_6$): δ 7.98-7.90 (m, 2H), 7.32-1.16 (m, 4H), 5.01 (s, 2H), 4.72-4.61 (m, 1H), 3.40 (t, 1H, J=5.45 Hz), 3.12-3.04 (m, 1H), 2.58 (t, 2H, J=7.62 Hz), 1.55 (p, 2H, J=7.62 Hz), 1.37-1.23 (m, 2H), 0.90 (t, 3H, J=7.34 Hz).

Example 27. 3-Phenylpropyl-N-[(3S)-2-oxoazetidin-3-yl]-carbamate

Step 1. Preparation of 3-phenylpropyl-2-pyridyl carbonate and 3-phenylpropyl-2-oxopyridine-1-carboxylate Under nitrogen atmosphere, to a stirred solution of commercially available 3-phenyl-1-propanol (0.20 mL, 1.46 mmol) in dry $CH_2Cl_2$ (15 mL), DMAP (0.02 g, 0.15 mmol) and 2-DPC (0.38 g, 1.76 mmol) were added. The reaction mixture was stirred at r.t. for 16 h, then diluted with $CH_2Cl_2$ (15 mL) and sequentially washed with sat. NH$_4$Cl solution (15 mL) and sat. NaHCO$_3$ solution (3×15 mL). The organic layer was dried over Na$_2$SO$_4$, filtered and concentrated to dryness giving an oily residue (0.45 g), as a mixture (1:2:2 ratio) of 3-phenylpropyl-2-pyridyl carbonate, 3-phenylpropyl-2-oxopyridine-1-carboxylate and 3-phenyl-1-propanol. The mixture of isomers and alcohol was not separated and used in the next step without any further purification. R$_t$=2.28 min. MS (ESI) m/z: 258 [M-H]$^+$, 280 [M−Na]$^+$, 296 [M−K]$^+$. MS (ESI) m/z: 256 [M-H]$^-$.

Step 2. Preparation of 3-phenylpropyl-N-[(3S)-2-oxoazetidin-3-yl]-carbamate

Under nitrogen atmosphere, to a suspension of [(3S)-2-oxoazetidin-3-yl]-ammonium acetate (0.05 g, 0.34 mmol) in dry CH$_2$Cl$_2$ (1.5 mL), DIPEA (0.08 mL, 0.46 mmol) was dropwise added. Subsequently, the crude mixture (0.40 g) containing 3-phenylpropyl-2-oxopyridine-1-carboxylate (0.09 g, 0.34 mmol) in dry CH$_2$Cl$_2$ (2.0 mL) was added. The reaction mixture was stirred at r.t. for 16 h, then diluted with CH$_2$Cl$_2$ and sequentially washed with sat. NH$_4$Cl solution (15 mL) and sat. NaHCO$_3$ solution (3×15 mL). The organic layer was dried over Na$_2$SO$_4$, filtered and concentrated to dryness to give a crude product. Trituration with Et$_2$O afforded the pure title compound (0.035 g, 41%), as a white solid. R$_t$=1.85 min. MS (ESI) m/z: 249 [M-H]$^+$, 271 [M−Na]$^+$. MS (ESI) m/z: 247 [M-H]$^-$. $^1$H NMR (DMSO-d$_6$) δ 7.91 (s, 1H), 7.85 (d, 1H, J=8.8 Hz), 7.32-7.26 (m, 2H), 7.23-7.15 (m, 3H), 4.75-4.54 (m, 1H), 3.96 (t, 2H, J=6.6 Hz), 3.38 (t, 1H, J=5.4 Hz), 3.08 (dd, 1H, J=5.3, 2.7 Hz), 2.72-2.56 (m, 2H), 1.98-1.72 (m, 2H).

Example 28.
Phenethyl-N-[(3S)-2-oxoazetidin-3-yl]-carbamate

Step 1. Preparation of phenethyl-2-pyridyl carbonate and phenethyl 2-oxopyridine-1-carboxylate Under nitrogen atmosphere, to a stirred solution of commercially available 2-phenyl-ethanol (0.20 mL, 1.64 mmol) in dry CH$_2$Cl$_2$ (15 mL), DMAP (0.02 g, 0.16 mmol) and 2-DPC (0.42 g, 1.96 mmol) were added. The reaction mixture was stirred at r.t. for 16 h, then diluted with CH$_2$Cl$_2$ (15 mL) and sequentially washed with sat. NH$_4$Cl solution (15 mL) and sat. NaHCO$_3$ solution (3×15 mL). The organic layer was dried over Na$_2$SO$_4$, filtered and concentrated to dryness giving an oily residue (0.41 g), as a mixture (1:2 ratio) of phenethyl-2-pyridyl carbonate and phenethyl 2-oxopyridine-1-carboxylate. The mixture of isomers was not separated and used in the next step without any further purification. R$_t$=2.05 min. MS (ESI) m/z: 244 [M-H]$^+$, 266 [M−Na]$^+$. MS (ESI) m/z: 242 [M-H]$^-$.

Step 2. Preparation of phenethyl-N-[(3S)-2-oxoazetidin-3-yl]-carbamate

Under nitrogen atmosphere, to a suspension of [(3S)-2-oxoazetidin-3-yl]-ammonium acetate (0.05 g, 0.34 mmol) in dry CH$_2$Cl$_2$ (1.5 mL), DIPEA (0.07 mL, 0.41 mmol) was dropwise added. Subsequently, the crude mixture (0.24 g) containing phenethyl-2-oxopyridine-1-carboxylate (0.08 g, 0.34 mmol) in dry CH$_2$Cl$_2$ (2.0 mL) was added. The reaction mixture was stirred at r.t. for 16 h, then diluted with CH$_2$Cl$_2$ and sequentially washed with sat. NH$_4$Cl solution (15 mL) and sat. NaHCO$_3$ solution (3×15 mL). The organic layer was dried over Na$_2$SO$_4$, filtered and concentrated to dryness to give a crude product. Purification by column chromatography using a Teledyne ISCO apparatus (Cy/EtOAc 20:80) afforded the pure title compound (0.03 g, 37%), as white powder. R$_t$=1.66 min. MS (ESI) m/z: 235 [M-H]$^+$, 252 [M-NH$_4$]$^+$, 257 [M−Na]$^+$. $^1$H NMR (DMSO-d$_6$) δ 7.90 (s, 1H), 7.83 (d, 1H, J=8.7 Hz), 7.33-7.18 (m, 5H), 4.67-4.57 (m, 1H), 4.17 (td, 2H, J=6.9, 2.4 Hz), 3.37 (t, 1H, J=5.5 Hz), 3.06 (dd, 1H, J=5.2, 2.8 Hz), 2.87 (t, 2H, J=6.9 Hz).

Example 29. 4-(o-Tolyl)-butyl-N-[(3S)-2-oxoazetidin-3-yl]-carbamate

Step 1. Preparation of 1-[(Z)-4-benzyloxybut-1-enyl]-2-methyl-benzene and 1-[(E)-4-benzyloxybut-1-enyl]-2-methyl-benzene Under nitrogen atmosphere, to a cooled (−30° C.), stirred solution of 3-benzyloxypropyl-(triphenyl)-phosphonium bromide (2.9 g, 6.0 mmol) in dry THF (75 mL), n-BuLi (2.5 M in hexane, 2.4 mL, 6.0 mmol) was added dropwise. The solution was stirred at −30° C. for 45 min, then commercially available o-tolualdehyde (0.65 g, 5.4 mmol) in dry THF (5.0 mL) was added dropwise. The reaction mixture was stirred at −30° C. for 30 min, and then at r.t. for 16 h. After dilution with CH$_2$Cl$_2$ (40 mL), the mixture was washed with sat. NH$_4$Cl solution (3×30 mL), and the organic layer was dried over Na$_2$SO$_4$, filtered and concentrated to dryness giving an oily residue (2.43 g). Purification by typical silica gel flash chromatography (CH$_2$Cl$_2$) afforded the pure title compounds (0.99 g, 73%), as a mixture (28:72 ratio) of E/Z diastereoisomers. R$_t$=2.33 min (minor) and 2.39 min (major). MS (ESI) m/z: 253 [M-H]$^+$, 270 [M-NH$_4$]$^+$. $^1$H NMR (DMSO-d$_6$): δ 7.44-7.04 (m, 18H), 6.66 (t, 1H, J=15.8, 1.7 Hz, minor), 6.53 (d, 1H, J=11.5, 1.3 Hz, major), 6.14 (dt, 1H, J=15.8, 6.9 Hz, minor), 5.81-5.73 (m, 1H, major), 4.50 (s, 2H, minor), 4.44 (s, 2H, major), 3.57 (t, 2H, J=6.6 Hz, minor), 3.50 (t, 2H, J=6.6 Hz, major), 2.53-2.46 (m, 2H, minor), 2.39 (qd, 2H, J=6.7, 1.8 Hz, major), 2.27 (s, 3H, minor), 2.19 (s, 3H, major).

Step 2. Preparation of 4-(o-tolyl)-butan-1-ol

A 0.05 M solution of 1-[(Z)-4-benzyloxybut-1-enyl]-2-methyl-benzene and 1-[(E)-4-benzyloxybut-1-enyl]-2-methyl-benzene (0.36 g, 1.43 mmol) in EtOH (28 mL) was passed through the H-Cube® hydrogenator flow reactor provided with a 20% Pd(OH)$_2$/C cartridge [flow rate: 1.0 mL/min; P=1.0 bar; T=60° C.]. The outcoming solution was concentrated to dryness, affording the title compound (0.23 g, quant.) as a colorless oil. R$_t$=2.23 min. $^1$H NMR (DMSO-d$_6$): δ 7.14-7.03 (m, 4H), 4.36 (t, 1H, J=5.2 Hz), 3.42 (qd, 2H, J=6.3, 1.1 Hz), 2.55 (t, 2H, J=7.9 Hz), 2.25 (s, 3H), 1.58-1.43 (m, 2H).

Step 3. Preparation of 4-(o-tolyl)-butyl-2-pyridyl carbonate and 4-(o-tolyl)-butyl-2-oxopyridine-1-carboxylate Under nitrogen atmosphere, to a stirred solution of 4-(o-tolyl)-butan-1-ol (0.23 g, 1.4 mmol) in dry CH$_2$Cl$_2$ (8.0 mL), DMAP (0.017 g, 0.14 mmol) and 2-DPC (0.364 g, 1.68 mmol) were added. The reaction mixture was stirred at r.t. for 16 h, then diluted with CH$_2$Cl$_2$ (50 mL) and sequentially washed with sat. NH$_4$Cl solution (15 mL) and sat. NaHCO$_3$ solution (3×15 mL). The organic layer was dried over Na$_2$SO$_4$, filtered and concentrated to dryness affording an oily residue (0.41 g), as a mixture (1:1.7 ratio) of 4-(o-tolyl)-butyl-2-pyridyl carbonate and 4-(o-tolyl)-butyl-2-oxopyridine-1-carboxylate. The mixture of isomers was not separated and used in the next step without any further purification. $R_t$=2.57 min. MS (ESI) m/z: 286 [M-H]$^+$, 308 [M−Na]$^+$, 324 [M−K]$^+$.

Step 4. Preparation of 4-(o-tolyl)-butyl-N-[(3S)-2-oxoazetidin-3-yl]-carbamate

Under nitrogen atmosphere, to a suspension of [(3S)-2-oxoazetidin-3-yl]-ammonium acetate (0.09 g, 0.62 mmol) in dry CH$_2$Cl$_2$ (8.0 mL), DIPEA (0.123 mL, 0.74 mmol) was added dropwise. Subsequently, the crude mixture (0.477 g) containing 4-(o-tolyl)-butyl-2-oxopyridine-1-carboxylate (0.177 g, 0.62 mmol) in dry CH$_2$Cl$_2$ (3.0 mL) was added. The reaction mixture was stirred at r.t. for 16 h, then concentrated to dryness giving an oily residue (0.16 g). Purification by typical silica gel flash chromatography (CH$_2$Cl$_2$/MeOH, from 100:00 to 96:4) afforded the pure title compound (0.065 g, 38%), as a white solid. $R_t$=2.17 min. MS (ESI) m/z: 277 [M-H]$^+$, 299 [M−Na]$^+$, 315 [M−K]$^+$. $^1$H NMR (DMSO-d$_6$): δ 7.90 (s, 1H), 7.80 (d, 1H, J=8.7 Hz), 7.15-7.04 (m, 4H), 4.66-4.49 (m, 1H), 4.01 (t, 2H, J=6.3 Hz), 3.37 (t, 1H, J=5.4 Hz), 3.08-3.04 (m, 1H), 2.57 (t, 2H, J=7.1 Hz), 2.25 (s, 3H), 1.66-1.49 (m, 4H).

Example 30.
Decyl-N-[(3S)-2-oxoazetidin-3-yl]-carbamate

Step 1. Preparation of decyl 2-pyridyl carbonate and decyl 2-oxopyridine-1-carboxylate Under nitrogen atmosphere, to a stirred solution of commercially available decan-1-ol (0.24 mL, 1.26 mmol) in dry CH$_2$Cl$_2$ (13 mL), DMAP (0.01 g, 0.13 mmol) and 2-DPC (0.33 g, 1.52 mmol) were added. The reaction mixture was stirred at r.t. for 16 h, then diluted with CH$_2$Cl$_2$ (15 mL) and sequentially washed with sat. NH$_4$Cl solution (15 mL) and sat. NaHCO$_3$ solution (3×15 mL). The organic layer was dried over Na$_2$SO$_4$, filtered and concentrated to dryness giving an oily residue (0.36 g), as a mixture (1:2 ratio) of decyl 2-pyridyl carbonate and decyl 2-oxopyridine-1-carboxylate. The mixture of isomers was not separated and used in the next step without any further purification. $R_t$=2.09 min. MS (ESI) m/z: 280 [M-H]$^+$. MS (ESI) m/z: 278 [M-H]$^−$.

Step 2. Preparation of octyl-N-[(3S)-2-oxoazetidin-3-yl]-carbamate

Under nitrogen atmosphere, to a suspension of [(3S)-2-oxoazetidin-3-yl]-ammonium acetate (0.05 g, 0.34 mmol) in dry CH$_2$Cl$_2$ (1.5 mL), DIPEA (0.07 mL, 0.41 mmol) was dropwise added. Subsequently, the crude mixture (0.30 g) containing decyl-2-oxopyridine-1-carboxylate (0.09 g, 0.34 mmol) in dry CH$_2$Cl$_2$ (2.0 mL) was added. The reaction mixture was stirred at r.t. for 16 h, then diluted with CH$_2$Cl$_2$ and sequentially washed with sat. NH$_4$Cl solution (15 mL) and sat. NaHCO$_3$ solution (3×15 mL). The organic layer was dried over Na$_2$SO$_4$, filtered and concentrated to dryness to give a crude product. Trituration with Et$_2$O afforded the pure title compound (0.05 g, 54%), as a white solid. $R_t$=2.82 min; MS (ESI) m/z: 271 [M-H]$^+$, 288 [M-NH$_4$]$^+$. MS (ESI) m/z: 269 [M-H]$^−$. $^1$H NMR (DMSO-d$_6$) δ 7.90 (s, 1H), 7.78 (d, 1H, J=8.8 Hz), 4.85-4.53 (m, 1H), 4.08-3.84 (m, 2H), 3.37 (t, 1H J=5.3 Hz), 3.07 (dd, 1H, J=5.1, 2.8 Hz), 1.64-1.43 (m, 2H), 1.26 (d, 14H, J=6.7 Hz), 0.86 (t, 3H, J=7.2 Hz).

Example 31. (4-Cyclohexylphenyl)-methyl-N-[(3S)-2-oxoazetidin-3-yl]-carbamate

Step 1. Preparation of (4-cyclohexylphenyl)-methanol

Under nitrogen atmosphere, to a cooled (0° C.) suspension of LiAlH$_4$ (2.0 M THF solution, 5.3 mL, 10.53 mmol) in dry Et$_2$O (10 mL), commercially available 4-cyclohexylbenzoic acid (0.5 g, 2.45 mmol) in dryEt$_2$O (5.0 mL) was added dropwise. The resulting reaction mixture was stirred at r.t. for 4 h, and then cooled to 0° C. H$_2$O (0.45 mL) was slowly added, followed by 3.0 M KOH solution (0.45 mL) and additional H$_2$O (2.0 mL). The mixture was stirred at 0° C. for 1 h and then filtered off. The organic layer was dried over Na$_2$SO$_4$, filtered and concentrated to dryness, affording the title compound (0.46 g, quant.), which was used in the next step without any further purification. $^1$H NMR (CDCl$_3$): δ 8.05-7.94 (m, 2H), 7.35-7.23 (m, 2H), 4.39 (q, 2H, J=7.12 Hz), 2.59 (tt, 1H J=11.41, 3.27 Hz), 1.97-1.73 (m, 5H), 1.53-1.34 (m, 6H).

Step 2. Preparation of (4-cyclohexylphenyl)-methyl-2-pyridyl carbonate and (4-cyclohexylphenyl)-methyl-2-oxopyridine-1-carboxylate Under nitrogen atmosphere, to a stirred mixture of (4-cyclohexylphenyl)-methanol (0.233 g, 1.23 mmol) in dry CH$_2$Cl$_2$ (8.0 mL), DMAP (0.015 g, 0.12 mmol) and 2-DPC (0.318 g, 1.47 mmol) were added. The reaction mixture was left at r.t. for 16 h, then diluted with CH$_2$Cl$_2$ (50 mL) and sequentially washed with sat. NH$_4$Cl solution (50 mL), sat. NaHCO$_3$ solution (3×50 mL) and brine (50 mL). The organic layer was dried over Na$_2$SO$_4$, filtered and concentrated to dryness to afford an oily crude product (0.426 g), as a mixture (1:1.7 ratio) of (4-cyclohexylphenyl)-methyl-2-pyridyl carbonate and (4-cyclohexylphenyl)-methyl-2-oxopyridine-1-carboxylate. The mixture of isomers was not separated and used in the next step without any further purification. $R_t$=1.73 min; MS (ESI) m/z: 268 [M-H]$^+$.

Step 3. Preparation of (4-cyclohexylphenyl)-methyl-N-[(3S)-2-oxoazetidin-3-yl]-carbamate Under nitrogen atmosphere, to a suspension of [(3S)-2-oxoazetidin-3-yl]-ammonium acetate (0.043 g, 0.29 mmol) in dry CH$_2$Cl$_2$ (5.0 mL), DIPEA (0.06 mL, 0.35 mmol) was dropwise added. Subsequently, the crude mixture (0.24 g) containing (4-cyclohexylphenyl)-methyl-2-oxopyridine-1-carboxylate (0.09 g, 0.29 mmol) in dry CH$_2$Cl$_2$ (2.0 mL) was added. The reaction mixture was stirred at r.t. for 16 h, concentrated to dryness affording an oily crude product. Purification by typical silica gel column chromatography (Cy/EtOAc 85:15) afforded the pure title compound (0.035 g, 38%), as a white solid. $R_t$=2.57 min; MS (ESI) m/z: 303 [M-H]$^+$, 320 [M-NH$_4$]$^+$. $^1$H NMR (DMSO-d$_6$): δ 7.95-7.88 (m, 2H), 7.29-7.17 (m, 4H), 4.98 (s, 2H), 4.65 (ddd, 1H, J=8.43, 5.30, 2.73 Hz), 3.39 (t, 1H, J=5.30 Hz), 3.07 (dd, 1H, J=5.30, 2.73 Hz), 2.47-2.44 (m, 1H), 1.83-1.72 (m, 4H), 1.72-1.64 (m, 1H), 1.47-1.27 (m, 4H), 1.27-1.13 (m, 1H).

Example 32. (3-Benzylphenyl)-methyl-N-[(3S)-2-oxoazetidin-3-yl]-carbamate

Step 1. Preparation of (3-benzylphenyl)-methanol

A solution of commercially available benzyl bromide (0.209 mL, 1.75 mmol), 3-hydroxymethylphenyl boronic acid (0.293 g, 1.93 mmol), bis-(triphenylphosphine)-palladium dichloride (0.039 g, 0.06 mmol) and K$_3$PO$_4$ (0.93 g, 4.39 mmol) in a 5:1 mixture of DMF/H$_2$O (10 mL) was purged by bubbling nitrogen for 5 min, then heated at 80° C. for 1 h. The reaction mixture was cooled to r.t. and diluted with Et$_2$O (30 mL). The organic layer was washed with H$_2$O (3×30 mL) and brine (30 mL), dried over Na$_2$SO$_4$, filtered and concentrated to dryness giving a crude product (0.596 g). Purification by typical silica gel flash chromatography (CH$_2$Cl$_2$) afforded the title compound (0.257 g, 74%), as a transparent oil. R$_t$=2.35 min. $^1$H NMR (DMSO-d$_6$): δ 7.33-7.07 (m, 9H), 5.11 (t, 1H, J=5.6 Hz), 4.45 (d, 1H, J=5.6 Hz), 3.92 (s, 2H).

Step 2. Preparation of (3-benzylphenyl)-methyl-2-pyridyl carbonate and (3-benzylphenyl)-methyl-2-oxopyridine-1-carboxylate Under nitrogen atmosphere, to a stirred solution of (3-benzylphenyl)-methanol (0.26 g, 1.3 mmol) in dry CH$_2$Cl$_2$ (8.0 mL), DMAP (0.017 g, 0.13 mmol) and 2-DPC (0.31 g, 1.43 mmol) were added. The reaction mixture was stirred at r.t. for 16 h, then diluted with CH$_2$Cl$_2$ (50 mL) and sequentially washed with sat. NH$_4$Cl solution (15 mL) and sat. NaHCO$_3$ solution (3×15 mL). The organic layer was dried over Na$_2$SO$_4$, filtered and concentrated to dryness affording an oily residue (0.39 g), as a mixture (1:1.7 ratio) of (3-benzylphenyl)-methyl-2-pyridyl carbonate and (3-benzylphenyl)-methyl-2-oxopyridine-1-carboxylate. The mixture of isomers was not separated and used in the next step without any further purification. R$_t$=2.61 min. MS (ESI) m/z: 320 [M-H]$^+$, 342 [M-Na]$^+$, 358 [M-K]$^+$.

Step 3. Preparation of (3-benzylphenyl)-methyl-N-[(3S)-2-oxoazetidin-3-yl]-carbamate Under nitrogen atmosphere, to a suspension of [(3S)-2-oxoazetidin-3-yl]-ammonium acetate (0.05 g, 0.34 mmol) in dry CH$_2$Cl$_2$ (4.0 mL), DIPEA (0.067 mL, 0.41 mmol) was added dropwise. Subsequently, the crude mixture (0.29 g) containing (3-benzylphenyl)-methyl-2-oxopyridine-1-carboxylate (0.108 g, 0.34 mmol) in dry CH$_2$Cl$_2$ (2.0 mL) was added. The reaction mixture was stirred at r.t. for 16 h, then concentrated to dryness giving a solid residue (0.22 g). Purification by typical silica gel flash chromatography (CH$_2$Cl$_2$/MeOH, from 100:00 to 98:2) afforded the pure title compound (0.035 g, 33%), as a white solid. R$_t$=2.26 min. MS (ESI) m/z: 311 [M-H]$^+$, 333 [M-Na]$^+$, 249 [M-K]$^+$. $^1$H NMR (DMSO-d$_6$): δ 8.00-7.90 (m, 2H), 7.32-7.14 (m, 9H), 5.05-4.96 (m, 2H), 4.68-4.60 (m, 1H), 3.94 (s, 2H), 3.38 (t, 1H, J=5.3 Hz), 3.07 (dd, 1H, J=5.3, 2.7 Hz).

Example 33. (4-Benzylphenyl)-N-[(3S)-2-oxoazetidin-3-yl]-carbamate

Step 1. Preparation of 4-benzylphenol

A solution of commercially available benzyl bromide (0.209 mL, 1.75 mmol), 4-hydroxyphenyl boronic acid (0.266 g, 1.93 mmol), bis-(triphenylphosphine)-palladium dichloride (0.04 g, 0.06 mmol) and K$_3$PO$_4$ (0.93 g, 4.4 mmol) in a 5:1 mixture of DMF/H$_2$O (10 mL) was purged by bubbling nitrogen for 5 min, then heated at 80° C. for 1 h. The reaction mixture was cooled to r.t. and diluted with Et$_2$O (30 mL). The organic layer was washed with H$_2$O (3×30 mL) and brine (30 mL), dried over Na$_2$SO$_4$, filtered and concentrated to dryness giving a crude product (0.54 g). Purification by typical silica gel flash chromatography (CH$_2$Cl$_2$) afforded the title compound (0.09 g, 28%), as a solid. R$_t$=2.41 min. $^1$H NMR (DMSO-d$_6$): δ 9.17 (s, 1H), 7.30-7.23 (m, 2H), 7.21-7.13 (m, 3H), 7.02-6.97 (m, 2H), 6.69-6.64 (m, 2H), 3.81 (s, 2H).

Step 2. Preparation of (4-benzylphenyl)-2-pyridyl carbonate and (4-benzylphenyl)-2-oxopyridine-1-carboxylate Under nitrogen atmosphere, to a stirred solution of 4-benzylphenol (0.09 g, 0.49 mmol) in dry CH$_2$Cl$_2$ (4.0 mL), DMAP (0.006 g, 0.05 mmol) and 2-DPC (0.127 g, 0.59 mmol) were added. The reaction mixture was stirred at r.t. for 16 h, then diluted with CH$_2$Cl$_2$ (50 mL) and sequentially washed with sat. NH$_4$Cl solution (15 mL) and sat. NaHCO$_3$ solution (3×15 mL). The organic layer was dried over Na$_2$SO$_4$, filtered and concentrated to dryness affording an oily residue (0.15 g), as a mixture (1:1.7 ratio) of (4-benzylphenyl)-2-pyridyl carbonate and (4-benzylphenyl)-2-oxopyridine-1-carboxylate. The mixture of isomers was not separated and used in the next step without any further purification. R$_t$=2.56 min. MS (ESI) m/z: 306 [M-H]$^+$, 328 [M-Na]$^+$, 344 [M-K]$^+$.

Step 3. Preparation of (4-benzylphenyl)-N-[(3S)-2-oxoazetidin-3-yl]-carbamate Under nitrogen atmosphere, to a suspension of [(3S)-2-oxoazetidin-3-yl]-ammonium acetate (0.05 g, 0.34 mmol) in dry CH$_2$Cl$_2$ (4.0 mL), DIPEA (0.067 mL, 0.41 mmol) was added dropwise. Subsequently, the crude mixture (0.28 g) containing (4-benzylphenyl)-2-oxopyridine-1-carboxylate (0.104 g, 0.34 mmol) in dry CH$_2$Cl$_2$ (2.0 mL) was added. The reaction mixture was stirred at r.t. for 16 h, then concentrated to dryness giving an solid residue (0.165 g). Trituration with MeOH afforded the pure title compound (0.021 g, 21%), as a white solid. R$_t$=2.18 min. MS (ESI) m/z: 297 [M-H]$^+$, 319 [M-Na]$^+$, 335 [M-K]$^+$. $^1$H NMR (DMSO-d$_6$): δ 8.42 (d, 1H, J=8.8 Hz), 7.99 (s, 1H), 7.33-7.15 (m, 7H), 7.05-6.98 (m, 2H), 4.71 (ddd, 1H, J=8.4, 5.4, 2.7 Hz), 3.93 (s, 2H), 3.44 (t, 1H, J=5.4 Hz), 3.14 (dd, 1H, J=5.4, 2.7 Hz).

Example 34. (4-Benzylphenyl)-methyl-N-[(3S)-2-oxoazetidin-3-yl]-carbamate

Step 1. Preparation of (4-benzylphenyl)-methanol

A solution of commercially available benzyl bromide (0.209 mL, 1.75 mmol), 4-hydroxymethylphenyl boronic acid (0.293 g, 1.93 mmol), bis-(triphenylphosphine)-palladium dichloride (0.04 g, 0.06 mmol) and K$_3$PO$_4$ (0.93 g, 4.39 mmol) in a 5:1 mixture of DMF/H$_2$O (10 mL) was purged by bubbling nitrogen for 5 min, then heated at 80° C. for 1 h. The reaction mixture was cooled to r.t. and diluted with Et$_2$O (30 mL). The organic layer was washed with H$_2$O (3×30 mL) and brine (30 mL), dried over Na$_2$SO$_4$, filtered and concentrated to dryness giving a crude product (0.645 g). Purification by typical silica gel flash chromatography (CH$_2$Cl$_2$) afforded the title compound (0.24 g, 68%), as an oil. R$_t$=2.35 min. $^1$H NMR (DMSO-d$_6$): δ 7.33-7.14 (m, 9H), 5.08 (t, 1H, J=5.7 Hz), 4.44 (d, 1H, J=5.7 Hz), 3.91 (s, 2H).

Step 2. Preparation of (4-benzylphenyl)-methyl-2-pyridyl carbonate and (4-benzylphenyl)-methyl-2-oxopyridine-1-carboxylate Under nitrogen atmosphere, to a stirred solution of (4-benzylphenyl)-methanol (0.236 g, 1.19 mmol) in dry $CH_2Cl_2$ (8.0 mL), DMAP (0.017 g, 0.14 mmol) and 2-DPC (0.308 g, 1.43 mmol) were added. The reaction mixture was stirred at r.t. for 16 h, then diluted with $CH_2Cl_2$ (50 mL) and sequentially washed with sat. $NH_4Cl$ solution (15 mL) and sat. $NaHCO_3$ solution (3×15 mL). The organic layer was dried over $Na_2SO_4$, filtered and concentrated to dryness affording an oily residue (0.37 g), as a mixture (1:1.7 ratio) of (4-benzylphenyl)-methyl-2-pyridyl carbonate and (4-benzylphenyl)-methyl-2-oxopyridine-1-carboxylate. The mixture of isomers was not separated and used in the next step without any further purification. $R_f$=2.62 min. MS (ESI) m/z: 320 [M-H]$^+$, 342 [M-Na]$^+$, 358 [M-K]$^+$.

Step 3. Preparation of (4-benzylphenyl)-methyl-N-[(3S)-2-oxoazetidin-3-yl]-carbamate Under nitrogen atmosphere, to a suspension of [(3S)-2-oxoazetidin-3-yl]-ammonium acetate (0.05 g, 0.34 mmol) in dry $CH_2Cl_2$ (4.0 mL), DIPEA (0.067 mL, 0.41 mmol) was added dropwise. Subsequently, the crude mixture (0.293 g) containing (4-benzylphenyl)-methyl-2-oxopyridine-1-carboxylate (0.108 g, 0.34 mmol) in dry $CH_2Cl_2$ (2.0 mL) was added. The reaction mixture was stirred at r.t. for 16 h, then concentrated to dryness giving a solid residue (0.21 g). Purification by typical silica gel flash chromatography ($CH_2Cl_2$/MeOH, from 100:00 to 98:2) afforded the pure title compound (0.034 g, 33%), as a white solid. $R_f$=2.27 min. MS (ESI) m/z: 311 [M-H]$^+$, 333 [M-Na]$^+$. $^1$H NMR (DMSO-d$_6$): δ 7.97-7.90 (m, 2H), 7.32-7.16 (m, 9H), 5.00 (s, 2H), 4.66 (ddd, 1H, J=8.5, 5.4, 2.9 Hz), 3.94 (s, 2H), 3.39 (t, 1H, J=5.4 Hz), 3.08 (dd, 1H, J=5.4, 2.9 Hz).

Example 35. (2-Cyclohexylphenyl)-methyl-N-[(3S)-2-oxoazetidin-3-yl]-carbamate

Step 1. Preparation of (2-cyclohexylphenyl)-methanol

Under nitrogen atmosphere, to a cooled (0° C.) suspension of LiAlH$_4$ (2.0 M THF solution, 4.9 mL, 9.80 mmol) in dryEt$_2$O (10 mL), commercially available 2-cyclohexylbenzoic acid (0.5 g, 2.45 mmol) in dryEt$_2$O (5.0 mL) was added dropwise. The resulting reaction mixture was stirred at r.t. for 4 h, and then cooled to 0° C. H$_2$O (0.45 mL) was slowly added, followed by 3.0 M KOH solution (0.45 mL) and additional H$_2$O (2.0 mL). The mixture was stirred at 0° C. for 1 h and then filtered off. The organic layer was dried over Na$_2$SO$_4$, filtered and concentrated to dryness, affording the title compound (0.46 g, quant.), which was used in the next step without any further purification. $^1$H NMR (CDCl$_3$): δ 7.44-7.18 (m, 2H), 4.83-4.69 (m, 2H), 2.93-2.74 (m, 1H), 1.97-1.74 (m, 5H), 1.56-1.39 (m, 6H).

Step 2. Preparation of (2-cyclohexylphenyl)-methyl-2-pyridyl carbonate and (2-cyclohexylphenyl)-methyl-2-oxopyridine-1-carboxylate Under nitrogen atmosphere, to a stirred mixture of (2-cyclohexylphenyl)-methanol (0.3 g, 1.58 mmol) in dry $CH_2Cl_2$ (8.0 mL), DMAP (0.019 g, 0.16 mmol) and 2-DPC (0.409 g, 1.90 mmol) were added. The reaction mixture was left at r.t. for 16 h, then diluted with $CH_2Cl_2$ (50 mL) and sequentially washed with sat. $NH_4Cl$ solution (50 mL), sat. $NaHCO_3$ solution (3×50 mL) and brine (50 mL). The organic layer was dried over $Na_2SO_4$, filtered and concentrated to dryness to afford an oily product (0.426 g), as a mixture (1:1.7 ratio) of (2-cyclohexylphenyl)-methyl-2-pyridyl carbonate and (2-cyclohexylphenyl)-methyl-2-oxopyridine-1-carboxylate. The mixture of isomers was not separated and used in the next step without any further purification. $R_f$=2.89 min; MS (ESI) m/z: 312 [M-H]$^+$, 334 [M-Na]$^+$.

Step 3. Preparation of (2-cyclohexylphenyl)-methyl-N-[(3S)-2-oxoazetidin-3-yl]-carbamate Under nitrogen atmosphere, to a suspension of [(3S)-2-oxoazetidin-3-yl]-ammonium acetate (0.067 g, 0.46 mmol) in dry $CH_2Cl_2$ (5.0 mL), DIPEA (0.096 mL, 0.55 mmol) was dropwise added. Subsequently, the crude mixture (0.39 g) containing (2-cyclohexylphenyl)-methyl-2-oxopyridine-1-carboxylate (0.14 g, 0.46 mmol) in dry $CH_2Cl_2$ (2.0 mL) was added. The reaction mixture was stirred at r.t. for 16 h, concentrated to dryness affording an oily crude product. Purification by typical silica gel column chromatography (Cy/EtOAc 85:15) afforded the pure title compound (0.062 g, 45%), as a white solid. $R_f$=2.47 min; MS (ESI) m/z: 303 [M-H]$^+$, 320 [M-Na]$^+$. $^1$H NMR (DMSO-d$_6$): δ 7.94-7.86 (m, 2H), 7.36-7.24 (m, 3H), 7.21-7.10 (m, 1H), 5.09 (s, 2H), 4.70-4.61 (m, 1H), 3.39 (t, 1H, J=5.37 Hz), 3.10-3.03 (m, 1H), 2.75-2.65 (m, 1H), 1.82-1.68 (m, 6H), 1.48-1.21 (m, 6H).

Example 36. 2-(4-Phenylphenyl)-ethyl-N-[(3S)-2-oxoazetidin-3-yl]-carbamate

Step 1. Preparation of 2-(4-phenylphenyl)-ethanol

Under nitrogen atmosphere, to a cooled (0° C.) suspension of LiAlH$_4$ (2.0 M in THF solution, 5.65 mL, 11.3 mmol) in dry Et$_2$O (20 mL), commercially available 4-biphenyl-acetic acid (0.6 g, 2.83 mmol) in dry Et$_2$O (8.0 mL) was added dropwise. The resulting reaction mixture was stirred at r.t. for 4 h, and then cooled to 0° C. H$_2$O (0.50 mL) was slowly added, followed by 3.0 M KOH solution (0.50 mL) and additional H$_2$O (1.5 mL). The mixture was stirred at 0° C. for 1 h and then filtered off. The organic layer was dried over Na$_2$SO$_4$, filtered and concentrated to dryness, affording the title compound (0.53 g, 87%), which was used in the next step without any further purification. $^1$H NMR (DMSO-d$_6$) δ 7.67-7.61 (m, 2H), 7.59-7.54 (m, 2H), 7.50-7.42 (m, 2H), 7.38-7.28 (m, 3H), 4.64 (t, 1H, J=5.2 Hz), 3.78-3.53 (m, 2H), 2.76 (t, 2H, J=7.0 Hz).

Step 2. Preparation of 2-(4-phenylphenyl)-ethyl-2-pyridyl carbonate and 2-(4-phenylphenyl)-ethyl-2-oxopyridine-1-carboxylate Under nitrogen atmosphere, to a stirred solution of 2-(4-phenylphenyl)-ethanol (0.30 g, 1.41 mmol) in dry $CH_2Cl_2$ (15 mL), DMAP (0.014 g, 0.11 mmol) and 2-DPC (0.37 g, 1.70 mmol) were added. The reaction mixture was stirred at r.t. for 16 h, then diluted with $CH_2Cl_2$ (15 mL) and sequentially washed with sat. $NH_4Cl$ solution (15 mL) and sat. $NaHCO_3$ solution (3×15 mL). The organic layer was dried over $Na_2SO_4$, filtered and concentrated to dryness giving an oily residue (0.46 g), as a mixture (1:1.7 ratio) of 2-(4-phenylphenyl)-ethyl-2-pyridyl carbonate and 2-(4-phenylphenyl)-ethyl-2-oxopyridine-1-carboxylate. The mixture of isomers was not separated and used in the next step without any further purification. $R_t$=2.63 min. MS (ESI) m/z: 244 [M-H]$^+$, 266 [M−Na]$^+$. MS (ESI) m/z: 242 [M-H]$^-$.

Step 3. Preparation of 2-(4-phenylphenyl)-ethyl-N-[(3S)-2-oxoazetidin-3-yl]-carbamate Under nitrogen atmosphere, to a suspension of [(3S)-2-oxoazetidin-3-yl]-ammonium acetate (0.05 g, 0.34 mmol) in dry CH$_2$Cl$_2$ (1.5 mL), DIPEA (0.07 mL, 0.41 mmol) was dropwise added. Subsequently, the crude mixture (0.27 g) containing 2-(4-phenylphenyl)-ethyl-2-oxopyridine-1-carboxylate (0.10 g, 0.34 mmol) in dry CH$_2$Cl$_2$ (2.0 mL) was added. The reaction mixture was stirred at r.t. for 16 h, then diluted with CH$_2$Cl$_2$ and sequentially washed with sat. NH$_4$Cl solution (15 mL) and sat. NaHCO$_3$ solution (3×15 mL). The organic layer was dried over Na$_2$SO$_4$, filtered and concentrated to dryness to give a crude product. Trituration with Et$_2$O afforded the pure title compound (0.05 g, 47%), as a white solid. $R_t$=2.28 min. MS (ESI) m/z: 311 [M-H]$^+$. MS (ESI) m/z: 309 [M-H]$^-$. $^1$H NMR (DMSO-d$_6$) δ 7.91 (s, 1H), 7.85 (d, 1H, J=8.7 Hz), 7.67-7.62 (m, 2H), 7.62-7.55 (m, 2H), 7.49-7.42 (m, 2H), 7.39-7.32 (m, 3H), 4.71-4.56 (m, 1H), 4.22 (td, 2H, J=6.7, 2.5 Hz), 3.37 (t, 1H, J=5.3 Hz), 3.07 (dd, 1H, J=5.2, 2.7 Hz), 2.92 (t, 2H, J=6.8 Hz).

Example 37. 4-(2-Pyridyl)-butyl-N-[(3S)-2-oxoazetidin-3-yl]-carbamate

Step 1. Preparation of 4-(2-pyridyl)-but-3-yn-1-ol

Under nitrogen atmosphere, and at r.t., CuI (0.06 g, 0.31 mmol), dry Et$_3$N (1.32 mL, 9.49 mmol) and bis-(triphenylphosphine)-palladium chloride (0.13 g, 0.18 mmol) were sequentially added to a solution of 2-bromopyridine (0.60 mL, 6.33 mmol) in 1,4-dioxane (10 mL). Then, but-3-yn-1-ol (0.57 mL, 7.59 mmol) was added dropwise at the same temperature. The resulting reaction mixture was left stirred overnight, then concentrated under reduced pressure, dissolved in EtOAc (80 mL) and washed with H$_2$O (3×10 mL). The organic layer was dried over Na$_2$SO$_4$ and concentrated to dryness to give an oily crude (1.1 g). Purification by typical silica gel flash chromatography using a Teledyne ISCO apparatus (Cy/EtOAc from 90:10 to 30:70) afforded the pure title compound (0.84 g, 90%), as a white solid. $R_t$=1.25 min. MS (ESI) m/z: 148 [M-H]$^+$, 170 [M−Na]$^+$, 186 [M−K]$^+$. $^1$H NMR (DMSO-d$_6$): δ 8.55-8.49 (m, 1H), 7.76 (td, 1H, J=7.8, 1.8 Hz), 7.44 (d, 1H, J=7.8 Hz), 7.33 (ddd, 1H, J=7.8, 4.9, 1.8 Hz), 4.92 (t, 1H, J=5.2 Hz), 3.62-3.58 (m, 2H), 2.58 (t, 2H, J=6.8 Hz).

Step 2. Preparation of 4-(2-pyridyl)-butan-1-ol

A 0.23 M solution of 4-(2-pyridyl)-but-3-yn-1-ol (0.4 g, 2.72 mmol) in EtOH (12 mL) was passed through the H-Cube® hydrogenator flow reactor provided with 10% Pd(OH)$_2$ cartridge (flow rate: 1.0 mL/min; P=1.0 bar, T=25° C.). The outcoming solution was concentrated to dryness, leading to the title compound (0.36 g, 88%), which was used in the next step without any further purification. $R_t$=1.11 min. MS (ESI) m/z: 152 [M-H]$^+$, 174 [M−Na]$^+$. $^1$H NMR (DMSO-d$_6$): δ=8.49-8.43 (m, 2H), 7.68 (td, 1H, J=7.6, 1.9 Hz), 7.23 (d, 1H, J=7.6 Hz), 7.18 (ddd, 1H, J=7.6, 5.4, 1.9 Hz), 3.40 (t, 2H, J=6.6 Hz), 2.71 (t, 2H, J=6.6 Hz), 1.74-1.63 (m, 2H), 1.50-1.39 (m, 2H).

Step 3. Preparation of 4-(2-pyridyl)-butyl-2-pyridyl carbonate and 4-(2-pyridyl)-butyl-2-oxopyridine-1-carboxylate Under nitrogen atmosphere, to a stirred solution of 4-(2-pyridyl)-butan-1-ol (0.30 g, 1.98 mmol) in dry CH$_2$Cl$_2$ (10 mL), DMAP (0.024 g, 0.19 mmol) and 2-DPC (0.12 g, 2.37 mmol) were added. The reaction mixture was left at r.t. for 16 h, then diluted with CH$_2$Cl$_2$ (50 mL) and sequentially washed with sat. NH$_4$Cl solution (15 mL), sat. NaHCO$_3$ solution (3×15 mL) and brine (15 mL). The organic layer was dried over Na$_2$SO$_4$, filtered and concentrated to dryness giving a grey oily residue (0.51 g), as a mixture (1:1.5 ratio) of 4-(2-pyridyl)-butyl-2-pyridyl carbonate and 4-(2-pyridyl)-butyl-2-oxopyridine-1-carboxylate. The mixture of isomers was not separated and used in the next step without any further purification. $R_t$=1.64. MS (ESI) m/z: 273 [M-H]$^+$, 295 [M−Na]$^+$, 311 [M−K]$^+$; MS (ESI) m/z: 271 [M-H]$^-$

Step 4. Preparation of 4-(2-pyridyl)-butyl-N-[(3S)-2-oxoazetidin-3-yl]-carbamate Under nitrogen atmosphere, to a suspension of [(3S)-2-oxoazetidin-3-yl]-ammonium acetate (0.05 g, 0.34 mmol) in dry CH$_2$Cl$_2$ (4.0 mL), DIPEA (0.067 mL, 0.41 mmol) was added dropwise. Subsequently, the crude mixture (0.18 g) containing 4-(2-pyridyl)-butyl-2-oxopyridine-1-carboxylate (0.073 g, 0.34 mmol) in dry CH$_2$Cl$_2$ (2.0 mL) was added. The reaction mixture was stirred at r.t. for 16 h, concentrated to dryness giving an oily crude (0.21 g). Purification by typical silica gel flash chromatography using a Teledyne ISCO apparatus (Cy/AcOEt, from 90:10 to 10:90) followed by preparative HPLC afforded the pure title compound (0.020 mg, 22%), as a white solid. $R_t$=1.28 min. MS (ESI) m/z: 264 [M-H]$^+$, 286 [M−Na]$^+$, 302 [M−K]$^+$. $^1$H NMR (DMSO-d$_6$): δ 8.50-8.44 (m, 1H), 7.90 (s, 1H), 7.79 (d, 1H, J=8.7 Hz), 7.68 (td, 1H, J=7.6, 1.9 Hz), 7.24 (d, 1H, J=7.6 Hz), 7.18 (ddd, 1H, J=7.6, 4.9, 0.8 Hz), 4.69-4.62 (m, 1H), 3.98 (t, 2H, J=6.5 Hz), 3.37 (t, 1H, J=5.3 Hz), 3.06 (dd, 1H, J=5.3, 2.7 Hz), 2.74 (t, 2H, J=7.6 Hz), 1.71 (p, 2H, J=8.0, 7.5 Hz), 1.62-1.52 (m, 2H).

Example 38. 4-[4-(Trifluoromethyl)-phenyl]-butyl-N-[(3S)-2-oxoazetidin-3-yl]-carbamate

Step 1. Preparation of 1-[(E)-4-benzyloxybut-1-enyl]-4-(trifluoromethyl)-benzene and 1-[(Z)-4 benzyloxybut-1-enyl]-4-(trifluoromethyl)-benzene Under nitrogen atmosphere, to a stirred and cooled (−30° C.) solution of commercially available 3-benzyloxypropyl-(triphenyl)-phosphonium bromide (2.18 g, 4.42 mmol) in dry THF (40 mL), n-BuLi (2.5 M in hexane, 1.77 mL, 4.42 mmol) was added dropwise. The resulting yellowish suspension was stirred at −30° C. for 45 min, then a solution of commercially available 4-(trifluoromethyl)-benzaldehyde (0.70 g, 4.02 mmol) in dry THF (2.0 mL) was slowly added. The reaction mixture was stirred at −30° C. for 30 min, and at r.t. for 16 h. The suspension was diluted with CH$_2$Cl$_2$ (120 mL), washed with sat. NH$_4$Cl solution (20 mL), sat. NaHCO$_3$ solution (2×10 mL) and brine (10 mL). The organic layer was dried over Na$_2$SO$_4$, filtered and concentrated to dryness giving a brown oily crude (2.84 g). Purification by typical silica gel flash chromatography using a Teledyne ISCO apparatus (Cy/EtOAc, from 100:0 to 90:10) afforded the title compounds (0.79 g, 64%), as a mixture (ratio 15:85) of E/Z diastereoisomers, as an oil. $^1$H NMR (DMSO-d$_6$): δ 7.69 (d, 2H, J=8.2 Hz, major), 7.64 (d, 2H, J=8.4 Hz, minor), 7.58 (d, 2H, J=8.4 Hz, minor), 7.52 (d, 2H, J=8.2 Hz, major), 7.37-7.23 (m, 10H), 6.56 (d, 1H, J=11.9 Hz, major), 6.50 (dt, 1H, J=16.0, 6.3 Hz), 5.90-5.86 (m, 2H), 4.50 (s, 2H, minor), 4.47 (s, 2H, major), 3.55 (t, 4H, J=6.4 Hz), 2.57 (qd, 4H, J=6.4, 1.8 Hz).

Step 2. Preparation of 4-[4-(trifluoromethyl)-phenyl]-butan-1-ol

A solution containing a mixture of 1-[(E)-4-benzyloxy-but-1-enyl]-4-(trifluoromethyl)-benzene and 1-[(Z)-4 benzyloxybut-1-enyl]-4-(trifluoromethyl)-benzene (0.5 g, 1.88 mmol) in EtOH (38.0 mL) was passed through the H-Cube® hydrogenator flow reactor provided with 20% Pd(OH)$_2$/C cartridge (flow rate: 1.0 mL/min; P=1.0 bar; T=60° C.). The outcoming solution was concentrated to dryness affording a crude product (0.44 g) which was purified by silica gel flash chromatography (Cy/EtOAc, from 100:0 to 70:30) giving the pure title compound (0.31 g, 76%), as a colorless liquid. $^1$H NMR (DMSO-d$_6$): δ 7.62 (d, 2H, J=8.1 Hz), 7.2 (d, 2H, J=8.1 Hz), 4.37 (t, 1H, J=5.2 Hz), 3.41 (q, 2H, J=6.4 Hz), 2.67 (t, 2H, J=7.6 Hz), 1.68-1.55 (m, 2H), 1.49-1.33 (m, 2H).

Step 3. Preparation of 4-[4-(trifluoromethyl)-phenyl]-butyl-2-pyridyl carbonate and 4-[4-(trifluoromethyl)-phenyl]-butyl-2-oxopyridine-1-carboxylate Under nitrogen atmosphere, to a stirred solution of 4-[4-(trifluoromethyl)-phenyl]-butan-1-ol (0.25 g, 1.14 mmol) in dry CH$_2$Cl$_2$ (6 mL), DMAP (0.014 g, 0.11 mmol) and 2-DPC (0.29 g, 1.37 mmol) were added. The reaction mixture was left at r.t. for 16 h, then diluted with CH$_2$Cl$_2$ (60 mL) and sequentially washed with a sat. NH$_4$Cl solution (15 mL), sat. NaHCO$_3$ solution (3×15 mL) and brine (15 mL). The organic layer was dried over Na$_2$SO$_4$, filtered and concentrated to dryness to afford a grey oily residue (0.34 g), as a mixture (1:1.5 ratio) of 4-[4-(trifluoromethyl)-phenyl]-butyl-2-pyridyl carbonate and 4-[4-(trifluoromethyl)-phenyl]-butyl-2-oxopyridine-1-carboxylate. The mixture of isomers was not separated and used in the next step without any further purification. R$_t$=2.70 min. MS (ESI) m/z: 340 [M-H]$^+$, 362 [M−Na]$^+$, 378 [M−K]$^+$; MS (ESI) m/z: 338 [M-H]$^-$.

Step 4. Preparation of 4-[4-(trifluoromethyl)-phenyl]-butyl-N-[(3S)-2-oxoazetidin-3-yl]-carbamate Under nitrogen atmosphere, to a suspension of [(3S)-2-oxoazetidin-3-yl]-ammonium acetate (0.06 g, 0.41 mmol) in dry CH$_2$Cl$_2$ (4.0 mL), DIPEA (0.081 mL, 0.49 mmol) was added dropwise. Subsequently, the crude mixture (0.35 g) containing 4-[4-(trifluoromethyl)-phenyl]-butyl-2-oxopyridine-1-carboxylate (0.139 g, 0.41 mmol) in dry CH$_2$Cl$_2$ (2.0 mL) was added. The reaction mixture was stirred at r.t. for 16 h, concentrated to dryness giving an oily crude (0.24 g). Purification by typical silica gel flash chromatography (Cy/EtOAc, from 90:10 to 40:60) afforded the pure title compound (0.071 g, 52%), as a white solid. R$_t$=2.35 min. MS (ESI) m/z: 331 [M-H]$^+$, 348 [M−NH$_4$]$^+$, 353 [M−Na]$^+$, 369 [M−K]$^+$. $^1$H NMR (DMSO-d$_6$): δ 7.91 (s, 1H), 7.80 (d, 1H, J=8.7 Hz), 7.63 (d, 2H, J=8.0 Hz), 7.43 (d, 2H, J=8.0 Hz), 4.64-4.60 (m, 1H), 3.99 (t, 2H, J=6.1 Hz), 3.37 (t, 1H, J=5.2), 3.06 (dd, 1H, J=5.2, 2.7 Hz), 2.69 (t, 2H, J=7.3 Hz), 1.73-1.48 (m, 4H).

Example 39. 4-(4-Ethylphenyl)-butyl-N-[(3S)-2-oxoazetidin-3-yl]-carbamate

Step 1. Preparation of 1-[(E)-4-benzyloxybut-1-enyl]-4-ethyl-benzene and 1-[(Z)-4 benzyloxybut-1-enyl]-4-ethyl-benzene Under nitrogen atmosphere, to a stirred and cooled (−30° C.) solution of commercially available 3-benzyloxypropyl-(triphenyl)-phosphonium bromide (2.83 g, 5.74 mmol) in dry THF (50 mL), n-BuLi (2.5 M in hexane, 2.29 mL, 5.74 mmol) was added dropwise. The resulting yellowish suspension was stirred for 45 min at −30° C., then a solution of commercially available 4-ethyl-benzaldehyde (0.70 g, 5.22 mmol) in dry THF (5.0 mL) was slowly added. The reaction mixture was stirred at −30° C. for 30 min, and at r.t. for 16 h. The suspension was diluted with CH$_2$Cl$_2$ (120 mL), washed with sat. NH$_4$Cl solution (20 mL), sat. NaHCO$_3$ solution (2×10 mL) and brine (10 mL). The organic layer was dried over Na$_2$SO$_4$, filtered and concentrated to dryness giving a brown oily crude (2.84 g). Purification by typical silica gel flash chromatography using a Teledyne ISCO apparatus (Cy/EtOAc 90:10) afforded the title compound (0.81 g, 58%), as mixture (45:55 ratio) of E/Z diastereoisomers, as a yellow oil. $^1$H NMR (DMSO-d$_6$): δ 7.39-7.05 (m, 18H), 6.44 (d, 1H, J=11.7 Hz, major), 6.42 (d, 1H, J=15.9 Hz, minor), 6.21 (dt, 1H, J=15.9, 6.9 Hz, minor), 5.65 (dt, 1H, J=11.7, 7.2 Hz, major), 4.49 (s, 2H, minor), 4.48 (s, 2H, major), 3.53 (td, 4H, J=6.6, 4.0 Hz), 2.63-2.53 (m, 4H), 2.57-.2.50 (m, 2H), 2.48-2.41 (m, 2H, minor), 1.24-1.12 (m, 6H).

Step 2. Preparation of 4-(4-ethylphenyl)-butan-1-ol

A solution containing a mixture of 1-[(E)-4-benzyloxybut-1-enyl]-4-ethyl-benzene and 1-[(Z)-4 benzyloxybut-1-enyl]-4-ethyl-benzene (0.61 g, 2.3 mmol) in EtOH (46 mL) was passed through the H-Cube® hydrogenator flow reactor provided with 20% Pd(OH)$_2$/C cartridge (flow rate: 1.0 mL/min; P=1.0 bar; T=60° C.). The outcoming solution was concentrated to dryness affording a crude product (0.39 g) which was purified by silica gel flash chromatography (Cy/EtOAc 100:0 to 70:30), giving the pure title compound (0.36 g, 89%), as a liquid. $^1$H NMR (DMSO-d$_6$): δ 7.13-7.03 (m, 4H), 4.34 (t, 1H, J=5.2 Hz), 3.42-3.37 (m, 2H), 2.59-2.50 (m, 4H), 1.61-1.51 (m, 2H), 1.47-1.37 (m, 2H), 1.15 (t, 3H, J=7.6 Hz).

Step 3. Preparation of 4-(4-ethylphenyl)-butyl-2-pyridyl carbonate and 4-(4-ethylphenyl)-butyl-2-oxopyridine-1-carboxylate Under nitrogen atmosphere, to a stirred solution of 4-(4-ethylphenyl)-butan-1-ol (0.36 g, 2.04 mmol) in dry CH$_2$Cl$_2$ (10 mL), DMAP (0.024 g, 0.20 mmol) and 2-DPC (0.530 g, 2.45 mmol) were added. The reaction mixture was left at r.t. for 16 h, then diluted with CH$_2$Cl$_2$ (50 mL) and sequentially washed with sat. NH$_4$Cl solution (15 mL), sat. NaHCO$_3$ solution (3×15 mL) and brine (15 mL). The organic layer was dried over Na$_2$SO$_4$, filtered and concentrated to dryness to afford a grey oily residue (0.57 g), as a mixture (1:1.5 ratio) of 4-(4-ethylphenyl)-butyl-2-pyridyl carbonate and 4-(4-ethylphenyl)-butyl-2-oxopyridine-1-carboxylate. The mixture of isomers was not separated and used in the next step without any further purification. R$_t$=2.79. MS (ESI) m/z: 300 [M-H]$^+$, 322 [M−Na]$^+$, 338 [M−K]$^+$; MS (ESI) m/z: 298 [M-H]$^-$.

Step 4. Preparation of 4-(4-ethylphenyl)-butyl-N-[(3S)-2-oxoazetidin-3-yl]-carbamate Under nitrogen atmosphere, to a suspension of [(3S)-2-oxoazetidin-3-yl]-ammonium acetate (0.06 g, 0.41 mmol) in dry $CH_2Cl_2$ (4.0 mL), DIPEA (0.081 mL, 0.49 mmol) was added dropwise. Subsequently, the crude mixture (0.29 g) containing 4-(4-ethylphenyl)-butyl-2-oxopyridine-1-carboxylate (0.118 g, 0.41 mmol) in dry $CH_2Cl_2$ (2.0 mL) was added. The reaction mixture was stirred at r.t. for 16 h, concentrated to dryness giving an oily crude (0.25 g). Purification by typical silica gel flash chromatography (Cy/AcOEt, from 90:10 to 40:60) afforded the pure title compound (0.061 mg, 51%), as a white solid. $R_t$=2.42 min. MS (ESI) m/z: 291 [M-H]$^+$, 308 [M-NH$_4$]$^+$, 329 [M-K]$^+$. MS (ESI) m/z: 289 [M-H]$^-$. $^1$H NMR (DMSO-d$_6$): δ 7.90 (s, 1H), 7.79 (d, 1H, J=8.7 Hz), 7.05-7.02 (m, 4H), 4.64-4.62 (m, 1H), 3.97 (t, 2H, J=5.8 Hz), 3.37 (t, 1H, J=5.2 Hz), 3.06 (dd, 1H, J=5.2, 2.7 Hz), 2.60-2.50 (m, 4H), 1.75-1.62 (m, 4H), 1.15 (t, 3H, J=7.6 Hz).

Example 40. [4-(o-Tolyl)-phenyl]-methyl-N-[(3S)-2-oxoazetidin-3-yl]-carbamate

Step 1. Preparation of 4-(o-tolyl)-benzoic acid

In a 35 mL microwave reaction vessel, commercially available 4-bromobenzoic acid (0.3 g, 1.5 mmol), o-tolylboronic acid (0.243 g, 1.80 mmol) and $Na_2HPO_4$ (1.065 g, 7.50 mmol) were sequentially added. $H_2O$ (9.0 mL) was added and the mixture stirred at 50° C. to dissolve most of the materials. Bis-(disodium 2-aminopyrimidine-4,6-diolate) palladium acetate [prepared as described in *J. Am. Chem. Soc.* 2009, 131, 16346-16347] (0.01 M in Pd(II), 1.50 mL, 0.015 mmol) was added to the reaction and the tube was heated to 120° C. under microwave irradiation for 10 min, under vigorous stirring. After cooling to r.t., the reaction was partitioned between 1.0 M HCl solution (50 mL) and EtOAc (50 mL). The organic layer was separated, dried over $Na_2SO_4$ and filtered through a short pad of silica gel and Celite. The collected organic phase was concentrated under reduced pressure affording the title compound (0.34 g, quant.) as a white solid, which was used in the next step without any further purification. $R_t$=2.02 min. MS (ESI) m/z: 211 [M-H]$^-$. $^1$H NMR (DMSO-d$_6$): δ 12.95 (s, 1H), 8.00 (dt, 2H, J=8.2, 1.8 Hz), 7.47 (dt, 2H, J=8.2, 1.8 Hz), 7.35-7.03 (m, 5H).

Step 2. Preparation of [4-(o-tolyl)-phenyl]-methanol

Under nitrogen atmosphere, to a cooled (0° C.) suspension of LiAlH$_4$ (2.0 M in THF, 3.3 mL, 6.6 mmol) in dry Et$_2$O (20.0 mL), a solution of 4-(o-tolyl)-benzoic acid (0.35 g, 1.65 mmol) in dry THF (8.0 mL) was added dropwise. The resulting mixture was stirred at r.t. for 1 h, then cooled to 0° C. and $H_2O$ (0.25 mL) was slowly and cautiously added, followed by a 3.0 M KOH solution (0.25 mL) and additional $H_2O$ (0.75 mL). The mixture was stirred at 0° C. for 1 h, filtered and the organic phase dried over $Na_2SO_4$, concentrated to dryness giving a solid residue (0.310 g). Purification by typical silica gel flash chromatography (Cy/EtOAc, 4:1) afforded the pure title compound (0.270 g, 83%), as a white solid. $R_t$=2.41 min. $^1$H NMR (DMSO-d$_6$): δ 7.40-7.35 (m, 2H), 7.31-7.21 (m, 5H), 7.20-7.16 (m, 1H), 5.20 (t, 1H, J=5.7 Hz), 4.55 (d, 2H, J=5.7 Hz), 2.23 (s, 3H).

Step 3. Preparation of [4-(o-tolyl)-phenyl]-methyl-2-pyridyl carbonate and [4-(o-tolyl)-phenyl]-methyl-2-oxopyridine-1-carboxylate Under nitrogen atmosphere, to a stirred solution of [4-(o-tolyl)-phenyl]-methanol (0.250 g, 1.26 mmol) in dry $CH_2Cl_2$ (10.0 mL), DMAP (0.015 g, 0.13 mmol) and 2-DPC (0.327 g, 1.52 mmol) were added. The reaction mixture was stirred at r.t. for 16 h, then diluted with $CH_2Cl_2$ (50 mL) and sequentially washed with sat. NH$_4$Cl solution (15 mL) and sat. NaHCO$_3$ solution (3×15 mL). The organic layer was dried over $Na_2SO_4$, filtered and concentrated to dryness affording a grey oily residue (0.42 g), as a mixture (1:1.9 ratio) of [4-(o-tolyl)-phenyl]-methyl-2-pyridyl carbonate and [4-(o-tolyl)-phenyl]-methyl-2-oxopyridine-1-carboxylate. The mixture of isomers was not separated and used in the next step without any further purification. $R_t$=1.30 min. MS (ESI) m/z: 342 [M-Na]$^+$, 358 [M-K]$^+$.

Step 4. Preparation of [4-(o-tolyl)-phenyl]-methyl-N-[(3S)-2-oxoazetidin-3-yl]-carbamate Under nitrogen atmosphere, to a suspension of [(3S)-2-oxoazetidin-3-yl]-ammonium acetate (0.05 g, 0.34 mmol) in dry $CH_2Cl_2$ (4.0 mL), DIPEA (0.067 mL, 0.41 mmol) was added dropwise. Subsequently, the crude mixture (0.314 g) containing [4-(o-tolyl)-phenyl]-methyl-2-oxopyridine-1-carboxylate (0.108 g, 0.34 mmol) in dry $CH_2Cl_2$ (2.0 mL) was added. The reaction mixture was stirred at r.t. for 16 h, then concentrated to dryness giving an oily residue (0.22 g). Trituration with Et$_2$O afforded the pure title compound (0.053 g, 50%), as a white solid. $R_t$=2.32 min. MS (ESI) m/z: 311 [M-H]$^+$, 333 [M-Na]$^+$, 349 [M-K]$^+$. $^1$H NMR (DMSO-d$_6$): δ 8.00 (d, 1H, J=8.8 Hz), 7.94 (s, 1H), 7.45-7.40 (m, 2H), 7.36-7.32 (m, 2H), 7.31-7.22 (m, 3H), 7.21-7.17 (m, 1H), 5.10 (s, 2H), 4.68 (ddd, 1H, J=8.6, 5.5, 2.8 Hz), 3.41 (t, 1H, J=5.5 Hz), 3.10 (dd, 1H, J=5.5, 2.8 Hz), 2.22 (s, 3H).

Example 41. [3-Methyl-4-(o-tolyl)-phenyl]-methyl-N-[(3S)-2-oxoazetidin-3-yl]-carbamate

Step 1. Preparation of 3-methyl-4-(o-tolyl)-benzoic acid

In a 35 mL microwave reaction vessel, commercially available 4-bromo-3-methylbenzoic acid (0.2 g, 0.93 mmol), o-tolylboronic acid (0.151 g, 1.12 mmol) and $Na_2HPO_4$ (0.66 g, 4.65 mmol) were sequentially added. $H_2O$ (6.0 mL) was added and the mixture stirred at 50° C. to dissolve most of the materials. Bis-(disodium 2-aminopyrimidine-4,6-diolate) palladium acetate [prepared as described in *J. Am. Chem. Soc.* 2009, 131, 16346-16347] (0.01 M in Pd(II), 1.50 mL, 0.015 mmol) was added to the reaction and the tube was heated to 120° C. under microwave irradiation for 10 min, under vigorous stirring. After cooling to r.t., the reaction was partitioned between 1.0 M HCl solution (100 mL) and EtOAc (100 mL). The organic layer was separated, dried over $Na_2SO_4$, filtered and concentrated affording a solid residue (0.304 g). Purification by typical silica gel flash chromatography ($CH_2Cl_2$) afforded the pure title compound (0.20 g, 95%) as a white wax. $R_t$=2.20 min. MS (ESI) m/z: 225 [M-H]$^-$. $^1$H NMR (DMSO-d$_6$): δ 12.90 (s, 1H), 7.90 (d, 1H, J=1.0 hz), 7.80 (dd, 1H, J=7.9, 1.6 Hz), 7.35-7.23 (m, 3H), 7.19 (d, 1H, J=7.9 Hz), 7.07 (dd, 1H, J=7.5, 1.4 Hz), 2.04 (s, 3H), 1.99 (s, 3H).

Step 2. Preparation of [3-methyl-4-(o-tolyl)-phenyl]-methanol

Under nitrogen atmosphere, to a cooled (0° C.) suspension of LiAlH$_4$ (2.0 M in THF, 1.77 mL, 3.54 mmol) in dry Et$_2$O (11.0 mL), a solution of 3-methyl-4-(o-tolyl)-benzoic acid (0.2 g, 0.88 mmol) in dry Et$_2$O (6.0 mL) was added dropwise. The resulting mixture was stirred at r.t. for 1 h, then cooled to 0° C. and H$_2$O (0.15 mL) was slowly and cautiously added, followed by a 3.0 M KOH solution (0.15 mL) and additional H$_2$O (0.50 mL). The mixture was stirred at 0° C. for 1 h, filtered and the organic phase dried over Na$_2$SO$_4$ and concentrated to dryness giving a solid residue (0.2 g). Purification by typical silica gel flash chromatography (Cy/EtOAc, 4:1) afforded the pure title compound (0.171 g, 92%), as a white solid. R$_t$=2.57 min. $^1$H NMR (DMSO-d$_6$): δ 7.31-7.15 (m, 5H), 7.06-6.98 (m, 2H), 5.15 (t, 1H, J=5.7 Hz), 4.51 (d, 1H, J=5.7 Hz), 1.99 (s, 3H), 1.98 (s, 3H).

Step 3. Preparation of [3-methyl-4-(o-tolyl)-phenyl]-methyl-2-pyridyl carbonate and [3-methyl-4-(o-tolyl)-phenyl]-methyl-2-oxopyridine-1-carboxylate Under nitrogen atmosphere, to a stirred solution of [3-methyl-4-(o-tolyl)-phenyl]-methanol (0.171 g, 0.81 mmol) in dry CH$_2$Cl$_2$ (8.0 mL), DMAP (0.01 g, 0.08 mmol) and 2-DPC (0.21 g, 0.97 mmol) were added. The reaction mixture was stirred at r.t. for 16 h, then diluted with CH$_2$Cl$_2$ (50 mL) and sequentially washed with sat. NH$_4$Cl solution (15 mL) and sat. NaHCO$_3$ solution (3×15 mL). The organic layer was dried over Na$_2$SO$_4$, filtered and concentrated to dryness affording a grey oily residue (0.26 g), as a mixture (1:2 ratio) of [3-methyl-4-(o-tolyl)-phenyl]-methyl-2-pyridyl carbonate and [3-methyl-4-(o-tolyl)-phenyl]-methyl-2-oxopyridine-1-carboxylate. The mixture of isomers was not separated and used in the next step without any further purification. R$_t$=1.50 min. MS (ESI) m/z: 356 [M+Na]$^+$, 372 [M+K]$^+$.

Step 4. Preparation of [3-methyl-4-(o-tolyl)-phenyl]-methyl-N-[(3S)-2-oxoazetidin-3-yl]-carbamate Under nitrogen atmosphere, to a suspension of [(3S)-2-oxoazetidin-3-yl]-ammonium acetate (0.035 g, 0.24 mmol) in dry CH$_2$Cl$_2$ (4.0 mL), DIPEA (0.048 mL, 0.29 mmol) was added dropwise. Subsequently, the crude mixture (0.240 g) containing [3-methyl-4-(o-tolyl)-phenyl]-methyl-2-oxopyridine-1-carboxylate (0.080 g, 0.24 mmol) in dry CH$_2$Cl$_2$ (2.0 mL) was added. The reaction mixture was stirred at r.t. for 16 h, then concentrated to dryness giving a solid residue (0.16 g). Trituration with Et$_2$O afforded the pure title compound (0.037 g, 48%), as a white solid. R$_t$=2.45 min. MS (ESI) m/z: 325 [M-H]$^+$, 347 [M−Na]$^+$, 363 [M−K]$^+$. MS (ESI) m/z: 323 [M−H]$^−$. $^1$H NMR (DMSO-d$_6$): δ 7.98 (d, 1H, J=8.8 Hz), 7.94 (s, 1H), 7.32-7.20 (m, 4H), 7.08-7.03 (m, 2H), 5.05 (s, 2H), 4.68 (ddd, 1H, J=8.5, 5.6, 2.9 Hz), 3.41 (t, 1H, J=5.6 Hz), 3.10 (dd, 1H, J=5.6, 2.9 Hz), 1.99 (s, 6H).

Example 42. [3-Methyl-4-(m-tolyl)-phenyl]-methyl-N-[(3S)-2-oxoazetidin-3-yl]-carbamate

Step 1. Preparation of 3-methyl-4-(m-tolyl)-benzoic acid

In a 35 mL microwave reaction vessel, commercially available 4-bromo-3-methylbenzoic acid (0.250 g, 1.16 mmol), m-tolylboronic acid (0.188 g, 1.40 mmol) and Na$_2$HPO$_4$ (0.826 g, 5.81 mmol) were sequentially added. H$_2$O (10 mL) was added and the mixture stirred at 50° C. to dissolve most of the materials. Bis-(disodium 2-aminopyrimidine-4,6-diolate) palladium acetate [prepared as described in J. Am. Chem. Soc. 2009, 131, 16346-16347] (0.01 M in Pd(II), 1.50 mL, 0.015 mmol) was added to the reaction and the tube was heated to 120° C. under microwave irradiation for 10 min, under vigorous stirring. After cooling to r.t., the reaction was partitioned between 1.0 M HCl solution (100 mL) and EtOAc (100 mL). The organic layer was separated, dried over Na$_2$SO$_4$, filtered and concentrated affording a crude residue (0.39 g). Purification by typical silica gel flash chromatography (CH$_2$Cl$_2$) afforded the pure title compound (0.275 g, quant.) as a white solid. R$_t$=2.22 min. MS (ESI) m/z: 225 [M−H]$^−$. $^1$H NMR (DMSO-d$_6$): δ 12.86 (s, 1H), 7.87 (s, 1H), 7.83-7.78 (m, 1H), 7.35 (t, 1H, J=7.5 Hz), 7.29 (d, 1H, J=7.9 Hz), 7.23-7.12 (m, 3H), 2.36 (s, 3H), 2.27 (s, 3H).

Step 2. Preparation of [3-methyl-4-(m-tolyl)-phenyl]-methanol

Under nitrogen atmosphere, to a cooled (0° C.) suspension of LiAlH$_4$ (2.0 M in THF, 2.30 mL, 4.60 mmol) in dry Et$_2$O (12 mL), a solution of 3-methyl-4-(m-tolyl)-benzoic acid (0.26 g, 1.15 mmol) in dry Et$_2$O (7.0 mL) was added dropwise. The resulting mixture was stirred at r.t. for 1 h, then cooled to 0° C. and H$_2$O (0.18 mL) was slowly and cautiously added, followed by a 3.0 M KOH solution (0.18 mL) and additional H$_2$O (0.75 mL). The mixture was stirred at 0° C. for 1 h, filtered and the organic phase dried over Na$_2$SO$_4$ and concentrated to dryness giving a solid residue (0.25 g). Purification by typical silica gel flash chromatography (Cy/EtOAc, 4:1) afforded the pure title compound (0.227 g, 93%), as a white solid. R$_t$=2.59 min. $^1$H NMR (DMSO-d$_6$): δ 7.31 (t, 1H, J=7.5 Hz), 7.24-7.07 (m, 6H), 5.14 (t, 1H, J=5.6 Hz), 4.50 (d, 1H, J=5.6 Hz), 2.35 (s, 3H), 2.21 (s, 3H).

Step 3. Preparation of [3-methyl-4-(m-tolyl)-phenyl]-methyl-2-pyridyl carbonate and [3-methyl-4-(m-tolyl)-phenyl]-methyl-2-oxopyridine-1-carboxylate Under nitrogen atmosphere, to a stirred solution of [3-methyl-4-(m-tolyl)-phenyl]-methanol (0.227 g, 1.07 mmol) in dry CH$_2$Cl$_2$ (9.0 mL), DMAP (0.013 g, 0.11 mmol) and 2-DPC (0.278 g, 1.28 mmol) were added. The reaction mixture was stirred at r.t. for 16 h, then diluted with CH$_2$Cl$_2$ (50 mL) and sequentially washed with sat. NH$_4$Cl solution (15 mL) and sat. NaHCO$_3$ solution (3×15 mL). The organic layer was dried over Na$_2$SO$_4$, filtered and concentrated to dryness affording a grey oily residue (0.345 g), as a mixture (1:1.8 ratio) of [3-methyl-4-(m-tolyl)-phenyl]-methyl-2-pyridyl carbonate and [3-methyl-4-(m-tolyl)-phenyl]-methyl-2-oxopyridine-1-carboxylate. The mixture of isomers was not separated and used in the next step without any further purification. R$_t$=1.54 min. MS (ESI) m/z: 356 [M−Na]$^+$, 372 [M−K]$^+$.

Step 4. Preparation of [3-methyl-4-(m-tolyl)-phenyl]-methyl-N-[(3S)-2-oxoazetidin-3-yl]-carbamate Under nitrogen atmosphere, to a suspension of [(3S)-2-oxoazetidin-3-yl]-ammonium acetate (0.050 g, 0.34 mmol) in dry CH$_2$Cl$_2$ (4.0 mL), DIPEA (0.067 mL, 0.41 mmol) was added dropwise. Subsequently, the crude mixture (0.317 g) containing [3-methyl-4-(m-tolyl)-phenyl]-methyl-2-oxopyridine-1-carboxylate (0.113 g, 0.34 mmol) in dry $CH_2Cl_2$ (2.0 mL) was added. The reaction mixture was stirred at r.t. for 16 h, then concentrated to dryness giving a solid residue (0.22 g). Trituration with $Et_2O$ afforded the pure title compound (0.040 g, 36%), as a white solid. $R_t$=2.48 min. MS (ESI) m/z: 325 [M-H]$^+$, 347 [M–Na]$^+$, 363 [M–K]$^+$. MS (ESI) m/z: 323 [M-H]$^-$. $^1$H NMR (DMSO-d$_6$): δ 7.96 (d, 1H, J=8.9 Hz), 7.94 (s, 1H), 7.32 (t, 1H, J=7.6 Hz), 7.27 (s, 1H), 7.25-7.09 (m, 5H), 5.04 (s, 2H), 4.68 (ddd, 1H, J=8.5, 5.5, 2.9 Hz), 3.41 (t, 1H, J=5.5 Hz), 3.09 (dd, 1H, J=5.5, 2.9 Hz), 2.35 (s, 3H), 2.22 (s, 3H).

Example 43. [4-(m-Tolyl)-phenyl]-methyl-N-[(3S)-2-oxoazetidin-3-yl]-carbamate

Step 1. Preparation of 4-(m-tolyl)-benzoic acid

In a 35 mL microwave reaction vessel, commercially available 4-bromobenzoic acid (0.3 g, 1.5 mmol), m-tolylboronic acid (0.243 g, 1.80 mmol) and $Na_2HPO_4$ (1.065 g, 7.50 mmol) were sequentially added. $H_2O$ (9.0 mL) was added and the mixture stirred at 50° C. to dissolve most of the materials. Bis-(disodium 2-aminopyrimidine-4,6-diolate) palladium acetate [prepared as described in J. Am. Chem. Soc. 2009, 131, 16346-16347] (0.01 M in Pd(II), 1.50 mL, 0.015 mmol) was added to the reaction solution and the tube was heated to 120° C. under microwave irradiation for 10 min, under vigorous stirring. After cooling to r.t., the reaction was partitioned between 1.0 M HCl solution (100 mL) and EtOAc (100 mL). The organic layer was separated, dried over $Na_2SO_4$, and filtered through a short pad of silica gel and Celite. The collected organic layer was concentrated under reduced pressure affording the title compound (0.34 g, quant.) as a white solid, which was used in the next step without any further purification. $R_t$=2.05 min. MS (ESI) m/z: 211 [M-H]$^-$. $^1$H NMR (DMSO-d$_6$): δ 12.95 (s, 1H), 8.01 (dt, 2H, J=8.3, 1.7 Hz), 7.78 (dt, 2H, J=8.3, 1.7 Hz), 7.57-7.49 (m, 2H), 7.38 (t, 1H, J=7.4 Hz), 7.26-7.22 (m, 1H), 2.39 (s, 3H).

Step 2. Preparation of [4-(m-tolyl)-phenyl]-methanol

Under nitrogen atmosphere, to a cooled (0° C.) stirred suspension of LiAlH$_4$ (2.0 M in THF, 3.20 mL, 6.42 mmol) in dry $Et_2O$ (22 mL), a solution of 4-(m-tolyl)-benzoic acid (0.340 g, 1.60 mmol) in dry THF (8.0 mL) was added dropwise. The resulting mixture was stirred at r.t. for 1 h, then cooled to 0° C. and $H_2O$ (0.25 mL) was slowly and cautiously added, followed by a 3.0 M KOH solution (0.25 mL) and additional $H_2O$ (0.75 mL). The mixture was stirred at 0° C. for 1 h, filtered and the organic phase dried over $Na_2SO_4$ and concentrated to dryness giving a solid residue (0.31 g). Purification by typical silica gel flash chromatography (Cy/EtOAc, 4:1) afforded the pure title compound (0.28 g, 88%), as a white solid. $R_t$=2.43 min. $^1$H NMR (DMSO-d$_6$): δ 7.60 (dt, 2H, J=8.2, 1.8 Hz), 7.48-7.37 (m, 3H), 7.33 (t, 1H, J=7.7 Hz), 7.18-7.14 (m, 1H), 5.19 (t, 1H, J=5.7 Hz), 4.53 (d, 1H, J=5.7 Hz), 2.37 (s, 3H).

Step 3. Preparation of [4-(m-tolyl)-phenyl]-methyl-2-pyridyl carbonate and [4-(m-tolyl)-phenyl]-methyl-2-oxopyridine-1-carboxylate Under nitrogen atmosphere, to a stirred solution of [4-(m-tolyl)phenyl]methanol (0.250 g, 1.26 mmol) in dry $CH_2Cl_2$ (10 mL), DMAP (0.015 g, 0.13 mmol) and 2-DPC (0.327 g, 1.52 mmol) were added. The reaction mixture was stirred at r.t. for 16 h, then diluted with $CH_2Cl_2$ (50 mL) and sequentially washed with sat. NH$_4$Cl solution (15 mL) and sat. NaHCO$_3$ solution (3×15 mL). The organic layer was dried over $Na_2SO_4$, filtered and concentrated to dryness affording a grey oily residue (0.40 g), as a mixture (1:1.8 ratio) of [4-(m-tolyl)-phenyl]-methyl-2-pyridyl carbonate and [4-(m-tolyl)-phenyl]-methyl-2-oxopyridine-1-carboxylate. The mixture of isomers was not separated and used in the next step without any further purification. $R_t$=1.34 min. MS (ESI) m/z: 342 [M–Na]$^+$, 358 [M–K]$^+$.

Step 4. Preparation of [4-(m-tolyl)-phenyl]-methyl-N-[(3S)-2-oxoazetidin-3-yl]-carbamate Under nitrogen atmosphere, to a suspension of [(3S)-2-oxoazetidin-3-yl]-ammonium acetate (0.050 g, 0.34 mmol) in dry $CH_2Cl_2$ (4.0 mL), DIPEA (0.067 mL, 0.41 mmol) was added dropwise. Subsequently, the crude mixture (0.304 g) containing [4-(m-tolyl)-phenyl]-methyl-2-oxopyridine-1-carboxylate (0.108 g, 0.34 mmol) in dry $CH_2Cl_2$ (2.0 mL) was added. The reaction mixture was stirred at r.t. for 16 h, then concentrated to dryness giving an solid residue (0.22 g). Trituration with $Et_2O$ afforded the pure title compound (0.054 g, 51%), as a white solid. $R_t$=2.35 min. MS (ESI) m/z: 311 [M-H]$^+$, 333 [M–Na]$^+$, 349 [M–K]$^+$. MS (ESI) m/z: 309 [M-H]$^-$. $^1$H NMR (DMSO-d$_6$): δ 7.99 (d, 1H, J=8.7 Hz), 7.94 (s, 1H), 7.67-7.63 (m, 2H), 7.50-7.40 (m, 4H), 7.35 (t, 1H, J=7.6 Hz), 7.21-7.16 (m, 1H), 5.08 (s, 2H), 4.67 (ddd, 1H, J=8.6, 5.5, 2.8 Hz), 3.40 (t, 1H, J=5.5 Hz), 3.09 (dd, 1H, J=5.5, 2.8 Hz), 2.38 (s, 3H).

Example 44. (3-Methyl-4-phenyl-phenyl)-methyl-N-[(3S)-2-oxoazetidin-3-yl]-carbamate

Step 1. Preparation of 3-methyl-4-phenyl-benzoic acid

In a 35 mL microwave reaction vessel, commercially available 4-bromo-3-methylbenzoic acid (0.25 g, 1.16 mmol), phenylboronic acid (0.17 g, 1.4 mmol) and $Na_2HPO_4$ (0.83 g, 5.8 mmol) were sequentially added. $H_2O$ (10 mL) was added and the mixture stirred at 50° C. to dissolve most of the materials. Bis-(disodium 2-aminopyrimidine-4,6-diolate) palladium acetate [prepared as described in J. Am. Chem. Soc. 2009, 131, 16346-16347] (0.01 M in Pd(II), 1.50 mL, 0.015 mmol) was added to the reaction and the tube was heated to 120° C. under microwave irradiation for 10 min, under vigorous stirring. After cooling to r.t., the reaction was partitioned between 1.0 M HCl solution (100 mL) and EtOAc (100 mL). The organic layer was separated, dried over $Na_2SO_4$, and filtered through a short pad of silica gel and Celite. The collected organic phase was concentrated under reduced pressure affording the title compound (0.29 g, quant.) as a white solid, which was used in the next step without any further purification. $R_t$=2.04 min. MS (ESI) m/z: 213 [M-H]$^+$. MS (ESI) m/z: 211 [M-H]$^-$. $^1$H NMR (DMSO-d$_6$): δ 12.88 (s, 1H), 7.90-7.86 (m, 1H), 7.84-7.76 (m, 1H), 7.50-7.44 (m, 2H), 7.43-7.29 (m, 4H), 2.28 (s, 3H).

Step 2. Preparation of (3-methyl-4-phenyl-phenyl)-methanol

Under nitrogen atmosphere, to a cooled (0° C.), stirred suspension of LiAlH$_4$ (2.0 M in THF, 2.74 mL, 5.47 mmol)

in dry Et$_2$O (12 mL), a solution of 3-methyl-4-phenyl-benzoic acid (0.290 g, 1.37 mmol) in dry Et$_2$O (7.0 mL) was added dropwise. The resulting mixture was stirred at r.t. for 1 h, then cooled to 0° C. and H$_2$O (0.21 mL) was slowly and cautiously added, followed by a 3.0 M KOH solution (0.21 mL) and additional H$_2$O (0.75 mL). The mixture was stirred at 0° C. for 1 h, filtered and the organic phase dried over Na$_2$SO$_4$ and concentrated to dryness giving a solid residue (0.27 g). Purification by typical silica gel flash chromatography (Cy/EtOAc, 4:1) afforded the pure title compound (0.211 g, 78%), as a white solid. R$_t$=2.40 min. $^1$H NMR (DMSO-d$_6$): δ 7.46-7.40 (m, 2H), 7.38-7.29 (m, 3H), 7.26-7.12 (m, 3H), 5.15 (t, 1H, J=5.7 Hz), 4.50 (d, 1H, J=5.7 Hz), 2.22 (s, 3H).

Step 3. Preparation of (3-methyl-4-phenyl-phenyl)-methyl-2-pyridyl carbonate and (3-methyl-4-phenyl-phenyl)-methyl-2-oxopyridine-1-carboxylate Under nitrogen atmosphere, to a stirred solution of (3-methyl-4-phenyl-phenyl)-methanol (0.211 g, 1.07 mmol) in dry CH$_2$Cl$_2$ (9.0 mL), DMAP (0.013 g, 0.11 mmol) and 2-DPC (0.276 g, 1.28 mmol) were added. The reaction mixture was stirred at r.t. for 16 h, then diluted with CH$_2$Cl$_2$ (50 mL) and sequentially washed with sat. NH$_4$Cl solution (15 mL) and sat. NaHCO$_3$ solution (3×15 mL). The organic layer was dried over Na$_2$SO$_4$, filtered and concentrated to dryness affording an oily residue (0.40 g), as a mixture (1:2.1 ratio) of (3-methyl-4-phenyl-phenyl)-methyl-2-pyridyl carbonate and (3-methyl-4-phenyl-phenyl)-methyl-2-oxopyridine-1-carboxylate. The mixture of isomers was not separated and used in the next step without any further purification. R$_t$=1.29 min. MS (ESI) m/z: 342 [M–Na]$^+$, 358 [M–K]$^+$.

Step 4. Preparation of (3-methyl-4-phenyl-phenyl)-methyl-N-[(3S)-2-oxoazetidin-3-yl]-carbamate Under nitrogen atmosphere, to a suspension of [(3S)-2-oxoazetidin-3-yl]-ammonium acetate (0.050 g, 0.34 mmol) in dry CH$_2$Cl$_2$ (4.0 mL), DIPEA (0.067 mL, 0.41 mmol) was added dropwise. Subsequently, the crude mixture (0.335 g) containing (3-methyl-4-phenyl-phenyl)-methyl-2-oxopyridine-1-carboxylate (0.108 g, 0.34 mmol) in dry CH$_2$Cl$_2$ (2.0 mL) was added. The reaction mixture was stirred at r.t. for 16 h, then concentrated to dryness giving a solid residue (0.21 g). Trituration with Et$_2$O afforded the pure title compound (0.037 g, 41%), as a white solid. R$_t$=2.31 min. MS (ESI) m/z: 311 [M-H]$^+$, 333 [M–Na]$^+$, 349 [M–K]$^+$. $^1$H NMR (DMSO-d$_6$): δ 7.97 (d, 1H, J=8.9 Hz), 7.94 (s, 1H), 7.47-7.41 (m, 2H), 7.39-7.31 (m, 3H), 7.28 (bs, 1H), 7.26-7.17 (m, 2H), 5.05 (s, 2H), 4.68 (ddd, 1H, J=8.5, 5.5, 2.8 Hz), 3.41 (t, 1H, J=5.5 Hz), 3.10 (dd, 1H, J=2.8 Hz, 5.5 Hz), 2.22 (s, 3H).

Example 45. [4-(4-Pyridyl)-phenyl]-methyl-N-[(3S)-2-oxoazetidin-3-yl]-carbamate

Step 1. Preparation of [4-(4-pyridyl)-phenyl]-methanol

Under nitrogen atmosphere, to a cooled (0° C.), stirred suspension of LiAlH$_4$ (2.0 M in THF, 5.02 mL, 10.05 mmol) in dry THF (40 mL), commercially available 4-(4-pyridyl)-benzoic acid (0.5 g, 2.51 mmol) was added in one portion. The resulting mixture was stirred at r.t. for 3 h, then cooled to 0° C. and H$_2$O (0.38 mL) was slowly and cautiously added, followed by a 3.0 M KOH solution (0.38 mL) and additional H$_2$O (1.2 mL). The mixture was stirred at 0° C. for 1 h, filtered and the organic phase dried over Na$_2$SO$_4$ and concentrated to dryness affording the title compound (0.28 g, 60%) as a yellow solid, which was used in the next step without any further purification. R$_t$=1.40 min. MS (ESI) m/z: 186 [M-H]$^+$. $^1$H NMR (DMSO-d$_6$): δ 8.63-8.61 (m, 2H), 7.80-7.75 (m, 2H), 7.72-7.68 (m, 2H), 7.48-7.44 (m, 2H), 5.27 (t, 1H, J=5.7 Hz), 4.56 (d, 1H, J=5.7 Hz).

Step 2. Preparation of [4-(4-pyridyl)-phenyl]-methyl-2-pyridyl carbonate and [4-(4-pyridyl)-phenyl]-methyl-2-oxopyridine-1-carboxylate Under nitrogen atmosphere, to a stirred solution of [4-(4-pyridyl)-phenyl]-methanol (0.2 g, 1.08 mmol) in dry CH$_2$Cl$_2$ (9.0 mL), DMAP (0.013 g, 0.11 mmol) and 2-DPC (0.280 g, 1.30 mmol) were added. The reaction mixture was stirred at r.t. for 16 h, then diluted with CH$_2$Cl$_2$ (50 mL) and sequentially washed with sat. NH$_4$Cl solution (15 mL) and sat. NaHCO$_3$ solution (3×15 mL). The organic layer was dried over Na$_2$SO$_4$, filtered and concentrated to dryness affording an oily residue (0.34 g), as a mixture (1:1.7 ratio) of [4-(4-pyridyl)-phenyl]-methyl-2-pyridyl carbonate and [4-(4-pyridyl)-phenyl]-methyl-2-oxopyridine-1-carboxylate. The mixture of isomers was not separated and used in the next step without any further purification. R$_t$=1.83 min. MS (ESI) m/z: 307 [M-H]$^+$, 329 [M–Na]$^+$, 345 [M–K]$^+$.

Step 3. Preparation of [4-(4-pyridyl)-phenyl]-methyl-N-[(3S)-2-oxoazetidin-3-yl]-carbamate Under nitrogen atmosphere, to a suspension of [(3S)-2-oxoazetidin-3-yl]-ammonium acetate (0.050 g, 0.34 mmol) in dry CH$_2$Cl$_2$ (4.0 mL), DIPEA (0.067 mL, 0.41 mmol) was added dropwise. Subsequently, the crude mixture (0.281 g) containing [4-(4-pyridyl)-phenyl]-methyl-2-oxopyridine-1-carboxylate (0.104 g, 0.34 mmol) in dry CH$_2$Cl$_2$ (2.0 mL) was added. The reaction mixture was stirred at r.t. for 16 h, then concentrated to dryness giving a solid residue (0.22 g). Purification by typical silica gel flash chromatography (CH$_2$Cl$_2$/MeOH, from 100:0 to 95:5) afforded the pure title compound (0.066 g, 66%), as a white solid. R$_t$=1.48 min. MS (ESI) m/z: 298 [M-H]$^+$, 320 [M–Na]$^+$, 336 [M–K]$^+$. $^1$H NMR (DMSO-d$_6$): δ 8.65-8.62 (m, 2H), 8.02 (d, 1H, J=8.7 Hz), 7.94 (s, 1H), 7.83-7.79 (m, 2H), 7.73-7.70 (m, 2H), 7.52-7.48 (m, 2H), 5.11 (s, 2H), 4.68 (ddd, 1H, J=8.3, 5.5, 2.8 Hz), 3.40 (t, 1H, J=5.5 Hz), 3.09 (dd, 1H, J=5.5, 2.8 Hz).

Example 46. [4-(3-Pyridyl)-phenyl]-methyl-N-[(3S)-2-oxoazetidin-3-yl]-carbamate

Step 1. Preparation of [4-(3-pyridyl)-phenyl]-methanol

Under nitrogen atmosphere, to a cooled (0° C.), stirred suspension of LiAlH$_4$ (2.0 M in THF, 5.02 mL, 10.05 mmol) in dry THF (45 mL), commercially available 4-(3-pyridyl) benzoic acid (0.5 g, 2.51 mmol) was added in one portion. The resulting mixture was stirred at r.t. for 2 h, then cooled to 0° C. and H$_2$O (0.35 mL) was slowly and cautiously added, followed by a 3.0 M KOH solution (0.35 mL) and additional H$_2$O (1.1 mL). The mixture was stirred at 0° C. for 1 h, filtered and the organic phase dried over Na$_2$SO$_4$ and concentrated to dryness giving a crude residue (0.402 g). Purification by typical silica gel flash chromatography (CH$_2$Cl$_2$/MeOH, from 100:0 to 90:10) afforded the pure title compound (0.327 g, 71%), as a solid. $R_t$=1.47 min. MS (ESI) m/z: 186 [M–H]$^+$. $^1$H NMR (DMSO-d$_6$): δ 8.89 (dd, 1H, J=2.4, 0.8 Hz), 8.55 (dd, 1H, J=4.8, 1.6 Hz), 8.06 (ddd, 1H, J=7.9, 2.4, 1.6 Hz), 7.71-7.66 (m, 2H), 7.50-7.42 (m, 3H), 5.25 (t, 1H, J=3.3 Hz), 4.56 (d, 2H, J=3.3 Hz).

Step 2. Preparation of [4-(3-pyridyl)-phenyl]-methyl-2-pyridyl carbonate and [4-(3-pyridyl)-phenyl]-methyl-2-oxopyridine-1-carboxylate Under nitrogen atmosphere, to a solution of [4-(3-pyridyl)-phenyl]-methanol (0.25 g, 1.35 mmol) in dry CH$_2$Cl$_2$ (14 mL), DMAP (0.016 g, 0.14 mmol) and 2-DPC (0.35 g, 1.62 mmol) were added. The reaction mixture was stirred at r.t. for 16 h, then diluted with CH$_2$Cl$_2$ (50 mL) and sequentially washed with sat. NH$_4$Cl solution (15 mL) and sat. NaHCO$_3$ solution (3×15 mL). The organic layer was dried over Na$_2$SO$_4$, filtered and concentrated to dryness affording an oily residue (0.41 g), as a mixture (1:1.7 ratio) of [4-(3-pyridyl)-phenyl]-methyl-2-pyridyl carbonate and [4-(3-pyridyl)-phenyl]-methyl-2-oxopyridine-1-carboxylate. The mixture of isomers was not separated and used in the next step without any further purification. $R_t$=1.86 min. MS (ESI) m/z: 307 [M–H]$^+$, 329 [M–Na]$^+$, 345 [M–K]$^+$.

Step 3. Preparation of [4-(3-pyridyl)]-methyl-N-[(3S)-2-oxoazetidin-3-yl]-carbamate Under nitrogen atmosphere, to a suspension of [(3S)-2-oxoazetidin-3-yl]-ammonium acetate (0.050 g, 0.34 mmol) in dry CH$_2$Cl$_2$ (4.0 mL), DIPEA (0.067 mL, 0.41 mmol) was added dropwise. Subsequently, the crude mixture (0.28 g) containing [4-(3-pyridyl)-phenyl]-methyl-2-oxopyridine-1-carboxylate (0.104 g, 0.34 mmol) in dry CH$_2$Cl$_2$ (2.0 mL) was added. The reaction mixture was stirred at r.t. for 16 h, then concentrated to dryness giving a solid residue (0.16 g). Purification by preparative HPLC afforded the pure title compound (0.014 g, 14%), as a white solid. $R_t$=1.54 min. MS (ESI) m/z: 298 [M–H]$^+$, 320 [M–Na]$^+$, 336 [M+K]$^+$. MS (ESI) m/z: 296 [M–H]$^-$. $^1$H NMR (DMSO-d$_6$): δ 8.90 (dd, 1H, J=2.4, 0.7 Hz), 8.57 (dd, 1H, J=4.8, 1.6 Hz), 8.08 (ddd, 1H, J=8.0, 2.4, 1.7 Hz), 8.02 (d, 1H, J=8.8 Hz), 7.96 (s, 1H), 7.77-7.71 (m, 2H), 7.52-7.46 (m, 3H), 5.10 (s, 2H), 4.67 (ddd, 1H, J=8.4, 5.5, 2.8 Hz), 3.40 (t, 1H, J=5.5 Hz), 3.10 (dd, 1H, J=5.5, 2.8 Hz).

Example 47. 4-(3-Pyridyl)-butyl-N-[(3S)-2-oxoazetidin-3-yl]-carbamate

Step 1. Preparation of 4-(3-pyridyl)-but-3-yn-1-ol

In a degassed 20 mL vial, commercially available 3-iodopyridine (0.5 g, 2.44 mmol), 3-butyn-1-ol (0.22 mL, 2.93 mmol), 10% Pd/C (0.01 g, 0.01 mmol) and sodium phosphate tribasic dodecahydrate (1.85 g, 4.88 mmol) were dissolved in a 1:1 mixture of i-PrOH/H$_2$O (10 mL). The suspension was vigorously stirred and heated at 80° C. for 30 min. The crude mixture was diluted with EtOAc (40 mL) and H$_2$O (40 mL), filtered and separated. The corresponding aqueous layer was washed with EtOAc (4×25 mL), and the collected organic layer was dried over Na$_2$SO$_4$, filtered and concentrated to dryness giving an oily residue (0.56 g). Purification by typical silica gel flash chromatography (Cy/EtOAc, 25:75) afforded the pure title compound (0.331 g, 77%), as an oil. $R_t$=1.22 min. MS (ESI) m/z: 148 [M–H]$^+$. $^1$H NMR (DMSO-d$_6$): δ 8.59-8.57 (m, 1H), 8.51 (dd, 1H, J=4.8, 1.7 Hz), 7.80 (dt, 1H, J=7.9, 1.7 Hz), 7.38 (ddd, 1H, J=7.9, 4.8, 0.7 Hz), 4.92 (t, 1H, J=5.8 Hz), 3.60 (q, 2H, J=5.8 Hz), 2.59 (t, 2H, J=6.7 Hz).

Step 2. Preparation of 4-(3-pyridyl)-butan-1-ol

A solution of 4-(3-pyridyl)-but-3-yn-1-ol (0.32 g, 2.2 mmol) in EtOH (44 mL) was passed through the H-Cube® hydrogenator flow reactor provided with a 10% Pd/C cartridge (flow rate: 1.0 mL/min; P=1.0 bar; T=35° C.). The outcoming solution was concentrated to dryness giving an oily residue (0.31 g). Purification by typical silica gel flash chromatography (CH$_2$Cl$_2$/MeOH, 95:5), afforded the pure title compound (0.294 g, 89%), as a colorless liquid. $R_t$=1.16 min. MS (ESI) m/z: 152 [M–H]$^+$. $^1$H NMR (DMSO-d$_6$): δ 8.43 (m, 1H), 8.38 (dd, 1H, J=4.8, 1.5 Hz), 7.61 (dt, 1H, J=7.8, 2.1 Hz), 7.30 (dd, 1H, J=7.8, 4.8 Hz), 4.37 (t, 1H, J=5.2 Hz), 3.41 (q, 2H, J=5.2 Hz), 2.59 (t, 2H, J=7.7 Hz), 1.64-1.55 (m, 2H), 1.47-1.38 (m, 2H).

Step 3. Preparation of 4-(3-pyridyl)-butyl-2-pyridyl carbonate and 4-(3-pyridyl)-butyl-2-oxopyridine-1-carboxylate Under nitrogen atmosphere, to a solution of 4-(3-pyridyl)-butanol (0.29 g, 1.92 mmol) in dry CH$_2$Cl$_2$ (18 mL), DMAP (0.023 g, 0.19 mmol) and 2-DPC (0.5 g, 2.3 mmol) were added. The reaction mixture was stirred at r.t. for 16 h, then diluted with CH$_2$Cl$_2$ (50 mL) and sequentially washed with sat. NH$_4$Cl solution (15 mL) and sat. NaHCO$_3$ solution (3×15 mL). The organic layer was dried over Na$_2$SO$_4$, filtered and concentrated to dryness affording an oily residue (0.52 g), as a mixture (1:1.17 ratio) of 4-(3-pyridyl)-butyl-2-pyridyl carbonate and 4-(3-pyridyl)-butyl-2-oxopyridine-1-carboxylate. The mixture of isomers was not separated and used in the next step without any further purification. $R_t$=1.64 min. MS (ESI) m/z: 273 [M–H]$^+$, 295 [M–Na]$^+$, 311 [M–K]$^+$.

Step 4. Preparation of 4-(3-pyridyl)-butyl-N-[(3S)-2-oxoazetidin-3-yl]-carbamate Under nitrogen atmosphere, to a suspension of [(3S)-2-oxoazetidin-3-yl]-ammonium acetate (0.050 g, 0.34 mmol) in dry CH$_2$Cl$_2$ (4.0 mL), DIPEA (0.067 mL, 0.41 mmol) was added dropwise. Subsequently, the crude mixture (0.250 g) containing 4-(3-pyridyl)-butyl-2-oxopyridine-1-carboxylate (0.092 g, 0.34 mmol) in dry CH$_2$Cl$_2$ (2.0 mL) was added. The reaction mixture was stirred at r.t. for 16 h, then concentrated to dryness giving a solid residue (0.21 g). Purification by typical silica gel flash chromatography (CH$_2$Cl$_2$/MeOH, from 100:0 to 90:10) afforded the pure title compound (0.054 g, 60%), as a white solid. $R_t$=1.31 min. MS (ESI) m/z: 264 [M–H]$^+$, 286 [M–Na]$^+$, 302 [M–K]$^+$. MS (ESI) m/z: 262 [M–H]$^-$. $^1$H NMR (DMSO-d$_6$): δ 8.44-8.42 (m, 1H), 8.39 (dd, 1H, J=4.8, 1.6 Hz), 7.93 (s, 1H), 7.82 (d, 1H, J=8.7 Hz), 7.62 (dt, 1H, J=7.7, 1.8 Hz), 7.30 (ddd, 1H, J=7.9, 4.9, 0.7 Hz), 4.62 (ddd, 1H, J=8.4, 5.5, 2.9 Hz), 3.98 (t, 2H, J=6.1 Hz), 3.36 (m, 1H), 3.06 (dd, 1H, J=5.5, 2.8 Hz), 2.61 (t, 2H, J=7.5 Hz), 1.67-1.50 (m, 4H).

Example 48. 4-Tetrahydropyran-4-yl-butyl-N-[(3S)-2-oxoazetidin-3-yl]-carbamate

Step 1. Preparation of 4-[(E)-4-benzyloxybut-1-enyl]-tetrahydropyran and 4-[(Z)-4-benzyloxybut-1-enyl]-tetrahydropyran Under nitrogen atmosphere, to a cooled (−30° C.), stirred solution of commercially available 3-benzyloxypropyl-(triphenyl)-phosphonium bromide (3.33 g, 6.75 mmol) in dry THF (70 mL), n-BuLi (2.5 M in hexane, 2.7 mL, 6.75 mmol) was added dropwise. The resulting yellowish suspension was stirred for 45 min at −30° C., then a solution of commercially available tetrahydro-2H-pyran-4-carbaldehyde (0.7 g, 6.14 mmol) in dry THF (15 mL) was slowly added. The reaction mixture was stirred at −30° C. for 30 min, and then at r.t. for 16 h. The reaction solution was diluted with $CH_2Cl_2$ (50 mL) and sequentially washed with sat. $NH_4Cl$ solution (3×15 mL), sat. $NaHCO_3$ solution (2×15 mL) and brine (20 mL). The organic layer was dried over $Na_2SO_4$, filtered and concentrated to dryness giving a brownish residue (2.1 g). Purification by typical silica gel flash chromatography ($CH_2Cl_2$) afforded the title compounds (0.73 g, 48%), as a mixture (8:92 ratio) of E/Z diastereoisomers, as a yellow oil. $R_t$=2.70 min (minor) and 2.82 min. $^1H$ NMR (DMSO-$d_6$): δ 7.41-7.19 (m, 10H), 5.49-5.22 (m, 4H), 4.46 (s, 4H), 3.87-3.75 (m, 4H), 3.43 (t, 4H, J=6.7 Hz, major), 3.32 (td, 4H, J=11.7, 2.2 Hz, major), 2.32 (qd, 2H, J=6.8, 0.8 Hz, major), 2.24 (qd, 2H, J=6.6, 1.1 Hz, minor), 1.69-1.21 (m, 10H).

Step 2. Preparation of 4-tetrahydropyran-4-yl-butan-1-ol

A solution containing a mixture of 4-[(E)-4-benzyloxybut-1-enyl]-tetrahydropyran and 4-[(Z)-4-benzyloxybut-1-enyl]-tetrahydropyran (0.5 g, 2.03 mmol) in EtOH (40 mL) was passed through the H-Cube® hydrogenator flow reactor provided with a 20% Pd(OH)$_2$/C cartridge [flow rate: 1.0 mL/min; P=1.0 bar; T=60° C.]. The outcoming solution was concentrated to dryness giving an oily residue (0.3 g). Purification by typical silica gel flash chromatography (Cy/EtOAc, from 83:17 to 33:67) afforded the pure title compound (0.18 g, 56%), as a colorless liquid. $^1H$ NMR (DMSO-$d_6$): δ 4.31 (t, 1H, J=5.2 Hz), 3.81 (dd, 2H, J=11.3, 4.2 Hz), 3.38 (dd, 2H, J=6.5, 1.2 Hz), 3.25 (td, 2H, J=12.0, 2.0 Hz), 1.58-1.03 (m, 11H).

Step 3. Preparation of 4-tetrahydropyran-4-yl-butyl-2-pyridyl carbonate and 4-tetrahydropyran-4-yl-butyl-2-oxopyridine-1-carboxylate Under nitrogen atmosphere, to a solution of 4-tetrahydropyran-4-yl-butan-1-ol (0.18 g, 1.14 mmol) in dry $CH_2Cl_2$ (8.0 mL), DMAP (0.017 g, 0.14 mmol) and 2-DPC (0.295 g, 1.37 mmol) were added. The reaction mixture was stirred at r.t. for 16 h, then diluted with $CH_2Cl_2$ (50 mL) and sequentially washed with sat. $NH_4Cl$ solution (15 mL) and sat. $NaHCO_3$ solution (3×15 mL). The organic layer was dried over $Na_2SO_4$, filtered and concentrated to dryness affording an oily residue (0.28 g), as a mixture (1:1.7 ratio) of 4-tetrahydropyran-4-yl-butyl-2-pyridyl carbonate and 4-tetrahydropyran-4-yl-butyl-2-oxopyridine-1-carboxylate. The mixture of isomers was not separated and used in the next step without any further purification. $R_t$=1.99 min. MS (ESI) m/z: 280 [M-H]$^+$, 302 [M−Na]$^+$, 318 [M−K]$^+$.

Step 4. Preparation of 4-tetrahydropyran-4-yl-butyl-N-[(3S)-2-oxoazetidin-3-yl]-carbamate Under nitrogen atmosphere, to a suspension of [(3S)-2-oxoazetidin-3-yl]-ammonium acetate (0.05 g, 0.34 mmol) in dry $CH_2Cl_2$ (4.0 mL), DIPEA (0.067 mL, 0.41 mmol) was added dropwise. Subsequently, the crude mixture (0.26 g) containing 4-tetrahydropyran-4-yl-butyl-2-oxopyridine-1-carboxylate (0.095 g, 0.34 mmol) in dry $CH_2Cl_2$ (2.0 mL) was added. The reaction mixture was stirred at r.t. for 16 h, then concentrated to dryness giving a solid residue (0.19 g). Purification by typical silica gel flash chromatography ($CH_2Cl_2$/MeOH, from 100:0 to 95:5) afforded the pure title compound (0.023 g, 25%), as a white solid. $R_t$=1.61 min. MS (ESI) m/z: 271 [M-H]$^+$, 293 [M−Na]$^+$, 309 [M−K]$^+$. $^1H$ NMR (DMSO-$d_6$): δ 7.90 (s, 1H), 7.78 (d, 1H, J=8.9 Hz), 4.66-4.49 (m, 1H), 3.95 (t, 2H, J=6.6 Hz), 3.81 (dd, 2H, J=11.5, 4.3 Hz), 3.37 (t, 1H, J=5.3 Hz), 3.25 (td, 2H, J=11.5, 2.9 Hz), 3.06 (dd, 1H, J=5.2, 2.8 Hz), 1.59-1.04 (m, 11H).

Example 49. 2-(Cyclohexylmethoxy)-ethyl-N-[(3S)-2-oxoazetidin-3-yl]-carbamate

Step 1. Preparation of 2-(cyclohexylmethoxy)-ethanol

A solution of (bromomethyl)-cyclohexane (0.95 mL, 6.78 mmol) and ethylene glycol (3.02 mL, 54.24 mmol) in a 25.5 M NaOH solution (1.11 mL, 28.3 mmol) was stirred and heated at 80° C. for 16 h. Then, the reaction mixture was diluted with $H_2O$ (30 mL) and the product was extracted with EtOAc (3×30 mL). The collected organic layer was dried over $Na_2SO_4$, filtered and concentrated to dryness giving an oily residue (1.2 g). Purification by typical silica gel flash chromatography (Cy/EtOAc, from 89:11 to 50:50) afforded the pure title compound (0.4 g, 37%), as an orange liquid. $^1H$ NMR (DMSO-$d_6$): δ 4.51 (t, 1H, J=5.5 Hz), 3.47 (q, 2H, J=5.5 Hz), 3.36 (t, 2H, J=5.5 Hz), 3.19 (d, 2H, J=6.5 Hz), 1.73-1.44 (m, 6H), 1.26-1.06 (m, 3H), 0.95-0.82 (m, 2H).

Step 2. Preparation of 2-(cyclohexylmethoxy)-ethyl-2-pyridyl carbonate and 2-(cyclohexylmethoxy)-ethyl-2-oxopyridine-1-carboxylate Under nitrogen atmosphere, to a solution of 2-(cyclohexylmethoxy)-ethanol (0.25 g, 1.58 mmol) in dry $CH_2Cl_2$ (12 mL), DMAP (0.019 g, 0.16 mmol) and 2-DPC (0.41 g, 1.9 mmol) were added. The reaction mixture was stirred at r.t. for 16 h, then diluted with $CH_2Cl_2$ (50 mL) and sequentially washed with sat. $NH_4Cl$ solution (15 mL) and sat. $NaHCO_3$ solution (3×15 mL). The organic layer was dried over $Na_2SO_4$, filtered and concentrated to dryness affording an oily residue (0.43 g), as a mixture (1:2.1 ratio) of 2-(cyclohexylmethoxy)-ethyl-2-pyridyl carbonate and 2-(cyclohexylmethoxy)-ethyl-2-oxopyridine-1-carboxylate. The mixture of isomers was not separated and used in the next step without any further purification. $R_t$=1.00 min. MS (ESI) m/z: 280 [M-H]$^+$, 302 [M−Na]$^+$, 318 [M−K]$^+$.

Step 3. Preparation of 2-(cyclohexylmethoxy)-ethyl-N-[(3S)-2-oxoazetidin-3-yl]-carbamate Under nitrogen atmosphere, to a suspension of [(3S)-2-oxoazetidin-3-yl]-ammonium acetate (0.050 g, 0.34 mmol) in dry $CH_2Cl_2$ (4.0 mL), DIPEA (0.067 mL, 0.41 mmol) was added dropwise. Subsequently, the crude mixture (0.294 g) containing 2-(cyclohexylmethoxy)-ethyl-2-oxopyridine-1-carboxylate (0.095 g, 0.34 mmol) in dry $CH_2Cl_2$ (2.0 mL) was added. The reaction mixture was stirred at r.t. for 16 h, then concentrated to dryness giving an oily residue (0.18 g). Purification by typical silica gel flash chromatography (Cy/EtOAc from 50:50 to 25:75) afforded the pure title compound (0.067 g, 73%), as a white solid. $R_t$=2.02 min. MS (ESI) m/z: 271 [M-H]$^+$, 293 [M−Na]$^+$, 309 [M−K]$^+$. $^1H$ NMR (DMSO-$d_6$): δ 7.93-7.86 (m, 2H), 4.63 (ddd, 1H, J=8.4, 5.5, 2.8 Hz), 4.12-4.01 (m, 2H), 3.52 (t, 2H, J=4.7 Hz), 3.38 (t, 1H, J=5.5 Hz), 3.20 (d, 2H, J=6.4 Hz), 3.07 (dd, 1H, J=5.5, 2.8 Hz), 1.73-1.57 (m, 5H), 1.56-1.43 (m, 1H), 1.28-1.05 (m, 3H), 0.95-0.82 (m, 2H).

Example 50. 3-(Cyclohexoxy)-propyl-N-[(3S)-2-oxoazetidin-3-yl]-carbamate

Step 1. Preparation of 7,11-dioxaspiro-[5.5]-undecane

A solution of cyclohexanone (1.06 mL, 10.20 mmol), iodine (0.002 g, 0.01 mmol) in 1,3-propanediol (0.15 mL, 2.06 mmol) was stirred at r.t. for 16 h. The reaction mixture was then diluted with $Et_2O$ (40 mL) and washed with 5% $Na_2S_2O_3$ solution (40 mL) and sat. $NaHCO_3$ solution (2×30 mL). The organic layer was dried over $Na_2SO_4$, filtered and concentrated to dryness, affording the title compound (0.85 g, 53%), which was used in the next step without any further purification. $^1$H NMR (DMSO-$d_6$): δ 3.78 (t, 4H, J=5.6 Hz), 1.69-1.63 (m, 4H), 1.56 (p, 2H, J=5.7 Hz), 1.45-1.30 (m, 6H).

Step 2. Preparation of 3-(cyclohexoxy)-propan-1-ol $AlCl_3$ (0.336 g, 2.53 mmol) was dried under vacuum/nitrogen cycles, then, dissolved in dry $Et_2O$ (2.0 mL) at 0° C. Successively, a solution of $LiAlH_4$ (2.0 M in THF, 0.32 mL, 0.63 mmol) was added dropwise followed, after 30 min, by a solution of 7,11-dioxaspiro-[5.5]-undecane (0.2 g, 1.27 mmol) in dry $Et_2O$ (1.0 mL). After stirring at r.t. for 2 h, the solution was cooled to 0° C. and $H_2O$ (0.33 mL) was slowly and cautiously added, followed by a 3.0 M KOH solution (0.33 mL) and additional $H_2O$ (1.10 mL). The mixture was stirred at 0° C. for 1 h, then diluted with $Et_2O$ (40 mL), washed with $H_2O$ (40 mL) and the product was extracted with $Et_2O$ (2×20 mL). The collected organic layer was dried over $Na_2SO_4$, filtered and concentrated to dryness giving an oily residue (0.186 g). Purification by typical silica gel flash chromatography (Cy/EtOAc 67:33) afforded the pure title compound (0.15 g, 75%), as a colorless liquid. $^1$H NMR (DMSO-$d_6$): δ 4.07 (bs, 1H), 3.43 (q, 4H, J=6.0 Hz), 3.22-3.14 (m, 1H), 1.85-1.74 (m, 2H), 1.69-1.56 (m, 4H), 1.51-1.41 (m, 1H), 1.28-1.10 (m, 5H).

Step 3. Preparation of 3-(cyclohexoxy)-propyl-2-pyridyl carbonate and 3-(cyclohexoxy)-propyl-2-oxopyridine-1-carboxylate Under nitrogen atmosphere, to a solution of 3-(cyclohexoxy)-propan-1-ol (0.15 g, 0.95 mmol) in dry $CH_2Cl_2$ (8.0 mL), DMAP (0.012 g, 0.09 mmol) and 2-DPC (0.246 g, 1.14 mmol) were added. The reaction mixture was stirred at r.t. for 16 h, then diluted with $CH_2Cl_2$ (50 mL) and sequentially washed with sat. $NH_4Cl$ solution (15 mL) and sat. $NaHCO_3$ solution (3×15 mL). The organic layer was dried over $Na_2SO_4$, filtered and concentrated to dryness affording an oily residue (0.24 g), as a mixture (1:1.7 ratio) of 3-(cyclohexoxy)-propyl-2-pyridyl carbonate and 3-(cyclohexoxy)-propyl-2-oxopyridine-1-carboxylate. The mixture of isomers was not separated and used in the next step without any further purification. $R_t$=2.30 min. MS (ESI) m/z: 280 [M-H]$^+$, 302 [M-Na]$^+$, 318 [M-K]$^+$.

Step 4. Preparation of 3-(cyclohexoxy)-propyl-N-[(3S)-2-oxoazetidin-3-yl]-carbamate Under nitrogen atmosphere, to a suspension of [(3S)-2-oxoazetidin-3-yl]-ammonium acetate (0.038 g, 0.26 mmol) in dry $CH_2Cl_2$ (4.0 mL), DIPEA (0.051 mL, 0.31 mmol) was added dropwise. Subsequently, the crude mixture (0.196 g) containing 3-(cyclohexoxy)-propyl-2-oxopyridine-1-carboxylate (0.073 g, 0.26 mmol) in dry $CH_2Cl_2$ (2.0 mL) was added. The reaction mixture was stirred at r.t. for 16 h, then concentrated to dryness giving an oily residue (0.14 g). Purification by typical silica gel flash chromatography ($CH_2Cl_2$/MeOH, from 100:0 to 95:5) afforded the pure title compound (0.025 g, 36%), as a white solid. $R_t$=1.84 min. MS (ESI) m/z: 271 [M-H]$^+$, 293 [M-Na]$^+$, 309 [M-K]$^+$. $^1$H NMR (DMSO-$d_6$): δ 7.90 (s, 1H), 7.80 (d, 1H, J=8.7 Hz), 4.66-4.50 (m, 1H), 4.01 (t, 2H, J=6.4 Hz), 3.43 (t, 2H, J=6.4 Hz), 3.37 (t, 1H, J=5.5 Hz), 3.25-3.16 (m, 1H), 3.07 (dd, 1H, J=5.2, 2.8 Hz), 1.85-1.70 (m, 4H), 1.69-1.58 (m, 2H), 1.51-1.41 (m, 1H), 1.28-1.11 (m, 5H).

Example 51. 2-(2-Cyclohexylethoxy)-ethyl-N-[(3S)-2-oxoazetidin-3-yl]-carbamate

Step 1. Preparation of 2-(2-cyclohexylethoxy)-ethanol

A solution of 1-bromo-2-cyclohexylethane (1.06 mL, 6.78 mmol), and ethylene glycol (3.02 mL, 54.24 mmol) in a 25.5 M NaOH solution (1.11 mL, 28.31 mmol) was stirred and heated at 80° C. for 16 h. Then, the reaction mixture was diluted with $H_2O$ (30 mL) and the organic material extracted with EtOAc (3×30 mL). The collected organic layer was dried over $Na_2SO_4$, filtered and concentrated to dryness affording an oily residue (1.1 g). Purification by typical silica gel flash chromatography (Cy/EtOAc from 89:11 to 50:50) afforded the pure title compound (0.58 g, 50%), as an orange liquid. $^1$H NMR (DMSO-$d_6$): δ 4.52 (t, 1H, J=5.5 Hz), 3.47 (q, 2H, J=5.5 Hz), 3.40 (t, 2H, J=6.7 Hz), 3.36 (d, 2H, J=5.2 Hz), 1.70-1.55 (m, 5H), 1.42-1.26 (m, 3H), 1.26-1.05 (m, 3H), 0.93-0.81 (m, 2H).

Step 2. Preparation of 2-(2-cyclohexylethoxy)-ethyl-2-pyridyl carbonate and 2-(2-cyclohexylethoxy)-ethyl-2-oxopyridine-1-carboxylate Under nitrogen atmosphere, to a solution of 2-(2-cyclohexylethoxy)-ethanol (0.250 g, 1.45 mmol) in dry $CH_2Cl_2$ (11 mL), DMAP (0.018 g, 0.15 mmol) and 2-DPC (0.377 g, 1.74 mmol) were added. The reaction mixture was stirred at r.t. for 16 h, then diluted with $CH_2Cl_2$ (50 mL) and sequentially washed with sat. $NH_4Cl$ solution (15 mL) and sat. $NaHCO_3$ solution (3×15 mL). The organic layer was dried over $Na_2SO_4$, filtered and concentrated to dryness affording an oily residue (0.41 g), as a mixture (1:2.1 ratio) of 2-(2-cyclohexylethoxy)-ethyl-2-pyridyl carbonate and 2-(2-cyclohexylethoxy)-ethyl-2-oxopyridine-1-carboxylate. The mixture of isomers was not separated and used in the next step without any further purification. $R_t$=1.20 min. MS (ESI) m/z: 294 [M-H]$^+$, 332 [M-K]$^+$.

Step 3. Preparation of 2-(2-cyclohexylethoxy)-ethyl-N-[(3S)-2-oxoazetidin-3-yl]-carbamate Under nitrogen atmosphere, to a suspension of [(3S)-2-oxoazetidin-3-yl]-ammonium acetate (0.050 g, 0.34 mmol) in dry $CH_2Cl_2$ (4.0 mL), DIPEA (0.067 mL, 0.41 mmol) was added dropwise. Subsequently, the crude mixture (0.309 g) containing 2-(2-cyclohexylethoxy)-ethyl-2-oxopyridine-1-carboxylate (0.100 g, 1.13 mmol) in dry $CH_2Cl_2$ (2.0 mL) was added. The reaction mixture was stirred at r.t. for 16 h, then concentrated to dryness giving an oily residue (0.16 g).

Purification by typical silica gel flash chromatography (CH$_2$Cl$_2$/MeOH from 100:0 to 94:6) afforded the pure title compound (0.064 g, 66%), as a white solid. R$_t$=2.20 min. MS (ESI) m/z: 285 [M-H]$^+$, 307 [M-Na]$^+$, 323 [M-K]$^+$. MS (ESI) m/z: 283 [M-H]$^-$. $^1$H NMR (DMSO-d$_6$): δ 7.93-7.86 (m, 2H), 4.63 (ddd, 1H, J=8.6, 5.5, 2.8 Hz), 4.11-4.03 (m, 2H), 3.51 (t, 2H, J=4.8 Hz), 3.41 (t, 2H, J=6.7 Hz), 3.38 (t, 1H, J=5.5 Hz), 3.07 (dd, 1H, J=5.5, 2.8 Hz), 1.70-1.55 (m, 5H), 1.42-1.26 (m, 3H), 1.25-1.05 (m, 3H), 0.93-0.81 (m, 2H).

Example 52. (4-Benzoylphenyl)-methyl-N-[(3S)-2-oxoazetidin-3-yl]-carbamate

Step 1. Preparation of methyl 4-benzoylbenzoate

Commercially available 4-benzoylbenzoic acid (1.0 g, 4.42 mmol) in MeOH (50 mL) was treated with concentrated sulfuric acid (14 drops, 0.35 mL, 6.6 mmol) and the reaction mixture was stirred until complete conversion of starting material. The solvent was then evaporated and crude was taken up in EtOAc (50 mL) and washed with sat. Na$_2$HCO$_3$ solution (2×50 mL). The organic layer was dried over Na$_2$SO$_4$, filtered and concentrated to dryness, affording the pure title compound (1.03 g, 97%), as a white solid, which was used in the next step without any further purification. R$_t$=2.59 min. MS (ESI) m/z: 241 [M-H]$^+$. $^1$H NMR (DMSO-d$_6$): δ 8.14-8.10 (m, 2H), 7.87-7.83 (m, 2H), 7.78-7.75 (m, 2H), 7.74-7.69 (m, 1H), 7.61-7.56 (m, 2H), 3.91 (s, 3H).

Step 2. Preparation of methyl 4-(2-phenyl-1,3-dioxolan-2-yl)-benzoate

A mixture of methyl 4-benzoylbenzoate (0.93 g, 3.84 mmol), ethylene glycol (4.71 mL, 84.55 mmol), p-toluensolfonic acid (0.051 g, 0.27 mmol) and bis-(trimethylsilyl)-ethylene glycol (10.3 mL, 42.27 mmol) in toluene (20 mL) was heated at 90° C. for 24 h. The reaction mixture was then cooled to r.t., diluted with additional toluene (40 mL), and the organic layer was washed with sat. NaHCO$_3$ solution (2×30 mL). The organic layer was dried over Na$_2$SO$_4$, filtered and concentrated to dryness giving a white precipitate. Filtration afforded the pure title compound (0.916 g, 84%), as a white solid. R$_t$=2.76 min. MS (ESI) m/z: 285 [M-H]$^+$. $^1$H NMR (DMSO-d$_6$): δ 7.96-7.92 (m, 2H), 7.61-7.57 (m, 2H), 7.46-7.42 (m, 2H), 7.38-7.27 (m, 3H), 4.04-3.96 (m, 4H), 3.84 (s, 3H).

Step 3. Preparation of [4-(2-phenyl-1,3-dioxolan-2-yl)-phenyl]-methanol

Under nitrogen atmosphere, to a cooled (0° C.) suspension of LiAlH$_4$ (2.0 M in THF, 7.04 mL, 14.08 mmol) in dry Et$_2$O (38 mL), a solution of methyl 4-(2-phenyl-1,3-dioxolan-2-yl)-benzoate (1.0 g, 3.52 mmol) in dry THF (8.0 mL) was added dropwise. The resulting reaction mixture was stirred at r.t. for 2.5 h, then cooled to 0° C. H$_2$O (0.54 mL) was slowly and cautiously added, followed by 3.0 M KOH solution (0.54 mL) and additional H$_2$O (1.2 mL). The mixture was stirred at 0° C. for additional 1 h and then filtered off. The organic layer was dried over Na$_2$SO$_4$, filtered and concentrated to dryness, giving a solid residue (0.951 g). Purification by typical silica gel flash chromatography (Cy/EtOAc 80:20) afforded the pure title compound (0.815 g, 91%), as a white solid. R$_t$=2.17 min. MS (ESI) m/z: 257 [M-H]$^+$, 279 [M-Na]$^+$. $^1$H NMR (DMSO-d$_6$): δ 7.44-7.25 (m, 9H), 5.14 (t, 1H, J=5.7 Hz), 4.46 (d, 2H, J=5.7 Hz), 3.99-3.95 (m, 4H).

Step 4. Preparation of 4-benzoylbenzyl alcohol

[4-(2-phenyl-1,3-dioxolan-2-yl)-phenyl]-methanol (0.610 g, 2.38 mmol) was dissolved in a 3:1 mixture of 70% aq. AcOH/THF (32 mL) and stirred at 65° C. for 16 h. The solution was then cooled to r.t., diluted with Et$_2$O (70 mL) and the organic layer was sequentially washed with cold sat. NaHCO$_3$ solution (3×100 mL) and cold sat. Na$_2$CO$_3$ solution (2×100 mL). The organic layer was dried over Na$_2$SO$_4$, filtered and concentrated to dryness, affording the title compound (0.465 g, 92%), as a white solid, which was used in the next step without any further purification. R$_t$=1.98 min. MS (ESI) m/z: 213 [M-H]$^+$, 235 [M-Na]$^+$, 251 [M-K]$^+$. $^1$H NMR (DMSO-d$_6$): δ 7.76-7.64 (m, 5H), 7.59-7.47 (m, 4H), 5.38 (t, 1H, J=5.6 Hz), 4.61 (d, 2H, J=5.6 Hz).

Step 5. Preparation of (4-benzoylphenyl)-methyl-2-pyridyl carbonate and (4-benzoylphenyl)-methyl-2-oxopyridine-1-carboxylate Under nitrogen atmosphere, to a solution of 4-benzoylbenzyl alcohol (0.22 g, 1.04 mmol) in dry CH$_2$Cl$_2$ (8.0 mL), DMAP (0.015 g, 0.12 mmol) and 2-DPC (0.269 g, 1.25 mmol) were added. The reaction mixture was stirred at r.t. for 16 h, then diluted with CH$_2$Cl$_2$ (50 mL) and sequentially washed with sat. NH$_4$Cl solution (15 mL) and sat. NaHCO$_3$ solution (3×15 mL). The organic layer was dried over Na$_2$SO$_4$, filtered and concentrated to dryness affording an oily residue (0.4 g), as a mixture (1:1.8 ratio) of (4-benzoylphenyl)-methyl-2-pyridyl carbonate and (4-benzoylphenyl)-methyl-2-oxopyridine-1-carboxylate. The mixture of isomers was not separated and used in the next step without any further purification. R$_t$=2.31 min. MS (ESI) m/z: 334 [M-H]$^+$, 356 [M-Na]$^+$, 372 [M-K]$^+$.

Step 6. Preparation of (4-benzoylphenyl)-methyl-N-[(3S)-2-oxoazetidin-3-yl]-carbamate Under nitrogen atmosphere, to a suspension of [(3S)-2-oxoazetidin-3-yl]-ammonium acetate (0.05 g, 0.34 mmol) in dry CH$_2$Cl$_2$ (4.0 mL), DIPEA (0.067 mL, 0.41 mmol) was added dropwise. Subsequently, the crude mixture (0.317 g) containing (4-benzoylphenyl)-methyl-2-oxopyridine-1-carboxylate (0.113 g, 0.34 mmol) in dry CH$_2$Cl$_2$ (2.0 mL) was added. The reaction mixture was stirred at r.t. for 16 h, then concentrated to dryness giving a solid residue (0.22 g). Purification by typical silica gel flash chromatography (CH$_2$Cl$_2$/MeOH from 100:0 to 90:10) afforded the pure title compound (0.044 g, 40%), as a white solid. R$_t$=1.94 min. MS (ESI) m/z: 325 [M-H]$^+$, 347 [M-Na]$^+$, 363 [M+K]$^+$. $^1$H NMR (DMSO-d$_6$): δ 8.07 (d, 1H, J=8.7 Hz), 7.95 (s, 1H), 7.77-7.72 (m, 4H), 7.71-7.66 (m, 1H), 7.60-7.50 (m, 4H), 5.16 (s, 2H), 4.68 (ddd, 1H, J=8.7, 5.5, 2.8 Hz), 3.41 (t, 1H, J=5.5 Hz), 3.10 (dd, 1H, J=5.5, 2.8 Hz).

Example 53. [4-(Morpholine-4-carbonyl)-phenyl]-methyl-N-[(3S)-2-oxoazetidin-3-yl]-carbamate Step 1. Preparation of [4-(hydroxymethyl)-phenyl]-morpholino-methanone To a stirred solution of commercially available 4-hydroxymethylbenzoic acid (0.200 g, 1.32 mmol), EDC (0.278 g, 1.45 mmol), dry Et₃N (0.403 mL, 2.89 mmol), HOBt (0.196 g, 1.45 mmol) and DMAP (0.002 g, 0.01 mmol) in dry CH$_2$Cl$_2$ (8.0 mL), morpholine (0.172 mL, 1.97 mmol) was added in one portion. The resulting solution was stirred at r.t. for 16 h, and then sequentially washed with sat. NH$_4$Cl solution (2×5.0 mL) and sat. NaHCO$_3$ solution (10.0 mL). The organic layer was dried over Na$_2$SO$_4$, filtered and concentrated to dryness, giving a solid residue (0.288 g). Purification by typical silica gel flash chromatography (CH$_2$Cl$_2$/MeOH from 100:0 to 95:5) afforded the title compound (0.152 g, 52%), as a white solid. $R_t$=1.07 min. MS (ESI) m/z: 222 [M-H]$^+$, 244 [M-Na]$^+$, 260 [M-K]$^+$. $^1$H NMR (DMSO-d$_6$): δ 7.40-7.34 (m, 4H), 5.26 (t, 1H, J=5.8 Hz), 4.53 (d, 2H, J=5.8 Hz), 3.80-3.20 (m, 8H).

Step 2. Preparation of [4-(morpholine-4-carbonyl)-phenyl]-methyl-2-pyridyl carbonate and [4-(morpholine-4-carbonyl)-phenyl]-methyl-2-oxopyridine-1-carboxylate Under nitrogen atmosphere, to a solution of [4-(hydroxymethyl)-phenyl]-morpholino-methanone (0.152 g, 0.69 mmol) in dry CH$_2$Cl$_2$ (9.0 mL), DMAP (0.008 g, 0.07 mmol) and 2-DPC (0.178 g, 0.83 mmol) were added. The reaction mixture was stirred at r.t. for 16 h, then diluted with CH$_2$Cl$_2$ (50 mL) and sequentially washed with sat. NH$_4$Cl solution (15 mL) and sat. NaHCO$_3$ solution (3×15 mL). The organic layer was dried over Na$_2$SO$_4$, filtered and concentrated to dryness affording an oily residue (0.4 g), as a mixture (1:1.5 ratio) of [4-(morpholine-4-carbonyl)-phenyl]-methyl-2-pyridyl carbonate and [4-(morpholine-4-carbonyl)-phenyl]-methyl-2-oxopyridine-1-carboxylate. The mixture of isomers was not separated and used in the next step without any further purification. $R_t$=1.49 min. MS (ESI) m/z: 343 [M-H]$^+$, 365 [M-Na]$^+$, 381 [M-K]$^+$.

Step 3. Preparation of [4-(morpholine-4-carbonyl)-phenyl]-methyl-N-[(3S)-2-oxoazetidin-3-yl]-carbamate Under nitrogen atmosphere, to a suspension of [(3S)-2-oxoazetidin-3-yl]-ammonium acetate (0.03 g, 0.21 mmol) in dry CH$_2$Cl$_2$ (4.0 mL), DIPEA (0.042 mL, 0.25 mmol) was added dropwise. Subsequently, the crude mixture (0.176 g) containing [4-(morpholine-4-carbonyl)-phenyl]-methyl-2-oxopyridine-1-carboxylate (0.070 g, 0.21 mmol) in dry CH$_2$Cl$_2$ (2.0 mL) was added. The reaction mixture was stirred at r.t. for 16 h, then concentrated to dryness giving a solid residue (0.21 g). Purification by preparative HPLC afforded the pure title compound (0.017 g, 24%), as a white solid. $R_t$=1.20 min. MS (ESI) m/z: 334 [M-H]$^+$, 356 [M-Na]$^+$, 372 [M-K]$^+$. $^1$H NMR (DMSO-d$_6$): δ 8.01 (d, 1H, J=8.7 Hz), 7.94 (s, 1H), 7.46-7.38 (m, 4H), 5.13-5.05 (m, 2H), 4.67 (ddd, 1H, J=8.5, 5.5, 2.7 Hz), 3.73-3.46 (m, 8H), 3.40 (t, 1H, J=5.5 Hz), 3.09 (dd, 1H, J=5.5, 2.7 Hz).

Example 54. [4-(1,3-Benzoxazol-2-yl)-phenyl]-methyl-N-[(3S)-2-oxoazetidin-3-yl]-carbamate Step 1. Preparation of methyl 4-(1,3-benzoxazol-2-yl)-benzoate Under nitrogen atmosphere, a mixture of benzoxazole (0.5 g, 4.07 mmol), methyl 4-iodobenzoate (1.32 g, 4.89 mmol), CuI (0.77 g, 4.07 mmol), PPh$_3$ (0.216 g, 0.81 mmol), and Na$_2$CO$_3$ (0.86 g, 8.14 mmol) in dry DMF (4.1 mL) was stirred at 160° C. for 2 h. A solution of ethylendiamine (8.25 mL) in H$_2$O (20 mL) was then added, and the crude mixture extracted with EtOAc (2×50 mL). The organic layer was dried over Na$_2$SO$_4$, concentrated to dryness to give a crude product which after Purification by typical silica gel flash chromatography (Cy/TBME from 100:0 to 90:10) afforded the pure title compound (0.26 g, 25%) as a solid. $R_t$=2.78 min; MS (ESI) m/z: 254 [M-H]$^+$. $^1$H NMR (CDCl$_3$): δ 8.34 (d, 2H, J=8.0 Hz), 8.20 (d, 2H, J=8.0 Hz), 7.81 (m, 1H), 7.62 (m, 1H), 7.39 (m, 2H), 3.97 (s, 3H)

Step 2. Preparation of [4-(1,3-benzoxazol-2-yl)-phenyl]-methanol

Under nitrogen atmosphere, at 0° C., to a suspension of LiAlH$_4$ (2.0 M in THF, 3.0 mL, 6.02 mmol) in dry THF (16 mL), a suspension of methyl 4-(1,3-benzoxazol-2-yl)-benzoate (0.38 g, 1.50 mmol) in dry THF (5.0 mL) was added dropwise. The resulting mixture was stirred at r.t. for 3 h, then cooled to 0° C. and H$_2$O (4.0 mL) was slowly added, followed by a 3.0 M KOH solution (4.0 mL) and additional H$_2$O (5.2 mL). The mixture was stirred at 0° C. for 1 h, filtered and the organic phase dried over Na$_2$SO$_4$, concentrated to dryness giving a solid crude product (0.23 g). Purification by typical silica gel flash chromatography (Cy/EtOAc, from 80:20 to 40:60) and then trituration in Et$_2$O afforded the pure title compound (0.18 g, 50%) as a white solid. $R_t$=2.09 min; MS (ESI) m/z: 226 [M-H]$^+$. $^1$H NMR (DMSO-d$_6$): δ 8.17 (d, 1H, J=8.3 Hz), 7.83-7.75 (m, 1H), 7.56 (d, 1H, J=8.3 Hz), 7.49-7.37 (m, 1H), 5.38 (t, 1H, J=5.3 Hz), 4.61 (d, 1H J=4.5, Hz).

Step 3. Preparation of [4-(1,3-benzoxazol-2-yl)-phenyl]-methyl-2-pyridyl carbonate and [4-(1,3-benzoxazol-2-yl)-phenyl]-methyl-2-oxopyridine-1-carboxylate Under nitrogen atmosphere, to a stirred mixture of [4-(1,3-benzoxazol-2-yl)-phenyl]-methanol (0.18 g, 0.80 mmol) in dry THF (8.0 mL), DMAP (0.098 g, 0.08 mmol) and 2-DPC (0.21 g, 0.96 mmol) were added. The reaction mixture was left at r.t. for 16 h, then diluted with EtOAc (50 mL) and sequentially washed with a sat. NH$_4$Cl solution (15 mL) and sat. NaHCO$_3$ solution (3×15 mL). The organic phase was dried over Na$_2$SO$_4$, filtered and concentrated to dryness to afford an oily product (0.27 g), as a mixture (1:2 ratio) of [4-(1,3-benzoxazol-2-yl)-phenyl]-methyl-2-pyridyl carbonate and [4-(1,3-benzoxazol-2-yl)-phenyl]-methyl-2-oxopyridine-1-carboxylate. The mixture of isomers was not separated and used in the next step without any further purification. $R_t$=2.12 min; MS (ESI) m/z: 347 [M-H]$^+$.

Step 4. Preparation of [4-(1,3-benzoxazol-2-yl)-phenyl]-methyl-N-[(3S)-2-oxoazetidin-3-yl]-carbamate Under nitrogen atmosphere, to a suspension of [(3S)-2-oxoazetidin-3-yl]-ammonium acetate (0.04 g, 0.27 mmol) in a dry 6:1 mixture of CH$_2$Cl$_2$/DMF (3.0 mL), DIPEA (0.06 mL, 0.32 mmol) was added dropwise. Subsequently, the crude mixture (0.27 g) containing [4-(1,3-benzoxazol-2-yl)-phenyl]-methyl-2-oxopyridine-1-carboxylate (0.095 g, 0.27 mmol) in a dry 6:1 mixture of CH$_2$Cl$_2$/DMF (1.0 mL) was added. The reaction mixture was stirred at r.t. for 16 h, concentrated to dryness affording an oily residue, which was portioned between EtOAc (15 mL) and sat. NaHCO$_3$ solution (15 mL). The organic fraction was dried over Na$_2$SO$_4$, filtered and concentrated to dryness to afford a crude product, which was triturated first in CH$_2$Cl$_2$ and then in MTBE to afford the pure title compound (0.052 g, 54%) as a white solid. R$_t$=2.05 min; MS (ESI) m/z: 338 [M-H]$^+$. $^1$H NMR (DMSO-d$_6$): δ 8.29-8.17 (m, 2H), 8.09 (d, 1H, J=8.8 Hz), 7.96 (s, 1H), 7.87-7.77 (m, 2H), 7.60 (d, 2H, J=8.1 Hz), 7.44 (tt, 2H, J=7.4, 5.7 Hz), 5.17 (s, 2H), 4.69 (ddd, 1H, J=8.1, 5.5, 2.6 Hz), 3.42 (t, 1H, J=5.4 Hz), 3.11 (dd, 1H, J=5.3, 2.7 Hz).

Example 55. (4-Cyclopentylphenyl)-methyl-N-[(3S)-2-oxoazetidin-3-yl]-carbamate

Step 1. Preparation of isopropyl 4-cyclopentylbenzoate

Under argon atmosphere, to a stirred suspension of 4-methoxycarbonyl-phenylboronic acid (2.13 g, 11.84 mmol), NiI$_2$ (0.185 g, 0.59 mmol) and trans-2-hydroxy-cyclohexylamine hydrochloride (0.091 g, 0.59 mmol) in i-PrOH (20 mL), sodium bis-(trimethylsilyl)-amide (1.0 M in THF, 20 mL, 19.73 mmol) was added and the mixture stirred at r.t. for 5 min. To the resulting suspension cyclopentylbromide (1.1 mL, 9.86 mmol) was added, and the reaction mixture stirred at 60° C. for 6 h. The crude reaction was diluted with a 1:1 mixture of CH$_2$Cl$_2$/MeOH (20 mL), then filtered through a short pad of Celite. After removal of the organics, the crude product was dissolved in EtOAc (150 mL), washed with 0.1 M HCl solution (100 mL), brine (100 mL), dried over Na$_2$SO$_4$ and concentrated to dryness. Purification by typical silica gel flash chromatography (Cy/MTBE from 100:0 to 90:10) afforded the title compound (0.47 g, 15%), as an oil [compound isolated as 75% weigh mass purity, with isopropyl benzoate as detected impurity]. R$_t$=2.12 min. $^1$H NMR (CDCl$_3$): δ 7.97 (d, 2H, J=8.0 Hz), 7.32 (d, 2H, J=8.0 Hz), 5.27 (hep, 1H, J=12.0 Hz), 3.14-3.00 (m, 1H), 2.20-2.04 (m, 2H), 1.91-1.79 (m, 2H), 1.79-1.68 (m, 2H), 1.68-1.56 (m, 2H), 1.39 (d, 6H, J=12.0 Hz).

Step 2. Preparation of (4-cyclopentylphenyl)-methanol

Under nitrogen atmosphere, at 0° C., to a suspension of LiAlH$_4$ (2.0 M in THF, 4.2 mL, 8.38 mmol)) in dry THF (12 mL), a suspension of isopropyl 4-cyclopentylbenzoate (0.47 g, 1.52 mmol) in dry THF (3.0 mL) was added dropwise. The resulting mixture was stirred at r.t. for 3 h, then cooled to 0° C. and H$_2$O (4.0 mL) was slowly added, followed by a 3.0 M KOH solution (4.0 mL) and additional H$_2$O (5.2 mL). The mixture was stirred at 0° C. for 1 h, filtered and the organic phase dried over Na$_2$SO$_4$, concentrated to dryness giving a solid crude product (0.31 g). Purification by typical silica gel flash chromatography (Cy/TBME from 95:5 to 60:40) afforded the pure title compound (0.225 g, 81%), as an oil. R$_t$=1.00 min; MS (ESI) m/z: not detected. $^1$H NMR (CDCl$_3$): δ 7.32 (d, 2H, J=8.2 Hz), 7.27 (d, 2H, J=8.2 Hz), 4.68 (s, 2H), 3.02 (tt, 1H, J=9.5, 7.5 Hz), 2.18-2.03 (m, 1H), 1.91-1.78 (m, 2H), 1.79-1.67 (m, 2H), 1.67-1.53 (m, 3H).

Step 3. Preparation of (4-cyclopentylphenyl)-methyl-2-pyridyl carbonate and (4-cyclopentylphenyl)-methyl-2-oxopyridine-1-carboxylate Under nitrogen atmosphere, to a stirred mixture of (4-cyclopentylphenyl)-methanol (0.225 g, 1.28 mmol) in dry CH$_2$Cl$_2$ (18 mL), DMAP (0.016 g, 0.13 mmol) and 2-DPC (0.33 g, 1.53 mmol) were added. The reaction mixture was left at r.t. for 16 h, then diluted with CH$_2$Cl$_2$ (50 mL) and sequentially washed with a sat. NH$_4$Cl solution (15 mL) and a sat. NaHCO$_3$ solution (3×15 mL). The organic fraction was dried over Na$_2$SO$_4$, filtered and concentrated to dryness to afford an oily product (0.38 g) as a mixture (1:2 ratio) of (4-cyclopentylphenyl)-methyl-2-pyridyl carbonate and (4-cyclopentylphenyl)-methyl-2-oxopyridine-1-carboxylate. The mixture of isomers was not separated and used in the next step without any further purification. R$_t$=2.79 min; MS (ESI) m/z: 298 [M-H]$^+$.

Step 4. Preparation of (4-cyclopentylphenyl)-methyl-N-[(3S)-2-oxoazetidin-3-yl]-carbamate Under nitrogen atmosphere, to a suspension of [(3S)-2-oxoazetidin-3-yl]-ammonium acetate (0.05 g, 0.34 mmol) in dry CH$_2$Cl$_2$ (2.0 mL), DIPEA (0.07 mL, 0.41 mmol) was added dropwise. Subsequently, the crude mixture (0.37 g) containing (4-cyclopentylphenyl)-methyl-2-oxopyridine-1-carboxylate (0.131 g, 0.34 mmol) in dry CH$_2$Cl$_2$ (4.0 mL) was added. The reaction mixture was stirred at r.t. for 16 h, diluted with CH$_2$Cl$_2$ (6 mL), washed with sat. NH$_4$Cl solution (2×20 mL), sat. NaHCO$_3$ solution (2×20 mL), and the organic layer dried over Na$_2$SO$_4$ and concentrated to dryness. Purification by typical silica gel flash chromatography (CH$_2$Cl$_2$/MeOH from 100:0 to 95:5) afforded the pure title compound (0.034 g, 35%) as a white solid. R$_t$=2.79 min; MS (ESI) m/z: 298 [M-H]$^+$. $^1$H NMR (DMSO-d$_6$): δ 7.92 (d, 2H, J=9.0 Hz), 7.32-7.17 (m, 4H), 4.99 (s, 2H), 4.66 (ddd, 1H, J=8.4, 5.4, 2.7 Hz), 3.39 (t, 1H, J=5.4 Hz), 3.08 (dd, 1H, J=5.2, 2.8 Hz), 2.97 (tt, 1H, J=9.7, 7.4 Hz), 2.07-1.94 (m, 2H), 1.76 (tdd, 2H, J=9.1, 6.9, 3.9 Hz), 1.71-1.58 (m, 2H), 1.58-1.44 (m, 2H).

Example 56. [4-(1R,2R,4S)- and (1S,2S,4R)-Norbornan-2-yl-phenyl)]-methyl-N-[(3S)-2-oxoazetidin-3-yl]-carbamate

Step 1. Preparation of exo-isopropyl isopropyl 4-norbornan-2-yl-benzoate

Under argon atmosphere, to a stirred suspension of 4-methoxycarbonyl-phenylboronic acid (1.81 g, 10.08 mmol), NiI$_2$ (0.185 g, 0.59 mmol) and trans-2-hydroxy-cyclohexylamine hydrochloride (0.157 g, 0.50 mmol) in i-PrOH (17 mL), sodium bis-(trimethylsilyl)-amide (1.0 M in THF, 17 mL, 16.79 mmol) was added and the mixture stirred at r.t. for 5 min. To the resulting suspension racemic exo-2-bromonorbornane (1.1 mL, 8.40 mmol) was added, and the reaction mixture stirred at 60° C. for 6 h. The crude reaction was diluted with a 1:1 mixture of CH$_2$Cl$_2$/MeOH (20 mL), then filtered through a short pad of Celite®. After removal of the organics, the crude product was dissolved in EtOAc (150 mL), washed with 0.1 M HCl solution (100 mL), brine (100 mL), dried over Na$_2$SO$_4$ and concentrated to dryness. Purification by typical silica gel flash chromatography (Cy/MTBE from 100:0 to 90:10) afforded the title compound (0.478 g, 17%), as an oil [compound isolated as 77% weigh mass purity, with isopropyl benzoate as detected impurity]. R$_t$=2.37 min; MS (ESI) m/z: not detected. $^1$H NMR (CDCl$_3$): δ 7.97 (d, 2H, J=8.0 Hz), 7.32 (d, 2H, J=8.0 Hz), 5.26 (hep, 1H, J=12.0 Hz), 2.84-2.78 (m, 1H), 2.40 (m, 2H), 1.86-1.76 (m, 1H), 1.70-1.50 (m, 5H), 1.37 (d, 6H, J=12.0 Hz), 1.35-1.20 (m, 2H).

Step 2. Preparation of [4-(1S*,2S*,4R*)-norbornan-2-yl-phenyl]-methanol

Under nitrogen atmosphere, at 0° C., to a suspension of LiAlH$_4$ (2.0 M in THF, 3.9 mL, 7.83 mmol) in dry THF (11 mL), a solution of exo-isopropyl 4-norbornan-2-yl-benzoate (0.478 g, 1.42 mmol) in dry THF (3.0 mL) was added dropwise. The resulting mixture was stirred at r.t. for 3 h, then cooled to 0° C. and $H_2O$ (4.0 mL) was slowly added, followed by a 3.0 M KOH solution (4.0 mL) and additional $H_2O$ (5.2 mL). The mixture was stirred at 0° C. for 1 h, filtered and the organic phase dried over $Na_2SO_4$, concentrated to dryness giving a solid crude product (0.35 g). Purification by typical silica gel flash chromatography (Cy/TBME from 80:20 to 60:40) afforded the title compound (0.2 g, 68%), as an oil. $R_t$=1.26 min; MS (ESI) m/z: not detected. $^1H$ NMR ($CDCl_3$): δ 7.28 (d, 2H, J=8.1 Hz), 7.22 (d, 2H, J=8.0 Hz), 4.65 (s, 2H), 2.75 (dd, 1H, J=9.1, 5.6 Hz), 2.39-2.31 (m, 2H), 1.77 (ddd, 1H, J=11.7, 9.0, 2.3 Hz), 1.71-1.49 (m, 3H), 1.47-1.14 (m, 4H).

Step 3. Preparation of [4-(1S*,2S*,4R*)-norbornan-2-yl-phenyl]-methyl-2-pyridyl carbonate and [4-(1S*,2S*,4R*)-norbornan-2-yl-phenyl]-methyl-2-oxopyridine-1-carboxylate Under nitrogen atmosphere, to a stirred mixture of [4-(1S*,2S*,4R*)-norbornan-2-yl-phenyl]-methanol (0.2 g, 1.0 mmol) in dry $CH_2Cl_2$ (18 mL), DMAP (0.012 g, 0.10 mmol) and 2-DPC (0.26 g, 1.20 mmol) were added. The reaction mixture was left at r.t. for 16 h, then diluted with $CH_2Cl_2$ (50 mL) and sequentially washed with a sat. $NH_4Cl$ solution (15 mL) and a sat. $NaHCO_3$ solution (3×15 mL). The organic fraction was dried over $Na_2SO_4$, filtered and concentrated to dryness to afford an oily product (0.32 g), as a mixture (2:1 ratio) of [4-(1S*,2S*,4R*)-norbornan-2-yl-phenyl]-methyl-2-pyridyl carbonate and [4-(1S*,2S*,4R*)-norbornan-2-yl-phenyl]-methyl-2-oxopyridine-1-carboxylate. The mixture of isomers was not separated and used in the next step without any further purification. $R_t$=3.00 min; MS (ESI) m/z: 324 $[M-H]^+$.

Step 4. Preparation of [4-(1R,2R,4S)-norbornan-2-yl-phenyl)]-methyl-N-[(3S)-2-oxoazetidin-3-yl]-carbamate and [4-(1S,2S,4R)-norbornan-2-yl-phenyl)]-methyl-N-[(3S)-2-oxoazetidin-3-yl]-carbamate Under nitrogen atmosphere, to a suspension of [(3S)-2-oxoazetidin-3-yl]-ammonium acetate (0.05 g, 0.34 mmol) in dry $CH_2Cl_2$ (2.0 mL), DIPEA (0.07 mL, 0.41 mmol) was added dropwise. Subsequently, the crude mixture (0.32 g) containing [4-(1S*,2S*,4R*)-norbornan-2-yl-phenyl]-methyl-2-oxopyridine-1-carboxylate (0.112 g, 0.34 mmol) in dry $CH_2Cl_2$ (4.0 mL) was added. The reaction mixture was stirred at r.t. for 16 h, diluted with $CH_2Cl_2$ (6 mL), washed with sat. $NH_4Cl$ solution (2×20 mL), sat. $NaHCO_3$ solution (2×20 mL), and the organic layer dried over $Na_2SO_4$ and concentrated to dryness. Purification by typical silica gel flash chromatography (Cy/EtOAc from 25:75 to 15:85) afforded the pure title compound (0.041 g, 38%) as a white solid. $R_t$=3.00 min; MS (ESI) m/z: 324 $[M-H]^+$. $^1H$ NMR (DMSO-$d_6$): δ 8.02-7.92 (m, 2H), 7.26 (d, 2H, J=8.2 Hz), 7.21 (d, 2H, J=8.2 Hz), 4.99 (s, 2H), 4.66 (ddd, 1H, J=8.6, 5.5, 2.7 Hz), 3.40 (m, 1H), 3.07 (dd, 1H, J=5.3, 2.8 Hz), 2.72 (dd, 1H, J=8.7, 5.8 Hz), 2.38-2.23 (m, 2H), 1.73 (ddd, 1H, J=11.6, 8.9, 2.3 Hz), 1.64-1.50 (m, 3H), 1.47 (ddd, 1H, J=11.6, 5.5, 3.1 Hz), 1.40-1.31 (m, 1H), 1.28-1.19 (m, 1H), 1.14 (dt, 1H, J=9.8, 1.9 Hz).

Example 57. (4-tert-Butylphenyl)-methyl-N-[(3S)-2-oxoazetidin-3-yl]-carbamate

Step 1. Preparation of (4-tert-butylphenyl)-methyl-2-pyridyl carbonate and (4-tert-butylphenyl)-methyl-2-oxopyridine-1-carboxylate Under nitrogen atmosphere, to a stirred mixture of commercially available 4-tert-butylbenzyl alcohol (0.22 mL, 1.19 mmol) in dry $CH_2Cl_2$ (6.3 mL), DMAP (0.015 g, 0.12 mmol) and 2-DPC (0.34 g, 1.55 mmol) were added. The reaction mixture was left at r.t. for 16 h, then diluted with $CH_2Cl_2$ (50 mL) and sequentially washed with a sat. $NH_4Cl$ solution (15 mL) and a sat. $NaHCO_3$ solution (3×15 mL). The organic fraction was dried over $Na_2SO_4$, filtered and concentrated to dryness to afford an oily product (0.34 g), as a mixture (2:1 ratio) of (4-tert-butylphenyl)-methyl-2-pyridyl carbonate and (4-tert-butylphenyl)-methyl-2-oxopyridine-1-carboxylate. The mixture of isomers was not separated and used in the next step without any further purification. $R_t$=2.65 min; MS (ESI) m/z: 286 $[M-H]^+$.

Step 2. Preparation of (4-tert-butylphenyl)-methyl-N-[(3S)-2-oxoazetidin-3-yl]-carbamate Under nitrogen atmosphere, to a suspension of [(3S)-2-oxoazetidin-3-yl]-ammonium acetate (0.05 g, 0.34 mmol) in dry $CH_2Cl_2$ (2.0 mL), DIPEA (0.07 mL, 0.41 mmol) was added dropwise. Subsequently, the crude mixture (0.34 g) containing (4-tert-butylphenyl)-methyl-2-oxopyridine-1-carboxylate (0.119 g, 0.34 mmol) in dry $CH_2Cl_2$ (4.0 mL) was added. The reaction mixture was stirred at r.t. for 16 h, diluted with $CH_2Cl_2$ (6.0 mL), washed with sat. $NH_4Cl$ solution (2×20 mL), sat. $NaHCO_3$ solution (2×20 mL), and the organic layer dried over $Na_2SO_4$ and concentrated to dryness. Purification by typical silica gel flash chromatography (Cy/TBME from 50:50 to 0:100) afforded the pure title compound (0.051 g, 54%) as a white solid. $R_t$=2.3 min; MS (ESI) m/z: 394 $[M-NH_4]^+$. $^1H$ NMR (DMSO-$d_6$): δ 7.95 (s, 1H), 7.91 (s, 1H), 7.39 (d, 2H, J=8.3 Hz), 7.28 (d, 2H, J=8.3 Hz), 5.00 (s, 2H), 4.66 (ddd, 1H, J=8.4, 5.4, 2.7 Hz), 3.40 (t, 1H, J=5.4 Hz), 3.08 (dd, 1H, J=5.3, 2.8 Hz), 1.28 (s, 9H).

Example 58. [4-(1-Adamantyl)-phenyl]-methyl-N-[(3S)-2-oxoazetidin-3-yl]-carbamate Step 1. Preparation of 1-[4-(bromomethyl)-phenyl]-adamantane Under argon atmosphere, at 0° C., to a solution of p-(1-adamantyl)-toluene (2.0 g, 8.39 mmol) in $CHCl_3$ (12.3 mL) benzoyl-peroxide (0.027 g, 0.084 mmol) and of N-bromosuccinimide (1.58 g, 8.81 mmol) were added stepwise. The reaction was stirred at reflux temperature for 6.5 h, then diluted with $CH_2Cl_2$ (50 mL), washed with sat. $Na_2CO_3$ solution (50 mL), dried over $Na_2SO_4$ and concentrated to dryness. Purification by typical silica gel flash chromatography (Cy/$CH_2Cl_2$ from 100:0 to 97:3) afforded the pure title compound (1.52 g, 59%) as a white solid. $R_t$ 2.52 min; MS (ESI) m/z: not detected. $^1H$-NMR ($CDCl_3$): δ 7.34 (s, 4H), 4.50 (s, 2H), 2.10 (m, 3H), 1.90 (m, 6H), 1.86-1.69 (m, 6H).

Step 2. Preparation of [4-(1-adamantyl)-phenyl]-methanol

Under nitrogen atmosphere, a suspension of 1-[4-(bromomethyl)-phenyl]-adamantane (1.5 g, 4.91 mmol) and Na₂CO₃ (2.66 g, 24.55 mmol) in a 1:1 mixture of 1,4-dioxane/H₂O (25 mL) was stirred at 100° C. for 16 h. The reaction mixture was portioned between EtOAc (25 mL) and 2.0 M HCl solution (25 mL); the organic layer was dried over Na₂SO₄ and concentrated to dryness at low pressure. The crude product was triturated in cyclohexane to afford the pure title compound (0.84 g, 69%) as a white solid. $R_t$=1.66 min; MS (ESI) m/z: not observed. ¹H NMR (DMSO-d₆): δ 7.29 (d, 2H, J=8.2 Hz), 7.23 (d, 2H, J=8.2 Hz), 5.04 (t, 1H, J=5.7 Hz), 4.44 (d, 2H, J=5.6 Hz), 2.05 (m, 3H), 1.85 (m, 6H), 1.73 (m, 6H).

Step 3. Preparation of [4-(1-adamantyl)-phenyl]-methyl-2-pyridyl carbonate and [4-(1-adamantyl)-phenyl]-methyl-2-oxopyridine-1-carboxylate Under nitrogen atmosphere, to a stirred mixture of [4-(1-adamantyl)-phenyl]-methanol (0.4 g, 1.65 mmol) in dry CH₂Cl₂ (8.7 mL), DMAP (0.02 g, 0.17 mmol) and 2-DPC (0.428 g, 1.98 mmol) were added. The reaction mixture was left at r.t. for 16 h, then diluted with CH₂Cl₂ (50 mL) and sequentially washed with a sat. NH₄Cl solution (15 mL) and a sat. NaHCO₃ solution (3×15 mL). The organic fraction was dried over Na₂SO₄, filtered and concentrated to dryness to afford an oily product (0.59 g), as a mixture (2:1 ratio) of [4-(1-adamantyl)-phenyl]-methyl-2-pyridyl carbonate and [4-(1-adamantyl)-phenyl]-methyl-2-oxopyridine-1-carboxylate. The mixture of isomers was not separated and used in the next step without any further purification. $R_t$=1.95 min; MS (ESI) m/z: 364 [M-H]⁺.

Step 4. Preparation of [4-(1-adamantyl)-phenyl]-methyl-N-[(3S)-2-oxoazetidin-3-yl]-carbamate Under nitrogen atmosphere, to a suspension of [(3S)-2-oxoazetidin-3-yl]-ammonium acetate (0.050 g, 0.34 mmol) in dry CH₂Cl₂ (2.0 mL), DIPEA (0.07 mL, 0.41 mmol) was added dropwise. Subsequently, the crude mixture (0.38 g) containing [4-(1-adamantyl)-phenyl]-methyl-2-oxopyridine-1-carboxylate (0.134 g, 0.41 mmol) in dry CH₂Cl₂ (4.0 mL) was added. The reaction mixture was stirred at r.t. for 16 h, diluted with CH₂Cl₂ (6.0 mL), washed with sat. NH₄Cl solution (2×20 mL), sat. NaHCO₃ solution (2×20 mL), and the organic layer dried over Na₂SO₄ and concentrated to dryness. Purification by typical silica gel flash chromatography (Cy/TBME from 50:50 to 0:100) afforded the pure title compound (0.062 g, 43%) as a white solid. $R_t$=1.47 min; MS (ESI) m/z: 372 [M-NH₄]⁺. ¹H NMR (DMSO-d₆): δ 7.92 (s, 1H), 7.90 (s, 1H), 7.35 (d, 2H, J=8.3 Hz), 7.28 (d, 2H, J=8.2 Hz), 4.99 (s, 2H), 4.65 (ddd, 1H, J=8.4, 5.5, 2.7 Hz), 3.42-3.36 (m, 1H), 3.07 (dd, 1H, J=5.4, 2.8 Hz), 2.08-2.02 (m, 3H), 1.87-1.83 (m, 6H), 1.78-1.68 (m, 6H).

Example 59. Tetralin-6-yl-methyl-N-[(3S)-2-oxoazetidin-3-yl]-carbamate

Step 1. Preparation of tetralin-6-yl-methanol

Under nitrogen atmosphere, at 0° C., to a suspension of LiAlH₄ (2.0 M in THF, 11 mL, 22.02 mmol) in dry THF (50 mL), a solution of 5,6,7,8-tetrahydro-2-naphthoic acid (1.0 g, 5.5 mmol,) in dry THF (5.0 mL) was added dropwise. The resulting mixture was stirred at r.t. for 3 h, then cooled to 0° C. and H₂O (10 mL) was slowly added, followed by a 3.0 M KOH solution (10 mL) and additional H₂O (15 mL). The mixture was stirred at 0° C. for 1 h, filtered and the organic phase dried over Na₂SO₄, concentrated to dryness giving the title compound as a white solid (0.876 g, 98%), which was used in the next step without any further purification. $R_t$=2.20 min; MS (ESI) m/z: not detected. ¹H NMR (DMSO-d₆): δ 6.99 (m, 3H), 5.01 (t, 1H, J=5.7 Hz), 4.40 (d, 2H, J=5.7 Hz), 2.77-2.61 (m, 4H), 1.76-1.68 (m, 4H).

Step 2. Preparation of 2-pyridyl-tetralin-6-ylmethyl carbonate and tetralin-6-yl-methyl-2-oxopyridine-1-carboxylate Under nitrogen atmosphere, to a stirred mixture of tetralin-6-yl-methanol (0.2 g, 1.23 mmol) in dry CH₂Cl₂ (6.5 mL), DMAP (0.015 g, 0.12 mmol) and 2-DPC (0.325 g, 1.48 mmol) were added. The reaction mixture was left at r.t. for 16 h, then diluted with CH₂Cl₂ (50 mL) and sequentially washed with a sat. NH₄Cl solution (15 mL) and a sat. NaHCO₃ solution (3×15 mL). The organic fraction was dried over Na₂SO₄, filtered and concentrated to dryness to afford an oily product (0.36 g), as a mixture (2:1 ratio) of 2-pyridyl-tetralin-6-ylmethyl carbonate and tetralin-6-yl-methyl-2-oxopyridine-1-carboxylate. The mixture of isomers was not separated and used in the next step without any further purification. $R_t$=2.57 min; MS (ESI) m/z: 284 [M-H]⁺.

Step 3. Preparation of tetralin-6-yl-methyl-N-[(3S)-2-oxoazetidin-3-yl]-carbamate Under nitrogen atmosphere, to a suspension of [(3S)-2-oxoazetidin-3-yl]-ammonium acetate (0.05 g, 0.34 mmol) in dry CH₂Cl₂ (2.0 mL), DIPEA (0.07 mL, 0.41 mmol) was added dropwise. Subsequently, the crude mixture (0.35 g) containing tetralin-6-yl-methyl-2-oxopyridine-1-carboxylate (0.125 g, 0.41 mmol) in dry CH₂Cl₂ (4.0 mL) was added. The reaction mixture was stirred at r.t. for 16 h, diluted with CH₂Cl₂ (10 mL), washed with sat. NH₄Cl solution (2×20 mL), sat. NaHCO₃ solution (2×20 mL), and the organic layer dried over Na₂SO₄ and concentrated to dryness. Purification by typical silica gel flash chromatography (Cy/EtOAc from 70:30 to 30:70) afforded the pure title compound (0.056 g, 56%) as a white solid. $R_t$=2.15 min; MS (ESI) m/z: 292 [M-NH₄]⁺. ¹H NMR (DMSO-d₆): δ 7.95-7.85 (m, 2H), 7.03 (s, 3H), 4.94 (s, 2H), 4.65 (ddd, 1H, J=8.5, 6.3, 2.7 Hz), 3.39 (t, 1H, J=5.4 Hz), 3.07 (dd, 1H, J=5.3, 2.8 Hz), 2.76-2.64 (m, 4H), 1.79-1.66 (m, 4H).

Example 60. (3-Fluoro-4-phenyl-phenyl)-methyl-N-[(3S)-2-oxoazetidin-3-yl]-carbamate

Step 1. Preparation of (3-fluoro-4-phenyl-phenyl)-methanol

Under nitrogen atmosphere, at 0° C., to a suspension of LiAlH₄ (2.0 M in THF, 4.5 mL, 8.97 mmol) in dry THF (17 mL), a solution of solution of 3-fluoro-4-phenyl-benzoic acid (0.5 g, 2.24 mmol) in dry THF (5.0 mL) was added dropwise. The resulting mixture was stirred at r.t. for 3 h, then cooled to 0° C. and H₂O (5.0 mL) was slowly added, followed by a 3.0 M KOH solution (5.0 mL) and additional H₂O (7.5 mL). The mixture was stirred at 0° C. for 1 h, filtered and the organic phase dried over Na₂SO₄, concentrated to dryness giving the title compound (0.425 g, 94%), as a white solid, which was used in the next step without any further purification. $R_t$=2.29 min; MS (ESI) m/z: not detected. ¹H NMR (DMSO-d₆): δ 7.54 (d, 2H, J=8.1 Hz), 7.48 (t, 3H, 8.1 Hz), 7.39 (t, 1H, 8.1 Hz), 7.25, (s, 1H), 7.22 (d, 2H, 8.1 Hz), 5.34 (t, J=5.8 Hz, 1H), 4.55 (d, J=5.7 Hz, 2H).

Step 2. Preparation of (3-fluoro-4-phenyl-phenyl)-methyl-2-pyridyl carbonate and 3-fluoro-4-phenyl-phenyl)-methyl-2-oxopyridine-1-carboxylate Under nitrogen atmosphere, to a stirred mixture of (3-fluoro-4-phenyl-phenyl)-methanol (0.25 g, 1.24 mmol) in dry $CH_2Cl_2$ (6.5 mL), DMAP (0.015 g, 0.12 mmol) and 2-DPC (0.3 g, 1.49 mmol) were added. The reaction mixture was left at r.t. for 16 h, then diluted with $CH_2Cl_2$ (50 mL) and sequentially washed with a sat. $NH_4Cl$ solution (15 mL) and a sat. $NaHCO_3$ solution (3×15 mL). The organic fraction was dried over $Na_2SO_4$, filtered and concentrated to dryness to afford an oily product (0.44 g), as a mixture (1:2 ratio) of (3-fluoro-4-phenyl-phenyl)-methyl-2-pyridyl carbonate and 3-fluoro-4-phenyl-phenyl)-methyl-2-oxopyridine-1-carboxylate. The mixture of isomers was not separated and used in the next step without any further purification. $R_t$=2.58 min; MS (ESI) m/z: 324 [M-H]$^+$.

Step 3. Preparation of (3-fluoro-4-phenyl-phenyl)-methyl-N-[(3S)-2-oxoazetidin-3-yl]-carbamate Under nitrogen atmosphere, to a suspension of [(3S)-2-oxoazetidin-3-yl]-ammonium acetate (0.05 g, 0.34 mmol) in dry $CH_2Cl_2$ (2.0 mL), DIPEA (0.07 mL, 0.41 mmol) was added dropwise. Subsequently, the crude mixture (0.43 g) containing 3-fluoro-4-phenyl-phenyl)-methyl-2-oxopyridine-1-carboxylate (0.153 g, 0.41 mmol) in dry $CH_2Cl_2$ (4.0 mL) was added. The reaction mixture was stirred at r.t. for 16 h, diluted with $CH_2Cl_2$ (10 mL), washed with sat. $NH_4Cl$ solution (2×20 mL), sat. $NaHCO_3$ solution (2×20 mL), and the organic layer dried over $Na_2SO_4$ and concentrated to dryness. Purification by typical silica gel flash chromatography (Cy/EtOAc from 50:50 to 0:100) afforded the pure title compound (0.071 g, 55%) as a white solid. $R_t$=2.22 min; MS (ESI) m/z: 315 [M-H]$^+$. $^1$H NMR (DMSO-d$_6$): δ 8.05 (d, 1H, J=8.8 Hz), 7.95 (s, 1H), 7.57-7.44 (m, 6H), 7.43-7.38 (m, 1H), 7.32-7.26 (m, 2H), 5.10 (s, 2H), 4.68 (ddd, 1H, J=8.5, 5.5, 2.7 Hz), 3.41 (t, 1H, J=5.4 Hz), 3.10 (dd, 1H, J=5.3, 2.8 Hz).

Example 61. (1s,4R) and (1r,4S)-(4-Butylcyclo-hexyl)-N-[(3S)-2-oxoazetidin-3-yl]-carbamate Step 1. Preparation of (1s,4R) and (1r,4S)-(4-butyl-cyclohexyl)-2-pyridyl carbonate and (1s,4R) and (1r,4S)-(4-butylcyclohexyl)-2-oxopyridine-1-carboxylate Under nitrogen atmosphere, to a stirred mixture of commercially available 4-butylcyclohexanol (0.275 mL, 1.60 mmol) in dry $CH_2Cl_2$ (8.0 mL), DMAP (0.017 g, 0.14 mmol) and 2-DPC (0.415 g, 1.92 mmol) were added. The reaction mixture was left at r.t. for 16 h, then diluted with $CH_2Cl_2$ (50 mL) and sequentially washed with sat. $NH_4Cl$ solution (50 mL), sat. $NaHCO_3$ solution (3×50 mL) and brine (50 mL). The organic layer was dried over $Na_2SO_4$, filtered and concentrated to dryness to afford an oily crude product (0.346 g), as a mixture (1:1.7 ratio) of (1s,4R) and (1r,4S)-(4-butylcyclohexyl)-2-pyridyl carbonate and (1s,4R) and (1r,4S)-(4-butylcyclohexyl)-2-oxopyridine-1-carboxylate. The mixture of isomers was not separated and used in the next step without any further purification. $R_t$=3.01 min; MS (ESI) m/z: 278 [M-H]$^+$, 300 [M-Na]$^+$.

Step 2. Preparation of (1s,4R) and (1r,4S)-(4-butyl-cyclohexyl)-N-[(3S)-2-oxoazetidin-3-yl]-carbamate Under nitrogen atmosphere, to a suspension of [(3S)-2-oxoazetidin-3-yl]-ammonium acetate (0.042 g, 0.29 mmol) in dry $CH_2Cl_2$ (5.0 mL), DIPEA (0.06 mL, 0.35 mmol) was dropwise added. Subsequently, the crude mixture containing (1s,4R) and (1r,4S)-(4-butylcyclohexyl)-2-oxopyridine-1-carboxylate (0.08 g, 0.29 mmol) in dry $CH_2Cl_2$ (3.0 mL) was added. The reaction mixture was stirred at r.t. for 16 h, concentrated to dryness affording an oily crude product. Purification by typical silica gel column chromatography (Cy/EtOAc 85:15) afforded the title compound (0.060 g, 79%), as a mixture (1:1 ratio) of two diastereoisomers, as a white solid. Isomer 1: $R_t$=2.50 min; MS (ESI) m/z: 269 [M-H]$^+$, 291 [M-Na]$^+$; Isomer 2: $R_t$=2.57 min; MS (ESI) m/z: 269 [M-H]$^+$, 291 [M-Na]$^+$. $^1$H NMR (DMSO-d$_6$): δ 7.93-7.88 (m, 2H), 7.74 (d, 2H, J=8.86 Hz), 4.76-4.71 (m, 1H), 4.69-4.59 (m, 2H), 4.42 (tt, 1H, J=11.02, 4.22 Hz), 3.38 (td, 2H, J=5.41, 1.65 Hz), 3.17-3.02 (m, 2H), 1.96-1.86 (m, 2H), 1.79-1.70 (m, 4H), 1.55-1.44 (m, 3H), 1.34-1.13 (m, 18H), 1.05-0.83 (m, 9H).

Example 62. (3-Phenylphenyl)-methyl-N-[(3S)-2-oxoazetidin-3-yl]-carbamate

Step 1. Preparation of (3-phenylphenyl)-methyl-2-pyridyl carbonate and (3-phenylphenyl)-methyl-2-oxopyridine-1-carboxylate Under nitrogen atmosphere, to a stirred mixture of commercially available (3-phenylphenyl)-methanol (0.30 g, 1.82 mmol) in dry $CH_2Cl_2$ (8.0 mL), DMAP (0.022 g, 0.18 mmol) and 2-DPC (0.471 g, 2.18 mmol) were added. The reaction mixture was left at r.t. for 16 h, then diluted with $CH_2Cl_2$ (50 mL) and sequentially washed with sat. $NH_4Cl$ solution (50 mL), sat. $NaHCO_3$ solution (3×50 mL) and brine (50 mL). The organic layer was dried over $Na_2SO_4$, filtered and concentrated to dryness to afford an oily product (0.426 g), as a mixture (1:1.7 ratio) of (3-phenylphenyl)-methyl-2-pyridyl carbonate and (3-phenylphenyl)-methyl-2-oxopyridine-1-carboxylate. The mixture of isomers was not separated and used in the next step without any further purification. $R_t$=2.33 min; MS (ESI) m/z: 306 [M-H]$^+$, 228 [M-Na]$^+$.

Step 2. Preparation of (4-cyclohexylphenyl)-methyl-N-[(3S)-2-oxoazetidin-3-yl]-carbamate Under nitrogen atmosphere, to a suspension of [(3S)-2-oxoazetidin-3-yl]-ammonium acetate (0.052 g, 0.36 mmol) in dry $CH_2Cl_2$ (5.0 mL), DIPEA (0.075 mL, 0.43 mmol) was dropwise added. Subsequently, the crude mixture (0.30 g) containing (3-phenylphenyl)-methyl-2-oxopyridine-1-carboxylate (0.11 g, 0.36 mmol) in dry $CH_2Cl_2$ (2.0 mL) was added. The reaction mixture was stirred at r.t. for 16 h, concentrated to dryness affording an oily crude product. Purification by typical silica gel column chromatography (Cy/EtOAc 85:15) afforded the pure title compound (0.064 g, 55%), as a white solid. $R_t$=2.18 min; MS (ESI) m/z: 297 [M-H]$^+$, 314 [M-NH$_4$]$^+$. $^1$H NMR (DMSO-d$_6$): δ 8.01 (d, 1H, J=8.79 Hz), 7.94 (s, 1H), 7.70-7.58 (m, 4H), 7.47 (td, J=7.45, 2.37 Hz, 3H), 7.45-7.32 (m, 2H), 5.12 (s, 2H), 4.72-4.63 (m, 1H), 3.40 (t, 1H, J=5.41 Hz), 3.13-3.05 (m, 1H).

Example 63. (4-Butoxyphenyl)-methyl-N-[(3S)-2-oxoazetidin-3-yl]-carbamate

Step 1. Preparation of (4-butoxyphenyl)-methyl-2-pyridyl carbonate and (4-butoxyphenyl)-methyl-2-oxopyridine-1-carboxylate Under nitrogen atmosphere, to a stirred mixture of commercially available (4-butoxyphenyl)-methanol (0.30 g, 1.66 mmol) in dry $CH_2Cl_2$ (8.0 mL), DMAP (0.020 g, 0.17 mmol) and 2-DPC (0.43 g, 1.99 mmol) were added. The reaction mixture was left at r.t. for 16 h, then diluted with $CH_2Cl_2$ (50 mL) and sequentially washed with sat. $NH_4Cl$ solution (50 mL), sat. $NaHCO_3$ solution (3×50 mL) and brine (50 mL). The organic layer was dried over $Na_2SO_4$, filtered and concentrated to dryness to afford an oily product (0.423 g), as a mixture (1.7:1 ratio) of (4-butoxyphenyl)-methyl-2-pyridyl carbonate and (4-butoxyphenyl)-methyl-2-oxopyridine-1-carboxylate. The mixture of isomers was not separated and used in the next step without any further purification. $R_t$=2.61 min; MS (ESI) m/z: 340 [M–K]$^+$.

Step 2. Preparation of (4-butoxyphenyl)-methyl-N-[(3S)-2-oxoazetidin-3-yl]-carbamate Under nitrogen atmosphere, to a suspension of [(3S)-2-oxoazetidin-3-yl]-ammonium acetate (0.048 g, 0.33 mmol) in dry $CH_2Cl_2$ (5.0 mL), DIPEA (0.068 mL, 0.40 mmol) was dropwise added. Subsequently, the crude mixture (0.25 g) containing (4-butoxyphenyl)-methyl-2-oxopyridine-1-carboxylate (0.091 g, 0.33 mmol) in dry $CH_2Cl_2$ (2.0 mL) was added. The reaction mixture was stirred at r.t. for 16 h, concentrated to dryness affording an oily crude product. Purification by typical silica gel column chromatography (Cy/EtOAc 85:15) afforded the pure title compound (0.060 g, 60%), as a white solid. $R_t$=2.24 min; MS (ESI) m/z: 310 [M-$NH_4$]$^+$, 331 [M–K]$^+$. $^1$H NMR (DMSO-$d_6$): δ 8.00-7.81 (m, 2H), 7.34-7.21 (m, 2H), 6.96-6.84 (m, 2H), 4.95 (s, 2H), 4.64 (dd, 1H, J=8.52, 3.62 Hz), 3.96 (t, 2H, J=6.49 Hz), 3.38 (t, 1H, J=5.40 Hz), 3.11-3.02 (m, 1H), 1.74-1.60 (m, 2H), 1.48-1.38 (m, 2H), 0.93 (t, 3H, J=7.40 Hz).

Example 64. [4-(Cyclohexoxy)-phenyl]-methyl-N-[(3S)-2-oxoazetidin-3-yl]-carbamate

Step 1. Preparation of ethyl 4-(cyclohexoxy)-benzoate

To a mixture of ethyl 4-hydroxybenzoate (0.5 g, 3.01 mmol) and cyclohexene (3.0 mL, 28.96 mmol), boron trifluoride diethyl etherate (0.19 mL, 1.51 mmol) was added. The resulting mixture was heated under reflux for 2 h, cooled to r.t., diluted with EtOAc (20 mL), and washed with 5% NaOH solution (3×40 mL) and with $H_2O$ (50 mL). The organic layer was dried with $Na_2SO_4$, filtered and concentrated to dryness to afford an oily product (0.7 g), which was used in the next step without any further purification. $R_t$=3.28 min; MS (ESI) m/z: 249 [M-H]$^+$; (ESI) m/z: 247 [M-H]$^-$.

Step 2. Preparation of [4-(cyclohexoxy)-phenyl]-methanol

Under nitrogen atmosphere, to a cooled (0° C.) suspension of $LiAlH_4$ (2.0 M THF solution, 4.8 mL, 9.66 mmol) in dry$Et_2O$ (10 mL), ethyl 4-(cyclohexoxy)-benzoate (0.6 g, 2.41 mmol) in dry$Et_2O$ (5.0 mL) was added dropwise. The resulting reaction mixture was stirred at r.t. for 4 h, and then cooled to 0° C. $H_2O$ (0.45 mL) was slowly added, followed by 3.0 M KOH solution (0.45 mL) and additional $H_2O$ (2.0 mL). The mixture was stirred at 0° C. for 1 h and then filtered off. The organic layer was dried over $Na_2SO_4$, filtered and concentrated to dryness, affording the title compound (0.55 g, quant.), which was used in the next step without any further purification. $^1$H NMR (CDCl$_3$): δ 7.34-7.26 (m, 2H), 6.96-6.87 (m, 2H), 4.63 (s, 2H), 4.26 (ddd, 1H, J=12.70, 8.86, 4.00 Hz), 2.06-1.95 (m, 2H), 1.83 (ddt, 2H, J=13.88, 8.86, 4.00 Hz), 1.64-1.24 (m, 6H).

Step 3. Preparation of [4-(cyclohexoxy)-phenyl]-methyl-2-pyridyl carbonate and [4-(cyclohexoxy)-phenyl]-methyl-2-oxopyridine-1-carboxylate Under nitrogen atmosphere, to a stirred mixture of [4-(cyclohexoxy)-phenyl]-methanol (0.55 g, 2.67 mmol) in dry $CH_2Cl_2$ (12.0 mL), DMAP (0.033 g, 0.27 mmol) and 2-DPC (0.692 g, 3.02 mmol) were added. The reaction mixture was left at r.t. for 16 h, then diluted with $CH_2Cl_2$ (100 mL) and sequentially washed with sat. $NH_4Cl$ solution (100 mL), sat. $NaHCO_3$ solution (3×100 mL) and brine (100 mL). The organic layer was dried over $Na_2SO_4$, filtered and concentrated to dryness to afford an oily product (0.70 g), as a mixture (1.7:1 ratio) of [4-(cyclohexoxy)-phenyl]-methyl-2-pyridyl carbonate and [4-(cyclohexoxy)-phenyl]-methyl-2-oxopyridine-1-carboxylate. The mixture of isomers was not separated and used in the next step without any further purification. $R_t$=2.79 min; MS (ESI) m/z: 366 [M–K]$^+$.

Step 4. Preparation of [4-(cyclohexoxy)-phenyl]-methyl-N-[(3S)-2-oxoazetidin-3-yl]-carbamate Under nitrogen atmosphere, to a suspension of [(3S)-2-oxoazetidin-3-yl]-ammonium acetate (0.052 g, 0.36 mmol) in dry $CH_2Cl_2$ (8.0 mL), DIPEA (0.09 mL, 0.51 mmol) was dropwise added. Subsequently, the crude mixture (0.32 g) containing [4-(cyclohexoxy)-phenyl]-methyl-2-oxopyridine-1-carboxylate (0.12 g, 0.36 mmol) in dry $CH_2Cl_2$ (2.0 mL) was added. The reaction mixture was stirred at r.t. for 16 h, concentrated to dryness affording an oily crude product. Purification by typical silica gel column chromatography (Cy/EtOAc 85:15) afforded the pure title compound (0.065 g, 57%), as a white solid. $R_t$=2.39 min; MS (ESI) m/z: 336 [M-$NH_4$]$^+$, 357 [M–K]$^+$. $^1$H NMR (DMSO-$d_6$): δ 7.88-7.79 (m, 2H), 7.26 (d, 2H, J=8.28 Hz), 6.91 (d, 2H, J=8.28 Hz), 4.96 (s, 2H), 4.70-4.61 (m, 1H), 4.38-4.27 (m, 1H), 3.44-3.36 (m, 1H), 3.12-3.05 (m, 1H), 1.96-1.86 (m, 2H), 1.77-1.66 (m, 2H), 1.59-1.23 (m, 6H).

Example 65. But-3-ynyl-N-[(3S)-2-oxoazetidin-3-yl]-carbamate

Step 1. Preparation of but-3-ynyl-2-pyridyl carbonate and but-3-ynyl-2-oxopyridine-1-carboxylate Under nitrogen atmosphere, to a stirred solution of commercially available 3-butyn-1-ol (0.133 mL, 1.76 mmol) in dry $CH_2Cl_2$ (9.0 mL), DMAP (0.021 g, 0.18 mmol) and 2-DPC (0.456 g, 2.11 mmol) were added. The reaction mixture was stirred at r.t. for 16 h, then diluted with $CH_2Cl_2$ (50 mL) and sequentially washed with sat. $NH_4Cl$ solution (15 mL) and sat. $NaHCO_3$ solution (3×15 mL). The organic layer was dried over Na$_2$SO$_4$, filtered and concentrated to dryness affording an oily residue (0.480 g), as a mixture (1:1.8 ratio) of but-3-ynyl-2-pyridyl carbonate and but-3-ynyl-2-oxopyridine-1-carboxylate. The mixture of isomers was not separated and used in the next step without any further purification. R$_t$=1.40 min. MS (ESI) m/z: 192 [M-H]$^+$, 214 [M-Na]$^+$, 230 [M-K]$^+$.

Step 2. Preparation of but-3-ynyl-N-[(3S)-2-oxoazetidin-3-yl]-carbamate

Under nitrogen atmosphere, to a suspension of [(3S)-2-oxoazetidin-3-yl]-ammonium acetate (0.05 g, 0.34 mmol) in dry CH$_2$Cl$_2$ (4.0 mL), DIPEA (0.067 mL, 0.41 mmol) was added dropwise. Subsequently, the crude mixture (0.182 g) containing but-3-ynyl-2-oxopyridine-1-carboxylate (0.065 g, 0.34 mmol) in dry CH$_2$Cl$_2$ (2.0 mL) was added. The reaction mixture was stirred at r.t. for 16 h, then concentrated to dryness giving a solid residue (0.18 g). Trituration with Et$_2$O afforded the pure title compound (0.014 g, 23%), as a white solid. R$_t$=0.98 min. MS (ESI) m/z: 183 [M-H]$^+$, 205 [M-Na]$^+$, 221 [M-K]$^+$. $^1$H NMR (DMSO-d$_6$): δ 7.98-7.88 (m, 2H), 4.66-4.60 (m, 1H), 4.06-3.99 (m, 2H), 3.38 (t, 1H, J=5.4 Hz), 3.10-3.06 (m, 1H), 2.86 (t, 1H, J=2.7 Hz), 2.46 (dd, 2H, J=6.6, 2.7 Hz).

Example 66. (4-Tetrahydropyran-4-yl-phenyl)-methyl-N-[(3S)-2-oxoazetidin-3-yl]-carbamate Step 1. Preparation of 4-phenyl-tetrahydropyran A stirred mixture of (S)-(+)-prolinol (0.414 g, 3.99 mmol), NiCl$_2$-glyme (0.449 g, 1.99 mmol), phenyl boronic acid (3.04 g, 24.98 mmol) and KHMDS (6.6 g, 33.3 mmol) was submitted to few cycles of vacuum/argon flow. i-PrOH (40 mL) was added and the resulting mixture was stirred at r.t. for 10 min, then 4-chlorotetrahydropyran (1.75 mL, 16.6 mmol) was added dropwise. The resulting yellowish mixture was heated at 65° C. for 50 h, then cooled at r.t., diluted with EtOAc (200 mL) and washed with 10% HCl solution (30 mL), sat. NaHCO$_3$ solution (30 mL×2) and brine (40 mL). The organic layer was dried over Na$_2$SO$_4$, filtered and concentrated to dryness to afford a solid crude (2.5 g). Purification by typical silica gel flash chromatography using a Teledyne ISCO apparatus (Cy/TBME from 100:0 to 80:20) afforded the pure title compound (1.29 g, 48%), as a liquid. R$_t$=2.36 min. $^1$H NMR (CDCl$_3$): δ 7.40-7.28 (m, 2H), 7.24-7.19 (m, 3H), 4.20-4.07 (m, 2H), 3.57 (td, 2H, J=11.5, 2.5 Hz), 2.80 (tt, 1H, J=11.5, 4.2 Hz), 1.94-1.75 (m, 4H).

Step 2. Preparation of methyl 4-tetrahydropyran-4-yl-benzoate

Under nitrogen atmosphere, oxalyl chloride (1.05 mL, 12.34 mmol) was added to a solution of 4-phenyl-tetrahydropyran (0.5 g, 3.09 mmol) in CH$_2$Cl$_2$ (20 mL) at −20° C. and stirred for 30 min. AlCl$_3$ (4.12 g, 30.86 mmol) was then added and stirring was maintained at the same temperature for 1 h and at r.t for additional 1 h. MeOH (4.4 mL) was slowly added at −20° C. and the mixture left stirring overnight. The reaction mixture was diluted with additional CH$_2$Cl$_2$ (60 mL), and sat. NaHCO$_3$ solution (20 mL). The aqueous layer was washed with EtOAc (40 mL) and the collected organic phases were additionally washed with brine (2×10 mL). The organic layers were dried over Na$_2$SO$_4$, filtered and concentrated giving the title compound (0.510, 75%), which was used without any further purification. R$_t$=2.26 min. $^1$H NMR (CDCl$_3$): δ 8.00 (d, 2H, J=8.3 Hz), 7.30 (d, 1H, J=8.3 Hz), 4.14-4.06 (m, 2 Hz), 3.92 (s, 3H), 3.55 (td, 2H, J=11.5, 2.6 Hz), 2.84 (tt, 1H, J=11.5, 4.6 Hz), 1.89-1.75 (m, 4H).

Step 3. Preparation of (4-tetrahydropyran-4-yl-phenyl)-methanol

Under nitrogen atmosphere, to a stirred and cooled (0° C.) suspension of LiAlH$_4$ (2.0 M THF solution, 6.35 mL, 12.7 mmol) in dry THF (30 mL), methyl 4-tetrahydropyran-4-yl-benzoate (0.70 g, 3.18 mmol) in dry THF (5.0 mL) was added dropwise. The resulting reaction mixture was stirred at r.t. for 4 h, and then cooled to 0° C. H$_2$O (5.0 mL) was slowly and cautiously added, followed by 3.0 M KOH solution (5.0 mL) and additional H$_2$O (0.5 mL). The mixture was stirred at 0° C. for 1 h and then filtered off. The organic layer was dried over Na$_2$SO$_4$, filtered and concentrated to dryness, affording a semi-solid crude (1.70 g). Purification by typical silica gel flash chromatography (Cy/TBME from 90:10 to 60:40) afforded the pure title compound (0.162 g, 27%) as a white solid. R$_t$=1.63 min. $^1$H NMR (DMSO-d$_6$): δ 7.24 (d, 2H, J=8.1 Hz), 7.19 (d, 2H, J=8.1 Hz), 5.05 (t, 1H, J=5.7 Hz), 4.45 (d, 2H, J=5.7 Hz), 3.95-3.92 (m, 2H), 3.45-3.39 (m, 2H), 2.82-2.64 (m, 1H), 1.73-1.57 (m, 4H).

Step 4. Preparation of 2-pyridyl-(4-tetrahydropyran-4-yl-phenyl)-methyl carbonate and (4-tetrahydropyran-4-yl-phenyl)-methyl-2-oxopyridine-1-carboxylate Under nitrogen atmosphere, to a stirred mixture of (4-tetrahydropyran-4-yl-phenyl)-methanol (0.16 g, 0.83 mmol) in dry CH$_2$Cl$_2$ (4.2 ml), DMAP (0.010 g, 0.08 mmol) and 2-DPC (0.22 g, 1.00 mmol) were added. The reaction mixture was stirred at r.t. for 16 h, then diluted with CH$_2$Cl$_2$ (10 ml) and sequentially washed with sat. NH$_4$Cl solution (2×15 ml) and sat. NaHCO$_3$ solution (2×15 ml). The organic layer was dried over Na$_2$SO$_4$, filtered and concentrated to dryness to afford an oily residue (0.27 g), as a mixture (1:2 ratio) of 2-pyridyl-(4-tetrahydropyran-4-yl-phenyl)-methyl carbonate and (4-tetrahydropyran-4-yl-phenyl)-methyl-2-oxopyridine-1-carboxylate. The mixture of isomers was not separated and used in the next step without any further purification. R$_t$=2.05 min; MS (ESI) m/z: 314 [M-H]$^+$.

Step 5. Preparation of (4-tetrahydropyran-4-yl-phenyl)-methyl-N-[(3S)-2-oxoazetidin-3-yl]-carbamate Under nitrogen atmosphere, to a suspension of [(3S)-2-oxoazetidin-3-yl]-ammonium acetate (0.04 g, 0.37 mmol) in dry CH$_2$Cl$_2$ (2.0 ml), DIPEA (0.06 ml, 0.44 mmol) was added dropwise. Subsequently, the crude mixture (0.27 g) containing (4-tetrahydropyran-4-yl-phenyl)-methyl-2-oxopyridine-1-carboxylate (116 mg, 0.37 mmol) in dry CH$_2$Cl$_2$ (2.0 ml) was added. The reaction mixture was stirred at r.t. for 16 h, then diluted with CH$_2$Cl$_2$ (10 ml) and washed with sat. NH$_4$Cl solution (2×20 ml) and sat. NaHCO$_3$ solution (2×20 ml). The organic layer was dried over Na$_2$SO$_4$ and concentrated to dryness giving a solid residue (0.130 g). Purification by typical silica gel flash chromatography (Cy/TBME from 30:70 to 0:100) afforded the pure title compound (0.049 g, 59%) as a white solid. R$_t$=1.38 min. MS (ESI) m/z: 305 [M-H]$^+$, 322 [M-NH$_4$]$^+$. $^1$H NMR (DMSO-d$_6$): δ 7.93 (s, 1H), 7.91 (s, 1H), 7.29 (d, 2H, J=8.2 Hz), 7.25 (d, 2H, J=8.2 Hz), 5.00 (s, 2H), 4.65 (m, 1H), 3.94

(dt, 2H, J=11.3, 3.1 Hz), 3.48-3.36 (m, 3H), 3.07 (dd, 1H, J=5.2, 2.8 Hz), 2.84-2.69 (m, 1H), 1.75-1.57 (m, 4H).

Example 67. (6-Phenyl-3-pyridyl)-methyl-N-[(3S)-2-oxoazetidin-3-yl]-carbamate

Step 1. Preparation of (6-phenyl-3-pyridyl)-methanol

Under nitrogen atmosphere, to a cooled (0° C.), stirred suspension of LiAlH$_4$ (2.0 M in THF, 5.02 mL, 10.05 mmol) in dry THF (45.0 mL), commercially available 6-phenylpyridine-3-carboxylic acid (0.5 g, 2.51 mmol) was added in one portion. The resulting mixture was stirred at r.t. for 2 h, then cooled to 0° C. and H$_2$O (0.35 mL) was slowly and cautiously added, followed by a 3.0 M KOH solution (0.35 mL) and additional H$_2$O (1.1 mL). The mixture was stirred at 0° C. for 1 h, filtered off and the organic phase dried over Na$_2$SO$_4$, filtered and concentrated to dryness giving a crude residue (0.402 g). Purification by typical silica gel flash chromatography (CH$_2$Cl$_2$/MeOH from 100:0 to 90:10) afforded the pure title compound (0.356 g, 77%), as a whitish solid. R$_t$=1.70 min. MS (ESI) m/z: 186 [M-H]$^+$. $^1$H NMR (DMSO-d$_6$): δ 8.63-8.59 (m, 1H), 8.07 (dd, 2H, J=7.4, 1.3 Hz), 7.93 (d, 1H, J=8.2 Hz), 7.81 (dd, 1H, J=8.2, 1.3 Hz), 7.52-7.45 (m, 2H), 7.45-3.39 (m, 1H), 5.34 (t, 1H, J=5.7 Hz), 4.58 (d, 2H, J=5.7 Hz).

Step 2. Preparation of (6-phenyl-3-pyridyl)-methyl-2-pyridyl carbonate and (6-phenyl-3-pyridyl)-methyl-2-oxopyridine-1-carboxylate Under nitrogen atmosphere, to a solution of (6-phenyl-3-pyridyl)-methanol (0.25 g, 1.35 mmol) in dry CH$_2$Cl$_2$ (14 mL), DMAP (0.016 g, 0.14 mmol) and 2-DPC (0.35 g, 1.62 mmol) were added. The reaction mixture was stirred at r.t. for 16 h, then diluted with CH$_2$Cl$_2$ (50 mL) and sequentially washed with sat. NH$_4$Cl solution (15 mL) and sat. NaHCO$_3$ solution (3×15 mL). The organic layer was dried over Na$_2$SO$_4$, filtered and concentrated to dryness affording an oily residue (0.41 g), as a mixture (1:1.9 ratio) of (6-phenyl-3-pyridyl)-methyl-2-pyridyl carbonate and (6-phenyl-3-pyridyl)-methyl-2-oxopyridine-1-carboxylate. The mixture of isomers was not separated and used in the next step without any further purification. R$_t$=2.10 min. MS (ESI) m/z: 307 [M-H]$^+$, 329 [M-Na]$^+$, 345 [M-K]$^+$.

Step 3. Preparation of (6-phenyl-3-pyridyl)-methyl-N-[(3S)-2-oxoazetidin-3-yl]-carbamate Under nitrogen atmosphere, to a suspension of [(3S)-2-oxoazetidin-3-yl]-ammonium acetate (0.05 g, 0.34 mmol) in dry CH$_2$Cl$_2$ (4.0 mL), DIPEA (0.067 mL, 0.41 mmol) was added dropwise. Subsequently, the crude mixture (0.302 g) containing (6-phenyl-3-pyridyl)-methyl-2-oxopyridine-1-carboxylate (0.104 g, 0.34 mmol) in dry CH$_2$Cl$_2$ (2.0 mL) was added. The reaction mixture was stirred at r.t. for 16 h, then concentrated to dryness giving a solid residue (0.17 g). Purification by preparative HPLC afforded the pure title compound (0.037 g, 37%), as a white solid. R$_t$=1.75 min. MS (ESI) m/z: 298 [M-H]$^+$, 320 [M-Na]$^+$, 336 [M+K]$^+$. MS (ESI) m/z: 296 [M-H]$^-$. $^1$H NMR (DMSO-d$_6$): δ 8.69-8.64 (bs, 1H), 8.11-8.06 (m, 2H), 8.03 (d, 1H, J=8.8 Hz), 7.98 (d, 1H, J=8.1 Hz), 7.95 (s, 1H), 7.87 (dd, 1H, J=8.1, 2.0 Hz), 7.53-7.42 (m, 3H), 5.12 (s, 2H), 4.67 (ddd, 1H, J=8.1, 5.5, 2.7 Hz), 3.40 (t, 1H, J=5.5 Hz), 3.09 (dd, 1H, J=5.5, 2.7 Hz).

Example 68. [4-(Cyclohexylcarbamoyl)-phenyl]-methyl-N-[(3S)-2-oxoazetidin-3-yl]-carbamate

Step 1. Preparation of N-cyclohexyl-4-(hydroxymethyl)-benzamide

To a stirred solution of commercially available 4-hydroxymethylbenzoic acid (0.200 g, 1.32 mmol), EDC (0.278 g, 1.45 mmol), dry Et$_3$N (0.403 mL, 2.89 mmol), HOBt (0.196 g, 1.45 mmol), DMAP (0.002 g, 0.01 mmol) in dry CH$_2$Cl$_2$ (8.0 mL), cyclohexylamine (0.224 mL, 1.97 mmol) was added in one portion. The resulting solution was stirred at r.t. for 16 h, and then sequentially washed with sat. NH$_4$Cl solution (2×5.0 mL) and sat. NaHCO$_3$ solution (10.0 mL). The organic layer was dried over Na$_2$SO$_4$, filtered and concentrated to dryness, giving a solid residue (0.263 g). Purification by typical silica gel flash chromatography (CH$_2$Cl$_2$/MeOH from 100:0 to 96:4) afforded the pure title compound (0.19 g, 83%), as a white solid. R$_t$=1.77 min. MS (ESI) m/z: 234 [M-H]$^+$, 256 [M-Na]$^+$, 272 [M-K]$^+$. $^1$H NMR (DMSO-d$_6$): δ 8.11 (d, 1H, J=8.0 Hz), 7.80 (d, 2H, J=8.3 Hz), 7.36 (d, 2H, J=8.3 Hz), 5.26 (t, 1H, J=5.7 Hz), 4.54 (d, 2H, J=5.7 Hz), 3.81-3.69 (m, 1H), 1.86-1.56 (m, 5H), 1.37-1.22 (m, 4H), 1.20-1.05 (m, 1H).

Step 2. Preparation of [4-(cyclohexylcarbamoyl)-phenyl]-methyl-2-pyridyl carbonate and [4-(cyclohexylcarbamoyl)-phenyl]-methyl-2-oxopyridine-1-carboxylate Under nitrogen atmosphere, to a solution of N-cyclohexyl-4-(hydroxymethyl)-benzamide (0.190 g, 0.82 mmol) in dry CH$_2$Cl$_2$ (12.0 mL), DMAP (0.01 g, 0.08 mmol) and 2-DPC (0.211 g, 0.98 mmol) were added. The reaction mixture was stirred at r.t. for 16 h, then diluted with CH$_2$Cl$_2$ (50 mL) and sequentially washed with sat. NH$_4$Cl solution (15 mL) and sat. NaHCO$_3$ solution (3×15 mL). The organic layer was dried over Na$_2$SO$_4$, filtered and concentrated to dryness affording an oily residue (0.29 g), as a mixture (1:1.6 ratio) of [4-(cyclohexylcarbamoyl)-phenyl]-methyl-2-pyridyl carbonate and [4-(cyclohexylcarbamoyl)-phenyl]-methyl-2-oxopyridine-1-carboxylate. The mixture of isomers was not separated and used in the next step without any further purification. R$_t$=2.11 min. MS (ESI) m/z: 355 [M-H]$^+$, 377 [M-Na]$^+$, 393 [M-K]$^+$. MS (ESI) m/z: 353 [M-H]$^-$.

Step 3. Preparation of [4-(cyclohexylcarbamoyl)-phenyl]-methyl-N-[(3S)-2-oxoazetidin-3-yl]-carbamate Under nitrogen atmosphere, to a suspension of [(3S)-2-oxoazetidin-3-yl]-ammonium acetate (0.040 g, 0.27 mmol) in dry CH$_2$Cl$_2$ (6.0 mL), DIPEA (0.053 mL, 0.32 mmol) was added dropwise. Subsequently, the crude mixture (0.24 g) containing [4-(cyclohexylcarbamoyl)-phenyl]-methyl-2-oxopyridine-1-carboxylate (0.093 g, 0.27 mmol) in dry CH$_2$Cl$_2$ (2.0 mL) was added. The reaction mixture was stirred at r.t. for 16 h, then concentrated to dryness giving a solid residue (0.31 g). Purification by preparative HPLC followed by trituration with Et$_2$O afforded the pure title compound (0.043 g, 45%), as a white solid. R$_t$=1.81 min. MS (ESI) m/z: 346 [M-H]$^+$, 368 [M-Na]$^+$, 384 [M-K]$^+$. MS (ESI) m/z: 344 [M-H]$^-$. $^1$H NMR (DMSO-d$_6$): δ 8.16 (d, 1H, J=8.0 Hz), 8.02 (d, 1H, J=8.7 Hz), 7.94 (s, 1H), 7.82 (d, 2H, J=8.2 Hz), 7.40 (d, 2H, J=8.2 Hz), 5.08 (s, 2H), 4.66 (ddd, 1H, J=8.5, 5.5, 2.7 Hz), 3.81-3.68 (m, 1H), 3.40 (t, 1H, J=5.5

Hz), 3.08 (dd, 1H, J=5.5, 2.7 Hz), 1.87-1.68 (m, 4H), 1.65-1.56 (m, 1H), 1.37-1.23 (m, 4H), 1.20-1.05 (m, 1H).

Example 69. [4-(Piperidine-1-carbonyl)-phenyl]-methyl-N-[(3S)-2-oxoazetidin-3-yl]-carbamate Step 1. Preparation of [4-(hydroxymethyl)-phenyl]-(1-piperidyl)-methanone To a stirred solution of commercially available 4-hydroxymethylbenzoic acid (0.200 g, 1.32 mmol), EDC (0.278 g, 1.45 mmol), dry Et$_3$N (0.403 mL, 2.89 mmol), HOBt (0.196 g, 1.45 mmol), DMAP (0.002 g, 0.01 mmol) in dry CH$_2$Cl$_2$ (8.0 mL), piperidine (0.195 mL, 1.97 mmol) was added in one portion. The resulting solution was stirred at r.t. for 16 h, and then sequentially washed with sat. NH$_4$Cl solution (2×5.0 mL) and sat. NaHCO$_3$ solution (10.0 mL). The organic layer was dried over Na$_2$SO$_4$, filtered and concentrated to dryness, giving a solid residue (0.242 g). Purification by typical silica gel flash chromatography (CH$_2$Cl$_2$/MeOH from 100:0 to 96:4) afforded the title compound (0.174 g, 60%), as a white solid. R$_t$=1.54 min. MS (ESI) m/z: 220 [M-H]$^+$, 242 [M-Na]$^+$, 258 [M-K]$^+$. $^1$H NMR (DMSO-d$_6$): δ 7.37 (d, 1H, J=8.1 Hz), 7.31 (d, 2H, J=8.1 Hz), 5.24 (t, 1H, J=5.7 Hz), 4.53 (d, 2H, J=5.7 Hz), 3.71-3.11 (m, 4H), 1.66-1.36 (m, 6H).

Step 2. Preparation of [4-(piperidine-1-carbonyl)-phenyl]-methyl-2-pyridyl carbonate and [4-(piperidine-1-carbonyl)-phenyl]-methyl-2-oxopyridine-1-carboxylate Under nitrogen atmosphere, to a solution of [4-(hydroxymethyl)-phenyl]-(1-piperidyl)-methanone (0.174 g, 0.79 mmol) in dry CH$_2$Cl$_2$ (11 mL), DMAP (0.01 g, 0.08 mmol) and 2-DPC (0.206 g, 0.95 mmol) were added. The reaction mixture was stirred at r.t. for 16 h, then diluted with CH$_2$Cl$_2$ (50 mL) and sequentially washed with sat. NH$_4$Cl solution (15 mL) and sat. NaHCO$_3$ solution (3×15 mL). The organic layer was dried over Na$_2$SO$_4$, filtered and concentrated to dryness affording an oily residue (0.27 g), as a mixture (1:1.6 ratio) of [4-(piperidine-1-carbonyl)-phenyl]-methyl-2-pyridyl carbonate and [4-(piperidine-1-carbonyl)-phenyl]-methyl-2-oxopyridine-1-carboxylate. The mixture of isomers was not separated and used in the next step without any further purification. R$_t$=1.89 min. MS (ESI) m/z: 341 [M-H]$^+$, 363 [M-Na]$^+$, 379 [M-K]$^+$.

Step 3. Preparation of [4-(piperidine-1-carbonyl)-phenyl]-methyl-N-[(3S)-2-oxoazetidin-3-yl]-carbamate Under nitrogen atmosphere, to a suspension of [(3S)-2-oxoazetidin-3-yl]-ammonium acetate (0.036 g, 0.25 mmol) in dry CH$_2$Cl$_2$ (6.0 mL), DIPEA (0.049 mL, 0.30 mmol) was added dropwise. Subsequently, the crude mixture (0.221 g) containing [4-(piperidine-1-carbonyl)-phenyl]-methyl-2-oxopyridine-1-carboxylate (0.085 g, 0.25 mmol) in dry CH$_2$Cl$_2$ (2.0 mL) was added. The reaction mixture was stirred at r.t. for 16 h, then concentrated to dryness giving a solid residue (0.33 g). Purification by preparative HPLC followed by trituration with a 20:1 mixture of Et$_2$O/MeOH afforded the pure title compound (0.021 g, 25%), as a white sticky solid. R$_t$=1.59 min. MS (ESI) m/z: 332 [M-H]$^+$, 354 [M-Na]$^+$, 370 [M-K]$^+$. MS (ESI) m/z: 330 [M-H]$^-$. $^1$H NMR (DMSO-d$_6$): δ 8.01 (d, 1H, J=8.7 Hz), 7.94 (s, 1H), 7.40 (d, 2H, J=8.1 Hz), 7.36 (d, 2H, J=8.1 Hz), 5.07 (s, 2H), 4.67 (ddd, 1H, J=8.3, 5.5, 2.8 Hz), 3.66-3.47 (m, 4H), 3.40 (t, 1H, J=5.5 Hz), 3.08 (dd, 1H, J=5.5, 2.8 Hz), 1.65-1.37 (m, 6H).

Example 70. [4-(Benzylcarbamoyl)-phenyl]-methyl-N-[(3S)-2-oxoazetidin-3-yl]-carbamate Step 1. Preparation of N-benzyl-4-(hydroxymethyl)-benzamide To a stirred solution of commercially available 4-hydroxymethylbenzoic acid (0.200 g, 1.32 mmol), EDC (0.278 g, 1.45 mmol), dry Et$_3$N (0.403 mL, 2.89 mmol), HOBt (0.196 g, 1.45 mmol), DMAP (0.002 g, 0.01 mmol) in dry CH$_2$Cl$_2$ (8.0 mL), benzylamine (0.215 mL, 1.97 mmol) was added in one portion. The resulting solution was stirred at r.t. for 16 h, and then sequentially washed with sat. NH$_4$Cl solution (2×5.0 mL) and sat. NaHCO$_3$ solution (10.0 mL). The organic layer was dried over Na$_2$SO$_4$, filtered and concentrated to dryness, giving a solid residue (0.258 g). Purification by typical silica gel flash chromatography (CH$_2$Cl$_2$/MeOH from 100:0 to 96:4) afforded the title compound (0.142 g, 43%), as a white solid. $^1$H NMR (DMSO-d$_6$): δ 8.98 (t, 1H, J=6.0 Hz), 7.86 (d, 2H, J=8.1 Hz), 7.40 (d, 2H, J=8.1 Hz), 7.34-7.20 (m, 5H), 5.29 (t, 1H, J=5.7 Hz), 4.60-4.51 (m, 2H), 4.48 (d, 2H, J=5.7 Hz).

Step 2. Preparation of [4-(benzylcarbamoyl)-phenyl]-methyl-2-pyridyl carbonate and [4-(benzylcarbamoyl)-phenyl]-methyl-2-oxopyridine-1-carboxylate Under nitrogen atmosphere, to a solution of N-benzyl-4-(hydroxymethyl)-benzamide (0.142 g, 0.59 mmol) in dry CH$_2$Cl$_2$ (7.0 mL), DMAP (0.007 g, 0.06 mmol) and 2-DPC (0.153 g, 0.71 mmol) were added. The reaction mixture was stirred at r.t. for 16 h, then diluted with CH$_2$Cl$_2$ (50 mL) and sequentially washed with sat. NH$_4$Cl solution (15 mL) and sat. NaHCO$_3$ solution (3×15 mL). The organic layer was dried over Na$_2$SO$_4$, filtered and concentrated to dryness affording an oily residue (0.145 g), as a mixture (1:1.2 ratio) of [4-(benzylcarbamoyl)-phenyl]-methyl-2-pyridyl carbonate and [4-(benzylcarbamoyl)-phenyl]-methyl-2-oxopyridine-1-carboxylate. The mixture of isomers was not separated and used in the next step without any further purification. R$_t$=2.0 min. MS (ESI) m/z: 364 [M-H]$^+$, 386 [M-Na]$^+$, 401 [M-K]$^+$. MS (ESI) m/z: 361 [M-H]$^-$.

Step 3. Preparation of [4-(benzylcarbamoyl)-phenyl]-methyl-N-[(3S)-2-oxoazetidin-3-yl]-carbamate Under nitrogen atmosphere, to a suspension of [(3S)-2-oxoazetidin-3-yl]-ammonium acetate (0.03 g, 0.21 mmol) in dry CH$_2$Cl$_2$ (6.0 mL), DIPEA (0.042 mL, 0.25 mmol) was added dropwise. Subsequently, the crude mixture (0.167 g) containing [4-(benzylcarbamoyl)-phenyl]-methyl-2-oxopyridine-1-carboxylate (0.076 g, 0.21 mmol) in dry CH$_2$Cl$_2$ (2.0 mL) was added. The reaction mixture was stirred at r.t. for 16 h, then concentrated to dryness giving a solid residue (0.334 g). Purification by preparative HPLC followed by trituration with Et$_2$O afforded the pure title compound (0.036 g, 49%), as a white solid. R$_t$=1.71 min. MS (ESI) m/z: 354 [M-H]$^+$, 376 [M-Na]$^+$, 392 [M-K]$^+$. MS (ESI) m/z: 352 [M-H]$^-$. $^1$H NMR (DMSO-d$_6$): δ 9.03 (t, 1H, J=6.0 Hz), 8.03 (d, 1H, J=8.7 Hz), 7.94 (s, 1H), 7.89 (d, 2H, J=8.2 Hz), 7.44 (d, 2H, J=8.2 Hz), 7.35-7.29 (m, 4H), 7.27-7.21 (m, 1H), 5.10 (s, 2H), 4.69-4.63 (m, 1H), 4.48 (d, 2H, J=6.0 Hz), 3.40 (t, 1H, J=5.3 Hz), 3.09 (dd, 1H, J=5.3, 2.8 Hz).

Example 71. [4-(2-Fluorophenyl)-phenyl]-methyl-N-[(3S)-2-oxoazetidin-3-yl]-carbamate Step 1. Preparation of [4-(2-fluorophenyl)-phenyl]-methanol Under nitrogen atmosphere, to a stirred and cooled (0° C.) suspension of $LiAlH_4$ (2.0 M THF solution, 5.08 mL, 10.16 mmol) in dry THF (22 mL), commercially available 4-(2-fluorophenyl)-benzoic acid (0.55 g, 2.54 mmol) in dry THF (5.0 mL) was added dropwise. The resulting reaction mixture was stirred at r.t. for 4 h, and then cooled to 0° C. $H_2O$ (0.3 mL) was slowly added, followed by 3.0 M KOH solution (0.3 mL) and additional $H_2O$ (0.3 mL). The mixture was stirred at 0° C. for 1 h and then filtered off. The organic layer was dried over $Na_2SO_4$, filtered and concentrated to dryness, affording the title compound (0.43 g, 85%), which was used in the next step without any further purification. $R_t$=2.26 min. $^1H$ NMR (DMSO-$d_6$): δ 7.54-7.47 (m, 1H), 7.45-7.36 (m, 5H), 7.30-7.23 (m, 2H), 4.59 (s, 2H).

Step 2. Preparation of [4-(2-fluorophenyl)-phenyl]-methyl-2-pyridyl carbonate and of [4-(2-fluorophenyl)-phenyl]-methyl-2-oxopyridine-1-carboxylate Under nitrogen atmosphere, to a stirred solution of [4-(2-fluorophenyl)-phenyl]-methanol (0.30 g, 1.48 mmol) in dry $CH_2Cl_2$ (8.0 mL), DMAP (0.018 g, 0.15 mmol) and 2-DPC (0.38 g, 1.77 mmol) were added. The reaction mixture was stirred at r.t. for 16 h, then diluted with $CH_2Cl_2$ and sequentially washed with sat. $NH_4Cl$ solution (20 mL), sat. $NaHCO_3$ solution (3×20 mL) and brine (10 mL). The organic layer was dried over $Na_2SO_4$, filtered and concentrated to dryness affording a grey oil (0.34 g), as a mixture (1:2 ratio) of [4-(2-fluorophenyl)-phenyl]-methyl-2-pyridyl carbonate and of [4-(2-fluorophenyl)-phenyl]-methyl-2-oxopyridine-1-carboxylate. The mixture of isomers was not separated and used in the next step without any further purification. $R_t$=2.55 min. MS (ESI) m/z: 324 [M-H]$^+$, 346 [M–Na]$^+$, 362 [M–K]$^+$.

Step 3. Preparation of [4-(2-fluorophenyl)-phenyl]-methyl-N-[(3S)-2-oxoazetidin-3-yl]-carbamate Under nitrogen atmosphere, to a suspension of [(3S)-2-oxoazetidin-3-yl]-ammonium acetate (0.060 g, 0.41 mmol) in dry $CH_2Cl_2$ (4.0 mL), DIPEA (0.080 mL, 0.49 mmol) was added dropwise. Subsequently, the crude mixture (0.396 g) containing [4-(2-fluorophenyl)-phenyl]-methyl-2-oxopyridine-1-carboxylate (0.132 g, 0.41 mmol) in dry $CH_2Cl_2$ (2.0 mL) was added. The reaction mixture was stirred at r.t. for 16 h, then diluted with $CH_2Cl_2$ (60 mL) and sequentially washed with sat. $NH_4Cl$ solution (10 mL), sat. $NaHCO_3$ solution (3×10 mL) and brine (10 mL). The organic layer was dried over $Na_2SO_4$ and concentrated to dryness giving a solid residue (0.2 g). Purification by silica gel flash chromatography using a Teledyne ISCO apparatus (Cy/AcOEt from 90:10 to 0:100) afforded the pure title compound (0.03 g, 31%), as a white solid. $R_t$=2.18 min. MS (ESI) m/z: 315 [M-H]$^+$, 332 [M-$NH_4$]$^+$, 337 [M–Na]$^+$, 353 [M–K]$^+$. $^1H$ NMR (DMSO-$d_6$): δ 8.01 (d, 1H, J=8.5 Hz), 7.94 (s, 1H), 7.58-7.50 (m, 3H), 7.47-7.39 (m, 3H), 7.35-7.27 (m, 2H), 5.10 (s, 2H), 4.68 (ddd, 1H, J=8.5, 5.3, 2.7 Hz), 3.41 (t, 1H, J=5.3 Hz), 3.10 (dd, 1H, J=5.3, 2.7 Hz).

Preparation of [(2S,3S)-2-methyl-4-oxo-azetidin-3-yl]-ammonium toluene-4-sulfonate Step 1. Preparation of benzyl-N-[(1S,2R)-2-hydroxy-1-(methoxycarbamoyl)-propyl]-carbamate To a suspension of commercially available N-carbobenzyloxy-L-threonine (3.39 g, 13.4 mmol) in dry THF (100 mL), methoxyamine hydrochloride (3.26 g, 40.2 mmol), EDC (7.7 g, 40.2 mmol) and $H_2O$ (30 mL) were sequentially added. The biphasic solution was stirred at r.t. for 3 h, and then sat. NaCl solution was added. The crude mixture was extracted with EtOAc (4×100 mL) and the combined organic extracts were dried over $Na_2SO_4$ and concentrated to dryness to afford a solid residue (3.60 g), as a mixture (75:25 ratio) of the title compound and unreacted starting material, which was used in the next step without any further purification. $R_t$=1.50 min; MS (ESI) m/z: 283 [M-H]$^+$; 305 [M–Na]$^+$; (ESI) m/z: 281 [M-H]$^-$. $^1H$ NMR (DMSO-$d_6$): δ 11.19 (s, 1H), 7.42-7.27 (m, 5H), 7.02 (d, 1H, J=8.5 Hz), 5.05 (d, 1H, J=12.0 Hz), 5.01 (d, 1H, J=12.0 Hz), 3.91-3.78 (m, 1H), 3.74 (dd, 1H, J=8.5, 5.3 Hz), 3.57 (s, 3H), 1.04 (d, 3H, J=6.3 Hz).

Step 2. Preparation of [(1S,2R)-2-(benzyloxycarbonylamino)-3-(methoxyamino)-1-methyl-3-oxo-propyl]-methanesulfonate The crude mixture (3.40 g) containing benzyl-N-[(1S,2R)-2-hydroxy-1-(methoxycarbamoyl)-propyl]-carbamate (2.64 g, 7.34 mmol) was dissolved in dry pyridine (30 mL) and cooled to −5° C. Methanesulfonyl chloride (1.62 g, 14.68 mmol) was added over a period of 15 min, the mixture was stirred for 3 h at 0° C., and then poured into iced $H_2O$ (50 mL). The aqueous solution was adjusted to pH 4 with 2.0 N HCl solution, washed with sat. NaCl solution and extracted with EtOAc (4×20 mL). The combined organic layer was dried over $Na_2SO_4$ and concentrated to dryness to afford a solid residue which was purified by column chromatography using a Teledyne ISCO apparatus (Cy/TBME from 100:0 to 0:100) to afford the pure title compound (2.38 g, 73%), as white solid. $R_t$=1.78 min; MS (ESI) m/z: 361 [M-H]$^+$, 399 [M–K]$^+$, (ESI) m/z: 359 [M-H]$^-$. $^1H$ NMR (DMSO-$d_6$): δ 11.55 (s, 1H), 7.77 (d, 1H, J=9.41 Hz), 7.47-7.25 (m, 5H), 5.07 (q, 2H, J=12.60 Hz), 4.83 (t, 1H, J=6.34 Hz), 4.14 (dd, 1H, J=9.41, 6.34 Hz), 3.60 (s, 3H), 3.09 (s, 3H), 1.31 (d, 3H, J=6.34 Hz).

Step 3. Preparation of benzyl-N-[(2S,3S)-1-methoxy-2-methyl-4-oxo-azetidin-3-yl]-carbamate To a refluxing (90° C.) slurry of powdered $K_2CO_3$ (2.44 g, 17.67 mmol) in acetone (100 mL), a solution of [(1S,2R)-2-(benzyloxycarbonylamino)-3-(methoxyamino)-1-methyl-3-oxo-propyl]-methanesulfonate (1.59 g, 4.42 mmol) in acetone (60 mL) was added. The resulting suspension was stirred at 100° C. for 3 h. Upon cooling, the thick slurry was filtered through celite, and the collected solid was extracted with EtOAc (50 mL). After being washed sequentially with 1.0 N HCl solution (60 mL), sat. $NaHCO_3$ solution (60 mL) and brine (60 mL), the organic solution was dried over $Na_2SO_4$ and concentrated to dryness. The crude product was purified using a Teledyne ISCO apparatus (Cy/TBME from 100:0 to 20:80) to afford the pure title compound (0.91 g, 78%). $R_t$=1.94 min; MS (ESI) m/z: 265 [M–H]$^+$, 287 [M–Na]$^+$. $^1$H NMR (DMSO-d$_6$): δ 8.03 (d, 1H, J=8.12 Hz), 7.45-7.29 (m, 5H), 5.06 (s, 2H), 4.09 (dd, 1H, J=8.12, 2.06 Hz), 3.95-3.84 (m, 1H), 3.74 (s, 3H), 1.39-1.29 (m, 3H).

Step 4. Preparation of benzyl-N-[(2S,3S)-2-methyl-4-oxo-azetidin-3-yl]-carbamate To a stirred mixture of benzyl-N-[(2S,3S)-1-methoxy-2-methyl-4-oxo-azetidin-3-yl]-carbamate (1.07 g, 4.0 mmol) in dry THF (25 mL), a 0.5 M solution of SmI$_2$ in THF (162 mL, 15.2 mmol) was dropwise added via cannula. The reaction mixture was left to stir at r.t. for 30 min until complete disappearance of starting material. The crude mixture was diluted with EtOAc and washed twice with a 10% Na$_2$S$_2$O$_3$ solution and brine. The organic fraction was dried over Na$_2$SO$_4$, filtered and concentrated to dryness to give a crude product. Purification by column chromatography using a Teledyne ISCO apparatus (Cy/MTBE from 100:0 to 0:100) afforded the pure title compound (0.57 g, 60%), as a white sticky solid. $R_t$=1.67 min. $^1$H NMR (DMSO-d$_6$): δ 8.08 (s, 1H), 7.96 (d, 1H, J=8.6 Hz), 7.42-7.28 (m, 5H), 5.05 (d, 1H, J=12.2 Hz), 5.01 (d, 1H, J=12.2 Hz), 4.11 (dd, 1H, J=8.6, 2.3 Hz), 3.56-3.48 (m, 1H), 1.24 (d, 3H, J=6.1 Hz).

Step 5. Preparation of [(2S,3S)-2-methyl-4-oxo-azetidin-3-yl]-ammonium toluene-4-sulfonate To a stirred mixture of benzyl-N-[(2S,3S)-2-methyl-4-oxo-azetidin-3-yl]-carbamate (0.44 g, 1.90 mmol) in EtOH (37 mL), previously submitted to few cycles of vacuum/argon flow, commercially available cyclohexadiene (1.79 mL, 18.99 mmol) and 10% Pd on charcoal (0.44 g) were added. The reaction mixture was left to react at r.t. for 2 h, diluted with EtOAc and filtered over a pad of Celite into a p-TsOH (0.38 g, 1.99 mmol) solution in EtOAc (37 mL). The solution was concentrated to dryness to give the pure title compound (0.54 g, quant.), as a white fluffy solid. $^1$H NMR (DMSO-d$_6$): δ 8.61 (s, 3H), 8.56 (s, 1H), 7.49 (d, 2H, J=7.9 Hz), 7.12 (d, 2H, J=7.9 Hz), 4.01 (s, 1H), 3.65-3.58 (m, 1H), 2.29 (s, 3H), 1.29 (d, 3H, J=6.1 Hz).

Preparation of [(2R,3S)-2-methyl-4-oxo-azetidin-3-yl]-ammonium toluene-4-sulfonate Step 1. Preparation of (2S,3S)-2-(benzyloxycarbonylamino)-3-hydroxy-butanoic acid To a stirred mixture of commercially available L-allo-threonine (1.0 g, 8.4 mmol) and a sat. NaHCO$_3$ solution (10 mL) in THF (10 mL), at 0° C., benzyl chloroformiate (1.08 mL, 7.56 mmol) was dropwise added. The reaction mixture was left to react at 0° C. for 2 h and subsequently diluted with H$_2$O and extracted with Et$_2$O (3×20 mL). The aqueous phase was acidified to pH of 2-3 with a 2.0 M HCl solution and extracted again with EtOAc (3×20 mL). The organics were dried over Na$_2$SO$_4$ and concentrated to dryness to afford the title compound (1.8 g, 85%), which was used in the next step without any further purification. $R_t$=1.16 min; MS (ESI) m/z: 254 [M–H]$^+$, 276 [M–Na]$^+$, 292 [M–K]$^+$. $^1$H NMR (DMSO-d$_6$): δ 7.42-7.27 (m, 6H), 5.04 (s, 2H), 3.99-3.86 (m, 2H), 1.09 (d, 3H, J=6.3 Hz).

Step 2. Preparation of benzyl-N-[(1S,2S)-2-hydroxy-1-(methoxycarbamoyl)-propyl]-carbamate The title compound was prepared in an analogous manner as for its (1S,2R)-isomer [step 1], starting from (2S,3S)-2-(benzyloxycarbonylamino)-3-hydroxy-butanoic acid (1.81 g, 7.15 mmol). A mixture (75:25 ratio) containing the title compound and unreacted starting material (1.82 g) was afforded and used in the next step without further purification. $R_t$=1.48 min; MS (ESI) m/z: 283 [M–H]$^+$, 305 [M–Na]$^+$, 321 [M–K]$^+$; (ESI) m/z: 281 [M–H]$^-$. $^1$H NMR (DMSO-d$_6$): δ 11.11 (s, 1H), 7.41-7.26 (m, 6H), 5.03 (s, 2H), 4.92 (d, 1H, J=5.20 Hz), 3.86-3.73 (m, 1H), 3.68 (t, 1H, J=8.29 Hz), 3.56 (s, 3H), 1.05 (d, 3H, J=6.19 Hz).

Step 3. Preparation of [(1S,2S)-2-(benzyloxycarbonylamino)-3-(methoxyamino)-1-methyl-3-oxo-propyl]-methanesulfonate The title compound was prepared in an analogous manner as for its (1S,2R)-isomer [step 2], starting from the crude mixture (1.82 g) containing benzyl-N-[(1S,2S)-2-hydroxy-1-(methoxycarbamoyl)-propyl]-carbamate (1.40 g, 4.96 mmol). The crude product was purified by column chromatography using a Teledyne ISCO apparatus (Cy/MTBE from 100:0 to 0:100) to give the pure title compound (1.71 g, 96%), as a white solid. $R_t$=1.78 min; MS (ESI) m/z: 361 [M–H]$^+$, 378 [M–NH$_4$]$^+$. $^1$H NMR (DMSO-d$_6$): δ 11.56 (s, 1H), 7.82 (d, 1H, J=9.19 Hz), 7.42-7.27 (m, 5H), 5.06 (s, 2H), 4.83 (p, 1H, J=6.40 Hz), 4.15 (dd, 1H, J=9.19, 6.40 Hz), 3.59 (s, 3H), 3.10 (s, 3H), 1.32 (d, 3H, J=6.40 Hz).

Step 4. Preparation of benzyl-N-[(2R,3S)-1-methoxy-2-methyl-4-oxo-azetidin-3-yl]-carbamate The title compound was prepared in an analogous manner as for its (2S,3S)-isomer [step 3], starting from [(1S,2S)-2-(benzyloxycarbonylamino)-3-(methoxyamino)-1-methyl-3-oxo-propyl]-methanesulfonate (1.10 g, 3.05 mmol). The crude product was purified by column chromatography using a Teledyne ISCO apparatus (Cy/MTBE from 100:0 to 0:100) to give the pure title compound (0.62 g, 77%), as a white solid. $R_t$=1.91 min; MS (ESI) m/z: 265 [M–H]$^+$, 287 [M–Na]$^+$, 303 [M–K]$^+$. $^1$H NMR (DMSO-d$_6$): δ 8.06 (d, 1H, J=9.12 Hz), 7.43-7.27 (m, 5H), 5.06 (d, 2H, J=3.67 Hz), 4.73 (dd, 1H, J=9.12, 5.11 Hz), 4.25-4.13 (m, 1H), 3.71 (s, 3H), 1.14 (d, 3H, J=6.17 Hz).

Step 5. Preparation of benzyl-N-[(2R,3S)-2-methyl-4-oxo-azetidin-3-yl]-carbamate The title compound was prepared in an analogous manner as for its (2S,3S)-isomer [step 4], starting from benzyl-N-[(2R,3S)-1-methoxy-2-methyl-4-oxo-azetidin-3-yl]-carbamate (0.43 g, 1.61 mmol). The crude product was purified by column chromatography using a Teledyne ISCO apparatus (Cy/MTBE from 100:0 to 0:100) to give the pure title compound (0.18 g, 48%), as a white solid. $R_t$=1.66 min; MS (ESI) m/z: 235 [M–H]$^+$, 257 [M–Na]$^+$, 273 [M–K]$^+$. $^1$H NMR (DMSO-d$_6$): δ 8.13 (s, 1H), 8.04 (d, 1H, J=9.55 Hz), 7.42-7.27 (m, 5H), 5.12-4.99 (m, 2H), 4.80 (dd, 1H, J=9.55, 4.98 Hz), 3.81-3.70 (m, 1H), 1.07 (d, 3H, J=6.24 Hz).

Step 6. Preparation of [(2R,3S)-2-methyl-4-oxo-azetidin-3-yl]-ammonium toluene-4-sulfonate The title compound was prepared in an analogous manner as for its (2S,3S)-isomer [step 5], starting from benzyl-N-[(2R,3S)-2-methyl-4-oxo-azetidin-3-yl]-carbamate (0.16 g, 0.66 mmol). Trituration with Et$_2$O gave the pure title compound (0.18 g, quant.), as a fluffy white solid. $^1$H NMR (DMSO-d$_6$): δ 8.72-8.42 (m, 4H), 7.51-7.43 (m, 2H), 7.11

(d, 2H, J=7.85 Hz), 4.46 (s, 1H), 3.93-3.82 (m, 1H), 2.29 (s, 3H), 1.26 (d, 3H, J=6.42 Hz).

Preparation of [(2R,3R)-2-methyl-4-oxo-azetidin-3-yl]-ammonium toluene-4-sulfonate Step 1. Preparation of benzyl-N-[(1R,2S)-2-hydroxy-1-(methoxycarbamoyl)-propyl]-carbamate The title compound was prepared in an analogous manner as for its (1S,2R)-enantiomer [step 1], starting from N-carbobenzyloxy-D-threonine (2.54 g, 10 mmol). The crude solid residue (3.6 g), as a mixture (75:25 ratio) of the title compound and unreacted starting material, was used in the next step without any further purification. $R_t$=1.50 min; MS (ESI) m/z: 283 [M-H]$^+$, 305 [M-Na]$^+$, 321 [M-K]$^+$. $^1$H NMR (DMSO-d$_6$): δ 11.19 (s, 1H), 7.42-7.27 (m, 5H), 7.02 (d, 1H, J=8.5 Hz), 5.05 (d, 1H, J=12.0 Hz), 5.01 (d, 1H, J=12.0 Hz), 3.91-3.78 (m, 1H), 3.74 (dd, 1H, J=8.5, 5.3 Hz), 3.57 (s, 3H), 1.04 (d, 3H, J=6.3 Hz).

Step 2. Preparation of [(1R,2S)-2-(benzyloxycarbonylamino)-3-(methoxyamino)-1-methyl-3-oxo-propyl]-methanesulfonate The title compound was prepared in an analogous manner as for its (1S,2R)-enantiomer [step 2], starting from the crude mixture (2.89 g) containing benzyl-N-[(1R,2S)-2-hydroxy-1-(methoxycarbamoyl)-propyl]-carbamate (2.17 g, 7.69 mmol). The crude product was purified by column chromatography using a Teledyne ISCO apparatus (Cy/MTBE from 100:0 to 0:100) to give the pure title compound (1.9 g, 68%), as a white solid. $R_t$=1.81 min; MS (ESI) m/z: 361 [M-H]$^+$, 399 [M-K]$^+$. $^1$H NMR (DMSO-d$_6$): δ 11.55 (s, 1H), 7.77 (d, 1H, J=9.4 Hz), 7.44-7.27 (m, 5H), 5.10 (d, 1H, J=12.5 Hz), 5.04 (d, 1H, J=12.5 Hz), 4.83 (p, 1H, J=6.3 Hz), 4.14 (dd, 1H, J=9.4, 6.3 Hz), 3.60 (s, 3H), 3.09 (s, 3H), 1.31 (d, 3H, J=6.3 Hz).

Step 3. Preparation of benzyl-N-[(2R,3R)-1-methoxy-2-methyl-4-oxo-azetidin-3-yl]-carbamate The title compound was prepared in an analogous manner as for its (2S,3S)-enantiomer [step 3], starting from [(1R,2S)-2-(benzyloxycarbonylamino)-3-(methoxyamino)-1-methyl-3-oxo-propyl]-methanesulfonate (1.9 g, 5.28 mmol). The crude product was purified by column chromatography using a Teledyne ISCO apparatus (Cy/MTBE from 100:0 to 0:100) to give the pure title compound (0.82 g, 66%), as a white solid. $R_t$=1.92 min; MS (ESI) m/z: 265 [M-H]$^+$, 287 [M-Na]$^+$, 303 [M-K]$^+$. $^1$H NMR (DMSO-d$_6$): δ 8.01 (d, 1H, J=8.1 Hz), 7.44-7.27 (m, 5H), 5.05 (s, 2H), 4.07 (d, 1H, J=8.1 Hz), 3.89 (q, 1H, J=6.1 Hz), 3.73 (s, 3H), 1.34 (d, 3H, J=6.1 Hz).

Step 4. Preparation of benzyl-N-[(2R,3R)-2-methyl-4-oxo-azetidin-3-yl]-carbamate The title compound was prepared in an analogous manner as for its (2S,3S)-enantiomer [step 4], starting from benzyl-N-[(2R,3R)-1-methoxy-2-methyl-4-oxo-azetidin-3-yl]-carbamate (0.82 g, 3.09 mmol). The crude product was purified by column chromatography using a Teledyne ISCO apparatus (Cy/MTBE from 100:0 to 0:100) to give the pure title compound (0.47 g, 65%), as a sticky solid. $R_t$=1.67 min; MS (ESI) m/z: 235 [M-H]$^+$, 257 [M-Na]$^+$, 273 [M-K]$^+$. $^1$H NMR (DMSO-d$_6$): δ 8.08 (s, 1H), 7.96 (d, 1H, J=8.7 Hz), 7.43-7.28 (m, 5H), 5.10 (d, 1H, J=12.5 Hz), 5.04 (d, 1H, J=12.5 Hz), 4.11 (dd, 1H, J=8.7, 2.3 Hz), 3.52 (dq, 1H, J=6.1, 2.3 Hz), 1.25 (d, 3H, J=6.1 Hz).

Step 5. Preparation of [(2R,3R)-2-methyl-4-oxo-azetidin-3-yl]-ammonium toluene-4-sulfonate The pure title compound was prepared in an analogous manner as for its (2S,3S)-enantiomer [step 5], starting from benzyl-N-[(2R,3R)-2-methyl-4-oxo-azetidin-3-yl]-carbamate (0.44 g, 1.90 mmol). Trituration with Et$_2$O gave the pure title compound (0.54 g, quant.), as a fluffy white solid. $^1$H NMR (DMSO-d$_6$): δ 8.72-8.49 (m, 4H), 7.48 (d, 2H, J=8.1 Hz), 7.12 (d, 2H, J=7.9 Hz), 4.02 (s, 1H), 3.65-3.56 (m, 1H), 2.29 (s, 3H), 1.30 (d, 3H, J=6.2 Hz).

Preparation of [(2S,3R)-2-methyl-4-oxo-azetidin-3-yl]-ammonium toluene-4-sulfonate Step 1. Preparation of (2R,3R)-2-(benzyloxycarbonylamino)-3-hydroxy-butanoic acid The title compound was prepared in an analogous manner as for its (2S,3S)-enantiomer [step 1], starting from D-allo-threonine (1.60 g, 13.43 mmol). The crude product, containing the title compound (3.39 g, quant.), was used in the next step without any further purification. $R_t$=1.78 min; MS (ESI) m/z: 254 [M-H]$^+$, 276 [M-Na]$^+$, 292 [M-K]$^+$; (ESI) m/z: 252 [M-H]$^-$. $^1$H NMR (DMSO-d$_6$): δ 13.83-11.43 (m, 1H), 7.42-7.28 (m, 6H), 5.03 (s, 2H), 4.00-3.84 (m, 2H), 1.08 (d, 3H, J=6.26 Hz).

Step 2. Preparation of benzyl-N-[(1R,2R)-2-hydroxy-1-(methoxycarbamoyl)-propyl]-carbamate The title compound was prepared in an analogous manner as for its (1S,2R)-isomer [step 1], starting from (2R,3R)-2-(benzyloxycarbonylamino)-3-hydroxy-butanoic acid (3.39 g, 13.40 mmol). A mixture (75:25 ratio) containing the title compound, and unreacted starting material (3.40 g), was afforded and used in the next step without further purification. $R_t$=1.48 min; MS (ESI) m/z: 283 [M-H]$^+$, 305 [M-Na]$^+$, 321 [M-K]$^+$; (ESI) m/z: 281 [M-H]$^-$. $^1$H NMR (DMSO-d$_6$): δ 11.11 (s, 1H), 7.41-7.26 (m, 6H), 5.03 (s, 2H), 4.92 (d, 1H, J=5.20 Hz), 3.86-3.73 (m, 1H), 3.68 (t, 1H, J=8.29 Hz), 3.56 (s, 3H), 1.05 (d, 3H, J=6.19 Hz).

Step 3. Preparation of [(1R,2R)-2-(benzyloxycarbonylamino)-3-(methoxyamino)-1-methyl-3-oxo-propyl]-methanesulfonate The title compound was prepared in an analogous manner as for its (1S,2R)-isomer [step 2], starting from the crude mixture (3.40 g) containing benzyl-N-[(1R,2R)-2-hydroxy-1-(methoxycarbamoyl)-propyl]-carbamate (2.61 g, 9.26 mmol). The crude product was purified by column chromatography using a Teledyne ISCO apparatus (Cy/MTBE from 100:0 to 0:100) to give the pure title compound (2.60 g, 78%), as a white solid. $R_t$=1.78 min; MS (ESI) m/z: 361 [M-H]$^+$, 378 [M-NH$_4$]$^+$. $^1$H NMR (DMSO-d$_6$): δ 11.56 (s, 1H), 7.82 (d, 1H, J=9.19 Hz), 7.42-7.27 (m, 5H), 5.06 (s, 2H), 4.83 (p, 1H, J=6.40 Hz), 4.15 (dd, 1H, J=9.19, 6.40 Hz), 3.59 (s, 3H), 3.10 (s, 3H), 1.32 (d, 3H, J=6.40 Hz).

Step 4. Preparation of benzyl-N-[(2S,3R)-1-methoxy-2-methyl-4-oxo-azetidin-3-yl]-carbamate The title compound was prepared in an analogous manner as for its (2S,3S)-isomer [step 3], starting from [(1R,2R)-2-

(benzyloxycarbonylamino)-3-(methoxyamino)-1-methyl-3-oxo-propyl]-methanesulfonate (1.59 g, 4.41 mmol). The crude product was purified by column chromatography using a Teledyne ISCO apparatus (Cy/MTBE from 100:0 to 0:100) to give the pure title compound (0.69 g, 59%), as a white solid. $R_t$=1.91 min; MS (ESI) m/z: 265 [M–H]$^+$, 287 [M–Na]$^+$, 303 [M–K]$^+$. $^1$H NMR (DMSO-d$_6$): δ 8.06 (d, 1H, J=9.12 Hz), 7.43-7.27 (m, 5H), 5.06 (d, 2H, J=3.67 Hz), 4.73 (dd, 1H, J=9.12, 5.11 Hz), 4.25-4.13 (m, 1H), 3.71 (s, 3H), 1.14 (d, 3H, J=6.17 Hz).

Step 5. Preparation of benzyl-N-[(2S,3R)-2-methyl-4-oxo-azetidin-3-yl]-carbamate The title compound was prepared in an analogous manner as for its (2S,3S)-isomer [step 4], starting from benzyl-N-[(2S,3R)-1-methoxy-2-methyl-4-oxo-azetidin-3-yl]-carbamate (0.69 g, 2.63 mmol). The crude product was purified by column chromatography using a Teledyne ISCO apparatus (Cy/MTBE from 100:0 to 0:100) to give the pure title compound (0.29 g, 46%), as a white solid. $R_t$=1.66 min; MS (ESI) m/z: 235 [M–H]$^+$, 257 [M–Na]$^+$, 273 [M–K]$^+$. $^1$H NMR (DMSO-d$_6$): δ 8.13 (s, 1H), 8.04 (d, 1H, J=9.55 Hz), 7.42-7.27 (m, 5H), 5.12-4.99 (m, 2H), 4.80 (dd, 1H, J=9.55, 4.98 Hz), 3.81-3.70 (m, 1H), 1.07 (d, 3H, J=6.24 Hz).

Step 6. Preparation of [(2S,3R)-2-methyl-4-oxo-azetidin-3-yl]-ammonium toluene-4-sulfonate The pure title compound was prepared in an analogous manner as for its (2S,3S)-isomer [step 5], starting from benzyl-N-[(2S,3R)-2-methyl-4-oxo-azetidin-3-yl]-carbamate (0.29 g, 0.66 mmol). The crude salt was triturated with Et$_2$O to give the title compound (0.34 g, quant.), as a fluffy white solid. $^1$H NMR (DMSO-d$_6$): δ 8.72-8.42 (m, 4H), 7.51-7.43 (m, 2H), 7.11 (d, 2H, J=7.85 Hz), 4.46 (s, 1H), 3.93-3.82 (m, 1H), 2.29 (s, 3H), 1.26 (d, 3H, J=6.42 Hz).

Example 72. 4-Cyclohexylbutyl-N-[(2S,3S)-2-methyl-4-oxo-azetidin-3-yl]-carbamate Step 1. Preparation of 4-cyclohexylbutyl-N-[(2S,3S)-2-methyl-4-oxo-azetidin-3-yl]-carbamate Under nitrogen atmosphere, to a stirred mixture of [(2S,3S)-2-methyl-4-oxo-azetidin-3-yl]-ammonium toluene-4-sulfonate (0.07 g, 0.25 mmol) in dry CH$_2$Cl$_2$ (1.0 mL), DIPEA (0.05 mL, 0.31 mmol) was added dropwise. Subsequently, the crude mixture (0.19 g) containing 4-cyclohexylbutyl-2-oxopyridine-1-carboxylate (0.069 g, 0.25 mmol) [obtained as described in example 5 (step 1)] in dry CH$_2$Cl$_2$ (3.0 mL) was added. The reaction mixture was stirred at r.t. for 15 h, concentrated to dryness and purified by column chromatography using a Teledyne ISCO apparatus (Cy/EtOAc from 100:0 to 0:100) to give the pure title compound (0.027 g, 40%), as a white solid. $R_t$=2.69 min; MS (ESI) m/z: 283 [M–H]$^+$, 305 [M–Na]$^+$, 321 [M–K]$^+$. $^1$H NMR (DMSO-d$_6$): δ 8.05 (s, 1H), 7.77 (d, 1H, J=8.68 Hz), 4.11-4.04 (m, 1H), 4.00-3.88 (m, 2H), 3.56-3.44 (m, 1H), 1.72-1.56 (m, 5H), 1.56-1.46 (m, 2H), 1.36-1.25 (m, 2H), 1.23 (d, 3H, J=6.07 Hz), 1.22-1.04 (m, 6H), 0.92-0.77 (m, 2H).

Example 73. (4-Phenylphenyl)-methyl-N-[(2S,3S)-2-methyl-4-oxo-azetidin-3-yl]-carbamate Step 1. Preparation of (4-phenylphenyl)-methyl-N-[(2S,3S)-2-methyl-4-oxo-azetidin-3-yl]-carbamate Under nitrogen atmosphere, to a stirred mixture of [(2S,3S)-2-methyl-4-oxo-azetidin-3-yl]-ammonium toluene-4-sulfonate (0.08 g, 0.29 mmol) in dry CH$_2$Cl$_2$ (1.0 mL), DIPEA (0.06 mL, 0.35 mmol) was added dropwise. Subsequently, the crude mixture (0.23 g) containing (4-phenylphenyl)-methyl-2-oxopyridine-1-carboxylate (0.09 g, 0.29 mmol) [obtained as described in example 17 (step 1)] in dry CH$_2$Cl$_2$ (3.0 mL) was added. The reaction mixture was stirred at r.t. for 15 h, concentrated to dryness and purified by column chromatography using a Teledyne ISCO apparatus (Cy/EtOAc from 100:0 to 0:100) to give the pure title compound (0.049 g, 54%), as a white solid. $R_t$=2.28 min; MS (ESI) m/z: 311 [M–H]$^+$, 333 [M–Na]$^+$, 349 [M–K]$^+$. $^1$H NMR (DMSO-d$_6$): δ 8.09 (s, 1H), 7.98 (d, 1H, J=8.6 Hz), 7.67 (d, 4H, J=7.82 Hz), 7.50-7.43 (m, 4H), 7.40-7.34 (m, 1H), 5.10 (d, 1H, J=12 Hz), 5.06 (d, 1H, J=12 Hz), 4.13 (dd, 1H J=8.6, 2.3 Hz), 3.53 (dq, 1H, J=5.92, 2.3 Hz), 1.25 (d, 3H, J=6.13 Hz).

Example 74. (4-Cyclohexylphenyl)-methyl-N-[(2S,3S)-2-methyl-4-oxo-azetidin-3-yl]-carbamate Step 1. Preparation of (4-cyclohexylphenyl)-methyl-N-[(2S,3S)-2-methyl-4-oxo-azetidin-3-yl]-carbamate Under nitrogen atmosphere, to a stirred mixture of [(2S,3S)-2-methyl-4-oxo-azetidin-3-yl]-ammonium toluene-4-sulfonate (0.09 g, 0.33 mmol) in dry CH$_2$Cl$_2$ (1.0 mL), DIPEA (0.06 mL, 0.40 mmol) was added dropwise. Subsequently, the crude mixture (0.27 g) containing (4-cyclohexylphenyl)-methyl-2-oxopyridine-1-carboxylate (0.10 g, 0.33 mmol) [obtained as described in example 31 (step 2)] in dry CH$_2$Cl$_2$ (3.0 mL) was added. The reaction mixture was stirred at r.t. for 15 h, concentrated to dryness and purified by column chromatography using a Teledyne ISCO apparatus (Cy/MTBE from 100:0 to 0:100) to give the pure title compound (0.025 g, 24%), as a white solid. $R_t$=2.67 min; MS (ESI) m/z: 317 [M–H]$^+$, 339 [M–Na]$^+$, 355 [M–K]$^+$. $^1$H NMR (DMSO-d$_6$): δ 8.07 (s, 1H), 7.91 (d, 1H, J=8.70 Hz), 7.30-7.17 (m, 4H), 5.05-4.93 (m, 2H), 4.11 (dd, 1H, J=8.70, 2.2 Hz), 3.51 (dq, 1H, J=6.0, 2.2 Hz), 1.87-1.62 (m, 5H), 1.48-1.15 (m, 5H), 1.24 (d, 1H, J=6.0 Hz).

Example 75. 5-Phenylpentyl-N-[(2S,3S)-2-methyl-4-oxo-azetidin-3-yl]-carbamate

Step 1. Preparation of 5-phenylpentyl-N-[(2S,3S)-2-methyl-4-oxo-azetidin-3-yl]-carbamate Under nitrogen atmosphere, to a stirred mixture of [(2S,3S)-2-methyl-4-oxo-azetidin-3-yl]-ammonium toluene-4-sulfonate (0.09 g, 0.33 mmol) in dry CH$_2$Cl$_2$ (1.0 mL), DIPEA (0.06 mL, 0.40 mmol) was added dropwise. Subsequently, the crude mixture (0.45 g) containing 5-phenylpentyl-2-oxopyridine-1-carboxylate (0.09 g, 0.33 mmol) [obtained as described in example 3 (step 1)] in dry CH$_2$Cl$_2$ (3.0 mL) was added. The reaction mixture was stirred at r.t. for 15 h, concentrated to dryness and purified by column chromatography using a Teledyne ISCO apparatus (Cy/MTBE from 100:0 to 0:100) to give the pure title compound (0.035 g, 36%), as a white solid. $R_t$=2.32 min; MS (ESI) m/z: 291 [M–H]$^+$, 329 [M–K]$^+$. $^1$H NMR (DMSO-d$_6$): δ 8.05 (s, 1H), 7.77 (d, 1H, J=8.67 Hz), 7.30-7.23 (m, 2H), 7.21-7.12 (m, 3H), 4.10-4.04 (m, 1H), 4.00-3.88 (m, 2H), 3.53-3.46 (m, 1H), 2.57 (t, 2H, J=7.66 Hz), 1.63-1.51 (m, 4H), 1.38-1.27 (m, 2H), 1.23 (d, 3H, J=6.08 Hz).

Example 76. 4-Cyclohexylbutyl-N-[(2R,3S)-2-methyl-4-oxo-azetidin-3-yl]-carbamate Step 1. Preparation of 4-cyclohexylbutyl-N-[(2R,3S)-2-methyl-4-oxo-azetidin-3-yl]-carbamate Under nitrogen atmosphere, to a stirred mixture of [(2R,3S)-2-methyl-4-oxo-azetidin-3-yl]-ammonium toluene-4-sulfonate (0.08 g, 0.30 mmol) in dry $CH_2Cl_2$ (2.0 mL), DIPEA (0.06 mL, 0.33 mmol) was added dropwise. Subsequently, the crude mixture (0.22 g) containing 4-cyclohexylbutyl-2-oxopyridine-1-carboxylate (0.083 g, 0.30 mmol) [obtained as described in example 5 (step 1)] in dry $CH_2Cl_2$ (3.0 mL) was added. The reaction mixture was stirred at r.t. for 15 h, concentrated to dryness and purified by typical silica gel column chromatography (Cy/EtOAc 97:3) to afford the pure title compound (0.031 g, 39%), as a white solid. $R_t$=2.71 min; MS (ESI) m/z: 283 [M-H]$^+$, 305 [M-Na]$^+$, 321 [M-K]$^+$. $^1$H NMR (DMSO-d$_6$): δ 8.10 (s, 1H), 7.85 (d, 1H, J=9.50 Hz), 4.87-4.65 (m, 1H), 4.01-3.90 (m, 2H), 3.79-3.68 (m, 1H), 1.72-1.56 (m, 5H), 1.56-1.46 (m, 2H), 1.36-1.10 (m, 8H), 1.06 (d, 3H, J=6.23 Hz), 0.91-0.77 (m, 2H).

Example 77. (4-Phenylphenyl)-methyl-N-[(2R,3S)-2-methyl-4-oxo-azetidin-3-yl]-carbamate Step 1. Preparation of (4-phenylphenyl)-methyl-N-[(2R,3S)-2-methyl-4-oxo-azetidin-3-yl]-carbamate Under nitrogen atmosphere, to a stirred mixture of [(2R,3S)-2-methyl-4-oxo-azetidin-3-yl]-ammonium toluene-4-sulfonate (0.074 g, 0.27 mmol) in dry $CH_2Cl_2$ (1.0 mL), DIPEA (0.057 mL, 0.33 mmol) was added dropwise. Subsequently, the crude mixture (0.22 g) containing (4-phenylphenyl)-methyl-2-oxopyridine-1-carboxylate (0.083 g, 0.27 mmol) [obtained as described in example 17 (step 1)] in dry $CH_2Cl_2$ (3.0 mL) was added. The reaction mixture was stirred at r.t. for 15 h, concentrated to dryness and purified by typical silica gel column chromatography (Cy/EtOAc 97:3) to afford the pure title compound (0.032 g, 40%), as a white solid. $R_t$=2.28 min; MS (ESI) m/z: 311 [M-H]$^+$, 328 [M-NH$_4$]$^+$, 349 [M-K]$^+$. $^1$H NMR (DMSO-d$_6$): δ 8.14 (s, 1H), 8.07 (d, 1H, J=9.52 Hz), 7.76-7.63 (m, 4H), 7.52-7.32 (m, 5H), 5.17-5.04 (m, 2H), 4.82 (ddd, 1H, J=9.53, 5.04, 1.13 Hz), 3.82-3.71 (m, 1H), 1.08 (d, 3H, J=6.24 Hz).

Example 78. (4-Cyclohexylphenyl)-methyl-N-[(2R,3S)-2-methyl-4-oxo-azetidin-3-yl]-carbamate Step 1. Preparation of (4-cyclohexylphenyl)-methyl-N-[(2R,3S)-2-methyl-4-oxo-azetidin-3-yl]-carbamate Under nitrogen atmosphere, to a stirred mixture of [(2R,3S)-2-methyl-4-oxo-azetidin-3-yl]-ammonium toluene-4-sulfonate (0.073 g, 0.27 mmol) in dry $CH_2Cl_2$ (1.0 mL), DIPEA (0.056 mL, 0.32 mmol) was added dropwise. Subsequently, the crude mixture (0.23 g) containing (4-cyclohexylphenyl)-methyl-2-oxopyridine-1-carboxylate (0.084 g, 0.27 mmol) [obtained as described in example 31 (step 2)] in dry $CH_2Cl_2$ (3.0 mL) was added. The reaction mixture was stirred at r.t. for 15 h, concentrated to dryness and purified by typical silica gel column chromatography (Cy/EtOAc 97:3) to afford the pure title compound (0.038 g, 40%), as a white solid. $R_t$=2.68 min; MS (ESI) m/z: 317 [M-H]$^+$, 339 [M-Na]$^+$, 355 [M-K]$^+$. $^1$H NMR (DMSO-d$_6$): δ 8.14 (s, 1H), 8.01 (d, 1H, J=9.55 Hz), 7.29-7.17 (m, 4H), 5.06-4.93 (m, 2H), 4.84-4.75 (m, 1H), 3.80-3.69 (m, 1H), 1.82-1.65 (m, 6H), 1.46-1.18 (m, 5H), 1.06 (d, 3H, J=6.25 Hz).

Example 79. 5-Phenylpentyl-N-[(2R,3S)-2-methyl-4-oxo-azetidin-3-yl]-carbamate Step 1. Preparation of 5-phenylpentyl-N-[(2R,3S)-2-methyl-4-oxo-azetidin-3-yl]-carbamate Under nitrogen atmosphere, to a stirred mixture of [(2R,3S)-2-methyl-4-oxo-azetidin-3-yl]-ammonium toluene-4-sulfonate (0.072 g, 0.26 mmol) in dry $CH_2Cl_2$ (1.0 mL), DIPEA (0.054 mL, 0.31 mmol) was added dropwise. Subsequently, the crude mixture (0.35 g) containing 5-phenylpentyl-2-oxopyridine-1-carboxylate (0.074 g, 0.26 mmol) [obtained as described in example 3 (step 1)] in dry $CH_2Cl_2$ (3.0 mL) was added. The reaction mixture was stirred at r.t. for 15 h, concentrated to dryness and purified by typical silica gel column chromatography (Cy/EtOAc 97:3) to afford the pure title compound (0.049 g, 54%), as a white solid. $R_t$=2.32 min; MS (ESI) m/z: 291 [M-H]$^+$, 313 [M-Na]$^+$, 329 [M-K]$^+$. $^1$H NMR (DMSO-d$_6$): δ 8.12 (s, 1H), 7.88 (d, 1H, J=9.57 Hz), 7.29-7.09 (m, 5H), 4.83-4.70 (m, 1H), 4.08-3.87 (m, 2H), 3.78-3.63 (m, 1H), 2.56 (t, 2H, J=7.66 Hz), 1.67-1.51 (m, 4H), 1.40-1.24 (m, 2H), 1.05 (d, 3H, J=6.24 Hz).

Example 80. 4-Cyclohexylbutyl-N-[(2R,3R)-2-methyl-4-oxo-azetidin-3-yl]-carbamate Step 1. Preparation of 4-cyclohexylbutyl-N-[(2R,3R)-2-methyl-4-oxo-azetidin-3-yl]-carbamate Under nitrogen atmosphere, to a stirred mixture of [(2R,3R)-2-methyl-4-oxo-azetidin-3-yl]-ammonium toluene-4-sulfonate (0.09 g, 0.33 mmol) in dry $CH_2Cl_2$ (2.0 mL), DIPEA (0.06 mL, 0.33 mmol) was added dropwise. Subsequently, the crude mixture (0.25 g) containing 4-cyclohexylbutyl-2-oxopyridine-1-carboxylate (0.091 g, 0.33 mmol) [obtained as described in example 5 (step 1)] in dry $CH_2Cl_2$ (3.0 mL) was added. The reaction mixture was stirred at r.t. for 15 h, concentrated to dryness and purified by column chromatography using a Teledyne ISCO apparatus (Cy/EtOAc from 100:0 to 0:100) to give the pure title compound (0.06 g, 64%), as a white solid. $R_t$=2.69 min; MS (ESI) m/z: 283 [M-H]$^+$, 305 [M-Na]$^+$, 321 [M-K]$^+$. $^1$H NMR (DMSO-d$_6$): δ 8.05 (s, 1H), 7.77 (d, 1H, J=8.68 Hz), 4.11-4.04 (m, 1H), 4.00-3.88 (m, 2H), 3.56-3.44 (m, 1H), 1.72-1.56 (m, 5H), 1.56-1.46 (m, 2H), 1.36-1.25 (m, 2H), 1.23 (d, 3H, J=6.07 Hz), 1.22-1.04 (m, 6H), 0.92-0.77 (m, 2H).

Example 81. (4-Phenylphenyl)-methyl-N-[(2R,3R)-2-methyl-4-oxo-azetidin-3-yl]-carbamate Step 1. Preparation of (4-phenylphenyl)-methyl-N-[(2R,3R)-2-methyl-4-oxo-azetidin-3-yl]-carbamate Under nitrogen atmosphere, to a stirred mixture of [(2R,3R)-2-methyl-4-oxo-azetidin-3-yl]-ammonium toluene-4-sulfonate (0.09 g, 0.33 mmol) in dry $CH_2Cl_2$ (1.0 mL), DIPEA (0.06 mL, 0.35 mmol) was added dropwise. Subsequently, the crude mixture (0.26 g) containing (4-phenylphenyl)-methyl-2-oxopyridine-1-carboxylate (0.01 g, 0.33 mmol) [obtained as described in example 17 (step 1)] in dry $CH_2Cl_2$ (3.0 mL) was added. The reaction mixture was stirred at r.t. for 15 h, concentrated to dryness and purified by column chromatography using a Teledyne ISCO apparatus (Cy/EtOAc from 100:0 to 0:100) to give the pure title compound (0.05 g, 49%), as a white solid. $R_t$=2.28 min; MS (ESI) m/z: 311 [M-H]$^+$, 333 [M–Na]$^+$, 349 [M–K]$^+$. $^1$H NMR (DMSO-d$_6$): δ 8.09 (s, 1H), 7.98 (d, 1H, J=8.6 Hz), 7.67 (d, 4H, J=7.82 Hz), 7.50-7.43 (m, 4H), 7.40-7.34 (m, 1H), 5.10 (d, 1H, J=12 Hz), 5.06 (d, 1H, J=12 Hz), 4.13 (dd, 1H, J=8.6, 2.3 Hz), 3.53 (dq, 1H, J=5.92, 2.3 Hz), 1.25 (d, 3H, J=6.13 Hz).

Example 82. (4-Cyclohexylphenyl)-methyl-N-[(2R, 3R)-2-methyl-4-oxo-azetidin-3-yl]-carbamate Step 1. Preparation of (4-cyclohexylphenyl)-methyl-N-[(2R,3R)-2-methyl-4-oxo-azetidin-3-yl]-carbamate Under nitrogen atmosphere, to a stirred mixture of [(2R, 3R)-2-methyl-4-oxo-azetidin-3-yl]-ammonium toluene-4-sulfonate (0.09 g, 0.33 mmol) in dry CH$_2$Cl$_2$ (1.0 mL), DIPEA (0.06 mL, 0.40 mmol) was added dropwise. Subsequently, the crude mixture (0.28 g) containing (4-cyclohexylphenyl)-methyl-2-oxopyridine-1-carboxylate (0.01 g, 0.33 mmol) [obtained as described in example 31 (step 2)] in dry CH$_2$Cl$_2$ (3.0 mL) was added. The reaction mixture was stirred at r.t. for 15 h, concentrated to dryness and purified by column chromatography using a Teledyne ISCO apparatus (Cy/MTBE from 100:0 to 0:100) to give the pure title compound (0.07 g, 67%), as a white solid. $R_t$=2.67 min; MS (ESI) m/z: 317 [M-H]$^+$, 339 [M–Na]$^+$, 355 [M–K]$^+$. $^1$H NMR (DMSO-d$_6$): δ 8.07 (s, 1H), 7.91 (d, 1H, J=8.70 Hz), 7.30-7.17 (m, 4H), 5.05-4.93 (m, 2H), 4.11 (dd, 1H, J=8.70, 2.2 Hz), 3.51 (dq, 1H, J=6, 2.2 Hz), 1.87-1.62 (m, 5H), 1.48-1.15 (m, 5H), 1.24 (d, 1H, J=6 Hz).

Example 83. 4-Cyclohexylbutyl-N-[(2S,3R)-2-methyl-4-oxo-azetidin-3-yl]-carbamate Step 1. Preparation of 4-cyclohexylbutyl-N-[(2S, 3R)-2-methyl-4-oxo-azetidin-3-yl]-carbamate Under nitrogen atmosphere, to a stirred mixture of [(2S, 3R)-2-methyl-4-oxo-azetidin-3-yl]-ammonium toluene-4-sulfonate (0.074 g, 0.27 mmol) in dry CH$_2$Cl$_2$ (2.0 mL), DIPEA (0.057 mL, 0.32 mmol) was added dropwise. Subsequently, the crude mixture (0.22 g) containing 4-cyclohexylbutyl-2-carboxylate (0.075 g, 0.27 mmol) [obtained as described in example 5 (step 1)] in dry CH$_2$Cl$_2$ (3.0 mL) was added. The reaction mixture was stirred at r.t. for 15 h, concentrated to dryness and purified by typical silica gel column chromatography (Cy/EtOAc 97:3) to afford the pure title compound (0.031 g, 39%), as a white solid. $R_t$=2.71 min; MS (ESI) m/z: 283 [M-H]$^+$, 305 [M–Na]$^+$, 321 [M–K]$^+$. $^1$H NMR (DMSO-d$_6$): δ 8.10 (s, 1H), 7.85 (d, 1H, J=9.50 Hz), 4.87-4.65 (m, 1H), 4.01-3.90 (m, 2H), 3.79-3.68 (m, 1H), 1.72-1.56 (m, 5H), 1.56-1.46 (m, 2H), 1.36-1.10 (m, 8H), 1.06 (d, 3H, J=6.23 Hz), 0.91-0.77 (m, 2H).

Example 84. (4-Phenylphenyl)-methyl-N-[(2S,3R)-2-methyl-4-oxo-azetidin-3-yl]-carbamate Step 1. Preparation of (4-phenylphenyl)-methyl-N-[(2S,3R)-2-methyl-4-oxo-azetidin-3-yl]-carbamate Under nitrogen atmosphere, to a stirred mixture of [(2S, 3R)-2-methyl-4-oxo-azetidin-3-yl]-ammonium toluene-4-sulfonate (0.074 g, 0.27 mmol) in dry CH$_2$Cl$_2$ (1.0 mL), DIPEA (0.057 mL, 0.33 mmol) was added dropwise. Subsequently, the crude mixture (0.22 g) containing (4-phenylphenyl)-methyl-2-oxopyridine-1-carboxylate (0.083 g, 0.27 mmol) [obtained as described in example 17 (step 1)] in dry CH$_2$Cl$_2$ (3.0 mL) was added. The reaction mixture was stirred at r.t. for 15 h, concentrated to dryness and purified by typical silica gel column chromatography (Cy/EtOAc 97:3) to afford the pure title compound (0.056 g, 67%), as a white solid. $R_t$=2.28 min; MS (ESI) m/z: 311 [M-H]$^+$, 328 [M–NH$_4$]$^+$, 349 [M–K]$^+$. $^1$H NMR (DMSO-d$_6$): δ 8.14 (s, 1H), 8.07 (d, 1H, J=9.52 Hz), 7.76-7.63 (m, 4H), 7.52-7.32 (m, 5H), 5.17-5.04 (m, 2H), 4.82 (ddd, 1H, J=9.53, 5.04, 1.13 Hz), 3.82-3.71 (m, 1H), 1.08 (d, 3H, J=6.24 Hz).

Example 85. (4-Cyclohexylphenyl)-methyl-N-[(2S, 3R)-2-methyl-4-oxo-azetidin-3-yl]-carbamate Step 1. Preparation of (4-cyclohexylphenyl)-methyl-N-[(2S,3R)-2-methyl-4-oxo-azetidin-3-yl]-carbamate Under nitrogen atmosphere, to a stirred mixture of [(2S, 3R)-2-methyl-4-oxo-azetidin-3-yl]-ammonium toluene-4-sulfonate (0.073 g, 0.27 mmol) in dry CH$_2$Cl$_2$ (1.0 mL), DIPEA (0.056 mL, 0.32 mmol) was added dropwise. Subsequently, the crude mixture (0.23 g) containing (4-cyclohexylphenyl)-methyl-2-oxopyridine-1-carboxylate (0.084 g, 0.27 mmol) [obtained as described in example 31 (step 2)] in dry CH$_2$Cl$_2$ (3.0 mL) was added. The reaction mixture was stirred at r.t. for 15 h, concentrated to dryness and purified by typical silica gel column chromatography (Cy/EtOAc 97:3) to afford the pure title compound (0.057 g, 67%), as a white solid. $R_t$=2.68 min; MS (ESI) m/z: 317 [M-H]$^+$, 339 [M–Na]$^+$, 355 [M–K]$^+$. $^1$H NMR (DMSO-d$_6$): δ 8.14 (s, 1H), 8.01 (d, 1H, J=9.55 Hz), 7.29-7.17 (m, 4H), 5.06-4.93 (m, 2H), 4.84-4.75 (m, 1H), 3.80-3.69 (m, 1H), 1.82-1.65 (m, 6H), 1.46-1.18 (m, 5H), 1.06 (d, 3H, J=6.25 Hz).

Preparation of (3S)-3-amino-1-[bis-(trimethylsilyl)-methyl]-4,4-dimethyl-azetidin-2-one Step 1. Preparation of N-[bis-(trimethylsilyl)-methyl]-propan-2-imine Under nitrogen atmosphere, bis-(trimethylsilyl)-methylamine (0.15 g, 0.85 mmol) was dissolved in acetone (1.7 mL) and the resulting solution was stirred at r.t. for 12 h. The solvent was removed under reduced pressure to afford the title compound (0.17 g, 92%), as colorless oil; which was used in the next step without further purification. $R_t$=1.95 min; MS (ESI) m/z: 216 [M-H]$^+$. $^1$H NMR (DMSO-d$_6$): δ 2.87 (s, 1H), 1.92 (s, 3H), 1.68 (s, 3H), 0.03 (s, 18H).

Step 2. Preparation of (4S)-3-[(3S)-1-[bis-(trimethylsilyl)-methyl]-2,2-dimethyl-4-oxo-azetidin-3-yl]-4-phenyl-oxazolidin-2-one Under nitrogen atmosphere, at 0° C., to a solution of the commercially available (S)-(+)-2-oxo-4-phenyl-3-oxazolidine acetic acid (0.33 g, 1.50 mmol) in dry CH$_2$Cl$_2$ (5.0 mL), oxalyl chloride (0.16 mL, 1.87 mmol) was added dropwise, followed by dry DMF (0.01 mL). After stirring for 1 h, the mixture was concentrated to dryness to afford the corresponding acid chloride. Under argon atmosphere, at 0° C., the crude mixture containing the acid chloride was dissolved in dry CH$_2$Cl$_2$ (1.80 mL) and added dropwise, to a mixture of 4 Å molecular sieves (0.11 g), bis-(trimethylsilyl)-methylamine (0.21 g, 0.97 mmol) and dry Et$_3$N (0.33 mL, 2.34 mmol) in dry CH$_2$Cl$_2$ (1.0 mL). The reaction mixture was heated to 55° C. and gently stirred for 12 h. The molecular sieves were filtered off and the filtrate diluted with CH$_2$Cl$_2$ (15 mL) and washed with 1.0 M HCl solution (10 mL). The aqueous phase was extracted with CH$_2$Cl$_2$ (3×15 mL) and the combined organic layers were sequentially washed with sat. NaHCO$_3$ solution (15 mL) and H$_2$O (15 mL). The organic phase was dried over Na$_2$SO$_4$ and the solvent removed under reduced pressure. The crude product was purified by column chromatography using a Teledyne ISCO apparatus (Cy/EtOAc from 70:30 to 60:40) to afford the title compound (0.25 g, 62%), as white solid. R$_t$=3.16 min; MS (ESI) m/z: 419 [M-H]$^+$. $^1$H NMR (DMSO-d$_6$): δ 7.45-7.37 (m, 5H), 5.05 (dd, 1H, J=8.9, 5.9 Hz), 4.71 (t, 1H, J=8.8 Hz), 4.12 (dd, 1H, J=8.7, 5.9 Hz), 3.66 (s, 1H), 2.15 (s, 1H), 1.21 (s, 3H), 1.16 (s, 3H), 0.06 (s, 9H), 0.02 (s, 9H).

Step 3. Preparation of (3S)-3-amino-1-[bis-(trimethylsilyl)-methyl]-4,4-dimethyl-azetidin-2-one Under nitrogen atmosphere, at 0° C., to a suspension of sodium-silica gel (Na-SG(I) 35-40%) (0.42 g, 6.41 mmol) in dry THF (4.0 mL), ethylendiamine (0.43 mL, 6.40 mmol) was added. The reaction mixture was stirred for 15 min, then 2-methyl-2-butanol (0.52 mL, 4.80 mmol) was added and the resulting suspension was stirred for additional 5 min. A solution of (4S)-3-[(3S)-1-[bis-(trimethylsilyl)-methyl]-2,2-dimethyl-4-oxo-azetidin-3-yl]-4-phenyl-oxazolidin-2-one (0.24 g, 0.57 mmol) in dry THF (2.0 mL) was added and the reaction was allowed to warm to r.t. and stirred for 2 h. The mixture was diluted with Et$_2$O (15 mL), filtered, and the organic phase washed with H$_2$O (15 mL). The aqueous phase was extracted with EtOAc (8×15 mL), and the combined organic phases were dried over Na$_2$SO$_4$ and concentrated to dryness to afford the title compound (0.14 g), which was used in the next step without further purification. R$_t$=2.53 min; MS (ESI) m/z: 273 [M-H]$^+$, 295 [M−Na]$^+$, 311 [M−K]$^+$. $^1$H NMR (DMSO-d$_6$): δ 3.51 (s, 1H), 2.10 (s, 1H), 1.18 (s, 3H), 1.09 (s, 3H), 0.11 (s, 9H), 0.10 (s, 9H).

Preparation of (3R)-3-amino-1-[bis-(trimethylsilyl)-methyl]-4,4-dimethyl-azetidin-2-one Step 1. Preparation of benzyl-2-[(4R)-2-oxo-4-phenyl-oxazolidin-3-yl]-acetate The title compound was obtained according to the procedure reported in the literature [US Pat. Appl. Publ., 20060211603, 21, Sep. 2006], starting from the commercially available (4R)-4-phenyloxazolidin-2-one (0.60 g, 3.7 mmol). The crude product was purified by column chromatography using a Teledyne ISCO apparatus (Cy/EtOAc from 70:30 to 60:40) to afford the pure title compound (0.93 g, 81%), as colorless oil. R$_t$=2.50 min; MS (ESI) m/z: 312 [M-H]$^+$, 329 [M-NH$_4$]$^+$. $^1$H NMR (DMSO-d$_6$): δ 7.50-7.24 (m, 9H), 5.12 (d, 2H, J=1.7 Hz), 4.99 (t, 1H, J=8.4 Hz), 4.74 (t, 1H, J=8.7 Hz), 4.14 (d, 1H, J=17.9 Hz), 4.08 (t, 1H, J=8.4 Hz), 3.51 (d, 1H, J=17.9 Hz).

Step 2. Preparation of 2-[(4R)-2-oxo-4-phenyl-oxazolidin-3-yl]-acetic acid

Under nitrogen atmosphere, to a solution of 2-[(4R)-2-oxo-4-phenyl-oxazolidin-3-yl]-acetate (0.83 g, 2.66 mmol) in EtOAc (13 mL), 1,4-cyclohexadiene (2.52 mL, 26.6 mmol) and 10% Pd on activated charcoal (0.83 g) were added. The reaction mixture was stirred at r.t. for 16 h; then the suspension was filtered through a pad of Celite. The filtrate was concentrated to dryness to afford the pure title compound (0.55 g, 93%), as a white semi-solid. R$_t$=1.08 min; MS (ESI) m/z: 222 [M-H]$^+$. MS (ESI) m/z: 220 [M-H]$^−$. $^1$H NMR (DMSO): δ 7.62-7.20 (m, 5H), 5.00 (t, 1H, J=8.5 Hz), 4.73 (t, 1H, J=8.7 Hz), 4.05 (t, 1H, J=8.5 Hz), 4.00 (d, 1H, J=17.9 Hz), 3.27 (d, 1H, J=17.9 Hz).

Step 3. Preparation of (4R)-3-[(3R)-1-[bis-(trimethylsilyl)-methyl]-2,2-dimethyl-4-oxo-azetidin-3-yl]-4-phenyl-oxazolidin-2-one Following the procedure described for the preparation of (3S)-3-amino-1-[bis-(trimethylsilyl)-methyl]-4,4-dimethyl-azetidin-2-one, starting from N-[bis-(trimethylsilyl)-methyl]-propan-2-imine (0.35 g, 1.62 mmol) and 2-[(4R)-2-oxo-4-phenyl-oxazolidin-3-yl]-acetic acid (0.54 g, 2.44), activated as acid chloride, purification by column chromatography using a Teledyne ISCO apparatus (Cy/EtOAc from 70:30 to 60:40) afforded the pure title compound (0.54 g, 68%), as white solid. R$_t$=3.16 min; MS (ESI) m/z: 419 [M-H]$^+$. $^1$H NMR (DMSO-d$_6$): δ 7.45-7.37 (m, 5H), 5.05 (dd, 1H, J=8.9, 5.9 Hz), 4.71 (t, 1H, J=8.8 Hz), 4.12 (dd, 1H, J=8.7, 5.9 Hz), 3.66 (s, 1H), 2.15 (s, 1H), 1.21 (s, 3H), 1.16 (s, 3H), 0.06 (s, 9H), 0.02 (s, 9H).

Step 4. Preparation of (3R)-3-amino-1-[bis-(trimethylsilyl)-methyl]-4,4-dimethyl-azetidin-2-one Following the procedure described for the preparation of (3S)-3-amino-1-[bis-(trimethylsilyl)-methyl]-4,4-dimethyl-azetidin-2-one, starting from (4R)-3-[(3R)-1-[bis(trimethylsilyl)methyl]-2,2-dimethyl-4-oxo-azetidin-3-yl]-4-phenyl-oxazolidin-2-one (0.44 g, 1.05 mmol), the title compound (0.25 g) was obtained and used in the next step without further purification. R$_t$=2.53 min; MS (ESI) m/z: 273 [M-H]$^+$, 295 [M−Na]$^+$, 311 [M−K]$^+$. $^1$H NMR (DMSO-d$_6$): δ 3.51 (s, 1H), 2.10 (s, 1H), 1.18 (s, 3H), 1.09 (s, 3H), 0.11 (s, 9H), 0.10 (s, 9H).

Example 86. 4-Cyclohexylbutyl-N-[(3S)-2,2-dimethyl-4-oxo-azetidin-3-yl]-carbamate Step 1. Preparation of 4-cyclohexylbutyl-N-[(3S)-1-[bis-(trimethylsilyl)-methyl]-2,2-dimethyl-4-oxo-azetidin-3-yl]-carbamate Under nitrogen atmosphere, to a solution of the crude (3S)-3-amino-1-[bis-(trimethylsilyl)-methyl]-4,4-dimethyl-azetidin-2-one (0.10 g, 0.37 mmol) in dry CH$_2$Cl$_2$ (2.0 mL), DIPEA (0.08 mL, 0.44 mmol) was added. Subsequently, the crude mixture (0.28 g) containing 4-cyclohexylbutyl-2-oxopyridine-1-carboxylate (0.105 g, 0.37 mmol) [obtained as described in example 5 (step 1)] in dry CH$_2$Cl$_2$ (2.0 mL) was added. The reaction mixture was stirred at r.t. for 16 h, then diluted with CH$_2$Cl$_2$ and sequentially washed with sat. NH$_4$Cl solution (15 mL) and sat. NaHCO$_3$ solution (3×15 mL). The organic layer was dried over Na$_2$SO$_4$, filtered and concentrated to dryness. The crude product was purified by column chromatography using a Teledyne ISCO apparatus (Cy/EtOAc 80:20) to afford a mixture (ratio 1:2.8:1) containing the title compound, 4-cyclohexylbutyl-2-oxopyridine-1-carboxylate and 4-cyclohexylbutan-1-ol (0.18 g), which was used in the next step without further purification.

Step 2. Preparation of 4-cyclohexylbutyl-N-[(3S)-2,2-dimethyl-4-oxo-azetidin-3-yl]-carbamate To a suspension of the mixture (0.18 g) containing 4-cyclohexylbutyl-N-[(3S)-1-[bis-(trimethylsilyl)-methyl]-2,2-dimethyl-4-oxo-azetidin-3-yl]-carbamate (0.063 g, 0.14 mmol) in MeCN (2.0 mL), cooled to 0° C., a solution of CAN (0.38 g, 0.70 mmol) in deionized $H_2O$ (0.5 mL) was added. The reaction mixture was stirred at r.t. for 1 h, and then diluted with EtOAc (15 mL) and $H_2O$ (15 mL). The two phases were separated and the aqueous layer was extracted with EtOAc (3×15 mL). The combined organic layers were sequentially washed with sat. $NaHCO_3$ solution (10 mL), 40% $NaHSO_3$ solution (5 mL) and with sat. $NaHCO_3$ solution (10 mL). The organic layer was dried over $Na_2SO_4$ concentrated to dryness to afford a crude mixture (0.175 g) mainly containing 4-cyclohexylbutyl-N-[(3S)-1-formyl-2,2-dimethyl-4-oxo-azetidin-3-yl]-carbamate. This crude was suspended in a 1:1 mixture acetone/sat. $NaHCO_3$ solution (4.0 mL) and stirred at r.t. for 16 h. The suspension was diluted with EtOAc (15 mL) and $H_2O$ (5 mL) was added. After extraction with EtOAc (3×15 mL) and the combined organic phases were dried over $Na_2SO_4$, filtered and concentrated to dryness. The crude product was purified by column chromatography using a Teledyne ISCO apparatus (Cy/EtOAc 50:50) to afford the pure title compound (0.04 g, 32% over three steps), as white powder. $R_t$=1.49 min; MS (ESI) m/z: 297 [M-H]$^+$, 314 [M-NH$_4$]$^+$, 319 [M-Na]$^+$, 335 [M-K]$^+$. $^1$H NMR (DMSO-d$_6$): δ 8.12 (s, 1H), 7.89 (d, 1H, J=9.2 Hz), 4.34 (d, 1H, J=9.2 Hz), 4.04-3.89 (m, 2H), 1.71-1.57 (m, 6H), 1.52 (m, 2H), 1.34-1.27 (m, 1H), 1.31 (s, 3H), 1.23-1.16 (m, 5H), 1.14 (s, 3H), 0.93-0.78 (m, 3H).

Example 87. (4-Phenylphenyl)-methyl-N-[(3S)-2,2-dimethyl-4-oxo-azetidin-3-yl]-carbamate Step 1. Preparation of (4-phenylphenyl)-methyl-N-[(3S)-1-[bis(trimethylsilyl)methyl]-2,2-dimethyl-4-oxo-azetidin-3-yl]-carbamate Under nitrogen atmosphere, to a solution of the crude (3S)-3-amino-1-[bis-(trimethylsilyl)-methyl]-4,4-dimethyl-azetidin-2-one (0.13 g, 0.48 mmol) in dry $CH_2Cl_2$ (2.0 mL), DIPEA (0.10 mL, 0.57 mmol) was added. Subsequently, the crude mixture (0.38 g) containing (4-phenylphenyl)-methyl-2-oxopyridine-1-carboxylate (0.15 g, 0.48 mmol) [obtained as described in example 17 (step 1)] in dry $CH_2Cl_2$ (2.8 mL) was added. The reaction mixture was stirred at r.t. for 16 h, then diluted with $CH_2Cl_2$ and sequentially washed with sat. $NH_4Cl$ solution (15 mL) and sat. $NaHCO_3$ solution (3×15 mL). The organic layer was dried over $Na_2SO_4$, filtered and concentrated to dryness. The crude product was purified by column chromatography using a Teledyne ISCO apparatus (Cy/EtOAc 70:30) to afford a mixture (1:1:1 ratio) containing the title compound, (4-phenylphenyl)-methyl-2-oxopyridine-1-carboxylate and (4-phenylphenyl)-methanol (0.18 g). The mixture was used in the next step without further purification.

Step 2. Preparation of (4-phenylphenyl)-methyl-N-[(3S)-2,2-dimethyl-4-oxo-azetidin-3-yl]-carbamate To a suspension of the mixture (0.18 g) containing (4-phenylphenyl)-methyl-N-[(3S)-1-[bis-(trimethylsilyl)-methyl]-2,2-dimethyl-4-oxo-azetidin-3-yl]-carbamate (0.09 g, 0.19 mmol) in MeCN (4.0 mL), cooled to 0° C., a solution of CAN (0.51 g, 0.93 mmol) in deionized $H_2O$ (1.0 mL) was added. The reaction mixture was stirred at r.t. for 1 h, and then diluted with EtOAc (15 mL) and $H_2O$ (15 mL). The two phases were separated and the aqueous layer was extracted with EtOAc (3×15 mL). The combined organic layers were sequentially washed with sat. $NaHCO_3$ solution (10 mL), 40% $NaHSO_3$ solution (5 mL) and with sat. $NaHCO_3$ solution (10 mL). The organic layer was dried over $Na_2SO_4$ concentrated to dryness to afford a crude mixture (0.14 g) mainly containing (4-phenylphenyl)-methyl-N-[(3S)-1-formyl-2,2-dimethyl-4-oxo-azetidin-3-yl]-carbamate. This crude was suspended in a 1:1 mixture acetone/sat. $NaHCO_3$ solution (4.0 mL) and stirred at r.t. for 16 h. The suspension was diluted with EtOAc (15 mL) and $H_2O$ (5 mL) was added. After extraction with EtOAc (3×15 mL) and the combined organic phases were dried over $Na_2SO_4$, filtered and concentrated to dryness. The crude product was purified by column chromatography using a Teledyne ISCO apparatus (Cy/EtOAc from 50:50 to 40:60) to afford the title compound (0.035 g, 26% over three steps), as white powder. $R_t$=2.39 min; MS (ESI) m/z: 325 [M-H]$^+$, 347 [M-Na]$^+$, 363 [M-K]$^+$. $^1$H NMR (DMSO-d$_6$): δ 8.16 (s, 1H), 8.11 (d, 1H, J=9.2 Hz), 7.71-7.63 (m, 4H), 7.50-7.43 (m, 4H), 7.40-7.32 (m, 1H), 5.28-4.98 (m, 2H), 4.39 (d, 1H, J=9.2 Hz), 1.33 (s, 3H), 1.17 (s, 3H).

Example 88. (4-Cyclohexylphenyl)-methyl-N-[(3S)-2,2-dimethyl-4-oxo-azetidin-3-yl]-carbamate Step 1. Preparation of (4-cyclohexylphenyl)-methyl-N-[(3S)-1-[bis-(trimethylsilyl)-methyl]-2,2-dimethyl-4-oxo-azetidin-3-yl]-carbamate Under nitrogen atmosphere, to a solution of the crude (3S)-3-amino-1-[bis-(trimethylsilyl)-methyl]-4,4-dimethyl-azetidin-2-one (0.10 g, 0.35 mmol) in dry $CH_2Cl_2$ (2.0 mL), DIPEA (0.07 mL, 0.42 mmol) was added. Subsequently, the crude mixture (0.30 g) containing (4-cyclohexylphenyl)-methyl-2-oxopyridine-1-carboxylate (0.11 g, 0.35 mmol) [obtained as described in example 31 (step 2)] in dry $CH_2Cl_2$ (1.5 mL) was added. The reaction mixture was stirred at r.t. for 16 h, then diluted with $CH_2Cl_2$ and sequentially washed with sat. $NH_4Cl$ solution (15 mL) and sat. $NaHCO_3$ solution (3×15 mL). The organic layer was dried over $Na_2SO_4$, filtered and concentrated to dryness. The crude product was purified by column chromatography using a Teledyne ISCO apparatus (Cy/EtOAc 70:30) to afford a mixture (ratio 1:2:0.3) containing the title compound, (4-cyclohexylphenyl)-methyl-2-oxopyridine-1-carboxylate and (4-cyclohexylphenyl)-methanol (0.15 g). The mixture was used in the next step without further purification.

Step 2. Preparation of (4-cyclohexylphenyl)-methyl-N-[(3S)-2,2-dimethyl-4-oxo-azetidin-3-yl]-carbamate To a suspension of the mixture (0.15 g) containing (4-cyclohexylphenyl)-methyl-N-[(3S)-1-[bis-(trimethylsilyl)-methyl]-2,2-dimethyl-4-oxo-azetidin-3-yl]-carbamate (0.063 g, 0.13 mmol) in MeCN (2.0 mL), cooled to 0° C., a solution of CAN (0.38 g, 0.70 mmol) in deionized $H_2O$ (0.5 mL) was added. The reaction mixture was stirred at r.t. for 1 h, and then diluted with EtOAc (15 mL) and $H_2O$ (15 mL). The two phases were separated and the aqueous layer was extracted with EtOAc (3×15 mL). The combined organic layers were sequentially washed with sat. NaHCO$_3$ solution (10 mL), 40% NaHSO$_3$ solution (5 mL) and with sat. NaHCO$_3$ solution (10 mL). The organic layer was dried over Na$_2$SO$_4$ concentrated to dryness to afford a crude mixture (0.12 g) mainly containing (4-phenylphenyl)-methyl-N-[(3S)-1-formyl-2,2-dimethyl-4-oxo-azetidin-3-yl]-carbamate. This crude was suspended in a 1:1 mixture acetone/sat. NaHCO$_3$ solution (4.0 mL) and stirred at r.t. for 16 h. The suspension was diluted with EtOAc (15 mL) and H$_2$O (5 mL) was added. After extraction with EtOAc (3×15 mL) and the combined organic phases were dried over Na$_2$SO$_4$, filtered and concentrated to dryness. The crude product was purified by column chromatography using a Teledyne ISCO apparatus (Cy/EtOAc from 50:50 to 40:60) to afford the title compound (0.033 g, 21% over three steps), as white solid. R$_t$=1.46 min; MS (ESI) m/z: 331 [M-H]$^+$, 348 [M-NH$_4$]$^+$, 369 [M−K]$^+$. $^1$H NMR (DMSO-d$_6$): δ 8.14 (s, 1H), 8.03 (d, 1H, J=9.3 Hz), 7.28-7.24 (m, 2H), 7.23-7.19 (m, 2H), 5.16-4.86 (m, 2H), 4.37 (d, 1H, J=9.2 Hz), 1.83-1.72 (m, 5H), 1.73-1.67 (m, 1H), 1.47-1.33 (m, 4H), 1.32 (s, 3H), 1.28-1.20 (m, 1H), 1.15 (s, 3H).

Example 89. 4-Cyclohexylbutyl-N-[(3R)-2,2-dimethyl-4-oxo-azetidin-3-yl]-carbamate Step 1. Preparation of 4-cyclohexylbutyl-N-[(3R)-2,2-dimethyl-4-oxo-azetidin-3-yl]-carbamate Under nitrogen atmosphere, to a solution of the crude (3R)-3-amino-1-[bis-(trimethylsilyl)-methyl]-4,4-dimethyl-azetidin-2-one (0.12 g, 0.45 mmol) in dry CH$_2$Cl$_2$ (2.0 mL), DIPEA (0.09 mL, 0.54 mmol) was added. Subsequently, the crude mixture (0.28 g) containing 4-cyclohexylbutyl-2-oxopyridine-1-carboxylate (0.11 g, 0.45 mmol) [obtained as described in example 5 (step 1)] in dry CH$_2$Cl$_2$ (2.5 mL) was added. The reaction mixture was stirred at r.t. for 16 h, then diluted with CH$_2$Cl$_2$ and sequentially washed with sat. NH$_4$Cl solution (15 mL) and sat. NaHCO$_3$ solution (3×15 mL). The organic layer was dried over Na$_2$SO$_4$, filtered and concentrated to dryness. The crude product was purified by column chromatography using a Teledyne ISCO apparatus (Cy/EtOAc 80:20) to afford a mixture (ratio 1:2:1) containing the title compound, 4-cyclohexylbutyl-2-oxopyridine-1-carboxylate and 4-cyclohexylbutan-1-ol (0.25 g), which was used in the next step without further purification.

Step 2. Preparation of 4-cyclohexylbutyl-N-[(3S)-2,2-dimethyl-4-oxo-azetidin-3-yl]-carbamate To a suspension of the mixture (0.25 g) containing 4-cyclohexylbutyl-N-[(3R)-1-[bis-(trimethylsilyl)-methyl]-2,2-dimethyl-4-oxo-azetidin-3-yl]-carbamate (0.103 g, 0.23 mmol) in MeCN (2.0 mL), cooled to 0° C., a solution of CAN (0.38 g, 0.70 mmol) in deionized H$_2$O (0.5 mL) was added. The reaction mixture was stirred at r.t. for 1 h, and then diluted with EtOAc (15 mL) and H$_2$O (15 mL). The two phases were separated and the aqueous layer was extracted with EtOAc (3×15 mL). The combined organic layers were sequentially washed with sat. NaHCO$_3$ solution (10 mL), 40% NaHSO$_3$ solution (5 mL) and with sat. NaHCO$_3$ solution (10 mL). The organic layer was dried over Na$_2$SO$_4$ concentrated to dryness to afford a crude mixture (0.175 g) mainly containing 4-cyclohexylbutyl-N-[(3S)-1-formyl-2,2-dimethyl-4-oxo-azetidin-3-yl]-carbamate. This crude was suspended in a 1:1 mixture acetone/sat. NaHCO$_3$ solution (4.0 mL) and stirred at r.t. for 16 h. The suspension was diluted with EtOAc (15 mL) and H$_2$O (5 mL) was added. After extraction with EtOAc (3×15 mL) and the combined organic phases were dried over Na$_2$SO$_4$, filtered and concentrated to dryness. The crude product was purified by column chromatography using a Teledyne ISCO apparatus (Cy/EtOAc 50:50) to afford the pure title compound (0.04 g, 26% over three steps), as white powder. R$_t$=1.49 min; MS (ESI) m/z: 297 [M-H]$^+$, 314 [M-NH$_4$]$^+$, 319 [M−Na]$^+$, 335 [M−K]$^+$. $^1$H NMR (DMSO-d$_6$): δ 8.12 (s, 1H), 7.89 (d, 1H, J=9.2 Hz), 4.34 (d, 1H, J=9.2 Hz), 4.04-3.89 (m, 2H), 1.71-1.57 (m, 6H), 1.52 (m, 2H), 1.34-1.27 (m, 1H), 1.31 (s, 3H), 1.23-1.16 (m, 5H), 1.14 (s, 3H), 0.93-0.78 (m, 3H).

Example 90. (4-Phenylphenyl)-methyl-N-[(3R)-2,2-dimethyl-4-oxo-azetidin-3-yl]-carbamate Step 1. Preparation of (4-phenylphenyl)-methyl-N-[(3R)-1-[bis(trimethylsilyl)methyl]-2,2-dimethyl-4-oxo-azetidin-3-yl]-carbamate Under nitrogen atmosphere, to a solution of the crude (3R)-3-amino-1-[bis-(trimethylsilyl)-methyl]-4,4-dimethyl-azetidin-2-one (0.13 g, 0.48 mmol) in dry CH$_2$Cl$_2$ (2.0 mL), DIPEA (0.10 mL, 0.57 mmol) was added. Subsequently, the crude mixture (0.38 g) containing (4-phenylphenyl)-methyl-2-oxopyridine-1-carboxylate (0.15 g, 0.48 mmol) [obtained as described in example 17 (step 1)] in dry CH$_2$Cl$_2$ (2.8 mL) was added. The reaction mixture was stirred at r.t. for 16 h, then diluted with CH$_2$Cl$_2$ and sequentially washed with sat. NH$_4$Cl solution (15 mL) and sat. NaHCO$_3$ solution (3×15 mL). The organic layer was dried over Na$_2$SO$_4$, filtered and concentrated to dryness. The crude product was purified by column chromatography using a Teledyne ISCO apparatus (Cy/EtOAc 70:30) to afford a mixture (ratio 1:0.7:0.8) containing the title compound, (4-phenylphenyl)-methyl-2-oxopyridine-1-carboxylate and (4-phenylphenyl)-methanol (0.2 g). The mixture was used in the next step without further purification.

Step 2. Preparation of (4-phenylphenyl)-methyl-N-[(3R)-2,2-dimethyl-4-oxo-azetidin-3-yl]-carbamate To a suspension of the mixture (0.2 g) containing (4-phenylphenyl)-methyl-N-[(3R)-1-[bis-(trimethylsilyl)-methyl]-2,2-dimethyl-4-oxo-azetidin-3-yl]-carbamate (0.11 g, 0.23 mmol) in MeCN (4.1 mL), cooled to 0° C., a solution of CAN (0.63 g, 1.16 mmol) in deionized H$_2$O (1.3 mL) was added. The reaction mixture was stirred at r.t. for 1 h, and then diluted with EtOAc (15 mL) and H$_2$O (15 mL). The two phases were separated and the aqueous layer was extracted with EtOAc (3×15 mL). The combined organic layers were sequentially washed with sat. NaHCO$_3$ solution (10 mL), 40% NaHSO$_3$ solution (5 mL) and with sat. NaHCO$_3$ solution (10 mL). The organic layer was dried over Na$_2$SO$_4$ concentrated to dryness to afford a crude mixture (0.15 g) mainly containing (4-phenylphenyl)-methyl-N-[(3R)-1-formyl-2,2-dimethyl-4-oxo-azetidin-3-yl]-carbamate. This crude was suspended in a 1:1 mixture acetone/sat. NaHCO$_3$ solution (6.0 mL) and stirred at r.t. for 16 h. The suspension was diluted with EtOAc (15 mL) and H$_2$O (5 mL) was added. After extraction with EtOAc (3×15 mL) and the combined organic phases were dried over Na$_2$SO$_4$, filtered and concentrated to dryness. The crude product was purified by column chromatography using a Teledyne ISCO apparatus (Cy/EtOAc from 50:50 to 40:60) to afford the title compound (0.041 g, 22% over three steps), as white powder. R$_t$=2.39 min; MS (ESI) m/z: 325 [M-H]$^+$, 347 [M−Na]$^+$, 363 [M−K]$^+$. $^1$H NMR (DMSO-d$_6$): δ 8.16 (s, 1H), 8.11 (d, 1H, J=9.2 Hz), 7.71-7.63 (m, 4H), 7.50-7.43 (m, 4H), 7.40-7.32 (m, 1H), 5.28-4.98 (m, 2H), 4.39 (d, 1H, J=9.2 Hz), 1.33 (s, 3H), 1.17 (s, 3H).

Example 91. (4-Cyclohexylphenyl)-methyl-N-[(3R)-2,2-dimethyl-4-oxo-azetidin-3-yl]-carbamate Step 1. Preparation of (4-cyclohexylphenyl)-methyl-N-[(3R)-1-[bis(trimethylsilyl)methyl]-2,2-dimethyl-4-oxo-azetidin-3-yl]-carbamate Under nitrogen atmosphere, to a solution of the crude (3R)-3-amino-1-[bis-(trimethylsilyl)-methyl]-4,4-dimethyl-azetidin-2-one (0.11 g, 0.42 mmol) in dry $CH_2Cl_2$ (2.0 mL), DIPEA (0.09 mL, 0.50 mmol) was added. Subsequently, the crude mixture (0.35 g) containing (4-cyclohexylphenyl)-methyl-2-oxopyridine-1-carboxylate (0.13 g, 0.42 mmol) [obtained as described in example 31 (step 2)] in dry $CH_2Cl_2$ (2.5 mL) was added. The reaction mixture was stirred at r.t. for 16 h, then diluted with $CH_2Cl_2$ and sequentially washed with sat. $NH_4Cl$ solution (15 mL) and sat. $NaHCO_3$ solution (3×15 mL). The organic layer was dried over $Na_2SO_4$, filtered and concentrated to dryness. The crude product was purified by column chromatography using a Teledyne ISCO apparatus (Cy/EtOAc 70:30) to afford a mixture (ratio 1:1.4:1) containing the title compound, (4-cyclohexylphenyl)-methyl-2-oxopyridine-1-carboxylate and (4-cyclohexylphenyl)-methanol (0.26 g). The mixture was used in the next step without further purification.

Step 2. Preparation of (4-cyclohexylphenyl)-methyl-N-[(3S)-2,2-dimethyl-4-oxo-azetidin-3-yl]-carbamate To a suspension of the mixture (0.26 g) containing (4-cyclohexylphenyl)-methyl-N-[(3R)-1-[bis-(trimethylsilyl)-methyl]-2,2-dimethyl-4-oxo-azetidin-3-yl]-carbamate (0.12 g, 0.24 mmol) in MeCN (2.0 mL), cooled to 0° C., a solution of CAN (0.38 g, 0.70 mmol) in deionized $H_2O$ (0.5 mL) was added. The reaction mixture was stirred at r.t. for 1 h, and then diluted with EtOAc (15 mL) and $H_2O$ (15 mL). The two phases were separated and the aqueous layer was extracted with EtOAc (3×15 mL). The combined organic layers were sequentially washed with sat. $NaHCO_3$ solution (10 mL), 40% $NaHSO_3$ solution (5 mL) and with sat. $NaHCO_3$ solution (10 mL). The organic layer was dried over $Na_2SO_4$ concentrated to dryness to afford a crude mixture (0.22 g) mainly containing (4-phenylphenyl)-methyl-N-[(3S)-1-formyl-2,2-dimethyl-4-oxo-azetidin-3-yl]-carbamate. This crude was suspended in a 1:1 mixture acetone/sat. $NaHCO_3$ solution (4.0 mL) and stirred at r.t. for 16 h. The suspension was diluted with EtOAc (15 mL) and $H_2O$ (5 mL) was added. After extraction with EtOAc (3×15 mL) and the combined organic phases were dried over $Na_2SO_4$, filtered and concentrated to dryness. The crude product was purified by column chromatography using a Teledyne ISCO apparatus (Cy/EtOAc from 50:50 to 40:60) to afford the title compound (0.043 g, 25% over three steps), as white solid. $R_t$=1.46 min; MS (ESI) m/z: 331 [M-H]⁺, 348 [M-$NH_4$]⁺, 369 [M−K]⁺. ¹H NMR (DMSO-$d_6$): δ 8.14 (s, 1H), 8.03 (d, 1H, J=9.3 Hz), 7.28-7.24 (m, 2H), 7.23-7.19 (m, 2H), 5.16-4.86 (m, 2H), 4.37 (d, 1H, J=9.2 Hz), 1.83-1.72 (m, 5H), 1.73-1.67 (m, 1H), 1.47-1.33 (m, 4H), 1.32 (s, 3H), 1.28-1.20 (m, 1H), 1.15 (s, 3H).

Example 92. (4-Oxazol-4-ylphenyl)-methyl-N-[(3S)-2-oxoazetidin-3-yl]-carbamate

Step 1. Preparation of methyl-4-(2-bromoacetyl)-benzoate

To a stirred solution of ethyl-4-acetylbenzoate (1.85 g, 9.53 mmol) in EtOAc (110 mL), $CuBr_2$ (3.87 g, 17.15 mmol) was added and the mixture stirred at reflux for 16 h. The crude reaction mixture was filtered through a short pad of Celite® and concentrated to dryness. Purification by typical silica gel flash chromatography (Cy/$CH_2Cl_2$ from 70:30 to 40:60) afforded the title compound (1.99 g, 81%), as a white solid. $R_t$=2.48 min; MS (ESI) m/z: not detected. ¹H NMR (DMSO-$d_6$): δ 8.30-7.94 (m, 4H), 5.00 (s, 2H), 4.36 (q, J=7.1 Hz, 2H), 1.35 (t, J=7.1 Hz, 3H)

Step 2. Preparation of ethyl-4-oxazol-4-yl-benzoate

To a stirred solution of 4-(2-bromoacetyl)-benzoate (1.80 g, 6.64 mmol) in HCOOH (10 mL), ammonium formate (1.21 g, 18.59 mmol) was added and the mixture stirred under nitrogen atmosphere at reflux for 7 h. The crude reaction was diluted with $H_2O$ (10 mL), basified with 5.0 M NaOH solution, washed with EtOAc (2×25 mL), and extracted with $CH_2Cl_2$ (2×25 mL). The combined organics were dried over $Na_2SO_4$ and concentrated to dryness under reduced pressure. Purification by typical silica gel flash chromatography (Cy/TBME from 100:0 to 85:15) afforded the title compound (0.520 g, 36%), as a white solid. $R_t$=2.26 min; MS (ESI) m/z: 218 [M-H]⁺. ¹H NMR ($CDCl_3$): δ 8.12-8.07 (m, 2H), 8.04 (s, 1H), 7.97 (s, 1H), 7.86-7.79 (m, 2H), 4.40 (q, J=7.1 Hz, 2H), 1.41 (t, J=7.1 Hz, 3H).

Step 3. Preparation of (4-oxazol-4-ylphenyl)-methanol

Under nitrogen atmosphere, at 0° C., to a suspension of $LiAlH_4$ (2.0 M in THF, 4.6 mL, 9.21 mmol) in dry THF (18 mL), a solution of ethyl 4-oxazol-4-yl-benzoate (0.50 g, 2.30 mmol) in dry THF (5.0 mL) was added dropwise. The resulting mixture was stirred at r.t. for 3 h, then cooled to 0° C. and $H_2O$ (5.0 mL) was slowly added, followed by a 3.0 M KOH solution (5.0 mL). The mixture was stirred at 0° C. for 1 h, the precipitate was filtered off through a short pad of Celite®, rinsed with THF, and then the filtrate was dried over $Na_2SO_4$ and concentrated to dryness at low pressure to afford the title compound as a white solid (0.380 g, 94% yield). $R_t$=1.40 min; MS (ESI) m/z: 176.1 [M-H]⁺. ¹H NMR (DMSO-$d_6$): δ 8.59 (s, 1H), 8.44 (s, 1H), 7.75 (d, J=8.1 Hz, 2H), 7.37 (d, J=8.0 Hz, 2H), 5.20 (t, J=5.7 Hz, 1H), 4.51 (d, J=5.7 Hz, 2H).

Step 4. Preparation of (4-oxazol-4-ylphenyl)-methyl-2-pyridyl carbonate and (4-oxazol-4-ylphenyl)-methyl-2-oxopyridine-1-carboxylate Under nitrogen atmosphere, to a stirred mixture of (4-oxazol-4-ylphenyl)-methanol (0.18 g, 1.03 mmol) in dry $CH_2Cl_2$ (5.1 mL), DMAP (0.012 g, 0.10 mmol) and 2-DPC (0.272 g, 1.24 mmol) were added. The reaction mixture was left at r.t. for 16 h, then diluted with $CH_2Cl_2$ (15 mL) and washed with a sat. $NaHCO_3$ solution (15 mL). The organic fraction was dried over $Na_2SO_4$, filtered and concentrated to dryness to afford an oily product (0.32 g), as a mixture (2:1 ratio) of (4-oxazol-4-ylphenyl)-methyl-2-pyridyl carbonate and (4-oxazol-4-ylphenyl)-methyl-2-oxopyridine-1-carboxylate. The mixture of isomers was not separated and used in the next step without any further purification. Rt=2.14 min; MS (ESI) m/z: 297 [M-H]$^+$.

Step 5. Preparation of (4-oxazol-4-ylphenyl)-methyl-N-[(3S)-2-oxoazetidin-3-yl]-carbamate Under nitrogen atmosphere, to a suspension of [(3S)-2-oxoazetidin-3-yl]-ammonium acetate (0.05 g, 0.34 mmol) in dry CH$_2$Cl$_2$ (4.0 mL), DIPEA (0.07 mL, 0.41 mmol) was added dropwise. Subsequently, the crude mixture (0.32 g) containing (4-oxazol-4-ylphenyl)-methyl-2-oxopyridine-1-carboxylate (0.101 g, 0.34 mmol) in dry CH$_2$Cl$_2$ (1.0 mL) was added. The reaction mixture was stirred at r.t. for 16 h, concentrated to dryness affording an oily residue which was portioned between EtOAc (15 ml) and NaHCO$_3$ sat. solution (15 ml), the organic layer dried over Na$_2$SO$_4$ and concentrated to dryness. The resulting crude was triturated in DCM (2 ml) to afford the pure title compound (0.032 g, 33%) as a white solid. R$_t$=1.49 min; MS (ESI) m/z: 288 [M-H]$^+$. $^1$H NMR (DMSO-d$_6$): δ 8.63 (s, 1H), 8.46 (s, 1H), 8.04-7.89 (m, 2H), 7.79 (d, J=8.1 Hz, 2H), 7.42 (d, J=8.0 Hz, 2H), 5.06 (s, 2H), 4.67 (m, 1H), 3.39 (m, 1H), 3.09 (m, 1H).

Example 93. [(1R)- and (1S)-1-(4-Cyclohexylphenyl)-ethyl]-N-[(3S)-2-oxoazetidin-3-yl]-carbamate Step 1. Preparation of (1R*)-1-(4-cyclohexylphenyl)-ethanol Under nitrogen atmosphere, at 0° C., to a stirred solution of 1-(4-cyclohexylphenyl)-ethanone (0.30 g, 1.50 mmol) in dry MeOH (15 mL), NaBH$_4$ (0.11 g, 3.00 mmol) was added in one portion. The resulting reaction mixture was stirred at r.t. for 30 min, and then acetone (0.1 mL) was added, followed by evaporation of the solvents. The residue was taken up in EtOAc (20 mL) and sequentially washed with sat. NH$_4$Cl solution (20 mL) and sat. NaHCO$_3$ solution (3×20 mL) and sat. NaCl solution (20 mL). The organic layer was dried over Na$_2$SO$_4$, filtered and concentrated to dryness, affording the title compound (0.29 g, 95%), which was used in the next step without any further purification. $^1$H NMR (DMSO-d$_6$): δ 7.23 (d, 2H, J=8.1 Hz), 7.14 (d, 2H, J=8.1 Hz), 5.01 (d, 1H, J=4.2 Hz), 4.70-4.62 (m, 1H), 2.48-2.41 (m, 1H), 1.84-1.65 (m, 5H), 1.46-1.32 (m, 4H), 1.29 (d, 3H, J=6.5 Hz), 1.27-1.16 (m, 1H).

Step 2. Preparation of (1R*)-1-(4-cyclohexylphenyl)-ethyl-2-pyridyl carbonate and (1R*)-1-(4-cyclohexylphenyl)-ethyl-2-oxopyridine-1-carboxylate Under nitrogen atmosphere, to a stirred solution of (1R*)-1-(4-cyclohexylphenyl)-ethanol (0.2 g, 1.0 mmol) in dry CH$_2$Cl$_2$ (8.0 mL), DMAP (0.012 g, 0.10 mmol) and 2-DPC (0.259 g, 1.2 mmol) were added. The reaction mixture was stirred at r.t. for 16 h, then diluted with CH$_2$Cl$_2$ and sequentially washed with sat. NH$_4$Cl solution (30 mL) and sat. NaHCO$_3$ solution (3×30 mL). The organic layer was dried over Na$_2$SO$_4$, filtered and concentrated to dryness affording a yellow oil (0.33 g), as a mixture (1:1.8 ratio) of 1-(4-cyclohexylphenyl)-ethyl-2-oxopyridine-1-carboxylate and 1-(4-cyclohexylphenyl)-ethyl-2-pyridyl carbonate. The mixture of isomers was not separated and used in the next step without any further purification.

Step 3. Preparation of (1R)-1-(4-cyclohexylphenyl)-ethyl-N-[(3S)-2-oxoazetidin-3-yl]-carbamate and (1S)-1-(4-cyclohexylphenyl)-ethyl-N-[(3S)-2-oxoazetidin-3-yl]-carbamate Under nitrogen atmosphere, to a suspension of [(3S)-2-oxoazetidin-3-yl]-ammonium acetate (0.05 g, 0.34 mmol) in dry CH$_2$Cl$_2$ (4.0 mL), DIPEA (0.067 mL, 0.41 mmol) was added dropwise. Subsequently, the crude mixture (0.33 g) containing (1R*)-1-(4-cyclohexylphenyl)-ethyl-2-oxopyridine-1-carboxylate (0.11 g, 0.34 mmol) in dry CH$_2$Cl$_2$ (2.0 mL) was added. The reaction mixture was stirred at r.t. for 16 h, then concentrated to dryness giving an oily residue (0.24 g). Purification by typical silica gel flash chromatography (CH$_2$Cl$_2$/MeOH from 100:0 to 95:5) afforded the pure title compounds (0.057 g, 53%), as white solid. R$_t$=2.65 min. MS (ESI) m/z: 317 [M-H]$^+$, 339 [M-Na]$^+$, 355 [M-K]$^+$. $^1$H NMR (DMSO-d$_6$): δ 7.98-7.86 (m, 2H), 7.27-7.23 (m, 2H), 7.22-7.17 (m, 2H), 5.69-5.61 (m, 1H), 4.66-4.58 (m, 1H), 3.41-3.33 (m, 1H), 3.07-3.01 (m, 1H), 1.84-1.65 (m, 5H), 1.47-1.15 (m, 9H).

Example 94. p-Tolylmethyl-N-[(3S)-2-oxoazetidin-3-yl]-carbamate

Step 1. Preparation of p-tolylmethyl-2-pyridyl carbonate and p-tolylmethyl-2-oxopyridine-1-carboxylate Under nitrogen atmosphere, to a stirred solution of p-tolylmethanol (0.21 g, 1.7 mmol) in dry CH$_2$Cl$_2$ (14.0 mL), DMAP (0.021 g, 0.17 mmol) and 2-DPC (0.44 g, 2.0 mmol) were added. The reaction mixture was stirred at r.t. for 16 h, then diluted with CH$_2$Cl$_2$ and sequentially washed with sat. NH$_4$Cl solution (40 mL) and sat. NaHCO$_3$ solution (3×40 mL). The organic layer was dried over Na$_2$SO$_4$, filtered and concentrated to dryness affording a yellow oil (0.43 g), as a mixture (1:1.9 ratio) of p-tolylmethyl 2-oxopyridine-1-carboxylate and p-tolylmethyl 2-pyridyl carbonate. The mixture of isomers was not separated and used in the next step without any further purification. R$_t$=2.15 min. MS (ESI) m/z: 244 [M-H]$^+$, 266 [M-Na]$^+$, 282 [M-K]$^+$.

Step 2. Preparation of p-tolylmethyl-N-[(3S)-2-oxoazetidin-3-yl]-carbamate

Under nitrogen atmosphere, to a suspension of [(3S)-2-oxoazetidin-3-yl]-ammonium acetate (0.05 g, 0.34 mmol) in dry CH$_2$Cl$_2$ (4.0 mL), DIPEA (0.067 mL, 0.41 mmol) was added dropwise. Subsequently, the crude mixture (0.24 g) containing p-tolylmethyl-2-oxopyridine-1-carboxylate (0.083 g, 0.34 mmol) in dry CH$_2$Cl$_2$ (2.0 mL) was added. The reaction mixture was stirred at r.t. for 16 h, then concentrated to dryness giving an oily residue (0.21 g). Purification by typical silica gel flash chromatography (CH$_2$Cl$_2$/MeOH from 100:0 to 95:5) afforded the pure title compounds (0.040 g, 50%), as white solid. R$_t$=1.75 min. MS (ESI) m/z: 235 [M-H]$^+$, 257 [M-Na]$^+$, 273 [M-K]$^+$. $^1$H NMR (DMSO-d$_6$): δ 7.97-7.88 (m, 2H), 7.24 (d, 2H, J=7.9 Hz), 7.17 (d, 2H, J=7.9 Hz), 4.98 (s, 2H), 4.68-4.61 (m, 1H), 3.39 (t, 1H, J=5.4 Hz), 3.09-3.05 (m, 1H), 2.29 (s, 3H).

Example 95. (4-Ethylphenyl)-methyl-N-[(3S)-2-oxoazetidin-3-yl]-carbamate

Step 1. Preparation of (4-ethylphenyl)-methyl-2-pyridyl carbonate and (4-ethylphenyl)-methyl-2-oxopyridine-1-carboxylate Under nitrogen atmosphere, to a stirred solution of commercially-available 4-ethyl-benzyl alcohol (0.23 mL, 1.7 mmol) in dry $CH_2Cl_2$ (14.0 mL), DMAP (0.021 g, 0.17 mmol) and 2-DPC (0.44 g, 2.0 mmol) were added. The reaction mixture was stirred at r.t. for 16 h, then diluted with $CH_2Cl_2$ and sequentially washed with sat. $NH_4Cl$ solution (40 mL) and sat. $NaHCO_3$ solution (3×40 mL). The organic layer was dried over $Na_2SO_4$, filtered and concentrated to dryness affording a yellow oil (0.43 g), as a mixture (1:2 ratio) of (4-ethylphenyl)-methyl-2-oxopyridine-1-carboxylate and (4-ethylphenyl)-methyl-2-pyridyl carbonate. The mixture of isomers was not separated and used in the next step without any further purification. $R_t$=2.36 min. MS (ESI) m/z: 258 [M-H]$^+$, 280 [M−Na]$^+$, 296 [M−K]$^+$.

Step 2. Preparation of (4-ethylphenyl)methyl-N-[(3S)-2-oxoazetidin-3-yl]-carbamate Under nitrogen atmosphere, to a suspension of [(3S)-2-oxoazetidin-3-yl]-ammonium acetate (0.05 g, 0.34 mmol) in dry $CH_2Cl_2$ (4.0 mL), DIPEA (0.067 mL, 0.41 mmol) was added dropwise. Subsequently, the crude mixture (0.26 g) containing (4-ethylphenyl)-methyl-2-oxopyridine-1-carboxylate (0.088 g, 0.34 mmol) in dry $CH_2Cl_2$ (2.0 mL) was added. The reaction mixture was stirred at r.t. for 16 h, then concentrated to dryness giving an oily residue (0.22 g). Purification by typical silica gel flash chromatography ($CH_2Cl_2$/MeOH from 100:0 to 95:5) afforded the pure title compounds (0.054 g, 64%), as white solid. $R_t$=1.96 min. MS (ESI) m/z: 249 [M-H]$^+$, 271 [M−Na]$^+$, 287 [M−K]$^+$. $^1$H NMR (DMSO-$d_6$): δ 7.97-7.88 (m, 2H), 7.26 (d, 2H, J=7.9 Hz), 7.20 (d, 2H, J=7.9 Hz), 4.99 (s, 2H), 4.69-4.61 (m, 1H), 3.39 (t, 1H, J=5.4 Hz), 3.10-3.04 (m, 1H), 2.59 (q, 2H, J=7.7 Hz), 1.17 (t, 3H, J=7.7 Hz).

Example 96. (4-Propylphenyl)-methyl-N-[(3S)-2-oxoazetidin-3-yl]-carbamate

Step 1. Preparation of (4-propylphenyl)-methanol

Under nitrogen atmosphere, at 0° C., to a suspension of $LiAlH_4$ (2.0 M THF solution, 6.1 mL, 12.2 mmol) in dry $Et_2O$ (30 mL), 4-propylbenzoic acid (0.5 g, 3.05 mmol) in dry $Et_2O$ (10 mL) was added dropwise. The resulting reaction mixture was stirred at r.t. for 1 h, and then cooled to 0° C. $H_2O$ (0.50 mL) was slowly and cautiously added, followed by 3.0 M KOH solution (0.50 mL) and additional $H_2O$ (2.2 mL). The mixture was stirred at 0° C. for 1 h and then filtered off. The organic layer was dried over $Na_2SO_4$, filtered and concentrated to dryness, affording the title compound (0.43 g, 95%), which was used in the next step without any further purification. $R_t$=2.22 min. $^1$H NMR (DMSO-$d_6$): δ 7.22 (d, 2H, J=7.9 Hz), 7.13 (d, 2H, J=7.9 Hz), 5.07 (t, 1H, J=5.8 Hz), 4.46 (d, 2H, J=5.8 Hz), 2.53 (t, 2H, J=7.5 Hz), 1.56 (sex, 2H, J=7.5 Hz), 0.89 (t, 3H, J=7.5 Hz).

Step 2. Preparation of (4-propylphenyl)-methyl-2-pyridyl carbonate and (4-propylphenyl)-methyl-2-oxopyridine-1-carboxylate Under nitrogen atmosphere, to a stirred solution of (4-propylphenyl)-methanol (0.20 mg, 1.33 mmol) in dry $CH_2Cl_2$ (10.0 mL), DMAP (0.016 g, 0.13 mmol) and 2-DPC (0.35 g, 1.60 mmol) were added. The reaction mixture was stirred at r.t. for 16 h, then diluted with $CH_2Cl_2$ and sequentially washed with sat. $NH_4Cl$ solution (40 mL) and sat. $NaHCO_3$ solution (3×40 mL). The organic layer was dried over $Na_2SO_4$, filtered and concentrated to dryness affording a yellow oil (0.36 g), as a mixture (1:1.6 ratio) of (4-propylphenyl)-methyl-2-oxopyridine-1-carboxylate and (4-propylphenyl)-methyl-2-pyridyl carbonate. The mixture of isomers was not separated and used in the next step without any further purification. $R_t$=2.57 min. MS (ESI) m/z: 272 [M-H]$^+$, 294 [M−Na]$^+$, 310 [M−K]$^+$.

Step 3. Preparation of (4-propylphenyl)-methyl-N-[(3S)-2-oxoazetidin-3-yl]-carbamate Under nitrogen atmosphere, to a suspension of [(3S)-2-oxoazetidin-3-yl]-ammonium acetate (0.05 g, 0.34 mmol) in dry $CH_2Cl_2$ (4.0 mL), DIPEA (0.067 mL, 0.41 mmol) was added dropwise. Subsequently, the crude mixture (0.24 g) containing (4-propylphenyl)-methyl-2-oxopyridine-1-carboxylate (0.092 g, 0.34 mmol) in dry $CH_2Cl_2$ (2.0 mL) was added. The reaction mixture was stirred at r.t. for 16 h, then concentrated to dryness giving an oily residue (0.20 g). Purification by typical silica gel flash chromatography ($CH_2Cl_2$/MeOH from 100:0 to 95:5) afforded the pure title compounds (0.047 g, 53%), as white solid. $R_t$=2.17 min. MS (ESI) m/z: 263 [M-H]$^+$, 285 [M−Na]$^+$, 301 [M−K]$^+$. $^1$H NMR (DMSO-$d_6$): δ 7.96-7.89 (m, 2H), 7.26 (d, 2H, J=7.7 Hz), 7.18 (d, 2H, J=7.7 Hz), 4.99 (s, 2H), 4.69-4.62 (m, 1H), 3.39 (t, 1H, J=5.3 Hz), 3.09-3.05 (m, 1H), 2.54 (t, 2H, J=7.5 Hz), 1.57 (sex, 2H, J=7.5 Hz), 0.88 (t, 3H, J=7.5 Hz).

Example 97. (4-Propoxyphenyl)-methyl-N-[(3S)-2-oxoazetidin-3-yl]-carbamate

Step 1. Preparation of ethyl 4-propoxybenzoate

Under nitrogen atmosphere, to a stirred solution of ethyl 4-hydroxybenzoate (0.26 mL, 1.8 mmol) in dry DMF (12 mL), 1-bromopropane (0.45 mL, 4.93 mmol) was added dropwise, followed by NaH (95% pure, 0.075 g, 3.13 mmol). The resulting solution was stirred at r.t. for 18 h and subsequently heated at 80° C. for 3 h. The reaction mixture was then diluted with EtOAc (50 mL) and washed with $H_2O$ (3×50 mL). The organic layer was dried over $Na_2SO_4$, filtered and concentrated to dryness. Purification by typical silica gel flash chromatography (100% Cy) afforded the pure title compound (0.34 g, 91%), as an oil. $R_t$=2.90 min. MS (ESI) m/z: 209 [M-H]$^+$. $^1$H-NMR (CDCl$_3$): δ 8.06-7.92 (m, 2H), 6.97-6.83 (m, 2H), 4.34 (q, J=7.11 Hz, 2H), 3.97 (t, J=7.00 Hz, 2H), 1.83 (h, J=7.00 Hz, 2H), 1.38 (t, J=7.11 Hz, 3H), 1.05 (t, J=7.44 Hz, 3H).

Step 2. Preparation of (4-propoxyphenyl)-methanol

Under nitrogen atmosphere, at 0° C., to a suspension of $LiAlH_4$ (2.0 M in THF, 2.6 mL, 5.18 mmol) in dry $Et_2O$ (11 mL), a solution of ethyl 4-propoxybenzoate (0.34 g, 1.30 mmol) in dry $Et_2O$ (4.0 mL) was added dropwise. The resulting mixture was stirred at r.t. for 4 h, then cooled to 0° C. and $H_2O$ (3.0 mL) was slowly added, followed by a 3.0 M KOH solution (3.0 mL) and additional $H_2O$ (4.1 mL). The mixture was stirred at 0° C. for 1 h, filtered and the organic phase dried over $Na_2SO_4$, concentrated to dryness giving a solid crude product (0.23 g), which was used in the next step without further purification. $R_t$=1.39 min; MS (ESI) m/z: not detected. $^1$H NMR (CDCl$_3$): δ 7.31-7.23 (m, 2H), 6.94-6.85 (m, 2H), 4.62 (s, 2H), 3.92 (t, J=7.04 Hz, 2H), 1.81 (h, J=7.04 Hz, 2H), 1.04 (t, J=7.41 Hz, 3H).

Step 3. Preparation of (4-propoxyphenyl)-methyl-2-pyridyl carbonate and (4-propoxyphenyl)-methyl-2-oxopyridine-1-carboxylate Under nitrogen atmosphere, to a stirred mixture of (4-propoxyphenyl)-methanol (0.23 g, 1.4 mmol) in dry CH$_2$Cl$_2$ (8 mL), DMAP (0.017 g, 0.14 mmol) and 2-DPC (0.36 g, 1.68 mmol) were added. The reaction mixture was left at r.t. for 16 h, then diluted with CH$_2$Cl$_2$ (50 mL) and sequentially washed with a sat. NH$_4$Cl solution (15 mL) and a sat. NaHCO$_3$ solution (3×15 mL). The organic fraction was dried over Na$_2$SO$_4$, filtered and concentrated to dryness to afford an oily product (0.26 g), as a mixture (1:2.4 ratio) of (4-propoxyphenyl)-methyl-2-pyridyl carbonate and (4-propoxyphenyl)-methyl-2-oxopyridine-1-carboxylate. The mixture of isomers was not separated and used in the next step without any further purification. R$_t$=2.41 min; MS (ESI) m/z: 286 [M-H]$^-$.

Step 4. Preparation of (4-propoxyphenyl)methyl N-[(3S)-2-oxoazetidin-3-yl]carbamate Under nitrogen atmosphere, to a suspension of [(3S)-2-oxoazetidin-3-yl]-ammonium acetate (0.025 g, 0.17 mmol) in dry CH$_2$Cl$_2$ (3.0 mL), DIPEA (0.044 mL, 0.25 mmol) was added dropwise. Subsequently, the crude mixture (0.26 g) containing (4-propoxyphenyl)-methyl-2-oxopyridine-1-carboxylate (0.07 g, 0.21 mmol) in dry CH$_2$Cl$_2$ (4.0 mL) was added. The reaction mixture was stirred at r.t. for 16 h, diluted with CH$_2$Cl$_2$ (6 mL), washed with sat. NH$_4$Cl solution (2×20 mL), sat. NaHCO$_3$ solution (2×20 mL), and the organic layer dried over Na$_2$SO$_4$ and concentrated to dryness. Purification by typical silica gel flash chromatography (Cy/EtOAc 50:50) afforded the pure title compound (0.038 g, 78%) as a white solid. R$_t$=2.02 min; MS (ESI) m/z: 296 [M-NH$_4$]$^+$, 301 [M–Na]$^+$, 317 [M–K]$^+$. $^1$H NMR (DMSO-d$_6$): δ 8.13-7.78 (m, 2H), 7.35-7.21 (m, 2H), 6.98-6.86 (m, 2H), 4.95 (s, 2H), 4.72-4.57 (m, 1H), 3.91 (t, J=7.00 Hz, 2H), 3.38 (t, J=5.27 Hz, 1H), 3.07 (dd, J=2.72, 5.27 Hz, 1H), 1.72 (h, J=7.00 Hz, 2H), 0.97 (t, J=7.40 Hz, 3H).

Example 98. (2-Phenylpyrimidin-5-yl)-methyl-N-[(3S)-2-oxoazetidin-3-yl]-carbamate Step 1. Preparation of (2-phenylpyrimidin-5-yl)-methyl-2-pyridyl carbonate and (2-phenylpyrimidin-5-yl)-methyl-2-oxopyridine-1-carboxylate Under nitrogen atmosphere, to a stirred mixture of (2-phenylpyrimidin-5-yl)-methanol (0.200 g, 1.07 mmol) in dry CH$_2$Cl$_2$ (5.4 mL), DMAP (0.013 g, 0.11 mmol) and 2-DPC (0.284 g, 1.29 mmol) were added. The reaction mixture was left at r.t. for 16 h, then diluted with CH$_2$Cl$_2$ (15 mL) and washed with a sat. NaHCO$_3$ solution (20 mL). The organic fraction was dried over Na$_2$SO$_4$, filtered and concentrated to dryness to afford an oily product (0.35 g), as a mixture (2:1 ratio) of (2-phenylpyrimidin-5-yl)-methyl-2-pyridyl carbonate and (2-phenylpyrimidin-5-yl)-methyl-2-oxopyridine-1-carboxylate. The mixture of isomers was not separated and used in the next step without any further purification. R$_t$=2.08 min; MS (ESI) m/z: 308 [M-H]$^+$.

Step 2. Preparation of (2-phenylpyrimidin-5-yl)-methyl-N-[(3S)-2-oxoazetidin-3-yl]-carbamate Under nitrogen atmosphere, to a suspension of [(3S)-2-oxoazetidin-3-yl]-ammonium acetate (0.05 g, 0.34 mmol) in dry CH$_2$Cl$_2$ (4.0 mL), DIPEA (0.07 mL, 0.41 mmol) was added dropwise. Subsequently, the crude mixture (0.35 g) containing (2-phenylpyrimidin-5-yl)-methyl-2-oxopyridine-1-carboxylate (0.105 g, 0.34 mmol) in dry CH$_2$Cl$_2$ (1.0 mL) was added. The reaction mixture was stirred at r.t. for 16 h, concentrated to dryness affording an oily residue which was portioned between EtOAc (15 ml) and sat. NaHCO$_3$ solution (15 ml). The organic layer was dried over Na$_2$SO$_4$ and concentrated to dryness under reduced pressure. Purification by typical silica gel flash chromatography (Cy/EtOAc from 50:50 to 0:100) afforded the pure title compound (0.030 g, 29%), as a white solid. R$_t$=1.69 min; MS (ESI) m/z: 299 [M-H]$^+$. $^1$H NMR (DMSO-d$_6$): δ 8.91 (s, 2H), 8.43-8.36 (m, 2H), 8.08 (d, J=8.7 Hz, 1H), 7.95 (s, 1H), 7.59-7.50 (m, 3H), 5.14 (s, 2H), 4.67 (ddd, J=8.6, 5.6, 2.7 Hz, 1H), 3.4 (m, 1H), 3.10 (dd, J=5.3, 2.8 Hz, 1H).

Example 99. (4,4-Difluorocyclohexyl)-methyl-N-[(3S)-2-oxoazetidin-3-yl]-carbamate Step 1. Preparation of (4,4-difluorocyclohexyl)-methanol Under nitrogen atmosphere, at 0° C., to a suspension of LiAlH$_4$ (2.0 M THF solution, 11.2 mL, 22.47 mmol) in dry Et$_2$O (55 mL), methyl 4,4-difluorocyclohexane carboxylate (1.0 g, 5.62 mmol) in dry Et$_2$O (10 mL) was added dropwise. The resulting reaction mixture was stirred at r.t. for 1 h, and then cooled to 0° C. H$_2$O (1.0 mL) was slowly and cautiously added, followed by 3.0 M KOH solution (1.0 mL) and additional H$_2$O (4.5 mL). The mixture was stirred at 0° C. for 1 h and then filtered off. The organic layer was dried over Na$_2$SO$_4$, filtered and concentrated to dryness, affording the title compound (0.68 g, 81%), which was used in the next step without any further purification. $^1$H NMR (DMSO-d$_6$): δ 4.51 (t, 1H, J=5.6 Hz), 3.26 (t, 2H, J=7.5 Hz), 2.05-1.93 (m, 2H), 1.86-1.66 (m, 4H), 1.55-1.41 (m, 1H), 1.21-1.08 (m, 2H).

Step 2. Preparation of (4,4-difluorocyclohexyl)-methyl-2-pyridyl carbonate and (4,4-difluorocyclohexyl)-methyl-2-oxopyridine-1-carboxylate Under nitrogen atmosphere, to a stirred solution of (4,4-difluorocyclohexyl)-methanol (0.20 g, 1.33 mmol) in dry CH$_2$Cl$_2$ (11.0 mL), DMAP (0.016 g, 0.13 mmol) and 2-DPC (0.35 g, 1.60 mmol) were added. The reaction mixture was stirred at r.t. for 16 h, then diluted with CH$_2$Cl$_2$ and sequentially washed with sat. NH$_4$Cl solution (40 mL) and sat. NaHCO$_3$ solution (3×40 mL). The organic layer was dried over Na$_2$SO$_4$, filtered and concentrated to dryness affording a yellow oil (0.33 g), as a mixture (1:2.1 ratio) of (4,4-difluorocyclohexyl)-methyl-2-oxopyridine-1-carboxylate and (4,4-difluorocyclohexyl)-methyl-2-pyridyl carbonate. The mixture of isomers was not separated and used in the next step without any further purification.

Step 3. Preparation of (4,4-difluorocyclohexyl)-methyl-N-[(3S)-2-oxoazetidin-3-yl]-carbamate Under nitrogen atmosphere, to a suspension of [(3S)-2-oxoazetidin-3-yl]-ammonium acetate (0.05 g, 0.34 mmol) in dry CH$_2$Cl$_2$ (4.0 mL), DIPEA (0.067 mL, 0.41 mmol) was added dropwise. Subsequently, the crude mixture (0.29 g) containing (4,4-difluorocyclohexyl)-methyl-2-oxopyridine-1-carboxylate (0.092 g, 0.34 mmol) in dry CH$_2$Cl$_2$ (2.0 mL) was added. The reaction mixture was stirred at r.t. for 16 h, then concentrated to dryness giving an oily residue (0.19 g). Purification by typical silica gel flash chromatography (CH$_2$Cl$_2$/MeOH from 100:0 to 95:5) afforded the pure title compounds (0.038 g, 53%), as white solid. R$_t$=1.66 min. MS (ESI) m/z: 263 [M–H]$^+$, 285 [M–Na]$^+$, 301 [M–K]$^+$. $^1$H NMR (DMSO-d$_6$): δ 7.92 (s, 1H), 7.85 (d, 1H, J=8.8 Hz), 4.67-4.59 (m, 1H), 3.90-3.82 (m, 2H), 3.38 (t, 1H, J=5.5 Hz), 3.07 (dd, 1H, J=5.2, 2.7 Hz), 2.07-1.94 (m, 2H), 1.89-1.65 (m, 5H), 1.30-1.16 (m, 2H).

Example 100. 4-(4,4-Difluorocyclohexyl)-butyl-N-[(3S)-2-oxoazetidin-3-yl]-carbamate Step 1. Preparation of (4,4-difluorocyclohexyl)-methanol Under nitrogen atmosphere, at 0° C., to a suspension of LiAlH$_4$ (2.0 M THF solution, 11.2 mL, 22.47 mmol) in dry Et$_2$O (55 mL), methyl 4,4-difluorocyclohexane carboxylate (1.0 g, 5.62 mmol) in dry Et$_2$O (10 mL) was added dropwise. The resulting reaction mixture was stirred at r.t. for 1 h, and then cooled to 0° C. H$_2$O (1.0 mL) was slowly and cautiously added, followed by 3.0 M KOH solution (1.0 mL) and additional H$_2$O (4.5 mL). The mixture was stirred at 0° C. for 1 h and then filtered off. The organic layer was dried over Na$_2$SO$_4$, filtered and concentrated to dryness, affording the title compound (0.68 g, 81%), which was used in the next step without any further purification. $^1$H NMR (DMSO-d$_6$): δ 4.51 (t, 1H, J=5.6 Hz), 3.26 (t, 2H, J=7.5 Hz), 2.05-1.93 (m, 2H), 1.86-1.66 (m, 4H), 1.55-1.41 (m, 1H), 1.21-1.08 (m, 2H).

Step 2. Preparation of 4,4-difluorocyclohexane-carboxyaldehyde

Under nitrogen atmosphere, at –78° C., to a solution of oxalyl chloride (0.35 mL, 4.16 mmol) in dry CH$_2$Cl$_2$ (15.0 mL), DMSO (0.27 mL, 3.84 mmol) was added dropwise. After stirring at –78° C. for 15 min, a solution of (4,4-difluorocyclohexyl)-methanol (0.48 g, 3.20 mmol) in dry CH$_2$Cl$_2$ (10 mL) was added dropwise. The reaction mixture was stirred at –78° C. for 1 h, then Et$_3$N (1.27 mL, 9.60 mmol) was added dropwise. The resulting reaction mixture was warmed up to r.t., then concentrated to dryness. The crude product was taken up in Et$_2$O (30 mL) and washed with sat. NH$_4$Cl solution (30 mL). The organic layer was dried over Na$_2$SO$_4$, filtered and concentrated to dryness affording the title compound (0.39 g, 82%), which was used in the next step without any further purification. $^1$H NMR (DMSO-d$_6$): δ 9.61 (s, 1H), 2.05-1.73 (m, 7H), 1.64-1.51 (m, 2H).

Step 3. Preparation of [(Z)-4-(4,4-difluorocyclohexyl)-but-3-enoxy]-methylbenzene and [(E)-4-(4,4-difluorocyclohexyl)-but-3-enoxy]-methylbenzene Under nitrogen atmosphere, at –30° C., to a solution of 3-benzyloxypropyl-(triphenyl)-phosphonium bromide (1.41 g, 2.87 mmol) in dry THF (20 mL), n-BuLi (2.5 M in hexane, 1.15 mL, 2.87 mmol) was added dropwise. The solution was stirred at –30° C. for 45 min, then 4,4-difluorocyclohexane-carboxyaldehyde (0.39 g, 2.61 mmol) in dry THF (10.0 mL) was slowly added. The reaction mixture stirred at –30° C. for 30 min and then at r.t. for 16 h. The solution was diluted with CH$_2$Cl$_2$ (20 mL) and washed with sat. NH$_4$Cl solution (3×30 mL). The organic layer was dried over Na$_2$SO$_4$, filtered and concentrated to dryness giving a crude residue (0.832 g). Purification by typical silica gel flash chromatography (100% CH$_2$Cl$_2$) afforded the pure title compounds (0.37 g, 50%), as a mixture (ratio 85:15) of E/Z diastereoisomers. R$_t$=3.15 min (minor) and 3.25 min (major). MS (ESI) m/z: 279 [M–H]$^+$, 301 [M–Na]$^+$, 317 [M–K]$^+$. $^1$H NMR (DMSO-d$_6$): δ 7.38-7.25 (m, 10H), 5.48-5.25 (m, 4H), 4.47 (s, 2H, major), 4.46 (s, 2H, minor), 3.47-3.41 (m, 4H), 2.34 (q, 4H, J=6.8 Hz), 2.04-1.57 (m, 14H), 1.37-1.23 (m, 4H).

Step 4. Preparation of (4,4-difluorocyclohexyl)-butan-1-ol

A solution containing a mixture of [(Z)-4-(4,4-difluorocyclohexyl)-but-3-enoxy]-methylbenzene and [(E)-4-(4,4-difluorocyclohexyl)-but-3-enoxy]methylbenzene (0.37 g, 1.33 mmol) in EtOH (30 mL) was passed through a H-Cube® hydrogenator flow reactor provided with a 20% Pd(OH)$_2$/C cartridge [flow rate: 1.0 mL/min; P=10.0 bar, T=60° C.]. The outcoming solution was concentrated to dryness. Purification by typical silica gel flash chromatography (Cy/EtOAc 4:1) afforded the pure title compound (0.12 g, 70%), as an oil. $^1$H NMR (DMSO-d$_6$): δ 4.33 (t, 1H, J=5.2 Hz), 3.44 (qd, 2H, J=6.2, 5.2 Hz), 2.03-1.91 (m, 2H), 1.85-1.66 (m, 4H), 1.45-1.05 (m, 9H).

Step 5. Preparation of (4,4-difluorocyclohexyl)-butyl-2-pyridyl carbonate and (4,4-difluorocyclohexyl)-butyl-2-oxopyridine-1-carboxylate Under nitrogen atmosphere, to a stirred solution of (4,4-difluorocyclohexyl)-butan-1-ol (0.12 g, 0.63 mmol) in dry CH$_2$Cl$_2$ (8.0 mL), DMAP (0.008 g, 0.06 mmol) and 2-DPC (0.16 g, 0.75 mmol) were added. The reaction mixture was stirred at r.t. for 16 h, then diluted with CH$_2$Cl$_2$ and sequentially washed with sat. NH$_4$Cl solution (20 mL) and sat. NaHCO$_3$ solution (3×20 mL). The organic layer was dried over Na$_2$SO$_4$, filtered and concentrated to dryness affording a yellow oil (0.22 g), as a mixture (1:2.5 ratio) of (4,4-difluorocyclohexyl)-butyl-2-oxopyridine-1-carboxylate and (4,4-difluorocyclohexyl)-butyl-2-pyridyl carbonate. The mixture of isomers was not separated and used in the next step without any further purification.

Step 6. Preparation of (4,4-difluorocyclohexyl)-butyl-N-[(3S)-2-oxoazetidin-3-yl]-carbamate Under nitrogen atmosphere, to a suspension of [(3S)-2-oxoazetidin-3-yl]-ammonium acetate (0.03 g, 0.21 mmol) in dry CH$_2$Cl$_2$ (4.0 mL), DIPEA (0.079 mL, 0.45 mmol) was added dropwise. Subsequently, the crude mixture (0.22 g) containing (4,4-difluorocyclohexyl)-butyl-2-oxopyridine-1-carboxylate (0.066 g, 0.21 mmol) in dry CH$_2$Cl$_2$ (2.0 mL) was added. The reaction mixture was stirred at r.t. for 16 h, then concentrated to dryness giving an oily residue (0.10 g). Purification by preparative HPLC afforded the pure title compound (0.028 g, 44%), as white solid. R$_t$=2.21 min. MS (ESI) m/z: 305 [M–H]$^+$, 327 [M–Na]$^+$, 343 [M–K]$^+$. $^1$H NMR (DMSO-d$_6$): δ 7.90 (s, 1H), 7.78 (d, 1H, J=8.8 Hz), 4.65-4.50 (m, 1H), 4.00-3.90 (m, 2H), 3.37 (t, 1H, J=5.4

Hz), 3.06 (dd, 1H, J=5.2, 2.8 Hz), 2.03-1.90 (m, 2H), 1.85-1.66 (m, 4H), 1.57-1.48 (m, 2H), 1.41-1.03 (m, 7H).

Example 101. (4-Iodophenyl)-methyl-N-[(3S)-2-oxoazetidin-3-yl]-carbamate

Step 1. Preparation of (4-iodophenyl)-methyl-2-pyridyl carbonate and (4-iodophenyl)-methyl-2-oxopyridine-1-carboxylate Under nitrogen atmosphere, to a stirred solution of commercially available (4-iodophenyl)-methanol (0.90 g, 3.85 mmol) in dry $CH_2Cl_2$ (20 mL), DMAP (0.047 g, 0.385 mmol) and 2-DPC (1.08 g, 5.0 mmol) were added. The reaction mixture was stirred at r.t. for 16 h, then diluted with $CH_2Cl_2$ (120 mL) and sequentially washed with sat. $NH_4Cl$ solution (20 mL), sat. $NaHCO_3$ solution (3×20 mL) and brine (20 mL). The organic layer was dried over $Na_2SO_4$, filtered and concentrated to dryness affording an oily residue (1.31 g, 96%), as a mixture (1.1:1 ratio) of (4-iodophenyl)-methyl-2-pyridyl carbonate and (4-iodophenyl)-methyl-2-oxopyridine-1-carboxylate. The mixture of isomers was not separated and used in the next step without any further purification. $R_t$=2.34 min. MS (ESI) m/z: 356 [M-H]$^+$, 378 [M–Na]$^+$, 394 [M–K]$^+$.

Step 4. Preparation of (4-iodophenyl)methyl N-[(3S)-2-oxoazetidin-3-yl]carbamate Under nitrogen atmosphere, to a suspension of [(3S)-2-oxoazetidin-3-yl]-ammonium acetate (0.25 g, 1.71 mmol) in dry $CH_2Cl_2$ (20 mL), DIPEA (0.31 mL, 1.88 mmol) was added dropwise. Subsequently, the crude mixture (1.24 g) containing (4-iodophenyl)-methyl-2-oxopyridine-1-carboxylate (0.591 g, 1.71 mmol) in dry $CH_2Cl_2$ (5.0 mL) was added and the resulting reaction mixture was stirred at r.t. for 16 h. The mixture was diluted with $CH_2Cl_2$ (120 mL), and washed with sat. $NH_4Cl$ solution (2×30 mL), sat. $NaHCO_3$ solution (2×20 mL), and brine (20 mL). The organic layer was dried over $Na_2SO_4$, filtered and concentrated to dryness giving a solid residue (0.40 g). Purification by silica gel flash chromatography using a Teledyne ISCO apparatus (Cy/TBME from 100:0 to 0:100) afforded the pure title compound (0.32 g, 54%), as a white solid. $R_t$=1.95 min; MS (ESI) m/z: 347 [M-H]$^+$, 364 [M–Na]$^+$, 369 [M–K]$^+$. (ESI) m/z: 345 [M-H]$^-$. $^1$H NMR (DMSO-$d_6$): δ 8.00 (d, 1H, J=8.7 Hz), 7.94 (s, 1H), 7.73 (d, 2H, J=8.2 Hz), 7.16 (d, 2H, J=8.2 Hz), 4.99 (s, 2H), 4.66 (ddd, 1H, J=8.6, 5.4, 2.7 Hz), 3.39 (t, 1H, J=5.4 Hz), 3.07 (dd, 1H, J=5.4, 2.7 Hz).

Example 102. 4-[(1R,2R,4S)- and (1S,2S,4R)-Norbornan-2-yl]-oxyphenyl]-methyl-N-[(3S)-2-oxoazetidin-3-yl]-carbamate Step 1. Preparation of ethyl 4-[(1R*,2R*,4S*)-norbornan-2-yl]-oxybenzoate Under nitrogen atmosphere, a solution of ethyl 4-hydroxybenzoate (1.0 g, 5.96 mmol), 2-norbornene (0.85 g, 8.94 mmol) and trifluoromethanesulfonic acid (0.005 mL, 0.06 mmol) in dry 1,4-dioxane (9.0 mL) was stirred at reflux for 16 h. The reaction mixture was then concentrated to dryness affording a solid residue, which was portioned between EtOAc (50 ml) and 0.1 M NaOH solution (50 ml). The resulting extracted organic layer dried over $Na_2SO_4$ and concentrated to dryness. Purification by typical silica gel flash chromatography (Cy/$CH_2Cl_2$ from 80:20 to 50:50) afforded the pure title compound (0.78 g, 50%), as a white solid. $R_t$=2.03 min; MS (ESI) m/z: 261 [M-H]$^+$. $^1$H NMR (CDCl$_3$): δ 8.06-7.88 (m, 2H), 6.93-6.77 (m, 2H), 4.34 (q, J=7.1 Hz, 2H), 4.22 (d, J=7.3 Hz, 1H), 2.46 (d, J=4.8 Hz, 1H), 2.37-2.29 (m, 1H), 1.78 (ddd, J=13.2, 6.7, 2.4 Hz, 1H), 1.67 (dt, J=10.0, 2.0 Hz, 1H), 1.64-1.44 (m, 3H), 1.37 (t, J=7.1 Hz, 3H), 1.27-1.10 (m, 3H).

Step 2. Preparation of [4-[(1R*,2R*,4S*)-norbornan-2-yl]-oxyphenyl]-methanol

Under nitrogen atmosphere, at 0° C., to a suspension of LiAlH$_4$ (2.0 M in THF, 5.3 mL, 10.53 mmol) in dry THF (19 mL), a solution of ethyl 4-[(1R*,2R*,4S*)-norbornan-2-yl]-oxybenzoate (0.685 g, 2.63 mmol) in dry THF (7.0 mL) was added dropwise. The resulting mixture was stirred at r.t. for 3 h, then cooled to 0° C. and H$_2$O (5.0 mL) was slowly added, followed by a 3.0 M KOH solution (5.0 mL). The mixture was stirred at 0° C. for 1 h, the precipitate was filtered off through a short pad of Celite®, rinsed with THF, and then the filtrate was dried over Na$_2$SO$_4$ and concentrated to dryness at low pressure to afford the title compound as a white solid (0.517 g, 90% yield). $R_t$=1.03 min; MS (ESI) m/z: not detected. $^1$H NMR (DMSO-$d_6$): δ 7.23-7.16 (m, 2H), 6.85-6.78 (m, 2H), 5.00 (t, J=5.7 Hz, 1H), 4.40 (d, J=5.6 Hz, 2H), 4.22 (d, J=7.3 Hz, 1H), 2.35 (d, J=4.6 Hz, 1H), 2.27 (t, J=4.4 Hz, 1H), 1.77 (ddd, J=13.0, 6.7, 2.4 Hz, 1H), 1.61-1.34 (m, 4H), 1.23-1.04 (m, 3H).

Step 3. Preparation of [4-[(1R*,2R*,4S*)-norbornan-2-yl]-oxyphenyl]-methyl-2-pyridyl carbonate and [4-[(1R*,2R*,4S*)-norbornan-2-yl]-oxyphenyl]-methyl-2-oxopyridine-1-carboxylate Under nitrogen atmosphere, to a stirred mixture of [4-[(1R*,2R*,4S*)-norbornan-2-yl]-oxyphenyl]-methanol (0.514 g, 2.35 mmol) in dry CH$_2$Cl$_2$ (11.8 mL), DMAP (0.029 g, 0.24 mmol) and 2-DPC (0.623 g, 2.82 mmol) were added. The reaction mixture was left at r.t. for 16 h, then diluted with CH$_2$Cl$_2$ (15 mL) and sequentially washed with a sat. NH$_4$Cl solution (25 mL) and a sat. NaHCO$_3$ solution (25 mL). The organic fraction was dried over Na$_2$SO$_4$, filtered and concentrated to dryness to afford an oily product (0.796 g), as a mixture (2:1 ratio) of [4-[(1R*,2R*,4S*)-norbornan-2-yl]-oxyphenyl]-methyl-2-pyridyl carbonate and [4-[(1R*,2R*,4S*)-norbornan-2-yl]-oxyphenyl]-methyl-2-oxopyridine-1-carboxylate. The mixture of isomers was not separated and used in the next step without any further purification. Rt=2.86 min; MS (ESI) m/z: 340 [M-H]$^+$.

Step 4. Preparation of [4-[(1R,2R,4S)-norbornan-2-yl]-oxyphenyl]-methyl-N-[(3S)-2-oxoazetidin-3-yl]-carbamate and [4-[(1S,2S,4R)-norbornan-2-yl]-oxyphenyl]-methyl-N-[(3S)-2-oxoazetidin-3-yl]-carbamate Under nitrogen atmosphere, to a suspension of [(3S)-2-oxoazetidin-3-yl]-ammonium acetate (0.12 g, 0.82 mmol) in dry CH$_2$Cl$_2$ (9.6 mL), DIPEA (0.16 mL, 0.98 mmol) was added dropwise. Subsequently, the crude mixture (0.796 g) containing [4-[(1R*,2R*,4S*)-norbornan-2-yl]-oxyphenyl]-methyl-2-oxopyridine-1-carboxylate (0.271 g, 0.82 mmol) in dry CH$_2$Cl$_2$ (2.4 mL) was added. The reaction mixture was stirred at r.t. for 16 h, concentrated to dryness affording an oily residue which was dissolved in EtOAc (15 ml), washed with sat. NH$_4$Cl solution (2×15 mL), sat. NaHCO$_3$ solution (2×15 mL), and brine (2×15 mL). The collected organic layers were dried over Na$_2$SO$_4$ and concentrated to dryness under reduced pressure. Purification by typical silica gel flash chromatography (Cy/TBME from 50:50 to 0:100) afforded a solid which was triturated in Et$_2$O (2.0 mL) to afford the pure title compound (0.089 g, 33%), as a white solid. R$_t$=2.47 min; MS (ESI) m/z: 329 [M-H]$^-$. $^1$H NMR (DMSO-d$_6$): δ 8.02-7.79 (m, 2H), 7.29-7.22 (m, 2H), 6.88-6.82 (m, 2H), 4.94 (s, 2H), 4.65 (ddd, J=8.6, 5.5, 2.7 Hz, 1H), 4.23 (d, J=7.3 Hz, 1H), 3.43-3.34 (m, 1H), 3.07 (dd, J=5.2, 2.8 Hz, 1H), 2.35 (d, J=4.6 Hz, 1H), 2.27 (t, J=4.3 Hz, 1H), 1.78 (ddd, J=13.0, 6.7, 2.4 Hz, 1H), 1.60-1.33 (m, 4H), 1.25-1.04 (m, 3H).

Example 103. Undec-10-ynyl-N-[(3S)-2-oxoazetidin-3-yl]-carbamate

Step 1. Preparation of 2-pyridyl-undec-10-ynyl carbonate and undec-10-ynyl-2-oxopyridine-1-carboxylate Under nitrogen atmosphere, to a stirred mixture of undec-10-yn-1-ol (0.35 g, 2.08 mmol) in dry CH$_2$Cl$_2$ (3.5 mL), DMAP (0.025 g, 0.20 mmol) and 2-DPC (0.54 g, 2.49 mmol) were added. The reaction mixture was left at r.t. for 16 h, then diluted with CH$_2$Cl$_2$ (10 mL) and sequentially washed with a sat. NH$_4$Cl solution (5 mL) and a sat. NaHCO$_3$ solution (3×5 mL). The organic fraction was dried over Na$_2$SO$_4$, filtered and concentrated to dryness to afford an oily product (0.6 g), as a mixture (1.6:1 ratio) of 2-pyridyl-undec-10-ynyl carbonate and undec-10-ynyl-2-oxopyridine-1-carboxylate. The mixture of isomers was not separated and used in the next step without any further purification. R$_t$=2.76 min; MS (ESI) m/z: 290 [M-H]$^+$.

Step 2. Preparation of undec-10-ynyl-N-[(3S)-2-oxoazetidin-3-yl]-carbamate

Under nitrogen atmosphere, to a suspension of [(3S)-2-oxoazetidin-3-yl]-ammonium acetate (0.06 g, 0.41 mmol) in dry CH$_2$Cl$_2$ (2.0 mL), DIPEA (0.08 mL, 0.49 mmol) was added dropwise. Subsequently, the crude mixture (0.35 g) containing undec-10-ynyl-2-oxopyridine-1-carboxylate (0.133 g, 0.46 mmol) in dry CH$_2$Cl$_2$ (2.0 mL) was added. The reaction mixture was stirred at r.t. for 16 h, diluted with CH$_2$Cl$_2$ (6 mL), washed with sat. NH$_4$Cl solution (1×10 mL), sat. NaHCO$_3$ solution (2×10 mL). The organic layer was dried over Na$_2$SO$_4$ and concentrated to dryness under reduced pressure. Purification by typical silica gel flash chromatography (Cy/EtOAc from 100:00 to 00:100) afforded the pure title compound (0.040 g, 35%) as a white solid. R$_t$=2.40 min; MS (ESI) m/z: 281 [M-H]$^+$. $^1$H NMR (DMSO-d$_6$): δ 7.90 (s, 1H), 7.77 (d, J=8.79 Hz, 1H), 4.65-4.59 (m, 1H), 3.94 (t, J=6.63 Hz, 2H), 3.37 (t, J=5.43 Hz, 1H), 3.07 (dd, J=5.1, 2.8 Hz, 1H), 2.71 (t, J=2.66 Hz, 1H), 2.17-2.10 (m, 2H), 1.58-1.48 (m, 2H), 1.47-1.38 (m, 2H), 1.38-1.20 (m, 10H).

Example 104. [(1s,4S)-(4-propylcyclohexyl]-methyl-N-[(3S)-2-oxoazetidin-3-yl]-carbamate Step 1. Preparation of [(1s,4r)-4-propylcyclohexyl]-methanol Under nitrogen atmosphere, at 0° C., to a suspension of LiAlH$_4$ (2.0 M THF solution, 8.82 mL, 17.65 mmol) in dry Et$_2$O (40 mL), (1s,4r)-4-propylcyclohexane carboxylic acid (1.0 g, 5.88 mmol) in dry Et$_2$O (5 mL) was added dropwise. The resulting reaction mixture was stirred at r.t. for 1 h, and then cooled to 0° C. H$_2$O (0.67 mL) was slowly and cautiously added, followed by 3.0 M KOH solution (0.67 mL) and additional H$_2$O (2.10 mL). The mixture was stirred at 0° C. for 1 h and then filtered off. The organic layer was dried over Na$_2$SO$_4$, filtered and concentrated to dryness, affording the title compound (0.94 g, quant.), which was used in the next step without any further purification. $^1$H NMR (DMSO-d$_6$): δ 4.31 (t, 1H, J=5.6 Hz), 3.19 (t, 2H, J=5.6 Hz), 1.77-1.66 (m, 4H), 1.35-1.21 (m, 3H), 1.18-1.10 (m, 3H), 0.90-0.77 (m, 7H).

Step 2. Preparation of [(1s,4r)-4-propylcyclohexyl]-methyl-2-pyridyl carbonate and [(1s,4r)-4-propylcyclohexyl]-methyl-2-oxopyridine-1-carboxylate Under nitrogen atmosphere, to a stirred solution of [(1s,4r)-4-propylcyclohexyl]-methanol (0.20 g, 1.64 mmol) in dry CH$_2$Cl$_2$ (10.0 mL), DMAP (0.02 g, 0.16 mmol) and 2-DPC (0.43 g, 1.97 mmol) were added. The reaction mixture was stirred at r.t. for 16 h, then diluted with CH$_2$Cl$_2$ and sequentially washed with sat. NH$_4$Cl solution (30 mL) and sat. NaHCO$_3$ solution (3×30 mL). The organic layer was dried over Na$_2$SO$_4$, filtered and concentrated to dryness affording a yellow oil (0.43 g), as a mixture (1.6:1 ratio) of [(1s,4r)-4-propylcyclohexyl]-methyl-2-pyridyl carbonate and [(1s,4r)-4-propylcyclohexyl]-methyl-2-oxopyridine-1-carboxylate. The mixture of isomers was not separated and used in the next step without any further purification. R$_t$=3.00 min. MS (ESI) m/z: 278 [M-H]$^+$, 300 [M-Na]$^+$, 316 [M-K]$^+$.

Step 3. Preparation of [(1s,4S)-(4-propylcyclohexyl]-methyl-N-[(3S)-2-oxoazetidin-3-yl]-carbamate Under nitrogen atmosphere, to a suspension of [(3S)-2-oxoazetidin-3-yl]-ammonium acetate (0.09 g, 0.62 mmol) in dry CH$_2$Cl$_2$ (8.0 mL), DIPEA (0.24 mL, 1.36 mmol) was added dropwise. Subsequently, the crude mixture (0.43 g) containing [(1s,4r)-4-propylcyclohexyl]-methyl-2-oxopyridine-1-carboxylate (0.17 g, 0.62 mmol) in dry CH$_2$Cl$_2$ (4.0 mL) was added. The reaction mixture was stirred at r.t. for 16 h, then concentrated to dryness giving an oily residue (0.16 g). Purification by preparative HPLC afforded the pure title compound (0.052 g, 20%), as white solid. R$_t$=2.55 min. MS (ESI) m/z: 269 [M-H]$^+$, 291 [M-Na]$^+$, 307 [M-K]$^+$. $^1$H NMR (DMSO-d$_6$): δ 7.90 (s, 1H), 7.78 (d, 1H, J=8.8 Hz), 4.66-4.47 (m, 1H), 3.82-3.73 (m, 2H), 3.37 (t, 1H, J=5.4 Hz), 3.07 (dd, 1H, J=5.1, 2.8 Hz), 1.75-1.65 (m, 3H), 1.55-1.42 (m, 1H), 1.34-1.22 (m, 2H), 1.20-1.09 (m, 3H), 1.01-0.78 (m, 6H).

Example 105. 1,3-Benzodioxol-5-ylmethyl-N-[(3S)-2-oxoazetidin-3-yl]-carbamate

Step 1. Preparation of 1,3-benzodioxol-5-ylmethyl-2-pyridyl carbonate and 1,3-benzodioxol-5-ylmethyl-2-oxopyridine-1-carboxylate Under nitrogen atmosphere, to a stirred solution of commercially available 1,3-benzodioxol-5-yl-methanol (0.30 g, 1.97 mmol) in dry CH$_2$Cl$_2$ (10 mL), DMAP (0.024 g, 0.197 mmol) and 2-DPC (0.55 g, 2.56 mmol) were added. The reaction mixture was stirred at r.t. for 16 h, then diluted with CH$_2$Cl$_2$ (80 mL) and sequentially washed with sat. NH$_4$Cl solution (20 mL), sat. NaHCO₃ solution (3×20 mL) and brine (20 mL). The organic layer was dried over Na₂SO₄, filtered and concentrated to dryness affording an oily residue (0.49 g, 93%), as a mixture (1.58:1 ratio) of 1,3-benzodioxol-5-ylmethyl-2-pyridyl carbonate and 1,3-benzodioxol-5-ylmethyl-2-oxopyridine-1-carboxylate. The mixture of isomers was not separated and used in the next step without any further purification. $R_t$=1.91 min. MS (ESI) m/z: 296 [M–Na]⁺, 312 [M–K]⁺.

Step 4. Preparation of 1,3-benzodioxol-5-ylmethyl N-[(3S)-2-oxoazetidin-3-yl]carbamate Under nitrogen atmosphere, to a suspension of [(3S)-2-oxoazetidin-3-yl]-ammonium acetate (0.060 g, 0.41 mmol) in dry CH₂Cl₂ (4.0 mL), DIPEA (0.074 mL, 0.45 mmol) was added dropwise. Subsequently, the crude mixture (0.28 g) containing 1,3-benzodioxol-5-ylmethyl-2-oxopyridine-1-carboxylate (0.11 g, 0.41 mmol) in dry CH₂Cl₂ (2.0 mL) was added and the resulting reaction mixture was stirred at r.t. for 16 h. The mixture was diluted with CH₂Cl₂ (60 mL), and washed with sat. NH₄Cl solution (2×10 mL), sat. NaHCO₃ solution (2×10 mL), and brine (10 mL). The organic layer was dried over Na₂SO₄, filtered and concentrated to dryness giving a solid residue (0.37 g). Purification by silica gel flash chromatography using a Teledyne ISCO apparatus (Cy/TBME from 100:0 to 0:100) and trituration with heptane afforded the pure title compound (0.053 g, 49%), as a white solid. $R_t$=1.51 min; MS (ESI) m/z: 265 [M–H]⁺, 282 [M–NH₄]⁺, 287 [M–Na]⁺, 303 [M–K]⁺. ¹H NMR (DMSO-d₆): δ 8.00-7.85 (m, 2H), 6.95-6.82 (m, 3H), 6.01 (s, 2H), 4.92 (s, 2H), 4.65 (ddd, 1H, J=8.3, 5.4, 2.7 Hz), 3.39 (t, 1H, J=5.4 Hz), 3.07 (dd, 1H, J=5.4, 2.7 Hz).

Example 106. (2,2-Difluoro-1,3-benzodioxol-5-yl)-methyl-N-[(3S)-2-oxoazetidin-3-yl]-carbamate Step 1. Preparation of (2,2-difluoro-1,3-benzodioxol-5-yl)-methanol Under nitrogen atmosphere, at 0° C., to a stirred suspension of LiAlH₄ (2.0 M THF solution, 6.94 mL, 13.88 mmol) in dry THF (29 mL), 2,2-difluoro-1,3-benzodioxole-5-carboxylic acid (0.70 g, 3.46 mmol) in dry THF (8.0 mL) was added dropwise. The resulting reaction mixture was stirred at r.t. for 4 h, and then cooled to 0° C. H₂O (1.5 mL) was slowly and cautiously added, followed by 3.0 M KOH solution (1.0 mL) and additional H₂O (1.0 mL). The mixture was stirred at 0° C. for 30 min and then filtered off. The organic layer was dried over Na₂SO₄, filtered and concentrated to dryness, affording the title compound (0.57 g, 84%), which was used in the next step without any further purification. $R_t$=1.99 min. ¹H NMR (DMSO-d₆): δ 7.35-7.29 (m, 2H), 7.14 (d, 1H, J=8.2 Hz), 5.33 (t, 1H, J=5.7 Hz), 4.49 (d, 2H, J=5.7 Hz).

Step 2. Preparation of (2,2-difluoro-1,3-benzodioxol-5-yl)-methyl-2-pyridyl carbonate and (2,2-difluoro-1,3-benzodioxol-5-yl)-methyl-2-oxopyridine-1-carboxylate Under nitrogen atmosphere, to a stirred solution of (2,2-difluoro-1,3-benzodioxol-5-yl)-methanol (0.30 g, 1.59 mmol) in dry CH₂Cl₂ (10 mL), DMAP (0.019 g, 0.16 mmol) and 2-DPC (0.45 g, 2.07 mmol) were added. The reaction mixture was stirred at r.t. for 16 h, then diluted with CH₂Cl₂ (90 mL) and sequentially washed with sat. NH₄Cl solution (20 mL), sat. NaHCO₃ solution (2×15 mL) and brine (15 mL). The organic layer was dried over Na₂SO₄, filtered and concentrated to dryness affording an oily residue (0.44 g, 90%), as a mixture (1.8:1 ratio) of (2,2-difluoro-1,3-benzodioxol-5-yl)-methyl-2-pyridyl carbonate and (2,2-difluoro-1,3-benzodioxol-5-yl)-methyl-2-oxopyridine-1-carboxylate. The mixture of isomers was not separated and used in the next step without any further purification. $R_t$=2.34 min. MS (ESI) m/z: 310 [M–H]⁺, 332 [M–Na]⁺, 348 [M–K]⁺.

Step 4. Preparation of (2,2-difluoro-1,3-benzodioxol-5-yl)-methyl-N-[(3S)-2-oxoazetidin-3-yl]-carbamate Under nitrogen atmosphere, to a suspension of [(3S)-2-oxoazetidin-3-yl]-ammonium acetate (0.060 g, 0.41 mmol) in dry CH₂Cl₂ (4.0 mL), DIPEA (0.074 mL, 0.45 mmol) was added dropwise. Subsequently, the crude mixture (0.34 g) containing (2,2-difluoro-1,3-benzodioxol-5-yl)-methyl-2-oxopyridine-1-carboxylate (0.12 g, 0.41 mmol) in dry CH₂Cl₂ (2.0 mL) was added and the resulting reaction mixture was stirred at r.t. for 16 h. The mixture was diluted with CH₂Cl₂ (60 mL), and washed with sat. NH₄Cl solution (2×10 mL), sat. NaHCO₃ solution (2×10 mL), and brine (10 mL). The organic layer was dried over Na₂SO₄, filtered and concentrated to dryness giving a solid residue (0.32 g). Purification by silica gel flash chromatography using a Teledyne ISCO apparatus (Cy/TBME from 100:0 to 0:100) afforded the pure title compound (0.053 g, 43%), as a white solid. $R_t$=1.97 min; MS (ESI) m/z: 301 [M–H]⁺, 318 [M–NH₄]⁺, 323 [M–Na]⁺, 339 [M–K]⁺. ¹H NMR (DMSO-d₆): δ 7.99 (d, 1H, J=8.5 Hz), 7.94 (bs, 1H), 7.45-7.33 (m, 2H), 7.22 (dd, 1H, J=8.3, 1.4 Hz), 5.04 (s, 2H), 4.66 (ddd, 1H, J=8.5, 5.4, 2.5 Hz), 3.39 (t, 1H, J=5.4 Hz), 3.08 (dd, 1H, J=5.4, 2.5 Hz).

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound having the structure of Formula I:

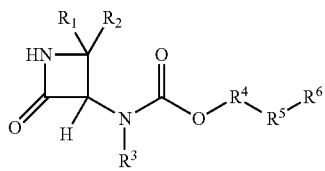

(I)

wherein:
R$^1$ and R$^2$ are each hydrogen,
R$^3$ is selected from the group consisting of hydrogen and alkyl;
R$^4$ is selected from the group consisting of alkylene, alkenylene, and alkynylene;
R$^5$ is selected from the group consisting of alkylene, alkenylene;
R$^6$ is 3 to 10 membered cycloalkyl;
or a pharmaceutically acceptable salt or ester thereof.

2. A compound of claim 1, having the structure:

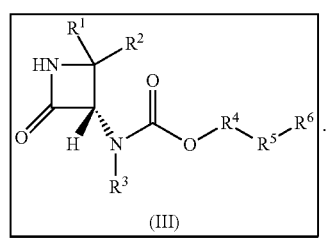

(III)

3. A compound of claim 1, wherein R$^4$ is alkylene.

4. A compound of claim 1, wherein R$^4$ is selected from the group consisting of methylene, ethylene, i-propylene, n-propylene, i-butylene, t-butylene, n-butylene, n-pentylene, i-pentylene, pentylene, hexylene, heptylene, octylene, nonylene, decylene, undecylene, and dodecylene.

5. A compound of claim 1, wherein the compound is selected from the group consisting of

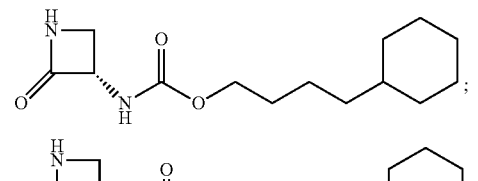

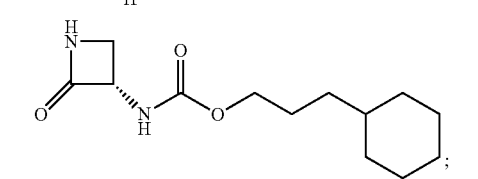

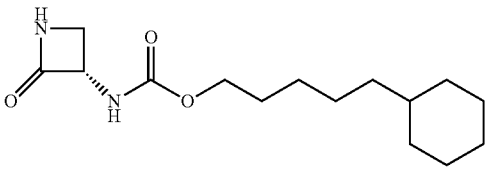

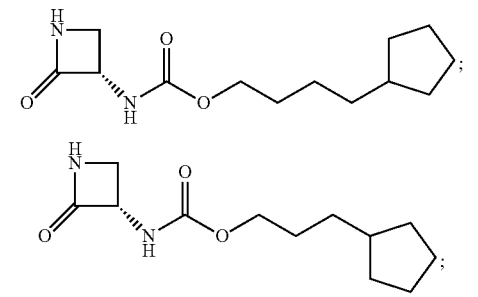

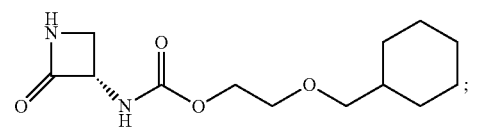

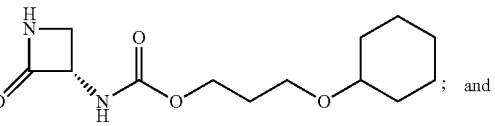

; and

-continued

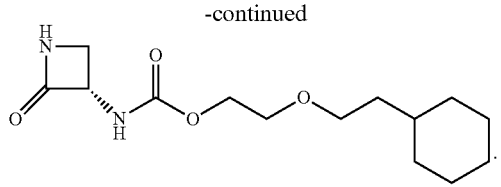

6. A pharmaceutical composition comprising a compound of claim 1, or a pharmaceutically acceptable salt thereof, and a pharmaceutically acceptable excipient, carrier or diluent.

7. A compound of claim 1, wherein the compound is of the formula:

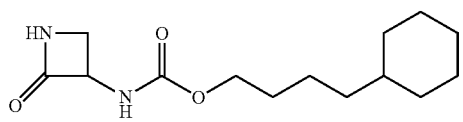 [SMILES: O=C(NC1CNC1=O)OCCCCC1CCCCC1]

or a pharmaceutically acceptable salt thereof.

8. A compound of claim 1, wherein the compound is

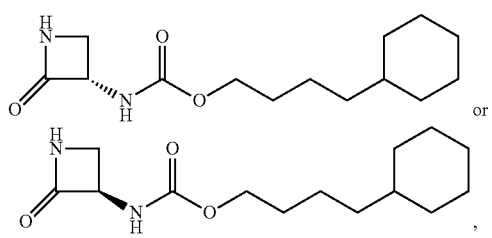

or a pharmaceutically acceptable salt thereof.

9. A compound of claim 1, wherein the compound is

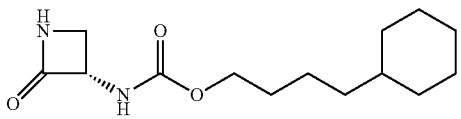 [SMILES: O=C(N[C@H]1CNC1=O)OCCCCC1CCCCC1]

or a pharmaceutically acceptable salt thereof.

10. A compound of claim 1, wherein the compound is

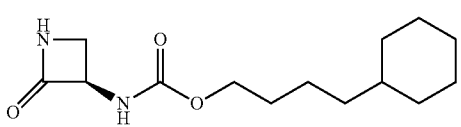

or a pharmaceutically acceptable salt thereof.

11. A compound of claim 1, wherein $R^4$-$R^5$ is ethylene, n-propylene, n-butylene, n-pentylene, or hexylene.

12. A compound of claim 1, wherein $R^4$-$R^5$ is n-propylene, n-butylene, or n-pentylene.

13. A compound of claim 1, wherein $R^3$ is hydrogen.

14. A compound of claim 1, wherein $R^6$ is cyclopentyl or cyclohexyl.

15. A compound of claim 1, wherein $R^6$ is cyclohexyl.

* * * * *

SEQUENCE LISTING

```
<160> NUMBER OF SEQ ID NOS: 2

<210> SEQ ID NO 1
<211> LENGTH: 19
<212> TYPE: DNA
<213> ORGANISM: Artificial Sequence
```

```
<220> FEATURE:
<223> OTHER INFORMATION: Synthetic polynucleotide

<400> SEQUENCE: 1
gaccatgctg ggccgtagt                                          19

<210> SEQ ID NO 2
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 2
ccagcctata caagggtct                                          19
```